US009434690B2

(12) United States Patent
Röhrig et al.

(10) Patent No.: US 9,434,690 B2
(45) Date of Patent: Sep. 6, 2016

(54) SUBSTITUTED OXOPYRIDINE DERIVATIVES AND USE THEREOF IN THE TREATMENT OF CARDIOVASCULAR DISORDERS

(71) Applicant: BAYER PHARMA AKTIENGESELLSCHAFT, Berlin (DE)

(72) Inventors: Susanne Röhrig, Hilden (DE); Alexander Hillisch, Solingen (DE); Julia Straßburger, Wuppertal (DE); Stefan Heitmeier, Wülfrath (DE); Martina Victoria Schmidt, Köln (DE); Karl-Heinz Schlemmer, Wuppertal (DE); Adrian Tersteegen, Wuppertal (DE); Anja Buchmüller, Essen (DE); Christoph Gerdes, Köln (DE); Martina Schäfer, Berlin (DE); Tom Kinzel, Düsseldorf (DE); Henrik Teller, Schwaan (DE); Hartmut Schirok, Langenfeld (DE); Jürgen Klar, Wuppertal (DE); Eloisa Jimenez Nunez, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 14/780,925

(22) PCT Filed: Mar. 27, 2014

(86) PCT No.: PCT/EP2014/056135
§ 371 (c)(1),
(2) Date: Sep. 28, 2015

(87) PCT Pub. No.: WO2014/154794
PCT Pub. Date: Oct. 2, 2014

(65) Prior Publication Data
US 2016/0052884 A1 Feb. 25, 2016

(30) Foreign Application Priority Data

Mar. 28, 2013 (EP) ..................................... 13161588
Oct. 30, 2013 (EP) ..................................... 13190944

(51) Int. Cl.
| | | |
|---|---|---|
| C07D 213/64 | (2006.01) | |
| C07D 401/12 | (2006.01) | |
| A61K 31/4412 | (2006.01) | |
| C07D 413/14 | (2006.01) | |
| C07D 213/85 | (2006.01) | |
| C07D 405/06 | (2006.01) | |
| C07D 409/06 | (2006.01) | |
| C07D 413/12 | (2006.01) | |
| C07D 417/12 | (2006.01) | |
| C07D 213/69 | (2006.01) | |
| C07D 213/84 | (2006.01) | |

(52) U.S. Cl.
CPC ........... *C07D 213/64* (2013.01); *C07D 213/69* (2013.01); *C07D 213/84* (2013.01); *C07D 213/85* (2013.01); *C07D 401/12* (2013.01); *C07D 405/06* (2013.01); *C07D 409/06* (2013.01); *C07D 413/12* (2013.01); *C07D 413/14* (2013.01); *C07D 417/12* (2013.01); *C07B 2200/05* (2013.01)

(58) Field of Classification Search
None
See application file for complete search history.

(56) References Cited

FOREIGN PATENT DOCUMENTS

| | | |
|---|---|---|
| WO | 2006/030032 A1 | 3/2006 |
| WO | 2007/131179 A1 | 11/2007 |
| WO | 2008/079787 A2 | 7/2008 |

OTHER PUBLICATIONS

International Preliminary Report on Patentability for International Patent Application No. PCT/EP2014/056135, Sep. 29, 2015, 6 pages.
"American College of Chest Physicians/Society of Critical Care Medicine Consensus Conference: Definitions for sepsis and organ failure and guidelines for the use of innovative therapies in sepsis", Critical Care Medicine, vol. 20, No. 6, 1992, pp. 864-874.
"Pschyrembel: Klinisches Worterbuch", 257.Auflage; Walter de Gruyter Verlag, Seite 610, Stichwort "Heparin", 1994, 2 pages.
"Rompp Lexikon Chemie", Version 1.5, Georg Thieme Verlag Stuttgart, 2 pages, 1998.
Ansell, Jack et al., "Managing Oral Anticoagulant Therapy", Chest, 119, 1 (Supplement), Jan. 2001, pp. S22-S38.
Aponick, Aaron et al., "Chirality Transfer in Au-Catalyzed Cyclization Reactions of Monoallylic Diols: Selective Access to Specific Enantiomers Based on Olefin Geometry", Organic Letters, vol. 13, No. 6, 2011, pp. 1330-1333.
Baker, Benjamin A. et al., "(BDP)CuH: a "Hot" Stryker's Reagent for Use in Achiral Conjugate Reductions", Organic Letters, vol. 10, No. 2, 2008, pp. 289-292.
Braunwald, Eugene, "Heart Disease: a Textbook of Cardiovascular Medicine (5th edition)", 5. Auflage; W.B. Saunders Company, Philadelphia, 1997, 23 pages.
Castells, Josep et al., "1-Alkoxycarbonylalkylidene-triphenylarsonanes: Preparation and Reactions", Tetrahedron, vol. 50, No. 48, 1994, pp. 13765-13774.
Dellinger, R. P., "Surviving Sepsis Campaign guidelines for management of severe sepsis and septic shock", Crit. Care. Med., vol. 32, No. 3, 2004, pp. 858-873.

(Continued)

*Primary Examiner* — Zinna Northington Davis
(74) *Attorney, Agent, or Firm* — Aseem V. Mehta

(57) ABSTRACT

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

8 Claims, No Drawings

(56) References Cited

OTHER PUBLICATIONS

European Patent Office, Written Opinion for International Patent Application No. PCT/EP2014/056135, Sep. 28, 2015, 10 pages.
European Patent Office, International Search Report for International Patent Application No. PCT/EP2014/056135, Oct. 2, 2014, 6 pages.
Hirsh, Jack et al., "Oral Anticoagulants: Mechanism of Action, Clinical Effectiveness, and Optimal Therapeutic Range", Chest, 119, 1 (Supplement), Jan. 2001, pp. 8S-21S.
Kinzel, Tom et al., "A New Palladium Precatalyst Allows for the Fast Suzuki-Miyaura Coupling Reactions of Unstable Polyfluorophenyl and 2-Heteroaryl Boronic Acids", J. Am. Chem. Soc., 132, 2010, pp. 14073-14075.
Levin, Vitalij V. et al., "Reaction of the Ruppert-Prakash reagent with perfluorosulfonic acids", Journal of Fluorine Chemistry, 130, 2009, pp. 667-670.
Levy, Mitchell M. et al., "2001 SCCM/ESICM/ACCP/ATS/SIS International Sepsis Definitions Conference", Crit. Care. Med., vol. 31, No. 4, 2003, pp. 1250-1256.
Wells, et al., "Interactions of Warfarin with Drugs and Food", Ann. Intern. Med., 121, 1994, pp. 676-683.

SUBSTITUTED OXOPYRIDINE DERIVATIVES AND USE THEREOF IN THE TREATMENT OF CARDIOVASCULAR DISORDERS

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood.

In the more recent past, the traditional theory of two separate regions of the coagulation cascade (extrinsic and intrinsic path) has been modified owing to new findings: In these models, coagulation is initiated by binding of activated factor VIIa to tissue factor (TF). The resulting complex activates factor X, which in turn leads to generation of thrombin with subsequent production of fibrin and platelet activation (via PAR-1) as injury-sealing end products of haemostasis. Compared to the subsequent amplification/propagation phase, the thrombin production rate is low and as a result of the occurrence of TFPI as inhibitor of the TF-FVIIa-FX complex is limited in time.

A central component of the transition from initiation to amplification and propagation of coagulation is factor XIa. In positive feedback loops, thrombin activates, in addition to factor V and factor VIII, also factor XI to factor XIa, whereby factor IX is converted into factor IXa, thus, via the factor IXa/factor VIIIa complex generated in this manner, rapidly producing relatively large amounts of factor Xa. This triggers the production of large amounts of thrombin, leading to strong thrombus growth and stabilizing the thrombus.

In addition, activation of the coagulation system may also occur at in particular negatively charged surfaces including artificial surfaces such as vessel prostheses, stents and extracorporeal circulation. On the surface, initially factor XII is activated to factor XIIa which subsequently, via kininogen or glycoprotein Ib, activates factor XI attached to cell surfaces. This leads to further activation of the coagulation cascade.

In addition, factor XIIa also activates bound plasma prekallikrein to plasma kallikrein. Plasma kallikrein in turn, in a potentiation loop, leads to further factor XII activation, overall resulting in amplification of the initiation of the coagulation cascade. In addition, plasma kallikrein is an important bradikinin-releasing protease which, inter alia, thus leads to increased endothelial permeability. Further substrates that have been described are prorenin and prourokinase, whose activation may trigger the regulatory processes of the renin-angiotensin system and fibrinolysis.

Uncontrolled activation of the coagulation system or defects in the inhibition of the activation processes may cause formation of local thromboses or embolisms in vessels (arteries, veins, lymph vessels) or heart chambers. This may lead to serious thrombotic or thromboembolic disorders. In addition, systemic hypercoaguability may lead to consumption coagulopathy in the context of a disseminated intravasal coagulation.

In the course of many cardiovascular and metabolic disorders, there is an increased tendency for coagulation and platelet activation owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis. This unwanted and excessive haemostasis may, by formation of fibrin- and platelet-rich thrombi, lead to thromboembolic disorders and thrombotic complications with life-threatening conditions. Inflammable processes may also be involved here.

Thromboembolic disorders are the most frequent cause of morbidity and mortality in most industrialized countries [Heart Disease: A Textbook of Cardiovascular Medicine, Eugene Braunwald, 5th edition, 1997, W.B. Saunders Company, Philadelphia].

The anticoagulants known from the prior art, for example substances for inhibiting or preventing blood coagulation, have various, frequently grave disadvantages. Accordingly, in practice, efficient treatment methods or the prophylaxis of thrombotic/thromboembolic disorders is frequently found to be very difficult and unsatisfactory.

In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral haemorrhages and bleeding in the gastrointestinal tract, and there may be thrombopenia, alopecia medicomentosa or osteoporosis [Pschyrembel, Klinisches Wörterbuch [clinical dictionary], 257th edition, 1994, Walter de Gruyter Verlag, page 610, keyword "Heparin"; Römpp Lexikon Chemie, version 1.5, 1998, Georg Thieme Verlag Stuttgart, keyword "Heparin"]. Low-molecular-weight heparins do have a lower probability of leading to the development of heparin-induced thrombocytopenia; however, they can likewise only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other cumarin derivatives which nonselectively inhibit the synthesis of various products of certain vitamin K-dependent coagulation factors in the liver. Owing to the mechanism of action, the onset of action is very slow (latency to the onset of action 36 to 48 hours). The compounds can be administered orally; however, owing to the high risk of bleeding and the narrow therapeutic index complicated individual adjustment and monitoring of the patient are required [J. Hirsch, J. Dalen, D. R. Anderson et al., "Oral anticoagulants: Mechanism of action, clinical effectiveness, and optimal therapeutic range" *Chest* 2001, 119, 8S-21S; J. Ansell, J. Hirsch, J. Dalen et al., "Managing oral anticoagulant therapy" *Chest* 2001, 119, 22S-38S; P. S. Wells, A. M. Holbrook, N. R. Crowther et al., "Interactions of warfarin with drugs and food" *Ann. Intern. Med.* 1994, 121, 676-683]. In addition, other side-effects such as gastrointestinal problems, hair loss and skin necroses have been described.

More recent approaches for oral anticoagulants are in various phases of clinical evaluation or in clinical use; however, they have also displayed disadvantages such as, for example, highly variable bioavailability, liver damage and bleeding complications.

For antithrombotic medicaments, the therapeutic width is of central importance: The distance between the therapeutically active dose for coagulation inhibition and the dose where bleeding may occur should be as big as possible so that maximum therapeutic activity is achieved at a minimum risk profile.

In various in vivo models with, for example, antibodies as factor XIa inhibitors, but also in factor XIa knock-out models, the antithrombotic effect with small/no prolongation of bleeding time or extension of blood volume was confirmed. In clinical studies, elevated factor XIa concentrations were associated with an increased event rate. However, factor XI deficiency (haemophilia C), in contrast to factor VIIIa or factor IXa (haemophilia A and B, respectively), did not lead to spontaneous bleeding and was only noticed during surgical interventions and traumata. Instead, protection against certain thromboembolic events was found.

Furthermore, for many disorders the combination of antithrombotic and antiinflammatory principles may also be particularly attractive to prevent the mutual enhancement of coagulation and inflammation.

Plasma kallikrein is associated with disorders accompanied by increased vessel permeability as is the case, for example, in diabetic retinopathy and macular oedema.

Diabetic retinopathy, a well-characterized chronic eye disorder, is the most frequent microvascular sequela of type 1 and type 2 diabetes mellitus. It is classified into two forms, non-proliferative retinopathy and proliferative retinopathy which in turn are classified according to their degree of severity.

Diabetic retinopathy is primarily caused by microvascular deficiency. These is an initial thickening of the basal membrane of the vessels and loss of vascularized pericytes, followed by vascular occlusion and retinal ischaemia. Further development is then controlled by the resulting retinal hypoxia, which causes preretinal neovascularization and increased vascular permeability with subsequent formation of a macular oedema. All this finally leads to the patient going blind.

From animal models, there are indications that inhibition of plasma kallikrein inhibits increased vascular permeability and may therefore prevent formation of a macular oedema and/or diabetic retinopathy.

It is therefore an object of the present invention to provide novel compounds for the treatment of cardiovascular disorders, in particular of thrombotic or thromboembolic and also oedematous disorders, and/or ophthalmic disorders, in particular diabetic retinopathy and/or macular oedema, in humans and animals, which compounds have a wide therapeutic bandwidth.

WO 2006/030032 describes inter alia substituted pyridinones as allosteric modulators of the mGluR2 receptor, and WO 2008/079787 describes substituted pyridin-2-ones and their use as glucokinase activators.

The invention provides compounds of the formula

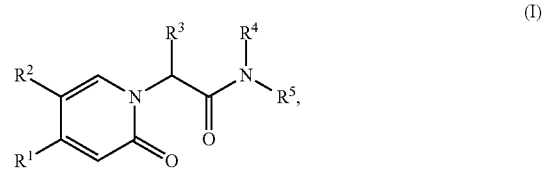

in which $R^1$ represents a group of the formula

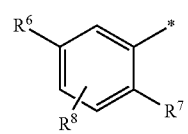

where * is the point of attachment to the oxopyridine ring, $R^6$ represents bromine, chlorine, fluorine, methyl, difluoromethyl, trifluoromethyl, methoxy, difluoromethoxy or trifluoromethoxy, $R^7$ represents bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl, $R^8$ represents hydrogen, chlorine or fluorine, $R^2$ represents hydrogen, bromine, chlorine, fluorine, cyano, $C_1$-$C_3$-alkyl, difluoromethyl, trifluoromethyl, 1,1-difluoroethyl, 2,2-difluoroethyl, 2,2,2-trifluoroethyl, $C_1$-$C_3$-alkoxy, difluoromethoxy, trifluoromethoxy, 1,1-difluoroethoxy, 2,2-difluoroethoxy, 2,2,2-trifluoroethoxy, methylcarbonyl or cyclopropyl, $R^3$ represents hydrogen, $C_1$-$C_5$-alkyl, $C_1$-$C_4$-alkoxy, difluoromethyl, trifluoromethyl, 1,1-difluoroethyl, 1,1,2,2,2-pentadeuteroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy, where alkyl may be substituted by a substituent selected from the group consisting of fluorine, cyano, hydroxy, difluoromethyl, trifluoromethyl, methoxy, ethoxy, difluoromethoxy, trifluoromethoxy, $C_3$-$C_6$-cycloalkyl, 4- to 6-membered oxoheterocyclyl, 4- to 6-membered thioheterocyclyl, 1,4-dioxanyl, phenyl and pyridyl, where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy, and where oxoheterocyclyl and thioheterocyclyl may be substituted by 1 to 2 substituents independently of one another selected from the group consisting of oxo, fluoro, methyl, ethyl, difluoromethyl and trifluoromethyl, R⁴ represents hydrogen,
R⁵ represents a group of the formula

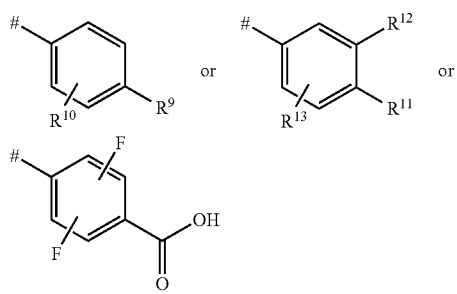

where # is the point of attachment to the nitrogen atom,
R⁹ represents hydroxycarbonyl or 5-membered heterocyclyl,
    where heterocyclyl may be substituted by 1 to 2 substituents independently of one another selected from the group consisting of oxo, hydroxy, thioxo, sulphanyl, methyl, difluoromethyl, trifluoromethyl, 2-hydroxycarbonyl-1,1,2,2-tetrafluoroethyl and 2-methoxycarbonyl-1,1,2,2-tetrafluoroethyl,
    where methyl may be substituted by a methoxy substituent,
R¹⁰ represents hydrogen, chlorine, fluorine or methyl,
R¹¹ and R¹² together with the carbon atoms to which they are attached form a 5-membered heterocycle,
    where the heterocycle may be substituted by 1 to 2 substituents independently of one another selected from the group consisting of oxo, chlorine, hydroxy, hydroxycarbonyl, methyl, difluoromethyl, trifluoromethyl, 1,1,2,2,2-pentafluoroethyl, 2-hydroxycarbonyl-1,1,2,2-tetrafluoroethyl and 2-methoxycarbonyl-1,1,2,2-tetrafluoroethyl,
R¹³ represents hydrogen, chlorine, fluorine, methyl or methoxy,
and the salts thereof, solvates thereof and the solvates of the salts thereof.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The compounds according to the invention may, depending on their structure, exist in different stereoisomeric forms, i.e. in the form of configurational isomers or else optionally as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention can occur in tautomeric forms, the present invention encompasses all the tautomeric forms.

In the context of the present invention, the term "enantiomerically pure" is to be understood as meaning that the compound in question with respect to the absolute configuration of the chiral centre is present in an enantiomeric excess of more than 95%, preferably more than 97%. The enantiomeric excess, ee, is calculated here by evaluating of the corresponding HPLC chromatogram on a chiral phase using the formula below:

$$ee=[E^A(\text{area \%})-E^B(\text{area \%})]\times 100\%/[E^A(\text{area \%})+E^B(\text{area \%})]$$

($E^A$: major enantiomer, $E^B$: minor enantiomer)

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

In the context of the present invention, preferred salts are physiologically acceptable salts of the compounds according to the invention. Also included, however, are salts which are themselves unsuitable for pharmaceutical applications but can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates refer to those forms of the compounds according to the invention which, in the solid or liquid state, form a complex by coordination with solvent molecules. Hydrates are a specific form of solvates in which the coordination is with water.

Moreover, the present invention also encompasses prodrugs of the compounds according to the invention. The term "prodrugs" includes compounds which may themselves be biologically active or inactive but are converted to compounds according to the invention while resident in the body (for example metabolically or hydrolytically).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

In the context of the present invention, the substituents, unless specified otherwise, are each defined as follows:

Alkyl represents a straight-chain or branched alkyl radical having 1 to 5 carbon atoms, preferably 1 to 3 carbon atoms, by way of example and with preference methyl, ethyl, n-propyl, isopropyl, 2-methylprop-1-yl, n-butyl, tert-butyl and 2,2-dimethylprop-1-yl.

Alkoxy represents a straight-chain or branched alkoxy radical having 1 to 4 carbon atoms, preferably 1 to 3 carbon atoms, by way of example and with preference methoxy, ethoxy, n-propoxy, isopropoxy, 2-methylprop-1-oxy, n-butoxy and tert-butoxy.

Cycloalkyl represents a monocyclic cycloalkyl group having 3 to 6 carbon atoms, by way of example and with preference cyclopropyl, cyclobutyl, cyclopentyl and cyclohexyl may be mentioned for cycloalkyl.

5-membered heterocyclyl in the definition of the radical $R^9$ represents a saturated, partially unsaturated or aromatic monocyclic radical having 5 ring atoms and up to 4 heteroatoms from the group consisting of S, O and N, where a nitrogen atom may also form an N-oxide, by way of example and with preference thienyl, furyl, pyrrolyl, thiazolyl, oxazolyl, isoxazolyl, oxadiazolyl, thiadiazolyl, pyrazolyl, imidazolyl, triazolyl, tetrazolyl, dihydrooxazolyl and dihydroimidazolyl.

5-membered heterocycle in the definition of the radicals $R^{11}$ and $R^{12}$ represents a saturated, partially unsaturated or aromatic monocyclic radical having 5 ring atoms and up to 2 heteroatoms from the group consisting of S, O and N, where a nitrogen atom may also form an N-oxide. This 5-membered heterocycle together with the phenyl ring to which it is attached represents, by way of example and with preference, 2,3-dihydro-1-benzothiophen-5-yl, 1,3-dihydro-2-benzothiophen-5-yl, 2,3-dihydro-1-benzofuran-5-yl, 1,3-dihydro-2-benzofuran-5-yl, indolin-5-yl, isoindolin-5-yl, 2,3-dihydro-1H-indazol-5-yl, 2,3-dihydro-1H-benzimidazol-5-yl, 1,3-dihydro-2,1-benzoxazol-5-yl, 2,3-dihydro-1,3-benzoxazol-5-yl, 1,3-dihydro-2,1-benzothiazol-5-yl, 2,3-dihydro-1,3-benzothiazol-5-yl, 1H-benzimidazol-5-yl, 1H-indazol-5-yl, 1,2-benzoxazol-5-yl, indol-5-yl, isoindol-5-yl, benzofuran-5-yl, benzothiophen-5-yl, 2,3-dihydro-1-benzothiophen-6-yl, 1,3-dihydro-2-benzothiophen-6-yl, 2,3-dihydro-1-benzofuran-6-yl, 1,3-dihydro-2-benzofuran-6-yl, indolin-6-yl, isoindolin-6-yl, 2,3-dihydro-1H-indazol-6-yl, 2,3-dihydro-1H-benzimidazol-6-yl, 1,3-dihydro-2,1-benzoxazol-6-yl, 2,3-dihydro-1,3-benzoxazol-6-yl, 1,3-dihydro-2,1-benzothiazol-6-yl, 2,3-dihydro-1,3-benzothiazol-6-yl, 1H-benzimidazol-6-yl, 1H-indazol-6-yl, 1,2-benzoxazol-6-yl, indol-6-yl, isoindol-6-yl, benzofuran-6-yl and benzothiophen-6-yl.

4- to 6-membered oxoheterocyclyl in the definition of the radical $R^3$ represents a saturated monocyclic radical having 4 to 6 ring atoms in which one ring atom is an oxygen atom, by way of example and with preference oxetanyl, tetrahydrofuranyl and tetrahydro-2H-pyranyl.

4- to 6-membered thioheterocyclyl in the definition of the radical $R^3$ represents a saturated monocyclic radical having 4 to 6 ring atoms in which one ring atom is an sulphur atom, by way of example and with preference thientanyl, tetrahydrothienyl and tetrahydro-2H-thiopyranyl.

In the formulae of the group which may represent $R^1$, the end point of the line marked by * does not represent a carbon atom or a $CH_2$ group, but is part of the bond to the atom to which $R^1$ is attached.

In the formulae of the group which may represent $R^5$, the end point of the line marked by # does not represent a carbon atom or a $CH_2$ group, but is part of the bond to the atom to which $R^5$ is attached.

Preference is given to compounds of the formula (I) in which
$R^1$ represents a group of the formula

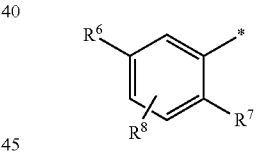

where * is the point of attachment to the oxopyridine ring,
$R^6$ represents chlorine,
$R^7$ represents bromine, chlorine, cyano, nitro, methyl, difluoromethyl, trifluoromethyl, difluoromethoxy, trifluoromethoxy, ethynyl or cyclopropyl,
$R^8$ represents hydrogen,
$R^2$ represents hydrogen, chlorine, fluorine, cyano, difluoromethyl, trifluoromethyl, 2,2,2-trifluoroethyl, methoxy, ethoxy, isopropoxy, difluoromethoxy or 2,2,2-trifluoroethoxy,
$R^3$ represents hydrogen, $C_1$-$C_5$-alkyl, ethoxy, 1,1,2,2,2-pentadeuteroethyl or prop-2-yn-1-yl,
where $C_1$-alkyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl, tetrahydro-2H-thiopyranyl, 1,4-dioxanyl, phenyl and pyridyl,
where cyclopropyl, cyclobutyl, cyclohexyl and oxetanyl may be substituted by 1 to 2 substituents independently of one another selected from the group consisting of fluorine, hydroxy, methyl, ethyl, methoxy and trifluoromethyl,
and
where tetrahydrofuranyl, tetrahydro-2H-pyranyl and tetrahydro-2H-thiopyranyl may be substituted by 1 to 2 substituents independently of one another selected from the group consisting of oxo, methyl and ethyl,
and
where $C_2$-$C_4$-alkyl may be substituted by a substituent selected from the group consisting of fluorine, hydroxy, trifluoromethyl, methoxy and trifluoromethoxy,
$R^4$ represents hydrogen,
$R^5$ represents a group of the formula

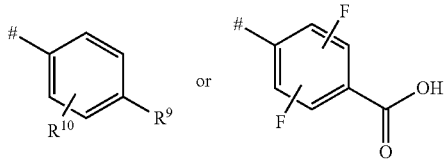

where # is the point of attachment to the nitrogen atom,
$R^9$ represents hydroxycarbonyl, oxazolyl, oxadiazolyl, thiadiazolyl, pyrazolyl, imidazolyl, triazolyl, tetrazolyl or dihydrooxazolyl,
where oxazolyl, oxadiazolyl, thiadiazolyl, pyrazolyl, imidazolyl, triazolyl and dihydrooxazolyl may be substituted by 1 to 2 substituents independently of one another selected from the group consisting of oxo, hydroxy, thioxo, sulphanyl, methyl, trifluoromethyl and 2-hydroxycarbonyl-1,1,2,2-tetrafluoroethyl,
where methyl may be substituted by a methoxy substituent,
$R^{10}$ represents hydrogen, chlorine, fluorine or methyl,
or
$R^5$ represents 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl or 1H-indazol-5-yl,
where the 5-membered heterocycle in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by 1 to 2 substituents independently of one another selected from the group consisting of oxo, chlorine, hydroxycarbonyl, methyl and trifluoromethyl,
and
where the benzyl ring in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by a substituent selected from the group consisting of fluorine and methoxy,
and the salts thereof, solvates thereof and the solvates of the salts thereof.

Preference is also given to compounds of the formula (I) in which
$R^1$ represents a group of the formula

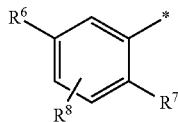

where * is the point of attachment to the oxopyridine ring, $R^6$ represents chlorine,
$R^7$ represents cyano or difluoromethoxy,
$R^8$ represents hydrogen,
$R^2$ represents chlorine, cyano, methoxy, ethoxy or difluoromethoxy,
$R^3$ represents methyl, ethyl, n-propyl, 2-methylprop-1-yl or n-butyl,
where methyl may be substituted by a substituent selected from the group consisting of difluoromethyl, trifluoromethyl, cyclopropyl, cyclobutyl, cyclohexyl, tetrahydrofuranyl, tetrahydro-2H-pyranyl, 1,4-dioxanyl, phenyl and pyridyl,
where cyclopropyl, cyclobutyl and cyclohexyl may be substituted by 1 to 2 substituents independently of one another selected from the group consisting of fluorine, hydroxy, methyl, methoxy and trifluoromethyl,
and
where ethyl, n-propyl and n-butyl may be substituted by a substituent selected from the group consisting of fluorine, methoxy and trifluoromethoxy,
$R^4$ represents hydrogen,
$R^5$ represents a group of the formula

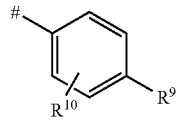

where # is the point of attachment to the nitrogen atom,
$R^9$ represents hydroxycarbonyl, oxadiazolyl, pyrazolyl, triazolyl or tetrazolyl,
where oxadiazolyl and pyrazolyl may be substituted by 1 to 2 substituents independently of one another selected from the group consisting of oxo, hydroxy and trifluoromethyl,
and
where triazolyl may be substituted by a substituent selected from the group consisting of trifluoromethyl and 2-hydroxycarbonyl-1,1,2,2-tetrafluoroethyl,
$R^{10}$ represents hydrogen or fluorine,
or
$R^5$ represents 2,3-dihydro-1H-indazol-6-yl, 1H-benzimidazol-6-yl, 2,3-dihydro-1H-benzimidazol-5-yl or 1H-indazol-5-yl,
where the 5-membered heterocycle in 2,3-dihydro-1H-indazol-6-yl may substituted by 1 to 2 substituents independently of one another selected from the group consisting of oxo and methyl,
and
where the benzyl ring in 2,3-dihydro-1H-indazol-6-yl may be substituted by a fluorine substituent,
and
where the 5-membered heterocycle in 1H-benzimidazol-6-yl may be substituted by a hydroxycarbonyl substituent,
and
where the 5-membered heterocycle in 2,3-dihydro-1H-benzimidazol-5-yl may be substituted by an oxo substituent,
and
where the 5-membered heterocycle in 1H-indazol-5-yl may be substituted by a chlorine substituent,
and the salts thereof, solvates thereof and the solvates of the salts thereof.

Preference is also given to compounds of the formula (I) in which

R³ represents hydrogen, C₁-C₅-alkyl, ethoxy, 1,1,2,2,2-pentadeuteroethyl or prop-2-yn-1-yl,
where C₁-alkyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl, tetrahydro-2H-thiopyranyl, 1,4-dioxanyl, phenyl and pyridyl,
where cyclopropyl, cyclobutyl, cyclohexyl and oxetanyl may be substituted by 1 to 2 substituents independently of one another selected from the group consisting of fluorine, hydroxy, methyl, ethyl, methoxy and trifluoromethyl,
and
where tetrahydrofuranyl, tetrahydro-2H-pyranyl and tetrahydro-2H-thiopyranyl may be substituted by 1 to 2 substituents independently of one another selected from the group consisting of oxo, methyl and ethyl,
and
where C₂-C₄-alkyl may be substituted by a substituent selected from the group consisting of fluorine, hydroxy, trifluoromethyl, methoxy and trifluoromethoxy.

Preference is also given to compounds of the formula (I) in which

R³ represents methyl, ethyl, n-propyl, 2-methylprop-1-yl or n-butyl,
where methyl may be substituted by a substituent selected from the group consisting of difluoromethyl, trifluoromethyl, cyclopropyl, cyclobutyl, cyclohexyl, tetrahydrofuranyl, tetrahydro-2H-pyranyl, 1,4-dioxanyl, phenyl and pyridyl,
where cyclopropyl, cyclobutyl and cyclohexyl may be substituted by 1 to 2 substituents independently of one another selected from the group consisting of fluorine, hydroxy, methyl, methoxy and trifluoromethyl,
and
where ethyl, n-propyl and n-butyl may be substituted by a substituent selected from the group consisting of fluorine, methoxy and trifluoromethoxy.

Preference is also given to compounds of the formula (I) in which

R⁵ represents a group of the formula

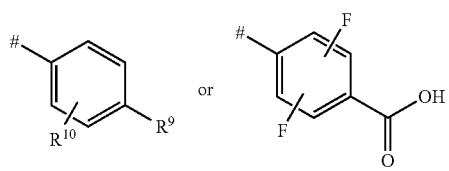

where # is the point of attachment to the nitrogen atom,
R⁹ represents hydroxycarbonyl, oxazolyl, oxadiazolyl, thiadiazolyl, pyrazolyl, imidazolyl, triazolyl, tetrazolyl or dihydrooxazolyl,
where oxazolyl, oxadiazolyl, thiadiazolyl, pyrazolyl, imidazolyl, triazolyl and dihydrooxazolyl may be substituted by 1 to 2 substituents independently of one another selected from the group consisting of oxo, hydroxy, thioxo, sulphanyl, methyl, trifluoromethyl and 2-hydroxycarbonyl-1,1,2,2-tetrafluoroethyl, where methyl may be substituted by a methoxy substituent,
R¹⁰ represents hydrogen, chlorine, fluorine or methyl.

Preference is also given to compounds of the formula (I) in which

R⁵ represents a group of the formula

where # is the point of attachment to the nitrogen atom.

Preference is also given to compounds of the formula (I) in which

R⁵ represents 2,3-dihydro-1H-indazol-6-yl, 1H-benzimidazol-6-yl, Indol-6-yl, 2,3-dihydro-1H-indazol-5-yl, 2,3-dihydro-1H-benzimidazol-5-yl, indol-5-yl, 1H-indazol-6-yl or 1H-indazol-5-yl,
where the 5-membered heterocycle in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by 1 to 2 substituents independently of one another selected from the group consisting of oxo, chlorine, hydroxycarbonyl, methyl and trifluoromethyl,
and
where the benzyl ring in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by a substituent selected from the group consisting of fluorine and methoxy.

Preference is also given to compounds of the formula (I) in which

R⁵ represents 2,3-dihydro-1H-indazol-6-yl, 1H-benzimidazol-6-yl, 2,3-dihydro-1H-benzimidazol-5-yl or 1H-indazol-5-yl,
where the 5-membered heterocycle in 2,3-dihydro-1H-indazol-6-yl may be substituted by 1 to 2 substituents independently of one another selected from the group consisting of oxo and methyl,
and
where the benzyl ring in 2,3-dihydro-1H-indazol-6-yl may be substituted by a fluorine substituent,
and
where the 5-membered heterocycle in 1H-benzimidazol-6-yl may be substituted by a hydroxycarbonyl substituent,
and
where the 5-membered heterocycle in 2,3-dihydro-1H-benzimidazol-5-yl may be substituted by an oxo substituent,
and
where the 5-membered heterocycle in 1H-indazol-5-yl may be substituted by a chlorine substituent.

Preference is also given to compounds of the formula (I) in which

R⁵ represents 2,3-dihydro-1H-indazol-6-yl, 1H-benzimidazol-6-yl, Indol-6-yl, 2,3-dihydro-1H-indazol-5-yl, 2,3-dihydro-1H-benzimidazol-5-yl or indol-5-yl, where the 5-membered heterocycle in 2,3-dihydro-1H-
indazol-6-yl, 1H-benzimidazol-6-yl, indol-6-yl, 2,3-di-
hydro-1H-indazol-5-yl, 2,3-dihydro-1H-benzimidazol-
5-yl and indol-5-yl may be substituted by 1 to 2
substituents independently of one another selected
from the group consisting of oxo, hydroxycarbonyl,
methyl and trifluoromethyl.

Preference is also given to compounds of the formula (I)
in which
$R^1$ represents a group of the formula

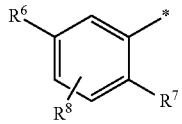

where * is the point of attachment to the oxopyridine ring,
$R^6$ represents bromine, chlorine, fluorine, methyl, difluo-
romethyl, trifluoromethyl, methoxy, difluoromethoxy
or trifluoromethoxy,
$R^7$ represents bromine, chlorine, fluorine, cyano, nitro,
hydroxy, methyl, difluoromethyl, trifluoromethyl,
methoxy, ethoxy, difluoromethoxy, trifluoromethoxy,
ethynyl, 3,3,3-trifluoroprop-1-yn-1-yl or cyclopropyl,
$R^8$ represents hydrogen, chlorine or fluorine,
$R^2$ represents hydrogen, bromine, chlorine, fluorine, cyano,
$C_1$-$C_3$-alkyl, difluoromethyl, trifluoromethyl, 1,1-difluo-
roethyl, 2,2-difluoroethyl, 2,2,2-trifluoroethyl, $C_1$-$C_3$-
alkoxy, difluoromethoxy, trifluoromethoxy, 1,1-difluo-
roethoxy, 2,2-difluoroethoxy, 2,2,2-trifluoroethoxy,
methylcarbonyl or cyclopropyl,
$R^3$ represents hydrogen, $C_1$-$C_5$-alkyl, $C_1$-$C_4$-alkoxy, difluo-
romethyl, trifluoromethyl, 1,1-difluoroethyl, 3,3,3-trif-
luoro-2-hydroxyprop-1-yl, 3,3,3-trifluoro-2-methoxy-
prop-1-yl, 3,3,3-trifluoro-2-ethoxyprop-1-yl, prop-2-yn-
1-yl, cyclopropyloxy or cyclobutyloxy,
where alkyl may be substituted by a substituent selected
from the group consisting of fluorine, cyano, hydroxy,
difluoromethyl, trifluoromethyl, methoxy, ethoxy, dif-
luoromethoxy, trifluoromethoxy, $C_3$-$C_6$-cycloalkyl, 4-
to 6-membered oxoheterocyclyl, 1,4-dioxanyl, phenyl
and pyridyl,
where cycloalkyl may be substituted by 1 to 2 substitu-
ents independently of one another selected from the
group consisting of fluorine, hydroxy, methyl, ethyl,
methoxy, ethoxy, difluoromethyl, trifluoromethyl,
difluoromethoxy and trifluoromethoxy,
$R^4$ represents hydrogen,
$R^5$ represents a group of the formula

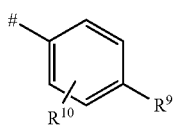 or 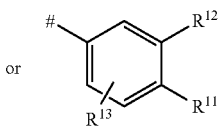

where # is the point of attachment to the nitrogen atom,
$R^9$ represents hydroxycarbonyl or 5-membered heterocy-
clyl,
where heterocyclyl may be substituted by 1 to 2 sub-
stituents independently of one another selected from
the group consisting of oxo, hydroxy, methyl, difluoromethyl, trifluoromethyl, 2-hydroxycarbonyl-1,
1,2,2-tetrafluoroethyl and 2-methoxycarbonyl-1,1,2,
2-tetrafluoroethyl,
where methyl may be substituted by a methoxy
substituent,
$R^{10}$ represents hydrogen, chlorine, fluorine or methyl,
$R^{11}$ and $R^{12}$ together with the carbon atoms to which they
are attached form a 5-membered heterocycle,
where the heterocycle may be substituted by 1 to 2
substituents independently of one another selected
from the group consisting of oxo, chlorine, hydroxy,
hydroxycarbonyl, methyl, difluoromethyl, trifluo-
romethyl, 1,1,2,2,2-pentafluoroethyl, 2-hydroxycar-
bonyl-1,1,2,2-tetrafluoroethyl and 2-methoxycarbo-
nyl-1,1,2,2-tetrafluoroethyl,
$R^{13}$ represents hydrogen, chlorine, fluorine or methyl,
and the salts thereof, solvates thereof and the solvates of the
salts thereof.

Preference is also given to compounds of the formula (I)
in which
$R^1$ represents a group of the formula

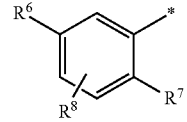

where * is the point of attachment to the oxopyridine ring,
$R^6$ represents chlorine,
$R^7$ represents bromine, chlorine, cyano, nitro, methyl,
difluoromethyl, trifluoromethyl, difluoromethoxy, trif-
luoromethoxy, ethynyl or cyclopropyl,
$R^8$ represents hydrogen,
$R^2$ represents hydrogen, chlorine, fluorine, cyano, difluo-
romethyl, trifluoromethyl, 2,2,2-trifluoroethyl, methoxy,
ethoxy, isopropoxy, difluoromethoxy or 2,2,2-trifluo-
roethoxy,
$R^3$ represents hydrogen, $C_1$-$C_5$-alkyl, ethoxy or prop-2-yn-
1-yl,
where $C_1$-alkyl may be substituted by a substituent
selected from the group consisting of difluoromethyl,
trifluoromethyl, cyclopropyl, cyclobutyl, cyclohexyl,
oxetanyl, tetrahydrofuranyl, tetrahydro-2H-pyranyl,
1,4-dioxanyl, phenyl and pyridyl,
where cyclopropyl, cyclobutyl, cyclohexyl and oxeta-
nyl may be substituted by 1 to 2 substituents inde-
pendently of one another selected from the group
consisting of fluorine, hydroxy, methyl and ethyl,
and
where $C_2$-$C_4$-alkyl may be substituted by a substituent
selected from the group consisting of fluorine, hydroxy,
trifluoromethyl, methoxy and trifluoromethoxy,
$R^4$ represents hydrogen,
$R^5$ represents a group of the formula

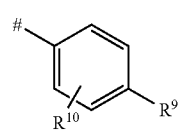

where # is the point of attachment to the nitrogen atom,
$R^9$ represents hydroxycarbonyl, oxadiazolyl, pyrazolyl,
imidazolyl, triazolyl, tetrazolyl or dihydrooxazolyl, where oxadiazolyl, pyrazolyl, imidazolyl, triazolyl and dihydrooxazolyl may be substituted by 1 to 2 substituents independently of one another selected from the group consisting of oxo, hydroxy, methyl, trifluoromethyl and 2-hydroxycarbonyl-1,1,2,2-tetrafluoroethyl, where methyl may be substituted by a methoxy substituent, $R^{10}$ represents hydrogen, chlorine, fluorine or methyl, or $R^5$ represents 2,3-dihydro-1H-indazol-6-yl, 1H-benzimidazol-6-yl, Indol-6-yl, 2,3-dihydro-1H-indazol-5-yl, 2,3-dihydro-1H-benzimidazol-5-yl or indol-5-yl, where 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl and indol-5-yl may be substituted by 1 to 2 substituents independently of one another selected from the group consisting of oxo, hydroxycarbonyl, methyl and trifluoromethyl, and the salts thereof, solvates thereof and the solvates of the salts thereof.

Preference is also given to compounds of the formula (I) in which $R^1$ represents a group of the formula

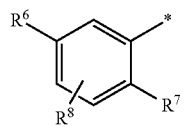

where * is the point of attachment to the oxopyridine ring,
$R^6$ represents chlorine,
$R^7$ represents cyano or difluoromethoxy,
$R^8$ represents hydrogen,
$R^2$ represents chlorine, cyano, methoxy, ethoxy or difluoromethoxy,
$R^3$ represents methyl, ethyl, n-propyl, 2-methylprop-1-yl or n-butyl, where methyl may be substituted by a substituent selected from the group consisting of difluoromethyl, trifluoromethyl, cyclopropyl, cyclobutyl, cyclohexyl, tetrahydrofuranyl, tetrahydro-2H-pyranyl, 1,4-dioxanyl, phenyl and pyridyl, where cyclopropyl, cyclobutyl and cyclohexyl may be substituted by 1 to 2 substituents independently of one another selected from the group consisting of fluorine, hydroxy and methyl, and where ethyl, n-propyl and n-butyl may be substituted by a substituent selected from the group consisting of fluorine, methoxy and trifluoromethoxy, $R^4$ represents hydrogen,
$R^5$ represents a group of the formula

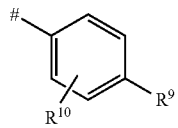

where # is the point of attachment to the nitrogen atom,
$R^9$ represents hydroxycarbonyl, oxadiazolyl, pyrazolyl, triazolyl or tetrazolyl, where oxadiazolyl and pyrazolyl may be substituted by 1 to 2 substituents independently of one another selected from the group consisting of oxo, hydroxy and trifluoromethyl, and where triazolyl may be substituted by a substituent selected from the group consisting of trifluoromethyl and 2-hydroxycarbonyl-1,1,2,2-tetrafluoroethyl, $R^{10}$ represents hydrogen or fluorine, or $R^5$ represents 2,3-dihydro-1H-indazol-6-yl, 1H-benzimidazol-6-yl or 2,3-dihydro-1H-benzimidazol-5-yl, where 2,3-dihydro-1H-indazol-6-yl may be substituted by 1 to 2 substituents independently of one another selected from the group consisting of oxo and methyl, and where 1H-benzimidazol-6-yl may be substituted by a hydroxycarbonyl substituent, and where 2,3-dihydro-1H-benzimidazol-5-yl may be substituted by an oxo substituent, and the salts thereof, solvates thereof and the solvates of the salts thereof.

Preference is also given to compounds of the formula (I) in which $R^1$ represents a group of the formula

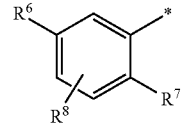

where * is the point of attachment to the oxopyridine ring,
$R^6$ represents chlorine,
$R^7$ represents cyano or difluoromethoxy,
$R^8$ represents hydrogen.

Preference is also given to compounds of the formula (I) in which $R^2$ represents chlorine, cyano, methoxy, ethoxy or difluoromethoxy.

Preference is also given to compounds of the formula (I) in which $R^3$ represents $C_1$-$C_5$-alkyl, $C_1$-$C_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy, where alkyl may be substituted by a substituent selected from the group consisting of fluorine, cyano, hydroxy, difluoromethyl, trifluoromethyl, methoxy, ethoxy, difluoromethoxy, trifluoromethoxy, $C_3$-$C_6$-cycloalkyl, 4- to 6-membered oxoheterocyclyl, 1,4-dioxanyl, phenyl and pyridyl, where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy.

Preference is also given to compounds of the formula (I) in which $R^3$ represents $C_1$-$C_5$-alkyl, ethoxy or prop-2-yn-1-yl, where $C_1$-alkyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl, 1,4-dioxanyl, phenyl and pyridyl,
where cyclopropyl, cyclobutyl, cyclohexyl and oxetanyl may be substituted by 1 to 2 substituents independently of one another selected from the group consisting of fluorine, hydroxy, methyl and ethyl,
and
where $C_2$-$C_4$-alkyl may be substituted by a substituent selected from the group consisting of fluorine, hydroxy, trifluoromethyl, methoxy and trifluoromethoxy.

Preference is also given to compounds of the formula (I) in which
$R^3$ represents methyl, ethyl, n-propyl, 2-methylprop-1-yl or n-butyl,
where methyl may be substituted by a substituent selected from the group consisting of difluoromethyl, trifluoromethyl, cyclopropyl, cyclobutyl, cyclohexyl, tetrahydrofuranyl, tetrahydro-2H-pyranyl, 1,4-dioxanyl, phenyl and pyridyl,
where cyclopropyl, cyclobutyl and cyclohexyl may be substituted by 1 to 2 substituents independently of one another selected from the group consisting of fluorine, hydroxy and methyl,
and
where ethyl, n-propyl and n-butyl may be substituted by a substituent selected from the group consisting of fluorine, methoxy and trifluoromethoxy.

Preference is also given to compounds of the formula (I) in which
$R^5$ represents a group of the formula

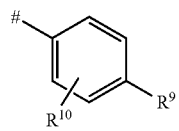

where # is the point of attachment to the nitrogen atom,
$R^9$ represents hydroxycarbonyl, oxadiazolyl, pyrazolyl, triazolyl or tetrazolyl,
where oxadiazolyl and pyrazolyl may be substituted by 1 to 2 substituents independently of one another selected from the group consisting of oxo, hydroxy and trifluoromethyl,
and
where triazolyl may be substituted by a substituent selected from the group consisting of trifluoromethyl and 2-hydroxycarbonyl-1,1,2,2-tetrafluoroethyl,
$R^{10}$ represents hydrogen or fluorine.

Preference is also given to compounds of the formula (I) in which
$R^5$ represents 2,3-dihydro-1H-indazol-6-yl, 1H-benzimidazol-6-yl or 2,3-dihydro-1H-benzimidazol-5-yl,
where 2,3-dihydro-1H-indazol-6-yl may be substituted by 1 to 2 substituents independently of one another selected from the group consisting of oxo and methyl,
and
where 1H-benzimidazol-6-yl may be substituted by a hydroxycarbonyl substituent,
and
where 2,3-dihydro-1H-benzimidazol-5-yl may be substituted by an oxo substituent.

Preference is also given to compounds of the formula (I) in which
$R^5$ represents 2,3-dihydro-1H-indazol-6-yl, 1H-benzimidazol-6-yl or 2,3-dihydro-1H-benzimidazol-5-yl,
where the 5-membered heterocycle in 2,3-dihydro-1H-indazol-6-yl may be substituted by 1 to 2 substituents independently of one another selected from the group consisting of oxo and methyl,
and
where the 5-membered heterocycle in 1H-benzimidazol-6-yl may be substituted by a hydroxycarbonyl substituent,
and
where the 5-membered heterocycle in 2,3-dihydro-1H-benzimidazol-5-yl may be substituted by an oxo substituent.

Preference is also given to compounds of the formula (I) in which
$R^1$ represents a group of the formula

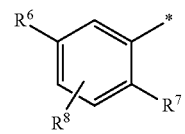

where * is the point of attachment to the oxopyridine ring,
$R^6$ represents bromine, chlorine, fluorine, methyl, difluoromethyl, trifluoromethyl, methoxy, difluoromethoxy or trifluoromethoxy,
$R^7$ represents bromine, chlorine, fluorine, cyano, nitro, hydroxy, methyl, difluoromethyl, trifluoromethyl, methoxy, difluoromethoxy, trifluoromethoxy, ethynyl, 3,3,3-trifluoroprop-1-yn-1-yl or cyclopropyl,
$R^8$ represents hydrogen, chlorine or fluorine,
$R^2$ represents hydrogen, bromine, chlorine, fluorine, cyano, $C_1$-$C_3$-alkyl, difluoromethyl, trifluoromethyl, 1,1-difluoroethyl, 2,2-difluoroethyl, 2,2,2-trifluoroethyl, $C_1$-$C_3$-alkoxy, difluoromethoxy, trifluoromethoxy, 1,1-difluoroethoxy, 2,2-difluoroethoxy, 2,2,2-trifluoroethoxy, methylcarbonyl or cyclopropyl,
$R^3$ represents $C_1$-$C_5$-alkyl, difluoromethyl, trifluoromethyl, 1,1-difluoroethyl or prop-2-yn-1-yl,
where alkyl may be substituted by a substituent selected from the group consisting of fluorine, cyano, hydroxy, difluoromethyl, trifluoromethyl, methoxy, difluoromethoxy, trifluoromethoxy, $C_3$-$C_6$-cycloalkyl, 4- to 6-membered oxoheterocyclyl, phenyl and pyridyl,
$R^4$ represents hydrogen,
$R^5$ represents a group of the formula

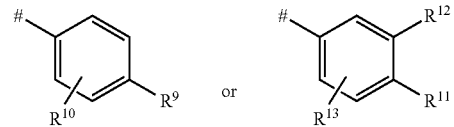

where # is the point of attachment to the nitrogen atom,
$R^9$ represents hydroxycarbonyl or 5-membered heterocyclyl,
where heterocyclyl may be substituted by 1 to 2 substituents selected from the group consisting of oxo, hydroxy, methyl, difluoromethyl and trifluoromethyl, where methyl may be substituted by a methoxy substituent, R¹⁰ represents hydrogen, chlorine, fluorine or methyl, R¹¹ and R¹² together with the carbon atoms to which they are attached form a 5-membered heterocycle,
where the heterocycle may be substituted by 1 to 2 substituents selected from the group consisting of oxo, hydroxy, methyl, difluoromethyl, trifluoromethyl and 1,1,2,2,2-pentafluoroethyl, R¹³ represents hydrogen, chlorine, fluorine or methyl, and the salts thereof, solvates thereof and the solvates of the salts thereof.

Preference is also given to compounds of the formula (I) in which

R¹ represents a group of the formula

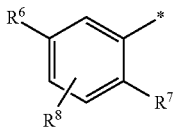

where * is the point of attachment to the oxopyridine ring,

R⁶ represents chlorine,

R⁷ represents bromine, chlorine, cyano, nitro, difluoromethyl, trifluoromethyl, trifluoromethoxy, ethynyl or cyclopropyl, R⁸ represents hydrogen, R² represents hydrogen, chlorine, fluorine, cyano, difluoromethyl, trifluoromethyl, 2,2,2-trifluoroethyl, methoxy or ethoxy, R³ represents $C_1$-$C_5$-alkyl or prop-2-yn-1-yl,
where $C_1$-alkyl may be substituted by a substituent selected from the group consisting of cyclopropyl, phenyl and pyridyl, R⁴ represents hydrogen, R⁵ represents a group of the formula

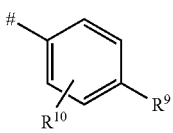

where # is the point of attachment to the nitrogen atom,

R⁹ represents hydroxycarbonyl, oxadiazolyl, pyrazolyl, imidazolyl, triazolyl or tetrazolyl,
where oxadiazolyl, pyrazolyl, imidazolyl and triazolyl may be substituted by 1 to 2 substituents selected from the group consisting of oxo, hydroxy, methyl and trifluoromethyl,
where methyl may be substituted by a methoxy substituent, R¹⁰ represents hydrogen, chlorine, fluorine or methyl, or R⁵ represents 2,3-dihydro-1H-indazol-6-yl, 1H-benzimidazol-6-yl or 2,3-dihydro-1H-indazol-5-yl,
where 2,3-dihydro-1H-indazol-6-yl, 1H-benzimidazol-6-yl and 2,3-dihydro-1H-indazol-5-yl may be substituted by 1 to 2 substituents selected from the group consisting of oxo, methyl and trifluoromethyl, and the salts thereof, solvates thereof and the solvates of the salts thereof.

Preference is also given to compounds of the formula (I) in which

R¹ represents a group of the formula

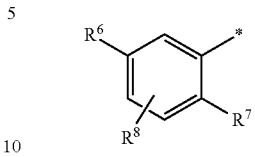

where * is the point of attachment to the oxopyridine ring,

R⁶ represents chlorine,

R⁷ represents cyano or trifluoromethyl,

R⁸ represents hydrogen,

R² represents hydrogen, chlorine, fluorine, cyano, 2,2,2-trifluoroethyl, methoxy or ethoxy, R³ represents methyl, ethyl or 2-methylprop-1-yl,
where methyl may be substituted by a cyclopropyl substituent, R⁴ represents hydrogen, R⁵ represents a group of the formula

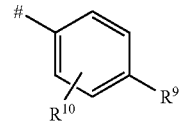

where # is the point of attachment to the nitrogen atom,

R⁹ represents hydroxycarbonyl, oxadiazolyl, pyrazolyl, imidazolyl, triazolyl or tetrazolyl,
where oxadiazolyl, pyrazolyl, imidazolyl and triazolyl may be substituted by 1 to 2 substituents selected from the group consisting of oxo, hydroxy, methyl and trifluoromethyl,
where methyl may be substituted by a methoxy substituent, R¹⁰ represents hydrogen, chlorine, fluorine or methyl, or R⁵ represents 2,3-dihydro-1H-indazol-6-yl and 1H-benzimidazol-6-yl,
where 2,3-dihydro-1H-indazol-6-yl and 1H-benzimidazol-6-yl may be substituted by 1 to 2 substituents selected from the group consisting of oxo, methyl and trifluoromethyl, and the salts thereof, solvates thereof and the solvates of the salts thereof.

Preference is also given to compounds of the formula (I) in which

R¹ represents a group of the formula

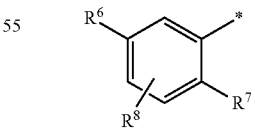

where * is the point of attachment to the oxopyridine ring,

R⁶ represents chlorine,

R⁷ represents cyano or trifluoromethoxy,

R⁸ represents hydrogen.

Preference is also given to compounds of the formula (I) in which R² represents hydrogen, chlorine, cyano, 2,2,2-trifluoroethyl, methoxy or ethoxy.

Preference is also given to compounds of the formula (I) in which R³ represents methyl, ethyl or 2-methylprop-1-yl, where methyl may be substituted by a cyclopropyl substituent.

Preference is also given to compounds of the formula (I) in which

R⁵ represents a group of the formula

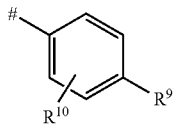

where # is the point of attachment to the nitrogen atom,

R⁹ represents hydroxycarbonyl, oxadiazolyl, pyrazolyl, imidazolyl, triazolyl or tetrazolyl, where oxadiazolyl, pyrazolyl, imidazolyl and triazolyl may be substituted by 1 to 2 substituents selected from the group consisting of oxo, hydroxy, methyl and trifluoromethyl, where methyl may be substituted by a methoxy substituent, R¹⁰ represents hydrogen, chlorine, fluorine or methyl.

Preference is also given to compounds of the formula (I) in which

R⁵ represents 2,3-dihydro-1H-indazol-6-yl, 1H-benzimidazol-6-yl or 2,3-dihydro-1H-indazol-5-yl, where the 5-membered heterocycle in 2,3-dihydro-1H-indazol-6-yl, 1H-benzimidazol-6-yl and 2,3-dihydro-1H-indazol-5-yl may be substituted by 1 to 2 substituents selected from the group consisting of oxo, methyl and trifluoromethyl.

Preference is also given to compounds of the formula (I) in which R⁵ represents 2,3-dihydro-1H-indazol-6-yl or 1H-benzimidazol-6-yl, where 2,3-dihydro-1H-indazol-6-yl and 1H-benzimidazol-6-yl may be substituted by 1 to 2 substituents selected from the group consisting of oxo, methyl and trifluoromethyl.

Preference is also given to compounds of the formula (I) in which R⁵ represents 2,3-dihydro-1H-indazol-6-yl or 1H-benzimidazol-6-yl, where the 5-membered heterocycle in 2,3-dihydro-1H-indazol-6-yl and 1H-benzimidazol-6-yl may be substituted by 1 to 2 substituents selected from the group consisting of oxo, methyl and trifluoromethyl.

Preference is also given to compounds of the formula (Ia)

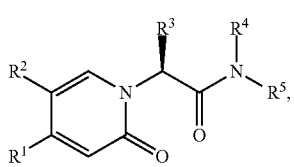

(Ia)

in which R¹, R², R³, R⁴ and R⁵ are as defined above.

The invention further provides a process for preparing the compounds of the formula (I), or the salts thereof, solvates thereof and the solvates of the salts thereof, wherein

[A] the compounds of the formula

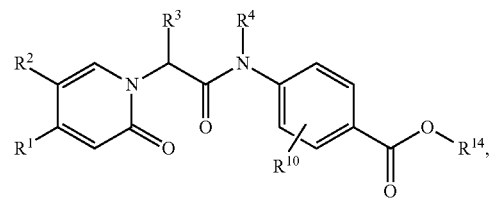

(IIa)

in which
R¹, R², R³, R⁴ and R¹⁰ have the meaning given above and
R¹⁴ represents tert-butyl,
are reacted with an acid to give compounds of the formula

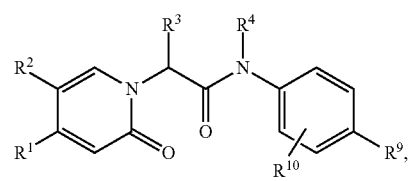

(Ib)

in which
R¹, R², R³, R⁴ and R¹⁰ have the meaning given above and
R⁹ represents hydroxycarbonyl,
or
[B] the compounds of the formula

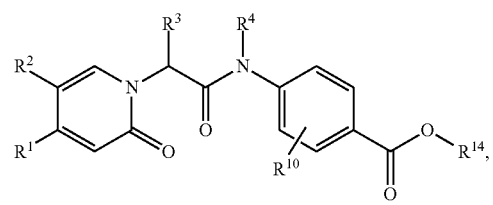

(IIb)

in which
R¹, R², R³, R⁴ and R¹⁰ have the meaning given above and
R¹⁴ represents methyl or ethyl,
are reacted with a base to give compounds of the formula

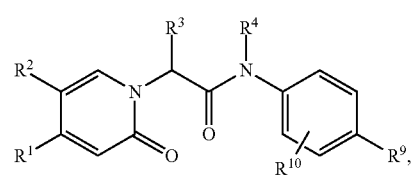

(Ib)

in which
R¹, R², R³, R⁴ and R¹⁰ have the meaning given above and
R⁹ represents hydroxycarbonyl,
or
[C] the compounds of the formula

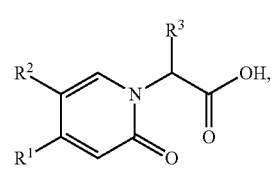

(III)

in which
R¹, R² and R³ have the meaning given above,
are reacted with compounds of the formula

(IV)

in which
R⁴ and R⁵ have the meaning given above,
in the presence of a dehydrating agent to give compounds of the formula (I),
or
[D] the compounds of the formula

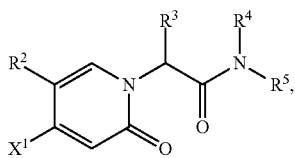
(V)

in which
R², R³, R⁴ and R⁵ have the meaning given above and
X¹ represents chlorine, bromine or iodine,
are reacted with compounds of the formula

R¹-Q (VI), in which
R¹ has the meaning given above and
Q represents —B(OH)₂, a boronic ester, preferably boronic acid pinacol ester, or —BF₃⁻K⁺,
under Suzuki coupling conditions to give compounds of the formula (I).

The compounds of the formula (Ib) are a subset of the compounds of the formula (I).

The compounds of the formulae (IIa) and (IIb) together form the group of the compounds of the formula (II).

The reaction according to process [A] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

The reaction according to process [B] is generally carried out in inert solvents, preferably in a temperature range from room temperature up to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to a mixture of tetrahydrofuran and water or a mixture of methanol and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide or caesium carbonate.

The reaction according to process [C] is generally carried out in inert solvents, if appropriate in the presence of a base, preferably in a temperature range from 0° C. to room temperature at atmospheric pressure.

Suitable dehydrating agents here are, for example, carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimid-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1 tetramethyluronium hexafluorophosphate (HATU), or 1-hydroxybenzotriazole (HOBt), or benzotriazol-1-yloxytris (dimethylamino)phosphonium hexafluorophosphate (BOP), or mixtures of these, with bases. The condensation is preferably carried out using HATU.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine. The condensation is preferably carried out using diisopropylethylamine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The reaction according to process [D] is generally carried out in inert solvents, in the presence of a catalyst, optionally in the presence of an additional reagent, optionally in a microwave, preferably in a temperature range from room temperature to 150° C. at atmospheric pressure to 3 bar.

Catalysts are, for example, palladium catalysts customary for Suzuki reaction conditions; preference is given to catalysts such as dichlorobis(triphenylphosphine)palladium, tetrakistriphenylphosphinepalladium(0), palladium(II) acetate/ triscyclohexylphosphine, tris(dibenzylideneacetone) dipalladium, bis(diphenylphosphaneferrocenyl)palladium (II) chloride, 1,3-bis(2,6-diisopropylphenyl)imidazol-2-ylidene(1,4-napththoquinone)palladium dimer, allyl(chloro) (1,3-dimesityl-1,3-dihydro-2H-imidazol-2-ylidene) palladium, palladium(II) acetate/dicyclohexyl-(2',4',6'-triisopropyl-biphenyl-2-yl)phosphine, [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2',4',6'-triisopropylbiphenyl-2-yl)phosphane (1:1)], preference is given to tetrakistriphenylphosphinepalladium(0), [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2',4',6'-triisopropylbiphenyl-2-yl)phosphane (1:1)].

Additional reagents are, for example, potassium acetate, caesium carbonate, potassium carbonate or sodium carbonate, potassium tert-butoxide, caesium fluoride or potassium phosphate, which may be present in aqueous solution; preferred are additional reagents such as potassium carbonate or aqueous potassium phosphate solution.

Inert solvents are, for example, ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, order N-methylpyrrolidone or acetonitrile, or mixtures of the solvents with alcohols such as methanol or ethanol and/or water; preference is given to tetrahydrofuran, dioxane or acetonitrile.

The compounds of the formula (IV) are known, can be synthesized from the corresponding starting compounds by known processes or can be prepared analogously to the processes described in the Examples section.

The compounds of the formula (VI) are known or can be synthesized by known processes from the appropriate starting materials.

The compounds of the formula (II) are known or can be prepared by reacting compounds of the formula

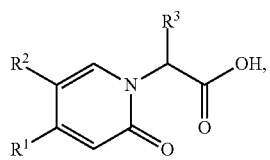
(III)

in which
$R^1$, $R^2$ and $R^3$ have the meaning given above,
with compounds of the formula

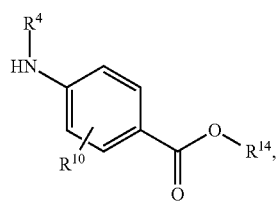
(VII)

in which
$R^4$ and $R^{10}$ have the meaning given above and
$R^{14}$ represents methyl, ethyl or tert-butyl,
in the presence of a dehydrating agent.

The reaction is carried out as described for process [C].

The compounds of the formula (VII) are known, can be synthesized from the corresponding starting compounds by known processes or can be prepared analogously to the processes described in the Examples section.

The compounds of the formula (III) are known or can be prepared by
[E] reacting compounds of the formula

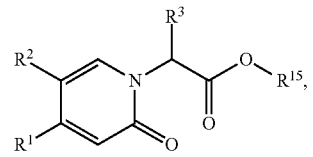
(VIIIa)

in which
$R^1$, $R^2$ and $R^3$ have the meaning given above and
$R^{15}$ represents tert-butyl,
with an acid
or
[F] reacting compounds of the formula

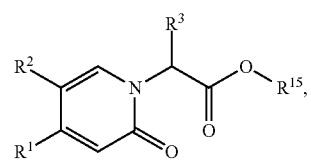
(VIIIb)

in which
$R^1$, $R^2$ and $R^3$ have the meaning given above and
$R^{15}$ represents methyl, ethyl or benzyl,
with a base.

The compounds of the formulae (VIIIa) and (VIIIb) together form the group of the compounds of the formula (VIII).

The reaction according to process [E] is carried out as described for process [A].

The reaction according to process [F] is carried out as described for process [B].

The compounds of the formula (VIII) are known or can be prepared by
[G] reacting compounds of the formula

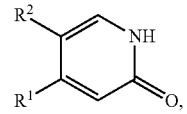
(IX)

in which
$R^1$ and $R^2$ have the meaning given above,
with compounds of the formula

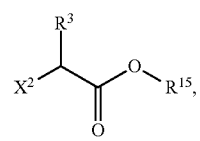
(X)

in which
$R^3$ has the meaning given above,
$R^{15}$ represents methyl, ethyl, benzyl or tert-butyl and $X^2$ represents chlorine, bromine, iodine, methanesulphonyloxy or trifluoromethanesulphonyloxy,
or
[H] reacting compounds of the formula

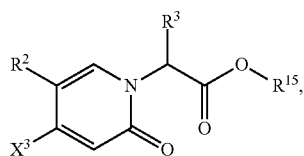

(XI)

in which
$R^2$ and $R^3$ have the meaning given above,
$R^{15}$ represents methyl, ethyl, benzyl or tert-butyl and
$X^3$ represents chlorine, bromine or iodine,
with compounds of the formula (VI) under Suzuki coupling conditions.

The reaction according to process [G] is generally carried out in inert solvents, optionally in the presence of a base, preferably in a temperature range from room temperature to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to dimethylformamide.

Bases are, for example, alkali metal hydroxides such as sodium hydroxide, lithium hydroxide or potassium hydroxide, or alkali metal carbonates such as caesium carbonate, sodium carbonate or potassium carbonate, or potassium tert-butoxide or sodium tert-butoxide, sodium hydride or a mixture of these bases or a mixture of sodium hydride and lithium bromide; preference is given to potassium carbonate or sodium hydride.

The compounds of the formula (X) are known or can be synthesized by known processes from the appropriate starting materials.

The reaction according to process [H] is carried out as described for process [D].

Further processes which can be used to prepare the compounds of the formula (VIII) can be found under the starting materials in Examples 32.1A-C, 41.1A-C, 43.1B, 43.1C, 44.1B and 44.1C.

The compounds of the formula (IX) are known or can be prepared by reacting compounds of the formula

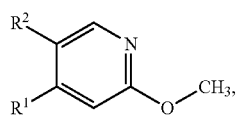

(XII)

in which
$R^1$ and $R^2$ have the meaning given above,
with pyridinium hydrochloride or pyridinium hydrobromide.

The reaction is generally carried out in inert solvents, preferably in a temperature range of from 80° C. to 120° C. at atmospheric pressure.

Inert solvents are, for example, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The compounds of the formula (XII) are known or can be prepared by reacting compounds of the formula

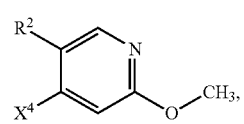

(XIII)

in which
$R^2$ has the meaning given above and
$X^4$ represents chlorine, bromine or iodine,
with compounds of the formula (VI) under Suzuki coupling conditions.

The reaction is carried out as described for process [D].

The compounds of the formula (XIII) are known or can be synthesized by known processes from the appropriate starting materials.

The compounds of the formula (XI) are known or can be prepared by reacting compounds of the formula

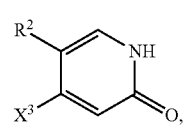

(XIV)

in which
$R^2$ has the meaning given above and
$X^3$ represents chlorine, bromine or iodine,
with compounds of the formula (X).

The reaction is carried out as described for process [G].

The compounds of the formula (XIV) are known or can be synthesized by known processes from the appropriate starting materials.

The compounds of the formula (V) are known or can be prepared by reacting compounds of the formula

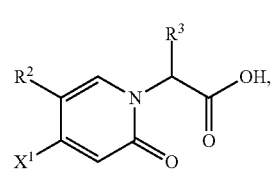

(XV)

in which
$R^2$ and $R^3$ have the meaning given above and
$X^1$ represents chlorine, bromine or iodine,
with compounds of the formula (IV) in the presence of a dehydrating agent.

The reaction is carried out as described for process [C].

The compounds of the formula (XV) are known or can be prepared by

[I] reacting compounds of the formula

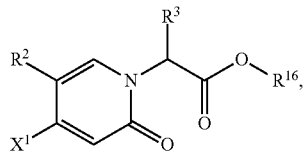
(XVIa)

in which
R² and R³ have the meaning given above,
R¹⁶ represents tert-butyl and
X¹ represents chlorine, bromine or iodine,
with an acid
or
[J] reacting compounds of the formula

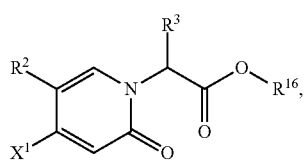
(XVIb)

in which
R² and R³ have the meaning given above,
R¹⁶ represents methyl, ethyl or benzyl and
X¹ represents chlorine, bromine or iodine,
with a base.

The compounds of the formulae (XVIa) and (XVIb) together form the group of the compounds of the formula (XVI).

The reaction according to process [I] is carried out as described for process [A].

The reaction according to process [J] is carried out as described for process [B].

The compounds of the formula (XVI) are known or can be prepared by reacting compounds of the formula

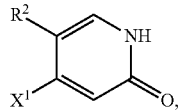
(XVII)

in which
R² has the meaning given above and
X¹ represents chlorine, bromine or iodine,
with compounds of the formula

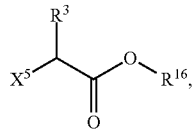
(XVIII)

in which
R³ has the meaning given above,
R¹⁶ represents methyl, ethyl, benzyl or tert-butyl and
X⁵ represents chlorine, bromine, iodine, methanesulphonyloxy or trifluoromethanesulphonyloxy.

The reaction is carried out as described for process [G].

The compounds of the formulae (XVII) and (XVIII) are known or can be synthesized by known processes from the appropriate starting materials.

In an alternative process, the compounds of the formula (VIII) can be prepared by reacting compounds of the formula

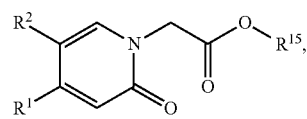
(XIX)

in which
R¹ and R² have the meaning given above and
R¹⁵ represents methyl, ethyl, benzyl or tert-butyl,
with compounds of the formula $R^3$—$X^6$ (XX), in which
R³ has the meaning given above and
X⁶ represents chlorine, bromine, iodine, methanesulphonyloxy, trifluoromethanesulphonyloxy or para-toluenesulphonyloxy.

The reaction is generally carried out in inert solvents, if appropriate in the presence of a base, preferably in a temperature range from −78° C. to room temperature at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride, N-butyllithium or bis(trimethylsilyl)lithium amide, preference is given to bis(trimethylsilyl)lithium amide.

The compounds of the formula (XIX) are known or can be synthesized by the processes described above, for example process [G], from the appropriate starting materials.

The compounds of the formula (XX) are known or can be synthesized by known processes from the appropriate starting materials.

In an alternative process, the compounds of the formula (III) can be prepared by reacting compounds of the formula

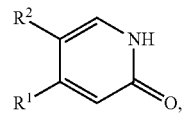
(IX)

in which
R¹ and R² have the meaning given above, with compounds of the formula

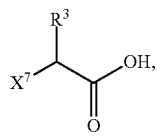
(XXI)

in which
R³ has the meaning given above and
X⁷ represents chlorine, bromine or iodine.

The reaction is generally carried out in inert solvents, if appropriate in the presence of a base, preferably in a temperature range from −10° C. to 90° C. at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride or bis(trimethylsilyl)lithium amide or a mixture of magnesium di-tert-butoxide and potassium tert-butoxide, preference is given to a mixture of magnesium di-tert-butoxide and potassium tert-butoxide.

The compounds of the formula (XXI) are known or can be synthesized by known processes from the appropriate starting materials.

In an alternative process, the compounds of the formula (XV) can be prepared by reacting compounds of the formula

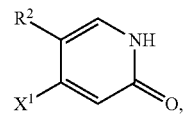
(XVII)

in which
R² has the meaning given above and
X¹ represents chlorine, bromine or iodine,
with compounds of the formula

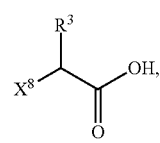
(XXII)

in which
R³ has the meaning given above and
X⁸ represents chlorine, bromine or iodine.

The reaction is carried out as described for the reaction of compounds of the formula (IX) with compounds of the formula (XXI).

The compounds of the formula (XXII) are known or can be synthesized by known processes from the appropriate starting materials.

The preparation of the starting compounds and of the compounds of the formula (I) can be illustrated by the synthesis scheme below.

Scheme 1:

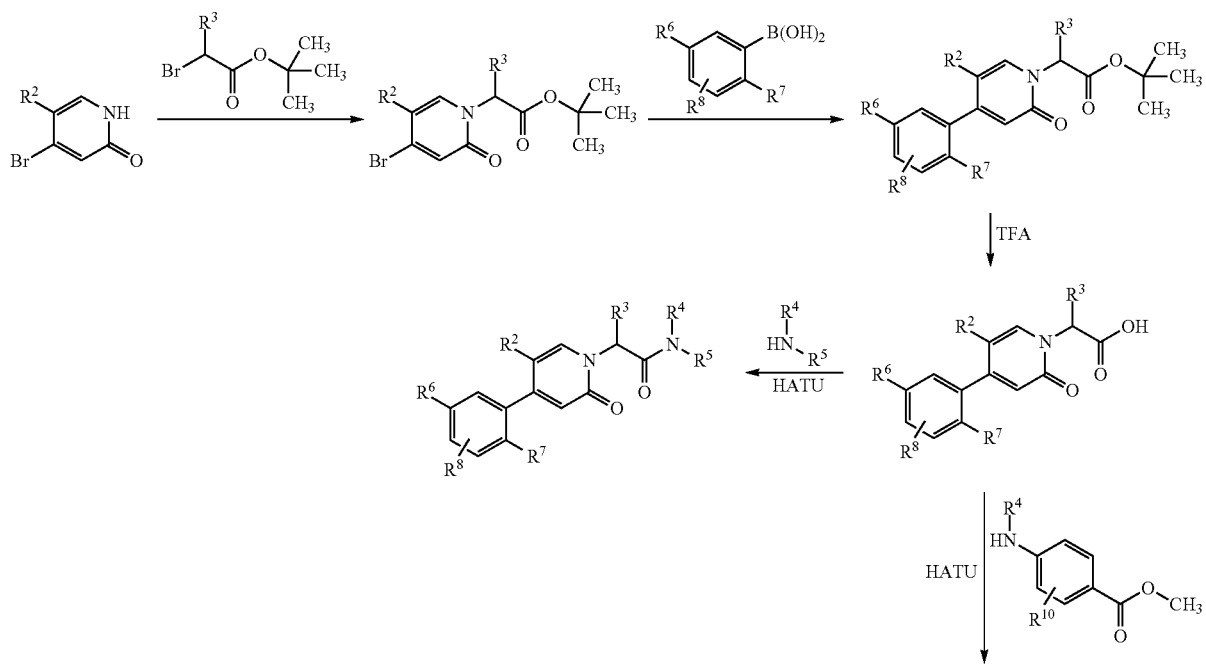

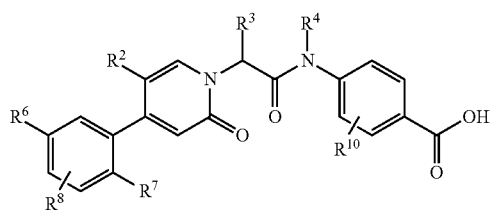
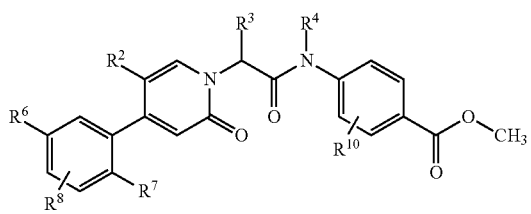

The compounds according to the invention have an unforeseeable useful spectrum of pharmacological and pharmacokinetic activity. They are compounds modulating the proteolytic activity of the serine protease FXIa. The compounds according to the invention inhibit the enzymatic cleavage of substrates playing an essential role in the activation of the blood coagulation cascade and platelet aggregation. Furthermore, some of the compounds also inhibit plasma kallikrein.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmologic disorders, in particular of diabetic retinopathy or macular oedema, and/or inflammatory disorders, in particular those associated with excess plasma kallikrein activity.

"Thromboembolic disorders" in the sense of the present invention include in particular disorders such as acute coronary syndrome (ACS), ST-segment elevation myocardial infarction (STEMI) and non-ST-segment elevation myocardial infarction (non-STEMI), stable angina pectoris, unstable angina pectoris, reocclusions and restenoses after coronary interventions such as angioplasty, stent implantation or aortocoronary bypass, peripheral arterial occlusion diseases, pulmonary embolisms, venous thromboses, in particular in deep leg veins and renal veins, transitory ischaemic attacks and also thrombotic and thromboembolic stroke.

Accordingly, the compounds according to the invention are also suitable for the prevention and treatment of cardiogenic thromboembolisms such as, for example, brain ischaemias, stroke and systemic thromboembolisms and ischaemias, in patients with acute, intermittent or persistent cardiac arrhythmias such as, for example, atrial fibrillation, and those undergoing cardioversion, furthermore in patients with heart valve disorders or with artificial heart valves.

In addition, the compounds according to the invention are suitable for the treatment and prevention of disseminated intravascular coagulation (DIC) which may occur inter alia associated with sepsis, but also owing to surgical interventions, tumour disorders, burns or other injuries and may lead to severe organ damage by microthrombosis.

Thromboembolic complications furthermore occur in microangiopathic haemolytical anaemias and by the blood coming into contact with foreign surfaces in the context of extracorporeal circulation such as, for example, haemodialysis, ECMO ("extracorporeal membrane oxygenation"), LVAD ("left ventricular assist device") and similar methods, AV fistulas, vascular and heart valve prostheses.

Moreover, the compounds according to the invention are also used for influencing wound healing, for the prophylaxis and/or treatment of atherosclerotic vascular disorders and inflammatory disorders, such as rheumatic disorders of the locomotive system, coronary heart diseases, of heart failure, of hypertension, of inflammatory disorders such as, for example, asthma, inflammatory pulmonary disorders, glomerulonephritis and inflammatory intestinal disorders such as, for example, Crohn's disease or ulcerative colitis, and additionally also for the prophylaxis and/or treatment of dementia disorders such as, for example, Alzheimer's disease. Moreover, the compounds according to the invention can be used for inhibiting tumour growth and the formation of metastases, for microangiopathies, age-related macular degeneration, diabetic retinopathy, diabetic nephropathy and other microvascular disorders, and also for the prevention and treatment of thromboembolic complications, such as, for example, venous thromboembolisms, for tumour patients, in particular those undergoing major surgical interventions or chemo- or radiotherapy.

The compounds according to the invention are also suitable for modulating disorders causing high vascular permeability and inflammation, for example hereditary angiooedema (HAE) which is due to dysregulation of vascular permeability triggered by excess plasma kallikrein activation.

Furthermore, the compounds according to the invention, in particular those acting on plasma kallikrein, are suitable for use in lung transplantations, orthotopic liver transplantations, complication associated with CABG (coronary artery bypass graft) operations. The compounds according to the invention are furthermore suitable for protecting organs during transplantation.

Moreover, the compounds according to the invention are also suitable for the prophylaxis and/or treatment of pulmonary hypertension.

The term "pulmonary hypertension" includes certain forms of pulmonary hypertension, as determined, for example, by the World Health Organization (WHO). Examples which may be mentioned are pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypersion" comprises idiopathic pulmonary arterial hypertension (IPAH, formally also referred to as primary pulmonary hypertension), familial pulmonary arterial hypertension (FPAH) and associated pulmonary-arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonatants.

Pulmonary hypertension associated with disorders of the left heart comprises a diseased left atrium or ventricle and mitral or aorta valve defects.

Pulmonary hyptertension associated with pulmonary disorders and/or hypoxia comprises chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention furthermore provides the use of the compounds according to the invention for preparing medicaments for the treatment and/or prophylaxis of pulmonary hypertension associated with sarcoidosis, histiocytosis X and lymphangiomatosis.

Moreover, the substances according to the invention may also be suitable for treating pulmonary and hepatic fibroses.

Moreover, the compounds according to the invention may also be suitable for the treatment and/or prophylaxis of sepsis (or septicaemia), systemic inflammatory syndrome (SIRS), septic organ dysfunction, septic organ failure and multiorgan failure, acute respiratory distress syndrome (ARDS), acute lung injury (ALI), septic shock, DIC (disseminated intravascular coagulation or consumption coagulopathy) and/or septic organ failure.

"Sepsis" is defined as the presence of an infection and a systemic inflammatory response syndrome (hereinbelow referred to as "SIRS"). SIRS occurs during infections, but also during other states such as injuries, burns, shock, surgical interventions, ischaemia, pancreatitis, reanimation or tumours. The definition of the ACCP/SCCM Consensus Conference Committee from 1992 (Crit Care Med 1992; 20:864-874) describes the diagnosis symptoms and measuring parameters required for the diagnosis of "SIRS" (inter alia body temperature change, increased pulse, breathing difficulties and changed blood picture). The later (2001) SCCM/ESICM/ACCP/ATS/SIS International Sepsis Definitions Conference essentially kept the criteria, but fine-tuned details (Levy et al., Crit Care Med 2003; 31:1250-1256).

In the course of sepsis, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and seeping of fluids and proteins into the extravasal lumen. As the sepsis progresses, there may be failure of an organ (for example kidney failure, liver failure, respiratory failure, central-nervous deficits and cardiovascular failure) or multiorgan failure. "Septic shock" is the occurrence of treatment-requiring hypotension which facilitates further organ damage and is associated with a worsening of the prognosis.

Pathogens can be bacteria (gram-negative and gram-positive), fungi, viruses and/or eukaryotes. The site of entry or primary infection may be pneumonia, an infection of the urinary tract or peritonitis, for example. The infection may, but need not necessarily, be associated with bacteriaemia.

DIC and/or SIRS may occur during sepsis, but also as a result of surgical interventions, tumour disorders, burns or other injuries. In the case of DIC, there is a massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

Therapy of sepsis consists, firstly, in the thorough elimination of the infectious cause, for example by operative focal reconstruction and antibiosis. Secondly, it consists in temporary intensive medical support of the affected organ systems. Treatments of the different stages of this disease have been described, for example, in the following publication (Dellinger et al., Crit Care Med 2004; 32:858-873). There are no proven effective treatments for DIC.

"Ophthalmic disorders" in the context of the present invention include in particular disorders such as diabetic retinopathy, diabetic macular oedema (DME), macular oedema, macular oedema associated with retinal vein occlusion, age-related macular degeneration (AMD), choroidal neovascularization (CNV), choroidal neovascular membranes (CNVM), cystoid macula oedema (CME), epiretinal membranes (ERM) and macula perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorder such as uveitis, scleritis or endophthalmitis, cataract, refraction anomalies such as myopia, hyperopia or astigmatism and keratoconus, disorders of the anterior eye such as corneal angiogenesis as sequela of, for example ceratitis, cornea transplantation or keratoplasty, corneal angiogenesis as sequela of hypoxia (for example by excessive use of contact lenses), pterygium conjunctivae, subcorneal oedema and intracorneal oedema.

The present invention further provides medicaments comprising a compound according to the invention and one or more further active compounds, especially for the treatment and/or prophylaxis of the disorders mentioned above. Preferred examples of suitable active compound combinations include:

Antibiotic therapy

Various antibiotics or antifungal medicament combinations are suitable, either as calculated therapy (prior to the presence of the microbial diagnosis) or as specific therapy.

Fluid therapy for example crystalloids or colloidal fluids.

Vasopressors for example norepinephrins, dopamines or vasopressin

Inotropic therapy for example dobutamine

Corticosteroids for example hydrocortisone, or fludrocortisone

Recombinant human activated protein C

Xigris

Blood products for example erythrocyte concentrates, platelet concentrates, erythropoietin or fresh frozen plasma Artificial ventilation in the case of sepsis-induced acute lung injury (ALI)

or acute respiratory distress syndrome (ARDS)

for example permissive hypercapnia, reduced tidal volumes

Sedation, analgesia and neuromuscular blockade

Sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium Glucose control for example insulin, glucose Renal replacement methods for example continuous veno-venous haemofiltration or intermittent haemodialysis. Low doses of dopamine for renal protection.

Anticoagulants for example for thrombosis prophylaxis or renal replacement methods, for example unfractionated heparins, low-molecular-weight heparins, heparinoids, hirudin, bivalirudin or argatroban.

Bicarbonate therapy

Stress ulcer prophylaxis for example H2-receptor inhibitors, antacids.

In addition, the compounds according to the invention can also be used for preventing coagulation ex vivo, for example for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa and/or plasma kallikrein.

The present invention further provides for the use of the compounds according to the invention for the treatment and/or prophylaxis of disorders, in particular the disorders mentioned above.

The present invention further provides for the use of the compounds according to the invention for producing a medicament for treatment and/or prophylaxis of disorders, in particular the disorders mentioned above.

The present invention further provides a method for the treatment and/or prophylaxis of disorders, especially the disorders mentioned above, using a therapeutically effective amount of a compound according to the invention.

The present invention further provides medicaments comprising a compound according to the invention and one or more further active compounds.

The present invention furthermore provides a method for preventing the coagulation of blood in vitro, in particular in banked blood or biological samples which may comprise factor XIa and/or plasma kallikrein, which method is characterized in that an anticoagulatory effective amount of the compound according to the invention is added.

The present invention further provides medicaments comprising a compound according to the invention and one or more further active compounds, especially for the treatment and/or prophylaxis of the disorders mentioned above. Preferred examples of suitable active compound combinations include:

- lipid-lowering substances, in particular HMG-CoA-(3-hydroxy-3-methylglutaryl-coenzyme A) reductase inhibitors such as, for example, lovastatin (Mevacor), simvastatin (Zocor), pravastatin (Pravachol), fluvastatin (Lescol) and atorvastatin (Lipitor);
- coronary therapeutics/vasodilatators, in particular ACE (angiotensin converting enzyme) inhibitors such as, for example, captopril, lisinopril, enalapril, ramipril, cilazapril, benazepril, fosinopril, quinapril and perindopril, or AII (angiotensin II) receptor antagonists such as, for example, embusartan, losartan, valsartan, irbesartan, candesartan, eprosartan and temisartan, or β-adrenoceptor antagonists such as, for example, carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists such as, for example, prazosine, bunazosine, doxazosine and terazosine, or diuretics such as, for example, hydrochlorothiazide, furosemide, bumetanide, piretanide, torasemide, amiloride and dihydralazine, or calcium channel blockers such as, for example, verapamil and diltiazem, or dihydropyridine derivatives such as, for example, nifedipin (Adalat) and nitrendipine (Bayotensin), or nitro preparations such as, for example, isosorbide 5-mononitrate, isosorbide dinitrate and glycerol trinitrate, or substances causing an increase in cyclic guanosine monophosphate (cGMP) such as, for example, stimulators of soluble guanylate cyclase, for example riociguat;
- plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA), streptokinase, reteplase and urokinase or plasminogen-modulating substances causing increased formation of plasmin;
- anticoagulatory substances (anticoagulants), such as, for example, heparin (UFH), low-molecular-weight heparins (NMH), such as, for example, tinzaparin, certoparin, parnaparin, nadroparin, ardeparin, enoxaparin, reviparin, dalteparin, danaparoid, semuloparin (AVE 5026), adomiparin (M118) and EP-42675/ORG42675,
- direct thrombin inhibitors (DTI) such as, for example, Pradaxa (dabigatran), atecegatran (AZD-0837), DP-4088 and SSR-182289A,
- direct factor Xa inhibitors such as, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux,
- substances which inhibit the aggregation of platelets (platelet aggregation inhibitors, thrombocyte aggregation inhibitors), such as, for example, acetylsalicylic acid (such as, for example, aspirin), P2Y12 antagonists such as, for example, ticlopidine (Ticlid), clopidogrel (Plavix), prasugrel, ticagrelor, cangrelor, elinogrel, PAR-1 antagonists such as, for example, vorapaxar, PAR-4 antagonists, EP3 antagonists such as, for example, DG041;
- platelet adhesion inhibitors such as GPVI and/or GPIb antagonists such as, for example, Revacept or caplacizumab;
- fibrinogen receptor antagonists (glycoprotein-IIb/IIIa antagonists), such as, for example, abciximab, eptifibatide, tirofiban, lamifiban, lefradafiban and fradafiban;
- and also antiarrhythmics;
- inhibitors of VEGF and/or PDGF signal paths such as, for example, aflibercept, ranibizumab, bevacizumab, KH-902, pegaptanib, ramucirumab, squalamin or bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, Vargatef and E-10030;
- inhibitors of angiopoietin-Tie signal paths such as, for example, AMG386;
- inhibitors of Tie2 receptor tyrosine kinase;

inhibitors of the integrin signal paths such as, for example, volociximab, cilengitide and ALG1001;
inhibitors of the PI3K-Akt-mTor signal paths such as, for example, XL-147, perifosine, MK2206, sirolimus, temsirolimus and everolimus;
corticosteroids such as, for example, anecortave, betamethasone, dexamethasone, triamcinolone, fluocinolone and fluocinolone acetonide;
inhibitors of the ALK1-Smad1/5 signal path such as, for example, ACE041;
cyclooxygenase inhibitors such as, for example, bromfenac and nepafenac;
inhibitors of the kallikrein-kinin system such as, for example, safotibant and ecallantide;
inhibitors of the sphingosine 1-phosphate signal paths such as, for example, sonepcizumab;
inhibitors of the complement-C5a receptor such as, for example, eculizumab;
inhibitors of the 5HT1a receptor such as, for example, tandospirone;
inhibitors of the Ras-Raf-Mek-Erk signal path; inhibitors of the MAPK signal paths; inhibitors of the FGF signal paths; inhibitors of endothelial cell proliferation; apoptosis-inducing active compounds;
photodynamic therapy consisting of an active compound and the action of light, the active compound being, for example, verteporfin.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, extraocular, intraocular or otic route, or as an implant or stent.

The compounds according to the invention can be administered in administration forms suitable for these administration routes.

Suitable administration forms for oral administration are those which function according to the prior art and deliver the compounds according to the invention rapidly and/or in modified fashion, and which contain the compounds according to the invention in crystalline and/or amorphized and/or dissolved form, for example tablets (uncoated or coated tablets, for example having enteric coatings or coatings which are insoluble or dissolve with a delay and control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

Suitable for extraocular (topic) administration are administration forms which operate in accordance with the prior art, which release the active compound rapidly and/or in a modified or controlled manner and which contain the active compound in crystalline and/or amorphized and/or dissolved form such as, for example, eye drops, sprays and lotions (e.g. solutions, suspensions, vesicular/colloidal systems, emulsions, aerosols), powders for eye drops, sprays and lotions (e.g. ground active compound, mixtures, lyophilizates, precipitated active compound), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable for intraocular administration are administration forms which operate in accordance with the prior art, which release the active compound rapidly and/or in a modified or controlled manner and which contain the active compound in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active compound, mixtures, lyophilizates, precipitated active compound), gels for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds according to the invention can be converted to the administration forms mentioned. This can be done in a manner known per se, by mixing with inert, nontoxic, pharmaceutically suitable excipients. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

The present invention further provides medicaments comprising at least one compound according to the invention, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary to deviate from the amounts specified, specifically depending on body weight, administration route, individual behaviour towards the active compound, type of formulation, and time or interval of administration.

The percentages in the tests and examples which follow are, unless indicated otherwise, percentages by weight; parts are parts by weight. Solvent ratios, dilution ratios and concentration figures for liquid/liquid solutions are each based on volume. "w/v" means "weight/volume". For example, "10% w/v" means: 100 ml of solution or suspension comprise 10 g of substance.

A) EXAMPLES

Abbreviations

CDI carbonyldiimidazole
d day(s), doublet (in NMR)
DAD diode array detector
TLC thin-layer chromatography
DCM dichloromethane
DCI direct chemical ionization (in MS)
dd doublet of doublets (in NMR)
DIC N,N'-diisopropylcarbodiimide
DIEA N,N-diisopropylethylamine
DMAP 4-dimethylaminopyridine
DMF N,N-dimethylformamide
DMSO dimethyl sulphoxide
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
HV high vacuum
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
oxima ethyl hydroxyiminocyanoacetate
quant. quantitative
RP reversed phase (in HPLC)
RT room temperature
$R_t$ retention time (in HPLC)
s singlet (in NMR)
SFC supercritical fluid chromatography (with supercritical carbon dioxide as mobile phase)
THF tetrahydrofuran
TFA trifluoroacetic acid
T3P 2,4,6-tripropyl-1,3,5,2,4,6-trioxatriphosphinane 2,4,6-trioxide
Xantphos 4,5-bis(diphenylphosphino)-9,9-dimethylxanthene
XPhos precatalyst [(2'-aminobiphenyl-2-yl)(chloro)palladium dicyclohexyl(2',4',6'-triisopropylbiphenyl-2-yl)phosphane (1:1)], J. Am. Chem. Soc. 2010, 132, 14073-14075

HPLC, LC/MS and GC Methods:

Method 1:
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2:
Instrument: Waters ACQUITY SQD UPLC System; column: Waters Acquity UPLC HSS T3 1.8µ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 3:
Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A; oven: 50° C.; flow rate: 0.3 ml/min; UV detection: 210 nm.

Method 4:
MS instrument: Waters (Micromass) Quattro Micro; HPLC instrument: Agilent 1100 series; column: YMC-Triart C18 3µ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 5:
MS instrument: Waters (Micromass) QM; HPLC instrument: Agilent 1100 series; column: Agient ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 6:
MS instrument: Waters (Micromass) ZQ; HPLC instrument: Agilent 1100 series; column: Agient ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7:
Instrument: Thermo DFS, Trace GC Ultra; column: Restek RTX-35, 15 m×200 µm×0.33 µm; constant flow rate with helium: 1.20 ml/min; oven: 60° C.; inlet: 220° C.; gradient: 60° C., 30° C./min→300° C. (hold for 3.33 min).

Method 8:
Instrument: Agilent MS Quad 6150; HPLC: Agilent 1290; column: Waters Acquity UPLC HSS T3 1.8µ 50 mm×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 9:
Instrument: Thermo Scientific DSQII, Thermo Scientific Trace GC Ultra; column: Restek RTX-35MS, 15 m×200 µm×0.33 µm; constant flow rate with helium: 1.20 ml/min; oven: 60° C.; inlet: 220° C.; gradient: 60° C., 30° C./min→300° C. (hold for 3.33 min).

Method 10:
MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.

Method 11:
MS instrument type: Waters Synapt G2S; UPLC instrument type: Waters Acquity I-CLASS; column: Waters, HSST3, 2.1 mm×50 mm, C18 1.8 µm; mobile phase A: 1 l of water+0.01% formic acid; mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm.

Microwave:

The microwave reactor used was a single-mode instrument of the Emrys™ Optimizer type.

Starting Materials

General Method 1A: Preparation of a Boronic Acid

At −78° C., LDA (2 molar in THF/heptane/ethylbenzene) was added to a solution of the appropriate pyridine derivative in THF (3 ml/mmol), the mixture was stirred for 2-4 h and triisopropyl borate was then added quickly. The reaction mixture was maintained at −78° C. for a further 2-3 h and then slowly thawed to RT overnight. After addition of water, the THF was removed under reduced pressure and the aqueous phase was extracted twice with ethyl acetate The aqueous phase was acidified with 2M hydrochloric acid, generally resulting in formation of a precipitate which was filtered off, washed with water and dried. The aqueous phase was extracted three times with ethyl acetate. The combined organic phases were dried (sodium sulphate), filtered and concentrated under reduced pressure.

General Method 2A: Suzuki Coupling

In a flask which had been dried by heating and flushed with argon, 1.0 eq. of the appropriate boronic acids, 1.0 eq. of the aryl bromide or aryl iodide, 3.0 eq. of potassium carbonate and 0.1 eq. of [1,1-bis-(diphenylphosphino)ferrocene]palladium(II) chloride/monodichloromethane adduct or tetrakis(triphenylphosphine)palladium(0) were initially charged. The flask was then evacuated three times and in each case vented with argon. Dioxane (6 ml/mmol) was added, and the reaction mixture was stirred at 110° C. for a number of hours until substantially complete conversion had been achieved. The reaction mixture was then filtered through Celite and the filtrate was concentrated under reduced pressure. Water was added to the residue. After addition of ethyl acetate and phase separation, the organic phase was washed once with water and once with saturated aqueous sodium chloride solution, dried (magnesium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 2B: Suzuki Coupling

In a flask which had been dried by heating and flushed with argon, 1.0 eq. of the appropriate boronic acids, 1.0 eq. of the aryl bromide or aryl iodide and 0.05 eq. of XPhos precatalyst [(2'-aminobiphenyl-2-yl)(chloro)palladium/dicyclohexyl(2',4',6'-triisopropylbiphenyl-2-yl)phosphane (1:1)], *J. Am. Chem. Soc.* 2010, 132, 14073-14075] were initially charged. The flask was then evacuated three times and in each case vented with argon. THF (about 12 ml/mmol) which had been degassed in an ultrasonic bath and 3.0 eq. of aqueous potassium phosphate solution (0.5 molar) were added, and the reaction mixture was stirred at 60° C. Water and ethyl acetate were then added to the reaction mixture. After phase separation, the aqueous phase was extracted once with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 3A: Methoxypyridine Cleavage 20 eq. of pyridinium hydrochloride or pyridinium hydrobromide were added to a solution of the appropriate methoxypyridine in DMF (12.5 ml/mmol) and the mixture was stirred at 100° C. for a number of hours to days, with further pyridinium hydrochloride or pyridinium hydrobromide being added, until substantially complete conversion had been achieved. Subsequently, the reaction solution was concentrated under reduced pressure and the residue was triturated with water. The precipitate formed was filtered off, washed with water and dried under reduced pressure.

General Method 4A: N-Alkylation of 2-Pyridinone Derivatives with the Appropriate 2-Bromo- or 2-Chloropropanoic Acid Derivatives Under argon, a suspension of 1.0 eq. of the appropriate 2-pyridinone derivative, 2.0 eq. of magnesium di-tert-butoxide and 1.05 eq. of potassium tert-butoxide in THF (5-10 ml/mmol) was stirred at RT for 10-20 min. The reaction mixture was cooled in an ice bath, and 1.5 eq. of the appropriate 2-bromo- or 2-chloropropanoic acid derivative were added. The reaction mixture was then stirred initially at RT for 2.5 h and then further at 35-90° C. overnight and then quenched with 6 N hydrochloric acid. After addition of ethyl acetate and phase separation, the organic phase was washed once with water and once with saturated aqueous sodium chloride solution, dried (magnesium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 4B: N-Alkylation of 2-Pyridinone Derivatives with the Appropriate 2-Bromo- or 2-Chloropropanoic Ester Derivatives in the Presence of Potassium Carbonate Under argon and at RT, 1.2 eq. of the appropriate 2-bromo- or 2-chloropropanoic ester derivative and 1.5 eq. of potassium carbonate were added to a solution of 1.0 eq. of the appropriate 2-pyridinone derivative in dimethylformamide (5-10 ml/mmol), and the mixture was stirred at 100° C. After removal of the DMF and addition of water/ethyl acetate and phase separation, the organic phase was washed with water and with saturated aqueous sodium chloride solution, dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 4C: N-Alkylation of 2-Pyridinone Derivatives with the Appropriate 2-Bromo- or 2-Chloropropanoic Ester Derivatives in the Presence of Sodium Hydride/Lithium Bromide Under argon and at 0° C., 1.25 eq. of sodium hydride (60% in mineral oil) were added to a solution of 1.0 eq. of the appropriate 2-pyridinone derivative in dimethylformamide (5-10 ml/mmol), and the mixture was stirred at 0° C. for 10-20 min 2.0 eq. of lithium bromide were then added, the reaction mixture was stirred at RT for 15 min, 1.25 eq. of the appropriate 2-bromo- or 2-chloropropanoic ester derivative were added and the mixture was stirred at 65° C. After removal of the DMF and addition of water/ethyl acetate and phase separation, the organic phase was washed with water, dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 4D: N-Alkylation of 2-Pyridinone Derivatives with the Appropriate 2-Bromo- or 2-Chloropropanoic Ester Derivatives in the Presence of Sodium Hydride Under argon and at RT, the appropriate 2-pyridinone derivative was added to a suspension of sodium hydride (1.2 eq.) in dimethylformamide (5-10 ml/mmol). The reaction mixture was stirred at RT for 30-90 min and then cooled to 0° C., the appropriate 2-bromo- or 2-chloropropanoic ester derivative (1.2 eq.) was added and the mixture was stirred at RT for 2-5 h. After addition of water and phase separation, the aqueous phase was extracted with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 4E: N-Alkylation of 2-Pyridinone Derivatives with the Appropriate Triflates in the Presence of Sodium Hydride Under argon and at RT, sodium hydride (1.1-1.5 eq.) was added to a solution of the appropriate 2-pyridinone derivative (1 eq.) in tetrahydrofuran (0.05-0.2M), and the mixture was stirred for 30-90 min. The appropriate triflate (1.0-2.0 eq.) was then added neat or as a solution in THF. The resulting reaction mixture was stirred at RT for another 1-5 h. Saturated aqueous ammonium chloride solution was added to the reaction mixture. After phase separation, the aqueous phase was extracted with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 5A: Amide Coupling Using HATU/DIEA

Under argon and at RT, the amine (1.1 eq.), N,N-diisopropylethylamine (2.2 eq.) and a solution of HATU (1.2 eq.) in a little DMF were added to a solution of the appropriate carboxylic acid (1.0 eq.) in dimethylformamide (7-15 ml/mmol). The reaction mixture was stirred at RT. After addition of water/ethyl acetate and phase separation, the organic phase was washed with water and with saturated aqueous sodium chloride solution, dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 5B: Amide Coupling Using OXIMA/DIC

N,N'-Diisopropylcarbodiimide (DIC) (1 eq.) was added dropwise to a degassed solution of the appropriate carboxylic acid (1 eq.), aniline (1 eq.) and ethyl hydroxyiminocyanoacetate (Oxima) (1 eq.) in dimethylformamide (0.1M), and the resulting reaction solution was stirred at RT-40° C. for 8-24 h. The solvent was removed under reduced pressure. The residue was either admixed with water and the desired product was filtered off or purified by normal phase chromatography (cyclohexane/ethyl acetate gradient) or preparative RP-HPLC (water/acetonitrile gradient or water/methanol gradient).

General Method 5C: Amide Coupling Using T3P/Pyridine

Under argon and at 0° C., propylphosphonic anhydride (T3P, 50% in ethyl acetate, 4 eq.) was added dropwise to a solution of the carboxylic acid (1 eq.) and the appropriate amine (1.5 eq.) in pyridine (0.15-0.05 M). This mixture was heated to 90° C. and stirred at 90° C. for 1-20 h. The reaction mixture was cooled to RT, and water and ethyl acetate were added. After phase separation, the aqueous phase was extracted with ethyl acetate. The combined organic phases were washed with aqueous buffer solution (pH 5), with saturated aqueous sodium bicarbonate solution and with saturated aqueous sodium chloride solution, dried (sodium sulphate or magnesium sulphate), filtered and concentrated under reduced pressure. The crude product was then optionally purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 6A: Hydrolysis of a Tert-Butyl Ester Using TFA

At RT, 20 eq. of TFA were added to a solution of 1.0 eq. of the appropriate tert-butyl ester derivative in dichloromethane (about 7 ml/mmol), and the mixture was stirred at RT for 1-8 h. The reaction mixture was then concentrated under reduced pressure and the residue was co-evaporated repeatedly with dichloromethane and/or toluene and dried under reduced pressure. The crude product was then optionally purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 6B: Hydrolysis of a Methyl/Ethyl or Tert-Butyl Ester with Lithium Hydroxide At RT, 3.0 eq. of lithium hydroxide were added to a solution of 1.0 eq. of the appropriate methyl or ethyl ester in tetrahydrofuran/water (3:1, about 10 ml/mmol). The reaction mixture was stirred at RT to 60° C. and then adjusted to pH 1 using aqueous 1 N hydrochloric acid solution. After addition of water/ethyl acetate and phase separation, the aqueous phase was extracted three times with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 6C: Hydrolysis of a Methyl or Ethyl Ester with Caesium Carbonate

Caesium carbonate (2 eq.) was added to a solution of the appropriate methyl or ethyl ester (1 eq.) in a mixture of methanol/water (4/1, 0.05-0.2M), and the resulting suspension was stirred at RT-60° C. for 3-8 h. The reaction mixture was then optionally cooled to RT and adjusted to pH 3 using aqueous hydrochloric acid (1N). Methanol was removed at 30° C. under reduced pressure. The aqueous phase was extracted with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 7A: Alkylation of Acetic Esters with Halides

Under argon and at −78° C., 1.1 eq. of bis(trimethylsilyl) lithium amide (1.0M in THF) were added to a solution of the appropriate acetic ester in THF (about 10 ml/mmol), and the mixture was stirred at −78° C. for 10 min. A solution of the appropriate iodide/bromide/chloride in THF was then added, and the reaction mixture was stirred at −78° C. for 10 min and further in an ice bath and then quenched with water. After addition of ethyl acetate and phase separation, the aqueous phase was extracted twice with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 7B: Alkylation of Acetic Esters with Triflates

Under argon and at −78° C., bis(trimethylsilyl)lithium amide (1.0M in THF, 1.1-1.3 eq.) was added dropwise to a solution of the appropriate acetic ester (1 eq.) in tetrahydrofuran (0.1-0.2M), and the mixture was stirred for 15 min. The appropriate alkyl triflate (1.5-2.0 eq.) was then added neat or as a solution in THF. The resulting reaction mixture was stirred at −78° C. for another 15 min and at RT for another 1 h. Saturated aqueous ammonium chloride solution was added to the reaction mixture. After phase separation, the aqueous phase was extracted with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 8A: Preparation of Triflates

A solution of the appropriate alcohol (1 eq.) was initially charged in dichloromethane (0.1M), and at −20° C. lutidine (1.1-1.5 eq.) or triethylamine (1.1-1.5 eq.) and trifluoromethanesulphonic anhydride (1.05-1.5 eq.) were added in succession. The reaction mixture was stirred at −20° C. for another 1 h and then diluted with triple the amount (based on the reaction volume) of methyl tert-butyl ether. The organic phase was washed three times with a 3:1 mixture of saturated aqueous sodium chloride solution/1N hydrochloric acid and finally with saturated aqueous sodium bicarbonate solution, dried (sodium sulphate or magnesium sulphate) and filtered, and the solvent was removed under reduced pressure. The crude product was used for the next step without further purification.

General Method 9A: Nitro Reduction with Iron/Ammonium Chloride 10 eq. of ammonium chloride were dissolved in an ethanol/water mixture (2:1) (about 2M), the mixture was heated to 95° C. and the nitroaryl compound (1 eq.) was added. 3 eq. of iron powder were added in small portions over a period of 1 h. The reaction mixture was then stirred at 95° C. for 30 min, and the hot mixture was then filtered through kieselguhr. The filter cake was washed with ethanol and the filtrate was freed from ethanol under reduced pressure. The aqueous phase that remained was extracted three times with diethyl ether. The combined organic phases were washed with saturated aqueous sodium chloride solution, dried (sodium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 10A: Preparation of Tert-Butyl Esters

A solution of the corresponding carboxylic acid (1 eq.) in toluene (0.15-0.05M) was heated to 60-100° C., and N,N-dimethylformamide di-tert-butyl acetal (4 eq.) was added dropwise. The reaction mixture was stirred at 60-100° C. for 1-5 h and cooled to RT, and ethyl acetate was added. The organic phase was washed with saturated aqueous sodium bicarbonate solution and with saturated aqueous sodium chloride solution, dried (sodium sulphate), filtered and concentrated under reduced pressure. The crude product was used for the next step without purification.

Example 1.1A

4-Nitrobenzenecarboximidohydrazide

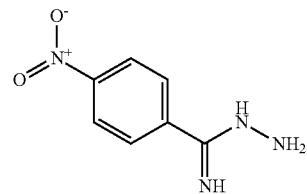 [SMILES: N=C(NN)c1ccc([N+](=O)[O-])cc1]

At 0° C., 5.2 ml (29.8 mmol, 3 eq.) of N,N-diisopropylethylamine and 0.62 g (purity 80%, 9.92 mmol, 1.0 eq.) of hydrazine monohydrate were added to a solution of 2.0 g (9.92 mmol) of 4-nitrobenzenecarboximidamide monohydrochloride in 20 ml of methanol, and the mixture was stirred at RT for 64 h. The reaction mixture was then added to 10% strength sodium chloride solution and, after addition of ethyl acetate and phase separation, was extracted twice with ethyl acetate. The combined organic phases were dried over sodium sulphate, filtered and concentrated under reduced pressure. Yield: 1.7 g (93% of theory)

LC/MS [Method 4]: $R_t$=1.77 min; MS (ESIpos): m/z=181 (M+H)$^+$

Example 1.1B 5-(4-Nitrophenyl)-3-(trifluoromethyl)-1H-1,2,4-triazole

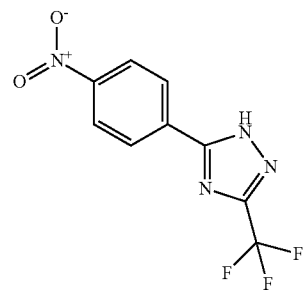 [SMILES: O=[N+]([O-])c1ccc(-c2nc(C(F)(F)F)n[nH]2)cc1]

At 0° C., 1.95 g (9.3 mmol, 1 eq.) of trifluoroacetic anhydride were added to a solution of 1.7 g (9.3 mmol) of 4-nitrobenzenecarboximidohydrazide in 50 ml of dichloromethane and the mixture was stirred at RT, with 50 ml of acetonitrile being added after 20 min to improve the solubility of the reaction mixture. The reaction mixture was stirred at 50° C. for 3 h and then concentrated under reduced pressure. The residue was coevaporated three times with dichloromethane and dried under reduced pressure. Yield: 2.7 g (quant.)

LC/MS [Method 1]: $R_t$=0.94 min; MS (ESIpos): m/z=259 $(M+H)^+$

Example 1.1C

4-[3-(Trifluoromethyl)-1H-1,2,4-triazol-5-yl]aniline

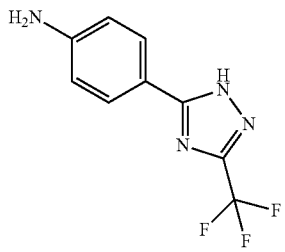 [SMILES: Nc1ccc(-c2nc(C(F)(F)F)n[nH]2)cc1]

8.9 g (39.7 mmol, 4 eq.) of tin(II) chloride dihydrate were added to a solution of 2.7 g (9.9 mmol) of 5-(4-nitrophenyl)-3-(trifluoromethyl)-1H-1,2,4-triazole in 110 ml of ethanol, and the mixture was stirred at 70° C. for 1 h. The reaction mixture was poured into ice-water, and sodium bicarbonate was added carefully until a pH of 8 had been reached. The mixture was filtered through a filter layer and the residue was washed with ethyl acetate. After phase separation, the aqueous phase was washed twice with ethyl acetate. The combined organic phases were washed with aqueous sodium chloride solution, dried (magnesium sulphate), filtered and concentrated under reduced pressure. Yield: 1.9 g (79% of theory)

LC/MS [Method 4]: $R_t$=1.66 min; MS (ESIpos): m/z=229 $(M+H)^+$

Example 1.2A 4-(1H-Imidazol-2-yl)aniline

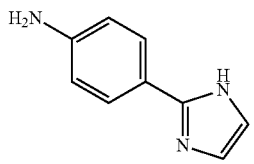 [SMILES: Nc1ccc(-c2ncc[nH]2)cc1]

A solution of 95 mg (0.5 mmol) of 2-(4-nitrophenyl)-1H-imidazole in 3 ml of ethanol was hydrogenated in the presence of 20 mg of palladium (10% on activated carbon) at RT and standard pressure. The reaction mixture was then filtered through Celite and the filtrate was concentrated under reduced pressure and dried. Yield: 91 mg (quant.)

LC/MS [Method 5]: $R_t$=1.06 min; MS (ESIpos): m/z=160 $(M+H)^+$

Example 1.3A 5-(4-Nitrophenyl)-2-(trifluoromethyl)-1H-imidazole

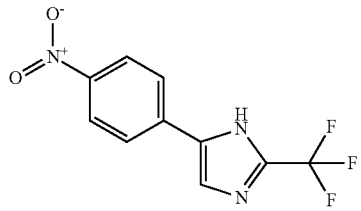 [SMILES: O=[N+]([O-])c1ccc(-c2cnc(C(F)(F)F)[nH]2)cc1]

324 mg (purity 85%, 2.5 mmol, 3 eq.) of 2,2,2-trifluoroethaneimidamide were added to a suspension of 200 mg (0.82 mmol) of 2-bromo-1-(4-nitrophenyl)ethanone and 500 mg of sodium sulphate in 10 ml of acetonitrile, and the mixture was treated in an ultrasonic bath for 1 h and then stirred at RT. The sodium sulphate was then filtered off and the filtrate was concentrated under reduced pressure. The residue was purified by preparative HPLC (Reprosil C18, water/methanol gradient). Yield: 104 mg (49% of theory)

LC/MS [Method 1]: $R_t$=0.96 min; MS (ESIpos): m/z=258 $(M+H)^+$

Example 1.3B

4-[2-(Trifluoromethyl)-1H-imidazol-5-yl]aniline

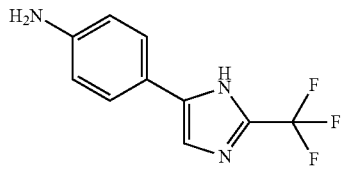 [SMILES: Nc1ccc(-c2cnc(C(F)(F)F)[nH]2)cc1]

A solution of 104 mg (0.4 mmol) of 5-(4-nitrophenyl)-2-(trifluoromethyl)-1H-imidazole in 10 ml of ethanol was hydrogenated in the presence of 15 mg of palladium (10% on activated carbon) at RT and standard pressure. The reaction mixture was then filtered through Celite and the filtrate was concentrated under reduced pressure and dried. Yield: 98 mg (quant.)

LC/MS [Method 1]: $R_t$=0.47 min; MS (ESIpos): m/z=228 $(M+H)^+$

Example 1.4A tert-Butyl 5-(4-nitrophenyl)-3-oxo-2,3-dihydro-1H-pyrazole-1-carboxylate

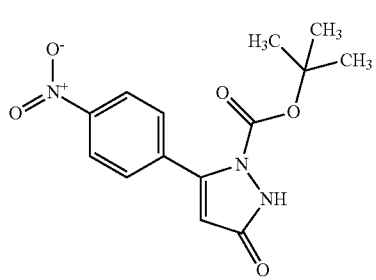 [SMILES: CC(C)(C)OC(=O)n1[nH]c(=O)cc1-c1ccc([N+](=O)[O-])cc1]

At RT, 2.7 g (12.2 mmol, 1.0 eq.) of di-tert-butyl dicarbonate and 1.7 ml (12.2 mmol, 1.0 eq.) of triethylamine were added to a solution of 2.5 g (12.2 mmol) of 5-(4-nitrophenyl)-1,2-dihydro-3H-pyrazol-3-one in 50 ml of dichloromethane, and the mixture was stirred at RT for 4 h. The reaction mixture was diluted with dichloromethane and water. After phase separation, the organic phase was dried (sodium sulphate), filtered and concentrated under reduced pressure. The crude product was purified by flash chromatography (silica gel 60, mobile phase: dichloromethane/methanol mixtures). Yield: 2.23 g (58% of theory).

LC/MS [Method 1]: $R_t$=1.07 min; MS (ESIpos): m/z=306 (M+H)$^+$

Example 1.4B tert-Butyl 5-(4-aminophenyl)-3-oxo-2,3-dihydro-1H-pyrazole-1-carboxylate

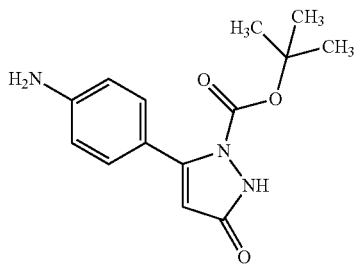 [SMILES: CC(C)(C)OC(=O)n1[nH]c(=O)cc1-c1ccc(N)cc1]

A solution of 2.2 g (7.1 mmol) of tert-butyl 5-(4-nitrophenyl)-3-oxo-2,3-dihydro-1H-pyrazole-1-carboxylate in 100 ml of ethanol was hydrogenated in the presence of 253 mg of palladium (10% on activated carbon) at RT and standard pressure. The reaction mixture was then filtered through Celite and the filtrate was concentrated under reduced pressure and dried. Yield: 1.99 g (purity 90%, 92% of theory)

LC/MS [Method 6]: $R_t$=2.06 min; MS (ESIpos): m/z=276 (M+H)$^+$

Example 1.5A 3-(4-Aminophenyl)-1,2,4-oxadiazol-5(4H)-one

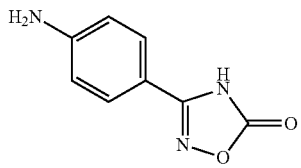 [SMILES: Nc1ccc(-c2noc(=O)[nH]2)cc1]

6.5 g (29 mmol, 4 eq.) of tin(II) chloride dihydrate were added to a solution of 1.5 g (7.2 mmol) of 3-(4-nitrophenyl)-1,2,4-oxadiazol-5(4H)-one in 75 ml of ethanol, and the mixture was stirred at 70° C. for 1 h. The reaction mixture was poured into ice-water, and sodium bicarbonate was added carefully until a pH of 8 had been reached. The mixture was filtered through a filter layer and the residue was washed with ethyl acetate. The combined filtrates were concentrated under reduced pressure. The residue was stirred with dichloromethane and methanol, treated in an ultrasonic bath for 10 min and then filtered. The filtrate was concentrated under reduced pressure and dried. Yield: 1.4 g (quant.)

LC/MS [Method 1]: $R_t$=0.44 min; MS (ESIpos): m/z=178 (M+H)$^+$ $^1$H-NMR (400 MHz, DMSO-d$_6$): δ [ppm]=7.42 (d, 2H), 6.51 (d, 2H), 5.23 (s, 2H), 4.13 (br. s, 1H).

Example 1.6A

1-Benzyl 2-tert-butyl 1-methylhydrazine-1,2-dicarboxylate

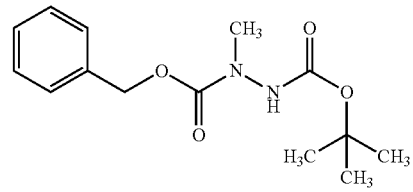 [SMILES: CN(NC(=O)OC(C)(C)C)C(=O)OCc1ccccc1]

At RT, 20.6 g (94.6 mmol, 1.2 eq.) of di-tert.-butyl dicarbonate in 42 ml of dichloromethane were added to a solution of 14.2 g (78.8 mmol) of benzyl 1-methylhydrazinecarboxylate in 100 ml of propan-2-ol, and the mixture was stirred at RT for 24 h. The reaction mixture was diluted with dichloromethane and water. After phase separation, the organic phase was dried (sodium sulphate), filtered and concentrated under reduced pressure. The crude product was purified by flash chromatography (silica gel 60, mobile phase: cyclohexane/ethyl acetate mixtures). Yield: 24.8 g (purity 80%, 90% of theory)

LC/MS [Method 1]: $R_t$=1.00 min; MS (ESIneg): m/z=279 (M−H)$^−$

Example 1.6B tert-Butyl 2-methylhydrazinecarboxylate

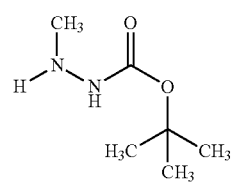

A solution of 24.8 g (70.8 mmol) of 1-benzyl 2-tert-butyl 1-methylhydrazine-1,2-dicarboxylate in 500 ml of ethanol was hydrogenated in the presence of 1.24 g of palladium (10% on activated carbon) at RT and standard pressure. The reaction mixture was then filtered through Celite and the filtrate was concentrated under reduced pressure and dried. Yield: 12.3 g (purity 48%, 57% of theory)

Example 1.6C tert-Butyl 2-(2-fluoro-4-nitrobenzoyl)-2-methylhydrazinecarboxylate

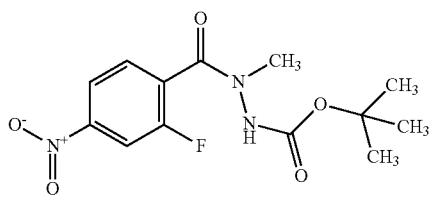 [SMILES: CN(NC(=O)OC(C)(C)C)C(=O)c1ccc([N+](=O)[O-])cc1F]

Under argon and at RT, 17.1 g (53.4 mmol, 1.3 eq.) of (benzotriazol-1-yloxy)bisdimethylaminomethylium fluoroborate and 21.4 ml (123.1 mol, 3.0 eq.) of N,N-diisopropylethylamine were added to a solution of 9.1 g (49.3 mmol, 1.2 eq.) of 2-fluoro-4-nitrobenzoic acid in 200 ml of DMF, and the mixture was stirred at RT for 20 min. A solution of 12.5 g (purity 48%, 41 mmol) of tert-butyl 2-methylhydrazinecarboxylate in 50 ml of DMF was added, and the reaction mixture was stirred at RT for 6 h. After removal of the DMF under reduced pressure and addition of water/ethyl acetate and phase separation, the organic phase was washed with 10% aqueous citric acid and with saturated aqueous sodium chloride solution, dried (sodium sulphate), filtered and concentrated under reduced pressure. The crude product was purified by flash chromatography (silica gel 60, mobile phase: cyclohexane/ethyl acetate mixtures). Yield: 8.35 g (65% of theory)

LC/MS [Method 1]: $R_t$=0.91 min; MS (ESIneg): m/z=312 (M−H)⁻

¹H-NMR (400 MHz, DMSO-d₆): δ [ppm]=9.78 (s, 1H), 8.20 (d, 1H), 8.11 (d, 1H), 7.59 (t, 1H), 3.13 (s, 3H), 1.24 (s, 9H).

Example 1.6D

2-Fluoro-N-methyl-4-nitrobenzohydrazide

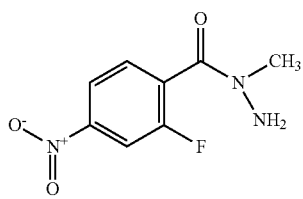

A solution of 3.6 g (11.5 mmol) of tert-butyl 2-(2-fluoro-4-nitrobenzoyl)-2-methylhydrazinecarboxylate in 57 ml of 4-molar hydrochloric acid/dioxane solution was stirred at RT for 3 h. The reaction mixture was concentrated under reduced pressure and the residue was taken up in ethyl acetate and washed with saturated aqueous sodium bicarbonate solution. The organic phase was dried (sodium sulphate), filtered and concentrated under reduced pressure. Yield: 2.0 g (81% of theory)

LC/MS [Method 1]: $R_t$=0.50 min; MS (ESIpos): m/z=214 (M+H)⁺

¹H-NMR (400 MHz, DMSO-d₆): δ [ppm]=8.09 (m, 2H), 7.61 (dd, 1H), 3.2 (s, 3H).

Example 1.6E

2-Methyl-6-nitro-1,2-dihydro-3H-indazol-3-one

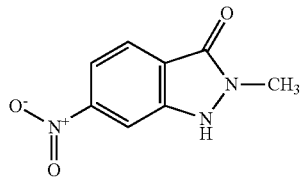

At RT, 6.6 ml (37.9 mmol, 3.5 eq.) of N,N-diisopropylethylamine were added to a solution of 2.4 g (10.9 mmol) of 2-fluoro-N-methyl-4-nitrobenzohydrazide in 25 ml of DMF, and the mixture was stirred at 80° C. overnight. The reaction mixture was concentrated under reduced pressure and the residue was taken up in ethyl acetate. The precipitated solid was filtered off and dried under reduced pressure. Yield: 595 mg (28% of theory)

LC/MS [Method 1]: $R_t$=0.49 min; MS (ESIpos): m/z=194 (M+H)⁺

¹H-NMR (400 MHz, DMSO-d₆): δ [ppm]=8.14 (s, 1H), 7.85 (d, 1H), 7.78 (dd, 1H), 3.48 (s. 3H).

Alternative Synthesis:

1.66 g (9.27 mmol) of 6-nitro-1,2-dihydro-3H-indazol-3-one were initially charged in 20 ml of DMF, and 1.75 ml (18.5 mmol, 2.0 eq.) of dimethyl sulphate were added. The reaction mixture was heated at 60° C. for 8 h and then diluted with dichloromethane and shaken with saturated aqueous sodium carbonate solution. The aqueous phase was washed three times each with dichloromethane and with ethyl acetate and the organic fractions were discarded. Using 4N aqueous hydrochloric acid, the aqueous phase was then carefully adjusted to pH 4.5 and extracted three times with ethyl acetate. These combined organic phases were dried over magnesium sulphate and concentrated under reduced pressure. The crude product was purified by flash chromatography (silica gel 50, mobile phase: gradient cyclohexane/ethyl acetate 1:1 to ethyl acetate/methanol 15:1), giving the title compound. Yield: 770 mg (43% of theory)

LC/MS [Method 1]: $R_t$=0.50 min; MS (ESIpos): m/z=194 (M+H)⁺,

¹H-NMR (400 MHz, DMSO-d₆): δ [ppm]=11.2 (br. s., 1H), 8.15 (d, 1H), 7.88 (d, 1H), 7.82 (dd, 1H), 3.48 (s, 3H).

Example 1.6F tert-Butyl 2-methyl-6-nitro-3-oxo-2,3-dihydro-1H-indazole-1-carboxylate

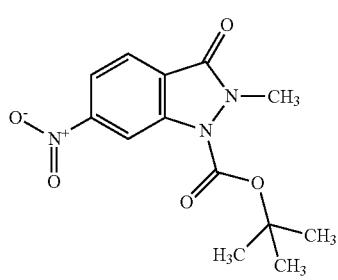 [SMILES: Cn1c(=O)c2ccc([N+](=O)[O-])cc2n1C(=O)OC(C)(C)C]

At RT, a solution of 0.8 g (3.7 mmol, 1.2 eq.) of di-tert.-butyl dicarbonate in 6 ml of dichloromethane was added to a solution of 595 mg (3.0 mmol) of 2-methyl-6-nitro-1,2-dihydro-3H-indazol-3-one in 25 ml of propan-2-ol, and the mixture was stirred at RT for 12 h. To improve the solubility of the reaction mixture, 6 ml of DMF were added. A further 4 eq. of di-tert-butyl dicarbonate were added, and the reaction mixture was stirred at RT for 24 h and then diluted with dichloromethane and water. After phase separation, the organic phase was dried (sodium sulphate), filtered and concentrated under reduced pressure. The crude product was purified by flash chromatography (silica gel 60, mobile phase: cyclohexane/ethyl acetate mixtures). Yield: 720 mg (80% of theory)

LC/MS [Method 1]: $R_t$=1.04 min; MS (ESIpos): m/z=194 (M+H-Boc)$^+$ $^1$H-NMR (400 MHz, DMSO-d$_6$): δ [ppm]=8.62 (d, 1H), 8.17 (dd, 1H), 8.05 (d, 1H), 3.58 (s. 3H), 1.63 (s, 9H).

Example 1.6G tert-Butyl 6-amino-2-methyl-3-oxo-2,3-dihydro-1H-indazole-1-carboxylate

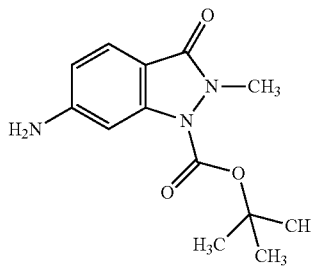

A solution of 715 mg (2.4 mmol) of tert-butyl 2-methyl-6-nitro-3-oxo-2,3-dihydro-1H-indazole-1-carboxylate in 30 ml of ethanol was hydrogenated in the presence of 52 mg of palladium (10% on activated carbon) at RT and standard pressure. The reaction mixture was then filtered through Celite and the filtrate was concentrated under reduced pressure and dried. Yield: 668 mg (100% of theory)

LC/MS [Method 1]: $R_t$=0.79 min; MS (ESIpos): m/z=264 (M+H)$^+$ $^1$H-NMR (400 MHz, DMSO-d$_6$): δ [ppm]=7.36 (d, 1H), 6.94 (d, 1H), 6.53 (dd, 1H), 6.21 (s, 2H), 1.58 (s, 9H).

Example 1.6H

6-Nitro-1,2-dihydro-3H-indazol-3-one

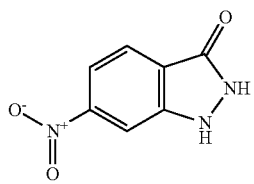 [SMILES: O=c1[nH][nH]c2cc([N+](=O)[O-])ccc12]

In two portions of equal size, a total of 2.00 g (10.0 mmol) of methyl 2-fluoro-4-nitrobenzoate and 2.51 g (50.2 mmol) of hydrazine monohydrate in 36 ml of ethanol were heated in a microwave reactor at 120° C. for 2 h. The combined reaction solutions were diluted with ethyl acetate and washed with water. The aqueous phase was extracted three times with ethyl acetate. The combined organic phases were dried over magnesium sulphate and concentrated under reduced pressure. Yield: 1.66 g (purity 95%, 88% of theory)

LC/MS [Method 11]: $R_t$=0.73 min; MS (ESIpos): m/z=180 (M+H)$^+$, $^1$H-NMR (400 MHz, DMSO-d$_6$): δ [ppm]=12.4 (s, 1H), 11.0 (br. s, 1H), 8.21 (d, 1H), 7.86 (d, 1H), 7.78 (dd, 1H).

Example 1.7A 1,3-Thiazolidine-2,4-dione potassium salt

At 50° C., a solution of 1.05 g (18.8 mmol, 1.1 eq.) of potassium hydroxide in 3 ml of ethanol was added to a solution of 2.0 g (17.1 mmol) of 1,3-thiazolidine-2,4-dione in 7 ml of ethanol, and the mixture was stirred at RT for 2 h. The precipitate formed was filtered off, washed with ethanol and dried under reduced pressure. Yield: 2.3 g (87% of theory)

Example 1.7B

3-[2-(4-Nitrophenyl)-2-oxoethyl]-1,3-thiazolidine-2,4-dione

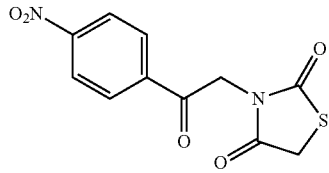 [SMILES: O=C(CN1C(=O)CSC1=O)c1ccc([N+](=O)[O-])cc1]

A little at a time, 1.3 g (8.4 mmol) of 1,3-thiazolidine-2,4-dione potassium salt were added to a solution of 2.0 g (8.2 mmol) of 2-bromo-1-(4-nitrophenyl)ethanone in 80 ml of acetone, and the mixture was stirred at 60° C. for 1 h. The reaction mixture was concentrated under reduced pressure and the residue was dissolved in water/dichloromethane. After phase separation, the organic phase was dried (sodium sulphate), filtered, concentrated under reduced pressure and dried. Yield: 2.3 g (98% of theory)

LC/MS [Method 3]: $R_t$=1.81 min; MS (ESIpos): m/z=281 (M+H)$^+$.

Example 1.7C 5-(4-Nitrophenyl)-1,3-oxazol-2(3H)-one

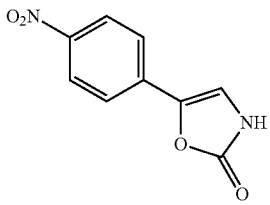

2.8 ml (20.1 mmol, 2.5 eq.) of triethylamine were added to a solution of 2.3 g (8.0 mmol) of 3-[2-(4-nitrophenyl)-2-oxoethyl]-1,3-thiazolidine-2,4-dione in 80 ml of ethanol, and the mixture was stirred under reflux for 14 h. The reaction mixture was concentrated under reduced pressure and the residue was dissolved in water/ethyl acetate. After phase separation, the organic phase was dried (sodium sulphate), filtered, concentrated under reduced pressure and dried. The residue was stirred in dichloromethane and the precipitate was filtered off and dried under reduced pressure. Yield: 1.1 g (67% of theory)

LC/MS [Method 1]: $R_t$=0.71 min; MS (ESIneg): m/z=205 (M–H)$^-$.

Example 1.7D 5-(4-Aminophenyl)-1,3-oxazol-2(3H)-one

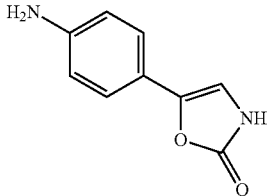 [SMILES: O=c1[nH]cc(-c2ccc([N+](=O)[O-])cc2)o1]

A solution of 1.1 g (5.4 mmol) of 5-(4-nitrophenyl)-1,3-oxazol-2(3H)-one in 40 ml of ethanol was hydrogenated in the presence of 111 mg of palladium (10% on activated carbon) at RT and standard pressure for 5 d. The reaction mixture was then filtered through Celite and the residue was washed with ethanol. The combined filtrates were concentrated under reduced pressure. The residue was used for the next step without further purification. Yield: 626 mg (purity 88%, 58% of theory)

LC/MS [Method 5]: $R_t$=1.23 min; MS (ESIpos): m/z=177 (M+H)$^+$.

Example 1.8A

6-Nitro-2-(trichloromethyl)-1H-benzimidazole

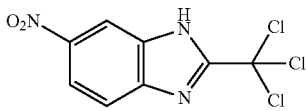 [SMILES: O=[N+]([O-])c1ccc2nc(C(Cl)(Cl)Cl)[nH]c2c1]

At 0° C., 6.3 g (35.9 mmol, 1.1 eq.) of methyl 2,2,2-trichloroethaneimidoate were added dropwise to a solution of 5.0 g (32.7 mmol) of 4-nitrobenzene-1,2-diamine in 150 ml of glacial acetic acid. The reaction mixture was stirred at RT for 3 h and then added to 400 ml of water, and 300 ml of ethyl acetate were added. After phase separation, the aqueous phase was extracted twice with ethyl acetate. The combined organic phases were washed twice with in each case 130 ml of saturated aqueous sodium bicarbonate solution and once with saturated aqueous sodium chloride solution, dried (sodium sulphate), filtered and concentrated under reduced pressure and dried. The crude product was triturated with pentane and left to stand overnight. The solid was then filtered off, washed with pentane and dried under reduced pressure. Yield: 10.1 g (purity 77%, 85% of theory)

LC/MS [Method 1]: $R_t$=0.91 min; MS (ESIpos): m/z=280 (M+H)$^+$.

Example 1.8B

Ethyl 6-nitro-1H-benzimidazole-2-carboxylate

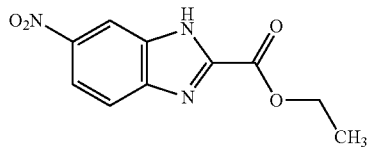 [SMILES: CCOC(=O)c1nc2ccc([N+](=O)[O-])cc2[nH]1]

15.4 g (90.7 mmol, 3.3 eq.) of silver(I) nitrate were added to a solution of 10.0 g (purity 77%, 27.5 mmol) of 6-nitro-2-(trichloromethyl)-1H-benzimidazole in 100 ml of ethanol, and the mixture was stirred under reflux for 15 h, cooled to RT and concentrated under reduced pressure. The residue was taken up in a mixture of 250 ml of hydrochloric acid (1N) and 220 ml of ethyl acetate, stirred for 1 h and filtered through silica gel. After phase separation, the organic phase was dried (sodium sulphate), filtered, concentrated under reduced pressure and dried. The residue was triturated with 30 ml of diisopropyl ether, filtered off, washed with diisopropyl ether and petroleum ether and dried under reduced pressure. Yield: 1.9 g (29% of theory)

LC/MS [Method 1]: $R_t$=0.70 min; MS (ESIpos): m/z=236 (M+H)$^+$.

Example 1.8C

Ethyl 6-amino-1H-benzimidazole-2-carboxylate

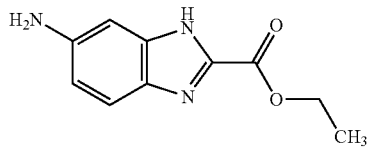

A solution of 1.9 g (8.1 mmol) of ethyl 6-nitro-1H-benzimidazole-2-carboxylate in 30 ml of ethanol was hydrogenated in the presence of 190 mg of palladium (10% on activated carbon) at RT and standard pressure for 3 h. The reaction mixture was then filtered through kieselguhr and the residue was washed with ethanol. The combined filtrates were concentrated under reduced pressure. The residue was dried under reduced pressure and then purified by flash chromatography (silica gel 50, mobile phase: dichloromethane/methanol 3-5%). Yield: 640 mg (39% of theory)

LC/MS [Method 5]: $R_t$=1.34 min; MS (ESIpos): m/z=206 (M+H)$^+$ $^1$H-NMR (400 MHz, DMSO-d$_6$): δ [ppm]=12.71 (s, 1H), 7.38 (d, 1H), 6.63 (dd, 1H), 6.58 (s, 1H), 5.29 (s, 2H), 4.34 (q, 2H), 1.34 (t, 3H).

Example 1.9A

5-Amino-3-chloro-1H-indazole

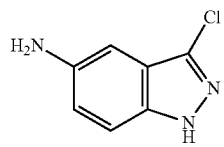 [SMILES: Nc1ccc2[nH]nc(Cl)c2c1]

1.00 g (5.06 mmol) of 3-chloro-5-nitro-1H-indazole was suspended in 50 ml of ethanol, and 5.71 g (25.3 mmol) of tin(II) chloride dihydrate were added. The mixture was left to stir at reflux overnight, saturated aqueous sodium bicarbonate solution was then added and the mixture was extracted three times with ethyl acetate. The combined organic phases were dried over magnesium sulphate and the solvent was removed under reduced pressure. The mixture was triturated with tert-butyl methyl ether and the solid was filtered off with suction. Yield: 544 mg (purity 90%, 58% of theory)

LC/MS [Method 5]: $R_t$=1.50 min; MS (ESIpos): m/z=168 (M+H)$^+$, $^1$H-NMR (400 MHz, DMSO-d$_6$): δ [ppm]=12.8 (s, 1H), 7.28 (d, 1H), 6.89 (dd, 1H), 6.66 (m, 1H), 5.46 (br. s, 2H).

Example 1.10A tert-Butyl 2-fluoro-4-nitrobenzoate

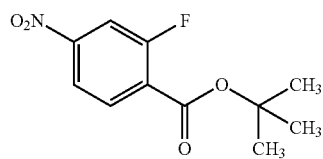 [SMILES: CC(C)(C)OC(=O)c1ccc([N+](=O)[O-])cc1F]

At 0° C., 0.258 ml (2.7 mmol, 1.0 eq.) of tert-butanol was added to a solution of 500 mg (2.7 mmol) of 2-fluoro-4-nitrobenzoic acid and 1.03 g (5.4 mmol, 2.0 eq.) of para-toluenesulphonyl chloride in 5.4 ml of pyridine, the mixture was stirred for 60 min and a further 0.258 ml (2.7 mmol, 1.0 eq.) of tert-butanol was added. The reaction mixture was stirred for another 18 h and concentrated under reduced pressure. Saturated aqueous sodium bicarbonate solution and ethyl acetate were added to the residue. After phase separation, the aqueous phase was extracted with ethyl acetate. The combined organic phases were washed with saturated aqueous sodium chloride solution, dried (sodium sulphate), filtered and concentrated under reduced pressure. The crude product was then purified by normal phase chromatography (mobile phase: cyclohexane/ethyl acetate 14%-20% mixtures). Yield: 524 mg (75% of theory).

LC/MS [Method 1]: $R_t$=1.16 min; MS (ESIneg): m/z=226 (M-CH$_3$)$^-$, $^1$H-NMR (400 MHz, DMSO-d$_6$): δ [ppm]=8.21 (dd, 1H), 8.16-8.12 (m, 1H), 8.06 (dd, 1H), 1.56 (s, 9H).

Example 1.10B tert-Butyl 4-amino-2-fluorobenzoate

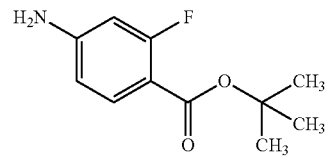

A solution of 1.109 g (20.73 mmol, 10 eq.) of ammonium chloride in 6.25 ml of ethanol and 3.125 ml of water was heated to 95° C., and 500 mg (2.07 mmol) of tert-butyl 2-fluoro-4-nitrobenzoate were added. 347 mg (6.22 mmol, 3 eq.) of iron powder were added in small portions over 1 h. The reaction mixture was then stirred at 95° C. for 30 min, and the hot mixture was then filtered through kieselguhr. The filter cake was washed with ethanol and the filtrate was freed from ethanol under reduced pressure. The aqueous phase was extracted three times with in each case 20 ml of diethyl ether. The combined organic phases were washed with saturated aqueous sodium chloride solution, dried (sodium sulphate), filtered and concentrated under reduced pressure. The crude product was purified by normal phase chromatography (mobile phase: cyclohexane/ethyl acetate 30%-50% mixtures). Yield: 280 mg (51% of theory).

LC/MS [Method 8]: $R_t$=1.18 min; MS (ESIneg): m/z=210 (M−H)$^-$, $^1$H-NMR (400 MHz, DMSO-d$_6$): δ [ppm]=7.49 (t, 1H), 6.36 (dd, 1H), 6.25 (dd, 1H), 6.15 (s, 2H), 1.48 (s, 9H).

Example 1.11A tert-Butyl 4-amino-3-fluorobenzoate

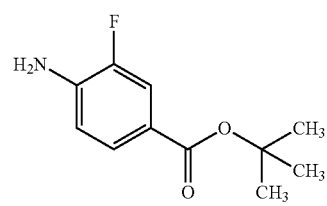

400 mg (1.66 mmol) of tert-butyl 3-fluoro-4-nitrobenzoate were reacted according to General Method 9A. The crude product was purified by normal phase chromatography (mobile phase: cyclohexane/ethyl acetate 15%-20% mixtures). Yield: 295 mg (82% of theory)

LC/MS [Method 1]: $R_t$=1.00 min; MS (ESIpos): m/z=212 (M+H)$^+$, $^1$H-NMR (400 MHz, DMSO-d$_6$): δ [ppm]=7.48-7.38 (m, 2H), 6.75 (t, 1H), 5.95 (br. s, 2H), 1.50 (s, 9H).

Example 1.12A tert-Butyl 2,5-difluoro-4-nitrobenzoate

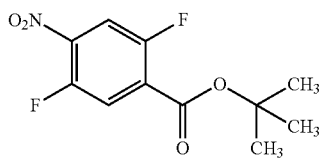

700 mg (3.45 mmol) of 2,5-difluoro-4-nitrobenzoate were reacted according to General Method 10A. The crude product was used for the next step without further purification. Yield: 1000 mg (purity 73%, 82% of theory)

HPLC [Method 3]: $R_t$=2.45 min, $^1$H-NMR (400 MHz, DMSO-$d_6$): δ [ppm]=8.24 (dd, 1H), 7.99 (dd, 1H), 1.56 (s, 9H).

Example 1.12B tert-Butyl 4-amino-2,5-difluorobenzoate

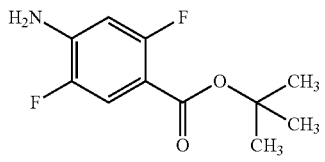 [SMILES: CC(C)(C)OC(=O)c1cc(F)c([N+](=O)[O-])cc1F]

A solution of 1000 mg (2.82 mmol) of tert-butyl 2,5-difluoro-4-nitrobenzoate in 8 ml of tetrahydrofuran and 8 ml of ethyl acetate was hydrogenated in the presence of 65.6 mg of palladium (10% on activated carbon) at RT and standard pressure. The reaction mixture was then filtered through Celite and the filtrate was concentrated under reduced pressure and dried. The crude product was purified by normal phase chromatography (mobile phase: cyclohexane/ethyl acetate 15%-20% mixtures). Yield: 155 mg (purity 85%, 20% of theory)

LC/MS [Method 8]: $R_t$=1.27 min; MS (ESIpos): m/z=230 (M+H)$^+$, $^1$H-NMR (400 MHz, DMSO-$d_6$): δ [ppm]=7.35 (dd, 1H), 6.47 (dd, 1H), 6.27 (s, 2H), 1.49 (s, 9H).

Example 1.13A

Methyl 4-[(tert-butoxycarbonyl)amino]-2,6-difluorobenzoate

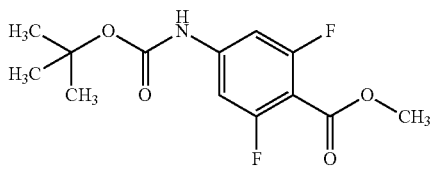 [SMILES: COC(=O)c1c(F)cc(NC(=O)OC(C)(C)C)cc1F]

Under argon, a microwave vessel was charged with 54 mg (0.22 mmol) of methyl 4-bromo-2,6-difluorobenzoate, 118 mg (1.01 mmol, 4.7 eq.) of tert-butyl carbamate, 4.6 mg (0.02 mmol, 0.1 eq.) of palladium(II) acetate, 15 mg (0.026 mmol, 0.13 eq.) of Xantphos, 137 mg (0.42 mmol, 2 eq.) of caesium carbonate and 2 ml of 1,4-dioxane. A stream of argon was passed through the suspension for 2 min. The reaction mixture was heated in the microwave at 140° C. for 20 min. After filtration through kieselguhr, the filtrate was concentrated under reduced pressure. The crude product was purified by normal phase chromatography (mobile phase: dichloromethane/methanol 10-50% mixtures). Yield: 37 mg (60% of theory)

LC/MS [Method 8]: $R_t$=1.35 min; MS (ESIneg): m/z=286 (M−H)$^−$, $^1$H-NMR (400 MHz, DMSO-$d_6$): δ [ppm]=10.10 (s, 1H), 7.28-7.22 (m, 2H), 3.83 (s, 3H), 1.49 (s, 9H).

Example 1.13B

Methyl 4-amino-2,6-difluorobenzoate

At RT, 0.5 ml of TFA was added to a solution of 36 mg (0.125 mmol) of methyl 4-[(tert-butoxycarbonyl)amino]-2,6-difluorobenzoate in 1 ml of dichloromethane, and the mixture was stirred at RT for 30 min. The reaction mixture was then concentrated under reduced pressure and the residue was co-evaporated repeatedly with dichloromethane and toluene and dried under reduced pressure. The crude product was used for the next step without purification. Yield: 24 mg (quant.)

LC/MS [Method 3]: $R_t$=1.56 min; MS (ESIpos): m/z=188 (M+H)$^+$, $^1$H-NMR (400 MHz, DMSO-$d_6$): δ [ppm]=6.44 (s, 2H), 6.24-6.15 (m, 2H), 3.73 (s, 3H).

Example 1.14A tert-Butyl [4-(N'-hydroxycarbamimidoyl)phenyl]carbamate

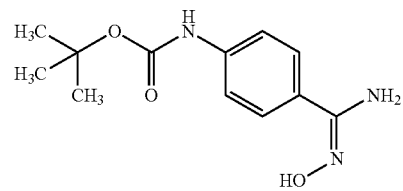 [SMILES: CC(C)(C)OC(=O)Nc1ccc(/C(N)=N\O)cc1]

At RT, 1.40 g (20.16 mmol, 2.2 eq.) of hydroxylammonium chloride and 2.81 ml (20.16 mmol, 2.2 eq.) of triethylamine were added to a solution of 2.0 g (9.16 mmol) of tert-butyl-(4-cyanophenyl)carbamate in 45 ml of ethanol. The reaction mixture was heated under reflux for 4 h and concentrated under reduced pressure. The residue was stirred with 100 ml of water at RT for 1 h. The reaction mixture was filtered and the filter cake was washed with water. The residue was dissolved in ethyl acetate. The aqueous phase that remained was separated off and the organic phase was dried (sodium sulphate), filtered and concentrated under reduced pressure. The crude product was used for the next step without purification. Yield: 2.10 g (purity 95%, 87% of theory)

LC/MS [Method 8]: Rt=0.68 min; MS (ESIpos): m/z=252 (M+H)+, $^{1}$H-NMR (400 MHz, DMSO-d$_{6}$): δ [ppm]=9.45 (s, 1H), 9.42 (br. s, 1H), 7.57-7.52 (m, 2H), 7.46-7.40 (m, 2H), 5.69 (s, 2H), 1.48 (s, 9H).

Example 1.14B tert-Butyl [4-(5-oxo-4,5-dihydro-1,2,4-thiadiazol-3-yl)phenyl]carbamate

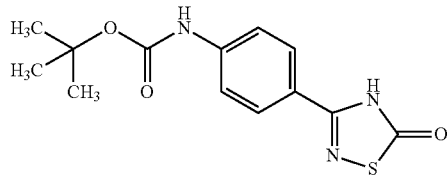

At RT, 560 mg (2.98 mmol, 1.5 eq.) of 1,1'-thiocarbonylimidazole were added to a solution of 500 mg (1.99 mmol) of tert-butyl [4-(N'-hydroxycarbamimidoyl)phenyl]carbamate in 16 ml of tetrahydrofuran, and the mixture was stirred at RT for 30 min. Water was then added to the reaction mixture. After phase separation, the aqueous phase was extracted with ethyl acetate. The combined organic phases were washed with saturated aqueous sodium chloride solution, dried (sodium sulphate), filtered and concentrated under reduced pressure. The residue was dissolved in 8 ml of tetrahydrofuran, and 0.76 ml (5.97 mmol, 3.0 eq.) of boron trifluoride/diethyl ether complex was added. The reaction mixture was stirred at RT for 1 h. After addition of water/ethyl acetate and phase separation, the aqueous phase was extracted three times with ethyl acetate. The combined organic phases were washed with saturated aqueous sodium chloride solution, dried (sodium sulphate), filtered and concentrated under reduced pressure. The crude product was used for the next step without purification. Yield: 130 mg (purity 70%, 15% of theory)

LC/MS [Method 8]: Rt=1.18 min; MS (ESIpos): m/z=294 (M+H)+, $^{1}$H-NMR (400 MHz, DMSO-d$_{6}$): δ [ppm]=13.24 (br. s, 1H), 9.70 (s, 1H), 7.87-7.80 (m, 2H), 7.61-7.54 (m, 2H), 1.49 (s, 9H).

Example 1.14C 3-(4-Aminophenyl)-1,2,4-thiadiazol-5(4H)-one

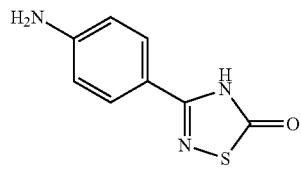

At 0° C., 0.8 ml of TFA was added to a solution of 129 mg (purity 70%, 0.44 mmol) of tert-butyl [4-(5-oxo-4,5-dihydro-1,2,4-thiadiazol-3-yl)phenyl]carbamate in 4 ml of dichloromethane, and the mixture was stirred at RT for 40 min Subsequently, the reaction mixture was concentrated under reduced pressure and the crude product was purified by preparative HPLC (water/acetonitrile/0.1% formic acid gradient). Yield: 54 mg (purity 90%, 57% of theory)

LC/MS [Method 8]: Rt=0.68 min; MS (ESIpos): m/z=194 (M+H)+, $^{1}$H-NMR (400 MHz, DMSO-d$_{6}$): δ [ppm]=12.93 (br. s, 1H), 7.65-7.60 (m, 2H), 6.64-6.58 (m, 2H), 5.58 (br. s, 2H).

Example 1.15A tert-Butyl [4-(5-thioxo-4,5-dihydro-1,2,4-oxadiazol-3-yl)phenyl]carbamate

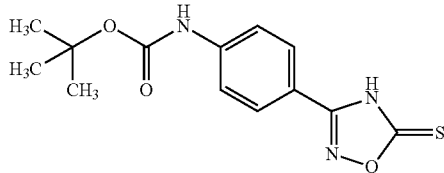 [SMILES: CC(C)(C)OC(=O)Nc1ccc(-c2nsc(=O)[nH]2)cc1]

At RT, 821 mg (4.37 mmol, 2.2 eq.) of 1,1'-thiocarbonylimidazole and 1.19 ml (7.96 mmol, 4.0 eq.) of 1,8-diazabicyclo[5.4.0]undec-7-ene were added to a solution of 500 mg (1.99 mmol) of tert-butyl [4-(N'-hydroxycarbamimidoyl)phenyl]carbamate in 20 ml of acetonitrile, and the mixture was stirred at RT for 24 h. The reaction mixture was then concentrated under reduced pressure and the residue was dissolved in ethyl acetate. The organic phase was washed with water and a potassium citrate/citric acid solution (pH 5). The organic phase was then washed with a saturated aqueous sodium chloride solution, dried (sodium sulphate), filtered and concentrated under reduced pressure. The crude product was purified by normal phase chromatography (mobile phase: dichloromethane/methanol 0-10% mixtures). Yield: 120 mg (20% of theory)

LC/MS [Method 8]: Rt=1.17 min; MS (ESIneg): m/z=292 (M−H)−, $^{1}$H-NMR (400 MHz, DMSO-d$_{6}$): δ [ppm]=9.80 (s, 1H), 7.81-7.76 (m, 2H), 7.67-7.62 (m, 2H), 1.49 (s, 9H).

Example 1.15B 3-(4-Aminophenyl)-1,2,4-oxadiazole-5(4H)-thione

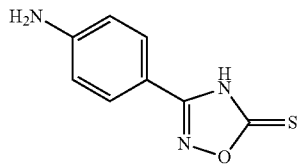

At 0° C., 0.8 ml of TFA was added to a solution of 119 mg (0.40 mmol) of tert-butyl [4-(5-thioxo-4,5-dihydro-1,2,4-oxadiazol-3-yl)phenyl]carbamate in 4 ml of dichlormethane, and the mixture was stirred at RT for 40 min. Subsequently, the reaction mixture was concentrated under reduced pressure. Ethyl acetate and a saturated aqueous sodium bicarbonate solution were added to the residue. After phase separation, the aqueous phase was extracted with ethyl acetate. The aqueous phase was concentrated and the crude product was purified by preparative HPLC (water/acetonitrile/0.1% formic acid gradient). Yield: 30 mg (38% of theory)

LC/MS [Method 8]: Rt=0.71 min; MS (ESIpos): m/z=194 (M+H)$^+$.

Example 1.16A 4-(1,3-Oxazol-2-yl)aniline

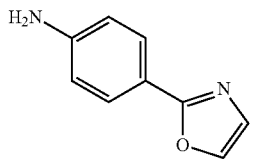 [SMILES: Nc1ccc(-c2ncco2)cc1]

250 mg (1.31 mmol) of 2-(4-nitrophenyl)-1,3-oxazole were reacted according to General Method 9A. The crude product was used for the next step without purification. Yield: 220 mg (99% of theory)

LC/MS [Method 1]: Rt=0.55 min; MS (ESIpos): m/z=161 (M+H)$^+$, $^1$H-NMR (400 MHz, DMSO-d$_6$): δ [ppm]=8.00 (d, 1H), 7.66-7.60 (m, 2H), 7.20 (d, 1H), 6.66-6.59 (m, 2H), 5.67 (br. s, 2H).

Example 1.17A

Methyl 3-[5-(4-aminophenyl)-4H-1,2,4-triazol-3-yl]-2,2,3,3-tetrafluoropropanoate

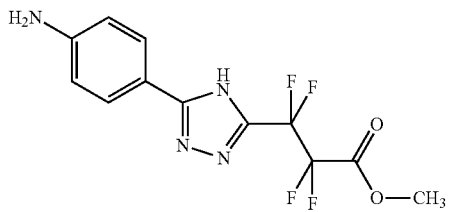 [SMILES: COC(=O)C(F)(F)C(F)(F)c1nnc(-c2ccc(N)cc2)[nH]1]

A mixture of 9.7 g (48.5 mmol) of 4-nitrobenzenecarboximidohydrazide in 150 ml of dichloromethane was stirred with 15.0 g (87.2 mmol) of 3,3,4,4-tetrafluorodihydrofuran-2,5-dione at RT for 2 min, 150 ml of acetonitrile were added to the suspension and the resulting solution was stirred at RT for 16 h. The reaction mixture was adsorbed on silica gel and separated by flash chromatography (dichloromethane/methanol mixtures). The product-containing fractions were combined and concentrated under reduced pressure. The residue was stirred with a little methanol, filtered and dried under reduced pressure.

The residue was dissolved in methanol, 1 ml of sulphuric acid was added and the mixture was stirred at 70° C. for 4 h. Methanol was removed from the reaction mixture under reduced pressure. The residue was taken up in ethyl acetate and extracted with saturated sodium bicarbonate solution. The organic phase was washed with a saturated sodium chloride solution, dried (sodium sulphate), filtered and concentrated under reduced pressure.

The residue was dissolved in 150 ml of ethanol, 43.2 g (191.8 mmol) of tin(II) chloride dihydrate were added and the mixture was stirred at 70° C. for 1 h. The reaction mixture was poured into ice-water, adjusted to pH 8 with solid sodium bicarbonate and filtered through kieselguhr to remove the precipitated salts. The filtrate was extracted with ethyl acetate. The combined organic phases were washed with saturated sodium chloride solution, dried (sodium sulphate), filtered and concentrated under reduced pressure. The residue was taken up in 600 ml of methanol, 200 mg of sodium methoxide were added, and the mixture was stirred at RT for 2 d. The reaction mixture was concentrated under reduced pressure and dried. Yield: 9.2 g (purity 91%, 99% of theory)

LC-MS (Method 1): R$_t$=0.77 min; MS (ESIpos): m/z=319 [M+H]$^+$.

Example 2.1A tert-Butyl 2-(4-bromo-2-oxopyridin-1(2H)-yl)propanoate (racemate)

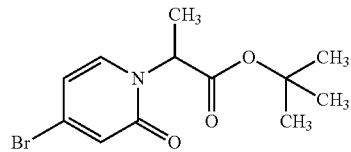 [SMILES: CC(C(=O)OC(C)(C)C)n1ccc(Br)cc1=O]

6.0 g (34.5 mmol) of 4-bromopyridin-2(1H)-one and 7.9 g (37.9 mmol) of tert-butyl 2-bromopropanoate (racemate) were reacted according to General Method 4B. After removal of the DMF, the desired product was precipitated with water and then purified further by flash chromatography (silica gel 60, mobile phase: cyclohexane/ethyl acetate mixtures). Yield: 7.4 g (69% of theory)

LC/MS [Method 1]: R$_t$=0.94 min; MS (ESIpos): m/z=302 (M+H)$^+$ $^1$H-NMR (400 MHz, DMSO-d$_6$): δ [ppm]=7.66 (d, 1H), 6.75 (d, 1H), 6.51 (dd, 1H), 5.04 (q, 1H), 1.51 (d, 3H), 1.37 (s, 9H).

Example 2.2A tert-Butyl 2-[4-(5-chloro-2-cyanophenyl)-2-oxopyridin-1(2H)-yl]propanoate (racemate)

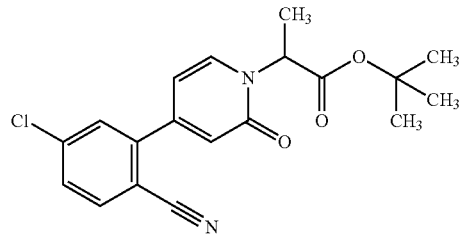 [SMILES: CC(C(=O)OC(C)(C)C)n1ccc(-c2cc(Cl)ccc2C#N)cc1=O]

2.4 g (purity 74%, 5.9 mmol) of tert-butyl 2-(4-bromo-2-oxopyridin-1(2H)-yl)propanoate (racemate) and 1.2 g (6.8 mmol) of 5-chloro-2-cyanophenylboronic acid in the presence of tetrakis(triphenylphosphine)palladium(0) were reacted according to General Method 2A. Yield: 1.86 g (purity 87%, 77% of theory)

LC/MS [Method 1]: R$_t$=1.07 min; MS (ESIpos): m/z=359 (M+H)$^+$ $^1$H-NMR (400 MHz, DMSO-d$_6$): δ [ppm]=8.03 (d, 1H), 7.84 (d, 1H), 7.81 (d, 1H), 7.75 (dd, 1H), 6.64 (d, 1H), 6.50 (dd, 1H), 5.14 (q, 1H), 1.58 (d, 3H), 1.40 (s, 9H).

Example 2.2B

2-[4-(5-Chloro-2-cyanophenyl)-2-oxopyridin-1(2H)-yl]propanoic acid (racemate)

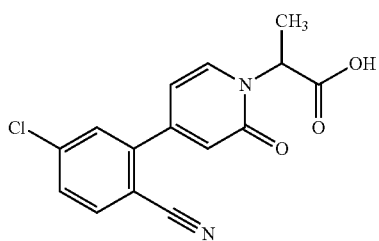 [SMILES: CC(C(=O)O)n1ccc(-c2cc(Cl)ccc2C#N)cc1=O]

2.2 g (purity 82%, 5.0 mmol) of tert-butyl 2-[4-(5-chloro-2-cyanophenyl)-2-oxopyridin-1(2H)-yl]propanoate (racemate) were hydrolysed with TFA according to General Method 6A. Yield: 1.5 g (94% of theory)

LC/MS [Method 1]: R$_t$=0.80 min; MS (ESIpos): m/z=303 (M+H)$^+$ $^1$H-NMR (400 MHz, DMSO-d$_6$): δ [ppm]=13.04 (br. s, 1H), 8.04 (d, 1H), 7.88 (d, 1H), 7.82 (d, 1H), 7.76 (dd, 1H), 6.65 (d, 1H), 6.51 (dd, 1H), 5.23 (q, 1H), 1.60 (d, 3H).

Example 2.2C tert-Butyl 4-({2-[4-(5-chloro-2-cyanophenyl)-2-oxopyridin-1(2H)-yl]propanoyl}amino)benzoate (racemate)

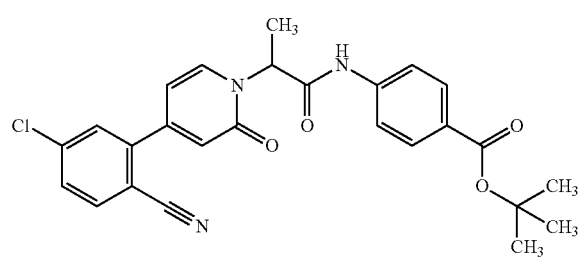 [SMILES: CC(C(=O)Nc1ccc(C(=O)OC(C)(C)C)cc1)n1ccc(-c2cc(Cl)ccc2C#N)cc1=O]

76 mg (purity 83%, 0.21 mmol) of 2-[4-(5-chloro-2-cyanophenyl)-2-oxopyridin-1(2H)-yl]propanoic acid (racemate) and 1.1 eq. of tert-butyl 4-aminobenzoate were reacted according to General Method 5A. Yield: 43 mg (43% of theory)

LC/MS [Method 1]: R$_t$=1.20 min; MS (ESIpos): m/z=478 (M+H)$^+$

Example 2.3A tert-Butyl 5-[4-({2-[4-(5-chloro-2-cyanophenyl)-2-oxopyridin-1(2H)-yl]propanoyl}amino)phenyl]-3-oxo-2,3-dihydro-1H-pyrazole-1-carboxylate (racemate)

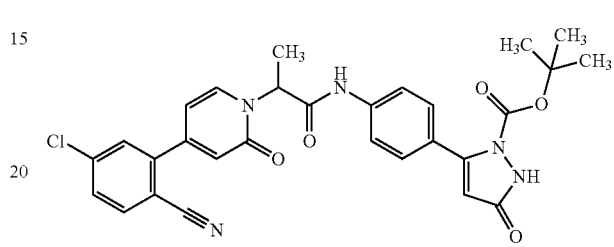

120 mg (purity 93%, 0.37 mmol) of 2-[4-(5-chloro-2-cyanophenyl)-2-oxopyridin-1(2H)-yl]propanoic acid (racemate) and 1.1 eq. of tert-butyl 5-(4-aminophenyl)-3-oxo-2,3-dihydro-1H-pyrazole-1-carboxylate were reacted according to General Method 5A. Yield: 110 mg (53% of theory)

LC/MS [Method 1]: R$_t$=1.10 min; MS (ESIpos): m/z=560 (M+H)$^+$ $^1$H-NMR (400 MHz, DMSO-d$_6$): δ [ppm]=12.95 (s, 1H), 10.61 (s, 1H), 8.05 (d, 1H), 7.96 (d, 1H), 7.83 (d, 1H), 7.77 (dd, 1H), 7.70 (m, 4H), 6.67 (d, 1H), 6.56 (dd, 1H), 6.49 (d, 1H), 5.59 (q, 1H), 1.70 (d, 3H), 1.50 (s, 9H).

Example 2.4A

Methyl 4-({2-[4-(5-chloro-2-cyanophenyl)-2-oxopyridin-1(2H)-yl]propanoyl}amino)-2-fluorobenzoate (racemate)

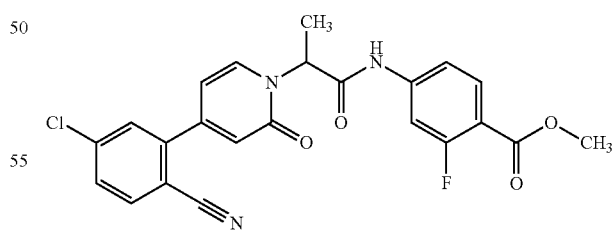

120 mg (0.39 mmol) of 2-[4-(5-chloro-2-cyanophenyl)-2-oxopyridin-1(2H)-yl]propanoic acid (racemate) and 1.1 eq. of methyl 4-amino-2-fluorobenzoate were reacted according to General Method 5A. Yield: 64 mg (36% of theory)

LC/MS [Method 1]: R$_t$=1.03 min; MS (ESIpos): m/z=454 (M+H)$^+$

Example 2.5A

Methyl 2-chloro-4-({2-[4-(5-chloro-2-cyanophenyl)-2-oxopyridin-1(2H)-yl]propanoyl}amino)benzoate (racemate)

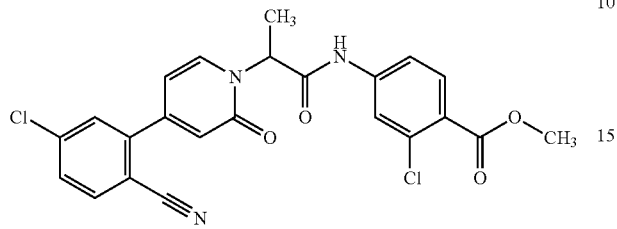

120 mg (0.39 mmol) of 2-[4-(5-chloro-2-cyanophenyl)-2-oxopyridin-1(2H)-yl]propanoic acid (racemate) and 1.1 eq. of methyl 4-amino-2-chlorobenzoate were reacted according to General Method 5A. Following aqueous work-up, the desired product was precipitated using a mixture of a little water, acetonitrile and DMF. Yield: 69 mg (38% of theory)

LC/MS [Method 1]: $R_t$=1.07 min; MS (ESIpos): m/z=470 (M+H)$^+$

Example 2.6A

Methyl 4-({2-[4-(5-chloro-2-cyanophenyl)-2-oxopyridin-1(2H)-yl]propanoyl}amino)-2-methylbenzoate (racemate)

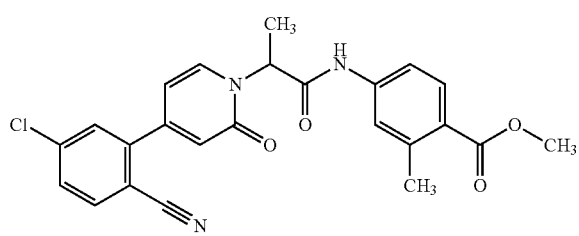 [SMILES: COC(=O)c1ccc(NC(=O)C(C)n2ccc(-c3cc(Cl)ccc3C#N)cc2=O)cc1C]

120 mg (0.39 mmol) of 2-[4-(5-chloro-2-cyanophenyl)-2-oxopyridin-1(2H)-yl]propanoic acid (racemate) and 1.1 eq. of methyl 4-amino-2-methylbenzoate were reacted according to General Method 5A. Following aqueous work-up, the desired product was precipitated using a mixture of a little water, acetonitrile and DMF. Yield: 120 mg (69% of theory)

LC/MS [Method 1]: $R_t$=1.06 min; MS (ESIpos): m/z=450 (M+H)$^+$ $^1$H-NMR (400 MHz, DMSO-d$_6$): δ [ppm]=10.69 (s, 1H), 8.04 (d, 1H), 7.94 (d, 1H), 7.85 (d, 1H), 7.82 (d, 1H), 7.77 (dd, 1H), 7.57 (m, 2H), 6.66 (d, 1H), 6.56 (dd, 1H), 5.56 (q, 1H), 3.8 (s, 3H), 1.69 (d, 3H).

Example 2.7A tert-Butyl 6-({2-[4-(5-chloro-2-cyanophenyl)-2-oxopyridin-1(2H)-yl]propanoyl}amino)-2-methyl-3-oxo-2,3-dihydro-1H-indazole-1-carboxylate (racemate)

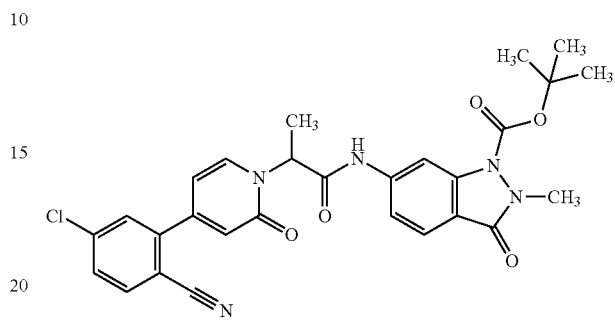

89 mg (purity 83%, 0.24 mmol) of 2-[4-(5-chloro-2-cyanophenyl)-2-oxopyridin-1(2H)-yl]propanoic acid (racemate) and 1.1 eq. of tert-butyl 6-amino-2-methyl-3-oxo-2,3-dihydro-1H-indazole-1-carboxylate were reacted according to General Method 5A. The crude product was purified by preparative HPLC (Reprosil C18, water/methanol gradient). Yield: 75 mg (56% of theory)

LC/MS [Method 1]: $R_t$=1.04 min; MS (ESIpos): m/z=548 (M+H)$^+$

Example 2.8A

[(2-Bromo-4-chlorophenyl)ethynyl](trimethyl)silane

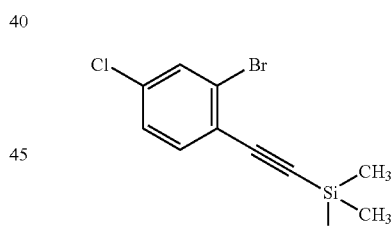

Under argon, 2.89 ml (20.7 mmol, 5.0 eq.) of triethylamine, 2.99 g (4.1 mmol) of 2-bromo-4-chloro-1-iodobenzene and 489 mg (4.97 mmol, 1.2 eq.) of ethynyl(trimethyl)silane were added successively to a solution of 73 mg (0.10 mmol, 0.025 eq.) of bis(triphenylphosphine)palladium(II) chloride and 20 mg (0.10 mmol, 0.025 eq.) copper(I) iodide in 27 ml of THF, and the mixture was stirred at RT overnight. The reaction mixture was then diluted with ethyl acetate and filtered through Celite, and the filtrate was concentrated under reduced pressure. After addition of ethyl acetate/water and phase separation, the organic phase was concentrated under reduced pressure. The crude product was purified by flash chromatography (silica gel 60, mobile phase: cyclohexane/ethyl acetate mixtures). Yield: 3.21 g (quant.)

$^1$H-NMR (400 MHz, DMSO-d$_6$): δ [ppm]=7.70 (d, 1H), 7.40 (d, 1H), 7.29 (dd, 1H), 0.07 (s, 9H).

Example 2.8B

4-{5-Chloro-2-[(trimethylsilyl)ethynyl]phenyl}-2-methoxypyridine

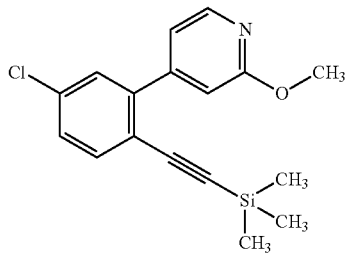 [SMILES: COc1cc(-c2cc(Cl)ccc2C#C[Si](C)(C)C)ccn1]

A solution of 333 mg (1.16 mmol) of [(2-bromo-4-chlorophenyl)ethynyl](trimethyl)silane, 195 mg (1.28 mmol, 1.1 eq.) of (2-methoxypyridin-4-yl)boronic acid, 401 mg (2.9 mmol, 2.5 eq.) of potassium carbonate and 14 mg (0.02 mmol, 0.015 eq.) of [1,1-bis(diphenylphosphino)ferrocene]palladium(II) chloride/monodichloromethane adduct in 18 ml of dioxane was irradiated in a microwave at 130° C. for 15 min. The reaction mixture was then filtered through Celite and the residue was washed with dioxane. The combined filtrates were concentrated under reduced pressure. After addition of water/ethyl acetate and phase separation, the organic phase was concentrated under reduced pressure. Yield: 550 mg (purity 41%, 62% of theory)

LC/MS [Method 1]: $R_t$=1.50 min; MS (ESIpos): m/z=316 (M+H)$^+$

Example 2.8C

4-{5-Chloro-2-[(trimethylsilyl)ethynyl]phenyl}pyridin-2(1H)-one

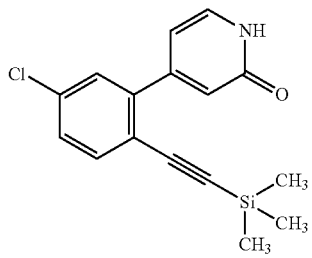 [SMILES: C[Si](C)(C)C#Cc1ccc(Cl)cc1-c1cc[nH]c(=O)c1]

550 mg (purity 41%, 0.71 mmol) of 4-{5-chloro-2-[(trimethylsilyl)ethynyl]phenyl}-2-methoxypyridine and 20 eq. of pyridinium hydrochloride were reacted according to General Method 3A. The reaction mixture was concentrated under reduced pressure and water was added to the residue. After addition of ethyl acetate and phase separation, the organic phase was washed once with water, dried (sodium sulphate), filtered and concentrated under reduced pressure. The crude product was purified by flash chromatography (silica gel 60, cyclohexane/ethyl acetate and dichloromethane/methanol mixtures). Yield: 141 mg (purity 91%, 59% of theory)

LC/MS [Method 1]: $R_t$=1.11 min; MS (ESIpos): m/z=302 (M+H)$^+$

Example 2.8D tert-Butyl 2-[4-{5-chloro-2-[(trimethylsilyl)ethynyl]phenyl}-2-oxopyridin-1(2H)-yl]propanoate

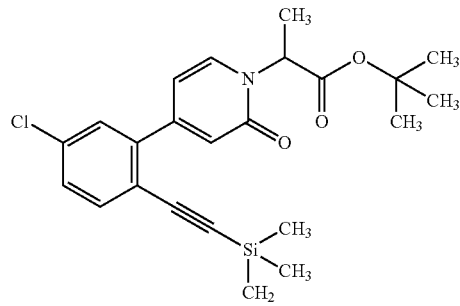 [SMILES: CC(C(=O)OC(C)(C)C)n1ccc(-c2cc(Cl)ccc2C#C[Si](C)(C)C)cc1=O]

125 mg (purity 91%, 0.38 mmol) of 4-{5-chloro-2-[(trimethylsilyl)ethynyl]phenyl}pyridin-2(1H)-one and 1.2 eq. of tert-butyl 2-bromopropanoate (racemate) were reacted at 80° C. according to General Method 4B. Yield: 56 mg (purity 89%, 31% of theory)

LC/MS [Method 1]: $R_t$=1.42 min; MS (ESIpos): m/z=430 (M+H)$^+$

Example 2.8E

2-[4-(5-Chloro-2-ethynylphenyl)-2-oxopyridin-1(2H)-yl]propanoic acid (racemate)

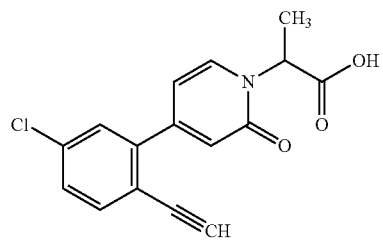

55 mg (purity 89%, 0.11 mmol) of tert-butyl 2-[4-{5-chloro-2-[(trimethylsilyl)ethynyl]phenyl}-2-oxopyridin-1(2H)-yl]propanoate (racemate) were hydrolysed with TFA according to General Method 6A. Yield: 50 mg (purity 82%, quant.)

LC/MS [Method 1]: $R_t$=0.90 min; MS (ESIpos): m/z=301 (M+H)$^+$

Example 2.8F

Methyl 4-({2-[4-(5-chloro-2-ethynylphenyl)-2-oxopyridin-1(2H)-yl]propanoyl}amino)benzoate

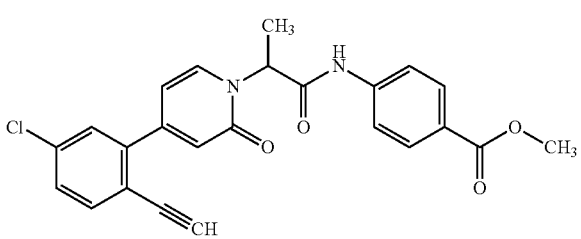 [SMILES: C#Cc1ccc(Cl)cc1-c1ccn(C(C)C(=O)Nc2ccc(C(=O)OC)cc2)c(=O)c1]

50 mg (purity 82%, 0.32 mmol) of 2-[4-(5-chloro-2-ethynylphenyl)-2-oxopyridin-1(2H)-yl]propanoic acid (racemate) and 1.2 eq. of methyl 4-aminobenzoate were reacted according to General Method 5A. Yield: 15 mg (25% of theory)

LC/MS [Method 1]: $R_t$=1.11 min; MS (ESIpos): m/z=435 (M+H)$^+$

Example 2.9A tert-Butyl 2-[4-(2,5-dichlorophenyl)-2-oxopyridin-1(2H)-yl]propanoate (racemate)

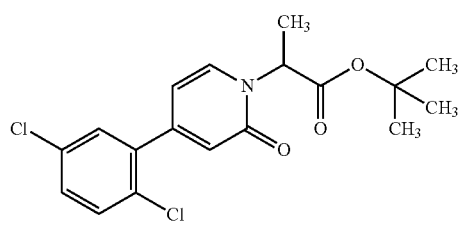 [SMILES: CC(C(=O)OC(C)(C)C)n1ccc(-c2cc(Cl)ccc2Cl)cc1=O]

2.5 g (8.0 mmol) of tert-butyl 2-(4-bromo-2-oxopyridin-1(2H)-yl)propanoate (racemate) and 1.76 g (9.2 mmol) of 2,5-dichlorophenylboronic acid in the presence of tetrakis(triphenylphosphine)palladium(0) were reacted according to General Method 2A. Yield: 2.3 g (77% of theory)

LC/MS [Method 1]: $R_t$=1.20 min; MS (ESIpos): m/z=368 (M+H)$^+$

Example 2.9B

2-[4-(2,5-Dichlorophenyl)-2-oxopyridin-1(2H)-yl]propanoic acid (racemate)

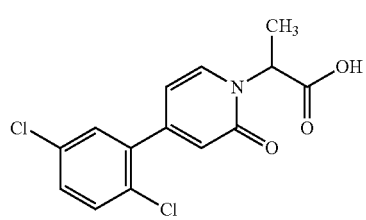 [SMILES: CC(C(=O)O)n1ccc(-c2cc(Cl)ccc2Cl)cc1=O]

A solution of 2.3 g (6.2 mmol) of tert-butyl 2-[4-(2,5-dichlorophenyl)-2-oxopyridin-1(2H)-yl]propanoate (racemate) in a 4-molar hydrochloric acid/dioxane solution was stirred at RT for 7 h and then concentrated under reduced pressure. The residue was coevaporated three times with dichloromethane and dried under reduced pressure. Yield: 2.0 g (99% of theory)

LC/MS [Method 1]: $R_t$=0.88 min; MS (ESIpos): m/z=312 (M+H)$^+$ $^1$H-NMR (400 MHz, DMSO-$d_6$): δ [ppm]=13.03 (br. s, 1H), 7.78 (d, 1H), 7.63 (d, 1H), 7.57 (d, 1H), 7.54 (dd, 1H), 6.46 (d, 1H), 6.36 (dd, 1H), 5.21 (q, 1H), 1.58 (d, 3H).

Example 2.9C tert-Butyl 4-({2-[4-(2,5-dichlorophenyl)-2-oxopyridin-1(2H)-yl]propanoyl}amino)benzoate (racemate)

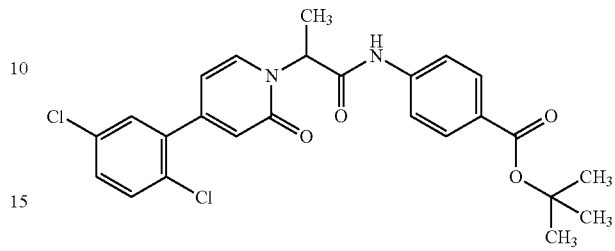

117 mg (0.36 mmol) of 2-[4-(2,5-dichlorophenyl)-2-oxopyridin-1(2H)-yl]propanoic acid (racemate) and 1.2 eq. of tert-butyl 4-aminobenzoate were reacted according to General Method 5A. Yield: 83 mg (47% of theory)

LC/MS [Method 1]: $R_t$=1.32 min; MS (ESIpos): m/z=487 (M+H)$^+$

Example 2.10A tert-Butyl 2-[4-(2-bromo-5-chlorophenyl)-2-oxopyridin-1(2H)-yl]propanoate (racemate)

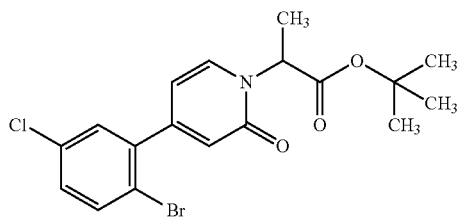 [SMILES: CC(C(=O)OC(C)(C)C)n1ccc(-c2cc(Cl)ccc2Br)cc1=O]

856 mg (2.75 mmol) of tert-butyl 2-(4-bromo-2-oxopyridin-1(2H)-yl)propanoate (racemate) and 776 mg (3.3 mmol) of 2-bromo-5-chlorophenylboronic acid in the presence of tetrakis(triphenylphosphine)palladium(0) were reacted according to General Method 2A. Yield: 921 mg (80% of theory)

LC/MS [Method 1]: $R_t$=1.21 min; MS (ESIpos): m/z=412 (M+H)$^+$

Example 2.10B

2-[4-(2-Bromo-5-chlorophenyl)-2-oxopyridin-1(2H)-yl]propanoic acid (racemate)

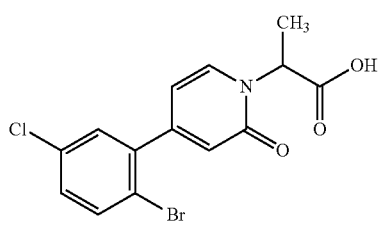

920 mg (2.2 mmol) of tert-butyl 2-[4-(2-bromo-5-chlorophenyl)-2-oxopyridin-1(2H)-yl]propanoate (racemate) were hydrolysed with TFA according to General Method 6A. Yield: 1110 mg (purity 93%, quant.)

LC/MS [Method 1]: $R_t$=0.91 min; MS (ESIpos): m/z=356 (M+H)$^+$

Example 2.10C tert-Butyl 4-({2-[4-(2-bromo-5-chlorophenyl)-2-oxopyridin-1(2H)-yl]propanoyl}amino)benzoate (racemate)

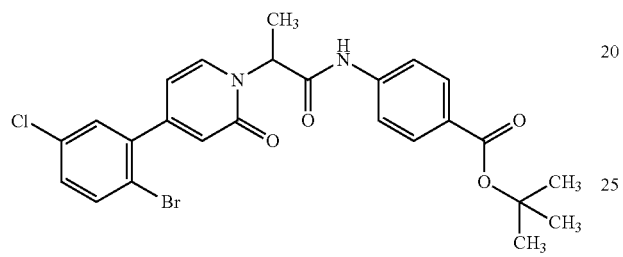

153 mg (purity 93%, 0.4 mmol) of 2-[4-(2-bromo-5-chlorophenyl)-2-oxopyridin-1(2H)-yl]propanoic acid (racemate) and 1.2 eq. of tert-butyl 4-aminobenzoate were reacted according to General Method 5A. Yield: 96 mg (44% of theory)

LC/MS [Method 1]: $R_t$=1.32 min; MS (ESIpos): m/z=531 (M+H)$^+$

Example 2.11A tert-Butyl 2-{4-[5-chloro-2-(trifluoromethyl)phenyl]-2-oxopyridin-1(2H)-yl}propanoate (racemate)

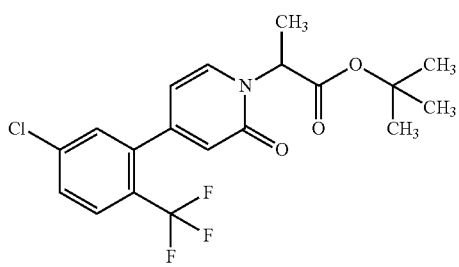 [SMILES: CC(C(=O)OC(C)(C)C)n1ccc(-c2cc(Cl)ccc2C(F)(F)F)cc1=O]

2.0 g (6.4 mmol) of tert-butyl 2-(4-bromo-2-oxopyridin-1(2H)-yl)propanoate (racemate) and 1.7 g (7.7 mmol) of 5-chloro-2-(trifluoromethyl)phenylboronic acid in the presence of tetrakis(triphenylphosphine)palladium(0) were reacted according to General Method 2A. Yield: 2.3 g (purity 91%, 82% of theory)

LC/MS [Method 1]: $R_t$=1.22 min; MS (ESIpos): m/z=402 (M+H)$^+$

Example 2.11B

2-{4-[5-Chloro-2-(trifluoromethyl)phenyl]-2-oxopyridin-1(2H)-yl}propanoic acid (racemate)

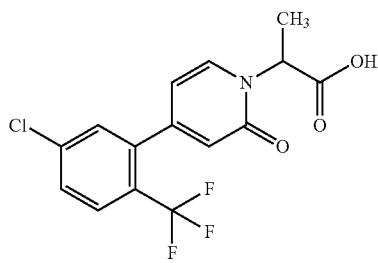 [SMILES: CC(C(=O)O)n1ccc(-c2cc(Cl)ccc2C(F)(F)F)cc1=O]

2.3 g (purity 91%, 5.2 mmol) of tert-butyl 2-[4-(5-chloro-2-cyanophenyl)-2-oxopyridin-1(2H)-yl]propanoate (racemate) were hydrolysed with TFA according to General Method 6A. Yield: 2.6 g (purity 93%, quant.)

LC/MS [Method 1]: $R_t$=0.91 min; MS (ESIpos): m/z=346 (M+H)$^+$

Example 2.11C tert-Butyl 4-[(2-{4-[5-chloro-2-(trifluoromethyl)phenyl]-2-oxopyridin-1(2H)-yl}propanoyl)amino]benzoate (racemate)

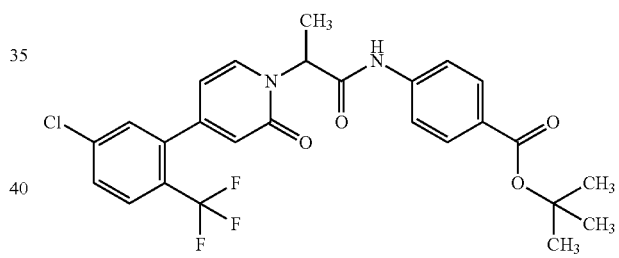

130 mg (purity 93%, 0.35 mmol) of 2-{4-[5-chloro-2-(trifluoromethyl)phenyl]-2-oxopyridin-1(2H)-yl}propanoic acid (racemate) and 1.2 eq. of tert-butyl 4-aminobenzoate were reacted according to General Method 5A. The crude product was purified by preparative HPLC (Reprosil C18, water/methanol gradient). Yield: 104 mg (56% of theory)

LC/MS [Method 1]: $R_t$=1.33 min; MS (ESIpos): m/z=521 (M+H)$^+$

Example 3.1A tert-Butyl 2-(4-bromo-2-oxopyridin-1(2H)-yl)butanoate (racemate)

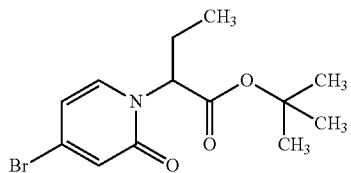 [SMILES: CCC(C(=O)OC(C)(C)C)n1ccc(Br)cc1=O]

348 mg (2.0 mmol) of 4-bromopyridin-2(1H)-one and 1.2 eq. of tert-butyl 2-bromobutanoate (racemate) were reacted according to General Method 4B at 120° C. After aqueous work-up, the desired product was reacted further as crude product. Yield: 608 mg (purity 82%, 79% of theory)

LC/MS [Method 1]: $R_t$=0.99 min; MS (ESIpos): m/z=316 (M+H)$^+$

Example 3.1B tert-Butyl 2-[4-(5-chloro-2-cyanophenyl)-2-oxopyridin-1(2H)-yl]butanoate (racemate)

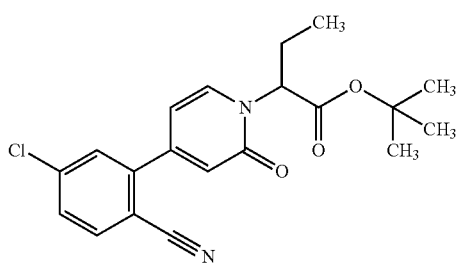 [SMILES: CCC(C(=O)OC(C)(C)C)n1ccc(-c2cc(Cl)ccc2C#N)cc1=O]

600 mg (purity 82%, 1.56 mmol) of tert-butyl 2-(4-bromo-2-oxopyridin-1(2H)-yl)butanoate (racemate) and 325 mg (1.8 mmol) of 5-chloro-2-cyanophenylboronic acid in the presence of tetrakis(triphenylphosphine)palladium(0) were reacted according to General Method 2A. Yield: 543 mg (purity 59%, 55% of theory)

LC/MS [Method 1]: $R_t$=1.10 min; MS (ESIpos): m/z=373 (M+H)$^+$

Example 3.1C

2-[4-(5-Chloro-2-cyanophenyl)-2-oxopyridin-1(2H)-yl]butanoic acid (racemate)

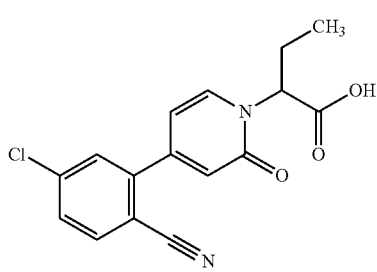 [SMILES: CCC(C(=O)O)n1ccc(-c2cc(Cl)ccc2C#N)cc1=O]

543 mg (purity 59%, 0.86 mmol) of tert-butyl 2-[4-(5-chloro-2-cyanophenyl)-2-oxopyridin-1(2H)-yl]butanoate (racemate) were hydrolysed with 20 eq. of TFA according to General Method 6A. Yield: 425 mg (purity 60%, 94% of theory)

LC/MS [Method 1]: $R_t$=0.78 min; MS (ESIpos): m/z=317 (M+H)$^+$

Example 4.1A

Ethyl 2-(4-bromo-2-oxopyridin-1(2H)-yl)-3-methylbutanoate (racemate)

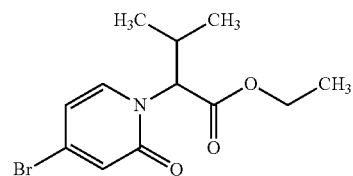 [SMILES: CCOC(=O)C(C(C)C)n1ccc(Br)cc1=O]

500 mg (2.9 mmol) of 4-bromopyridin-2(1H)-one and 841 mg (4.02 mmol) of ethyl 2-bromo-3-methylbutanoate (racemate) in the presence of 1.15 eq. of sodium hydride and 2.3 eq. of lithium bromide were reacted according to General Method 4C. Yield: 260 mg (purity 92%, 28% of theory)

LC/MS [Method 3]: $R_t$=2.05 min; MS (ESIpos): m/z=302 (M+H)$^+$

Example 4.1B

Ethyl 2-[4-(5-chloro-2-cyanophenyl)-2-oxopyridin-1(2H)-yl]-3-methylbutanoate (racemate)

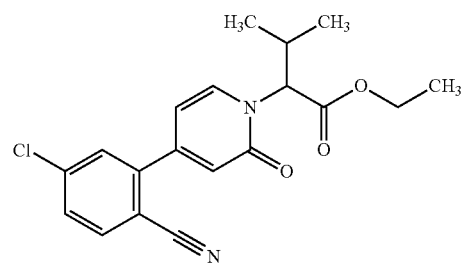 [SMILES: CCOC(=O)C(C(C)C)n1ccc(-c2cc(Cl)ccc2C#N)cc1=O]

240 mg (purity 92%, 0.73 mmol) of ethyl 2-(4-bromo-2-oxopyridin-1(2H)-yl)-3-methylbutanoate (racemate) and 172 mg (0.95 mmol) of 5-chloro-2-cyanophenylboronic acid in the presence of [1,1-bis(diphenylphosphino)ferrocene] palladium(II) chloride/monodichloromethane adduct were reacted according to General Method 2A. Yield: 117 mg (purity 81%, 36% of theory)

LC/MS [Method 1]: $R_t$=1.10 min; MS (ESIpos): m/z=359 (M+H)$^+$

Example 4.1C

2-[4-(5-Chloro-2-cyanophenyl)-2-oxopyridin-1(2H)-yl]-3-methylbutanoic acid (racemate)

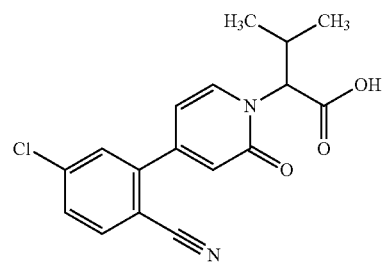 [SMILES: CC(C)C(C(=O)O)n1ccc(-c2cc(Cl)ccc2C#N)cc1=O]

117 mg (purity 81%, 0.26 mmol) of ethyl 2-[4-(5-chloro-2-cyanophenyl)-2-oxopyridin-1(2H)-yl]-3-methylbutanoate (racemate) were hydrolysed with lithium hydroxide according to General Method 6B. Yield: 79 mg (purity 86%, 78% of theory)

LC/MS [Method 1]: Rt=0.89 min; MS (ESIpos): m/z=331 (M+H)$^+$

Example 5.1A

Ethyl 2-(4-iodo-2-oxopyridin-1(2H)-yl)hexanoate (racemate)

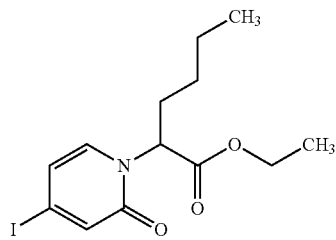 [SMILES: CCCCC(C(=O)OCC)n1ccc(I)cc1=O]

500 mg (2.3 mmol) of 4-iodopyridin-2(1H)-one and 706 mg (3.2 mmol) of ethyl 2-bromohexanoate (racemate) in the presence of 1.15 eq. of sodium hydride and 2.3 eq. of lithium bromide were reacted according to General Method 4C. Yield: 352 mg (43% of theory)

LC/MS [Method 1]: R$_t$=1.08 min; MS (ESIpos): m/z=364 (M+H)$^+$ $^1$H-NMR (400 MHz, DMSO-d$_6$): δ [ppm]=7.45 (d, 1H), 6.96 (d, 1H), 6.63 (dd, 1H), 5.10 (dd, 1H), 4.10 (q, 1H), 2.03 (m, 2H), 1.24 (m, 3H), 1.15 (t, 3H), 1.02 (m, 1H), 0.84 (t, 3H).

Example 5.1B

Ethyl 2-[4-(5-chloro-2-cyanophenyl)-2-oxopyridin-1(2H)-yl]hexanoate (racemate)

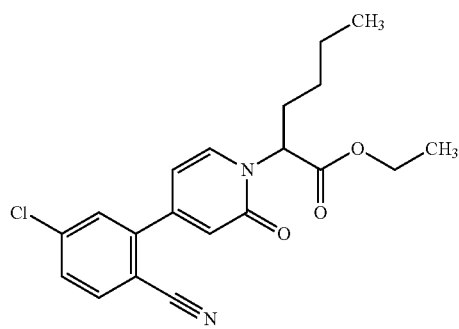 [SMILES: CCCCC(C(=O)OCC)n1ccc(-c2cc(Cl)ccc2C#N)cc1=O]

150 mg (0.41 mmol) of ethyl 2-(4-iodo-2-oxopyridin-1(2H)-yl)hexanoate (racemate) and 97 mg (0.53 mmol) of 5-chloro-2-cyanophenylboronic acid in the presence of [1,1-bis(diphenylphosphino)ferrocene]palladium(II) chloride/dichloromethane monoadduct were reacted according to General Method 2A. Yield: 114 mg (purity 95%, 70% of theory)

LC/MS [Method 1]: R$_t$=1.15 min; MS (ESIpos): m/z=373 (M+H)$^+$

Example 5.1C

2-[4-(5-Chloro-2-cyanophenyl)-2-oxopyridin-1(2H)-yl]hexanoic acid (racemate)

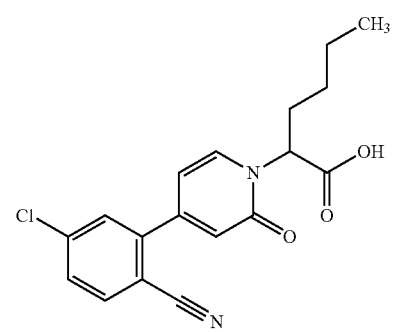 [SMILES: CCCCC(C(=O)O)n1ccc(-c2cc(Cl)ccc2C#N)cc1=O]

113 mg (purity 95%, 0.29 mmol) of ethyl 2-[4-(5-chloro-2-cyanophenyl)-2-oxopyridin-1(2H)-yl]hexanoate (racemate) were hydrolysed with lithium hydroxide according to General Method 6B. Yield: 64 mg (purity 78%, 50% of theory)

LC/MS [Method 1]: R$_t$=0.98 min; MS (ESIpos): m/z=345 (M+H)$^+$

Example 6.1A

Bromo(cyclopropylmethyl)magnesium

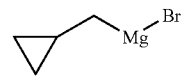

1.2 g (48.1 mmol) of magnesium turnings were initially charged in 30 ml of THF, a spatula tip of iodine was added and a solution of 6.5 g (48.1 mmol, 1.0 eq.) of bromomethylcyclopropane in 15 ml of THF was slowly added dropwise. The reaction mixture was then stirred under reflux for 2 h. After cooling to RT, the reaction solution was decanted from the remaining magnesium turnings and the crude solution was reacted further.

Example 6.1B

Ethyl 3-cyclopropyl-2-hydroxypropanoate (racemate)

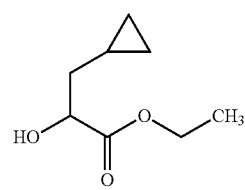

Under argon and with ice cooling, a solution of 5.4 g (purity 50%, 26.7 mmol) of ethyl oxoacetate in 50 ml of THF was quickly added dropwise to 7.6 g (48 mmol, 1.8 eq.) of bromo(cyclopropylmethyl)magnesium. The reaction mixture was stirred for another 48 h, diluted with ethyl acetate and quenched with water. Celite was added, and the reaction mixture was stirred for 5 min and then filtered. After phase separation, the organic phase was washed once with water, dried (sodium sulphate), filtered and concentrated under reduced pressure. Yield: 2.6 g (60% of theory)

GC [Method 7]: $R_f$=2.49 min; MS (EI): m/z=158 (M)$^+$

Example 6.1C

Ethyl 3-cyclopropyl-2-[(methylsulphonyl)oxy]propanoate (racemate)

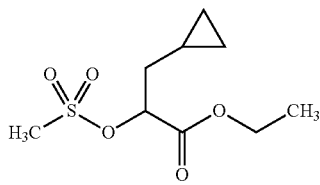

At RT, 2 ml (11.5 mmol, 2.4 eq.) of N-ethyl-N-(propan-2-yl)propan-2-amine were added to a solution of 1.9 g (purity 40%, 4.8 mmol) of ethyl 3-cyclopropyl-2-hydroxypropanoate (racemate) in 100 ml of dichloromethane, followed by the quick addition, at 0° C., of 0.45 ml (5.8 mmol, 1.2 eq.) of methanesulphonyl chloride. The reaction mixture was stirred at RT for 2 h and then quenched with ice. After phase separation, the organic phase was washed with three times with water and once with saturated sodium chloride solution. The combined organic phases were dried (sodium sulphate), filtered and concentrated under reduced pressure. The crude product was used for the next step without further purification.

Example 6.1D

Ethyl 2-(4-bromo-2-oxopyridin-1(2H)-yl)-3-cyclopropylpropanoate (racemate)

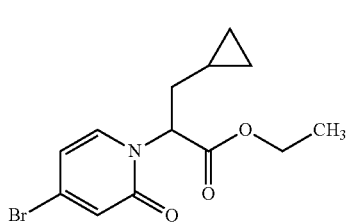 [SMILES: CCOC(=O)C(CC1CC1)n1ccc(Br)cc1=O]

1.02 g (5.87 mmol) of 4-bromopyridin-2(1H)-one and 2.23 g (purity 56%, 5.28 mmol) of ethyl 3-cyclopropyl-2-[(methylsulphonyl)oxy]propanoate (racemate) in the presence of 1.15 eq. of sodium hydride and 2.3 eq. of lithium bromide were reacted according to General Method 4C (stirred at 65° C. overnight). Yield: 246 mg (13% of theory)

$^1$H-NMR (400 MHz, DMSO-d$_6$): δ [ppm]=7.67 (d, 1H), 6.76 (d, 1H), 6.54 (dd, 1H), 5.76 (m, 1H), 5.12 (dd, 1H), 4.97 (m, 2H), 4.11 (q, 2H), 2.15 (q, 2H), 1.92 (m, 2H), 1.15 (t, 3H).

Example 6.1E

Ethyl 2-{4-[5-chloro-2-(trifluoromethyl)phenyl]-2-oxopyridin-1(2H)-yl}-3-cyclopropylpropanoate (racemate)

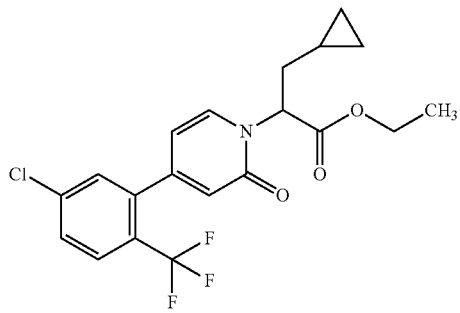 [SMILES: CCOC(=O)C(CC1CC1)n1ccc(-c2cc(Cl)ccc2C(F)(F)F)cc1=O]

250 mg (0.8 mmol) of ethyl 2-(4-bromo-2-oxopyridin-1(2H)-yl)-3-cyclopropylpropanoate (racemate) and 214 mg (0.96 mmol) of 5-chloro-2-trifluoromethylphenylboronic acid in the presence of tetrakis(triphenylphosphine)palladium(0) were reacted according to General Method 2A. Yield: 35 mg (purity 87%, 9% of theory) of the title compound and 70 mg (22% of theory) of the product which is already hydrolysed (Example 6.1F)

LC/MS [Method 1]: $R_t$=1.23 min; MS (ESIpos): m/z=414 (M+H)$^+$

Example 6.1F

2-{4-[5-Chloro-2-(trifluoromethyl)phenyl]-2-oxopyridin-1(2H)-yl}-3-cyclopropylpropanoic acid (racemate)

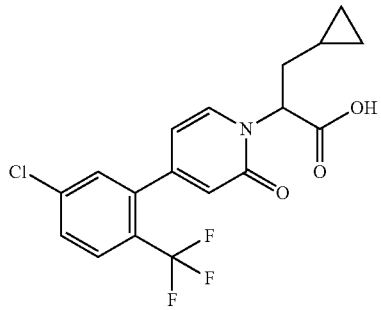 [SMILES: O=C(O)C(CC1CC1)n1ccc(-c2cc(Cl)ccc2C(F)(F)F)cc1=O]

35 mg (purity 87%, 0.07 mmol) of ethyl 2-{4-[5-chloro-2-(trifluoromethyl)phenyl]-2-oxopyridin-1(2H)-yl}-3-cyclopropylpropanoate (racemate) were hydrolysed with lithium hydroxide according to General Method 6B. Yield: 60 mg (purity 88%, quant.)

LC/MS [Method 1]: $R_t$=1.05 min; MS (ESIpos): m/z=386 (M+H)$^+$

Example 6.1G

Methyl 4-[(2-{4-[5-chloro-2-(trifluoromethyl)phenyl]-2-oxopyridin-1(2H)-yl}-3-cyclopropylpropanoyl)amino]benzoate (racemate)

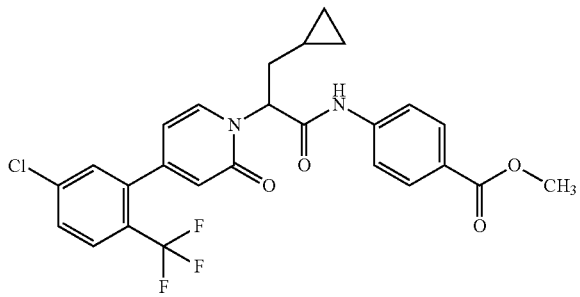 [SMILES: COC(=O)c1ccc(NC(=O)C(CC2CC2)n2ccc(-c3cc(Cl)ccc3C(F)(F)F)cc2=O)cc1]

105 mg (purity 94%, 0.26 mmol) of 2-{4-[5-chloro-2-(trifluoromethyl)phenyl]-2-oxopyridin-1(2H)-yl}-3-cyclopropylpropanoic acid (racemate) and 1.1 eq. of methyl 4-aminobenzoate were reacted according to General Method 5A. After aqueous work-up, the crude product was reacted further without further purification. Yield: 200 mg (purity 48%, 72% of theory)

LC/MS [Method 1]: $R_t$=1.27 min; MS (ESIpos): m/z=519 (M+H)$^+$

Example 6.2A 2-(4-Bromo-2-oxopyridin-1(2H)-yl)-3-cyclopropylpropanoic acid (racemate)

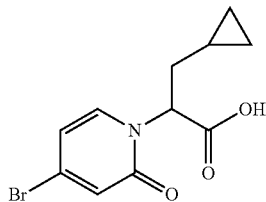 [SMILES: O=C(O)C(CC1CC1)n1ccc(Br)cc1=O]

350 mg (1.1 mmol) of ethyl 2-(4-bromo-2-oxopyridin-1(2H)-yl)-3-cyclopropylpropanoate (racemate) were hydrolysed with lithium hydroxide according to General Method 6B. Yield: 290 mg (purity 94%, 86% of theory)

LC/MS [Method 1]: $R_t$=0.76 min; MS (ESIpos): m/z=286 (M+H)$^+$ $^1$H-NMR (400 MHz, DMSO-d$_6$): δ [ppm]=13.14 (s, 1H), 7.65 (d, 1H), 6.74 (d, 1H), 6.51 (dd, 1H), 5.75 (m, 1H), 5.11 (t, 1H), 4.98 (m, 2H), 2.15 (q, 2H), 1.91 (m, 2H).

Example 6.2B tert-Butyl 4-{[2-(4-bromo-2-oxopyridin-1(2H)-yl)-3-cyclopropylpropanoyl]amino}benzoate (racemate)

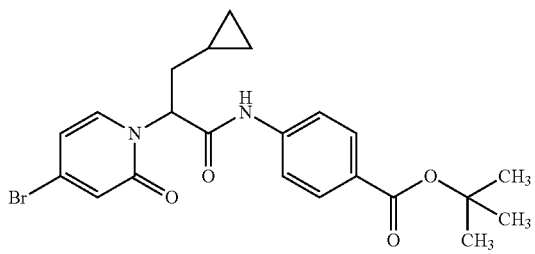 [SMILES: CC(C)(C)OC(=O)c1ccc(NC(=O)C(CC2CC2)n2ccc(Br)cc2=O)cc1]

290 mg (purity 94%, 0.95 mmol) of 2-(4-bromo-2-oxopyridin-1(2H)-yl)-3-cyclopropylpropanoic acid (racemate) and 1.1 eq. of tert-butyl 4-aminobenzoate were reacted according to General Method 5A. Yield: 114 mg (purity 80%, 21% of theory)

LC/MS [Method 1]: $R_t$=1.25 min; MS (ESIpos): m/z=461 (M+H)$^+$

Example 6.2C tert-Butyl 4-[(2-{4-[5-chloro-2-(trifluoromethoxy)phenyl]-2-oxopyridin-1(2H)-yl}-3-cyclopropylpropanoyl)amino]benzoate (racemate)

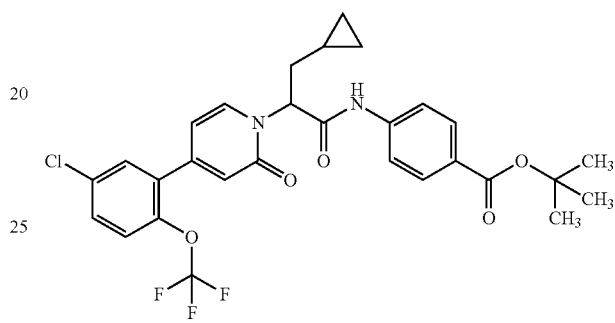

110 mg (purity 80%, 0.19 mmol) of tert-butyl 4-{[2-(4-bromo-2-oxopyridin-1(2H)-yl)-3-cyclopropylpropanoyl]amino}benzoate (racemate), 46 mg (0.19 mmol) of 5-chloro-2-trifluoromethoxyphenylboronic acid and 22 mg (0.02 mmol) of tetrakis(triphenylphosphine)palladium(0) were taken up in 2.5 ml of dioxane and 2.5 ml of saturated aqueous sodium carbonate solution and irradiated in a microwave at 130° C. for 12 min. The crude product was purified by flash chromatography (silica gel 60, cyclohexane/ethyl acetate mixtures). Yield: 77 mg (purity 92%, 64% of theory)

LC/MS [Method 1]: $R_t$=1.46 min; MS (ESIpos): m/z=577 (M+H)$^+$

Example 7.1A

Ethyl 2-(4-bromo-2-oxopyridin-1(2H)-yl)-3-phenylpropanoate (racemate)

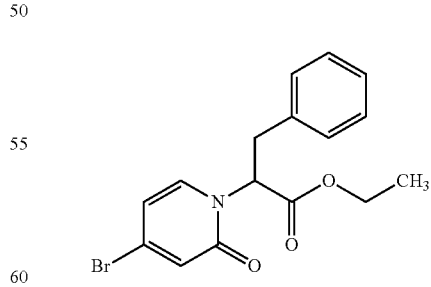

544 mg (3.13 mmol) of 4-bromopyridin-2(1H)-one and 845 mg (3.3 mmol) of ethyl 2-bromo-3-phenylpropanoate (racemate) in the presence of 1.15 eq. of sodium hydride and 2.3 eq. of lithium bromide were reacted according to General Method 4C (stirred at 65° C. for 1.5 h). Yield: 572 mg (51% of theory)

LC/MS [Method 1]: $R_t$=1.03 min; MS (ESIpos): m/z=350 (M+H)$^+$

Example 7.1B

Ethyl 2-[4-(5-chloro-2-cyanophenyl)-2-oxopyridin-1(2H)-yl]-3-phenylpropanoate (racemate)

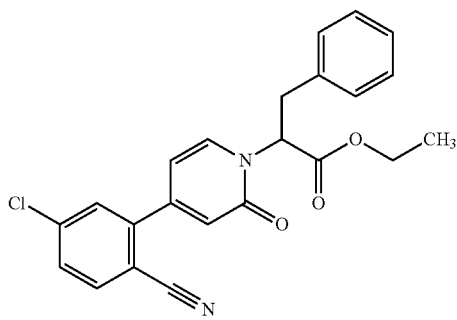 [SMILES: CCOC(=O)C(Cc1ccccc1)n1ccc(-c2cc(Cl)ccc2C#N)cc1=O]

572 mg (1.6 mmol) of ethyl 2-(4-bromo-2-oxopyridin-1(2H)-yl)-3-phenylpropanoate (racemate) and 330 mg (1.8 mmol) of 5-chloro-2-cyanophenylboronic acid in the presence of tetrakis(triphenylphosphine)palladium(0) were reacted according to General Method 2A. Yield: 300 mg (purity 94%, 43% of theory)

LC/MS [Method 1]: $R_t$=1.12 min; MS (ESIpos): m/z=407 (M+H)$^+$

Example 7.1C

2-[4-(5-Chloro-2-cyanophenyl)-2-oxopyridin-1(2H)-yl]-3-phenylpropanoic acid (racemate)

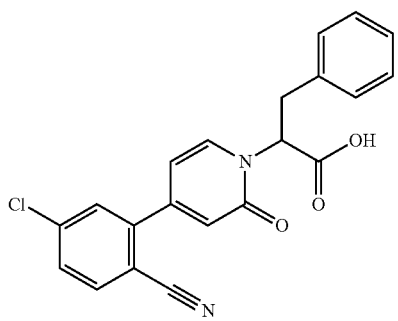 [SMILES: N#Cc1ccc(Cl)cc1-c1ccn(C(Cc2ccccc2)C(=O)O)c(=O)c1]

300 mg (purity 94%, 0.69 mmol) of ethyl 2-[4-(5-chloro-2-cyanophenyl)-2-oxopyridin-1(2H)-yl]-3-phenylpropanoate (racemate) were hydrolysed with lithium hydroxide according to General Method 6B. Yield: 129 mg (purity 89%, 43% of theory)

LC/MS [Method 1]: $R_t$=0.96 min; MS (ESIpos): m/z=379 (M+H)$^+$

Example 8.1A

Ethyl (4-bromo-2-oxopyridin-1(2H)-yl)acetate

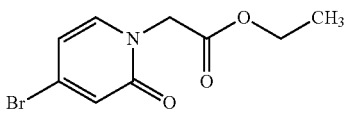

5.0 g (28.7 mmol) of 4-bromopyridin-2(1H)-one and 5.3 g (31.6 mmol) of ethyl bromoacetate were reacted according to General Method 4B. Yield: 6.2 g (83% of theory)

LC/MS [Method 3]: $R_t$=1.57 min; MS (ESIpos): m/z=260 (M+H)$^+$

Example 8.1B

Ethyl {4-[5-chloro-2-(trifluoromethyl)phenyl]-2-oxopyridin-1(2H)-yl}acetate

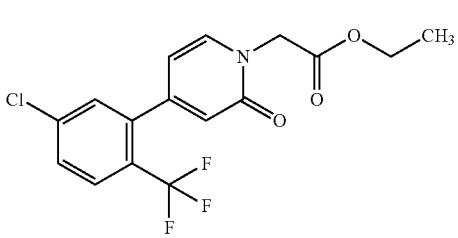 [SMILES: CCOC(=O)Cn1ccc(-c2cc(Cl)ccc2C(F)(F)F)cc1=O]

2.04 g (7.8 mmol) of ethyl (4-bromo-2-oxopyridin-1(2H)-yl)acetate and 1.98 g (8.6 mmol) of 5-chloro-2-trifluoromethylphenylboronic acid in the presence of [1,1-bis(diphenylphosphino)ferrocene]palladium(II) chloride/dichloromethane monoadduct were reacted according to General Method 2A. Yield: 2.89 g (quant.)

LC/MS [Method 1]: $R_t$=1.05 min; MS (ESIpos): m/z=360 (M+H)$^+$

Example 8.1C

Ethyl 2-{4-[5-chloro-2-(trifluoromethyl)phenyl]-2-oxopyridin-1(2H)-yl}-3-(pyridin-2-yl)propanoate (racemate)

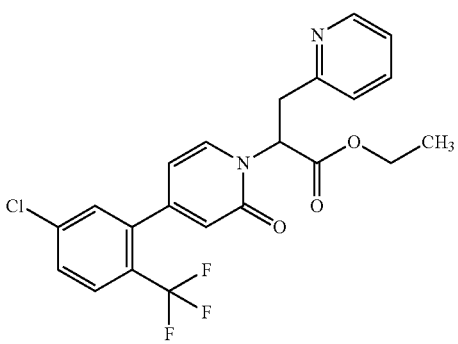 [SMILES: CCOC(=O)C(Cc1ccccn1)n1ccc(-c2cc(Cl)ccc2C(F)(F)F)cc1=O]

440 mg (1.22 mmol) of ethyl {4-[5-chloro-2-(trifluoromethyl)phenyl]-2-oxopyridin-1(2H)-yl}acetate and 464 mg (1.84 mmol) of 2-(bromomethyl)pyridine monohydrobromide were reacted according to General Method 7A. Yield: 371 mg (purity 65%, 44% of theory) of the title compound and 270 mg (50% of theory) of the product which is already hydrolysed (Example 8.1D)

LC/MS [Method 2]: $R_t$=3.07 min; MS (ESIpos): m/z=451 (M+H)$^+$

Example 8.1D

2-{4-[5-Chloro-2-(trifluoromethyl)phenyl]-2-oxopyridin-1(2H)-yl}-3-(pyridin-2-yl)propanoic acid (racemate)

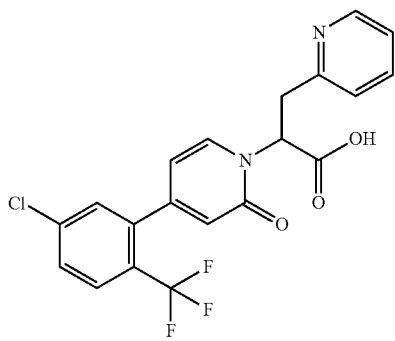 [SMILES: O=C(O)C(Cc1ccccn1)n1ccc(-c2cc(Cl)ccc2C(F)(F)F)cc1=O]

350 mg (purity 65%, 0.51 mmol) of ethyl 2-{4-[5-chloro-2-(trifluoromethyl)phenyl]-2-oxopyridin-1(2H)-yl}-3-(pyridin-2-yl)propanoate (racemate) were hydrolysed with lithium hydroxide according to General Method 6B. Yield: 240 mg (purity 80%, 90% of theory)

LC/MS [Method 1]: $R_t$=0.80 min; MS (ESIpos): m/z=423 (M+H)$^+$

Example 8.1E tert-Butyl 4-{[2-{4-[5-chloro-2-(trifluoromethyl)phenyl]-2-oxopyridin-1(2H)-yl}-3-(pyridin-2-yl)propanoyl]amino}benzoate (racemate)

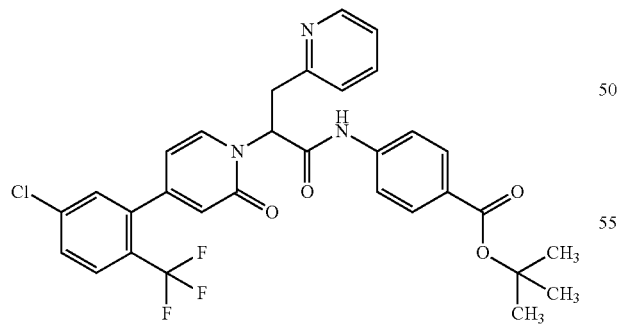

Under argon and at 0° C., 707 mg (50% strength in ethyl acetate, 1.11 mmol) of T3P and 0.29 ml (1.67 mmol) of N,N-diisopropylethylamine were added to a solution of 470 mg (purity 50%, 0.56 mmol) of 2-{4-[5-chloro-2-(trifluoromethyl)phenyl]-2-oxopyridin-1(2H)-yl}-3-(pyridin-2-yl)propanoic acid (racemate) and 129 mg (0.67 mmol) of tert-butyl 4-aminobenzoate in 45 ml of ethyl acetate. The reaction mixture was stirred at 60° C. for 1 h, another 353 mg (50% strength in ethyl acetate, 0.56 mmol) of T3P and 0.1 ml (0.56 mmol) of N,N-diisopropylethylamine were added and the mixture was stirred at 60° C. for 1 h. After addition of water/ethyl acetate and phase separation, the aqueous phase was extracted three times with ethyl acetate. The combined organic phases were dried (sodium sulphate), filtered and concentrated under reduced pressure. The crude product was purified by flash chromatography (silica gel 60, dichloromethane/methanol mixtures). Yield: 163 mg (purity 93%, 46% of theory)

LC/MS [Method 1]: $R_t$=1.29 min; MS (ESIpos): m/z=598 (M+H)$^+$

Example 9.1A

Ethyl 2-{4-[5-chloro-2-(trifluoromethyl)phenyl]-2-oxopyridin-1(2H)-yl}-3-(pyridin-3-yl)propanoate (racemate)

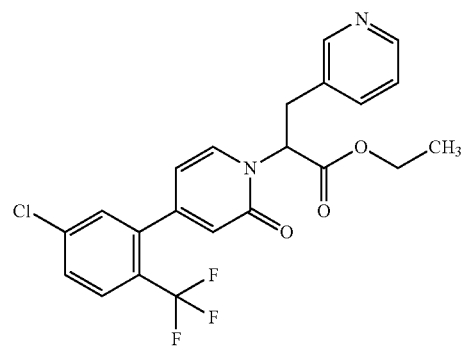 [SMILES: CCOC(=O)C(Cc1cccnc1)n1ccc(-c2cc(Cl)ccc2C(F)(F)F)cc1=O]

216 mg (0.6 mmol) of ethyl {4-[5-chloro-2-(trifluoromethyl)phenyl]-2-oxopyridin-1(2H)-yl}acetate and 228 mg (0.9 mmol) of 3-(bromomethyl)pyridine monohydrobromide were reacted according to General Method 7A. Yield: 39 mg (14% of theory)

LC/MS [Method 1]: $R_t$=0.94 min; MS (ESIpos): m/z=451 (M+H)$^+$

Example 9.1B

2-{4-[5-Chloro-2-(trifluoromethyl)phenyl]-2-oxopyridin-1(2H)-yl}-3-(pyridin-3-yl)propanoic acid (racemate)

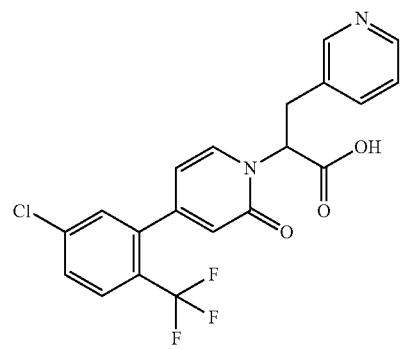 [SMILES: O=C(O)C(Cc1cccnc1)n1ccc(-c2cc(Cl)ccc2C(F)(F)F)cc1=O]

39 mg (0.09 mmol) of ethyl 2-{4-[5-chloro-2-(trifluoromethyl)phenyl]-2-oxopyridin-1(2H)-yl}-3-(pyridin-3-yl)propanoate (racemate) were hydrolysed with lithium hydroxide according to General Method 6B. Yield: 28 mg (purity 92%, 70% of theory)

LC/MS [Method 1]: $R_t$=0.74 min; MS (ESIpos): m/z=423 (M+H)$^+$

Example 9.1C tert-Butyl 4-{[2-{4-[5-chloro-2-(trifluoromethyl)phenyl]-2-oxopyridin-1(2H)-yl}-3-(pyridin-3-yl)propanoyl]amino}benzoate (racemate)

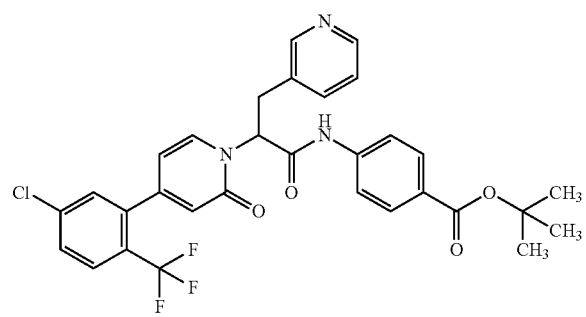 [SMILES: CC(C)(C)OC(=O)c1ccc(NC(=O)C(Cc2cccnc2)n2ccc(-c3cc(Cl)ccc3C(F)(F)F)cc2=O)cc1]

26 mg (purity 92%, 0.06 mmol) of 2-{4-[5-chloro-2-(trifluoromethyl)phenyl]-2-oxopyridin-1(2H)-yl}-3-(pyridin-3-yl)propanoic acid (racemate) and 1.1 eq. of tert-butyl 4-aminobenzoate were reacted according to General Method 5A. The reaction mixture was freed from DMF and the residue was stirred with ice-water. The crystals obtained were filtered off, washed with water and dried under reduced pressure. Yield: 33 mg (purity 94%, 92% of theory)

LC/MS [Method 1]: $R_t$=1.22 min; MS (ESIpos): m/z=598 (M+H)$^+$

Example 9.2A tert-Butyl (4-bromo-2-oxopyridin-1(2H)-yl)acetate

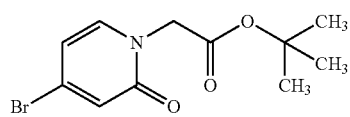 [SMILES: CC(C)(C)OC(=O)Cn1ccc(Br)cc1=O]

4.9 g (28.4 mmol) of 4-bromopyridin-2(1H)-one and 1.2 eq. of tert-butyl 2-bromoacetate were reacted according to General Method 4B at 120° C. After aqueous work-up, the crude product was reacted further without further purification. Yield: 8.6 g (purity 91%, 95% of theory)

LC/MS [Method 1]: $R_t$=0.89 min; MS (ESIpos): m/z=288 (M+H)$^+$

Example 9.2B tert-Butyl [4-(2-bromo-5-chlorophenyl)-2-oxopyridin-1(2H)-yl]acetate

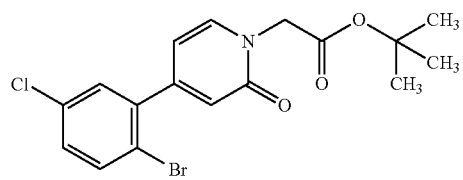 [SMILES: CC(C)(C)OC(=O)Cn1ccc(-c2cc(Cl)ccc2Br)cc1=O]

3.8 g (12 mmol) of tert-butyl (4-bromo-2-oxopyridin-1(2H)-yl)acetate and 3.4 g (14.4 mmol) of 2-bromo-5-chlorophenylboronic acid in the presence of tetrakis(triphenylphosphine)palladium(0) were reacted according to General Method 2A. Yield: 3.9 g (purity 94%, 76% of theory)

LC/MS [Method 1]: $R_t$=1.15 min; MS (ESIpos): m/z=398 (M+H)$^+$

Example 9.2C tert-Butyl 2-[4-(2-bromo-5-chlorophenyl)-2-oxopyridin-1(2H)-yl]-3-(pyridin-3-yl)propanoate (racemate)

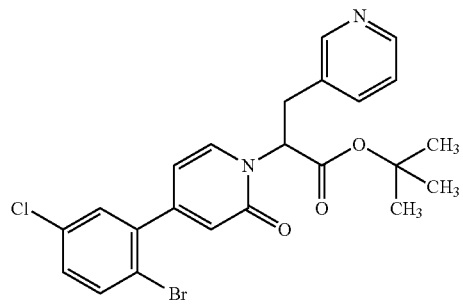 [SMILES: CC(C)(C)OC(=O)C(Cc1cccnc1)n1ccc(-c2cc(Cl)ccc2Br)cc1=O]

206 mg (purity 94%, 0.49 mmol) of tert-butyl [4-(2-bromo-5-chlorophenyl)-2-oxopyridin-1(2H)-yl]acetate and 184 mg (0.73 mmol) of 3-(bromomethyl)pyridine monohydrobromide were reacted according to General Method 7A. Yield: 274 mg (purity 88%, quant.)

LC/MS [Method 1]: $R_t$=1.02 min; MS (ESIpos): m/z=489 (M+H)$^+$

Example 9.2D

2-[4-(2-Bromo-5-chlorophenyl)-2-oxopyridin-1(2H)-yl]-3-(pyridin-3-yl)propanoic acid (racemate

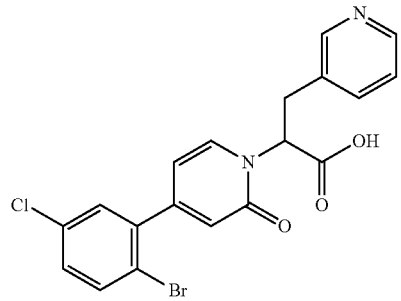 [SMILES: O=C(O)C(Cc1cccnc1)n1ccc(-c2cc(Cl)ccc2Br)cc1=O]

274 mg (purity 88%, 0.49 mmol) of tert-butyl 2-[4-(2-bromo-5-chlorophenyl)-2-oxopyridin-1(2H)-yl]-3-(pyridin- 3-yl)propanoate (racemate) were hydrolysed with TFA according to General Method 6A. Yield: 244 mg (purity 57%, 65% of theory)

LC/MS [Method 1]: $R_t$=0.73 min; MS (ESIpos): m/z=433 (M+H)$^+$

Example 9.2E

Methyl 4-({2-[4-(2-bromo-5-chlorophenyl)-2-oxopyridin-1(2H)-yl]-3-(pyridin-3-yl)propanoyl}amino)benzoate (racemate)

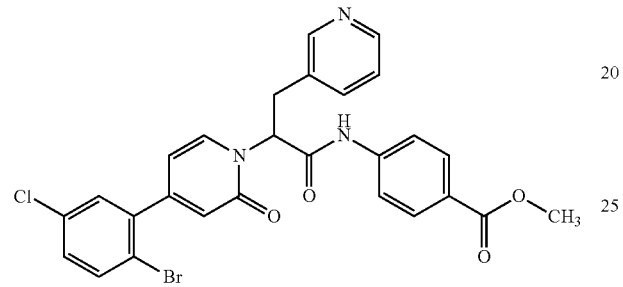

244 mg (purity 57%, 0.32 mmol) of 2-[4-(2-bromo-5-chlorophenyl)-2-oxopyridin-1(2H)-yl]-3-(pyridin-3-yl)propanoic acid (racemate) and 1.2 eq. of methyl 4-aminobenzoate were reacted according to General Method 5A. Yield: 65 mg (purity 85%, 30% of theory)

LC/MS [Method 1]: $R_t$=1.02 min; MS (ESIpos): m/z=566 (M+H)$^+$

Example 10.1A

Ethyl 2-{4-[5-chloro-2-(trifluoromethyl)phenyl]-2-oxopyridin-1(2H)-yl}-3-(pyridin-4-yl)propanoate (racemate)

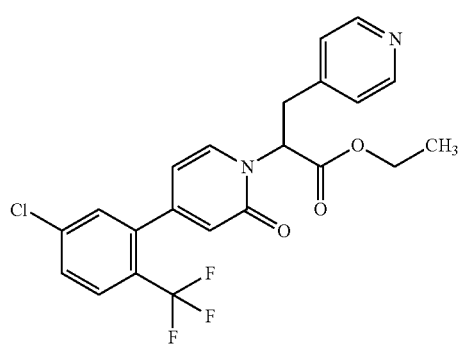 [SMILES: CCOC(=O)C(Cc1ccncc1)n1ccc(-c2cc(Cl)ccc2C(F)(F)F)cc1=O]

1.8 g (5.05 mmol) of ethyl {4-[5-chloro-2-(trifluoromethyl)phenyl]-2-oxopyridin-1(2H)-yl}acetate and 1.9 g (7.6 mmol) of 4-(bromomethyl)pyridine monohydrobromide were reacted according to General Method 7A. Yield: 0.45 g (20% of theory)

LC/MS [Method 2]: $R_t$=2.42 min; MS (ESIpos): m/z=451 (M+H)$^+$

Example 10.1B

2-{4-[5-Chloro-2-(trifluoromethyl)phenyl]-2-oxopyridin-1(2H)-yl}-3-(pyridin-4-yl)propanoic acid (racemate)

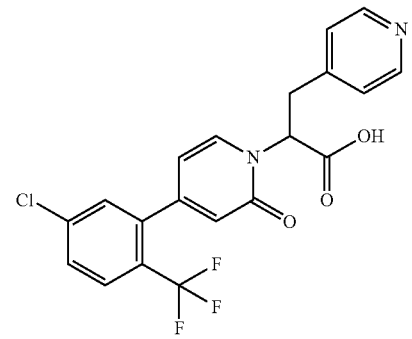 [SMILES: O=C(O)C(Cc1ccncc1)n1ccc(-c2cc(Cl)ccc2C(F)(F)F)cc1=O]

452 mg (1.0 mmol) of ethyl 2-{4-[5-chloro-2-(trifluoromethyl)phenyl]-2-oxopyridin-1(2H)-yl}-3-(pyridin-4-yl)propanoate (racemate) were hydrolysed with lithium hydroxide according to General Method 6B. Yield: 289 mg (68% of theory)

LC/MS [Method 1]: $R_t$=0.70 min; MS (ESIpos): m/z=423 (M+H)$^+$

Example 10.1C tert-Butyl 4-{[2-{4-[5-chloro-2-(trifluoromethyl)phenyl]-2-oxopyridin-1(2H)-yl}-3-(pyridin-4-yl)propanoyl]amino}benzoate (racemate)

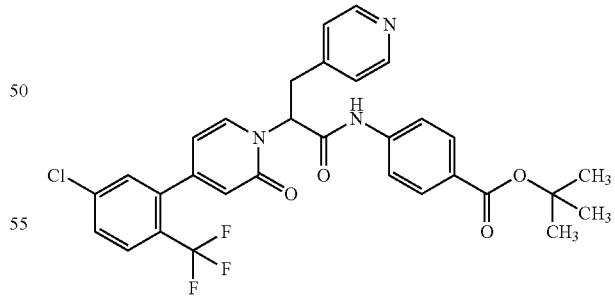

626 mg (purity 50%, 0.74 mmol) of 2-{4-[5-chloro-2-(trifluoromethyl)phenyl]-2-oxopyridin-1(2H)-yl}-3-(pyridin-4-yl)propanoic acid (racemate) and 1.2 eq. of tert-butyl 4-aminobenzoate were reacted according to General Method 5A. Yield: 155 mg (purity 94%, 33% of theory)

LC/MS [Method 1]: $R_t$=1.17 min; MS (ESIpos): m/z=598 (M+H)$^+$

Example 10.2A tert-Butyl 2-[4-(2-bromo-5-chlorophenyl)-2-oxopyridin-1(2H)-yl]-3-(pyridin-4-yl)propanoate (racemate)

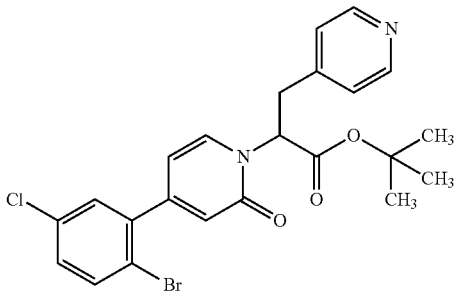 [SMILES: CC(C)(C)OC(=O)C(Cc1ccncc1)n1ccc(-c2cc(Cl)ccc2Br)cc1=O]

1.3 g (purity 94%, 3.0 mmol) of tert-butyl [4-(2-bromo-5-chlorophenyl)-2-oxopyridin-1(2H)-yl]acetate and 1.2 g (4.5 mmol) of 4-(bromomethyl)pyridine monohydrobromide were reacted according to General Method 7A. Yield: 1.7 g (purity 89%, quant.)

LC/MS [Method 1]: $R_t$=0.98 min; MS (ESIpos): m/z=489 (M+H)$^+$

Example 10.2B

2-[4-(2-Bromo-5-chlorophenyl)-2-oxopyridin-1(2H)-yl]-3-(pyridin-4-yl)propanoic acid (racemate

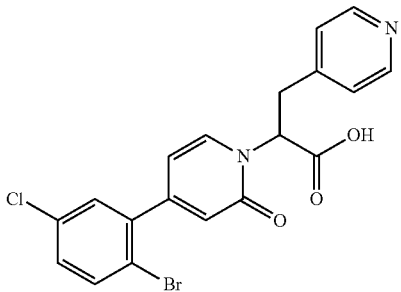 [SMILES: O=C(O)C(Cc1ccncc1)n1ccc(-c2cc(Cl)ccc2Br)cc1=O]

1.7 g (purity 89%, 3.2 mmol) of tert-butyl 2-[4-(2-bromo-5-chlorophenyl)-2-oxopyridin-1(2H)-yl]-3-(pyridin-4-yl)propanoate (racemate) were hydrolysed with TFA according to General Method 6A. After work-up, the residue was triturated with diethyl ether and the solid was filtered off and dried under reduced pressure. Yield: 1.8 g (purity 76%, 99% of theory)

LC/MS [Method 1]: $R_t$=0.64 min; MS (ESIpos): m/z=433 (M+H)$^+$

Example 10.2C tert-Butyl 4-({2-[4-(2-bromo-5-chlorophenyl)-2-oxopyridin-1(2H)-yl]-3-(pyridin-4-yl)propanoyl}amino)benzoate (racemate)

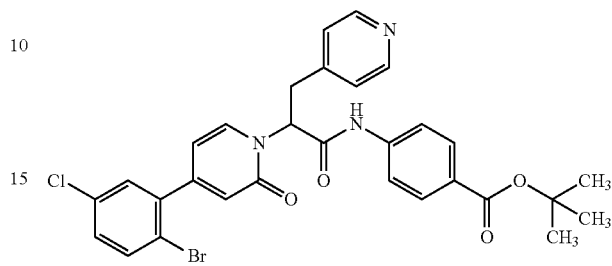

1.8 g (purity 76%, 3.2 mmol) of 2-[4-(2-bromo-5-chlorophenyl)-2-oxopyridin-1(2H)-yl]-3-(pyridin-4-yl)propanoic acid (racemate) and 1.1 eq. of tert-butyl 4-aminobenzoate were reacted according to General Method 5A. Yield: 734 mg (purity 92%, 35% of theory)

LC/MS [Method 1]: Rt=1.16 min; MS (ESIpos): m/z=608 (M+H)$^+$

Example 11.1A

4-Chloro-2-(5-fluoro-2-methoxypyridin-4-yl)benzonitrile

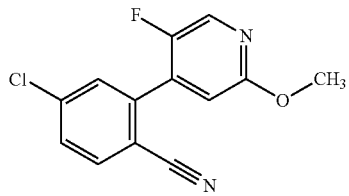

256 mg (1.5 mmol) of 5-fluoro-2-methoxypyridin-4-ylboronic acid and 295 mg (1.34 mmol) of 2-bromo-4-chlorobenzonitrile were reacted according to General Method 2A. The product was precipitated with water. Yield: 146 mg (37% of theory)

LC/MS [Method 1]: $R_t$=1.10 min; MS (ESIpos): m/z=263 (M+H)$^+$

Example 11.1B

4-Chloro-2-(5-fluoro-2-oxo-1,2-dihydropyridin-4-yl)benzonitrile

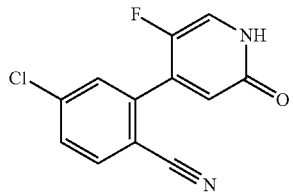

210 mg (0.77 mmol) of 4-chloro-2-(5-fluoro-2-methoxypyridin-4-yl)benzonitrile and pyridinium hydrochloride were reacted according to General Method 3A. Yield: 126 mg (66% of theory)

LC/MS [Method 1]: $R_t$=0.76 min; MS (ESIpos): m/z=249 (M+H)$^+$

Example 11.1C tert-Butyl 2-[4-(5-chloro-2-cyanophenyl)-5-fluoro-2-oxopyridin-1(2H)-yl]propanoate (racemate)

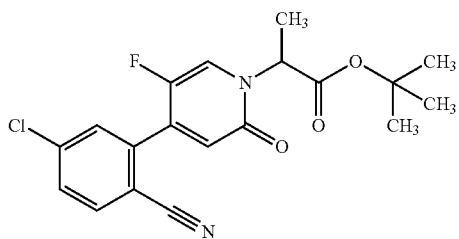 [SMILES: CC(C(=O)OC(C)(C)C)n1cc(F)c(-c2cc(Cl)ccc2C#N)cc1=O]

126 mg (0.51 mmol) of 4-chloro-2-(5-fluoro-2-oxo-1,2-dihydropyridin-4-yl)benzonitrile and 1.05 eq. of tert-butyl 2-bromopropanoate (racemate) were reacted according to General Method 4B at 100° C. Yield: 48 mg (25% of theory)

LC/MS [Method 1]: $R_t$=1.09 min; MS (ESIpos): m/z=377 (M+H)$^+$

Example 11.1D

2-[4-(5-Chloro-2-cyanophenyl)-5-fluoro-2-oxopyridin-1(2H)-yl]propanoic acid (racemate)

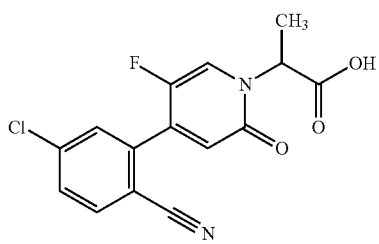 [SMILES: CC(C(=O)O)n1cc(F)c(-c2cc(Cl)ccc2C#N)cc1=O]

46 mg (0.12 mmol) of tert-butyl 2-[4-(5-chloro-2-cyanophenyl)-5-fluoro-2-oxopyridin-1(2H)-yl]propanoate (racemate) were hydrolysed with TFA according to General Method 6A. Yield: 54 mg (purity 90%, quant.)

LC/MS [Method 1]: $R_t$=0.78 min; MS (ESIpos): m/z=321 (M+H)$^+$

Example 11.1E tert-Butyl 4-({2-[4-(5-chloro-2-cyanophenyl)-5-fluoro-2-oxopyridin-1(2H)-yl]propanoyl}amino)benzoate (racemate)

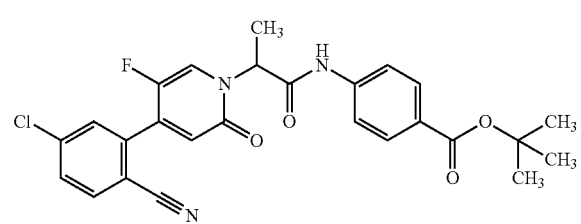 [SMILES: CC(C(=O)Nc1ccc(C(=O)OC(C)(C)C)cc1)n1cc(F)c(-c2cc(Cl)ccc2C#N)cc1=O]

54 mg (purity 90%, 0.15 mmol) of 2-[4-(5-chloro-2-cyanophenyl)-5-fluoro-2-oxopyridin-1(2H)-yl]propanoic acid (racemate) and 1.1 eq. of tert-butyl 4-aminobenzoate were reacted according to General Method 5A. Yield: 51 mg (67% of theory)

LC/MS [Method 1]: Rt=1.23 min; MS (ESIpos): m/z=496 (M+H)$^+$

Example 12.1A (5-Chloro-2-methoxypyridin-4-yl)boronic acid

10.0 g (69.65 mmol) of 5-chloro-2-methoxypyridine were reacted according to General Method 1A. The desired product precipitated on acidification with hydrochloric acid (2N). Yield: 10.44 g (purity 91%, 73% of theory)

LC/MS [Method 1]: $R_t$=0.50 min; MS (ESIpos): m/z=188 (M+H)$^+$ $^1$H-NMR (400 MHz, DMSO-d$_6$): δ [ppm]=8.64 (br. s, 2H), 8.12 (s, 1H), 6.81 (s, 1H), 3.82 (s, 3H).

Example 12.1B

4-Chloro-2-(5-chloro-2-methoxypyridin-4-yl)benzonitrile

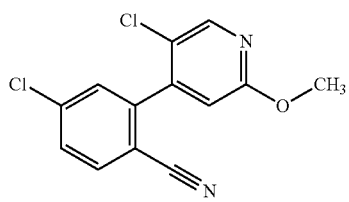 [SMILES: COc1cc(-c2cc(Cl)ccc2C#N)c(Cl)cn1]

5.36 g (purity 91%, 26.03 mmol) of 5-chloro-2-methoxypyridin-4-ylboronic acid and 5.12 g (23.66 mmol) of 2-bromo-4-chlorobenzonitrile in the presence of [1,1-bis(diphenylphosphino)ferrocene]palladium(II) chloride/dichloromethane monoadduct were reacted according to General Method 2A. After work-up, the crude product was then purified by flash chromatography (silica gel 60, cyclohexane/dichloromethane mixtures). Yield: 4.11 g (purity 91%, 52% of theory)

LC/MS [Method 1]: $R_t$=1.17 min; MS (ESIpos): m/z=279 (M+H)$^+$

Example 12.1C

4-Chloro-2-(5-chloro-2-oxo-1,2-dihydropyridin-4-yl)benzonitrile

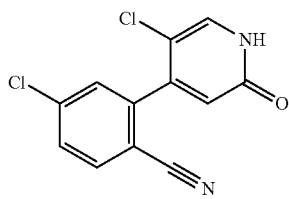 [SMILES: N#Cc1ccc(Cl)cc1-c1cc(=O)[nH]cc1Cl]

6.34 g (purity 93%, 21.12 mmol) of 4-chloro-2-(2,5-dimethoxypyridin-4-yl)benzonitrile and pyridinium hydrochloride were reacted according to General Method 3A. Yield: 4.23 g (76% of theory)

LC/MS [Method 1]: $R_t$=0.82 min; MS (ESIpos): m/z=265 (M+H)$^+$

Example 12.1D

2-[5-Chloro-4-(5-chloro-2-cyanophenyl)-2-oxopyridin-1(2H)-yl]propanoic acid (racemate)

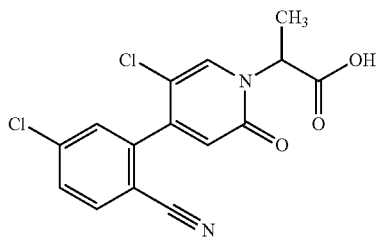

910 mg (purity 57%, 1.96 mmol) of 4-chloro-2-(5-chloro-2-oxo-1,2-dihydropyridin-4-yl)benzonitrile and 1.5 eq. of 2-bromopropanoic acid (racemate) were reacted according to General Method 4A, initially at RT for 2.5 h and then at 45° C. overnight. The desired product was obtained by precipitation with hydrochloric acid. Yield: 1.06 g (purity 78%, quant.)

LC/MS [Method 1]: $R_t$=0.86 min; MS (ESIpos): m/z=337 (M+H)$^+$

Example 12.1E tert-Butyl 4-({2-[5-chloro-4-(5-chloro-2-cyanophenyl)-2-oxopyridin-1(2H)-yl]propanoyl}amino)benzoate (racemate)

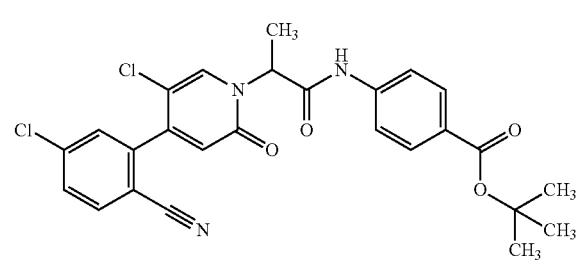 [SMILES: CC(C(=O)Nc1ccc(C(=O)OC(C)(C)C)cc1)n1cc(Cl)c(-c2cc(Cl)ccc2C#N)cc1=O]

135 mg (purity 93%, 0.37 mmol) of 2-[5-chloro-4-(5-chloro-2-cyanophenyl)-2-oxopyridin-1(2H)-yl]propanoic acid (racemate) and 1.2 eq. of tert-butyl 4-aminobenzoate were reacted according to General Method 5A. Yield: 281 mg (purity 58%, 85% of theory)

LC/MS [Method 3]: $R_t$=2.69 min; MS (ESIpos): m/z=512 (M+H)$^+$

Example 12.2A tert-Butyl 5-[4-({2-[5-chloro-4-(5-chloro-2-cyanophenyl)-2-oxopyridin-1(2H)-yl]propanoyl}amino)phenyl]-3-oxo-2,3-dihydro-1H-pyrazole-1-carboxylate (racemate)

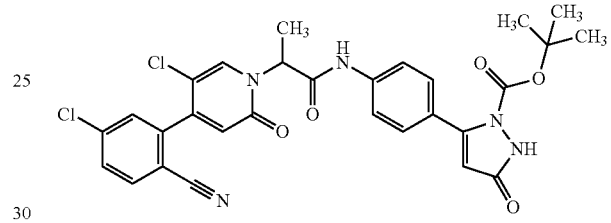

150 mg (purity 82%, 0.37 mmol) of 2-[5-chloro-4-(5-chloro-2-cyanophenyl)-2-oxopyridin-1(2H)-yl]propanoic acid (racemate) and 1.2 eq. of tert-butyl 5-(4-aminophenyl)-3-oxo-2,3-dihydro-1H-pyrazole-1-carboxylate were reacted according to General Method 5A. Yield: 17.8 mg (purity 78%, 6% of theory)

LC/MS [Method 1]: $R_t$=1.17 min; MS (ESIpos): m/z=594 (M+H)$^+$

Example 13.1A tert-Butyl [5-chloro-4-(5-chloro-2-cyanophenyl)-2-oxopyridin-1(2H)-yl]acetate

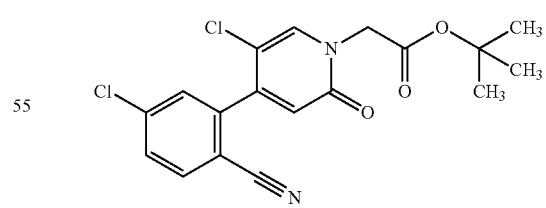

400 mg (purity 91%, 1.37 mmol) of 4-chloro-2-(5-chloro-2-oxo-1,2-dihydropyridin-4-yl)benzonitrile and 1.2 eq. of tert-butyl bromoacetate were reacted according to General Method 4B at 100° C. Yield: 421 mg (80% of theory)

LC/MS [Method 1]: $R_t$=1.11 min; MS (ESIneg): m/z=377 (M−H)$^-$

Example 13.1B tert-Butyl 2-[5-chloro-4-(5-chloro-2-cyanophenyl)-2-oxopyridin-1(2H)-yl]-3-cyclopropylpropanoate (racemate)

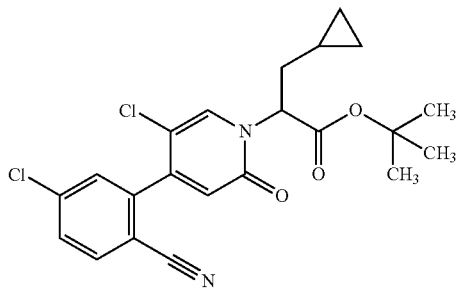 [SMILES: CC(C)(C)OC(=O)C(CC1CC1)n1cc(Cl)c(-c2cc(Cl)ccc2C#N)cc1=O]

349 mg (0.91 mmol) of tert-butyl [5-chloro-4-(5-chloro-2-cyanophenyl)-2-oxopyridin-1(2H)-yl]acetate and 216 mg (1.18 mmol) of (iodomethyl)cyclopropane were reacted according to General Method 7A. Yield: 245 mg (62% of theory)

LC/MS [Method 3]: $R_t$=2.75 min; MS (ESIpos): m/z=433 (M+H)$^+$

Example 13.1C

2-[5-Chloro-4-(5-chloro-2-cyanophenyl)-2-oxopyridin-1(2H)-yl]-3-cyclopropylpropanoic acid (racemate)

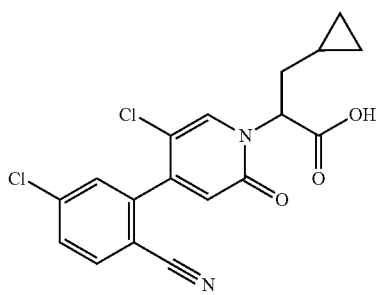 [SMILES: N#Cc1ccc(Cl)cc1-c1cc(=O)n(C(CC2CC2)C(=O)O)cc1Cl]

245 mg (0.57 mmol) of tert-butyl 2-[5-chloro-4-(5-chloro-2-cyanophenyl)-2-oxopyridin-1(2H)-yl]-3-cyclopropylpropanoate (racemate) were hydrolysed with 20 eq. of TFA according to General Method 6A. Yield: 268 mg (quant.)

LC/MS [Method 3]: $R_t$=2.21 min; MS (ESIpos): m/z=377 (M+H)$^+$

Example 13.1D tert-Butyl 4-({2-[5-chloro-4-(5-chloro-2-cyanophenyl)-2-oxopyridin-1(2H)-yl]-3-cyclopropylpropanoyl}amino)benzoate (racemate)

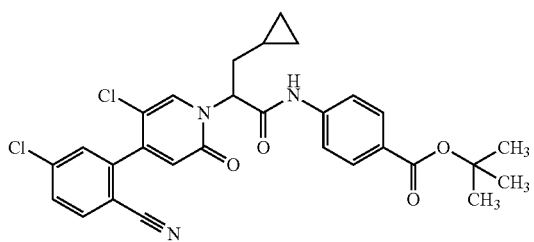 [SMILES: CC(C)(C)OC(=O)c1ccc(NC(=O)C(CC2CC2)n2cc(Cl)c(-c3cc(Cl)ccc3C#N)cc2=O)cc1]

268 mg (0.68 mmol) of 2-[5-chloro-4-(5-chloro-2-cyanophenyl)-2-oxopyridin-1(2H)-yl]-3-cyclopropylpropanoic acid (racemate) and 1.2 eq. of tert-butyl 4-aminobenzoate were reacted according to General Method 5A. Yield: 192 mg (51% of theory)

LC/MS [Method 1]: $R_t$=1.40 min; MS (ESIpos): m/z=552 (M+H)$^+$

Example 14.1A

2-Bromo-4-chloro-1-(difluoromethyl)benzene

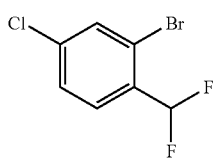 [SMILES: FC(F)c1ccc(Cl)cc1Br]

At 0° C., 0.9 ml (6.83 mmol) of diethylaminosulphur trifluoride was added to a solution of 1.0 g (4.56 mmol) of 2-bromo-4-chlorobenzaldehyde in 12 ml of dichloromethane. The reaction mixture was stirred at RT overnight and then added dropwise to a saturated sodium bicarbonate solution until no more evolution of carbon dioxide was noticeable. After addition of ethyl acetate and phase separation, the aqueous phase was extracted twice with ethyl acetate. The combined organic phases were washed with saturated aqueous sodium chloride solution, dried (sodium sulphate), filtered and briefly (!) concentrated under reduced pressure and dried. Yield: 872 mg (79% of theory)

GC/MS [Method 7]: $R_t$=2.98 min; MS (EI): m/z=240 (M)$^+$

Example 14.1B

5-Chloro-4-[5-chloro-2-(difluoromethyl)phenyl]-2-methoxypyridine

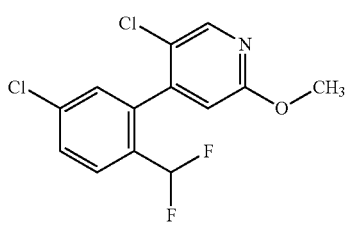 [SMILES: COc1cc(-c2cc(Cl)ccc2C(F)F)c(Cl)cn1]

463 mg (purity 93%, 2.3 mmol) of (5-chloro-2-methoxypyridin-4-yl)boronic acid and 515 mg (2.1 mmol) of 2-bromo-4-chloro-1-(difluoromethyl)benzene in the presence of [1,1-bis(diphenylphosphino)ferrocene]palladium(II) chloride/dichloromethane monoadduct were reacted according to General Method 2A. Yield: 305 mg (purity 77%, 34% of theory)

LC/MS [Method 1]: $R_t$=1.30 min; MS (ESIpos): m/z=304 (M+H)$^+$

Example 14.1C

5-Chloro-4-[5-chloro-2-(difluoromethyl)phenyl]pyridin-2(1H)-one

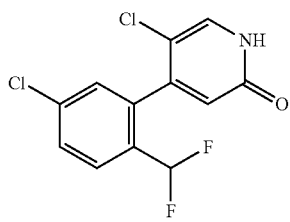 [SMILES: O=c1cc(-c2cc(Cl)ccc2C(F)F)c(Cl)c[nH]1]

305 mg (purity 77%, 0.77 mmol) of 5-chloro-4-[5-chloro-2-(difluoromethyl)phenyl]-2-methoxypyridine and 20 eq. of pyridinium chloride were reacted according to General Method 3A. After work-up, the crude product was purified by preparative HPLC (Reprosil C18, water/acetonitrile gradient). Yield: 179 mg (80% of theory)

LC/MS [Method 1]: $R_t$=0.90 min; MS (ESIpos): m/z=290 (M+H)$^+$

Example 14.1D

2-{5-Chloro-4-[5-chloro-2-(difluoromethyl)phenyl]-2-oxopyridin-1(2H)-yl}propanoic acid

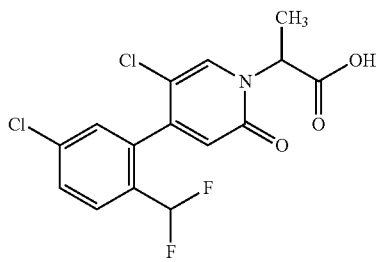 [SMILES: CC(C(=O)O)n1cc(Cl)c(-c2cc(Cl)ccc2C(F)F)cc1=O]

118 mg (0.41 mmol) of 5-chloro-4-[5-chloro-2-(difluoromethyl)phenyl]pyridin-2(1H)-one and 1.5 eq. of 2-bromopropanoic acid (racemate) were reacted according to General Method 4A at 35° C. Yield: 112 mg (76% of theory)

LC/MS [Method 1]: $R_t$=0.96 min; MS (ESIpos): m/z=362 (M+H)$^+$

Example 14.1E tert-Butyl 4-[(2-{5-chloro-4-[5-chloro-2-(difluoromethyl)phenyl]-2-oxopyridin-1(2H)-yl}propanoyl)amino]benzoate (racemate)

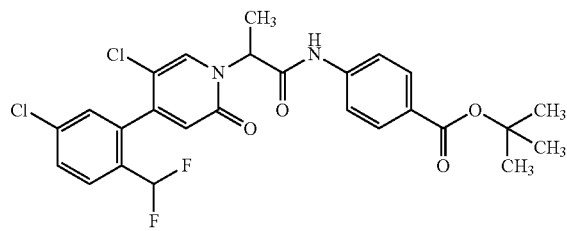 [SMILES: CC(C(=O)Nc1ccc(C(=O)OC(C)(C)C)cc1)n1cc(Cl)c(-c2cc(Cl)ccc2C(F)F)cc1=O]

115 mg (0.32 mmol) of 2-{5-chloro-4-[5-chloro-2-(difluoromethyl)phenyl]-2-oxopyridin-1(2H)-yl}propanoic acid (racemate) and 1.2 eq. of tert-butyl 4-aminobenzoate were reacted according to General Method 5A. After work-up, the crude product was purified by preparative HPLC (Reprosil C18, water/acetonitrile gradient). Yield: 79 mg (46% of theory)

LC/MS [Method 1]: $R_t$=1.31 min; MS (ESIpos): m/z=537 (M+H)$^+$

Example 15.1A

5-Chloro-4-[5-chloro-2-(trifluoromethyl)phenyl]-2-methoxypyridine

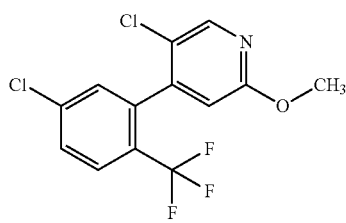 [SMILES: COc1cc(-c2cc(Cl)ccc2C(F)(F)F)c(Cl)cn1]

443 mg (2.20 mmol) of 5-chloro-2-methoxypyridin-4-ylboronic acid and 571 mg (2.20 mmol) of 2-bromo-4-chloro-1-(trifluoromethyl)benzene in the presence of XPhos precatalyst were reacted according to General Method 2B. Yield: 193 mg (purity 93%, 25% of theory)

LC/MS [Method 1]: $R_t$=1.36 min; MS (ESIpos): m/z=322 (M+H)$^+$

Example 15.1B

5-Chloro-4-[5-chloro-2-(trifluoromethyl)phenyl]pyridin-2(1H)-one

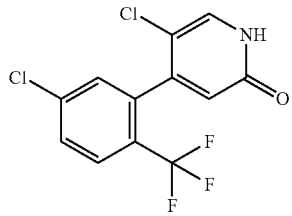 [SMILES: O=c1cc(-c2cc(Cl)ccc2C(F)(F)F)c(Cl)c[nH]1]

193 mg (purity 93%, 0.56 mmol) of 5-chloro-4-[5-chloro-2-(trifluoromethyl)phenyl]-2-methoxypyridine and pyridinium hydrochloride were reacted according to General Method 3A. Yield: 123 mg (72% of theory)

LC/MS [Method 1]: $R_t$=0.97 min; MS (ESIpos): m/z=308 (M+H)$^+$

Example 15.1C tert-Butyl 2-{5-chloro-4-[5-chloro-2-(trifluoromethyl)phenyl]-2-oxopyridin-1(2H)-yl}propanoate

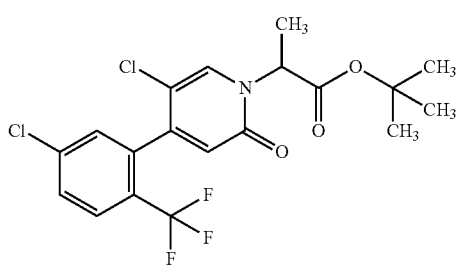 [SMILES: CC(C(=O)OC(C)(C)C)n1cc(Cl)c(-c2cc(Cl)ccc2C(F)(F)F)cc1=O]

123 mg (0.4 mmol) of 5-chloro-4-[5-chloro-2-(trifluoromethyl)phenyl]pyridin-2(1H)-one and 1.05 eq. of tert-butyl 2-bromopropanoate (racemate) were reacted according to General Method 4B at 100° C. Yield: 81 mg (47% of theory)

LC/MS [Method 1]: $R_t$=1.27 min; MS (ESIpos): m/z=436 (M+H)$^+$

Example 15.1D

2-{5-Chloro-4-[5-chloro-2-(trifluoromethyl)phenyl]-2-oxopyridin-1(2H)-yl}propanoic acid (racemate)

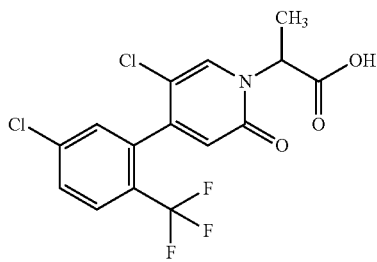 [SMILES: CC(C(=O)O)n1cc(Cl)c(-c2cc(Cl)ccc2C(F)(F)F)cc1=O]

81 mg (0.19 mmol) of 2-{5-chloro-4-[5-chloro-2-(trifluoromethyl)phenyl]-2-oxopyridin-1(2H)-yl}propanoic acid (racemate) were hydrolysed with TFA according to General Method 6A. Yield: 78 mg (purity 94%, quant.)

LC/MS [Method 1]: $R_t$=0.98 min; MS (ESIpos): m/z=380 (M+H)$^+$

Example 15.1E

2-{5-Chloro-4-[5-chloro-2-(trifluoromethyl)phenyl]-2-oxopyridin-1(2H)-yl}propanoic acid

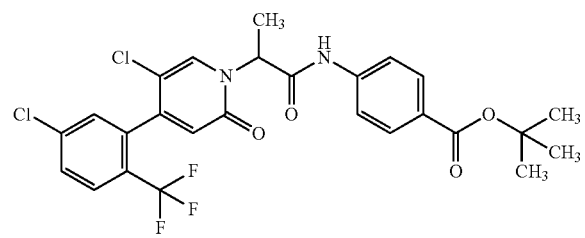 [SMILES: CC(C(=O)Nc1ccc(C(=O)OC(C)(C)C)cc1)n1cc(Cl)c(-c2cc(Cl)ccc2C(F)(F)F)cc1=O]

78 mg (purity 94%, 0.19 mmol) of 2-{5-chloro-4-[5-chloro-2-(trifluoromethyl)phenyl]-2-oxopyridin-1(2H)-yl}propanoic acid (racemate) and 1.2 eq. of tert-butyl 4-aminobenzoate were reacted according to General Method 5A. Yield: 75 mg (70% of theory)

LC/MS [Method 1]: $R_t$=1.37 min; MS (ESIpos): m/z=555 (M+H)$^+$

Example 16.1A (5-Cyano-2-methoxypyridin-4-yl)boronic acid

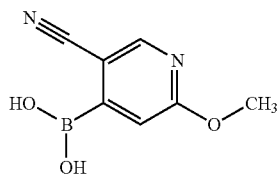

10.0 g (74.6 mmol) of 6-methoxypyridine-3-carbonitrile were reacted according to General Method 1A. Yield: 10.5 g (purity 89%, 70% of theory)

LC/MS [Method 1]: $R_t$=0.51 min; MS (ESIpos): m/z=179 (M+H)$^+$

Example 16.1B 4-(5-Chloro-2-cyanophenyl)-6-methoxypyridine-3-carbonitrile

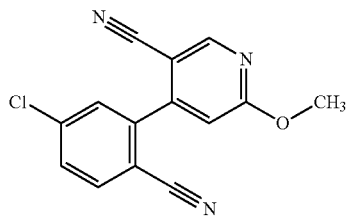 [SMILES: COc1cc(-c2cc(Cl)ccc2C#N)c(C#N)cn1]

600 mg (purity 89%, 3.0 mmol) of 5-cyano-2-methoxypyridin-4-ylboronic acid and 649 mg (3.0 mmol) of 2-bromo-4-chlorobenzonitrile in the presence of [1,1-bis(diphenylphosphino)ferrocene]palladium(II) chloride/dichloromethane monoadduct were reacted according to General Method 2A. After aqueous work-up, the crude product was triturated with water and then with cyclohexane/ethyl acetate (7:3), and the solid was filtered off and dried under high vacuum. Yield: 399 mg (purity 94%, 46% of theory)

LC/MS [Method 1]: $R_t$=1.02 min; MS (ESIpos): m/z=270 (M+H)$^+$

Example 16.1C 4-(5-Chloro-2-cyanophenyl)-6-oxo-1,6-dihydropyridine-3-carbonitrile

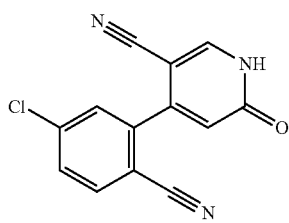 [SMILES: N#Cc1ccc(Cl)cc1-c1cc(=O)[nH]cc1C#N]

414 mg (purity 94%, 1.14 mmol) of 4-(5-chloro-2-cyanophenyl)-6-methoxypyridin-3-carbonitrile and pyridinium hydrochloride were reacted according to General Method 3A. Yield: 312 mg (purity 91%, 77% of theory)

LC/MS [Method 1]: $R_t$=0.71 min; MS (ESIpos): m/z=256 (M+H)$^+$

Example 16.1D

2-[4-(5-Chloro-2-cyanophenyl)-5-cyano-2-oxopyridin-1(2H)-yl]propanoic acid (racemate)

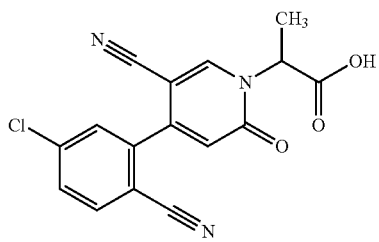 [SMILES: CC(C(=O)O)n1cc(C#N)c(-c2cc(Cl)ccc2C#N)cc1=O]

312 mg (purity 91%, 1.11 mmol) of 4-(5-chloro-2-cyanophenyl)-6-oxo-1,6-dihydropyridin-3-carbonitrile and 1.5 eq. of 2-bromopropanoic acid (racemate) were reacted according to General Method 4A at 45° C. Yield: 240 mg (purity 85%, 56% of theory)

LC/MS [Method 1]: $R_t$=0.78 min; MS (ESIpos): m/z=328 (M+H)$^+$

Example 16.1E tert-Butyl 4-({2-[4-(5-chloro-2-cyanophenyl)-5-cyano-2-oxopyridin-1(2H)-yl]propanoyl}amino)benzoate (racemate)

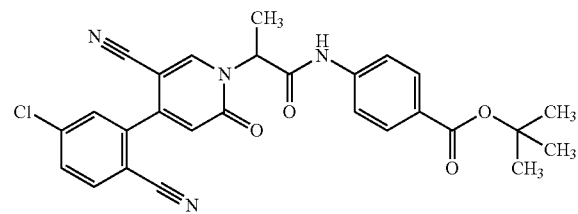 [SMILES: CC(C(=O)Nc1ccc(C(=O)OC(C)(C)C)cc1)n1cc(C#N)c(-c2cc(Cl)ccc2C#N)cc1=O]

240 mg (purity 85%, 0.62 mmol) of 2-[4-(5-chloro-2-cyanophenyl)-5-cyano-2-oxopyridin-1(2H)-yl]propanoic acid (racemate) and 1.1 eq. of tert-butyl 4-aminobenzoate were reacted according to General Method 5A. Yield: 93 mg (30% of theory)

LC/MS [Method 1]: $R_t$=1.17 min; MS (ESIneg): m/z=501 (M−H)$^−$

Example 17.1A

4-[5-Chloro-2-(difluoromethyl)phenyl]-6-methoxypyridine-3-carbonitrile

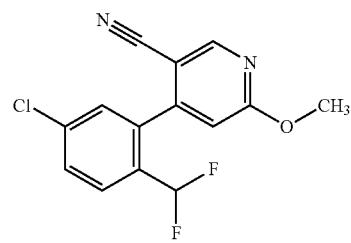 [SMILES: COc1cc(-c2cc(Cl)ccc2C(F)F)c(C#N)cn1]

724 mg (3.0 mmol) of 5-chloro-2-methoxypyridin-4-yl-boronic acid and 600 mg (3.0 mmol) of 2-bromo-4-chloro-1-(difluoromethyl)benzene in the presence of XPhos precatalyst were reacted according to General Method 2B. Yield: 143 mg (purity 65%, 11% of theory)

LC/MS [Method 1]: $R_t$=1.15 min; MS (ESIpos): m/z=295 (M+H)$^+$

Example 17.1B

4-[5-Chloro-2-(difluoromethyl)phenyl]-6-oxo-1,6-dihydropyridine-3-carbonitrile

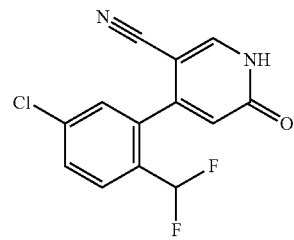 [SMILES: N#Cc1c[nH]c(=O)cc1-c1cc(Cl)ccc1C(F)F]

143 mg (purity 65%, 0.32 mmol) of 4-[5-chloro-2-(difluoromethyl)phenyl]-6-methoxypyridin-3-carbonitrile and pyridinium hydrochloride were reacted according to General Method 3A. Yield: 88 mg (99% of theory)

LC/MS [Method 1]: $R_t$=0.82 min; MS (ESIpos): m/z=281 (M+H)$^+$

Example 17.1C

2-{4-[5-Chloro-2-(difluoromethyl)phenyl]-5-cyano-2-oxopyridin-1(2H)-yl}propanoic acid (racemate)

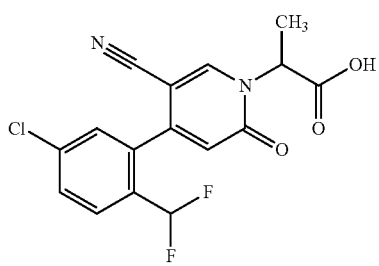 [SMILES: CC(C(=O)O)n1cc(C#N)c(-c2cc(Cl)ccc2C(F)F)cc1=O]

88 mg (0.31 mmol) of 4-[5-chloro-2-(difluoromethyl)phenyl]-6-oxo-1,6-dihydropyridin-3-carbonitrile and 1.5 eq. of 2-bromopropanoic acid (racemate) were reacted according to General Method 4A at 45° C. Yield: 88 mg (purity 92%, 73% of theory)

LC/MS [Method 1]: $R_t$=0.87 min; MS (ESIpos): m/z=353 $(M+H)^+$

Example 17.1D tert-Butyl 4-[(2-{4-[5-chloro-2-(difluoromethyl)phenyl]-5-cyano-2-oxopyridin-1(2H)-yl}propanoyl)amino]benzoate (racemate)

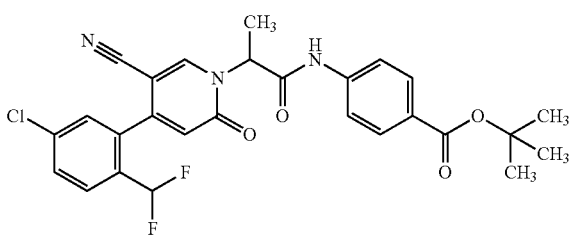 [SMILES: CC(C(=O)Nc1ccc(C(=O)OC(C)(C)C)cc1)n1cc(C#N)c(-c2cc(Cl)ccc2C(F)F)cc1=O]

88 mg (purity 92%, 0.23 mmol) of 2-{4-[5-chloro-2-(difluoromethyl)phenyl]-5-cyano-2-oxopyridin-1(2H)-yl}propanoic acid (racemate) and 1.1 eq. of tert-butyl 4-aminobenzoate were reacted according to General Method 5A. Yield: 48 mg (36% of theory)

LC/MS [Method 1]: $R_t$=1.24 min; MS (ESIpos): m/z=528 $(M+H)^+$

Example 18.1A

4-Iodo-6-methoxypyridine-3-carbonitrile

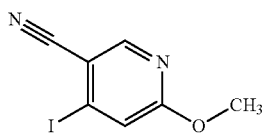

At −78° C., 19.4 ml of lithium diisopropylamide (2 molar in THF/heptane/ethylbenzene, 1.3 eq.) were added to a solution of 4.0 g (29.8 mmol) of 6-methoxypyridine-3-carbonitrile in 120 ml of THF, and the mixture was stirred at −78° C. for 1 h. At −78° C., a solution of 9.1 g (35.8 mmol) of iodine in 20 ml of THF was then added, and the reaction mixture was stirred at −78° C. for 1 h and then carefully added to saturated aqueous ammonium chloride solution. After addition of ethyl acetate, the reaction mixture was extracted three times with ethyl acetate. The combined organic phases were dried (magnesium sulphate), filtered and concentrated under reduced pressure. The crude product was purified by flash chromatography (silica gel 60, mobile phase: cyclohexane/ethyl acetate mixtures). Yield: 4.0 g (purity 92%, 48% of theory)

GC [Method 7]: $R_t$=5.08 min; MS (EI) m/z=260 $(M)^+$ $^1$H-NMR (400 MHz, DMSO-$d_6$): δ [ppm]=8.63 (s, 1H), 7.61 (s, 1H), 3.92 (s, 1H).

Example 18.1B

4-Bromo-6-oxo-1,6-dihydropyridine-3-carbonitrile

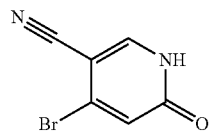

4.5 g (purity 90%, 15.6 mmol) of 4-iodo-6-methoxypyridin-3-carbonitrile and 20 eq. of pyridinium hydrobromide were reacted according to General Method 3A. After aqueous work-up, the crude product was reacted further without further purification. Yield: 1.99 g (purity 77%, 49% of theory) of the title compound as a mixture with 11% of the analogous iodine compound.

LC/MS [Method 1]: $R_t$=0.48 min; MS (ESIpos): m/z=199 $(M+H)^+$

Example 18.1C 2-(4-Bromo-5-cyano-2-oxopyridin-1(2H)-yl)propanoic acid (racemate)

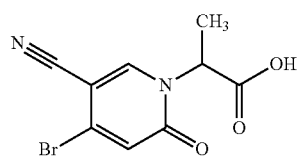

1.0 g (purity 77%, 3.87 mmol) of 4-bromo-6-oxo-1,6-dihydropyridin-3-carbonitrile and 1.5 eq. of 2-bromopropanoic acid (racemate) were reacted according to General Method 4A at 35-45° C. After aqueous work-up, the crude product was triturated with cyclohexane/dichloromethane, and the solid was filtered off and dried under high vacuum. Yield: 648 mg (purity 66%, 41% of theory)

The filtrate was concentrated under reduced pressure and the residue was purified by preparative HPLC (Reprosil C18, water/acetonitrile gradient). Yield: 110 mg (purity 91%, 10% of theory)

LC/MS [Method 1]: $R_t$=0.58 min; MS (ESIpos): m/z=271 $(M+H)^+$

Example 18.1D tert-Butyl 4-{[2-(4-bromo-5-cyano-2-oxopyridin-1(2H)-yl)propanoyl]amino}benzoate (racemate)

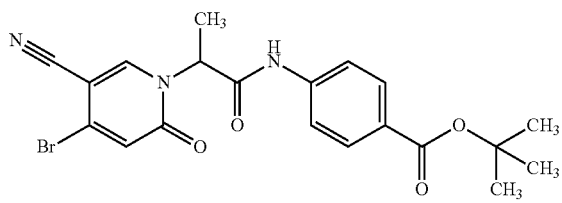 [SMILES: CC(C(=O)Nc1ccc(C(=O)OC(C)(C)C)cc1)n1cc(C#N)c(Br)cc1=O]

750 mg (purity 70%, 1.94 mmol) of 2-(4-bromo-5-cyano-2-oxopyridin-1(2H)-yl)propanoic acid (racemate) and 1.2 eq. of tert-butyl 4-aminobenzoate were reacted according to General Method 5A. Yield: 704 mg (purity 70%, 57% of theory)

LC/MS [Method 1]: $R_t$=1.12 min; MS (ESIneg): m/z=444 (M–H)⁻

Example 18.1E tert-Butyl 4-[(2-{4-[5-chloro-2-(trifluoromethyl)phenyl]-5-cyano-2-oxopyridin-1(2H)-yl}propanoyl)amino]benzoate (racemate)

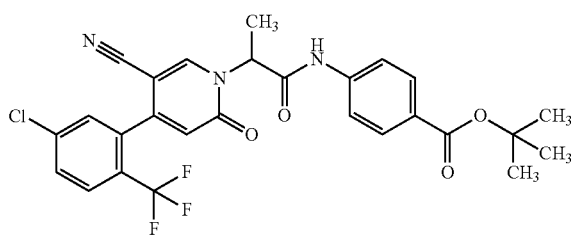 [SMILES: CC(C(=O)Nc1ccc(C(=O)OC(C)(C)C)cc1)n1cc(C#N)c(-c2cc(Cl)ccc2C(F)(F)F)cc1=O]

127 mg (purity 70%, 0.2 mmol) of tert-butyl 4-{[2-(4-bromo-5-cyano-2-oxopyridin-1(2H)-yl)propanoyl]amino}benzoate (racemate) and 54 mg (0.24 mmol) of 5-chloro-2-trifluoromethylphenylboronic acid in the presence of [1,1-bis(diphenylphosphino)ferrocene]palladium(II) chloride/dichloromethane monoadduct were reacted according to General Method 2A. After aqueous work-up, the crude product was triturated with water and the solid was filtered off, dried and purified further by flash chromatography (silica gel 60, mobile phase: cyclohexane/ethyl acetate mixtures). Yield: 124 mg (quant.)

LC/MS [Method 1]: $R_t$=1.28 min; MS (ESIpos): m/z=546 (M+H)⁺

¹H-NMR (400 MHz, DMSO-d₆): δ [ppm]=10.84 (d, 1H), 8.79 (s, 1H), 7.96 (dd, 1H), 7.89 (d, 2H), 7.84 (m, 2H), 7.71 (d, 2H), 6.58 (s, 1H), 5.57 (m, 1H), 1.76 (d, 3H), 1.54 (s, 9H).

Example 18.2A tert-Butyl 4-[(2-{4-[5-chloro-2-(trifluoromethoxy)phenyl]-5-cyano-2-oxopyridin-1(2H)-yl}propanoyl)amino]benzoate (racemate)

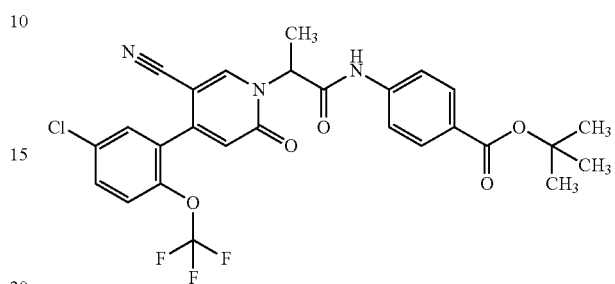

127 mg (purity 70%, 0.2 mmol) of tert-butyl 4-{[2-(4-bromo-5-cyano-2-oxopyridin-1(2H)-yl)propanoyl]amino}benzoate (racemate) and 58 mg (0.24 mmol) of 5-chloro-2-trifluoromethoxyphenylboronic acid in the presence of [1,1-bis(diphenylphosphino)ferrocene]palladium(II) chloride/dichloromethane monoadduct were reacted according to General Method 2A. Yield: 107 mg (purity 94%, 89% of theory)

LC/MS [Method 1]: $R_t$=1.29 min; MS (ESIpos): m/z=562 (M+H)⁺

Example 18.3A tert-Butyl 4-({2-[4-(5-chloro-2-cyclopropylphenyl)-5-cyano-2-oxopyridin-1(2H)-yl]propanoyl}amino)benzoate (racemate)

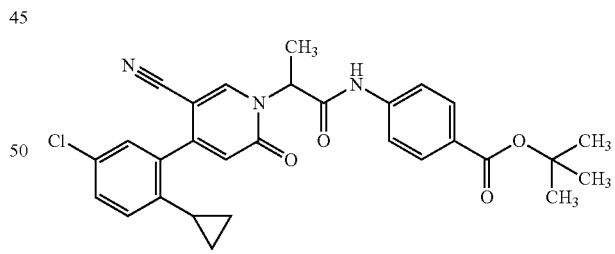

127 mg (purity 70%, 0.2 mmol) of tert-butyl 4-{[2-(4-bromo-5-cyano-2-oxopyridin-1(2H)-yl)propanoyl]amino}benzoate (racemate) and 67 mg (0.24 mmol) of 2-(5-chloro-2-cyclopropylphenyl)-4,4,5,5-tetramethyl-1,3,2-dioxaborolane in the presence of [1,1-bis(diphenylphosphino)ferrocene]palladium(II) chloride/dichloromethane monoadduct were reacted according to General Method 2A. Yield: 66 mg (62% of theory)

LC/MS [Method 1]: $R_t$=1.28 min; MS (ESIpos): m/z=518 (M+H)⁺

Example 19.1A

4-Iodo-6-methoxypyridine-3-carbaldehyde

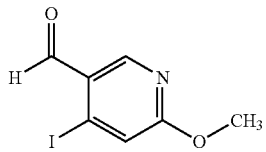

At −78° C., 25.1 ml (40.1 mmol, 1.1 eq.) of n-butyllithium were added to a solution of 5.7 ml (43.8 mmol, 1.2 eq.) of N,N,N'-trimethylethylenediamine in 135 ml of THF, the mixture was stirred for 45 min and 5.0 g (36.5 mmol) of 6-methoxypyridine-3-carbaldehyde were added. After 45 min at −78° C., a further 45.6 ml (72.9 mmol, 2.0 eq.) of n-butyllithium were added, the reaction mixture was stirred for 1 h, allowing the temperature to rise to −40° C., the mixture was stirred at −40° C. for a further 1 h and then cooled back to −78° C., and a solution of 18.5 g (72.9 mmol) of iodine in 90 ml of THF was added over a period of 50 min. The temperature was maintained at −78° C. for a further 4 h and then slowly allowed to rise to RT overnight. The reaction mixture was poured into 300 ml of saturated aqueous sodium chloride solution and, after phase separation, the aqueous phase was extracted twice with ethyl acetate. The combined organic phases were dried (sodium sulphate), filtered and concentrated under reduced pressure. The residue was stirred with acetonitrile and filtered off, and the precipitate was dried under HV. Yield: 647 mg (purity 91%, 6% of theory)

Further precipitate from the mother liquor was filtered off and dried under reduced pressure. Yield: 1050 mg (purity 70%, 8% of theory)

The combined mother liquors were concentrated under reduced pressure and the residue was further purified by flash chromatography (silica gel 60, mobile phase: cyclohexane/ethyl acetate mixtures). Yield: 1188 mg (purity 75%, 9% of theory)

LC/MS [Method 1]: $R_t$=0.90 min; MS (ESIpos): m/z=264 (M+H)$^+$ $^1$H-NMR (400 MHz, DMSO-d$_6$): δ [ppm]=9.89 (s, 1H), 8.52 (s, 1H), 7.56 (s, 1H), 3.94 (s, 3H).

Example 19.1B 5-(Difluoromethyl)-4-iodo-2-methoxypyridine

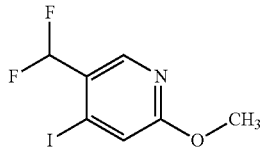

At 0° C., 0.7 ml (5.1 mmol, 1.5 eq.) of diethylaminosulphur trifluoride were added to a solution of 1.0 g (purity 91%, 3.46 mmol) of 4-iodo-6-methoxypyridin-3-carbaldehyde in 30 ml dichloromethane, and the mixture was stirred at RT overnight. The reaction mixture was added dropwise to a saturated sodium bicarbonate solution until no more evolution of carbon dioxide was noticeable. After addition of ethyl acetate and phase separation, the aqueous phase was extracted twice with ethyl acetate. The combined organic phases were washed with saturated aqueous sodium chloride solution, dried (sodium sulphate), filtered and briefly (!) concentrated under reduced pressure and dried. Yield: 616 mg (purity 83%, 52% of theory)

LC/MS [Method 1]: $R_t$=1.04 min; MS (ESIpos): m/z=286 (M+H)$^+$

Example 19.1C

4-Chloro-2-[5-(difluoromethyl)-2-methoxypyridin-4-yl]benzonitrile

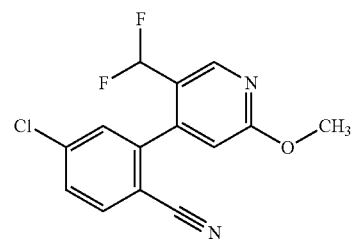 [SMILES: COc1cc(-c2cc(Cl)ccc2C#N)c(C(F)F)cn1]

616 mg (purity 83%, 1.79 mmol) of 5-(difluoromethyl)-4-iodo-2-methoxypyridine and 325 mg (1.79 mmol) of 5-chloro-2-cyanophenylboronic acid in the presence of [1,1-bis(diphenylphosphino)ferrocene]palladium(II) chloride/dichloromethane monoadduct were reacted according to General Method 2A. Yield: 223 mg (42% of theory)

LC/MS [Method 1]: $R_t$=1.11 min; MS (ESIpos): m/z=295 (M+H)$^+$

Example 19.1D

4-Chloro-2-[5-(difluoromethyl)-2-oxo-1,2-dihydropyridin-4-yl]benzonitrile

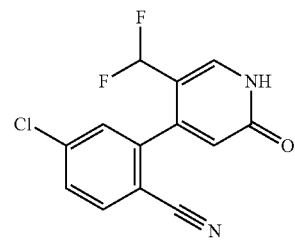 [SMILES: N#Cc1ccc(Cl)cc1-c1cc(=O)[nH]cc1C(F)F]

216 mg (0.73 mmol) of 4-chloro-2-[5-(difluoromethyl)-2-methoxypyridin-4-yl]benzonitrile and pyridinium hydrobromide were reacted according to General Method 3A. Yield: 215 mg (purity 64%, 67% of theory)

LC/MS [Method 1]: $R_t$=0.81 min; MS (ESIpos): m/z=281 (M+H)$^+$

Example 19.1E

2-[4-(5-Chloro-2-cyanophenyl)-5-(difluoromethyl)-2-oxopyridin-1(2H)-yl]propanoic acid (racemate)

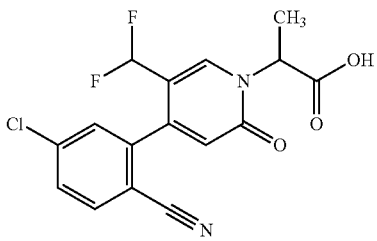 [SMILES: CC(C(=O)O)n1cc(C(F)F)c(-c2cc(Cl)ccc2C#N)cc1=O]

215 mg (purity 64%, 0.5 mmol) of 4-chloro-2-[5-(difluoromethyl)-2-oxo-1,2-dihydropyridin-4-yl]benzonitrile and 1.5 eq. of 2-bromopropanoic acid (racemate) were reacted according to General Method 4A at 50° C. Yield: 256 mg of crude product (purity 64%, 95% of theory)

LC/MS [Method 1]: $R_t$=0.86 min; MS (ESIpos): m/z=353 (M+H)$^+$

Example 19.1F tert-Butyl 4-({2-[4-(5-chloro-2-cyanophenyl)-5-(difluoromethyl)-2-oxopyridin-1(2H)-yl]propanoyl}amino)benzoate (racemate)

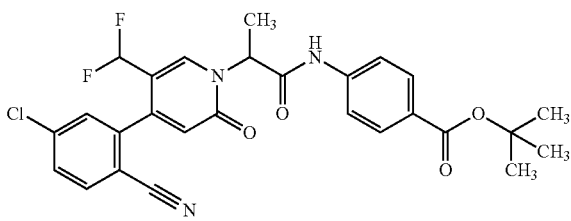 [SMILES: CC(C(=O)Nc1ccc(C(=O)OC(C)(C)C)cc1)n1cc(C(F)F)c(-c2cc(Cl)ccc2C#N)cc1=O]

65 mg (purity 88%, 0.16 mmol) of 2-[4-(5-chloro-2-cyanophenyl)-5-(difluoromethyl)-2-oxopyridin-1(2H)-yl]propanoic acid (racemate) and 1.2 eq. of tert-butyl 4-aminobenzoate were reacted according to General Method 5A. Yield: 65 mg (76% of theory)

LC/MS [Method 1]: $R_t$=1.23 min; MS (ESIpos): m/z=528 (M+H)$^+$ $^1$H-NMR (400 MHz, DMSO-d$_6$): δ [ppm]=10.85 (s, 1H), 8.30 (s, 1H), 8.02 (d, 1H), 7.88 (d, 2H), 7.74 (m, 4H), 6.85 (br. t, 1H), 6.56 (s, 1H), 5.58 (q, 1H), 1.74 (d, 3H), 1.55 (s, 9H).

Example 20.1A

2-Methoxy-5-trifluoromethylpyridin-4-ylboronic acid

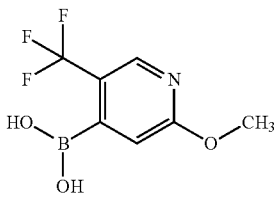

10 g (56.5 mmol) of 2-methoxy-5-(trifluoromethyl)pyridine were reacted according to General Method 1A. Yield: 4.4 g (34% of theory)

$^1$H-NMR (400 MHz, DMSO-d$_6$): δ [ppm]=8.63 (br. s, 2H), 8.50 (s, 1H), 6.91 (s, 1H), 3.92 (s, 3H).

Example 20.1B

4-Chloro-2-[2-methoxy-5-(trifluoromethyl)pyridin-4-yl]benzonitrile

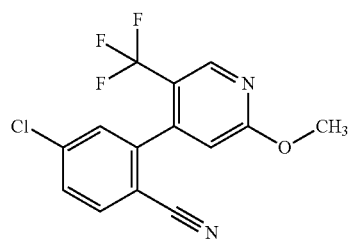 [SMILES: COc1cc(-c2cc(Cl)ccc2C#N)c(C(F)(F)F)cn1]

1.0 g (4.4 mmol) of 2-methoxy-5-trifluoromethylpyridin-4-ylboronic acid and 0.95 g (4.4 mmol) of 2-bromo-4-chlorobenzonitrile in the presence of [1,1-bis(diphenylphosphino)ferrocene]palladium(II) chloride/dichloromethane monoadduct were reacted according to General Method 2A. Yield: 351 mg (purity 71%, 18% of theory)

LC/MS [Method 1]: $R_t$=1.19 min; MS (ESIpos): m/z=313 (M+H)$^+$ $^1$H-NMR (400 MHz, DMSO-d$_6$): δ [ppm]=8.76 (s, 1H), 8.07 (d, 1H), 7.81 (dd, 1H), 7.77 (s, 1H), 7.16 (s, 1H), 4.01 (s, 3H).

Example 20.1C

4-Chloro-2-[2-oxo-5-(trifluoromethyl)-1,2-dihydropyridin-4-yl]benzonitrile

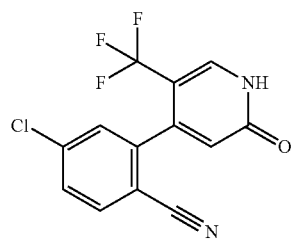 [SMILES: N#Cc1ccc(Cl)cc1-c1cc(=O)[nH]cc1C(F)(F)F]

450 mg (purity 71%, 1.02 mmol) of 4-chloro-2-[2-methoxy-5-(trifluoromethyl)pyridin-4-yl]benzonitrile and 20 eq. of pyridinium hydrochloride were reacted according to General Method 3A. After aqueous work-up, the crude product was purified by flash chromatography (silica gel 60, dichloromethane/methanol mixtures). Yield: 456 mg (purity 86%, quant.)

LC/MS [Method 1]: $R_t$=0.89 min; MS (ESIpos): m/z=299 (M+H)$^+$ $^1$H-NMR (400 MHz, DMSO-d$_6$): δ [ppm]=12.58 (br. s, 1H), 8.09 (s, 1H), 8.03 (d, 1H), 7.77 (dd, 1H), 7.74 (s, 1H), 6.51 (s, 1H).

Example 20.1D

2-[4-(5-Chloro-2-cyanophenyl)-2-oxo-5-(trifluoromethyl)pyridin-1(2H)-yl]propanoic acid (racemate)

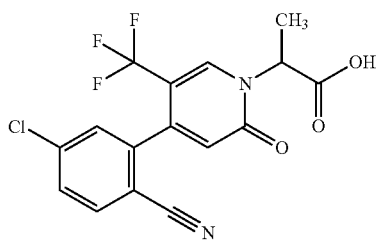 [SMILES: CC(C(=O)O)n1cc(C(F)(F)F)c(-c2cc(Cl)ccc2C#N)cc1=O]

456 mg (purity 86%, 1.31 mmol) of 4-chloro-2-[2-oxo-5-(trifluoromethyl)-1,2-dihydropyridin-4-yl]benzonitrile and 1.5 eq. of 2-bromopropanoic acid (racemate) were reacted according to General Method 4A at 50° C. Yield: 515 mg (purity 51%, 54% of theory)

LC/MS [Method 1]: $R_t$=0.91 min; MS (ESIpos): m/z=371 (M+H)$^+$

Example 20.1E tert-Butyl 4-({2-[4-(5-chloro-2-cyanophenyl)-2-oxo-5-(trifluoromethyl)pyridin-1(2H)-yl]propanoyl}amino)benzoate (racemate)

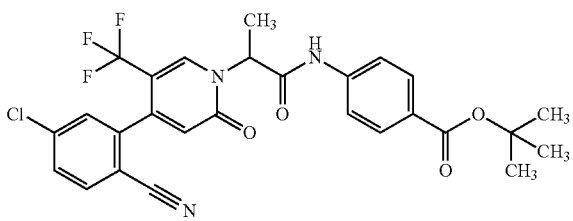 [SMILES: CC(C(=O)Nc1ccc(C(=O)OC(C)(C)C)cc1)n1cc(C(F)(F)F)c(-c2cc(Cl)ccc2C#N)cc1=O]

515 mg (purity 51%, 0.71 mmol) of 2-[4-(5-chloro-2-cyanophenyl)-2-oxo-5-(trifluoromethyl)pyridin-1(2H)-yl]propanoic acid (racemate) and 1.2 eq. of tert-butyl 4-aminobenzoate were reacted according to General Method 5A. Yield: 251 mg (purity 79%, 51% of theory)

LC/MS [Method 1]: $R_t$=1.30 min; MS (ESIpos): m/z=546 (M+H)$^+$

Example 21.1A 2,5-Dimethoxypyridin-4-ylboronic acid

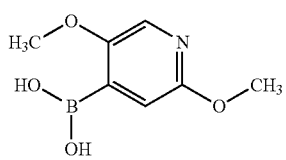

11.53 g (82.9 mmol) of 2,5-dimethoxypyridine were reacted according to General Method 1A. The desired product precipitated out after acidification of the aqueous phase. Yield: 9.53 g (61% of theory)

LC/MS [Method 1]: $R_t$=0.47 min; MS (ESIpos): m/z=184 (M+H)$^+$

Example 21.1B

4-Chloro-2-(2,5-dimethoxypyridin-4-yl)benzonitrile

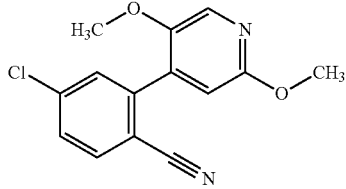 [SMILES: COc1cc(-c2cc(Cl)ccc2C#N)c(OC)cn1]

7.87 g (purity 95%, 40.86 mmol) of 2,5-dimethoxypyridin-4-ylboronic acid and 8.85 g (40.86 mmol) of 2-bromo-4-chlorobenzonitrile in the presence of [1,1-bis(diphenylphosphino)ferrocene]palladium(II) chloride/dichloromethane monoadduct were reacted according to General Method 2A. Yield: 6.23 g (purity 92%, 51% of theory)

LC/MS [Method 1]: $R_t$=1.08 min; MS (ESIpos): m/z=275 (M+H)$^+$

Example 21.1C

4-Chloro-2-(5-methoxy-2-oxo-1,2-dihydropyridin-4-yl)benzonitrile

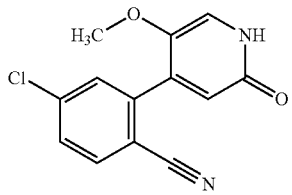 [SMILES: COc1c[nH]c(=O)cc1-c1cc(Cl)ccc1C#N]

7.23 g (purity 92%, 24.21 mmol) of 4-chloro-2-(2,5-dimethoxypyridin-4-yl)benzonitrile and pyridinium hydrochloride were reacted according to General Method 3A. Yield: 6.66 g (purity 91%, 96% of theory)

LC/MS [Method 1]: $R_t$=0.76 min; MS (ESIpos): m/z=261 (M+H)$^+$ $^1$H-NMR (400 MHz, DMSO-d$_6$): δ [ppm]=11.45 (br. s, 1H), 7.98 (d, 1H), 7.75-7.67 (m, 2H), 7.29 (br. s, 1H), 6.43 (s, 1H), 3.64 (s, 3H).

Example 21.1D

2-[4-(5-Chloro-2-cyanophenyl)-5-methoxy-2-oxopyridin-1(2H)-yl]propanoic acid (racemate)

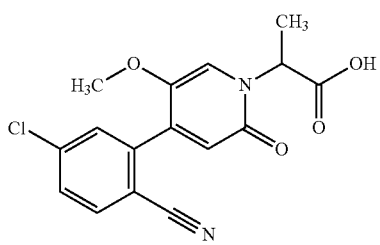 [SMILES: COc1cn(C(C)C(=O)O)c(=O)cc1-c1cc(Cl)ccc1C#N]

599 mg (purity 87%, 2.00 mmol) of 4-chloro-2-(5-methoxy-2-oxo-1,2-dihydropyridin-4-yl)benzonitrile and 1.5 eq. of 2-bromopropanoic acid (racemate) were reacted according to General Method 4A at 90° C. Yield: 716 mg (purity 68%, 73% of theory)

LC/MS [Method 1]: $R_t$=0.80 min; MS (ESIpos): m/z=333 (M+H)$^+$ $^1$H-NMR (400 MHz, DMSO-$d_6$): δ [ppm]=7.99 (d, 1H), 7.73 (m, 2H), 7.48 (s, 1H), 6.50 (s, 1H), 5.17 (q, 1H), 3.65 (s, 3H), 1.61 (d, 3H).

Example 21.1E tert-Butyl 4-({2-[4-(5-Chloro-2-cyanophenyl)-5-methoxy-2-oxopyridin-1(2H)-yl]propanoyl}amino)benzoate (racemate)

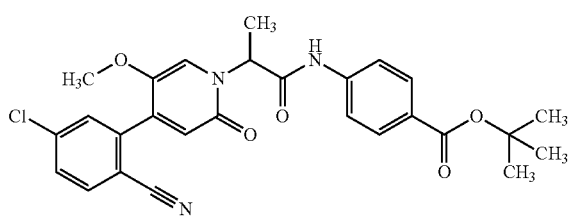 [SMILES: COc1cn(C(C)C(=O)Nc2ccc(C(=O)OC(C)(C)C)cc2)c(=O)cc1-c1cc(Cl)ccc1C#N]

1.53 g (purity 73%, 3.35 mmol) of 2-[4-(5-chloro-2-cyanophenyl)-5-methoxy-2-oxopyridin-1(2H)-yl]propanoic acid (racemate) and 1.1 eq. of tert-butyl 4-aminobenzoate were reacted according to General Method 5A. Yield: 1.52 g (purity 93%, 83% of theory)

LC/MS [Method 1]: $R_t$=1.19 min; MS (ESIpos): m/z=508 (M+H)$^+$ $^1$H-NMR (400 MHz, DMSO-$d_6$): δ [ppm]=10.72 (s, 1H), 8.01 (d, 1H), 7.87 (d, 2H), 7.74 (m, 4H), 7.46 (s, 1H), 6.53 (s, 1H), 5.59 (q, 1H), 3.70 (s, 3H), 1.74 (d, 3H), 1.54 (s, 9H).

Example 21.2A 4-(5-Chloro-2-nitrophenyl)-2,5-dimethoxypyridine

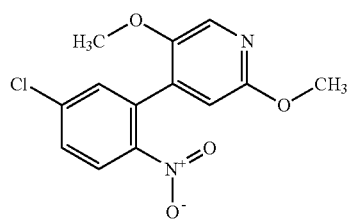

215 mg (purity 85%, 1.0 mmol) of 2,5-dimethoxypyridin-4-ylboronic acid and 236 mg (1.0 mmol) of 2-bromo-4-chloro-1-nitrobenzene in the presence of XPhos precatalyst were reacted according to General Method 2B. Yield: 124 mg (purity 93%, 39% of theory)

LC/MS [Method 2]: $R_t$=3.22 min; MS (ESIpos): m/z=295 (M+H)$^+$

Example 21.2B 4-(5-Chloro-2-nitrophenyl)-5-methoxypyridin-2(1H)-one

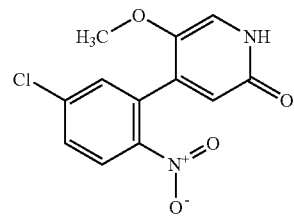

124 mg (purity 93%, 0.39 mmol) of 4-(5-chloro-2-nitrophenyl)-2,5-dimethoxypyridine and pyridinium hydrochloride were reacted according to General Method 3A. Yield: 115 mg (purity 85%, 89% of theory)

LC/MS [Method 1]: $R_t$=0.74 min; MS (ESIpos): m/z=281 (M+H)$^+$

Example 21.2C

2-[4-(5-Chloro-2-nitrophenyl)-5-methoxy-2-oxopyridin-1(2H)-yl]propanoic acid (racemate)

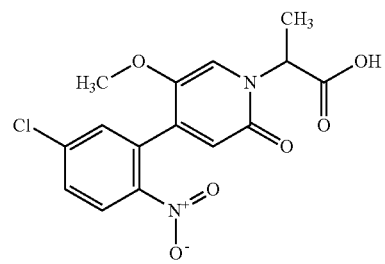

115 mg (purity 85%, 0.35 mmol) of 4-(5-chloro-2-nitrophenyl)-5-methoxypyridin-2(1H)-one and 1.5 eq. of 2-bromopropanoic acid (racemate) were reacted according to General Method 4A at 50° C. Yield: 43 mg (35% of theory)

LC/MS [Method 1]: $R_t$=0.80 min; MS (ESIpos): m/z=353 (M+H)$^+$

Example 21.2D tert-Butyl 4-({2-[4-(5-chloro-2-nitrophenyl)-5-methoxy-2-oxopyridin-1(2H)-yl]propanoyl}amino)benzoate (racemate)

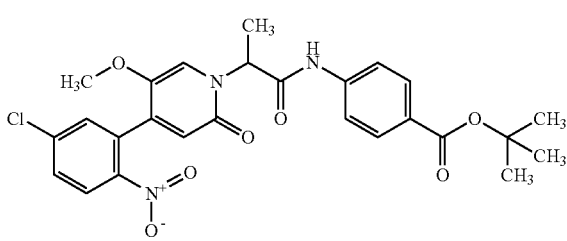

Under argon and at RT, 25 mg (0.13 mmol) of tert-butyl 4-aminobenzoate, 44 µl (0.26 mmol) of N,N-diisopropylethylamine and 74 µl (50% strength in DMF, 0.13 mmol) of T3P were added to a solution of 30 mg (0.09 mmol) of 2-[4-(5-chloro-2-nitrophenyl)-5-methoxy-2-oxopyridin-1(2H)-yl]propanoic acid (racemate) in 2 ml of DMF, and the mixture was stirred at RT for 2 h. The reaction mixture was concentrated under reduced pressure and the residue was purified by preparative HPLC (Reprosil C18, water/acetonitrile gradient). Yield: 32 mg (71% of theory)

LC/MS [Method 1]: $R_t$=1.19 min; MS (ESIpos): m/z=528 (M+H)$^+$

Example 22.1A tert-Butyl [4-(5-chloro-2-cyanophenyl)-5-methoxy-2-oxopyridin-1(2H)-yl]acetate

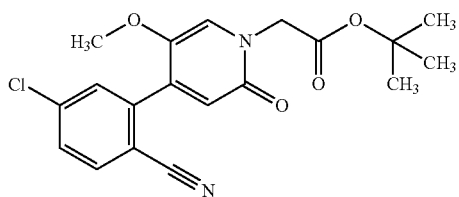 [SMILES: COc1cn(CC(=O)OC(C)(C)C)c(=O)cc1-c1cc(Cl)ccc1C#N]

516 mg (purity 91%, 1.8 mmol) of 4-chloro-2-(5-methoxy-2-oxo-1,2-dihydropyridin-4-yl)benzonitrile and 1.2 eq. of tert-butyl bromoacetate were reacted according to General Method 4B at 100° C. Yield: 464 mg (68% of theory)

LC/MS [Method 1]: $R_t$=1.00 min; MS (ESIpos): m/z=375 (M+H)$^+$

Example 22.1B tert-Butyl 2-[4-(5-chloro-2-cyanophenyl)-5-methoxy-2-oxopyridin-1(2H)-yl]-3-cyclopropylpropanoate (racemate)

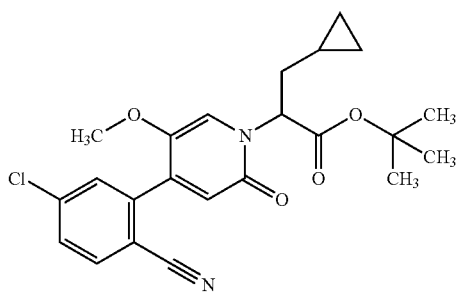 [SMILES: COc1cn(C(CC2CC2)C(=O)OC(C)(C)C)c(=O)cc1-c1cc(Cl)ccc1C#N]

464 mg (1.24 mmol) of tert-butyl [4-(5-chloro-2-cyanophenyl)-5-methoxy-2-oxopyridin-1(2H)-yl]acetate and 293 mg (1.61 mmol) of (iodomethyl)cyclopropane were reacted according to General Method 7A. Yield: 379 mg (71% of theory)

LC/MS [Method 1]: $R_t$=1.18 min; MS (ESIpos): m/z=429 (M+H)$^+$

Example 22.1C

2-[4-(5-Chloro-2-cyanophenyl)-5-methoxy-2-oxopyridin-1(2H)-yl]-3-cyclopropylpropanoate (racemate)

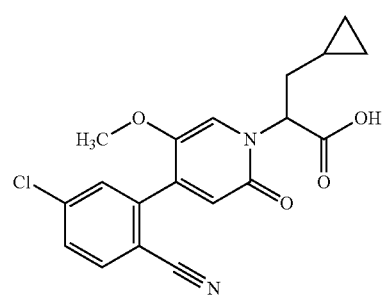 [SMILES: COc1cn(C(CC2CC2)C(=O)O)c(=O)cc1-c1cc(Cl)ccc1C#N]

378 mg (0.88 mmol) of tert-butyl 2-[4-(5-chloro-2-cyanophenyl)-5-methoxy-2-oxopyridin-1(2H)-yl]-3-cyclopropylpropanoate (racemate) were hydrolysed with 20 eq. of TFA according to General Method 6A. Yield: 420 mg (purity 92%, quant.)

LC/MS [Method 1]: $R_t$=0.90 min; MS (ESIpos): m/z=373 (M+H)$^+$

Example 22.1D tert-Butyl 4-({2-[4-(5-chloro-2-cyanophenyl)-5-methoxy-2-oxopyridin-1(2H)-yl]-3-cyclopropylpropanoyl}amino)benzoate (racemate)

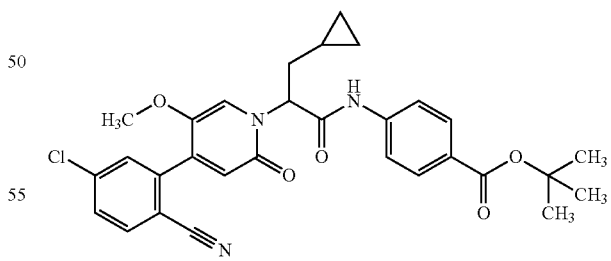

420 mg (purity 92%, 1.04 mmol) of 2-[4-(5-chloro-2-cyanophenyl)-5-methoxy-2-oxopyridin-1(2H)-yl]-3-cyclopropylpropanoic acid (racemate) and 1.2 eq. of tert-butyl 4-aminobenzoate were reacted according to General Method 5A. Yield: 348 mg (61% of theory)

LC/MS [Method 1]: $R_t$=1.29 min; MS (ESIpos): m/z=548 (M+H)$^+$

Example 23.1A tert-Butyl 2-[4-(5-chloro-2-cyanophenyl)-5-methoxy-2-oxopyridin-1(2H)-yl]pent-4-ynoate (racemate)

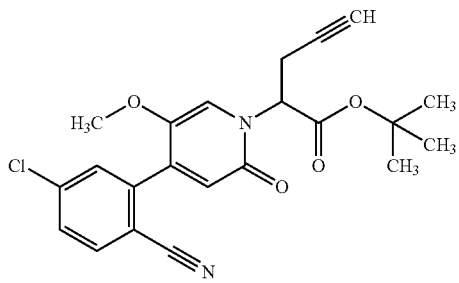 [SMILES: C#CCC(C(=O)OC(C)(C)C)n1cc(OC)c(-c2cc(Cl)ccc2C#N)cc1=O]

309 mg (0.8 mmol) of tert-butyl [4-(5-chloro-2-cyanophenyl)-5-methoxy-2-oxopyridin-1(2H)-yl]acetate and 155 mg (1.04 mmol) of 3-bromoprop-1-yne were reacted according to General Method 7A. Yield: 288 mg (87% of theory)

LC/MS [Method 1]: $R_t$=1.08 min; MS (ESIpos): m/z=413 (M+H)$^+$

Example 23.1B

2-[4-(5-Chloro-2-cyanophenyl)-5-methoxy-2-oxopyridin-1(2H)-yl]pent-4-ynoic acid (racemate)

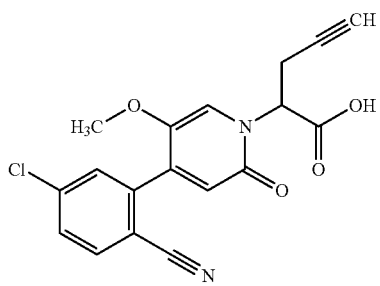 [SMILES: C#CCC(C(=O)O)n1cc(OC)c(-c2cc(Cl)ccc2C#N)cc1=O]

288 mg (0.7 mmol) of tert-butyl 2-[4-(5-chloro-2-cyanophenyl)-5-methoxy-2-oxopyridin-1(2H)-yl]pent-4-ynoate (racemate) were hydrolysed with TFA according to General Method 6A. Yield: 295 mg (purity 85%, quant.)

LC/MS [Method 1]: $R_t$=0.81 min; MS (ESIpos): m/z=357 (M+H)$^+$

Example 23.1C tert-Butyl 4-({2-[4-(5-chloro-2-cyanophenyl)-5-methoxy-2-oxopyridin-1(2H)-yl]pent-4-ynoyl}amino)benzoate (racemate)

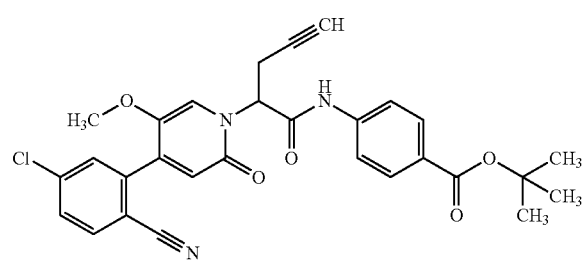 [SMILES: C#CCC(C(=O)Nc1ccc(C(=O)OC(C)(C)C)cc1)n1cc(OC)c(-c2cc(Cl)ccc2C#N)cc1=O]

295 mg (purity 85%, 0.70 mmol) of 2-[4-(5-chloro-2-cyanophenyl)-5-methoxy-2-oxopyridin-1(2H)-yl]pent-4-ynoic acid (racemate) and 1.1 eq. of tert-butyl 4-aminobenzoate were reacted according to General Method 5A. Yield: 91 mg (24% of theory)

LC/MS [Method 1]: $R_t$=1.23 min; MS (ESIpos): m/z=532 (M+H)$^+$

Example 24.1A

6-Methoxypyridin-3-ol

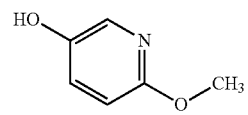

At RT, 50 g (327 mmol) of 6-methoxypyridin-3-ylboronic acid were added to a solution of 46.0 g (392 mmol) of N-methylmorpholine N-oxide in 500 ml of dichloromethane, and the mixture was stirred at 50° C. for 14 h. Additional N-methylmorpholine N-oxide was added until the reaction had gone to completion. The reaction mixture was concentrated under reduced pressure and the crude product was purified by flash chromatography (silica gel 60, cyclohexane/ethyl acetate mixtures). Yield: 32.9 g (80% of theory)

LC/MS [Method 1]: $R_t$=0.37 min; MS (ESIpos): m/z=126 (M+H)$^+$ $^1$H-NMR (400 MHz, DMSO-d$_6$): δ [ppm]=9.27 (s, 1H), 7.67 (d, 1H), 7.16 (dd, 1H), 6.66 (d, 1H), 3.74 (s, 3H).

Example 24.1B

2-Methoxy-5-(tetrahydro-2H-pyran-2-yloxy)pyridine

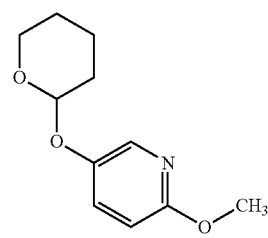

10.1 g (119.9 mmol, 1.5 eq.) of 3,4-dihydro-2H-pyran and 1.4 g (8.0 mmol, 0.1 eq.) of 4-toluenesulphonic acid were added to a solution of 10.0 g (79.9 mmol) of 6-methoxypyridin-3-ol in 150 ml of dichloromethane, and the mixture was stirred at RT for 5 d. After addition of water/dichloromethane and phase separation, the aqueous phase was extracted with dichloromethane. The combined organic phases were dried (sodium sulphate), filtered and concentrated under reduced pressure. Yield: 17.3 g (100% of theory)

LC/MS [Method 1]: $R_t$=0.95 min; MS (ESIpos): m/z=210 (M+H)$^+$

Example 24.1C

4-Iodo-2-methoxy-5-(tetrahydro-2H-pyran-2-yloxy)pyridine

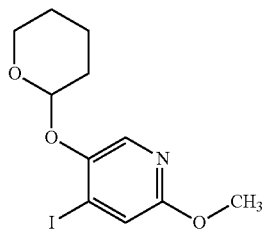 [SMILES: COc1cc(I)c(OC2CCCCO2)cn1]

At −78° C., 13.6 ml (90.1 mmol, 1.2 eq.) of 1,2-bis(dimethylamino)ethane and 54.0 ml (86.4 mmol, 1.15 eq.) of n-butyllithium were added to a solution of 16.2 g (75.1 mmol) of 2-methoxy-5-(tetrahydro-2H-pyran-2-yloxy)pyridine in 250 ml of THF, and the mixture was stirred at −78° C. for 1 h. 24.8 g (97.6 mmol, 1.3 eq.) of iodine were then added, and the reaction mixture was stirred at −78° C. for 1 h and then allowed to warm to RT overnight. The reaction mixture was quenched with water and extracted three times with ethyl acetate. The combined organic phases were washed with saturated aqueous sodium thiosulphate solution, dried (sodium sulphate), filtered and concentrated under reduced pressure. Yield: 25.1 g (purity 82%, 82% of theory)

LC/MS [Method 1]: $R_t$=1.18 min; MS (ESIpos): m/z=336 (M+H)$^+$

Example 24.1D

4-Iodo-6-methoxypyridin-3-ol

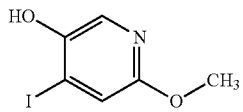

50 ml (3 molar, 150 mmol) of hydrochloric acid were added to a solution of 25.1 g (purity 82%, 61.3 mmol) of 4-iodo-2-methoxy-5-(tetrahydro-2H-pyran-2-yloxy)pyridine in 50 ml of dioxane and 50 ml of water, and the mixture was stirred at RT for 2 h. The reaction mixture was then filtered and the precipitate was rinsed with water and dried under high vacuum. Yield: 13.5 g (purity 93%, 81% of theory)

LC/MS [Method 1]: $R_t$=0.76 min; MS (ESIpos): m/z=252 (M+H)$^+$ $^1$H-NMR (400 MHz, DMSO-d$_6$): δ [ppm]=7.70 (s, 1H), 7.22 (s, 1H), 3.74 (s, 3H).

Example 24.1E

4-Iodo-5-isopropoxy-2-methoxypyridine

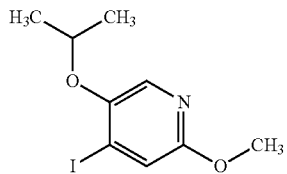

At 0° C., 758 mg (4.5 mmol) of 2-iodopropane and 948 mg (6.9 mmol, 2 eq.) of potassium carbonate were added to a solution of 861 mg (3.4 mmol) of 4-iodo-6-methoxypyridin-3-ol in 15 ml of acetone and the mixture was stirred at 80° C. overnight and concentrated under reduced pressure. After addition of water/ethyl acetate and phase separation, the aqueous phase was extracted with ethyl acetate. The combined organic phases were dried (sodium sulphate), filtered and concentrated under reduced pressure. Yield: 741 mg (73% of theory)

LC/MS [Method 1]: $R_t$=1.16 min; MS (ESIpos): m/z=294 (M+H)$^+$

Example 24.1F

4-Iodo-5-isopropoxypyridin-2(1H)-one

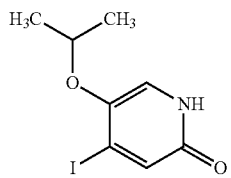

741 mg (2.53 mmol) of 4-iodo-2-methoxy-5-(propan-2-yloxy)pyridine and 20 eq. of pyridinium hydrobromide were reacted according to General Method 3A. Yield: 413 mg (purity 92%) of a mixture (1.4:1) of the iodine compound 24.1F and the analogous bromine compound LC/MS [Method 1]: bromine compound: $R_t$=0.71 min; MS (ESIpos): m/z=232 (M+H)$^+$; iodine compound: $R_t$=0.74 min; MS (ESIpos): m/z=280 (M+H)$^+$

Example 24.1G 2-(4-Iodo-5-isopropoxy-2-oxopyridin-1(2H)-yl)propanoic acid (racemate)

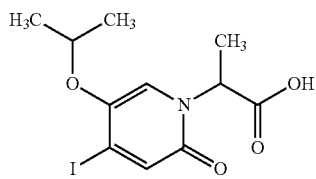 [SMILES: CC(C)Oc1cn(C(C)C(=O)O)c(=O)cc1I]

414 mg (purity 92%) of a mixture (1.4:1) of 4-iodo-5-(propan-2-yloxy)pyridin-2(1H)-one and the analogous bromine compound were reacted with 1.5 eq. of 2-bromopropanoic acid (racemate) according to General Method 4A at 50° C. Yield: 771 mg (purity 90%) of a mixture (1.6:1) of the iodine compound 24.1G and the analogous bromine compound LC/MS [Method 1]: bromine compound: $R_t$=0.78 min; MS (ESIpos): m/z=304 (M+H)$^+$; iodine compound: $R_t$=0.80 min; MS (ESIpos): m/z=352 (M+H)$^+$ Example 24.1H tert-Butyl 4-{[2-(4-iodo-5-isopropoxy-2-oxopyridin-1(2H)-yl)propanoyl]amino}benzoate (racemate)

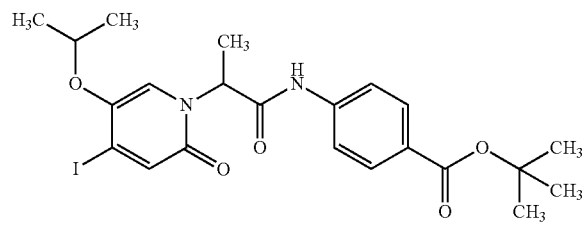 [SMILES: CC(C)Oc1cn(C(C)C(=O)Nc2ccc(C(=O)OC(C)(C)C)cc2)c(=O)cc1I]

771 mg (purity 90%) of a mixture (1.6:1) of 2-[4-iodo-2-oxo-5-(propan-2-yloxy)pyridin-1(2H)-yl]propanoic acid (racemate) and the analogous bromine compound were reacted with 1.2 eq. of tert-butyl 4-aminobenzoate according to General Method 5A. Yield: 100 mg of a mixture (3:1) of the iodine compound 24.1H and the analogous bromine compound LC/MS [Method 1]: bromine compound: $R_t$=1.22 min; MS (ESIpos): m/z=479 (M+H)$^+$; iodine compound: $R_t$=1.24 min; MS (ESIpos): m/z=527 (M+H)$^+$ Example 24.1I tert-Butyl 4-({2-[4-(5-chloro-2-cyanophenyl)-5-isopropoxy-2-oxopyridin-1(2H)-yl]propanoyl}amino)benzoate (racemate)

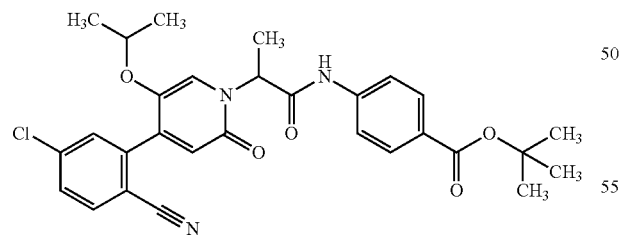

100 mg of a mixture (3:1) of tert-butyl 4-({2-[4-iodo-2-oxo-5-(propan-2-yloxy)pyridin-1(2H)-yl]propanoyl}amino)benzoate (racemate) and the analogous bromine compound and 41 mg (0.23 mmol) of 5-chloro-2-cyanophenylboronic acid in the presence of [1,1-bis(diphenylphosphino)ferrocene]palladium(II) chloride/dichloromethane monoadduct were reacted according to General Method 2A. Yield: 31 mg (29% of theory)

LC/MS [Method 1]: $R_t$=1.31 min; MS (ESIpos): m/z=536 (M+H)$^+$

Example 25.1A tert-Butyl 2-[4-(5-chloro-2-cyanophenyl)-5-methoxy-2-oxopyridin-1(2H)-yl]-4-methylpentanoate (racemate)

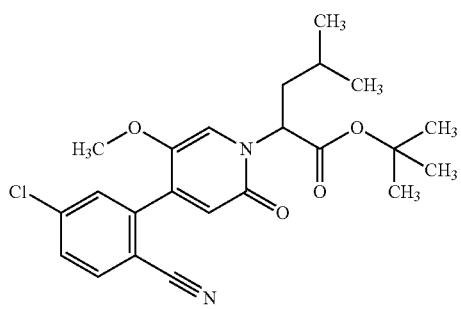 [SMILES: COc1cn(C(CC(C)C)C(=O)OC(C)(C)C)c(=O)cc1-c1cc(Cl)ccc1C#N]

309 mg (0.80 mmol) of tert-butyl [4-(5-chloro-2-cyanophenyl)-5-methoxy-2-oxopyridin-1(2H)-yl]acetate and 191 mg (1.04 mmol) of isobutyl iodide were reacted according to General Method 7A. Yield: 178 mg (purity 92%, 48% of theory) of product.

LC/MS [Method 1]: $R_t$=1.25 min; MS (ESIpos): m/z=431 (M+H)$^+$

Example 25.1B

2-[4-(5-Chloro-2-cyanophenyl)-5-methoxy-2-oxopyridin-1(2H)-yl]-4-methylpentanoic acid (racemate)

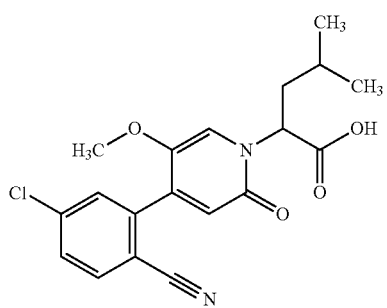 [SMILES: COc1cn(C(CC(C)C)C(=O)O)c(=O)cc1-c1cc(Cl)ccc1C#N]

178 mg (purity 92%, 0.38 mmol) of tert-butyl 2-[4-(5-chloro-2-cyanophenyl)-5-methoxy-2-oxopyridin-1(2H)-yl]-4-methylpentanoic acid (racemate) were hydrolysed with TFA according to General Method 6A. Yield: 165 mg (purity 85%, 98% of theory)

LC/MS [Method 1]: $R_t$=0.95 min; MS (ESIpos): m/z=375 (M+H)$^+$

Example 25.1C tert-Butyl 4-({2-[4-(5-chloro-2-cyanophenyl)-5-methoxy-2-oxopyridin-1(2H)-yl]-4-methylpentanoyl}amino)benzoate (racemate)

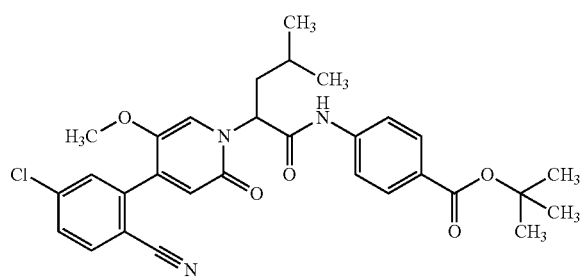 [SMILES: COc1cn(C(CC(C)C)C(=O)Nc2ccc(C(=O)OC(C)(C)C)cc2)c(=O)cc1-c1cc(Cl)ccc1C#N]

166 mg (purity 85%, 0.38 mmol) of 2-[4-(5-chloro-2-cyanophenyl)-5-methoxy-2-oxopyridin-1(2H)-yl]-4-methylpentanoic acid (racemate) and 1.1 eq. of tert-butyl 4-aminobenzoate were reacted according to General Method 5A. Yield: 127 mg (60% of theory)

LC/MS [Method 1]: $R_t$=1.33 min; MS (ESIpos): m/z=550 (M+H)$^+$

Example 26.1A

2-[4-(5-Chloro-2-cyanophenyl)-5-methoxy-2-oxopyridin-1(2H)-yl]butanoic acid (racemate)

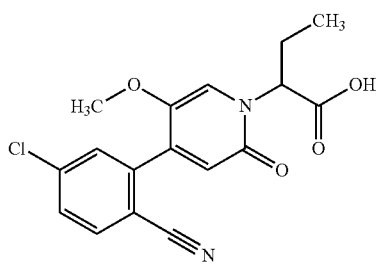 [SMILES: CCC(C(=O)O)n1cc(OC)c(-c2cc(Cl)ccc2C#N)cc1=O]

159 mg (purity 82%, 0.5 mmol) of 4-chloro-2-(5-methoxy-2-oxo-1,2-dihydropyridin-4-yl)benzonitrile and 1.5 eq. of 2-bromobutanoic acid (racemate) were reacted according to General Method 4A at 50° C. Yield: 55 mg (32% of theory)

LC/MS [Method 1]: $R_t$=0.85 min; MS (ESIpos): m/z=347 (M+H)$^+$

Alternative Synthesis:

Under argon and at RT, 7.8 ml (101.8 mmol, 10 eq.) of trifluoroacetic acid were added to a solution of 4.1 g (10.2 mmol) of tert-butyl 2-[4-(5-chloro-2-cyanophenyl)-5-methoxy-2-oxopyridin-1(2H)-yl]butanoate (racemate) in 40 ml of dichloromethane, the mixture was stirred at RT for 1 h, a further 7.8 ml (101.8 mmol, 10 eq.) of trifluoroacetic acid were added, the mixture was stirred at RT for 1 h, a further 7.8 ml (101.8 mmol, 10 eq.) of trifluoroacetic acid were added and the mixture was stirred at RT for 1 h. Once the reaction had gone to completion, the reaction mixture was concentrated under reduced pressure and the residue was co-evaporated in each case three times with dichloromethane and once with toluene and dried under reduced pressure. The residue was taken up in 100 ml of ethyl acetate and washed repeatedly with a strongly diluted aqueous sodium bicarbonate solution (where the pH of the washing water should not exceed pH 3-4 since otherwise the product is well soluble in water). The organic phase was subsequently dried (sodium sulphate), filtered and concentrated under reduced pressure. The residue was triturated with methyl tert-butyl ether, filtered, washed twice with methyl tert-butyl ether and dried under reduced pressure. Yield: 2.9 g (83% of theory)

LC/MS [Method 1]: $R_t$=0.81 min; MS (ESIpos): m/z=347 (M+H)$^+$, $^1$H-NMR (400 MHz, DMSO-d$_6$): δ [ppm]=12.97 (s, 1H), 7.99 (d, 1H), 7.77-7.70 (m, 2H), 7.41 (s, 1H), 6.49 (s, 1H), 5.09 (dd, 1H), 3.64 (s, 3H), 2.21-2.09 (m, 2H), 0.84 (t, 3H).

Example 26.1B tert-Butyl 4-({2-[4-(5-chloro-2-cyanophenyl)-5-methoxy-2-oxopyridin-1(2H)-yl]butanoyl}amino)benzoate (racemate)

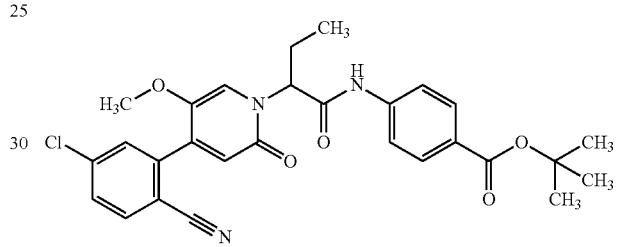

55 mg (0.16 mmol) of 2-[4-(5-chloro-2-cyanophenyl)-5-methoxy-2-oxopyridin-1(2H)-yl]butanoic acid (racemate) and 1.1 eq. of tert-butyl 4-aminobenzoate were reacted according to General Method 5A. Yield: 68 mg (82% of theory)

LC/MS [Method 1]: $R_t$=1.23 min; MS (ESIpos): m/z=522 (M+H)$^+$

Example 26.2A tert-Butyl 5-[4-({2-[4-(5-chloro-2-cyanophenyl)-5-methoxy-2-oxopyridin-1(2H)-yl]butanoyl}amino)phenyl]-3-oxo-2,3-dihydro-1H-pyrazole-1-carboxylate (racemate)

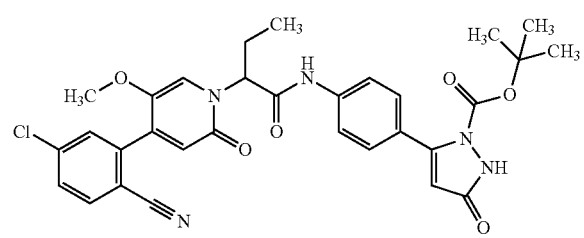 [SMILES: CCC(C(=O)Nc1ccc(-c2cc(=O)[nH]n2C(=O)OC(C)(C)C)cc1)n1cc(OC)c(-c2cc(Cl)ccc2C#N)cc1=O]

87 mg (0.25 mmol) of 2-[4-(5-chloro-2-cyanophenyl)-5-methoxy-2-oxopyridin-1(2H)-yl]butanoic acid (racemate) and 84 mg (purity 90%, 0.28 mmol, 1.1 eq.) of tert-butyl 5-(4-aminophenyl)-3-oxo-2,3-dihydro-1H-pyrazole-1-carboxylate were reacted according to General Method 5A. The crude product was purified by preparative HPLC (Reprosil C18, water/acetonitrile gradient). Yield: 17 mg (purity 70%, 8% of theory)

LC/MS [Method 1]: $R_t$=1.13 min; MS (ESIpos): m/z=604 (M+H)$^+$.

Example 26.3A tert-Butyl 6-({2-[4-(5-chloro-2-cyanophenyl)-5-methoxy-2-oxopyridin-1(2H)-yl]butanoyl}amino)-2-methyl-3-oxo-2,3-dihydro-1H-indazole-1-carboxylate (racemate)

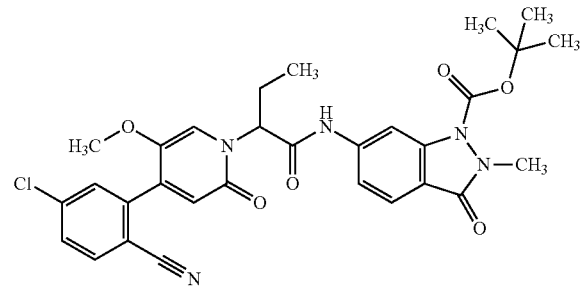 [SMILES: CCC(C(=O)Nc1ccc2c(=O)n(C)n(C(=O)OC(C)(C)C)c2c1)n1cc(OC)c(-c2cc(Cl)ccc2C#N)cc1=O]

87 mg (0.25 mmol) of 2-[4-(5-chloro-2-cyanophenyl)-5-methoxy-2-oxopyridin-1(2H)-yl]butanoic acid (racemate) and 74 mg (0.27 mmol, 1.1 eq.) of tert-butyl 6-amino-2-methyl-3-oxo-2,3-dihydro-1H-indazole-1-carboxylate were reacted according to General Method 5A. The crude product was purified by preparative HPLC (Reprosil C18, water/acetonitrile gradient). Yield: 112 mg (77% of theory)

LC/MS [Method 1]: $R_t$=1.14 min; MS (ESIpos): m/z=592 (M+H)$^+$.

Example 26.4A

Ethyl 6-({2-[4-(5-chloro-2-cyanophenyl)-5-methoxy-2-oxopyridin-1(2H)-yl]butanoyl}amino)-1H-benzimidazole-2-carboxylate (racemate)

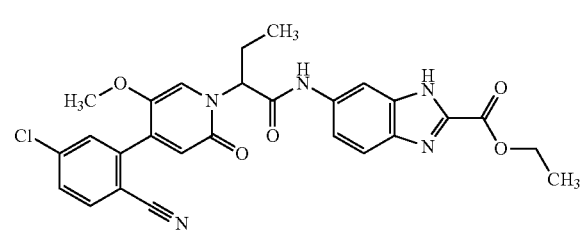 [SMILES: CCOC(=O)c1nc2ccc(NC(=O)C(CC)n3cc(OC)c(-c4cc(Cl)ccc4C#N)cc3=O)cc2[nH]1]

87 mg (0.25 mmol) of 2-[4-(5-chloro-2-cyanophenyl)-5-methoxy-2-oxopyridin-1(2H)-yl]butanoic acid (racemate) and 56 mg (0.28 mmol, 1.1 eq.) of ethyl 6-amino-1H-benzimidazole-2-carboxylate were reacted according to General Method 5A. The crude product was purified by preparative HPLC (Reprosil C18, acetonitrile/water+0.1% formic acid gradient). Yield: 86 mg (64% of theory)

LC/MS [Method 1]: $R_t$=0.96 min; MS (ESIpos): m/z=534 (M+H)$^+$.

Example 26.5A

Ethyl 6-({2-[4-(5-chloro-2-cyanophenyl)-5-methoxy-2-oxopyridin-1(2H)-yl]butanoyl}amino)-1H-indole-2-carboxylate (racemate)

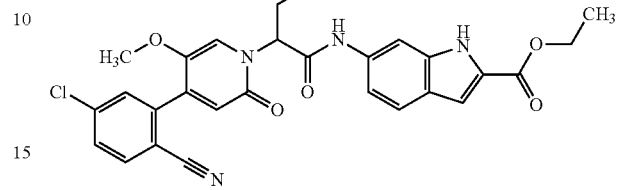

87 mg (0.25 mmol) of 2-[4-(5-chloro-2-cyanophenyl)-5-methoxy-2-oxopyridin-1(2H)-yl]butanoic acid (racemate) and 56 mg (0.28 mmol, 1.1 eq.) of ethyl 6-amino-1H-indole-2-carboxylate were reacted according to General Method 5A. The crude product was purified by preparative HPLC (Reprosil C18, water/acetonitrile gradient). Yield: 75 mg (55% of theory)

LC/MS [Method 1]: $R_t$=1.09 min; MS (ESIpos): m/z=533 (M+H)$^+$.

Example 26.6A

Ethyl 5-({2-[4-(5-chloro-2-cyanophenyl)-5-methoxy-2-oxopyridin-1(2H)-yl]butanoyl}amino)-1H-indole-2-carboxylate (racemate)

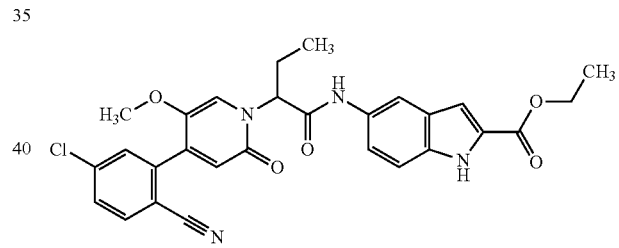

87 mg (0.25 mmol) of 2-[4-(5-chloro-2-cyanophenyl)-5-methoxy-2-oxopyridin-1(2H)-yl]butanoic acid (racemate) and 56 mg (0.28 mmol, 1.1 eq.) of ethyl 5-amino-1H-indole-2-carboxylate were reacted according to General Method 5A. The crude product was purified by preparative HPLC (Reprosil C18, water/acetonitrile gradient). Yield: 94 mg (70% of theory)

LC/MS [Method 1]: $R_t$=1.09 min; MS (ESIpos): m/z=533 (M+H)$^+$.

Example 27.1A 1,3-Dithiane-2-carboxylic acid

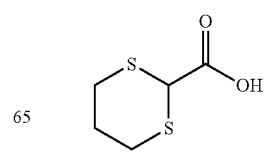

9.20 g (100 mmol) of glyoxalic acid monohydrate, 11.1 ml (110 mmol) of 1,3-propanedithiol and 1.72 g (10.0 mmol) of para-toluenesulphonic acid were heated in 200 ml of toluene under reflux for 3 h. The reaction mixture was cooled to RT and extracted three times with 100 ml of saturated aqueous sodium bicarbonate solution. The combined aqueous phases were washed with 200 ml of diethyl ether, acidified with aqueous hydrochloric acid (6N) and extracted four times with 200 ml of ethyl acetate. The combined organic phases were dried over magnesium sulphate and filtered, and the solvent was removed under reduced pressure. The residue was used for the next step without further purification. Yield: 8.0 g (47% of theory)

LC/MS [Method 4]: $R_t$=0.78 min; MS (ESIneg): m/z=163 (M−H)⁻

¹H-NMR (400 MHz, DMSO-$d_6$): δ [ppm]=13.0 (br. s, 1H), 4.59 (s, 1H), 3.17-3.08 (m, 2H), 2.76-2.68 (m, 2H), 1.98-1.79 (m, 2H).

Example 27.1B tert-Butyl 1,3-dithiane-2-carboxylate

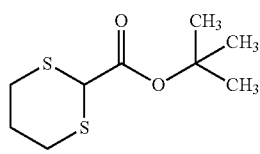

A little at a time, 10.5 g (48.2 mmol) of di-tert-butyl dicarbonate and 1.68 g (13.8 mmol) of dimethylaminopyridine were added to a solution of 7.54 mmol (45.9 mmol) of 1,3-dithiane-2-carboxylic acid in 28 ml of THF/tert-butanol (1:1). The resulting reaction mixture was stirred at RT overnight and diluted with 150 ml of ethyl acetate. The organic phase was washed successively with 100 ml of saturated aqueous ammonium chloride solution, 100 ml of water and 100 ml of saturated aqueous sodium chloride solution, dried over sodium sulphate and filtered, and the solvent was removed under reduced pressure. The residue was purified by flash chromatography and the title compound was obtained as a crystalline solid. Yield: 6.79 g (66% of theory)

LC/MS [Method 4]: $R_t$=2.28 min; MS (ESIpos): m/z=221 (M+H)⁺

¹H-NMR (400 MHz, DMSO-$d_6$): δ [ppm]=4.50 (s, 1H), 3.20-3.12 (m, 2H), 2.73-2.65 (m, 2H), 1.92-1.80 (m, 2H), 1.45 (s, 9H).

Example 27.1C

1-Iodo-2-methoxyethane

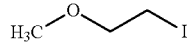

10.4 g (75.0 mmol) of 1-bromo-2-methoxyethane and 13.5 g (90.0 mmol) of sodium iodide were stirred in 75 ml of acetone at RT for 14 h. The solvent was then removed at 25° C. and 220 mbar and the residue was taken up in 100 ml of ethyl acetate. The organic phase was twice washed with 50 ml of water, dried over sodium sulphate and filtered, and the solvent was removed under reduced pressure. The crude product was used for the next step without further purification. Yield: 12.5 g (90% of theory)

GC/MS [Method 9]: Rt=1.56 min; MS: m/z=186 (M)⁺

¹H-NMR (400 MHz, CDCl₃): δ [ppm]=3.66 (t, 2H), 3.41 (s, 3H), 3.26 (t, 2H).

Example 27.1D tert-Butyl 2-(2-methoxyethyl)-1,3-dithiane-2-carboxylate

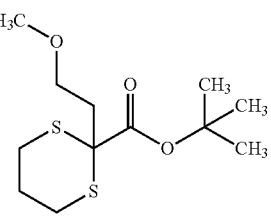

10.2 g (46.1 mmol) of tert-butyl 1,3-dithiane-2-carboxylate and 12.0 g (64.5 mmol) of 1-iodo-2-methoxyethane were initially charged in 127 ml of dimethylformamide, the mixture was cooled to 0° C. and 6.21 g (55.3 mmol) of potassium tert-butoxide were added. The resulting reaction mixture was stirred at 0° C. for 1 h and at RT for 16 h. The reaction mixture was added to 1.5 l of a 1:2 mixture of ice and saturated aqueous ammonium chloride solution and extracted three times with 300 ml of diethyl ether. The combined organic phases were dried over magnesium sulphate and filtered, and the solvent was removed under reduced pressure. The crude product was used for the next step without further purification. Yield: 11.1 g (87% of theory)

LC/MS [Method 1]: $R_t$=1.14 min; MS (ESIpos): m/z=177 (M-COO-tert-Butyl)⁺

¹H-NMR (400 MHz, DMSO-$d_6$): δ [ppm]=3.46 (t, 2H), 3.19 (s, 3H), 3.13-3.06 (m, 2H), 2.78-2.72 (m, 2H), 2.15 (t, 2H), 2.08-1.98 (m, 1H), 1.75-1.64 (m, 1H), 1.45 (s, 9H).

Example 27.1E tert-Butyl 4-methoxy-2-oxobutanoate

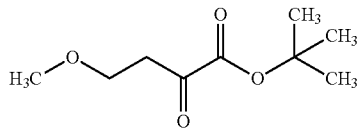

A solution of 10.6 g (38.1 mmol) of tert-butyl 2-(2-methoxyethyl)-1,3-dithiane-2-carboxylate in 365 ml of acetone and 18 ml of water was added dropwise to a solution, cooled to −18° C., of 54.2 g (305 mmol) of N-bromosuccinimide in 365 ml of acetone and 18 ml of water such that the internal temperature did not exceed −5° C. After the addition had ended, the mixture was stirred for another 10 min and the reaction was then terminated using 630 ml of sodium sulphite solution (1N). 420 ml of n-heptane were added to the reaction mixture and, after phase separation, the aqueous phase was extracted three times with 315 ml of ethyl acetate. The combined organic phases were dried over sodium sulphate and filtered, and the solvent was removed at 25° C. and 75 mbar. The resulting suspension was stirred with 100 ml of n-hexane and the precipitate was filtered off. The solvent was removed under reduced pressure, giving the target compound. Yield: 5.28 g (59% of theory)

GC/MS [Method 9]: Rt=3.20 min; MS: m/z=188 (M)$^+$ $^1$H-NMR (400 MHz, CDCl$_3$): δ [ppm]=3.70 (t, 2H), 3.34 (s, 3H), 3.04 (t, 2H), 1.55 (s, 9H).

Example 27.1F tert-Butyl 2-hydroxy-4-methoxybutanoate (racemate)

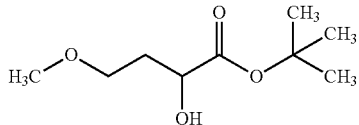

At 0° C., 1.05 g (27.6 mmol) of sodium borohydride were added a little at a time to a solution of 5.20 g (27.6 mmol) of tert-butyl 4-methoxy-2-oxobutanoate in 68.5 ml of methanol. The reaction mixture was stirred for another 5 min, 5 ml of water were added and the pH was adjusted to 6 using aqueous hydrochloric acid (1N). Methanol was removed under reduced pressure at 30° C. and the aqueous phase that remained was extracted three times with 50 ml of diethyl ether. The combined organic phases were dried over magnesium sulphate and filtered, and the solvent was removed under reduced pressure (25° C., 70 mbar). Yield: 4.48 g (77% of theory)

GC/MS [Method 9]: Rt=3.07 min; MS: m/z=190 (M)$^+$ $^1$H-NMR (400 MHz, CDCl$_3$): δ [ppm]=4.19-4.15 (m, 1H), 3.55 (t, 2H), 3.33 (s, 3H), 3.08 (d, 1H), 2.10-2.02 (m, 1H), 1.91-1.83 (m, 1H), 1.49 (s, 9H).

Example 27.1G tert-Butyl 4-methoxy-2-{[(trifluoromethyl)sulphonyl]oxy}butanoate (racemate)

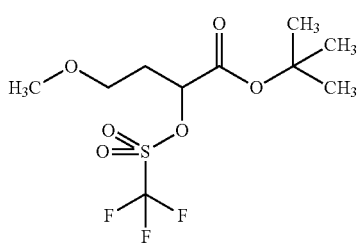 [SMILES: COCCC(OS(=O)(=O)C(F)(F)F)C(=O)OC(C)(C)C]

3.15 g (16.6 mmol) of tert-butyl 2-hydroxy-4-methoxybutanoate (racemate) in 158 ml of dichloromethane and 2.89 ml (24.8 mmol) of lutidine and 4.20 ml (24.8 mmol) of trifluoromethanesulphonic anhydride were reacted according to General Method 8A. Yield: 4.44 g (83% of theory)

$^1$H-NMR (400 MHz, CDCl$_3$): δ [ppm]=5.18 (dd, 1H), 3.56-3.44 (m, 2H), 3.34 (s, 3H), 2.31-2.23 (m, 1H), 2.21-2.12 (m, 1H), 1.51 (s, 9H).

Example 27.1H tert-Butyl 2-[4-(5-chloro-2-cyanophenyl)-5-methoxy-2-oxopyridin-1(2H)-yl]-4-methoxybutanoate (racemate)

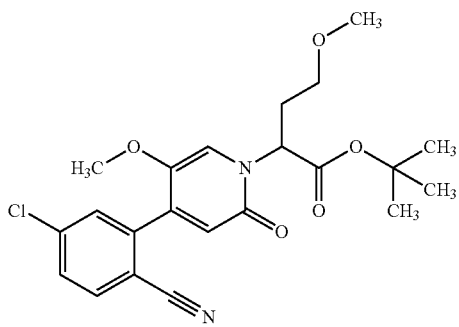 [SMILES: COCCC(C(=O)OC(C)(C)C)n1cc(OC)c(-c2cc(Cl)ccc2C#N)cc1=O]

A little at a time, 405 mg (10.1 mmol) of sodium hydride (60% in mineral oil) were added to a suspension of 2.4 g (9.2 mmol) of 4-chloro-2-(5-methoxy-2-oxo-1,2-dihydropyridin-4-yl)benzonitrile in 70 ml of tetrahydrofuran, and the mixture was stirred at RT for another 1 h. 4.45 g (13.8 mmol) of tert-butyl 4-methoxy-2-{[(trifluoromethyl)sulphonyl]oxy}butanoate (racemate) as a solution in 20 ml of THF were quickly added dropwise to the resulting reaction solution, and after the addition had ended the mixture was stirred at RT for another 1.5 h. The reaction was terminated by addition of 150 ml of saturated aqueous ammonium chloride solution and 150 ml of methyl tert-butyl ether. The phases were separated and the aqueous phase was extracted three times with 130 ml of methyl tert-butyl ether. The combined organic phases were dried over magnesium sulphate and filtered, and the solvent was removed under reduced pressure. The crude product was purified by flash chromatography (120 g silica cartridge, 85 ml/min, cyclohexane/ethyl acetate gradient), giving the title compound. Yield: 1.73 g (43% of theory)

LC/MS [Method 1]: R$_t$=1.07 min; MS (ESIpos): m/z=433 (M+H)$^+$ $^1$H-NMR (400 MHz, DMSO-d$_6$): δ [ppm]=7.99 (d, 1H), 7.74 (s, 1H), 7.73 (dd, 1H), 7.38 (s, 1H), 6.49 (s, 1H), 5.11 (t, 1H), 3.64 (s, 3H), 3.41-3.35 (m, 1H), 3.23-3.13 (m, 1H), 3.20 (s, 3H), 2.36-2.31 (m, 2H), 1.40 (s, 9H).

Example 27.1I

2-[4-(5-Chloro-2-cyanophenyl)-5-methoxy-2-oxopyridin-1(2H)-yl]-4-methoxybutanoic acid (racemate)

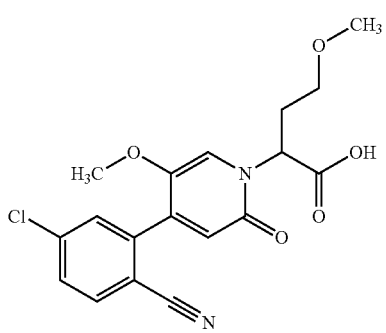 [SMILES: COCCC(C(=O)O)n1cc(OC)c(-c2cc(Cl)ccc2C#N)cc1=O]

1.99 g (4.60 mmol) of tert-butyl 2-[4-(5-chloro-2-cyanophenyl)-5-methoxy-2-oxopyridin-1(2H)-yl]-4-methoxybutanoic acid (racemate) in 46 ml of dichloromethane and 13.3 ml (172 mmol) of TFA were reacted according to General Method 6A. Yield: 1.58 g (91% of theory)

LC/MS [Method 1]: $R_t$=0.82 min; MS (ESIneg): m/z=374 (M−H)⁻

¹H-NMR (400 MHz, DMSO-$d_6$): δ [ppm]=13.0 (br. s, 1H), 7.99 (d, 1H), 7.75-7.72 (m, 2H), 7.42 (s, 1H), 6.48 (s, 1H), 5.13 (t, 1H), 3.63 (s, 3H), 3.41-3.31 (m, 1H), 3.19 (s, 3H), 3.15-3.10 (m, 1H), 2.38-2.33 (m, 2H).

Example 27.1J

Ethyl 4-({2-[4-(5-chloro-2-cyanophenyl)-5-methoxy-2-oxopyridin-1(2H)-yl]-4-methoxybutanoyl}amino)benzoate (racemate)

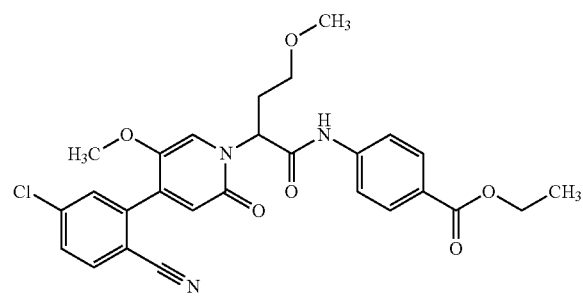 [SMILES: CCOC(=O)c1ccc(NC(=O)C(CCOC)n2cc(OC)c(-c3cc(Cl)ccc3C#N)cc2=O)cc1]

1.50 g (3.98 mmol) of 2-[4-(5-chloro-2-cyanophenyl)-5-methoxy-2-oxopyridin-1(2H)-yl]-4-methoxybutanoic acid (racemate), 658 mg (3.98 mmol) of ethyl 4-aminobenzoate, 566 mg (3.98 mmol) of Oxima and 620 μl (3.98 mmol) of DIC in 39 ml of dimethylformamide were reacted according to General Method 5B. Filtration gave the title compound. Yield: 1.87 g (85% of theory)

LC/MS [Method 1]: $R_t$=1.10 min; MS (ESIpos): m/z=524 (M+H)⁺

¹H-NMR (400 MHz, DMSO-$d_6$): δ [ppm]=10.8 (s, 1H), 8.00 (d, 1H), 7.94 (d, 2H), 7.79 (d, 2H), 7.65 (s, 1H), 7.74 (dd, 1H), 7.51 (s, 1H), 6.53 (s, 1H), 5.76 (t, 1H), 4.29 (q, 2H), 3.69 (s, 3H), 3.43-3.25 (m, 2H), 3.21 (s, 3H), 2.45-2.40 (m, 2H), 1.31 (t, 3H).

Example 28.1A (2S)-2-Methoxypropyltrifluoromethanesulphonate

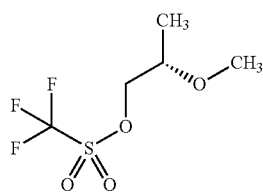

645 mg (7.16 mmol) of (S)-(+)-2-methoxypropanol and 1.27 ml (7.52 mmol, 1.05 eq.) of trifluoromethanesulphonic anhydride in the presence of 917 μl (7.87 mmol, 1.1 eq.) of 2,6-dimethylpyridine were reacted according to General Method 8A. The crude product was reacted in the next step without further purification.

Example 28.1B tert-Butyl 2-[4-(5-chloro-2-cyanophenyl)-5-methoxy-2-oxopyridin-1(2H)-yl]-2,3,5-trideoxy-4-O-methyl-L-glycero-pentonate (mixture of enantiomerically pure diastereomers 1 and 2)

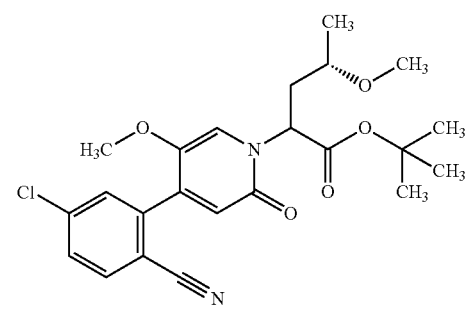 [SMILES: COc1cn(C(C[C@H](C)OC)C(=O)OC(C)(C)C)c(=O)cc1-c1cc(Cl)ccc1C#N]

450 mg (1.15 mmol) of tert-butyl [4-(5-chloro-2-cyanophenyl)-5-methoxy-2-oxopyridin-1(2H)-yl]acetate in the presence of 1.27 ml (1.27 mmol, 1.1 eq.) of bis(trimethylsilyl)lithium amide (1M in THF) and 384 mg (1.73 mmol, 1.5 eq.) of (2S)-2-methoxypropyl trifluoromethanesulphonate were reacted according to General Method 7B. Yield: 375 mg (73% of theory)

LC/MS [Method 1]: $R_t$=1.09 min; MS (ESIpos): m/z=447 (M+H)⁺.

Example 28.1C

2-[4-(5-Chloro-2-cyanophenyl)-5-methoxy-2-oxopyridin-1(2H)-yl]-2,3,5-trideoxy-4-O-methyl-L-glycero-pentonic acid (mixture of enantiomerically pure diastereomers 1 and 2)

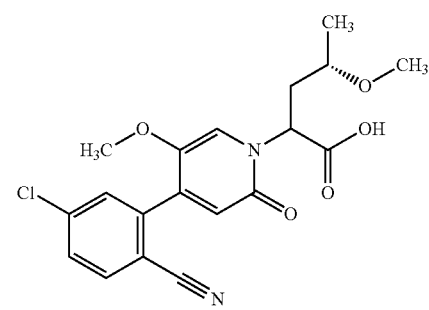 [SMILES: COc1cn(C(C[C@H](C)OC)C(=O)O)c(=O)cc1-c1cc(Cl)ccc1C#N]

375 mg (0.84 mmol) of tert-butyl 2-[4-(5-chloro-2-cyanophenyl)-5-methoxy-2-oxopyridin-1(2H)-yl]-2,3,5-trideoxy-4-O-methyl-L-glycero-pentonate (mixture of enantiomerically pure diastereomers 1 and 2) were hydrolysed with TFA according to General Method 6A. Yield: 391 mg (purity 92%, quant.)

LC/MS [Method 2]: diastereomer 1: $R_t$=2.28 min; MS (ESIpos): m/z=391 (M+H)⁺; diastereomer 2: $R_t$=2.36 min; MS (ESIpos): m/z=391 (M+H)⁺.

Example 28.1D tert-Butyl 4-({(4S)-2-[4-(5-chloro-2-cyanophenyl)-5-methoxy-2-oxopyridin-1(2H)-yl]-4-methoxypentanoyl}amino)benzoate (mixture of enantiomerically pure diastereomers 1 and 2)

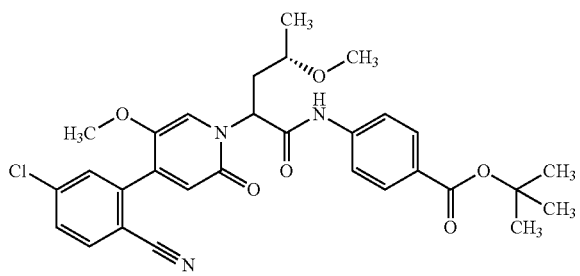 [SMILES: COc1cn(C(C[C@H](C)OC)C(=O)Nc2ccc(C(=O)OC(C)(C)C)cc2)c(=O)cc1-c1cc(Cl)ccc1C#N]

391 mg (purity 92%, 0.92 mmol) of 2-[4-(5-chloro-2-cyanophenyl)-5-methoxy-2-oxopyridin-1(2H)-yl]-2,3,5-trideoxy-4-O-methyl-L-glycero-pentonic acid (mixture of enantiomerically pure diastereomers 1 and 2) and 196 mg (1.01 mmol, 1.1 eq.) of tert-butyl 4-aminobenzoate were reacted according to General Method 5A. Yield: 387 mg (71% of theory)

LC/MS [Method 1]: diastereomer 1: $R_t$=1.23 min; MS (ESIpos): m/z=566 (M+H)$^+$; diastereomer 2: $R_t$=1.24 min; MS (ESIpos): m/z=566 (M+H)$^+$.

Example 29.1A (2R)-2-Methoxypropan-1-ol

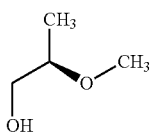

Under argon and at 0° C., 858 µl (8.39 mmol, 1.8 eq.) of borane/dimethyl sulphide complex were added dropwise to a solution of 500 mg (4.66 mmol) of (R)-(+)-2-methoxypropionic acid in 10 ml of dichloromethane, the reaction mixture was stirred at RT overnight and aqueous sodium hydroxide solution (2M) was then added dropwise. After phase separation, the aqueous phase was extracted with dichloromethane. The combined organic phases were dried (sodium sulphate), filtered, concentrated under reduced pressure (water bath <20° C., pressure >300 mbar) and dried. Yield: 490 mg (quant.)

$^1$H-NMR (400 MHz, DMSO-d$_6$): δ [ppm]=4.55 (t, 1H), 3.40-3.31 (m, 1H), 3.30-3.20 (m, 2H), 3.24 (s, 3H), 1.02 (d, 3H).

Example 29.1B (2R)-2-Methoxypropyl trifluoromethanesulphonate

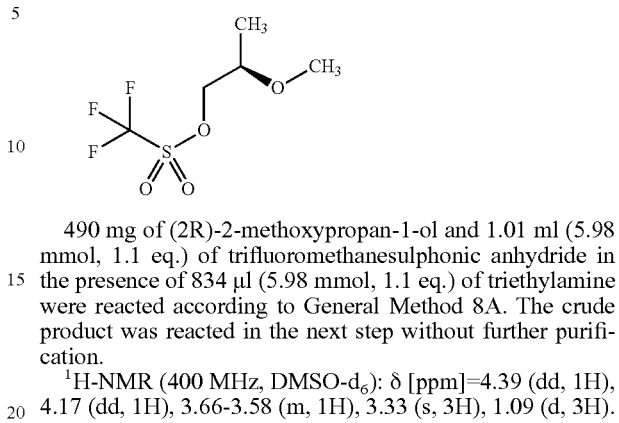

490 mg of (2R)-2-methoxypropan-1-ol and 1.01 ml (5.98 mmol, 1.1 eq.) of trifluoromethanesulphonic anhydride in the presence of 834 µl (5.98 mmol, 1.1 eq.) of triethylamine were reacted according to General Method 8A. The crude product was reacted in the next step without further purification.

$^1$H-NMR (400 MHz, DMSO-d$_6$): δ [ppm]=4.39 (dd, 1H), 4.17 (dd, 1H), 3.66-3.58 (m, 1H), 3.33 (s, 3H), 1.09 (d, 3H).

Example 29.1C tert-Butyl 2-[4-(5-chloro-2-cyanophenyl)-5-methoxy-2-oxopyridin-1(2H)-yl]-2,3,5-trideoxy-4-O-methyl-D-glycero-pentonate (mixture of enantiomerically pure diastereomers 1 and 2)

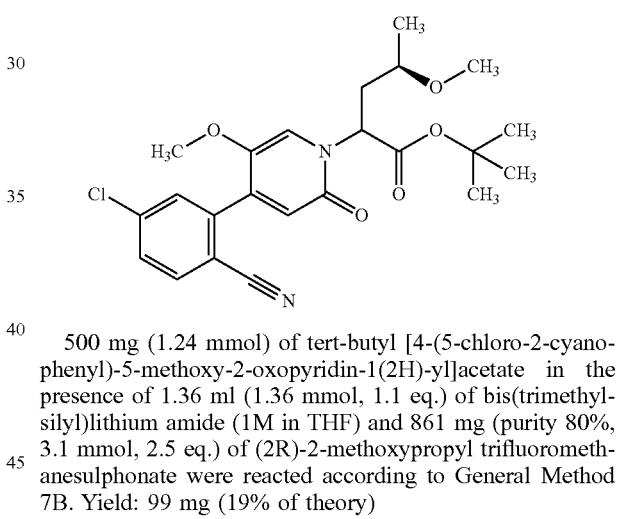

500 mg (1.24 mmol) of tert-butyl [4-(5-chloro-2-cyanophenyl)-5-methoxy-2-oxopyridin-1(2H)-yl]acetate in the presence of 1.36 ml (1.36 mmol, 1.1 eq.) of bis(trimethylsilyl)lithium amide (1M in THF) and 861 mg (purity 80%, 3.1 mmol, 2.5 eq.) of (2R)-2-methoxypropyl trifluoromethanesulphonate were reacted according to General Method 7B. Yield: 99 mg (19% of theory)

Example 29.1D

2-[4-(5-Chloro-2-cyanophenyl)-5-methoxy-2-oxopyridin-1(2H)-yl]-2,3,5-trideoxy-4-O-methyl-D-glycero-pentonic acid (mixture of enantiomerically pure diastereomers 1 and 2)

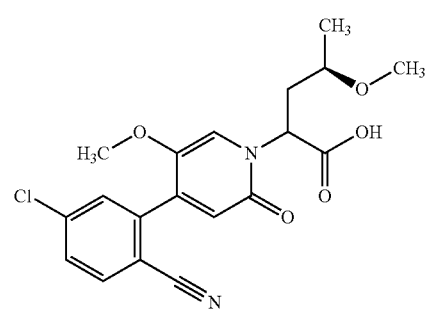 [SMILES: COc1cn(C(C[C@@H](C)OC)C(=O)O)c(=O)cc1-c1cc(Cl)ccc1C#N]

99 mg (0.22 mmol) of tert-butyl 2-[4-(5-chloro-2-cyano-phenyl)-5-methoxy-2-oxopyridin-1(2H)-yl]-2,3,5-trideoxy-4-O-methyl-D-glycero-pentonate (mixture of enantiomerically pure diastereomers 1 and 2) were hydrolysed with TFA according to General Method 6A. Yield: 88 mg (purity 88%, 91% of theory)

LC/MS [Method 8]: diastereomer 1: $R_t$=1.05 min; MS (ESIpos): m/z=391 (M+H)$^+$; diastereomer 2: $R_t$=1.07 min; MS (ESIpos): m/z=391 (M+H)$^+$.

Example 29.1E tert-Butyl 4-({(4R)-2-[4-(5-chloro-2-cyanophenyl)-5-methoxy-2-oxopyridin-1(2H)-yl]-4-methoxypentanoyl}amino)benzoate (mixture of enantiomerically pure diastereomers 1 and 2)

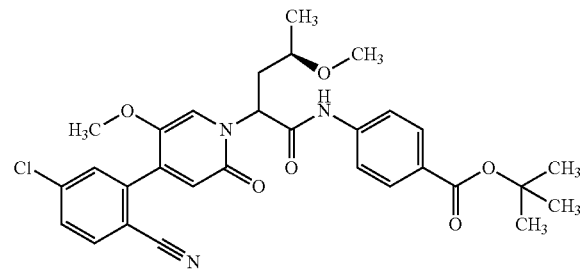 [SMILES: COc1cn(C(C[C@@H](C)OC)C(=O)Nc2ccc(C(=O)OC(C)(C)C)cc2)c(=O)cc1-c1cc(Cl)ccc1C#N]

88 mg (purity 88%, 0.20 mmol) of 2-[4-(5-chloro-2-cyanophenyl)-5-methoxy-2-oxopyridin-1(2H)-yl]-2,3,5-trideoxy-4-O-methyl-D-glycero-pentonic acid (mixture of enantiomerically pure diastereomers 1 and 2) and 42 mg (0.22 mmol, 1.1 eq.) of tert-butyl 4-aminobenzoate were reacted according to General Method 5A. Yield: 51 mg (46% of theory) mixture of enantiomerically pure diastereomers 1 and 2 and 26 mg (23% of theory) of diastereomer 1.

LC/MS [Method 8]: diastereomer 1: $R_t$=1.51 min; MS (ESIneg): m/z=564 (M–H)$^-$; diastereomer 2: $R_t$=1.52 min; MS (ESIneg): m/z=564 (M–H)$^-$.

Example 30.1A (2R)-Tetrahydrofuran-2-ylmethyl trifluoromethanesulphonate

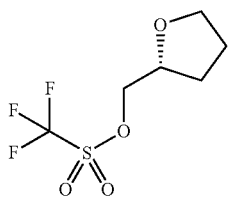 [SMILES: O=S(=O)(OC[C@H]1CCCO1)C(F)(F)F]

300 mg (2.9 mmol) of (2R)-tetrahydrofuran-2-ylmethanol and 512 µl (3.0 mmol, 1.05 eq.) of trifluoromethanesulphonic anhydride in the presence of 369 µl (3.2 mmol, 1.1 eq.) of 2,6-dimethylpyridine were reacted according to General Method 8A. The crude product was reacted in the next step without further purification.

$^1$H-NMR (400 MHz, DMSO-d$_6$): δ [ppm]=4.35 (dd, 1H), 4.17 (dd, 1H), 4.09 (dq, 1H), 3.86-3.70 (m, 2H), 2.00-1.79 (m, 3H), 1.61-1.47 (m, 1H).

Example 30.1B tert-Butyl 2-[4-(5-chloro-2-cyanophenyl)-5-methoxy-2-oxopyridin-1(2H)-yl]-3-[(2R)-tetrahydrofuran-2-yl]propanoate (mixture of enantiomerically pure diastereomers 1 and 2)

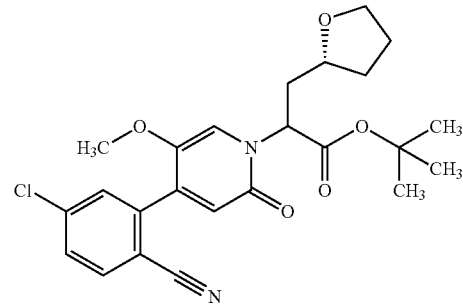 [SMILES: COc1cn(C(C[C@H]2CCCO2)C(=O)OC(C)(C)C)c(=O)cc1-c1cc(Cl)ccc1C#N]

450 mg (purity 94%, 1.1 mmol) of tert-butyl [4-(5-chloro-2-cyanophenyl)-5-methoxy-2-oxopyridin-1(2H)-yl]acetate in the presence of 1.35 ml (1.35 mmol, 1.2 eq.) of bis(trimethylsilyl)lithium amide (1M in THF) and 396 mg (1.7 mmol, 1.5 eq.) of (2R)-tetrahydrofuran-2-ylmethyl trifluoromethanesulphonate were reacted according to General Method 7B. Yield: 625 mg (purity 76%, 92% of theory)

LC/MS [Method 1]: $R_t$=1.09 min; MS (ESIpos): m/z=459 (M+H)$^+$.

Example 30.1C

2-[4-(5-Chloro-2-cyanophenyl)-5-methoxy-2-oxopyridin-1(2H)-yl]-3-[(2R)-tetrahydrofuran-2-yl]propanoic acid (mixture of enantiomerically pure diastereomers 1 and 2)

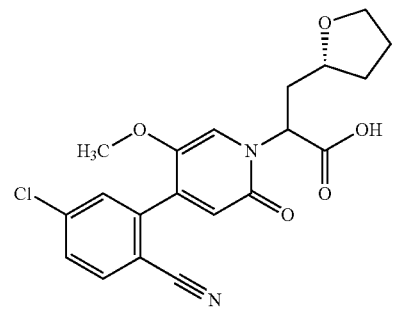 [SMILES: COc1cn(C(C[C@H]2CCCO2)C(=O)O)c(=O)cc1-c1cc(Cl)ccc1C#N]

625 mg (purity 76%, 1.0 mmol) of tert-butyl 2-[4-(5-chloro-2-cyanophenyl)-5-methoxy-2-oxopyridin-1(2H)-yl]-3-[(2R)-tetrahydrofuran-2-yl]propanoate (mixture of enantiomerically pure diastereomers 1 and 2) were hydrolysed with TFA according to General Method 6A. Yield: 585 mg (purity 73%, quant.)

LC/MS [Method 1]: diastereomer 1: $R_t$=2.33 min; MS (ESIpos): m/z=403 (M+H)$^+$; diastereomer 2: $R_t$=2.38 min; MS (ESIpos): m/z=403 (M+H)$^+$.

Example 30.1D tert-Butyl 4-({2-[4-(5-chloro-2-cyanophenyl)-5-methoxy-2-oxopyridin-1(2H)-yl]-3-[(2R)-tetrahydrofuran-2-yl]propanoyl}amino)benzoate (mixture of enantiomerically pure diastereomers 1 and 2)

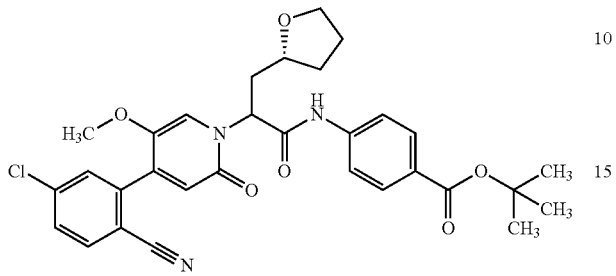

585 mg (purity 73%, 1.1 mmol) of 2-[4-(5-chloro-2-cyanophenyl)-5-methoxy-2-oxopyridin-1(2H)-yl]-3-[(2R)-tetrahydrofuran-2-yl]propanoic acid (mixture of enantiomerically pure diastereomers 1 and 2) and 225 mg (1.2 mmol, 1.1 eq.) of tert-butyl 4-aminobenzoate were reacted according to General Method 5A. Yield: 327 mg (53% of theory)
LC/MS [Method 1]: $R_t$=1.27 min; MS (ESIpos): m/z=578 (M+H)$^+$.

Example 31.1A (2S)-Tetrahydrofuran-2-ylmethanol

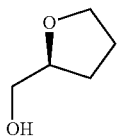

Under argon and at 0° C., 3.3 ml (32.4 mmol, 1.8 eq.) of borane/dimethyl sulphide complex were added dropwise to a solution of 2.13 g (18.0 mmol) of (2S)-tetrahydrofuran-2-carboxylic acid in 35 ml of dichloromethane, the reaction mixture was stirred at RT overnight and aqueous sodium hydroxide solution (2M) was then added dropwise. After phase separation, the aqueous phase was extracted with dichloromethane. The combined organic phases were dried (sodium sulphate), filtered, concentrated under reduced pressure and dried. Yield: 2.19 g (assumed purity of 80%, quant.)

Example 31.1B (2S)-Tetrahydrofuran-2-ylmethyl trifluoromethanesulphonate

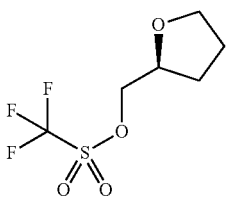 [SMILES: O=S(=O)(OC[C@@H]1CCCO1)C(F)(F)F]

2.19 g (assumed purity of 80%, 17.2 mmol) of (2S)-tetrahydrofuran-2-ylmethanol and 3.1 ml (18.0 mmol, 1.05 eq.) of trifluoromethanesulphonic anhydride in the presence of 2.2 ml (18.9 mmol, 1.1 eq.) of 2,6-dimethylpyridine were reacted according to General Method 8A. The crude product was reacted in the next step without further purification.
$^1$H-NMR (400 MHz, DMSO-d$_6$): δ [ppm]=4.35 (dd, 1H), 4.17 (dd, 1H), 4.09 (dq, 1H), 3.86-3.70 (m, 2H), 2.00-1.79 (m, 3H), 1.60-1.47 (m, 1H).

Example 31.1C tert-Butyl 2-[4-(5-chloro-2-cyanophenyl)-5-methoxy-2-oxopyridin-1(2H)-yl]-3-[(2,9-tetrahydrofuran-2-yl]propanoate (mixture of enantiomerically pure diastereomers 1 and 2)

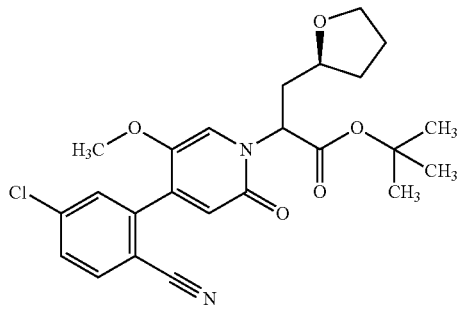 [SMILES: COc1cn(C(C[C@@H]2CCCO2)C(=O)OC(C)(C)C)c(=O)cc1-c1cc(Cl)ccc1C#N]

3.0 g (purity 93%, 7.4 mmol) of tert-butyl [4-(5-chloro-2-cyanophenyl)-5-methoxy-2-oxopyridin-1(2H)-yl]acetate in the presence of 8.9 ml (8.9 mmol, 1.2 eq.) of bis(trimethylsilyl)lithium amide (1M in THF) and 3.5 g (assumed purity 80%, 11.9 mmol, 1.6 eq.) of (2S)-tetrahydrofuran-2-ylmethyl trifluoromethanesulphonate were reacted according to General Method 7B. Yield: 1.7 g (49% of theory)
LC/MS [Method 8]: $R_t$=1.09 min; MS (ESIpos): m/z=403 (M-tert.-Butyl+H)$^+$.

Example 31.1D

2-[4-(5-Chloro-2-cyanophenyl)-5-methoxy-2-oxopyridin-1(2H)-yl]-3-[(2S)-tetrahydrofuran-2-yl]propanoic acid (mixture of enantiomerically pure diastereomers 1 and 2)

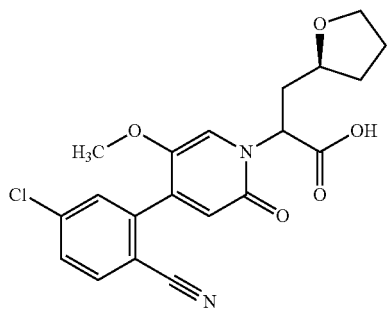 [SMILES: COc1cn(C(C[C@@H]2CCCO2)C(=O)O)c(=O)cc1-c1cc(Cl)ccc1C#N]

1.57 g (3.36 mmol) of tert-butyl 2-[4-(5-chloro-2-cyanophenyl)-5-methoxy-2-oxopyridin-1(2H)-yl]-3-[(2S)-tetrahydrofuran-2-yl]propanoate (mixture of enantiomerically pure diastereomers 1 and 2) were hydrolysed with TFA according to General Method 6A. Yield: 1.41 g (purity 92%, 96% of theory)

LC/MS [Method 8]: diastereomer 1: R$_t$=1.09 min; MS (ESIpos): m/z=403 (M+H)$^+$; diastereomer 2: R$_t$=1.11 min; MS (ESIpos): m/z=403 (M+H)$^+$.

Example 31.1E tert-Butyl 4-({2-[4-(5-chloro-2-cyanophenyl)-5-methoxy-2-oxopyridin-1(2H)-yl]-3-[(2,9-tetrahydrofuran-2-yl]propanoyl}amino)benzoate (mixture of enantiomerically pure diastereomers 1 and 2)

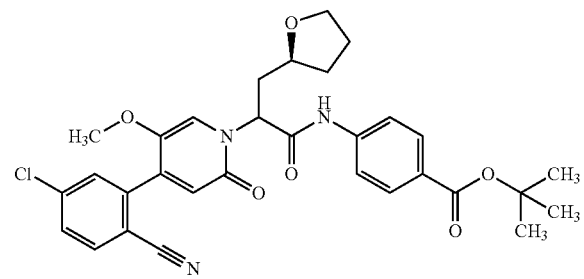 [SMILES: COc1cn(C(C[C@@H]2CCCO2)C(=O)Nc2ccc(C(=O)OC(C)(C)C)cc2)c(=O)cc1-c1cc(Cl)ccc1C#N]

1.54 g (purity 92%, 3.52 mmol) of 2-[4-(5-chloro-2-cyanophenyl)-5-methoxy-2-oxopyridin-1(2H)-yl]-3-[(2S)-tetrahydrofuran-2-yl]propanoic acid (mixture of enantiomerically pure diastereomers 1 and 2) and 747 mg (3.87 mmol, 1.1 eq.) of tert-butyl 4-aminobenzoate were reacted according to General Method 5A. Yield: 1.61 g (79% of theory)

LC/MS [Method 1]: R$_t$=1.23 min; MS (ESIpos): m/z=578 (M+H)$^+$.

Example 32.1A tert-Butyl 2-[4-(5-chloro-2-cyanophenyl)-5-methoxy-2-oxopyridin-1(2H)-yl]-3-hydroxy-3-(tetrahydrofuran-3-yl)propanoate (diastereomer mixture)

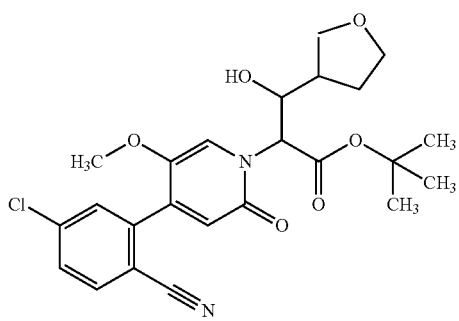 [SMILES: COc1cn(C(C(=O)OC(C)(C)C)C(O)C2CCOC2)c(=O)cc1-c1cc(Cl)ccc1C#N]

At −70° C., 6.94 ml (6.94 mmol, 1.3 eq.) of bis(trimethylsilyl)lithium amide (1M in THF) were added dropwise to a solution of 2.00 g (5.34 mmol) of tert-butyl [4-(5-chloro-2-cyanophenyl)-5-methoxy-2-oxopyridin-1(2H)-yl]acetate in 50 ml of tetrahydrofuran, the mixture was stirred at −70° C. for 10 min, a solution of 801 mg (8.00 mmol, 1.5 eq.) of tetrahydrofuran-3-carbaldehyde in 4 ml of tetrahydrofuran was added and the mixture was stirred at −70° C. for 90 min. The reaction mixture was warmed to −20° C., and 25 ml of semisaturated aqueous ammonium chloride solution were added. After phase separation, the aqueous phase was extracted with diethyl ether. The combined organic phases were washed with saturated aqueous sodium chloride solution, dried (sodium sulphate), filtered, concentrated under reduced pressure and dried. The crude product was purified by flash chromatography (KP-SIL, petroleum ether/ethyl acetate 33-75%). Yield: 1.49 g (56% of theory)

LC/MS [Method 1]: R$_t$=0.99 min; MS (ESIpos): m/z=475 (M+H)$^+$.

Example 32.1B tert-Butyl 2-[4-(5-chloro-2-cyanophenyl)-5-methoxy-2-oxopyridin-1(2H)-yl]-3-(tetrahydrofuran-3-yl)acrylate (diastereomer mixture)

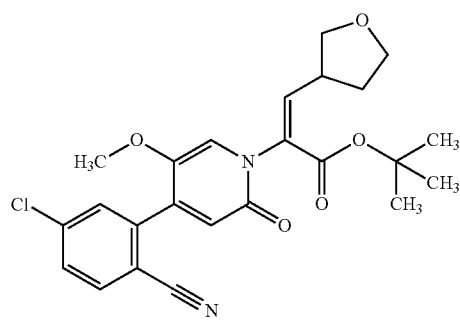 [SMILES: COc1cn(/C(=C/C2CCOC2)C(=O)OC(C)(C)C)c(=O)cc1-c1cc(Cl)ccc1C#N]

At RT, 0.5 ml (3.8 mmol, 1.2 eq.) of diethylaminosulphur trifluoride was added dropwise to a solution of 1.55 mg (3.13 mmol) of tert-butyl 2-[4-(5-chloro-2-cyanophenyl)-5-methoxy-2-oxopyridin-1(2H)-yl]-3-hydroxy-3-(tetrahydrofuran-3-yl)propanoate (diastereomer mixture) in 48 ml of dichloromethane, the mixture was stirred at RT for 90 min and 50 ml of dichloromethane and 50 ml of saturated aqueous sodium bicarbonate solution were then added. After phase separation, the aqueous phase was extracted with dichloromethane. The combined organic phases were washed with saturated aqueous sodium chloride solution, dried (sodium sulphate), filtered, concentrated under reduced pressure and dried. Yield: 1.38 g (93% of theory)

LC/MS [Method 1]: R$_t$=1.03 min/1.05 min; MS (ESIpos): m/z=457 (M+H)$^+$/457 (M+H)$^+$.

Example 32.1C tert-Butyl 2-[4-(5-chloro-2-cyanophenyl)-5-methoxy-2-oxopyridin-1(2H)-yl]-3-(tetrahydrofuran-3-yl)propanoate (mixture of racemic diastereomers)

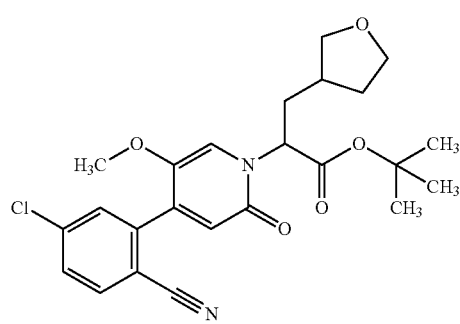 [SMILES: COc1cn(C(CC2CCOC2)C(=O)OC(C)(C)C)c(=O)cc1-c1cc(Cl)ccc1C#N]

At RT, 1.38 g (2.90 mmol) of tert-butyl 2-[4-(5-chloro-2-cyanophenyl)-5-methoxy-2-oxopyridin-1(2H)-yl]-3-(tetrahydrofuran-3-yl)acrylate (diastereomer mixture) were admixed with 100 ml of a "Hot Stryker's" reagent solution [B. A. Baker et al. *Org. Lett.* 2008, 10, 289-292]. The reaction mixture was stirred at RT for 6 h and then concentrated under reduced pressure. Four times, the crude product was stirred with in each case 50 ml of acetonitrile and decanted. The combined organic phases were concentrated under reduced pressure. The residue was purified by flash chromatography (PF-50SIHC, petroleum ether/ethyl acetate 40-66%). Yield: 930 mg (70% of theory)

LC/MS [Method 1]: $R_t$=1.06 min; MS (ESIpos): m/z=459 (M+H)$^+$.

Example 32.1D

2-[4-(5-Chloro-2-cyanophenyl)-5-methoxy-2-oxopyridin-1(2H)-yl]-3-(tetrahydrofuran-3-yl)propanoic acid (mixture of racemic diastereomers)

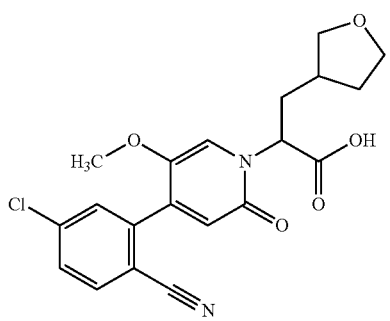 [SMILES: COc1cn(C(CC2CCOC2)C(=O)O)c(=O)cc1-c1cc(Cl)ccc1C#N]

930 mg (2.0 mmol) of tert-butyl 2-[4-(5-chloro-2-cyanophenyl)-5-methoxy-2-oxopyridin-1(2H)-yl]-3-(tetrahydrofuran-3-yl)propanoate (mixture of racemic diastereomers) were hydrolysed with TFA according to General Method 6A. Yield: 974 mg (purity 94%, quant.)

LC/MS [Method 1]: $R_t$=0.77 min; MS (ESIpos): m/z=403 (M+H)$^+$.

Example 32.1E tert-Butyl 4-({2-[4-(5-chloro-2-cyanophenyl)-5-methoxy-2-oxopyridin-1(2H)-yl]-3-(tetrahydrofuran-3-yl)propanoyl}amino)benzoate (mixture of racemic diastereomers)

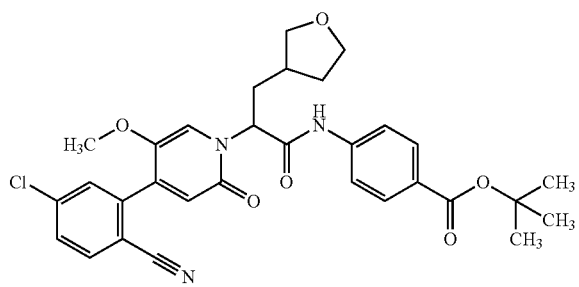 [SMILES: COc1cn(C(CC2CCOC2)C(=O)Nc2ccc(C(=O)OC(C)(C)C)cc2)c(=O)cc1-c1cc(Cl)ccc1C#N]

900 mg (purity 94%, 2.1 mmol) of 2-[4-(5-chloro-2-cyanophenyl)-5-methoxy-2-oxopyridin-1(2H)-yl]-3-(tetrahydrofuran-3-yl)propanoic acid (mixture of racemic diastereomers) and 446 mg (2.3 mmol, 1.1 eq.) of tert-butyl 4-aminobenzoate were reacted according to General Method 5A. Yield: 682 mg (purity 97%, 54% of theory) and 113 mg (purity 92%, 9% of theory)

LC/MS [Method 1]: $R_t$=1.20 min; MS (ESIpos): m/z=578 (M+H)$^+$.

Example 33.1A

Tetrahydro-2H-pyran-4-ylmethyl trifluoromethanesulphonate

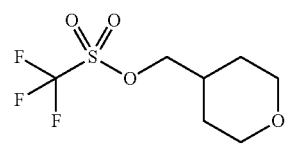 [SMILES: O=S(=O)(OCC1CCOCC1)C(F)(F)F]

5.00 g (43.0 mmol) of tetrahydro-2H-pyran-4-ylmethanol in 75 ml of dichloromethane and 5.52 ml (47.3 mmol) of lutidine and 7.65 ml (45.2 mmol) of trifluoromethanesulphonic anhydride were reacted according to General Method 8A. The crude product was used for the next step without further purification. Yield: 12.4 g (quant.)

GC/MS [Method 9]: Rt=3.15 min; MS: m/z=248 (M)$^+$ $^1$H-NMR (400 MHz, CDCl$_3$): δ [ppm]=4.37 (d, 2H), 4.03 (dd, 2H), 3.41 (dt, 2H), 2.16-2.02 (m, 1H), 1.72-1.65 (m, 2H), 1.48-1.37 (m, 2H).

Example 33.1B tert-Butyl 2-[4-(5-chloro-2-cyanophenyl)-5-methoxy-2-oxopyridin-1(2H)-yl]-3-(tetrahydro-2H-pyran-4-yl)propanoate (racemate)

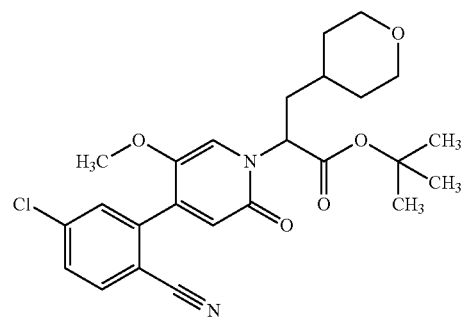 [SMILES: COc1cn(C(CC2CCOCC2)C(=O)OC(C)(C)C)c(=O)cc1-c1cc(Cl)ccc1C#N]

1.65 g (4.41 mmol) of tert-butyl [4-(5-chloro-2-cyanophenyl)-5-methoxy-2-oxopyridin-1(2H)-yl]acetate, 1.64 g (6.61 mmol) of tetrahydro-2H-pyran-4-ylmethyl trifluoromethanesulphonate and 5.73 ml (5.73 mmol) of bis(trimethylsilyl)lithium amide (1M in THF) in 37 ml of THF were reacted according to General Method 7B. Purification by column chromatography (80 g silica cartridge, flow rate: 60 ml/min, cyclohexane/ethyl acetate gradient) gave the title compound. Yield: 1.57 g (73% of theory)

LC/MS [Method 1]: $R_t$=1.10 min; MS (ESIpos): m/z=473 (M+H)$^+$ $^1$H-NMR (400 MHz, DMSO-d$_6$): δ [ppm]=7.99 (d, 1H), 7.77-7.71 (m, 2H), 7.40 (s, 1H), 6.51 (s, 1H), 5.32-5.26 (m, 1H), 3.85-3.76 (m, 2H), 3.64 (s, 3H), 3.23-3.13 (m, 2H), 2.22-2.12 (m, 1H), 2.02-1.93 (m, 1H), 1.73-1.66 (m, 1H), 1.51-1.45 (m, 1H), 1.40 (s, 9H), 1.36-1.13 (m, 3H).

Example 33.1C

2-[4-(5-Chloro-2-cyanophenyl)-5-methoxy-2-oxopyridin-1(2H)-yl]-3-(tetrahydro-2H-pyran-4-yl) propanoic acid (racemate)

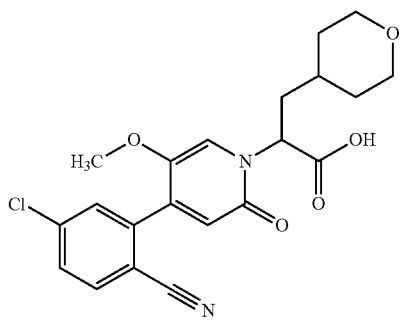 [SMILES: COc1cn(C(CC2CCOCC2)C(=O)O)c(=O)cc1-c1cc(Cl)ccc1C#N]

1.57 g (3.32 mmol) of tert-butyl 2-[4-(5-chloro-2-cyanophenyl)-5-methoxy-2-oxopyridin-1(2H)-yl]-3-(tetrahydro-2H-pyran-4-yl)propanoate (racemate) in 25 ml of dichloromethane and 5.12 ml (66.4 mmol) of TFA were reacted according to General Method 6A. Yield: 1.60 g (quant.)

LC/MS [Method 1]: $R_t$=0.80 min; MS (ESIpos): m/z=417 (M+H)$^+$ $^1$H-NMR (400 MHz, DMSO-d$_6$): δ [ppm]=13.1 (s, 1H), 7.99 (d, 1H), 7.77-7.71 (m, 2H), 7.45 (s, 1H), 6.50 (s, 1H), 5.38-5.30 (m, 1H), 3.85-3.74 (m, 2H), 3.63 (s, 3H), 3.22-3.12 (m, 2H), 2.26-2.16 (m, 1H), 2.05-1.96 (m, 1H), 1.73-1.65 (m, 1H), 1.48-1.40 (m, 1H), 1.36-1.11 (3H).

Example 33.1D 4-({2-[4-(5-Chloro-2-cyanophenyl)-5-methoxy-2-oxopyridin-1(2H)-yl]-3-(tetrahydro-2H-pyran-4-yl) propanoyl}amino)benzoic acid (racemate)

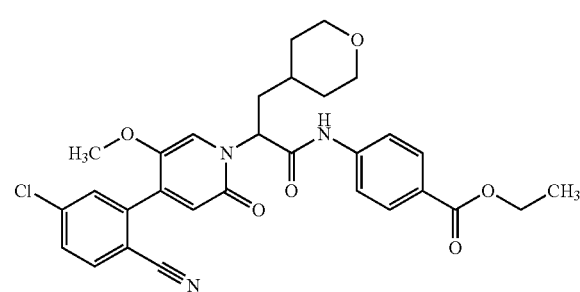 [SMILES: CCOC(=O)c1ccc(NC(=O)C(CC2CCOCC2)n2cc(OC)c(-c3cc(Cl)ccc3C#N)cc2=O)cc1]

1.38 g (3.31 mmol) of 2-[4-(5-chloro-2-cyanophenyl)-5-methoxy-2-oxopyridin-1(2H)-yl]-3-(tetrahydro-2H-pyran-4-yl)propanoic acid (racemate), 547 mg (3.31 mmol) of ethyl 4-aminobenzoate, 471 mg (3.31 mmol) of Oxima and 516 μl (3.31 mmol) of DIC in 33 ml of dimethylformamide were reacted according to General Method 5B. The crude product was purified by flash chromatography (120 g cartridge, 85 ml/min, cyclohexane/ethyl acetate gradient). Yield: 1.10 g (58% of theory)

LC/MS [Method 1]: $R_t$=1.14 min; MS (ESIpos): m/z=564 (M+H)$^+$ $^1$H-NMR (400 MHz, DMSO-d$_6$): δ [ppm]=10.9 (s, 1H), 8.00 (d, 1H), 7.94 (d, 2H), 7.81-7.72 (m, 4H), 7.52 (s, 1H), 6.54 (s, 1H), 5.92-5.85 (m, 1H), 4.33-4.25 (q, 2H), 3.87-3.77 (m, 2H), 3.69 (s, 3H), 3.25-3.11 (m, 2H), 2.31-2.21 (m, 1H), 2.03-1.94 (m, 1H), 1.65-1.57 (m, 2H), 1.39-1.19 (m, 3H), 1.32 (t, 3H).

Example 34.1A

Tetrahydro-2H-pyran-3-ylmethyl trifluoromethanesulphonate (racemate)

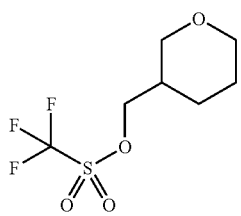 [SMILES: O=S(=O)(OCC1CCCOC1)C(F)(F)F]

232 mg (2.00 mmol) of tetrahydro-2H-pyran-3-ylmethanol and 355 μl (2.10 mmol, 1.05 eq.) of trifluoromethanesulphonic anhydride in the presence of 256 μl (2.20 mmol, 1.1 eq.) of 2,6-dimethylpyridine were reacted according to General Method 8A. The crude product was reacted in the next step without further purification.

$^1$H-NMR (400 MHz, DMSO-d$_6$): δ [ppm]=4.21-4.12 (m, 2H), 3.77 (dd, 1H), 3.74-3.66 (m, 1H), 3.40-3.30 (m, 1H), 3.20 (dd, 1H), 2.00-1.87 (m, 1H), 1.79-1.69 (m, 1H), 1.64-1.53 (m, 1H), 1.53-1.41 (m, 1H), 1.36-1.24 (m, 1H).

Example 34.1B tert-Butyl 2-[4-(5-chloro-2-cyanophenyl)-5-methoxy-2-oxopyridin-1(2H)-yl]-3-(tetrahydro-2H-pyran-3-yl)propanoate (mixture of racemic diastereomers)

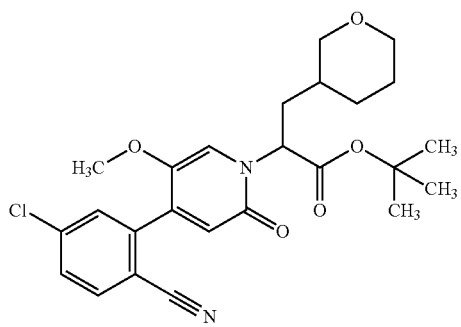 [SMILES: COc1cn(C(CC2CCCOC2)C(=O)OC(C)(C)C)c(=O)cc1-c1cc(Cl)ccc1C#N]

450 mg (purity 94%, 1.13 mmol) of tert-butyl [4-(5-chloro-2-cyanophenyl)-5-methoxy-2-oxopyridin-1(2H)-yl] acetate in the presence of 1.24 ml (1.24 mmol, 1.1 eq.) of bis(trimethylsilyl)lithium amide (1M in THF) and 467 mg (1.69 mmol, 1.5 eq.) of tetrahydro-2H-pyran-3-ylmethyl trifluoromethanesulphonate (racemate) were reacted according to General Method 7B. Yield: 451 mg (purity 82%, 69% of theory)

LC/MS [Method 1]: $R_t$=1.13 min; MS (ESIpos): m/z=473 (M+H)$^+$.

Example 34.1C

2-[4-(5-Chloro-2-cyanophenyl)-5-methoxy-2-oxopyridin-1(2H)-yl]-3-(tetrahydro-2H-pyran-3-yl)propanoic acid (mixture of racemic diastereomers)

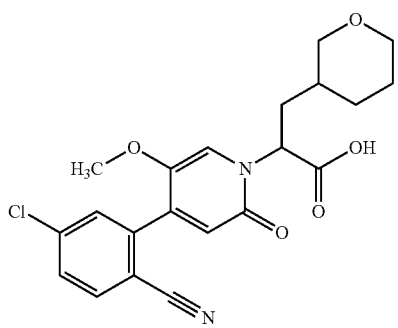 [SMILES: COc1cn(C(CC2CCCOC2)C(=O)O)c(=O)cc1-c1cc(Cl)ccc1C#N]

451 mg (purity 82%, 0.78 mmol) of tert-butyl 2-[4-(5-chloro-2-cyanophenyl)-5-methoxy-2-oxopyridin-1(2H)-yl]-3-(tetrahydro-2H-pyran-3-yl)propanoate (mixture of racemic diastereomers) were hydrolysed with TFA according to General Method 6A. Yield: 440 mg (purity 82%, quant.)

LC/MS [Method 1]: racemic diastereomer 1: $R_t$=0.84 min; MS (ESIpos): m/z=417 (M+H)$^+$; racemic diastereomer 2: $R_t$=0.86 min; MS (ESIpos): m/z=417 (M+H)$^+$.

Example 34.1D tert-Butyl 4-({2-[4-(5-chloro-2-cyanophenyl)-5-methoxy-2-oxopyridin-1(2H)-yl]-3-(tetrahydro-2H-pyran-3-yl)propanoyl}amino)benzoate (mixture of racemic diastereomers)

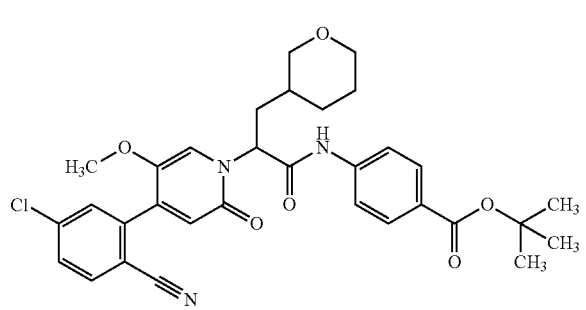 [SMILES: COc1cn(C(CC2CCCOC2)C(=O)Nc2ccc(C(=O)OC(C)(C)C)cc2)c(=O)cc1-c1cc(Cl)ccc1C#N]

440 mg (purity 82%, 0.87 mmol) of 2-[4-(5-chloro-2-cyanophenyl)-5-methoxy-2-oxopyridin-1(2H)-yl]-3-(tetrahydro-2H-pyran-3-yl)propanoic acid (mixture of racemic diastereomers) and 184 mg (0.95 mmol, 1.1 eq.) of tert-butyl 4-aminobenzoate were reacted according to General Method 5A. Yield: 742 mg (purity 85%, quant.)

LC/MS [Method 1]: diastereomer 1: $R_t$=1.28 min; MS (ESIpos): m/z=592 (M+H)+; diastereomer 2: $R_t$=1.29 min; MS (ESIpos): m/z=592 (M+H)$^+$.

Example 35.1A

Tetrahydro-2H-pyran-2-ylmethyl trifluoromethanesulphonate (racemate)

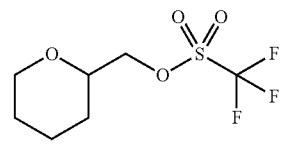 [SMILES: O=S(=O)(OCC1CCCCO1)C(F)(F)F]

5.85 g (50.4 mmol) of tetrahydro-2H-pyran-2-ylmethanol in 88 ml of dichloromethane and 6.45 ml (55.4 mmol) of lutidine and 8.95 ml (52.9 mmol) of trifluoromethanesulphonic anhydride were reacted according to General Method 8A. The crude product was used for the next step without further purification. Yield: 14.8 g (quant.)

$^1$H-NMR (400 MHz, DMSO-$d_6$): δ [ppm]=4.32 (dd, 1H), 4.18 (dd, 1H), 3.96-3.93 (m, 1H), 3.59-3.52 (m, 1H), 3.47-3.40 (m, 1H), 1.84-1.74 (m, 1H), 1.55-1.39 (m, 4H), 1.27-1.15 (m, 1H).

Example 35.1B tert-Butyl 2-[4-(5-chloro-2-cyanophenyl)-5-methoxy-2-oxopyridin-1(2H)-yl]-3-(tetrahydro-2H-pyran-2-yl)propanoate (mixture of racemic diastereomers)

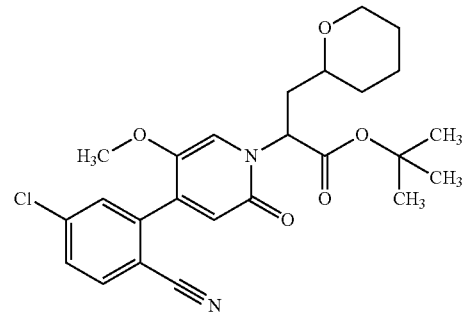 [SMILES: COc1cn(C(CC2CCCCO2)C(=O)OC(C)(C)C)c(=O)cc1-c1cc(Cl)ccc1C#N]

4.20 g (11.2 mmol) of tert-butyl [4-(5-chloro-2-cyanophenyl)-5-methoxy-2-oxopyridin-1(2H)-yl]acetate, 4.17 g (16.8 mmol) of tetrahydro-2H-pyran-2-ylmethyl trifluoromethanesulphonate (racemate) and 11.8 ml (11.8 mmol) of bis(trimethylsilyl)lithium amide (1M in THF) in 125 ml of THF were reacted according to General Method 7B. Purification by column chromatography (100 g silica cartridge, flow rate: 50 ml/min, cyclohexane/ethyl acetate gradient) gave the title compound. Yield: 2.6 g (49% of theory)

LC/MS [Method 1]: $R_t$=1.21 min; MS (ESIpos): m/z=473 (M+H)$^+$.

Example 35.1C

2-[4-(5-Chloro-2-cyanophenyl)-5-methoxy-2-oxopyridin-1(2H)-yl]-3-[tetrahydro-2H-pyran-2-yl]propanoic acid (mixture of racemic diastereomers)

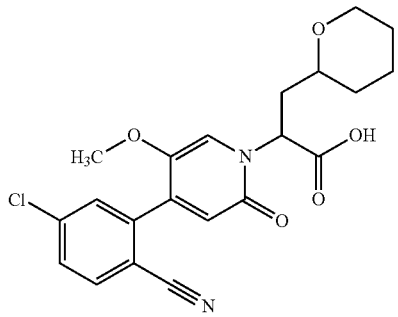 [SMILES: COc1cn(C(CC2CCCCO2)C(=O)O)c(=O)cc1-c1cc(Cl)ccc1C#N]

2.50 g (5.29 mmol) of tert-butyl 2-[4-(5-chloro-2-cyanophenyl)-5-methoxy-2-oxopyridin-1(2H)-yl]-3-(tetrahydro-2H-pyran-2-yl)propanoate (mixture of racemic diastereomers) in 60 ml of dichloromethane and 15.3 ml (198 mmol) of TFA were reacted according to General Method 6A. Yield: 2.20 g (71% of theory)

LC/MS [Method 1]: $R_t$=0.93-0.94 min; MS (ESIpos): m/z=417 (M+H)$^+$.

Example 35.1D

Methyl ({2-[4-(5-chloro-2-cyanophenyl)-5-methoxy-2-oxopyridin-1(2H)-yl]-3-[tetrahydro-2H-pyran-2-yl]propanoyl}amino)benzoate (mixture of racemic diastereomers)

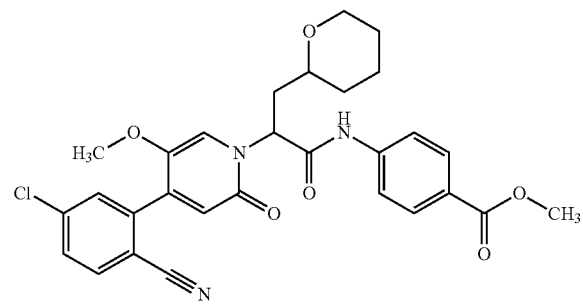 [SMILES: COC(=O)c1ccc(NC(=O)C(CC2CCCCO2)n2cc(OC)c(-c3cc(Cl)ccc3C#N)cc2=O)cc1]

2.20 g (5.28 mmol) of 2-[4-(5-chloro-2-cyanophenyl)-5-methoxy-2-oxopyridin-1(2H)-yl]-3-[tetrahydro-2H-pyran-2-yl]propanoic acid (mixture of racemic diastereomers), 798 mg (5.28 mmol) of methyl 4-aminobenzoate, 750 mg (5.28 mmol) of Oxima and 822 µl (5.28 mmol) of DIC in 110 ml of dimethylformamide were reacted according to General Method 5B. The reaction mixture was purified by flash chromatography (80 g cartridge, 60 ml/min, cyclohexane/ethyl acetate gradient). Yield: 905 mg (31% of theory)

LC/MS [Method 1]: $R_t$=1.14-1.16 min; MS (ESIpos): m/z=550 (M+H)$^+$.

Example 36.1A 1,4-Dioxan-2-ylmethyl trifluoromethanesulphonate (racemate)

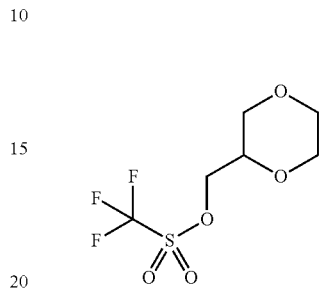

249 mg (2.00 mmol) of 1,4-dioxan-2-ylmethanol (racemate) and 355 µl (2.10 mmol, 1.05 eq.) of trifluoromethanesulphonic anhydride in the presence of 256 µl (2.20 mmol, 1.1 eq.) of 2,6-dimethylpyridine were reacted according to General Method 8A. The crude product was reacted in the next step without further purification.

$^1$H-NMR (400 MHz, DMSO-d$_6$): δ [ppm]=4.35 (dd, 1H), 4.27 (dd, 1H), 3.88-3.76 (m, 2H), 3.75-3.61 (m, 3H), 3.55-3.45 (m, 1H), 3.30 (t, 1H).

Example 36.1B tert-Butyl 2-[4-(5-chloro-2-cyanophenyl)-5-methoxy-2-oxopyridin-1(2H)-yl]-3-(1,4-dioxan-2-yl)propanoate (mixture of racemic diastereomers)

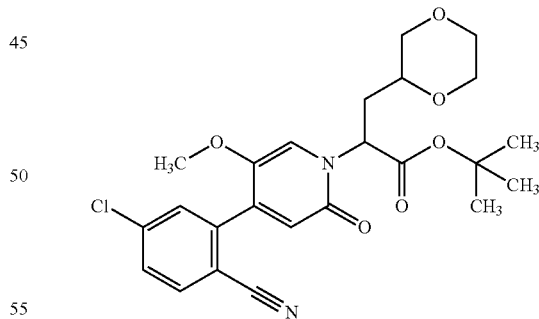

346 mg (purity 93%, 0.86 mmol) of tert-butyl [4-(5-chloro-2-cyanophenyl)-5-methoxy-2-oxopyridin-1(2H)-yl]acetate in the presence of 0.95 ml (0.95 mmol, 1.1 eq.) of bis(trimethylsilyl)lithium amide (1M in THF) and 430 mg (purity 90%, 1.55 mmol, 1.8 eq.) of 1,4-dioxan-2-ylmethyl trifluoromethanesulphonate (racemate) were reacted according to General Method 7B. Yield: 133 mg (33% of theory)

LC/MS [Method 1]: $R_t$=1.04 min; MS (ESIpos): m/z=475 (M+H)$^+$.

Example 36.1C

2-[4-(5-Chloro-2-cyanophenyl)-5-methoxy-2-oxopyridin-1(2H)-yl]-3-(1,4-dioxan-2-yl)propanoic acid (mixture of racemic diastereomers)

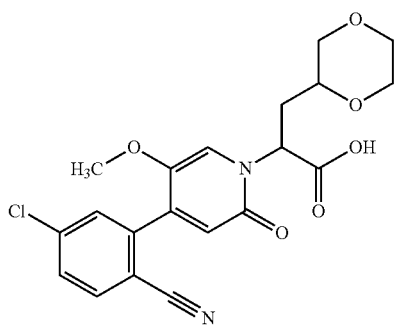 [SMILES: COc1cn(C(CC2COCCO2)C(=O)O)c(=O)cc1-c1cc(Cl)ccc1C#N]

133 mg (0.28 mmol) of tert-butyl 2-[4-(5-chloro-2-cyanophenyl)-5-methoxy-2-oxopyridin-1(2H)-yl]-3-(1,4-dioxan-2-yl)propanoate (mixture of racemic diastereomers) were hydrolysed with TFA according to General Method 6A. Yield: 132 mg (purity 60%, 68% of theory)

LC/MS [Method 8]: $R_t$=0.99 min; MS (ESIpos): m/z=419 (M+H)$^+$.

Example 36.1D tert-Butyl 4-({2-[4-(5-chloro-2-cyanophenyl)-5-methoxy-2-oxopyridin-1(2H)-yl]-3-(1,4-dioxan-2-yl)propanoyl}amino)benzoate (mixture of racemic diastereomers)

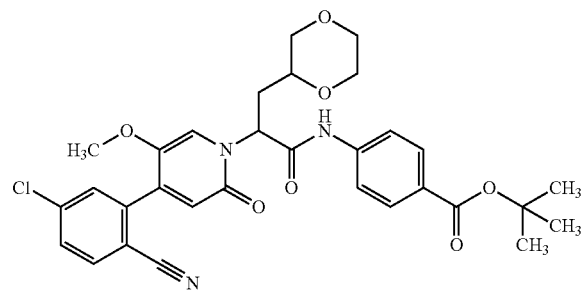 [SMILES: COc1cn(C(CC2COCCO2)C(=O)Nc2ccc(C(=O)OC(C)(C)C)cc2)c(=O)cc1-c1cc(Cl)ccc1C#N]

132 mg (purity 60%, 0.19 mmol) of 2-[4-(5-chloro-2-cyanophenyl)-5-methoxy-2-oxopyridin-1(2H)-yl]-3-(1,4-dioxan-2-yl)propanoic acid (mixture of racemic diastereomers) and 40 mg (0.21 mmol, 1.1 eq.) of tert-butyl 4-aminobenzoate were reacted according to General Method 5A. Yield: 106 mg (94% of theory)

LC/MS [Method 8]: racemic diastereomer 1: $R_t$=1.44 min; MS (ESIneg): m/z=592 (M–H)$^-$; racemic diastereomer 2: $R_t$=1.46 min; MS (ESIneg): m/z=592 (M–H)$^-$.

Example 37.1A

2-Fluoroethyl trifluoromethanesulphonate

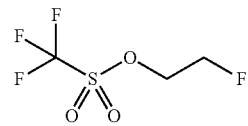 [SMILES: O=S(=O)(OCCF)C(F)(F)F]

At −78° C., a solution of 1.00 g (15.6 mmol) of 2-fluoroethanol and 2.39 ml (17.2 mmol) of triethylamine in 5 ml of dichloromethane was added dropwise to 2.89 ml (17.2 mmol) of trifluoromethanesulphonic anhydride in 5 ml of dichloromethane such that the internal temperature did not exceed −50° C. The mixture was stirred at −78° C. for another 15 min and spontaneously warmed to RT. The reaction mixture was diluted with 50 ml of methyl tert-butyl ether, washed three times with 25 ml of a mixture of saturated aqueous sodium chloride solution/1N hydrochloric acid (3:1), dried over magnesium sulphate, filtered and concentrated at 25° C. and a pressure of ≥100 mbar. Yield: 2.3 g (75% of theory)

$^1$H-NMR (400 MHz, DMSO-$d_6$): δ [ppm]=4.78-4.74 (m, 1H), 4.66-4.62 (m, 1H), 4.61-4.58 (m, 1H), 4.54-4.50 (m, 1H).

Example 37.1B tert-Butyl 2-[4-(5-chloro-2-cyanophenyl)-5-methoxy-2-oxopyridin-1(2H)-yl]-4-fluorobutanoate (racemate)

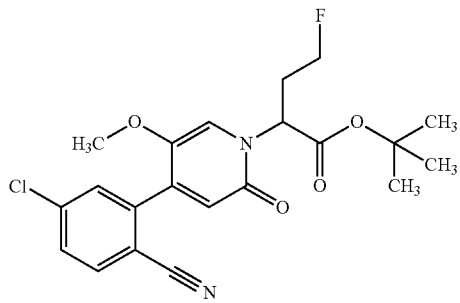 [SMILES: COc1cn(C(CCF)C(=O)OC(C)(C)C)c(=O)cc1-c1cc(Cl)ccc1C#N]

500 mg (1.26 mmol) of tert-butyl [4-(5-chloro-2-cyanophenyl)-5-methoxy-2-oxopyridin-1(2H)-yl]acetate, 445 mg (2.27 mmol) of 2-fluoroethyl trifluoromethanesulphonate and 1.39 ml (1.39 mmol) of bis(trimethylsilyl)lithium amide (1M in THF) in 10 ml of THF were reacted according to General Method 7B. Purification by column chromatography (120 g silica cartridge, flow rate: 80 ml/min, cyclohexane/ethyl acetate gradient) gave the title compound. Yield: 360 mg (67% of theory)

LC/MS [Method 1]: $R_t$=1.07 min; MS (ESIpos): m/z=421 (M+H)$^+$ $^1$H-NMR (400 MHz, DMSO-$d_6$): δ [ppm]=7.99 (d, 1H), 7.75-7.72 (m, 2H), 7.44 (s, 1H), 6.51 (s, 1H), 5.17 (dd, 1H), 4.66-4.49 (m, 1H), 4.44-4.27 (m, 1H), 3.63 (s, 3H), 2.62-2.40 (m, 2H), 1.40 (s, 9H).

Example 37.1C

2-[4-(5-Chloro-2-cyanophenyl)-5-methoxy-2-oxopyridin-1(2H)-yl]-4-fluorobutanoic acid (racemate)

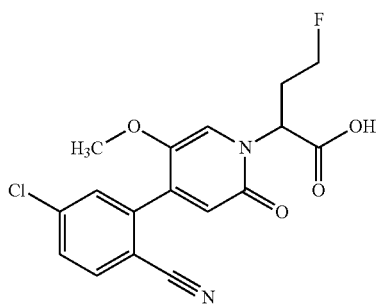 [SMILES: COc1cn(C(CCF)C(=O)O)c(=O)cc1-c1cc(Cl)ccc1C#N]

359 mg (853 µmol) of tert-butyl 2-[4-(5-chloro-2-cyanophenyl)-5-methoxy-2-oxopyridin-1(2H)-yl]-4-fluorobutanoate (racemate) in 8.5 ml of dichloromethane and 2.5 ml (32 mmol) of TFA were reacted according to General Method 6A. Yield: 306 mg (96% of theory)

LC/MS [Method 1]: $R_t$=0.80 min; MS (ESIneg): m/z=363 (M–H)⁻

$^1$H-NMR (400 MHz, DMSO-$d_6$): δ [ppm]=13.1 (s, 1H), 7.99 (d, 1H), 7.74 (s, 1H), 7.73 (dd, 1H), 7.49 (s, 1H), 6.50 (s, 1H), 5.22 (dd, 1H), 4.66-4.48 (m, 1H), 4.42-4.24 (m, 1H), 3.63 (s, 3H), 2.65-2.42 (m, 2H).

Example 37.1D tert-Butyl 4-({2-[4-(5-chloro-2-cyanophenyl)-5-methoxy-2-oxopyridin-1(2H)-yl]-4-fluorobutanoyl}amino)benzoate (racemate)

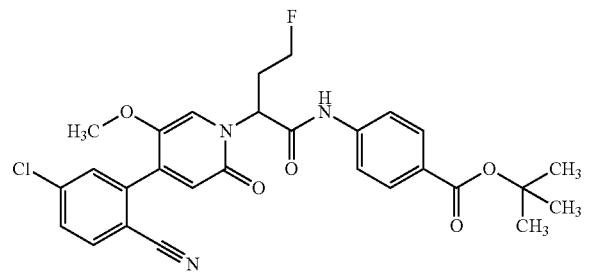 [SMILES: COc1cn(C(CCF)C(=O)Nc2ccc(C(=O)OC(C)(C)C)cc2)c(=O)cc1-c1cc(Cl)ccc1C#N]

100 mg (274 µmol) of 2-[4-(5-chloro-2-cyanophenyl)-5-methoxy-2-oxopyridin-1(2H)-yl]-4-fluorobutanoic acid (racemate), 53.0 mg (274 µmol) of tert-butyl 4-aminobenzoate, 39.0 mg (274 µmol) of Oxima and 43.0 µl (274 µmol) of DIC in 5 ml of dimethylformamide were reacted according to General Method 5B. Filtration gave the title compound. Yield: 117 mg (78% of theory)

LC/MS [Method 1]: $R_t$=1.20 min; MS (ESIpos): m/z=540 (M+H)⁺

$^1$H-NMR (400 MHz, DMSO-$d_6$): δ [ppm]=10.8 (s, 1H), 8.00 (d, 1H), 7.87 (d, 2H), 7.77-7.73 (m, 4H), 7.51 (s, 1H), 6.55 (s, 1H), 5.85 (t, 1H), 4.67-4.49 (m, 1H), 4.47-4.28 (m, 1H), 3.69 (s, 3H), 2.69-2.55 (m, 2H), 1.54 (s, 9H).

Example 38.1A 2,2-Difluoroethyl trifluoromethanesulphonate

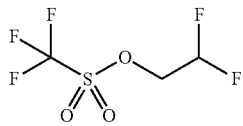

At –78° C., a solution of 1.00 g (12.2 mmol) of 2,2-difluoroethanol and 1.87 ml (13.4 mmol) of triethylamine in 5 ml of dichloromethane was added dropwise to 2.26 ml (13.4 mmol) of trifluoromethanesulphonic anhydride in 5 ml of dichloromethane such that the internal temperature did not exceed –50° C. The mixture was stirred at –78° C. for another 15 min and spontaneously warmed to RT. The reaction mixture was diluted with 50 ml of methyl tert-butyl ether and washed three times with 25 ml of a mixture of saturated aqueous sodium chloride solution/1N hydrochloric acid (3:1), dried over magnesium sulphate, filtered and concentrated at 25° C. and a pressure of ≥100 mbar. Yield: 1.48 g (51% of theory)

$^1$H-NMR (400 MHz, CDCl$_3$): δ [ppm]=6.05 (tt, 1H), 4.59 (dt, 2H).

Example 38.1B tert-Butyl 2-[4-(5-chloro-2-cyanophenyl)-5-methoxy-2-oxopyridin-1(2H)-yl]-4,4-difluorobutanoate (racemate)

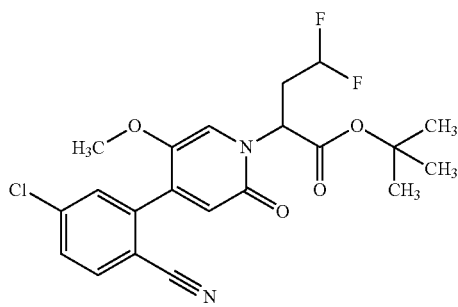 [SMILES: COc1cn(C(CC(F)F)C(=O)OC(C)(C)C)c(=O)cc1-c1cc(Cl)ccc1C#N]

150 mg (388 µmol) of tert-butyl [4-(5-chloro-2-cyanophenyl)-5-methoxy-2-oxopyridin-1(2H)-yl]acetate, 125 mg (582 µmol) of 2,2-difluoroethyl trifluoromethanesulphonate and 427 µl (427 µmol) of bis(trimethylsilyl)lithium amide (1M in THF) in 3 ml of THF were reacted according to General Method 7B. Purification by column chromatography (24 g silica cartridge, flow rate: 35 ml/min, cyclohexane/ethyl acetate gradient) gave the title compound. Yield: 122 mg (71% of theory)

LC/MS [Method 1]: $R_t$=1.10 min; MS (ESIpos): m/z=439 (M+H)⁺

$^1$H-NMR (400 MHz, DMSO-$d_6$): δ [ppm]=7.99 (d, 1H), 7.74-7.70 (m, 2H), 7.50 (s, 1H), 6.52 (s, 1H), 6.19 (tt, 1H), 5.29-5.20 (m, 1H), 3.64 (s, 3H), 2.83-2.65 (m, 2H), 1.39 (s, 9H).

Example 38.1C

2-[4-(5-Chloro-2-cyanophenyl)-5-methoxy-2-oxopyridin-1(2H)-yl]-4,4-difluorobutanoic acid (racemate)

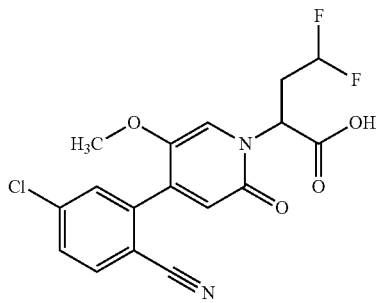

114 mg (260 µmol) of tert-butyl 2-[4-(5-chloro-2-cyanophenyl)-5-methoxy-2-oxopyridin-1(2H)-yl]-4,4-difluorobutanoate (racemate) in 8 ml of dichloromethane and 400 µl (5.20 mmol) of TFA were reacted according to General Method 6A. Yield: 99 mg (91% of theory)

LC/MS [Method 1]: $R_t$=0.85 min; MS (ESIneg): m/z=381 (M−H)−

$^1$H-NMR (400 MHz, DMSO-$d_6$): δ [ppm]=13.4 (s, 1H), 7.99 (d, 1H), 7.73 (dd, 1H), 7.72 (s, 1H), 7.55 (s, 1H), 6.51 (s, 1H), 6.18 (tt, 1H), 5.31-5.25 (m, 1H), 3.63 (s, 3H), 2.83-2.65 (m, 2H).

Example 38.1D

Ethyl 4-({2-[4-(5-chloro-2-cyanophenyl)-5-methoxy-2-oxopyridin-1(2H)-yl]-4,4-difluorobutanoyl}amino)benzoate (racemate)

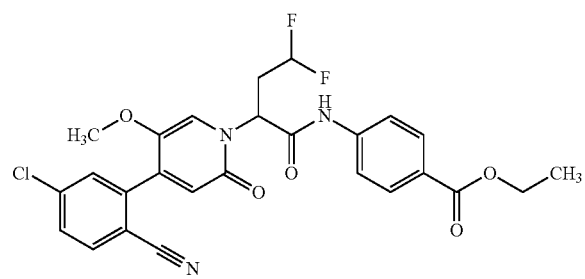 [SMILES: CCOC(=O)c1ccc(NC(=O)C(CC(F)F)n2cc(OC)c(-c3cc(Cl)ccc3C#N)cc2=O)cc1]

97.0 mg (253 µmol) of 2-[4-(5-chloro-2-cyanophenyl)-5-methoxy-2-oxopyridin-1(2H)-yl]-4,4-difluorobutanoic acid (racemate), 42.0 mg (253 µmol) of ethyl 4-aminobenzoate, 36.0 mg (253 µmol) of Oxima and 39.0 µl (253 µmol) of DIC in 2.5 ml of dimethylformamide were reacted according to General Method 5B. The crude product was purified by preparative HPLC [column: Chromatorex C18, 10 µm, 125×30 mm, mobile phase: acetonitrile/0.05% formic acid gradient (0 to 3 min 10% acetonitrile, to 35 min 90% acetonitrile and a further 3 min 90% acetonitrile)]. Yield: 81.7 mg (60% of theory)

LC/MS [Method 1]: $R_t$=1.12 min; MS (ESIpos): m/z=530 (M+H)+

$^1$H-NMR (400 MHz, DMSO-$d_6$): δ [ppm]=10.8 (s, 1H), 8.00 (d, 1H), 7.94 (d, 2H), 7.76 (d, 2H), 7.75-7.71 (m, 2H), 7.56 (s, 1H), 6.55 (s, 1H), 6.15 (tt, 1H), 5.90 (dd, 1H), 4.29 (q, 2H), 3.69 (s, 3H), 2.97-2.78 (m, 2H), 1.31 (t, 3H).

Example 39.1A 2,2,2-Trifluoroethyl trifluoromethanesulphonate

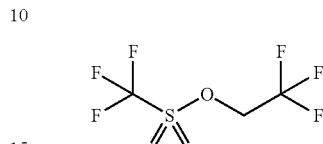

At −78° C., a solution of 1.00 g (10.0 mmol) of 2,2,2-trifluoroethanol and 1.53 ml (11.0 mmol) of triethylamine in 5 ml of dichloromethane was added dropwise to 1.85 ml (11.0 mmol) of trifluoromethanesulphonic anhydride in 5 ml of dichloromethane such that the internal temperature did not exceed −50° C. The mixture was stirred at −78° C. for another 15 min and spontaneously warmed to RT. The reaction mixture was diluted with 50 ml of methyl tert-butyl ether and washed three times with 25 ml of a mixture of saturated aqueous sodium chloride solution/1N hydrochloric acid (3:1), dried over magnesium sulphate, filtered and concentrated at 25° C. and a pressure of ≥100 mbar. Yield: 1.0 g (43% of theory)

$^1$H-NMR (400 MHz, CDCl$_3$): δ [ppm]=4.71 (q, 2H).

Example 39.1B tert-Butyl 2-[4-(5-chloro-2-cyanophenyl)-5-methoxy-2-oxopyridin-1(2H)-yl]-4,4,4-trifluorobutanoate (racemate)

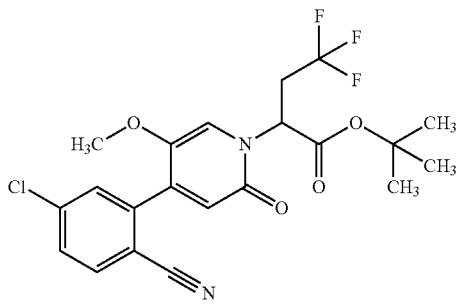

500 mg (1.29 mmol) of tert-butyl [4-(5-chloro-2-cyanophenyl)-5-methoxy-2-oxopyridin-1(2H)-yl]acetate, 360 mg (1.55 mmol) of 2,2,2-trifluoromethyl trifluoromethanesulphonate and 1.42 ml (1.42 mmol) of bis(trimethylsilyl)lithium amide (1M in THF) in 10 ml of THF were reacted according to General Method 7B. Purification by column chromatography (24 g silica cartridge, flow rate: 35 ml/min, cyclohexane/ethyl acetate gradient) gave the title compound. Yield: 66 mg (11% of theory)

LC/MS [Method 1]: $R_t$=1.12 min; MS (ESIpos): m/z=457 (M+H)+.

Example 39.1C

2-[4-(5-Chloro-2-cyanophenyl)-5-methoxy-2-oxopyridin-1(2H)-yl]-4,4,4-trifluorobutanoic acid (racemate)

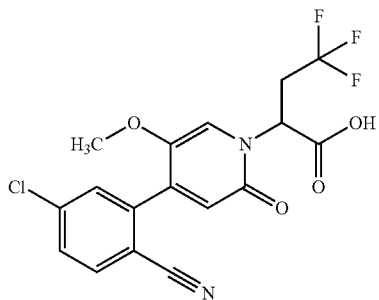 [SMILES: COc1cn(C(CC(F)(F)F)C(=O)O)c(=O)cc1-c1cc(Cl)ccc1C#N]

65.0 mg (142 µmol) of tert-butyl 2-[4-(5-chloro-2-cyanophenyl)-5-methoxy-2-oxopyridin-1(2H)-yl]-4,4,4-trifluorobutanoate (racemate) in 1.6 ml of dichloromethane and 411 µl (5.34 mmol) of TFA were reacted according to General Method 6A. Yield: 53 mg (81% of theory)

LC/MS [Method 1]: $R_t$=0.89 min; MS (ESIpos): m/z=401 (M+H)$^+$ $^1$H-NMR (400 MHz, DMSO-d$_6$): δ [ppm]=13.5 (br. s, 1H), 7.99 (d, 1H), 7.74-7.72 (m, 2H), 7.59 (s, 1H), 6.52 (s, 1H), 5.43-5.38 (m, 1H), 3.63 (s, 3H), 3.33-3.14 (m, 2H).

Example 39.1D

Ethyl 4-({2-[4-(5-chloro-2-cyanophenyl)-5-methoxy-2-oxopyridin-1(2H)-yl]-4,4,4-trifluorobutanoyl}amino)benzoate (racemate)

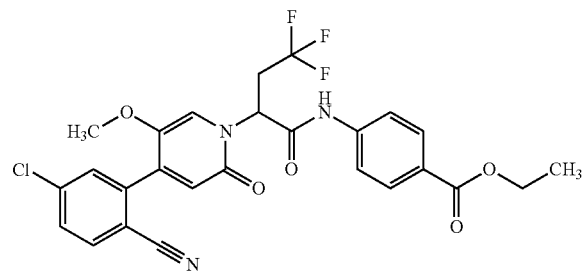 [SMILES: CCOC(=O)c1ccc(NC(=O)C(CC(F)(F)F)n2cc(OC)c(-c3cc(Cl)ccc3C#N)cc2=O)cc1]

63.0 mg (157 µmol) of 2-[4-(5-chloro-2-cyanophenyl)-5-methoxy-2-oxopyridin-1(2H)-yl]-4,4,4-trifluorobutanoic acid (racemate), 26.0 mg (157 µmol) of ethyl 4-aminobenzoate, 22.3 mg (157 µmol) of Oxima and 24.0 µl (157 µmol) of DIC in 1.6 ml of dimethylformamide were reacted according to General Method 5B. The reaction product was purified by preparative HPLC [column: Chromatorex C18, 10 µm, 125×30 mm, mobile phase: acetonitrile/0.05% formic acid gradient (0 to 3 min 10% acetonitrile, to 35 min 90% acetonitrile and a further 3 min 90% acetonitrile)]. Yield: 25.1 mg (28% of theory)

LC/MS [Method 1]: $R_t$=1.15 min; MS (ESIpos): m/z=548 (M+H)$^+$ $^1$H-NMR (400 MHz, DMSO-d$_6$): δ [ppm]=10.9 (s, 1H), 8.00 (d, 1H), 7.95 (d, 2H), 7.78 (d, 2H), 7.74 (dd, 1H), 7.72 (s, 1H), 7.62 (s, 1H), 6.56 (s, 1H), 6.11-6.03 (m, 1H), 4.29 (q, 2H), 3.69 (s, 3H), 3.57-3.44 (m, 1H), 3.38-3.26 (m, 1H), 1.31 (t, 3H).

Example 40.1A

2-Fluoropropyl trifluoromethanesulphonate (racemate)

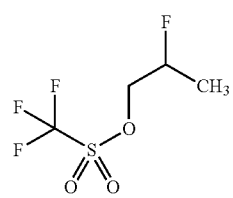

156 mg (1.94 mmol) of 2-fluoropropan-1-ol and 361 µl (2.13 mmol, 1.1 eq.) of trifluoromethanesulphonic anhydride in the presence of 297 µl (2.13 mmol, 1.1 eq.) of triethylamine were reacted according to General Method 8A. The crude product was reacted in the next step without further purification.

Example 40.1B tert-Butyl 2-[4-(5-chloro-2-cyanophenyl)-5-methoxy-2-oxopyridin-1(2H)-yl]-4-fluoropentanoate (mixture of racemic diastereomers)

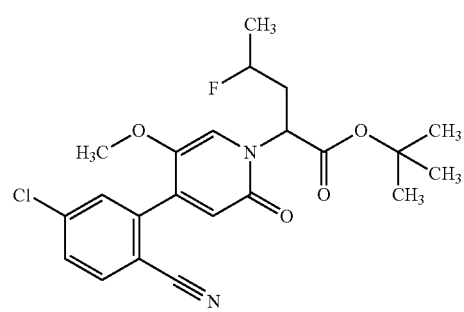 [SMILES: COc1cn(C(CC(C)F)C(=O)OC(C)(C)C)c(=O)cc1-c1cc(Cl)ccc1C#N]

450 mg (purity 94%, 1.13 mmol) of tert-butyl [4-(5-chloro-2-cyanophenyl)-5-methoxy-2-oxopyridin-1(2H)-yl] acetate in the presence of 1.24 ml (1.24 mmol, 1.1 eq.) of bis(trimethylsilyl)lithium amide (1M in THF) and 356 mg (1.69 mmol, 1.5 eq.) of 2-fluoropropyl trifluoromethanesulphonate (racemate) were reacted according to General Method 7B. Yield: 270 mg (52% of theory)

LC/MS [Method 1]: $R_t$=1.09 min; MS (ESIpos): m/z=435 (M+H)$^+$.

Example 40.1C

2-[4-(5-Chloro-2-cyanophenyl)-5-methoxy-2-oxopyridin-1(2H)-yl]-4-fluoropentanoic acid (mixture of racemic diastereomers)

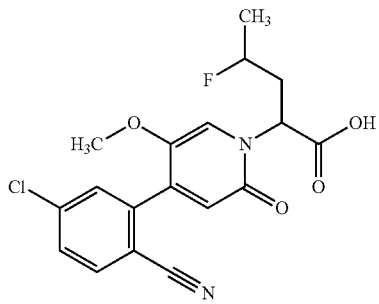 [SMILES: COc1cn(C(CC(C)F)C(=O)O)c(=O)cc1-c1cc(Cl)ccc1C#N]

270 mg (0.59 mmol) of tert-butyl 2-[4-(5-chloro-2-cyanophenyl)-5-methoxy-2-oxopyridin-1(2H)-yl]-4-fluoropentanoate (mixture of racemic diastereomers) were hydrolysed with TFA according to General Method 6A. Yield: 222 mg (purity 85%, 84% of theory)

LC/MS [Method 1]: $R_t$=0.86 min; MS (ESIpos): m/z=379 (M+H)$^+$.

Example 40.1D

Ethyl 4-({2-[4-(5-chloro-2-cyanophenyl)-5-methoxy-2-oxopyridin-1(2H)-yl]-4-fluoropentanoyl}amino)benzoate (mixture of racemic diastereomers)

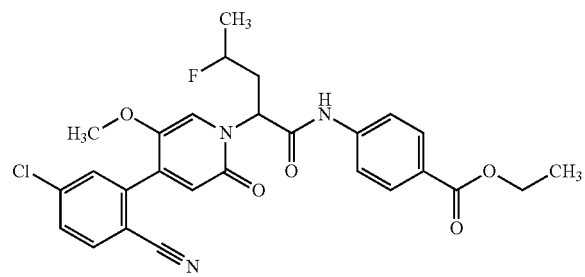 [SMILES: CCOC(=O)c1ccc(NC(=O)C(CC(C)F)n2cc(OC)c(-c3cc(Cl)ccc3C#N)cc2=O)cc1]

222 mg (purity 85%, 0.50 mmol) of 2-[4-(5-chloro-2-cyanophenyl)-5-methoxy-2-oxopyridin-1(2H)-yl]-4-fluoropentanoic acid (mixture of racemic diastereomers) and 91 mg (0.55 mmol, 1.1 eq.) of ethyl 4-aminobenzoate were reacted according to General Method 5A. Yield: 180 mg (purity 91%, 63% of theory)

LC/MS [Method 1]: $R_t$=1.12 min; MS (ESIpos): m/z=526 (M+H)$^+$.

Example 41.1A tert-Butyl 2-[4-(5-chloro-2-cyanophenyl)-5-methoxy-2-oxopyridin-1(2H)-yl]-2,4,5-trideoxy-5,5,5-trifluoro-4-methylpentonate (diastereomer mixture)

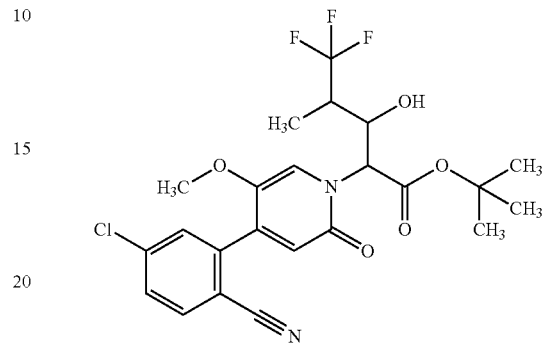

At −70° C., 1.17 ml (1.17 mmol, 1.1 eq.) of bis(trimethylsilyl)lithium amide (1M in THF) were added dropwise to a solution of 400 mg (1.07 mmol) of tert-butyl [4-(5-chloro-2-cyanophenyl)-5-methoxy-2-oxopyridin-1(2H)-yl]acetate in 10.8 ml of tetrahydrofuran, the mixture was stirred at −70° C. for 10 min, a solution of 175 mg (1.39 mmol, 1.3 eq.) of 2-(trifluoromethyl)propionaldehyde in 0.8 ml of tetrahydrofuran was added and the mixture was stirred at −70° C. for 1 h. The reaction mixture was warmed to RT and stirred at RT for a further 30 min, and 5 ml of saturated aqueous ammonium chloride solution were added. After phase separation, the aqueous phase was extracted twice with ethyl acetate. The combined organic phases were washed with saturated aqueous sodium chloride solution, dried (sodium sulphate), filtered, concentrated under reduced pressure and dried. The crude product was purified by flash chromatography (KP-SIL, ethyl acetate/cyclohexane 20-50%). Yield: 274 mg (purity 75%, 38% of theory)

LC/MS [Method 1]: $R_t$=1.15 min; MS (ESIpos): m/z=501 (M+H)$^+$.

Example 41.1B tert-Butyl 2-[4-(5-chloro-2-cyanophenyl)-5-methoxy-2-oxopyridin-1(2H)-yl]-5,5,5-trifluoro-4-methylpent-2-enate (diastereomer mixture)

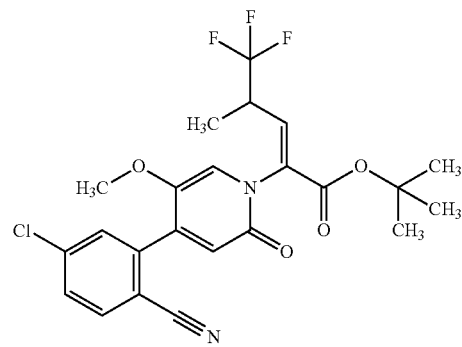 [SMILES: COc1cn(/C(=C\C(C)C(F)(F)F)C(=O)OC(C)(C)C)c(=O)cc1-c1cc(Cl)ccc1C#N]

At RT, 64 µl (0.48 mmol, 1.2 eq.) of diethylaminosulphur trifluoride were added dropwise to a solution of 270 mg (0.40 mmol) of tert-butyl 2-[4-(5-chloro-2-cyanophenyl)-5-methoxy-2-oxopyridin-1(2H)-yl]-2,4,5-trideoxy-5,5,5-trifluor-4-methylpentonate (diastereomer mixture) in 6 ml of dichloromethane, the mixture was stirred at RT for 90 min and 3 ml of dichloromethane and 6 ml of saturated aqueous sodium bicarbonate solution were then added. After phase separation, the aqueous phase was extracted with ethyl acetate. The combined organic phases were washed with saturated aqueous sodium chloride solution, dried (sodium sulphate), filtered, concentrated under reduced pressure and dried. Yield: 224 mg (purity 72%, 83% of theory)

LC/MS [Method 2]: $R_t$=3.78 min; MS (ESIpos): m/z=483 (M+H)$^+$.

Example 41.1C tert-Butyl 2-[4-(5-chloro-2-cyanophenyl)-5-methoxy-2-oxopyridin-1(2H)-yl]-5,5,5-trifluoro-4-methylpentanoate (mixture of racemic diastereomers)

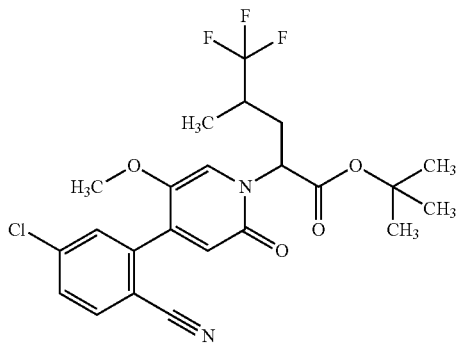 [SMILES: COc1cn(C(CC(C)C(F)(F)F)C(=O)OC(C)(C)C)c(=O)cc1-c1cc(Cl)ccc1C#N]

At RT, 193 mg (purity 72%, 0.29 mmol) of tert-butyl 2-[4-(5-chloro-2-cyanophenyl)-5-methoxy-2-oxopyridin-1(2H)-yl]-5,5,5-trifluoro-4-methylpent-2-enoate (diastereomer mixture) were admixed with 10 ml of a "Hot Stryker's" reagent solution [B. A. Baker et al. *Org. Lett.* 2008, 10, 289-292], and the reaction mixture was stirred at RT for 6 h. After addition of a further 8 ml of a "Hot Stryker's" reagent solution, the reaction mixture was stirred at RT overnight and then concentrated under reduced pressure. Three times, the crude product was stirred with in each case 15 ml of acetonitrile and decanted. The combined organic phases were concentrated under reduced pressure. The residue was purified by flash chromatography (KP-SIL, ethyl acetate/cyclohexane 20-33%). Yield: 169 mg (purity 92%, quant.)

LC/MS [Method 1]: $R_t$=1.21 min; MS (ESIpos): m/z=485 (M+H)$^+$.

Example 41.1D

2-[4-(5-Chloro-2-cyanophenyl)-5-methoxy-2-oxopyridin-1(2H)-yl]-5,5,5-trifluor-4-methylpentanoic acid (mixture of racemic diastereomers)

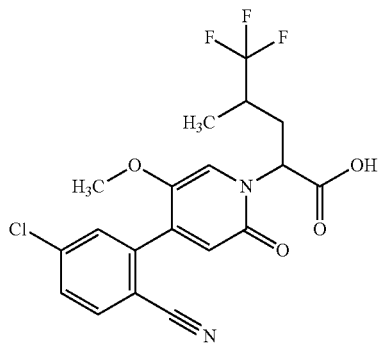 [SMILES: COc1cn(C(CC(C)C(F)(F)F)C(=O)O)c(=O)cc1-c1cc(Cl)ccc1C#N]

190 mg (purity 92%, 0.36 mmol) of tert-butyl 2-[4-(5-chloro-2-cyanophenyl)-5-methoxy-2-oxopyridin-1(2H)-yl]-5,5,5-trifluor-4-methylpentanoate (mixture of racemic diastereomers) were hydrolysed with TFA according to General Method 6A. The crude product was reacted in the next step without further purification. Yield: 129 mg Example 41.1E tert-Butyl 4-({2-[4-(5-chloro-2-cyanophenyl)-5-methoxy-2-oxopyridin-1(2H)-yl]-5,5,5-trifluoro-4-methylpentanoyl}amino)benzoate (mixture of racemic diastereomers)

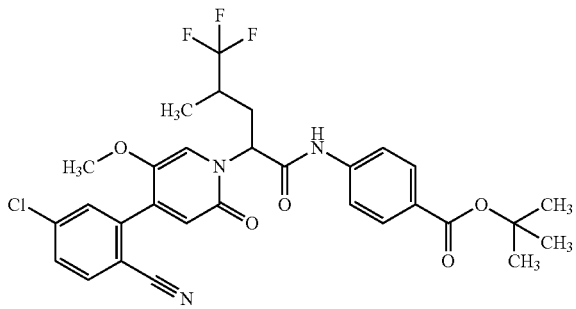 [SMILES: COc1cn(C(CC(C)C(F)(F)F)C(=O)Nc2ccc(C(=O)OC(C)(C)C)cc2)c(=O)cc1-c1cc(Cl)ccc1C#N]

129 mg of 2-[4-(5-chloro-2-cyanophenyl)-5-methoxy-2-oxopyridin-1(2H)-yl]-5,5,5-trifluoro-4-methylpentanoic acid (mixture of racemic diastereomers) and 59 mg (0.31 mmol, 1.1 eq.) of tert-butyl 4-aminobenzoate were reacted according to General Method 5A. Yield: 51 mg (30% of theory)

LC/MS [Method 1]: $R_t$=1.37 min; MS (ESIpos): m/z=604 (M+H)$^+$.

Example 42.1A

2-Hydroxy-4,4-dimethylpentanoic acid (racemate)

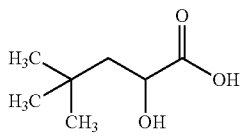

805 mg (5.54 mmol) of 4-methylleucine (racemate) were initially charged in 11 ml of sulphuric acid (1M) and cooled to 0° C. 2.30 g (33.3 mmol) of sodium nitrite as a solution in 6.5 ml of water were then slowly added dropwise over a period of 90 min. The solution was stirred at RT for another 24 h. The mixture was carefully diluted with 10 ml of water and the aqueous phase was extracted five times with 10 ml of methyl tert-butyl ether. The combined organic phases were washed with 25 ml of saturated aqueous sodium chloride solution, dried over sodium sulphate and filtered, and the solvent was removed under reduced pressure. The crude product was used for the next step without further purification. Yield: 667 mg (82% of theory)

$^1$H-NMR (400 MHz, DMSO-$d_6$): δ [ppm]=3.99 (dd, 1H), 1.56 (dd, 1H), 1.40 (dd, 1H), 0.93 (s, 9H).

Example 42.1B

Benzyl 2-hydroxy-4,4-dimethylpentanoate (racemate)

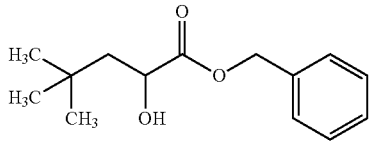 [SMILES: CC(C)(C)CC(O)C(=O)OCc1ccccc1]

743 mg (2.28 mmol) of caesium carbonate were added to a solution of 667 mg (4.56 mmol) of 2-hydroxy-4,4-dimethylpentanoic acid (racemate) in 8.7 ml of methanol and 1.7 ml of water The reaction mixture was stirred at RT for 60 min and the solvent was then removed under reduced pressure. The residue was dried under high vacuum (4 h) and then taken up in 10 ml of dimethylformamide. At 0° C., 516 μl (4.33 mmol) of benzyl bromide were slowly added dropwise. The reaction mixture was stirred at RT for 12 h, the reaction was terminated by addition of 25 ml of water and the reaction mixture was extracted three times with 20 ml of ethyl acetate. The combined organic phases were dried over magnesium sulphate and filtered, and the solvent was removed under reduced pressure. The residue was purified by flash chromatography (40 g silica cartridge, 35 ml/min, cyclohexane/ethyl acetate gradient). Yield: 584 mg (54% of theory)

$^1$H-NMR (400 MHz, CDCl$_3$): δ [ppm]=7.39-7.33 (m, 5H), 5.23 (d, 1H), 5.18 (d, 1H), 4.29 (ddd, 1H), 2.62 (d, 1H), 1.73 (dd, 1H), 1.49 (dd, 1H), 0.99 (s, 9H).

Example 42.1C

Benzyl 4,4-dimethyl-2-{[(trifluoromethyl)sulphonyl]oxy}pentanoate (racemate)

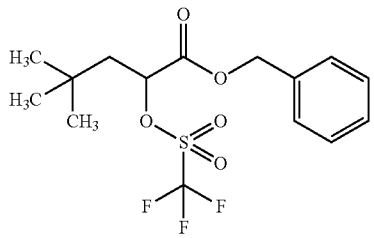 [SMILES: CC(C)(C)CC(OS(=O)(=O)C(F)(F)F)C(=O)OCc1ccccc1]

236 mg (1.00 mmol) of benzyl 2-hydroxy-4,4-dimethylpentanoate (racemate) in 10 ml of dichloromethane and 175 μl (1.50 mmol) of lutidine and 254 μl (1.50 mmol) of trifluoromethanesulphonic anhydride were reacted according to General Method 8A. The crude product was used for the next step without further purification. Yield: 365 mg (99% of theory)

Example 42.1D

Benzyl 2-[4-(5-chloro-2-cyanophenyl)-5-methoxy-2-oxopyridin-1(2H)-yl]-4,4-dimethylpentanoate

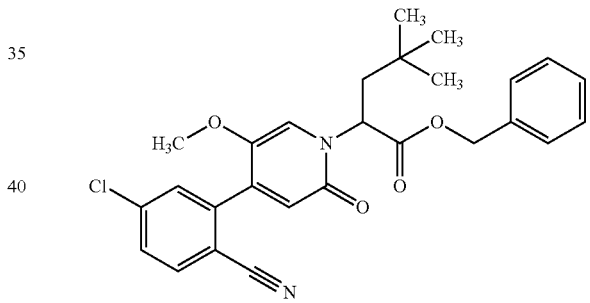

A little at a time, 41.8 mg (1.04 mmol) of sodium hydride (60% in mineral oil) were added to a suspension of 261 mg (purity 87%, 870 μmol) of 4-chloro-2-(5-methoxy-2-oxo-1,2-dihydropyridin-4-yl)benzonitrile in 10 ml of THF, and the mixture was stirred at RT for another 1 h. 481 mg (1.31 mmol) of benzyl 4,4-dimethyl-2-{[(trifluoromethyl)sulphonyl]oxy}pentanoate (racemate) as a solution in 3 ml of THF were quickly added dropwise to the resulting reaction solution, and after the addition had ended the mixture was stirred at RT for another 1.5 h. The reaction was terminated by addition of 10 ml of saturated aqueous ammonium chloride solution and 15 ml of methyl tert-butyl ether. The phases were separated and the aqueous phase was extracted three times with 10 ml of methyl tert-butyl ether. The combined organic phases were dried over magnesium sulphate and filtered, and the solvent was removed under reduced pressure. The crude product was purified by flash chromatography (80 g silica cartridge, 60 ml/min, cyclohexane/ethyl acetate gradient). Yield: 294 mg (71% of theory)

LC/MS [Method 1]: R$_t$=1.29 min; MS (ESIpos): m/z=479 (M+H)$^+$

¹H-NMR (400 MHz, DMSO-d₆): δ [ppm]=7.99 (d, 1H), 7.74-7.70 (m, 2H), 7.55 (s, 1H), 7.39-7.30 (m, 5H), 6.53 (s, 1H), 5.56-5.50 (m, 1H), 5.18 (s, 2H), 3.63 (s, 3H), 2.19-2.10 (m, 2H), 0.87 (s, 9H).

Example 42.1E

2-[4-(5-Chloro-2-cyanophenyl)-5-methoxy-2-oxopyridin-1(2H)-yl]-4,4-dimethylpentanoic acid

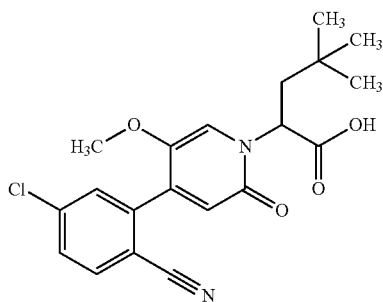 [SMILES: COc1cn(C(CC(C)(C)C)C(=O)O)c(=O)cc1-c1cc(Cl)ccc1C#N]

17.5 mg (438 µmol, 60% in mineral oil) of sodium hydride were added to a solution of 140 mg (292 µmol) of benzyl 2-[4-(5-chloro-2-cyanophenyl)-5-methoxy-2-oxopyridin-1(2H)-yl]-4,4-dimethylpentanoate (racemate) in 5 ml of THF (not dry), and the mixture was stirred for another 15 min. The reaction was terminated by addition of 5 ml of saturated aqueous ammonium chloride solution, 10 ml of dichloromethane and 0.5 ml of hydrochloric acid (1N). The phases were separated and the aqueous phase was extracted three times with 5 ml of dichloromethane. The combined organic phases were dried over sodium sulphate and filtered, and the solvent was removed under reduced pressure. The residue corresponded to the title compound and was used for the next step without further purification. Yield: 110 mg (83% of theory, purity 86%)

LC/MS [Method 1]: $R_t$=0.99 min; MS (ESIneg): m/z=387 (M−H)⁻

¹H-NMR (400 MHz, DMSO-d₆): δ [ppm]=13.1 (s, 1H), 7.97 (d, 1H), 7.73 (s, 1H), 7.72 (dd, 1H), 7.52 (s, 1H), 6.48 (s, 1H), 5.50-5.38 (br. s, 1H), 3.65 (s, 3H), 2.16-2.10 (m, 2H), 0.86 (s, 9H).

Example 42.1F tert-Butyl 4-({2-[4-(5-chloro-2-cyanophenyl)-5-methoxy-2-oxopyridin-1(2H)-yl]-4,4-dimethylpentanoyl}amino)benzoate (racemate)

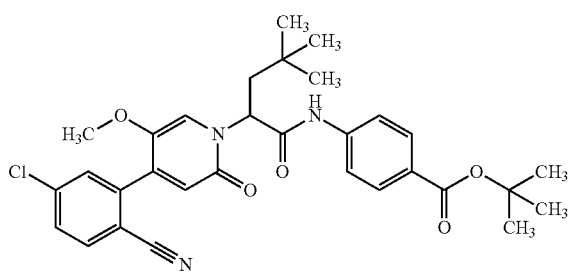 [SMILES: COc1cn(C(CC(C)(C)C)C(=O)Nc2ccc(C(=O)OC(C)(C)C)cc2)c(=O)cc1-c1cc(Cl)ccc1C#N]

110 mg (283 µmol) of 2-[4-(5-chloro-2-cyanophenyl)-5-methoxy-2-oxopyridin-1(2H)-yl]-4,4-dimethylpentanoic acid (racemate), 65.6 mg (339 µmol) of tert-butyl 4-aminobenzoate, 129 mg (339 µmol) of HATU and 148 µl (849 µmol) of N,N-diisopropylethylamine in 9 ml of dimethylformamide were reacted according to General Method 5A. The solvent was removed and the residue was purified by preparative HPLC [column: Chromatorex C18, 10 µm, 125× 30 mm, mobile phase: acetonitrile/0.05% formic acid gradient (0 to 3 min 10% acetonitrile, to 35 min 90% acetonitrile and a further 3 min 90% acetonitrile)]. Yield: 100 mg (62% of theory)

LC/MS [Method 4]: $R_t$=2.90 min; MS (ESIpos): m/z=564 (M+H)⁺

¹H-NMR (400 MHz, DMSO-d₆): δ [ppm]=10.9 (s, 1H), 7.99 (d, 1H), 7.88 (d, 2H), 7.77 (d, 2H), 7.74-7.71 (m, 2H), 7.60 (s, 1H), 6.53 (s, 1H), 5.98 (dd, 1H), 3.70 (s, 3H), 2.14 (dd, 1H), 2.02 (dd, 1H), 1.54 (s, 9H), 0.92 (s, 9H).

Example 43.1A 2,2-Difluorocyclopropanecarbaldehyde

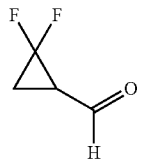

484 µl (5.55 mmol) of oxalyl chloride with 4A molecular sieve were initially charged in 5 ml of dichloromethane, and the mixture was cooled to −78° C. At −78° C., 410 µl (5.78 mmol) of DMSO were added dropwise, and the mixture was stirred for another 5 min. A solution of 500 mg (4.63 mmol) of 2,2-difluorocyclopropanemethanol in 5 ml of dichloromethane was then added, and the mixture was stirred at −78° C. for 30 min. After addition of 1.93 ml (13.9 ml) of triethylamine, the reaction solution was stirred at RT for another 10 min and then diluted with 30 ml of water and 30 ml of dichloromethane. The phases were separated and the aqueous phase was extracted twice with 50 ml of dichloromethane. The combined organic phases were washed with saturated aqueous sodium chloride solution, dried over magnesium sulphate and filtered, and the solvent was removed under reduced pressure. The crude product was used for the next step without further purification.

Example 43.1B tert-Butyl 2-[4-(5-chloro-2-cyanophenyl)-5-methoxy-2-oxopyridin-1(2H)-yl]-3-(2,2-difluorocyclopropyl)prop-2-enoate (diastereomer mixture)

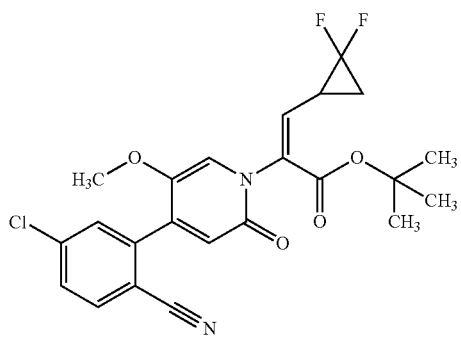 [SMILES: COc1cn(/C(=C/C2CC2(F)F)C(=O)OC(C)(C)C)c(=O)cc1-c1cc(Cl)ccc1C#N]

At −78° C., 1.87 ml (1.87 mmol) of bis(trimethylsilyl) lithium amide (1M in THF) were added dropwise to a solution of 500 mg (1.33 mmol) of tert-butyl [4-(5-chloro-2-cyanophenyl)-5-methoxy-2-oxopyridin-1(2H)-yl]acetate in 10 ml of THF, and the mixture was stirred for another 10 min 488 mg (4.60 mmol) of 2,2-difluorocyclopropanecarbaldehyde were then added, and after a further 10 min the mixture was warmed to −20° C. After 3 h at −20° C., the reaction was terminated by addition of 30 ml of saturated aqueous ammonium chloride solution and the reaction mixture was extracted three times with 20 ml of ethyl acetate. The combined organic phases were washed with saturated aqueous sodium chloride solution, dried over magnesium sulphate and filtered, and the solvent was removed under reduced pressure. The residue was taken up in a little dichloromethane and purified by flash chromatography (24 g silica cartridge, 35 ml/min, cyclohexane/ethyl acetate gradient). Yield: 240 mg (purity 78%, 30% of theory)

LC/MS [Method 1]: $R_t$=1.12 min; MS (ESIpos): m/z=463 (M+H)⁺.

Example 43.1C tert-Butyl 2-[4-(5-chloro-2-cyanophenyl)-5-methoxy-2-oxopyridin-1(2H)-yl]-3-[2,2-difluorocyclopropyl]propanoate (mixture of two racemic diastereomers)

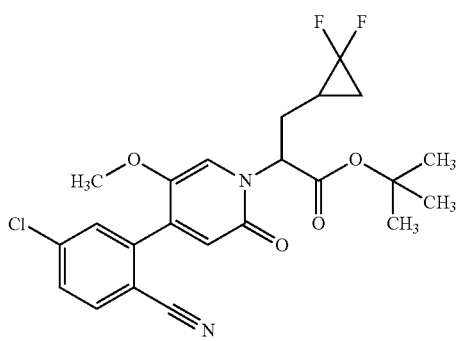 [SMILES: COc1cn(C(CC2CC2(F)F)C(=O)OC(C)(C)C)c(=O)cc1-c1cc(Cl)ccc1C#N]

At RT, 240 mg (purity 78%, 404 μmol) of tert-butyl 2-[4-(5-chloro-2-cyanophenyl)-5-methoxy-2-oxopyridin-1(2H)-yl]-3-(2,2-difluorocyclopropyl)prop-2-enoate (diastereomer mixture) were admixed with 30 ml of a "Hot Stryker's" reagent solution [B. A. Baker et al. Org. Lett. 2008, 10, 289-292]. The reaction mixture was stirred at RT for 2 h, and 20 ml of saturated aqueous ammonium chloride solution were then added. The phases were separated and the aqueous phase was extracted three times with 25 ml of ethyl acetate. The combined organic phases were dried over magnesium sulphate and filtered, and the solvent was removed under reduced pressure. The residue was purified by flash chromatography (40 g silica cartridge, 40 ml/min, cyclohexane/ethyl acetate gradient). Yield: 216 mg (quant.)

LC/MS [Method 1]: $R_t$=1.14 min; MS (ESIpos): m/z=465 (M+H)⁺.

Example 43.1D

2-[4-(5-Chloro-2-cyanophenyl)-5-methoxy-2-oxopyridin-1(2H)-yl]-3-[2,2-difluorocyclopropyl]propanoic acid (mixture of two racemic diastereomers)

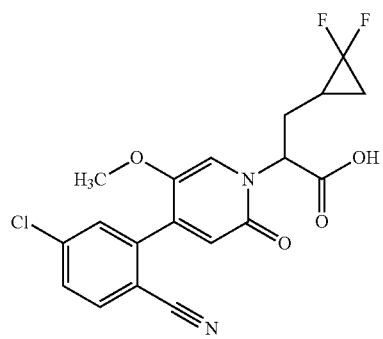 [SMILES: COc1cn(C(CC2CC2(F)F)C(=O)O)c(=O)cc1-c1cc(Cl)ccc1C#N]

216 mg (465 μmol) of tert-butyl 2-[4-(5-chloro-2-cyanophenyl)-5-methoxy-2-oxopyridin-1(2H)-yl]-3-[2,2-difluorocyclopropyl]propanoate (mixture of two racemic diastereomers) in 1 ml of dichloromethane and 537 μl (6.97 mmol) of TFA were reacted according to General Method 6A. The crude product was purified by preparative HPLC [column: Chromatorex C18, 10 μm, 125×30 mm, mobile phase: acetonitrile/0.1% formic acid gradient (0 to 3 min 10% acetonitrile, to 35 min 90% acetonitrile and a further 3 min 90% acetonitrile)]. Yield: 88 mg (44% of theory)

LC/MS [Method 1]: $R_t$=0.86/0.88 min; MS (ESIpos): m/z=409 (M+H)⁺.

Example 43.1E tert-Butyl 4-({2-[4-(5-chloro-2-cyanophenyl)-5-methoxy-2-oxopyridin-1(2H)-yl]-3-[2,2-difluorocyclopropyl]propanoyl}amino)benzoate (mixture of two racemic diastereomers)

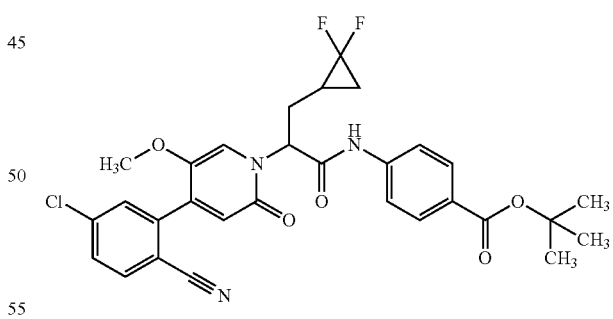

88.0 mg (215 μmol) of 2-[4-(5-chloro-2-cyanophenyl)-5-methoxy-2-oxopyridin-1(2H)-yl]-3-[2,2-difluorocyclopropyl]propanoic acid (mixture of two racemic diastereomers), 41.6 mg (215 μmol) of tert-butyl 4-aminobenzoate, 30.6 mg (215 μmol) of Oxima and 34.0 μl (215 μmol) of DIC in 2.1 ml of dimethylformamide were reacted according to General Method 5B. Yield: 101 mg (66% of theory)

LC/MS [Method 1]: $R_t$=1.25 min; MS (ESIpos): m/z=584 (M+H)⁺

¹H-NMR (400 MHz, DMSO-d₆): δ [ppm]=10.8/10.7 (2×s, 1H), 8.00 (d, 1H), 7.90-7.85 (m, 2H), 7.77-7.71 (m, 4H), 7.53 (s, 1H), 6.55 (s, 1H), 5.80-5.69 (m, 1H), 3.70/3.69 (2×s, 3H), 2.63-2.38 (m, 1H), 2.34-2.07 (2×m, 1H), 1.71-1.46 (m, 2H), 1.54 (s, 9H), 1.35-1.04 (2×m, 1H).

Example 44.1A

1-Methylcyclopropanecarbaldehyde

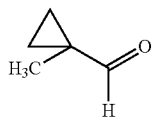

608 µl (6.97 mmol) of oxalyl chloride with 4A molecular sieve were initially charged in 5 ml of dichloromethane, and the mixture was cooled to −78° C. At −78° C., 515 µl (7.26 mmol) of DMSO were added dropwise, and the mixture was stirred for another 5 min. A solution of 500 mg (5.81 mmol) of (1-methylcyclopropyl)methanol in 5 ml of dichloromethane was then added, and the mixture was stirred at −78° C. for 30 min. After addition of 2.43 ml (17.4 ml) of triethylamine, the reaction solution was stirred at RT for another 10 min and then diluted with 30 ml of water and 30 ml of dichloromethane. The phases were separated and the aqueous phase was extracted twice with 50 ml of dichloromethane. The combined organic phases were washed with saturated aqueous sodium chloride solution, dried over magnesium sulphate and filtered, and the solvent was removed under reduced pressure. The crude product was used for the next step without further purification.

Example 44.1B tert-Butyl 2-[4-(5-chloro-2-cyanophenyl)-5-methoxy-2-oxopyridin-1(2H)-yl]-3-(1-methylcyclopropyl)prop-2-enoate (isomer mixture)

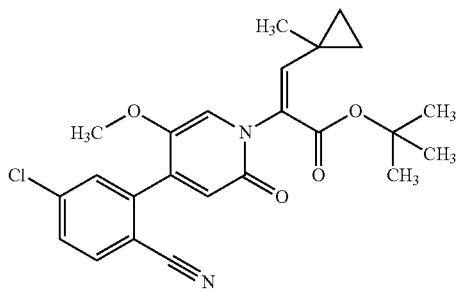 [SMILES: COc1cn(/C(=C/C2(C)CC2)C(=O)OC(C)(C)C)c(=O)cc1-c1cc(Cl)ccc1C#N]

At −78° C., 1.87 ml (1.87 mmol) of bis(trimethylsilyl) lithium amide (1M in THF) were added dropwise to a solution of 500 mg (1.33 mmol) of tert-butyl [4-(5-chloro-2-cyanophenyl)-5-methoxy-2-oxopyridin-1(2H)-yl]acetate in 10 ml of THF, and the mixture was stirred for another 10 min 488 mg (5.80 mmol) of 1-methylcyclopropanecarbaldehyde were then added, and after a further 10 min the mixture was warmed to −20° C. After 3 h at −20° C., the reaction was terminated by addition of 30 ml of saturated aqueous ammonium chloride solution and the reaction mixture was extracted three times with 20 ml of ethyl acetate. The combined organic phases were washed with saturated aqueous sodium chloride solution, dried over magnesium sulphate and filtered, and the solvent was removed under reduced pressure. The residue was taken up in a little dichloromethane and purified by flash chromatography (24 g silica cartridge, 35 ml/min, cyclohexane/ethyl acetate gradient). Yield: 257 mg (44% of theory)

LC/MS [Method 1]: $R_t$=1.15 min; MS (ESIpos): m/z=441 (M+H)$^+$.

Example 44.1C tert-Butyl 2-[4-(5-chloro-2-cyanophenyl)-5-methoxy-2-oxopyridin-1(2H)-yl]-3-(1-methylcyclopropyl)propanoate (racemate)

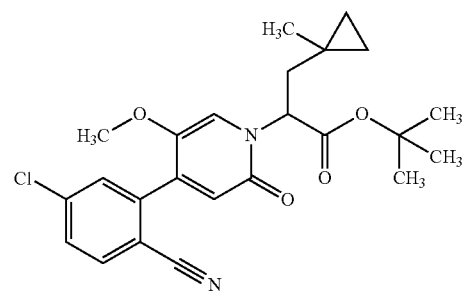 [SMILES: COc1cn(C(CC2(C)CC2)C(=O)OC(C)(C)C)c(=O)cc1-c1cc(Cl)ccc1C#N]

At RT, 257 mg (583 µmol) of tert-butyl 2-[4-(5-chloro-2-cyanophenyl)-5-methoxy-2-oxopyridin-1(2H)-yl]-3-(1-methylcyclopropyl)prop-2-enoate (isomer mixture) were admixed with 30 ml of a "Hot Stryker's" reagent solution [B. A. Baker et al. *Org. Lett.* 2008, 10, 289-292]. The reaction mixture was stirred at RT for 2 h, and 20 ml of saturated aqueous ammonium chloride solution were then added. The phases were separated and the aqueous phase was extracted three times with 25 ml of ethyl acetate. The combined organic phases were dried over magnesium sulphate and filtered, and the solvent was removed under reduced pressure. The residue was purified by flash chromatography (40 g silica cartridge, 35 ml/min, cyclohexane/ethyl acetate gradient). Yield: 247 mg (96% of theory)

LC/MS [Method 1]: $R_t$=1.21 min; MS (ESIpos): m/z=443 (M+H)$^+$.

Example 44.1D

2-[4-(5-Chloro-2-cyanophenyl)-5-methoxy-2-oxopyridin-1(2H)-yl]-3-(1-methylcyclopropyl)propanoic acid (racemate)

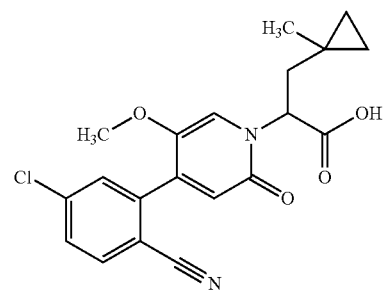 [SMILES: COc1cn(C(CC2(C)CC2)C(=O)O)c(=O)cc1-c1cc(Cl)ccc1C#N]

247 mg (558 µmol) of tert-butyl 2-[4-(5-chloro-2-cyanophenyl)-5-methoxy-2-oxopyridin-1(2H)-yl]-3-(1-methylcyclopropyl)propanoate (racemate) in 1 ml of dichloromethane and 859 µl (11.2 mmol) of TFA were reacted according to General Method 6A. The crude product was purified by preparative HPLC [column: Chromatorex C18, 10 µm, 125×30 mm, mobile phase: acetonitrile/0.1% formic acid gradient (0 to 3 min 10% acetonitrile, to 35 min 90% acetonitrile and a further 3 min 90% acetonitrile)]. Yield: 95 mg (43% of theory)

LC/MS [Method 2]: $R_t$=2.70 min; MS (ESIpos): m/z=387 (M+H)$^+$.

Example 44.1E tert-Butyl 4-({2-[4-(5-chloro-2-cyanophenyl)-5-methoxy-2-oxopyridin-1(2H)-yl]-3-(1-methylcyclopropyl)propanoyl}amino)benzoate (racemate)

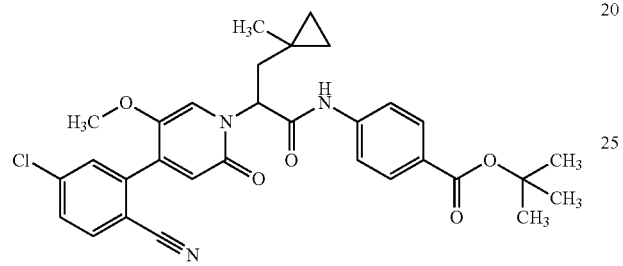

95.0 mg (246 µmol) of 2-[4-(5-chloro-2-cyanophenyl)-5-methoxy-2-oxopyridin-1(2H)-yl]-3-(1-methylcyclopropyl) propanoic acid (racemate), 47.5 mg (246 µmol) of tert-butyl 4-aminobenzoate, 34.9 mg (246 µmol) of Oxima and 38.3 µl (246 µmol) of DIC in 2.5 ml of dimethylformamide were reacted according to General Method 5B. Yield: 101 mg (66% of theory)

LC/MS [Method 1]: $R_t$=1.32 min; MS (ESIpos): m/z=562 (M+H)$^+$ $^1$H-NMR (400 MHz, DMSO-$d_6$): δ [ppm]=10.8 (s, 1H), 8.00 (d, 1H), 7.88 (d, 2H), 7.77 (d, 2H), 7.75-7.72 (m, 2H), 7.54 (s, 1H), 6.53 (s, 1H), 5.97 (dd, 1H), 3.68 (s, 3H), 2.20 (dd, 1H), 2.05 (dd, 1H), 1.54 (s, 9H), 1.07 (s, 3H), 0.35-0.25 (m, 2H), 0.21-0.12 (m, 2H).

Example 45.1A

Ethyl 3-cyclobutyl-2-hydroxypropanoate (racemate)

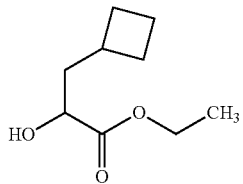

359 mg (14.8 mmol, 1.1 eq.) of magnesium turnings were covered with diethyl ether and etched by addition of a small piece of iodine for 3-4 min. Under argon and at RT, 5 ml of a solution of 2.0 g (13.4 mmol) of (bromomethyl)cyclobutane in 30 ml of diethyl ether were added with stirring to this mixture, the reaction was stirred for 5 min (until the reaction is initiated) and the remainder of the (bromomethyl)cyclobutane/diethyl ether solution is added dropwise over a further 10 min. The reaction mixture was stirred under reflux for 1 h, cooled under a stream of argon and, with ice-water cooling, added dropwise to a solution of 2.4 ml (12.1 mmol, 0.9 eq.) of ethyl glyoxylate (50% in toluene). The reaction mixture was stirred at RT for 1 h, carefully quenched to pH 7 with 20 ml of a potassium citrate/citric acid solution (pH 5) and then adjusted to pH 4-5 with aqueous hydrochloric acid (1N). After phase separation, the aqueous phase was extracted with diethyl ether. The combined organic phases were dried (sodium sulphate), filtered and concentrated under reduced pressure. The residue was purified by flash chromatography (silica gel 50, mobile phase: cyclohexane/ethyl acetate 20%-33%). Yield: 110 mg (purity 94%, 5% of theory)

LC/MS [Method 8]: $R_t$=3.37 min; MS (ESIpos): m/z=172 (M)$^+$.

Example 45.1B

Ethyl 3-cyclobutyl-2-{[(trifluoromethyl)sulphonyl]oxy}propanoate (racemate)

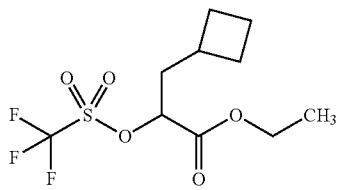

110 mg (purity 94%, 0.60 mmol) of ethyl 3-cyclobutyl-2-hydroxypropanoate (racemate) and 142 µl (0.84 mmol, 1.4 eq.) of trifluoromethanesulphonic anhydride in the presence of 105 µl (0.90 mmol, 1.5 eq.) of 2,6-dimethylpyridine were reacted according to General Method 8A. The crude product was reacted in the next step without further purification.

Example 45.1C

Ethyl 2-[4-(5-chloro-2-cyanophenyl)-5-methoxy-2-oxopyridin-1(2H)-yl]-3-cyclobutylpropanoate (racemate)

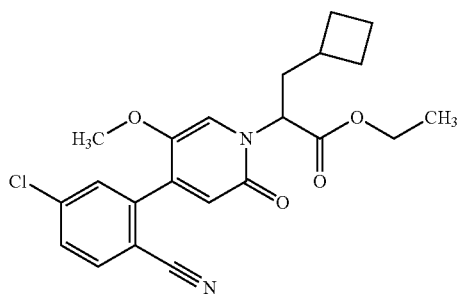 [SMILES: CCOC(=O)C(CC1CCC1)n1cc(OC)c(-c2cc(Cl)ccc2C#N)cc1=O]

122 mg (purity 87%, 0.41 mmol) of 4-chloro-2-(5-methoxy-2-oxo-1,2-dihydropyridin-4-yl)benzonitrile in the presence of 1.3 eq. of sodium hydride and 161 mg (0.53 mmol, 1.3 eq.) of ethyl 3-cyclobutyl-2-{[(trifluoromethyl) sulphonyl]oxy}propanoate (racemate) were reacted at RT according to General 4E. The crude product was purified by flash chromatography (KP-SIL, cyclohexane/ethyl acetate 15-33%). Yield: 140 mg (82% of theory)

LC/MS [Method 1]: $R_t$=1.15 min; MS (ESIpos): m/z=415 (M+H)$^+$ $^1$H-NMR (400 MHz, DMSO-d$_6$): δ [ppm]=7.99 (d, 1H), 7.78-7.69 (m, 2H), 7.42 (s, 1H), 6.48 (s, 1H), 5.12 (dd, 1H), 4.21-4.07 (m, 2H), 3.64 (s, 3H), 2.38-2.24 (m, 1H), 2.23-2.11 (m, 2H), 2.05-1.93 (m, 1H), 1.89-1.61 (m, 4H), 1.60-1.47 (m, 1H), 1.18 (t, 3H).

Example 45.1D

2-[4-(5-Chloro-2-cyanophenyl)-5-methoxy-2-oxopyridin-1(2H)-yl]-3-cyclobutylpropanoic acid (racemate)

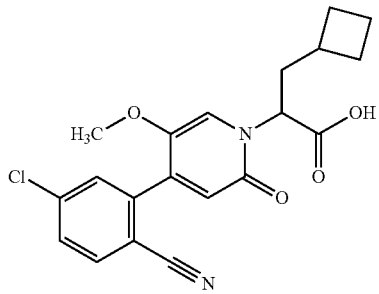 [SMILES: COc1cn(C(CC2CCC2)C(=O)O)c(=O)cc1-c1cc(Cl)ccc1C#N]

138 mg (0.33 mmol) of ethyl 2-[4-(5-chloro-2-cyanophenyl)-5-methoxy-2-oxopyridin-1(2H)-yl]-3-cyclobutylpropanoate (racemate) were hydrolysed with lithium hydroxide according to General Method 6B. Yield: 104 mg (82% of theory)

LC/MS [Method 1]: $R_t$=0.95 min; MS (ESIpos): m/z=387 (M+H)$^+$.

Example 45.1E tert-Butyl 4-({2-[4-(5-chloro-2-cyanophenyl)-5-methoxy-2-oxopyridin-1(2H)-yl]-3-cyclobutylpropanoyl}amino)benzoate (racemate)

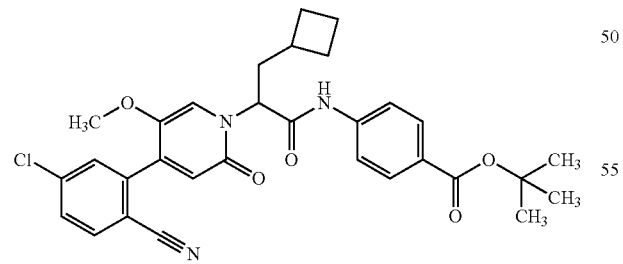

104 mg (0.27 mmol) of 2-[4-(5-chloro-2-cyanophenyl)-5-methoxy-2-oxopyridin-1(2H)-yl]-3-cyclobutylpropanoic acid (racemate) and 57 mg (0.30 mmol, 1.1 eq.) of tert-butyl 4-aminobenzoate were reacted according to General Method 5A. Yield: 66 mg (purity 86%, 38% of theory)

LC/MS [Method 1]: $R_t$=1.38 min; MS (ESIpos): m/z=562 (M+H)$^+$.

Example 46.1A

Ethyl [4-(5-chloro-2-cyanophenyl)-5-methoxy-2-oxopyridin-1(2H)-yl](ethoxy)acetate (racemate)

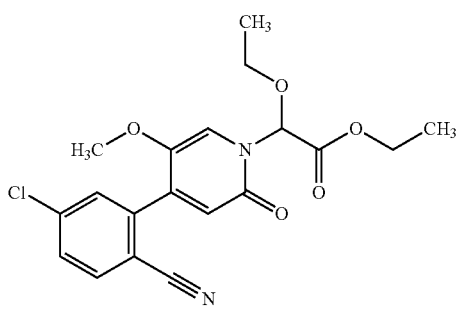 [SMILES: CCOC(=O)C(OCC)n1cc(OC)c(-c2cc(Cl)ccc2C#N)cc1=O]

Under argon and at 0° C., 10 min apart two portions of in total 350 mg (purity 82%, 1.10 mmol) of 4-chloro-2-(5-methoxy-2-oxo-1,2-dihydropyridin-4-yl)benzonitrile were added to a suspension of 53 mg (1.32 mmol, 1.2 eq.) of sodium hydride (60% in mineral oil) in 2.1 ml of dimethylformamide. The reaction mixture was stirred at RT for 60 min and then cooled back to 0° C., 245 mg (purity 90%, 1.32 mmol, 1.2 eq.) of ethyl 2-chloro-2-ethoxyacetate were added and the mixture was stirred at RT for 2 h. This batch together with an analogous test batch was combined with 50 mg (purity 82%, 0.16 mmol) of 4-chloro-2-(5-methoxy-2-oxo-1,2-dihydropyridin-4-yl)benzonitrile. After addition of 20 ml of water and phase separation, the aqueous phase was extracted twice with ethyl acetate. The combined organic phases were dried (sodium sulphate), filtered and concentrated under reduced pressure. The crude product was purified by flash chromatography (IR-50Si, petroleum ether/ethyl acetate 15-50%). Yield: 277 mg (55% of theory based on in total 1.26 mmol of 4-chloro-2-(5-methoxy-2-oxo-1,2-dihydropyridin-4-yl)benzonitrile employed)

LC/MS [Method 1]: $R_t$=1.01 min; MS (ESIpos): m/z=391 (M+H)$^+$.

Example 46.1B

[4-(5-Chloro-2-cyanophenyl)-5-methoxy-2-oxopyridin-1(2H)-yl](ethoxy)acetic acid (racemate)

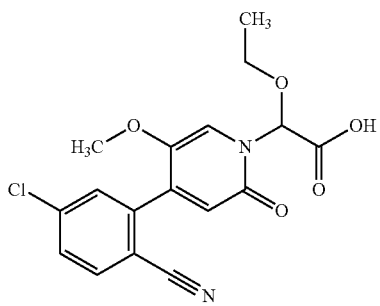 [SMILES: CCOC(C(=O)O)n1cc(OC)c(-c2cc(Cl)ccc2C#N)cc1=O]

277 mg (0.69 mmol) of ethyl [4-(5-chloro-2-cyanophenyl)-5-methoxy-2-oxopyridin-1(2H)-yl](ethoxy)acetate (racemate) were hydrolysed with lithium hydroxide according to General Method 6B. Yield: 180 mg (71% of theory)

Example 46.1C tert-Butyl 4-({[4-(5-chloro-2-cyanophenyl)-5-methoxy-2-oxopyridin-1(2H)-yl](ethoxy)acetyl}amino)benzoate (racemate)

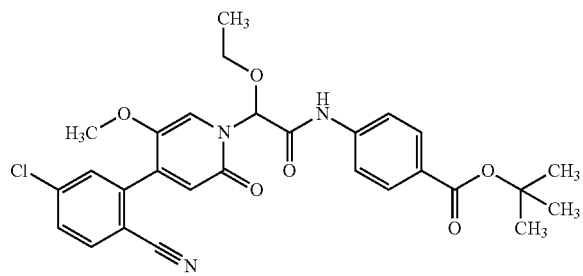 [SMILES: CCOC(C(=O)Nc1ccc(C(=O)OC(C)(C)C)cc1)n1cc(OC)c(-c2cc(Cl)ccc2C#N)cc1=O]

180 mg (0.50 mmol) of [4-(5-chloro-2-cyanophenyl)-5-methoxy-2-oxopyridin-1(2H)-yl](ethoxy)acetic acid (racemate) and 105 mg (0.55 mmol, 1.1 eq.) of tert-butyl 4-aminobenzoate were reacted according to General Method 5A. Yield: 265 mg (quant.)

LC/MS [Method 1]: $R_t$=1.22 min; MS (ESIpos): m/z=538 (M+H)$^+$ $^1$H-NMR (400 MHz, DMSO-d$_6$): δ [ppm]=10.74 (s, 1H), 8.01 (d, 1H), 7.90 (d, 2H), 7.80 (d, 2H), 7.79-7.71 (m, 2H), 7.35 (s, 1H), 6.57 (s, 1H), 6.40 (s, 1H), 3.82-3.72 (m, 1H), 3.72-3.60 (m, 1H), 3.67 (s, 3H), 1.54 (s, 9H), 1.27 (t, 3H).

Example 47.1A

[4-(5-Chloro-2-cyanophenyl)-5-methoxy-2-oxopyridin-1(2H)-yl]acetic acid

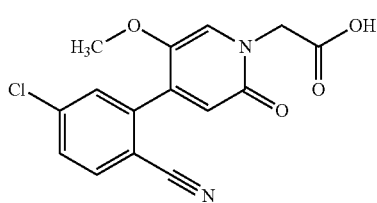 [SMILES: COc1cn(CC(=O)O)c(=O)cc1-c1cc(Cl)ccc1C#N]

187 mg (500 µmol) of tert-butyl [4-(5-chloro-2-cyanophenyl)-5-methoxy-2-oxopyridin-1(2H)-yl]acetate and 770 µl (10.0 mmol) of TFA were reacted according to General Method 6A. Yield: 159 mg (93% of theory)

LC/MS [Method 1]: $R_t$=0.72 min; MS (ESIneg): m/z=317 (M–H)$^-$ $^1$H-NMR (400 MHz, DMSO-d$_6$): δ [ppm]=13.1 (s, 1H), 8.00 (d, 1H), 7.74 (dd, 1H), 7.72 (s, 1H), 7.58 (s, 1H), 6.51 (s, 1H), 4.64 (s, 2H), 3.62 (s, 3H).

Example 47.1B tert-Butyl 4-({[4-(5-chloro-2-cyanophenyl)-5-methoxy-2-oxopyridin-1(2H)-yl]acetyl}amino)benzoate

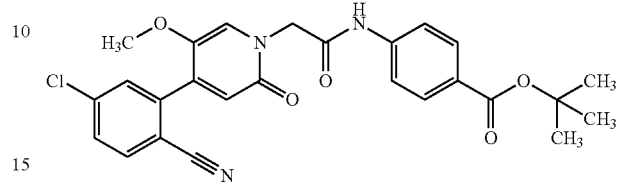

159 mg (499 µmol) of [4-(5-chloro-2-cyanophenyl)-5-methoxy-2-oxopyridin-1(2H)-yl]acetic acid, 116 mg (599 µmol) of tert-butyl 4-aminobenzoate, 228 mg (599 µmol) of HATU and 261 µl (1.50 mmol) of N,N-diisopropylethylamine in 8 ml of dimethylformamide were reacted according to General Method 5A. The solvent was removed and the residue was purified by preparative HPLC [column: Chromatorex C18, 10 µm, 125 mm×30 mm, mobile phase: acetonitrile/0.1% formic acid gradient (0 to 3 min 10% acetonitrile, to 35 min 90% acetonitrile and a further 3 min 90% acetonitrile)]. Yield: 54.5 mg (22% of theory)

LC/MS [Method 1]: $R_t$=1.09 min; MS (ESIpos): m/z=494 (M+H)$^+$ $^1$H-NMR (400 MHz, DMSO-d$_6$): δ [ppm]=10.7 (s, 1H), 8.00 (d, 1H), 7.88 (d, 2H), 7.75-7.71 (m, 4H), 7.60 (s, 1H), 6.52 (s, 1H), 4.81 (s, 2H), 3.64 (s, 3H), 1.54 (s, 9H).

Example 48.1A

Methyl 4-{[tert-butyl(dimethyl)silyl]oxy}cyclohexanecarboxylate (trans/cis mixture)

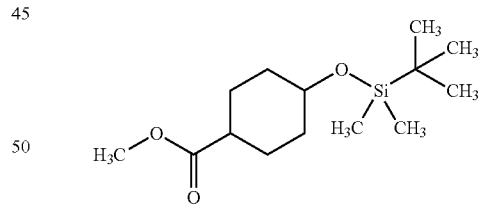

5.0 g (32 mmol) of methyl 4-hydroxycyclohexanecarboxylate were initially charged in 100 ml of dimethylformamide. 6.7 g (44 mmol) of tert-butyldimethylsilyl chloride and 4.1 g (60 mmol) of imidazole were then added, and the mixture was stirred at RT for another 14 h. The solvent was removed under reduced pressure and the residue was taken up in 100 ml of methyl tert-butyl ether and 100 ml of saturated aqueous sodium bicarbonate solution. The phases were separated, the organic phase was dried over magnesium sulphate and filtered and the solvent was removed under reduced pressure. Yield: 8.1 g (93% of theory)

GC/MS [Method 9]: $R_t$=4.79 min; MS: m/z=272 (M)$^+$.

Example 48.1B (4-{[tert-Butyl(dimethyl)silyl]oxy}cyclohexyl)methanol (trans/cis mixture)

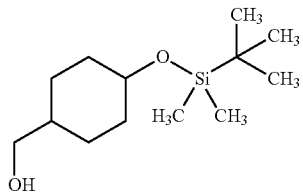 [SMILES: CC(C)(C)[Si](C)(C)OC1CCC(CO)CC1]

At 0° C., 8.1 g (29.7 mmol) of methyl 4-{[tert-butyl(dimethyl)silyl]oxy}cyclohexanecarboxylate (trans/cis mixture) as a solution in 50 ml of THF were added dropwise to a solution of 50 ml (100 mmol) of lithium aluminium hydride (2M in THF). The mixture was stirred at 0° C. for another 1 h and at RT for another 2 h. 3.8 ml of water, 3.8 ml of aqueous sodium hydroxide solution (15%) and 11.4 ml of water were then added to the reaction in succession, and the precipitate was filtered off. The organic phase was washed with 50 ml of saturated aqueous sodium chloride solution, dried over magnesium sulphate and filtered, and the solvent was removed under reduced pressure. Yield: 7.00 g (92% of theory)

GC/MS [Method 9]: $R_t$=4.74 min; MS: m/z=244 (M)$^+$.

Example 48.1C (4-{[tert-Butyl(dimethyl)silyl]oxy}cyclohexyl)methyl trifluoromethanesulphonate (trans/cis mixture)

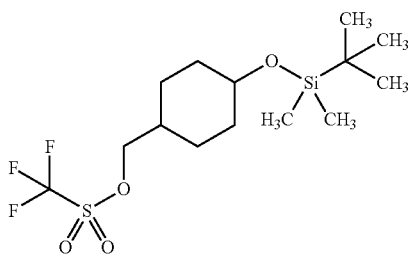 [SMILES: CC(C)(C)[Si](C)(C)OC1CCC(COS(=O)(=O)C(F)(F)F)CC1]

1.00 g (4.09 mmol) of (4-{[tert-butyl(dimethyl)silyl]oxy}cyclohexyl)methanol (trans/cis mixture) in 25 ml of dichloromethane were reacted with 715 µl (6.14 mmol) of lutidine and 1.04 ml (6.14 mmol) of trifluoromethanesulphonic anhydride according to General Method 8A. The crude product was used for the next step without further purification. Yield: 1.47 g (91% of theory)

Example 48.1D tert-Butyl 3-(4-[tert-butyl(dimethyl)silyl]oxy cyclohexyl)-2-[4-(5-chloro-2-cyanophenyl)-5-methoxy-2-oxopyridin-1(2H)-yl]propanoate (mixture of two racemic diastereomers)

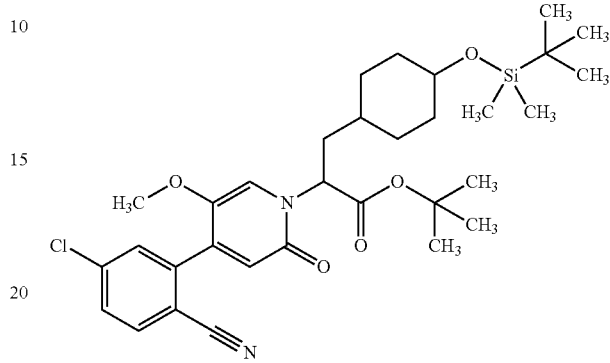

500 mg (1.26 mmol) of tert-butyl [4-(5-chloro-2-cyanophenyl)-5-methoxy-2-oxopyridin-1(2H)-yl]acetate, 712 mg (1.89 mmol) of (4-{[tert-butyl(dimethyl)silyl]oxy}cyclohexyl)methyl trifluoromethanesulphonate (trans/cis mixture) and 1.39 ml (1.39 mmol) of bis(trimethylsilyl)lithium amide (1M in THF) in 10 ml of THF were reacted according to General Method 7B. Purification by column chromatography (120 g silica cartridge, flow rate: 85 ml/min, cyclohexane/ethyl acetate gradient) gave the title compound. Yield: 479 mg (63% of theory)

LC/MS [Method 1]: $R_t$=1.56/1.59 min; MS (ESIpos): m/z=601 (M+H)$^+$.

Example 48.1E 3-(4-{[tert-Butyl(dimethyl)silyl]oxy}cyclohexyl)-2-[4-(5-chloro-2-cyanophenyl)-5-methoxy-2-oxopyridin-1(2H)-yl]propanoic acid (mixture of two racemic diastereomers)

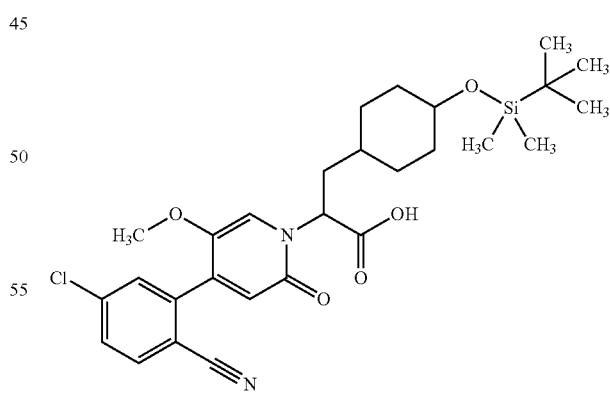

479 mg (797 µmol) of tert-butyl 3-(4-{[tert-butyl(dimethyl)silyl]oxy}cyclohexyl)-2-[4-(5-chloro-2-cyanophenyl)-5-methoxy-2-oxopyridin-1(2H)-yl]propanoate (mixture of two racemic diastereomers) were reacted with 4 ml of aqueous lithium hydroxide solution (1N) according to General Method 6B, giving the title compound. Yield: 400 mg (80% of theory)

Example 48.1F tert-Butyl 4-({3-(4-{[tert-butyl(dimethyl)silyl]oxy}cyclohexyl)-2-[4-(5-chloro-2-cyanophenyl)-5-methoxy-2-oxopyridin-1(2H)-yl]propanoyl}amino)benzoate (mixture of two racemic diastereomers)

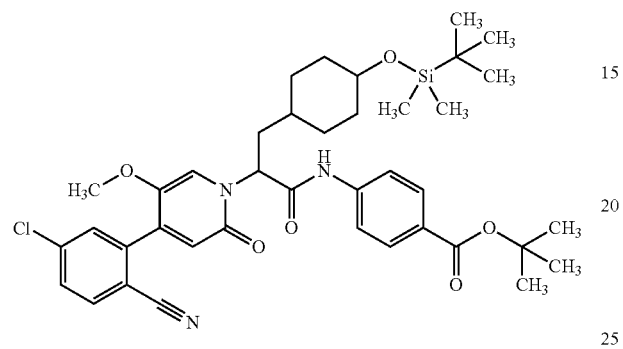

400 mg (734 µmol) of 3-(4-{[tert-butyl(dimethyl)silyl]oxy}cyclohexyl)-2-[4-(5-chloro-2-cyanophenyl)-5-methoxy-2-oxopyridin-1(2H)-yl]propanoic acid (mixture of two racemic diastereomers), 142 mg (734 µmol) of tert-butyl 4-aminobenzoate, 104 mg (734 µmol) of Oxima and 114 µl (734 µmol) of DIC in 7.3 ml of dimethylformamide were reacted according to General Method 5B. The crude product was purified by flash chromatography (40 g cartridge, 40 ml/min, cyclohexane/ethyl acetate gradient). Yield: 341 mg (64% of theory)

LC/MS [Method 1]: $R_t$=1.61/1.64 min; MS (ESIpos): m/z=720 (M+H)$^+$.

Example 49.1A tert-Butyl 2-[4-(5-chloro-2-cyanophenyl)-5-methoxy-2-oxopyridin-1(2H)-yl]-4-(trifluoromethoxy)butanoate (racemate)

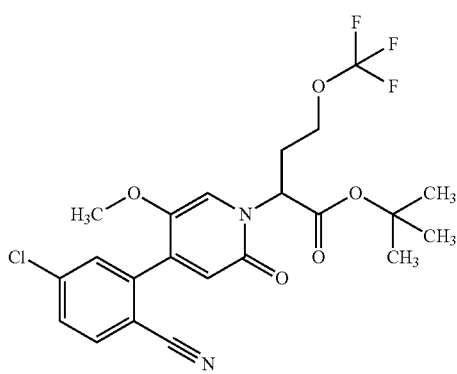 [SMILES: COc1cn(C(CCOC(F)(F)F)C(=O)OC(C)(C)C)c(=O)cc1-c1cc(Cl)ccc1C#N]

500 mg (1.29 mmol) of tert-butyl [4-(5-chloro-2-cyanophenyl)-5-methoxy-2-oxopyridin-1(2H)-yl]acetate, 495 mg (1.89 mmol) of 2-(trifluoromethoxy)ethyl trifluoromethanesulphonate and 1.39 ml (1.39 mmol) of bis(trimethylsilyl)lithium amide (1M in THF) in 10 ml of THF were reacted according to General Method 7B. Purification by column chromatography (24 g silica cartridge, flow rate: 35 ml/min, cyclohexane/ethyl acetate gradient) gave the title compound. Yield: 386 mg (62% of theory)

LC/MS [Method 1]: $R_t$=1.18 min; MS (ESIpos): m/z=487 (M+H)$^+$ $^1$H-NMR (400 MHz, DMSO-d$_6$): δ [ppm]=7.99 (d, 1H), 7.75-7.70 (m, 2H), 7.45 (s, 1H), 6.52 (s, 1H), 5.14 (dd, 1H), 4.22-4.16 (m, 1H), 4.04-3.98 (m, 1H), 3.63 (s, 3H), 2.59-2.51 (m, 2H), 1.40 (s, 9H).

Example 49.1B

2-[4-(5-Chloro-2-cyanophenyl)-5-methoxy-2-oxopyridin-1(2H)-yl]-4-(trifluoromethoxy)butanoic acid (racemate)

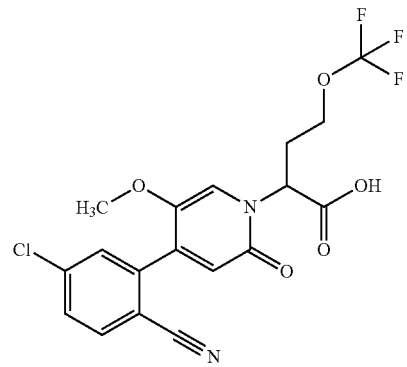 [SMILES: COc1cn(C(CCOC(F)(F)F)C(=O)O)c(=O)cc1-c1cc(Cl)ccc1C#N]

384 mg (789 µmol) of tert-butyl 2-[4-(5-chloro-2-cyanophenyl)-5-methoxy-2-oxopyridin-1(2H)-yl]-4-(trifluoromethoxy)butanoate (racemate) in 7.9 ml of dichloromethane and 2.28 ml (29.6 mmol) of TFA were reacted according to General Method 6A. Yield: 330 mg (96% of theory)

LC/MS [Method 1]: $R_t$=0.94 min; MS (ESIpos): m/z=431 (M+H)$^+$ $^1$H-NMR (400 MHz, DMSO-d$_6$): δ [ppm]=13.2 (s, 1H), 7.99 (d, 1H), 7.74-7.71 (m, 2H), 7.50 (s, 1H), 6.51 (s, 1H), 5.18 (dd, 1H), 4.22-4.15 (m, 1H), 4.02-3.95 (m, 1H), 3.63 (s, 3H), 2.62-2.51 (m, 2H).

Example 49.1C tert-Butyl 4-({2-[4-(5-chloro-2-cyanophenyl)-5-methoxy-2-oxopyridin-1(2H)-yl]-4-(trifluoromethoxy)butano-yl}amino)benzoate (racemate)

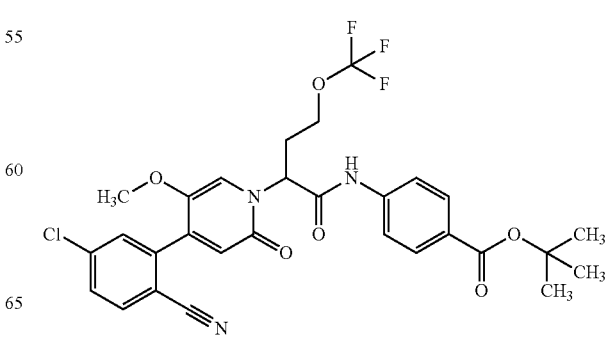

330 mg (766 μmol) of 2-[4-(5-chloro-2-cyanophenyl)-5-methoxy-2-oxopyridin-1(2H)-yl]-4-(trifluoromethoxy)butanoic acid (racemate), 148 mg (766 μmol) of tert-butyl 4-aminobenzoate, 109 mg (766 μmol) of Oxima and 120 μl (766 μmol) of DIC in 7.7 ml of dimethylformamide were reacted according to General Method 5B. The crude product was purified by flash chromatography (40 g cartridge, 40 ml/min, cyclohexane/ethyl acetate gradient). Yield: 329 mg (64% of theory)

LC/MS [Method 1]: $R_t$=1.27 min; MS (ESIpos): m/z=606 (M+H)$^+$ $^1$H-NMR (400 MHz, DMSO-d$_6$): δ [ppm]=10.8 (s, 1H), 8.00 (d, 1H), 7.88 (d, 2H), 7.77-7.71 (m, 4H), 7.51 (s, 1H), 6.56 (s, 1H), 5.81 (dd, 1H), 4.20-4.14 (m, 1H), 4.03-3.95 (m, 1H), 3.69 (s, 3H), 2.68-2.60 (m, 2H), 1.54 (s, 9H).

Example 50.1A

4-Bromo-2,5-dimethoxypyridine

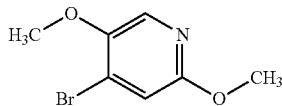

A mixture of 2.25 g (12.05 mmol) of 2,5-dimethoxypyridin-4-ylboronic acid and 4.04 g (18.08 mmol, 1.5 eq.) copper(II) bromide in 48 ml of methanol/water (1:1) was irradiated in a microwave at 100° C. for 60 min. After cooling, the precipitate was filtered, washed with water and then stirred in 600 ml of methanol at 65° C. for 1 h and filtered. The residue was dissolved in dichloromethane, this solution was washed with dilute ammonia solution, dried (sodium sulphate), filtered, concentrated under reduced pressure and dried. Yield: 1.71 g (65% of theory)

LC/MS [Method 3]: $R_t$=2.12 min; MS (ESIpos): m/z=218 (M+H)$^+$.

Example 50.1B

4-Bromo-5-methoxypyridin-2(1H)-one

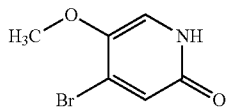

2.82 g (176 mmol, 20 eq.) of pyridinium hydrobromide were added to a solution of 1.94 g (8.81 mmol) of 4-bromo-2,5-dimethoxypyridine in 80 ml of dimethylformamide, the mixture was stirred at 100° C. for 3 h and concentrated under reduced pressure. The residue was triturated with 50 ml of water, filtered off, washed with water and dried under reduced pressure. The filtrate was extracted twice with dichloromethane/methanol (10:1). The combined organic phases were dried (sodium sulphate), filtered, concentrated under reduced pressure and dried. Yield: 771 mg (43% of theory) and 465 mg (purity 88%, 23% of theory)

LC/MS [Method 3]: $R_t$=1.38 min; MS (ESIpos): m/z=204 (M+H)$^+$.

Example 50.1C 2-(4-Bromo-5-methoxy-2-oxopyridin-1(2H)-yl)propanoic acid (racemate)

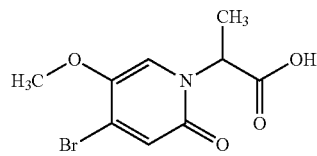

Under argon, a suspension of 1.76 g (10.3 mmol, 2.0 eq.) of magnesium di-tert-butoxide, 1.24 g (5.15 mmol) of 4-bromo-5-methoxypyridin-2(1H)-one and 607 mg (5.41 mmol, 1.05 eq.) of potassium tert-butoxide in 30 ml of tetrahydrofuran was stirred at RT for 10 min. The reaction mixture was cooled in an ice bath, and 695 μl (7.72 mmol, 1.5 eq.) of 2-bromopropionic acid (racemate) were added. The reaction mixture was then stirred initially at RT for another 2.5 h and then further at 50° C. overnight, acidified with aqueous hydrochloric acid (6N) and diluted by addition of ethyl acetate/water. The precipitate formed was filtered off and dried under reduced pressure. Yield: 205 mg (14% of theory)

After phase separation of the filtrate, the aqueous phase was extracted with ethyl acetate. The combined organic phases were dried (sodium sulphate), filtered and concentrated under reduced pressure. The crude product was then once more reacted as described above with 1.05 g (6.18 mmol) of magnesium di-tert-butylate, 376 mg (3.35 mmol) of potassium tert-butylate and 371 μl (4.12 mmol) of 2-bromopropionic acid (racemate) in 30 ml of tetrahydrofuran and worked up analogously, with a further precipitate being able to be isolated. Yield: 571 mg (39% of theory)

LC/MS [Method 1]: $R_t$=0.57 min; MS (ESIpos): m/z=276 (M+H)$^+$.

Example 50.1D tert-Butyl 4-{[2-(4-bromo-5-methoxy-2-oxopyridin-1(2H)-yl)propanoyl]amino}benzoate (racemate)

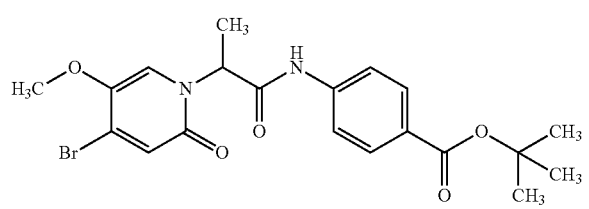 [SMILES: COc1cn(C(C)C(=O)Nc2ccc(C(=O)OC(C)(C)C)cc2)c(=O)cc1Br]

571 mg (2.01 mmol) of 2-(4-bromo-5-methoxy-2-oxopyridin-1(2H)-yl)propanoic acid (racemate) and 426 mg (2.21 mmol, 1.1 eq.) of tert-butyl 4-aminobenzoate were reacted according to General Method 5A. Yield: 562 mg (61% of theory)

LC/MS [Method 1]: $R_t$=1.10 min; MS (ESIpos): m/z=451 (M+H)$^+$.

Example 50.1E tert-Butyl 4-[(2-{4-[5-chloro-2-(trifluoromethoxy)phenyl]-5-methoxy-2-oxopyridin-1(2H)-yl}propanoyl)amino]benzoate (racemate)

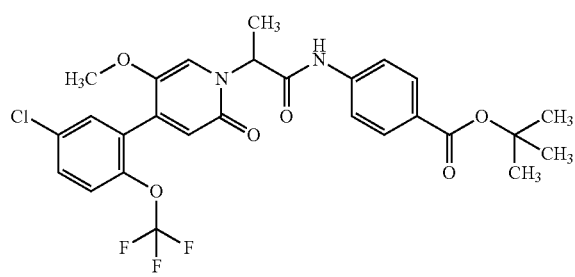 [SMILES: COc1cn(C(C)C(=O)Nc2ccc(C(=O)OC(C)(C)C)cc2)c(=O)cc1-c1cc(Cl)ccc1OC(F)(F)F]

Under argon (in a flask dried by heating), 125 mg (0.28 mmol) of tert-butyl 4-{[2-(4-bromo-5-methoxy-2-oxopyridin-1(2H)-yl)propanoyl]amino}benzoate (racemate), 80 mg (0.33 mmol, 1.2 eq.) of 5-chloro-2-trifluoromethoxyphenylboronic acid, 115 mg (0.83 mmol, 3.0 eq.) of potassium carbonate and 23 mg (0.03 mmol, 0.1 eq.) of [1,1-bis(diphenylphosphino)ferrocene]palladium(II) chloride/dichloromethane monoadduct were suspended in 5.0 ml of dioxane and stirred overnight in an oil bath already preheated to 110° C. The reaction mixture was filtered through Celite and the residue was washed with dioxane. The combined filtrates were concentrated under reduced pressure. The residue was triturated with water, filtered off, washed with water and dried under reduced pressure. Yield: 155 mg (purity 83%, 82% of theory)

LC/MS [Method 1]: $R_t$=1.34 min; MS (ESIpos): m/z=567 (M+H)$^+$.

Example 50.2A tert-Butyl 4-({2-[4-(2-bromo-5-chlorophenyl)-5-methoxy-2-oxopyridin-1(2H)-yl]propanoyl}amino)benzoate (racemate)

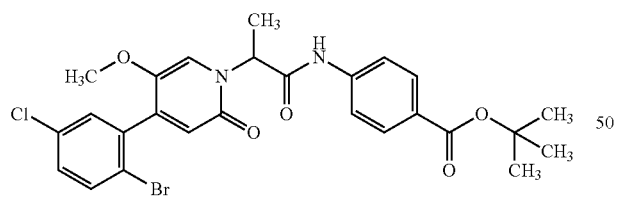

Under argon (in a flask dried by heating), 113 mg (0.25 mmol) of tert-butyl 4-{[2-(4-bromo-5-methoxy-2-oxopyridin-1(2H)-yl)propanoyl]amino}benzoate (racemate), 70 mg (0.30 mmol, 1.2 eq.) of 2-bromo-5-chlorophenylboronic acid, 103 mg (0.74 mmol, 3.0 eq.) of potassium carbonate and 20 mg (0.03 mmol, 0.1 eq.) of [1,1-bis(diphenylphosphino)ferrocene]palladium(II) chloride/dichloromethane monoadduct were suspended in 5.0 ml of dioxane and stirred overnight in an oil bath already preheated to 110° C. A further 10 mg (0.01 mmol, 0.05 eq.) of [1,1-bis-(diphenylphosphino)ferrocene]palladium(II) chloride/dichloromethane monoadduct and 29 mg (0.12 mmol, 0.5 eq.) of 2-bromo-5-chlorophenylboronic acid were added and the reaction mixture was stirred at 110° C. for a further night and then filtered through Celite. The residue was washed with dioxane. The combined filtrates were concentrated under reduced pressure. The residue was triturated with water, filtered off, dried under reduced pressure and purified by flash chromatography (silica gel 50, cyclohexane/ethyl acetate gradient). Yield: 72 mg (purity 73%, 38% of theory)

LC/MS [Method 1]: $R_t$=1.27 min; MS (ESIpos): m/z=561 (M+H)$^+$.

Example 50.3A tert-Butyl 4-({2-[4-(5-chloro-2-methylphenyl)-5-methoxy-2-oxopyridin-1(2H)-yl]propanoyl}amino)benzoate (racemate)

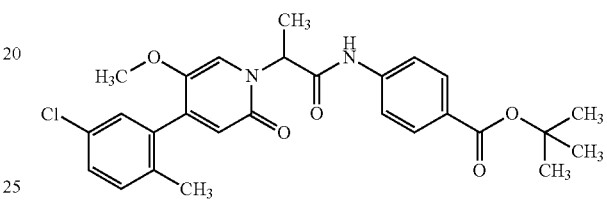

Under argon (in a flask dried by heating), 92 mg (0.20 mmol) of tert-butyl 4-{[2-(4-bromo-5-methoxy-2-oxopyridin-1(2H)-yl)propanoyl]amino}benzoate (racemate), 41 mg (0.24 mmol, 1.2 eq.) of 5-chloro-2-methylphenylboronic acid, 84 mg (0.61 mmol, 3.0 eq.) of potassium carbonate and 16 mg (0.02 mmol, 0.1 eq.) of [1,1-bis(diphenylphosphino)ferrocene]palladium(II) chloride/dichloromethane monoadduct were suspended in 5.0 ml of dioxane and stirred overnight in an oil bath already preheated to 110° C. The reaction mixture was filtered through Celite and the residue was washed with dioxane. The combined filtrates were concentrated under reduced pressure. The residue was triturated with water, filtered off, washed with water and dried under reduced pressure. Yield: 105 mg (purity 91%, 95% of theory)

LC/MS [Method 1]: $R_t$=1.26 min; MS (ESIpos): m/z=497 (M+H)$^+$.

Example 50.4A tert-Butyl 4-[(2-{4-[5-chloro-2-(trifluoromethyl)phenyl]-5-methoxy-2-oxopyridin-1(2H)-yl}propanoyl)amino]benzoate (racemate)

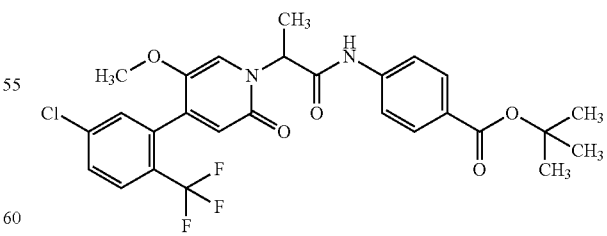

Under argon (in a flask dried by heating), 113 mg (0.25 mmol) of tert-butyl 4-{[2-(4-bromo-5-methoxy-2-oxopyridin-1(2H)-yl)propanoyl]amino}benzoate (racemate), 67 mg (0.30 mmol, 1.2 eq.) of 5-chloro-2-trifluoromethylphenylboronic acid, 103 mg (0.74 mmol, 3.0 eq.) of potassium carbonate and 20 mg (0.03 mmol, 0.1 eq.) of [1,1-bis (diphenylphosphino)ferrocene]palladium(II) chloride/dichloromethane monoadduct were suspended in 5.0 ml of dioxane and stirred overnight in an oil bath already preheated to 110° C. A further 10 mg (0.01 mmol, 0.05 eq.) of [1,1-bis-(diphenylphosphino)ferrocene]palladium(II) chloride/dichloromethane monoadduct and 22 mg (0.10 mmol, 0.4 eq.) of 5-chloro-2-trifluoromethylphenylboronic acid were added and the reaction mixture was stirred at 110° C. for a further 20 h and then filtered through Celite. The residue was washed with dioxane. The combined filtrates were concentrated under reduced pressure. The residue was triturated with water, filtered off, washed with water and dried under reduced pressure. Yield: 145 mg (purity 84%, 89% of theory)

LC/MS [Method 1]: $R_t$=1.26 min; MS (ESIpos): m/z=551 (M+H)$^+$.

Example 50.5A tert-Butyl 4-({2-[4-(5-chloro-2-cyclopropylphenyl)-5-methoxy-2-oxopyridin-1(2H)-yl]propanoyl}amino)benzoate (racemate)

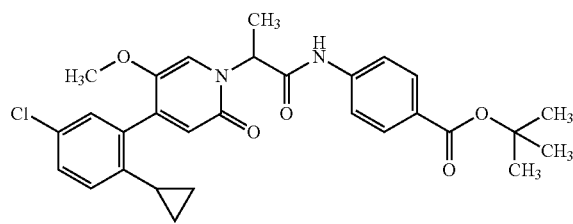 [SMILES: COc1cn(C(C)C(=O)Nc2ccc(C(=O)OC(C)(C)C)cc2)c(=O)cc1-c1cc(Cl)ccc1C1CC1]

Under argon (in a flask dried by heating), 125 mg (0.27 mmol) of tert-butyl 4-{[2-(4-bromo-5-methoxy-2-oxopyridin-1(2H)-yl)propanoyl]amino}benzoate (racemate), 92 mg (0.33 mmol, 1.2 eq.) of 2-(5-chloro-2-cyclopropylphenyl)-4,4,5,5-tetramethyl-1,3,2-dioxaborolane, 114 mg (0.82 mmol, 3.0 eq.) of potassium carbonate and 22 mg (0.03 mmol, 0.1 eq.) of [1,1-bis(diphenylphosphino)ferrocene]palladium(II) chloride/dichloromethane monoadduct were suspended in 5.0 ml of dioxane and stirred overnight in an oil bath already preheated to 110° C. The reaction mixture was filtered through Celite and the residue was washed with dioxane. The combined filtrates were concentrated under reduced pressure. The residue was triturated with water, filtered off, washed with water, dried under reduced pressure and purified by flash chromatography (silica gel-50, cyclohexane/ethyl acetate gradient). Yield: 114 mg (79% of theory)

LC/MS [Method 1]: $R_t$=1.30 min; MS (ESIpos): m/z=523 (M+H)$^+$.

Example 51.1A

2-Bromo-4-chlorophenyl difluoromethyl ether

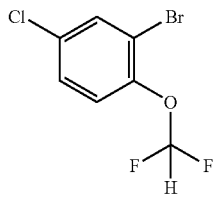 [SMILES: FC(F)Oc1ccc(Cl)cc1Br]

36 ml of aqueous potassium hydroxide solution (6M) were added to a solution of 3.5 g (16.9 mmol) of 2-bromo-4-chlorophenol in 36 ml of acetonitrile, the mixture was cooled in an ice bath and 6.5 ml (26.9 mmol, 1.6 eq.) of difluoromethyl trifluormethanesulphonate [*Angew. Chem. Int. Ed.* 2013, 52, 1-5; *Journal of Fluorine Chemistry* 2009, 130, 667-670] were added dropwise with vigorous stirring. The reaction mixture was stirred for 5 min and diluted with 200 ml of water. The aqueous phase was extracted twice with in each case 150 ml of diethyl ether. The combined organic phases were dried (sodium sulphate), filtered, concentrated under reduced pressure and dried. The aqueous phase was once more extracted with diethyl ether. The organic phase was dried (sodium sulphate), filtered, concentrated under reduced pressure and dried. Yield of the two combined residues: 3.4 g (80% of theory)

LC/MS [Method 9]: $R_t$=3.51 min; MS (ESIpos): m/z=256 (M+H)$^+$ $^1$H-NMR (400 MHz, DMSO-d$_6$): δ [ppm]=7.91 (d, 1H), 7.55 (dd, 1H), 7.37 (d, 1H), 7.30 (t, 1H).

Example 51.1B

4-[5-Chloro-2-(difluoromethoxy)phenyl]-2,5-dimethoxypyridine

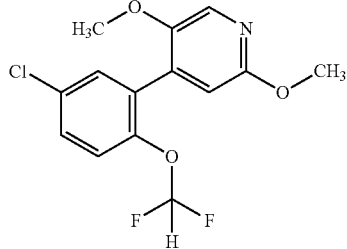 [SMILES: COc1cc(-c2cc(Cl)ccc2OC(F)F)c(OC)cn1]

417 mg (2.19 mmol, 1.2 eq.) of 2,5-dimethoxypyridin-4-ylboronic acid and 494 mg (1.82 mmol) of 2-bromo-4-chlorophenyl difluoromethyl ether in the presence of [1,1-bis(diphenylphosphino)ferrocene]palladium(II) chloride/dichloromethane monoadduct were reacted according to General Method 2A. The crude product was purified by flash chromatography (KP-SIL, petroleum ether/ethyl acetate 15-20%). Yield: 170 mg (purity 90%, 27% of theory)

LC/MS [Method 1]: $R_t$=1.16 min; MS (ESIpos): m/z=316 (M+H)$^+$ $^1$H-NMR (400 MHz, DMSO-d$_6$): δ [ppm]=7.96 (s, 1H), 7.57 (dd, 1H), 7.45 (d, 1H), 7.30 (d, 1H), 7.11 (t, 1H), 6.74 (s, 1H), 3.83 (s, 3H), 3.75 (s, 3H).

Example 51.1C

4-[5-Chloro-2-(difluoromethoxy)phenyl]-5-methoxypyridin-2(1H)-one

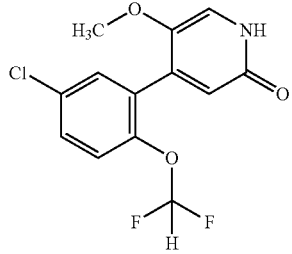 [SMILES: COc1c[nH]c(=O)cc1-c1cc(Cl)ccc1OC(F)F]

170 mg (purity 90%, 0.49 mmol) of 4-[5-chloro-2-(difluoromethoxy)phenyl]-2,5-dimethoxypyridine and pyridinium hydrobromide were reacted according to General Method 3A. Yield: 127 mg (87% of theory)

LC/MS [Method 1]: $R_t$=0.84 min; MS (ESIpos): m/z=302 (M+H)$^+$.

Example 51.1D

2-{4-[5-Chloro-2-(difluoromethoxy)phenyl]-5-methoxy-2-oxopyridin-1(2H)-yl}propanoic acid (racemate)

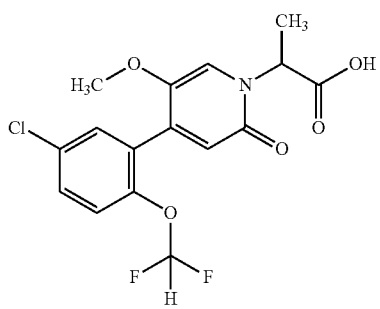 [SMILES: COc1cn(C(C)C(=O)O)c(=O)cc1-c1cc(Cl)ccc1OC(F)F]

127 mg (0.42 mmol) of 4-[5-chloro-2-(difluoromethoxy)phenyl]-5-methoxypyridin-2(1H)-one and 1.5 eq. of 2-bromopropanoic acid (racemate) were reacted according to General Method 4A at 90° C. Yield: 220 mg of crude product which was reacted in the next step without further purification Example 51.1E tert-Butyl 4-[(2-{4-[5-chloro-2-(difluoromethoxy)phenyl]-5-methoxy-2-oxopyridin-1(2H)-yl}propanoyl)amino]benzoate (racemate)

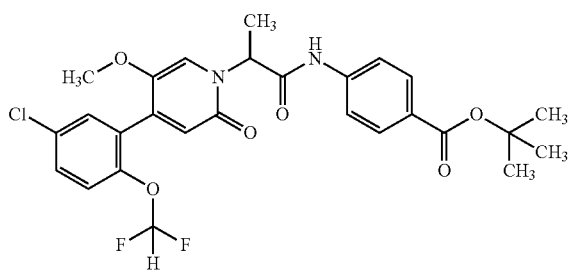

220 mg of crude product of 2-{4-[5-chloro-2-(difluoromethoxy)phenyl]-5-methoxy-2-oxopyridin-1(2H)-yl}propanoic acid (racemate) and 89 mg (0.46 mmol, 1.1 eq.) of tert-butyl 4-aminobenzoate were reacted according to General Method 5A. Yield: 48 mg (21% of theory)

LC/MS [Method 1]: $R_t$=1.26 min; MS (ESIpos): m/z=549 (M+H)$^+$ $^1$H-NMR (400 MHz, DMSO-d$_6$): δ [ppm]=10.70 (s, 1H), 7.87 (d, 2H), 7.73 (d, 2H), 7.58 (dd, 1H), 7.48 (d, 1H), 7.35 (s, 1H), 7.30 (d, 1H), 7.16 (t, 1H), 6.38 (s, 1H), 5.58 (q, 1H), 3.65 (s, 3H), 1.71 (d, 3H), 1.54 (s, 9H).

Example 51.2A

Ethyl 2-{4-[5-chloro-2-(difluoromethoxy)phenyl]-5-methoxy-2-oxopyridine-1(2H)-yl}butanoate (racemate)

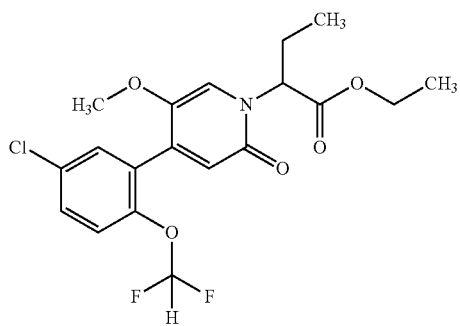 [SMILES: CCOC(=O)C(CC)n1cc(OC)c(-c2cc(Cl)ccc2OC(F)F)cc1=O]

Under argon and at RT, 105 mg (2.64 mmol, 1.3 eq.) of sodium hydride (60% in mineral oil) were added to a solution of 618 mg (2.03 mmol) of 4-[5-chloro-2-(difluoromethoxy)phenyl]-5-methoxypyridin-2(1H)-one in 25 ml of tetrahydrofuran, the mixture was stirred at RT for 60 min 871 mg (2.64 mmol, 1.3 eq.) of ethyl 2-{[(trifluoromethyl)sulphonyl]oxy}butanoate (racemate) [J. Castells et al. *Tetrahedron*, 1994, 50, 13765-13774] were then added dropwise and the mixture was stirred at RT for 1 h. A further 38 mg (0.96 mmol) of sodium hydride (60% in mineral oil) were added, the reaction mixture was stirred at RT for 5 min, a further 871 mg (2.64 mmol, 1.3 eq.) of ethyl 2-{[(trifluoromethyl)sulphonyl]oxy}butanoate (racemate) were added dropwise, and the reaction mixture was stirred at RT for 15 min and then quenched with water. After phase separation, the aqueous phase was extracted twice with ethyl acetate. The combined organic phases were washed with saturated aqueous sodium chloride solution, dried (sodium sulphate), filtered and concentrated under reduced pressure. The residue was purified by flash chromatography (silica gel 50, cyclohexane/ethyl acetate gradient). Yield: 415 mg (48% of theory)

LC/MS [Method 1]: $R_t$=1.08 min; MS (ESIpos): m/z=416 (M+H)$^+$.

Example 51.2B

2-{4-[5-Chloro-2-(difluoromethoxy)phenyl]-5-methoxy-2-oxopyridine-1(2H)-yl}butanoic acid (racemate)

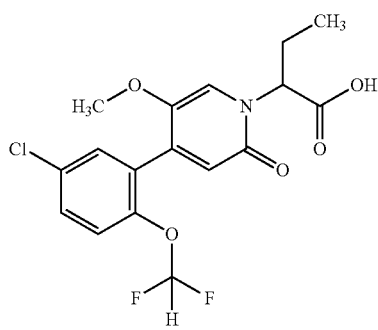 [SMILES: CCC(C(=O)O)n1cc(OC)c(-c2cc(Cl)ccc2OC(F)F)cc1=O]

415 mg (0.97 mmol) of ethyl 2-{4-[5-Chloro-2-(difluoromethoxy)phenyl]-5-methoxy-2-oxopyridin-1(2H)-yl}butanoate (racemate) were hydrolysed with lithium hydroxide according to General Method 6B. Yield: 348 mg (93% of theory)

LC/MS [Method 1]: R$_t$=0.91 min; MS (ESIpos): m/z=388 (M+H)$^+$ $^1$H-NMR (400 MHz, DMSO-d$_6$): δ [ppm]=12.96 (br. s, 1H), 7.57 (dd, 1H), 7.50 (d, 1H), 7.34-7.25 (m, 2H), 7.12 (t, 1H), 6.35 (s, 1H), 5.06 (dd, 1H), 3.58 (s, 3H), 2.20-2.06 (m, 2H), 0.82 (t, 3H).

Example 51.2C tert-Butyl 4-[(2-{4-[5-chloro-2-(difluoromethoxy)phenyl]-5-methoxy-2-oxopyridin-1(2H)-yl}butanoyl)amino]benzoate (racemate)

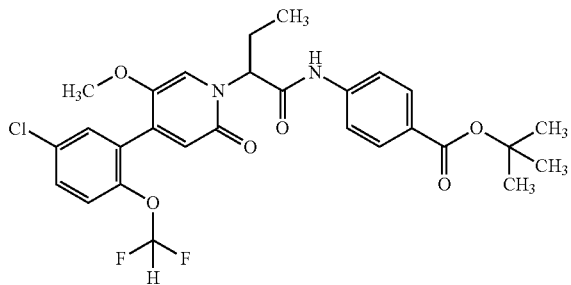 [SMILES: CCC(C(=O)Nc1ccc(C(=O)OC(C)(C)C)cc1)n1cc(OC)c(-c2cc(Cl)ccc2OC(F)F)cc1=O]

116 mg (0.30 mmol) of 2-{4-[5-chloro-2-(difluoromethoxy)phenyl]-5-methoxy-2-oxopyridin-1(2H)-yl}butanoic acid (racemate) and 64 mg (0.33 mmol, 1.1 eq.) of tert-butyl 4-aminobenzoate were reacted according to General Method 5A. Yield: 127 mg (75% of theory)

LC/MS [Method 1]: R$_t$=1.32 min; MS (ESIpos): m/z=563 (M+H)$^+$.

Example 52.1A

5-Ethoxy-4-iodo-2-methoxypyridine

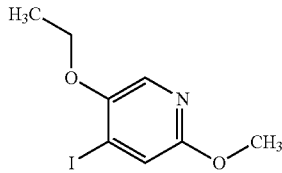

At 0° C., 304 mg (1.95 mmol, 1.3 eq.) of iodoethane and 415 mg (3.0 mmol, 2.0 eq.) of potassium carbonate were added to a solution of 405 mg (1.5 mmol) of 4-iodo-6-methoxypyridin-3-ol in 10 ml of acetone and the mixture was stirred at 80° C. overnight and concentrated under reduced pressure. The residue was triturated with water, filtered and dried under reduced pressure. Yield: 322 mg (purity 93%, 72% of theory)

LC/MS [Method 1]: R$_t$=1.07 min; MS (ESIpos): m/z=280 (M+H)$^+$.

Example 52.1B

4-Chloro-2-(5-ethoxy-2-methoxypyridin-4-yl)benzonitrile

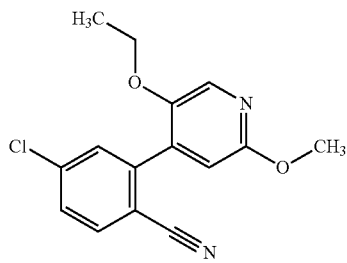 [SMILES: CCOc1cnc(OC)cc1-c1cc(Cl)ccc1C#N]

322 mg (purity 93%, 1.07 mmol) of 5-ethoxy-4-iodo-2-methoxypyridine and 234 mg (1.29 mmol, 1.2 eq.) of 5-chloro-2-cyanophenylboronic acid in the presence of [1,1-bis(diphenylphosphino)ferrocene]palladium(II) chloride/dichloromethane monoadduct were reacted according to General Method 2A. The crude product was purified by flash chromatography (silica gel 50, cyclohexane/ethyl acetate gradient). Yield: 135 mg (41% of theory)

LC/MS [Method 1]: R$_t$=1.15 min; MS (ESIpos): m/z=289 (M+H)$^+$.

Example 52.1C

4-Chloro-2-(5-ethoxy-2-oxo-1,2-dihydropyridin-4-yl)benzonitrile

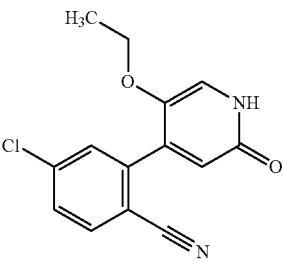 [SMILES: CCOc1c[nH]c(=O)cc1-c1cc(Cl)ccc1C#N]

135 mg (0.44 mmol) of 4-chloro-2-(5-ethoxy-2-methoxypyridin-4-yl)benzonitrile and pyridinium hydrobromide were reacted according to General Method 3A. Yield: 134 mg (purity 76%, 83% of theory)

LC/MS [Method 1]: R$_t$=0.81 min; MS (ESIpos): m/z=275 (M+H)$^+$.

Example 52.1D

2-[4-(5-Chloro-2-cyanophenyl)-5-ethoxy-2-oxopyridin-1(2H)-yl]propanoic acid (racemate)

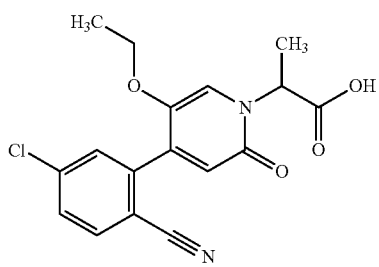 [SMILES: CCOc1cn(C(C)C(=O)O)c(=O)cc1-c1cc(Cl)ccc1C#N]

134 mg (0.37 mmol) of 4-chloro-2-(5-ethoxy-2-oxo-1,2-dihydropyridin-4-yl)benzonitrile and 1.5 eq. of 2-bromopropanoic acid (racemate) were reacted according to General Method 4A at 50° C. The crude product was purified by preparative HPLC (Reprosil C18, water/acetonitrile gradient). Yield: 89 mg (purity 86%, 60% of theory)

LC/MS [Method 1]: $R_t$=0.87 min; MS (ESIpos): m/z=347 (M+H)$^+$.

Example 52.1E tert-Butyl 4-({2-[4-(5-chloro-2-cyanophenyl)-5-ethoxy-2-oxopyridin-1(2H)-yl]propanoyl}amino)benzoate (racemate)

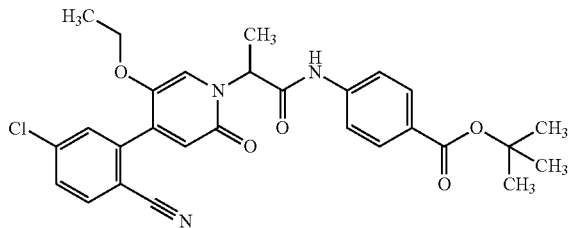 [SMILES: CCOc1cn(C(C)C(=O)Nc2ccc(C(=O)OC(C)(C)C)cc2)c(=O)cc1-c1cc(Cl)ccc1C#N]

89 mg (purity 86%, 0.22 mmol) of 2-[4-(5-chloro-2-cyanophenyl)-5-ethoxy-2-oxopyridin-1(2H)-yl]propanoic acid (racemate) and 47 mg (0.24 mmol, 1.1 eq.) of tert-butyl 4-aminobenzoate were reacted according to General Method 5A. Yield: 32 mg (purity 89%, 25% of theory)

LC/MS [Method 3]: $R_t$=2.77 min; MS (ESIpos): m/z=522 (M+H)$^+$.

Example 53.1A 5-(Difluoromethoxy)-4-iodo-2-methoxypyridine

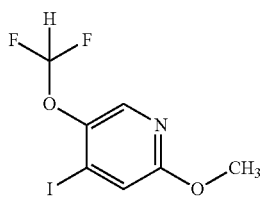

4.8 ml of aqueous potassium hydroxide solution (6M) were added to a solution of 600 mg (purity 93%, 2.22 mmol) of 4-iodo-6-methoxypyridin-3-ol in 4.8 ml of acetonitrile, the mixture was cooled in an ice bath and 863 µl (purity 75%, 3.56 mmol, 1.6 eq.) of difluoromethyl trifluoromethanesulphonate [*Angew. Chem. Int. Ed.* 2013, 52, 1-5; *Journal of Fluorine Chemistry* 2009, 130, 667-670] were added with vigorous stirring. The reaction mixture was stirred for 2 min and diluted with 33 ml of water. The aqueous phase was extracted twice with in each case 40 ml of diethyl ether. The combined organic phases were dried (sodium sulphate), filtered, concentrated under reduced pressure and dried. The crude product was purified by flash chromatography (IR-50SI, petroleum ether/ethyl acetate 12-20%). Yield: 407 mg (purity 90%, 55% of theory)

$^1$H-NMR (400 MHz, DMSO-d$_6$): δ [ppm]=8.1 (s, 1H), 7.45 (s, 1H), 7.16 (t, 1H), 3.84 (s, 3H).

Example 53.1B

4-Chloro-2-[5-(difluoromethoxy)-2-methoxypyridin-4-yl]benzonitrile

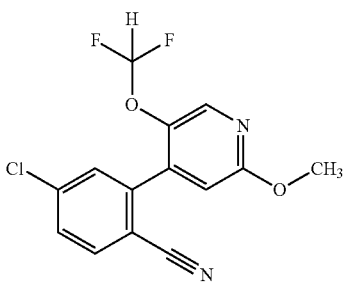 [SMILES: COc1cc(-c2cc(Cl)ccc2C#N)c(OC(F)F)cn1]

460 mg (purity 90%, 1.38 mmol) of 5-(difluoromethoxy)-4-iodo-2-methoxypyridine and 299 mg (1.65 mmol, 1.2 eq.) of 5-chloro-2-cyanophenylboronic acid in the presence of [1,1-bis(diphenylphosphino)ferrocene]palladium(II) chloride/dichloromethane monoadduct were reacted according to General Method 2A. The crude product was purified by flash chromatography (IR-50SI, petroleum ether/ethyl acetate 10-15%). Yield: 230 mg (purity 80%, 43% of theory)

LC/MS [Method 1]: $R_t$=1.12 min; MS (ESIpos): m/z=311 (M+H)$^+$.

$^1$H-NMR (400 MHz, DMSO-d$_6$): δ [ppm]=8.26 (s, 1H), 8.06 (d, 1H), 7.82-7.74 (m, 2H), 7.09 (s, 1H), 7.06 (t, 1H), 3.91 (s, 3H).

Example 53.1C

4-Chloro-2-[5-(difluoromethoxy)-2-oxo-1,2-dihydropyridin-4-yl]benzonitrile

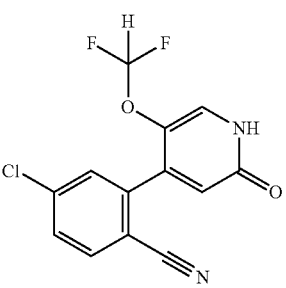 [SMILES: N#Cc1ccc(Cl)cc1-c1cc(=O)[nH]cc1OC(F)F]

230 mg (purity 80%, 0.59 mmol) of 4-chloro-2-[5-(difluoromethoxy)-2-methoxypyridin-4-yl]benzonitrile and pyridinium hydrobromide were reacted according to General Method 3A. The crude product was purified by flash chromatography (IR-50SI, dichloromethane/methanol 3-25%). Yield: 167 mg (95% of theory)

LC/MS [Method 1]: $R_t$=0.79 min; MS (ESIpos): m/z=297 (M+H)$^+$ $^1$H-NMR (400 MHz, DMSO-d$_6$): δ [ppm]=11.88 (br. s, 1H), 8.03 (d, 1H), 7.80-7.65 (m, 3H), 6.87 (t, 1H), 6.56 (s, 1H).

Example 53.1D

2-[4-(5-Chloro-2-cyanophenyl)-5-(difluoromethoxy)-2-oxopyridin-1(2H)-yl]propanoic acid (racemate)

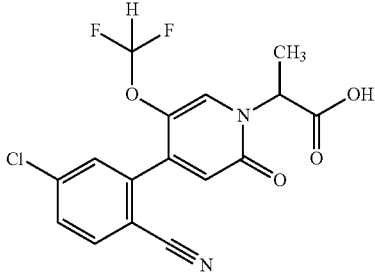 [SMILES: CC(C(=O)O)n1cc(OC(F)F)c(-c2cc(Cl)ccc2C#N)cc1=O]

163 mg (0.55 mmol) of 4-chloro-2-[5-(difluoromethoxy)-2-oxo-1,2-dihydropyridin-4-yl]benzonitrile, 2.0 eq. of magnesium di-tert-butoxide, 1.05 eq. of potassium tert-butoxide and 1.5 eq. of 2-bromopropanoic acid (racemate) were reacted at 45° C. and worked up according to General Method 4A. Owing to incomplete conversion, the crude product was then once more reacted as described above with 1.2 eq. of magnesium di-tert-butoxide, 0.65 eq. of potassium tert-butoxide and 0.8 eq. of 2-bromopropionic acid (racemate) in 3.5 ml of tetrahydrofuran and worked up analogously. Yield: 270 mg (purity 63%, 84% of theory)

LC/MS [Method 1]: $R_t$=0.86 min; MS (ESIpos): m/z=369 (M+H)$^+$.

Example 53.1E tert-Butyl 4-({2-[4-(5-chloro-2-cyanophenyl)-5-(difluoromethoxy)-2-oxopyridin-1(2H)-yl]propanoyl}amino)benzoate (racemate)

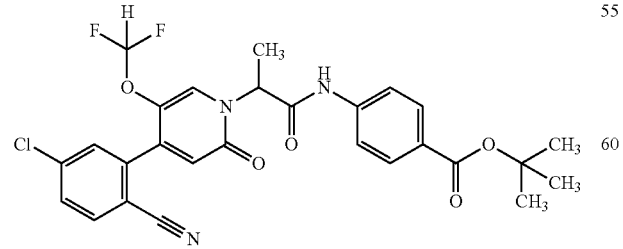

270 mg (purity 63%, 0.46 mmol) of 2-[4-(5-chloro-2-cyanophenyl)-5-(difluoromethoxy)-2-oxopyridin-1(2H)-yl]propanoic acid (racemate) and 98 mg (0.51 mmol, 1.1 eq.) of tert-butyl 4-aminobenzoate were reacted according to General Method 5A. Yield: 100 mg (40% of theory)

LC/MS [Method 1]: $R_t$=1.23 min; MS (ESIpos): m/z=544 (M+H)$^+$ $^1$H-NMR (400 MHz, DMSO-d$_6$): δ [ppm]=10.78 (s, 1H), 8.05 (d, 1H), 7.99 (s, 1H), 7.88 (d, 2H), 7.82-7.69 (m, 4H), 6.89 (t, 1H), 6.65 (s, 1H), 5.56 (q, 1H), 1.72 (d, 3H), 1.54 (s, 9H).

Example 54.1A

4-Iodo-2-methoxy-5-(2,2,2-trifluoroethoxy)pyridine

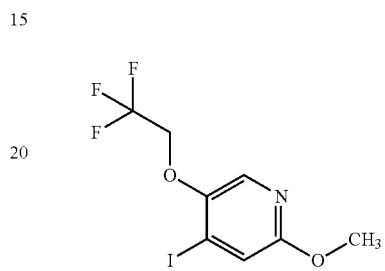

466 mg (3.4 mmol, 2.0 eq.) of potassium carbonate and 567 mg (2.5 mmol, 1.5 eq.) of 2,2,2-trifluoroethyl trifluoromethanesulphonate were added to a solution of 455 mg (purity 93%, 1.7 mmol) of 4-iodo-6-methoxypyridin-3-ol in 10 ml of dimethylformamide and 0.4 ml of acetonitrile, and the mixture was irradiated in a microwave at 150° C. for 30 min. A further 393 mg (1.7 mmol, 1.0 eq.) of 2,2,2-trifluoroethyl trifluoromethanesulphonate were added, and the reaction mixture was once more irradiated in the microwave at 150° C. for 30 min. After addition of water/ethyl acetate and phase separation, the aqueous phase was extracted twice with ethyl acetate. The combined organic phases were washed with saturated aqueous sodium chloride solution, dried (sodium sulphate), filtered, concentrated under reduced pressure and dried. Yield: 500 mg (purity 94%, 94% of theory)

LC/MS [Method 1]: $R_t$=1.11 min; MS (ESIpos): m/z=334 (M+H)$^+$.

Example 54.1B

4-Chloro-2-[2-methoxy-5-(2,2,2-trifluoroethoxy)pyridin-4-yl]benzonitrile

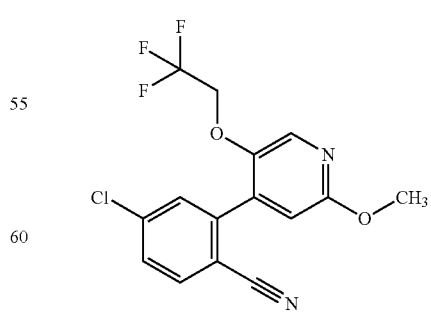

500 mg (purity 94%, 1.41 mmol) of 4-iodo-2-methoxy-5-(2,2,2-trifluoroethoxy)pyridine and 282 mg (1.55 mmol, 1.1 eq.) of 5-chloro-2-cyanophenylboronic acid in the presence of [1,1-bis(diphenylphosphino)ferrocene]palladium(II) chloride/dichloromethane monoadduct were reacted according to General Method 2A. The crude product was purified by flash chromatography (silica gel 50, cyclohexane/ethyl acetate gradient). Yield: 168 mg (33% of theory)

LC/MS [Method 1]: $R_t$=1.16 min; MS (ESIpos): m/z=343 (M+H)$^+$.

Example 54.1C

4-Chloro-2-[2-oxo-5-(2,2,2-trifluoroethoxy)-1,2-dihydropyridin-4-yl]benzonitrile

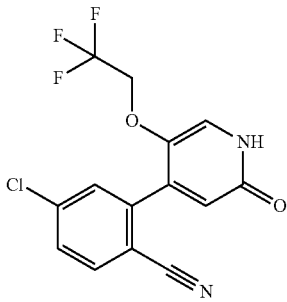 [SMILES: N#Cc1ccc(Cl)cc1-c1cc(=O)[nH]cc1OCC(F)(F)F]

168 mg (0.47 mmol) of 4-chloro-2-[2-methoxy-5-(2,2,2-trifluoroethoxy)pyridin-4-yl]benzonitrile and pyridinium hydrobromide were reacted according to General Method 3A. Yield: 112 mg (purity 92%, 67% of theory)

LC/MS [Method 1]: $R_t$=0.87 min; MS (ESIpos): m/z=329 (M+H)$^+$.

Example 54.1D

2-[4-(5-Chloro-2-cyanophenyl)-2-oxo-5-(2,2,2-trifluoroethoxy)pyridin-1(2H)-yl]propanoic acid (racemate)

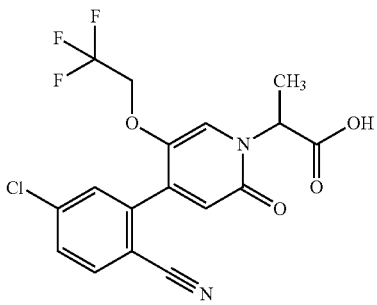 [SMILES: CC(C(=O)O)n1cc(OCC(F)(F)F)c(-c2cc(Cl)ccc2C#N)cc1=O]

140 mg (purity 87%, 0.37 mmol) of 4-chloro-2-[2-oxo-5-(2,2,2-trifluoroethoxy)-1,2-dihydropyridin-4-yl]benzonitrile, 2.0 eq. of magnesium di-tert-butoxide, 1.05 eq. of potassium tert-butoxide and 1.5 eq. of 2-bromopropanoic acid (racemate) were reacted according to General Method 4A at 50° C. and, after aqueous work-up, used without purification for the next step. Yield: 214 mg (purity 73%, quant.)

LC/MS [Method 1]: $R_t$=0.91 min; MS (ESIpos): m/z=401 (M+H)$^+$.

Example 54.1E tert-Butyl 4-({2-[4-(5-chloro-2-cyanophenyl)-2-oxo-5-(2,2,2-trifluoroethoxy)pyridin-1(2H)-yl]propanoyl}amino)benzoate (racemate)

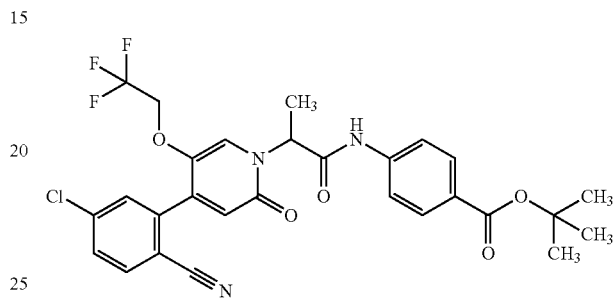

214 mg (purity 73%, 0.39 mmol) of 2-[4-(5-chloro-2-cyanophenyl)-2-oxo-5-(2,2,2-trifluoroethoxy)pyridin-1(2H)-yl]propanoic acid (racemate) and 83 mg (0.43 mmol, 1.1 eq.) of tert-butyl 4-aminobenzoate were reacted according to General Method 5A. Yield: 113 mg (purity 70%, 35% of theory)

LC/MS [Method 1]: $R_t$=1.23 min; MS (ESIpos): m/z=576 (M+H)$^+$.

Example 55.1A

2-Methoxybutyl trifluoromethanesulphonate (racemate)

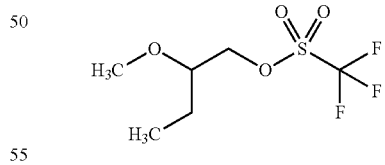

1.0 g (9.6 mmol) of 2-methoxybutanol and 1.78 ml (10.6 mmol, 1.1 eq.) of trifluoromethanesulphonic anhydride in the presence of 1.47 ml (10.6 mmol, 1.1 eq.) of triethylamine were reacted according to General Method 8A. The crude product was reacted in the next step without further purification.

$^1$H-NMR (400 MHz, CDCl$_3$): δ [ppm]=4.51 (dd, 1H), 4.43 (dd, 1H), 3.44 (s, 3H), 3.44-3.39 (m, 1H), 1.65-1.54 (m, 2H), 0.98 (t, 3H).

Example 55.1B tert-Butyl 2-[4-(5-chloro-2-cyanophenyl)-5-methoxy-2-oxopyridin-1(2H)-yl]-4-methoxyhexanoate (mixture of racemic diastereomers)

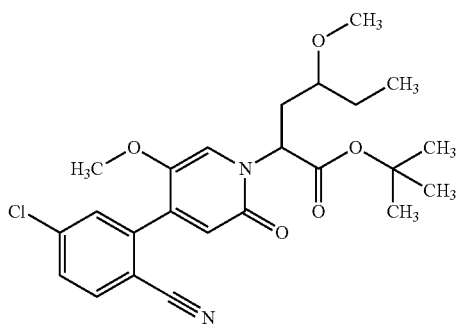 [SMILES: CCC(CC(C(=O)OC(C)(C)C)n1cc(OC)c(-c2cc(Cl)ccc2C#N)cc1=O)OC]

1.00 g (2.67 mmol) of tert-butyl [4-(5-chloro-2-cyanophenyl)-5-methoxy-2-oxopyridin-1(2H)-yl]acetate in the presence of 2.94 ml (2.94 mmol, 1.1 eq.) of bis(trimethylsilyl)lithium amide (1M in tetrahydrofuran) and 945 mg (4.00 mmol, 1.5 eq.) of 2-methoxybutyl trifluoromethanesulphonate (racemate) were reacted according to General Method 7B. Yield: 669 mg (54% of theory)

LC/MS [Method 1]: $R_t$=1.15 min; MS (ESIpos): m/z=461 (M+H)$^+$.

$^1$H-NMR (400 MHz, DMSO-d$_6$): δ [ppm]=7.98 (d, 1H), 7.75-7.70 (m, 2H), 7.44/7.40 (2×s, 1H), 6.49/6.48 (2×s, 1H), 5.24-5.17 (m, 1H), 3.64 (2×s, 3H), 3.19/3.16 (2×s, 3H), 2.81-2.74 (m, 1H), 2.45-2.28 (m, 1H), 2.16-2.03 (m, 1H), 1.57-1.38 (m, 2H), 1.41 (2×s, 9H), 0.84/0.80 (2×t, 3H).

Example 55.1C

2-[4-(5-Chloro-2-cyanophenyl)-5-methoxy-2-oxopyridin-1(2H)-yl]-4-methoxyhexanoic acid (mixture of racemic diastereomers)

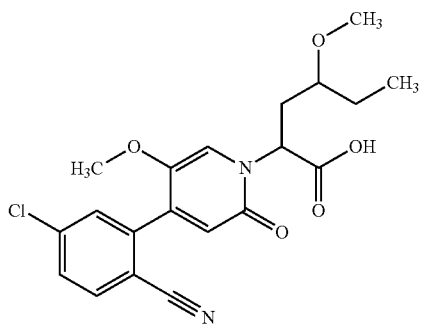 [SMILES: CCC(CC(C(=O)O)n1cc(OC)c(-c2cc(Cl)ccc2C#N)cc1=O)OC]

668 mg (1.45 mmol) of tert-butyl 2-[4-(5-chloro-2-cyanophenyl)-5-methoxy-2-oxopyridin-1(2H)-yl]-4-methoxyhexanoate (mixture of racemic diastereomers) were hydrolysed with trifluoroacetic acid according to General Method 6A. Yield: 623 mg (purity 94%, quant.)

LC/MS [Method 1]: $R_t$=0.89 min; MS (ESIpos): m/z=405 (M+H)$^+$ $^1$H-NMR (400 MHz, DMSO-d$_6$): δ [ppm]=13.0 (br. s, 1H), 7.98 (d, 1H), 7.77-7.70 (m, 2H), 7.50/7.44 (2×s, 1H), 6.48/6.47 (2×s, 1H), 5.28-5.20 (m, 1H), 3.64 (2×s, 3H), 3.16/3.15 (2×s, 3H), 2.78-2.71 (m, 1H), 2.48-2.28 (m, 1H), 2.24-2.06 (m, 1H), 1.55-1.41 (m, 2H), 0.83/0.79 (2×t, 3H).

Example 55.1D

Ethyl 4-({2-[4-(5-chloro-2-cyanophenyl)-5-methoxy-2-oxopyridin-1(2H)-yl]-4-methoxyhexanoyl}amino)-benzoate (mixture of racemic diastereomers)

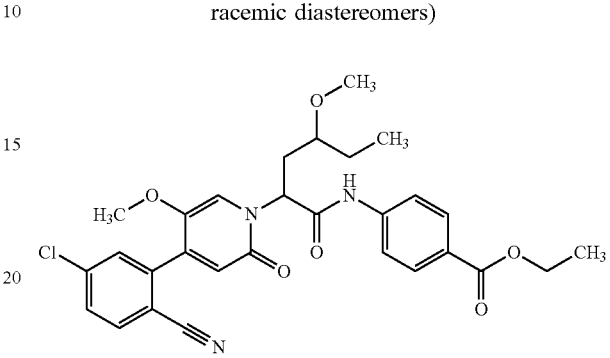

620 mg (1.53 mmol) of 2-[4-(5-chloro-2-cyanophenyl)-5-methoxy-2-oxopyridin-1(2H)-yl]-4-methoxyhexanoic acid (mixture of racemic diastereomers), 253 mg (1.53 mmol) of ethyl 4-aminobenzoate, 218 mg (1.53 mmol) of Oxima and 239 µl (1.53 mmol) of DIC in 15.3 ml of dimethylformamide were reacted according to General Method 5B. The crude product was purified by flash chromatography (120 g cartridge, 85 ml/min, cyclohexane/ethyl acetate gradient). Yield: 634 mg (70% of theory)

LC/MS [Method 2]: diastereomer 1: $R_t$=3.75 min; MS (ESIpos): m/z=552 (M+H)$^+$; diastereomer 2: $R_t$=3.81 min; MS (ESIpos): m/z=552 (M+H)$^+$.

$^1$H-NMR (400 MHz, DMSO-d$_6$): δ [ppm]=10.8 (2×s, 1H), 8.01-7.98 (m, 1H), 7.95-7.91 (m, 2H), 7.83-7.79 (m, 2H), 7.76-7.72 (m, 2H), 7.59/7.51 (2×s, 1H), 6.54 (s, 1H), 5.87-5.80 (m, 1H), 4.31/4.29 (2×q, 2H), 3.69 (s, 3H), 3.19/3.13 (2×s, 3H), 3.08-2.88 (2×m, 1H), 2.44-2.17 (m, 2H), 1.62-1.44 (m, 2H), 1.31/1.28 (2×t, 3H), 0.86/0.85 (2×t, 3H).

Example 56.1A

Benzyl [4-(5-chloro-2-cyanophenyl)-5-methoxy-2-oxopyridin-1(2H)-yl]acetate

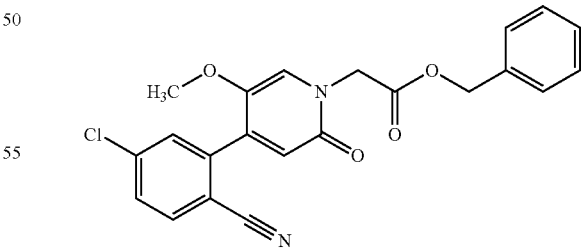

3.18 g (23.0 mmol) of potassium carbonate were added to a solution of 4.00 g (15.3 mmol) of 4-chloro-2-(5-methoxy-2-oxo-1,2-dihydropyridin-4-yl)benzonitrile and 2.92 ml (18.4 mmol) of benzyl bromoacetate in 53.3 ml of dimethylformamide, and the mixture was then stirred at 100° C. for 45 min. The reaction mixture was cooled to RT and the reaction was ended by adding 530 ml of water and 10.0 g (236 mmol) of lithium chloride. The mixture was extracted three times with 200 ml of ethyl acetate. The combined organic phases were dried over magnesium sulphate and filtered, and the solvent was removed under reduced pressure. The residue was dissolved in 50 ml of dichloromethane, applied to diatomaceous earth and purified by flash chromatography (120 g cartridge, 80 ml/min, ethyl acetate/cyclohexane gradient). Yield: 3.90 g (61% of theory)

LC/MS [Method 1]: $R_t$=1.02 min; MS (ESIpos): m/z=409 (M+H)$^+$ $^1$H-NMR (400 MHz, DMSO-d$_6$): δ [ppm]=8.00 (d, 1H), 7.75-7.72 (m, 2H), 7.61 (s, 1H), 7.42-7.33 (m, 5H), 6.54 (s, 1H), 5.22 (s, 2H), 4.81 (s, 2H), 3.62 (s, 3H).

Example 57.1A

2-{[tert-Butyl(diphenyl)silyl]oxy}ethanol

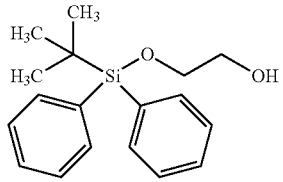 [SMILES: CC(C)(C)[Si](OCCO)(c1ccccc1)c1ccccc1]

10.0 g (36.4 mmol) of chloro-tert-butyl(diphenyl)silane dissolved in 88 ml of tetrahydrofuran were added dropwise over a period of 6 h to a solution of 10.1 ml (182 mmol) of 1,2-ethanediol and 2.97 g (43.7 mmol) of imidazole in 12 ml of tetrahydrofuran, and the mixture was then stirred further at RT overnight. The solvent was removed under reduced pressure and the residue was purified by flash chromatography (340 g silica cartridge, 100 ml/min, cyclohexane/ethyl acetate gradient). Yield: 8.34 g (76% of theory)

LC/MS [Method 1]: $R_t$=1.57 min; MS (ESIpos): m/z=323 (M+Na)$^+$ $^1$H-NMR (400 MHz, DMSO-d$_6$): δ [ppm]=7.66-7.62 (m, 4H), 7.49-7.40 (m, 6H), 4.64 (t, 1H), 3.67-3.61 (m, 2H), 3.54-3.49 (m, 2H), 0.99 (s, 9H).

Example 57.1B

2-{[tert-Butyl(diphenyl)silyl]oxy}ethyl trifluoromethansulphonate

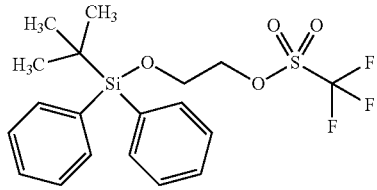 [SMILES: CC(C)(C)[Si](OCCOS(=O)(=O)C(F)(F)F)(c1ccccc1)c1ccccc1]

At −78° C., a solution of 1.50 g (4.99 mmol) of 2-{[tert-butyl(diphenyl)silyl]oxy}ethanol and 765 µl (5.49 mmol) of triethylamine in 5 ml of dichloromethane was added dropwise to 924 µl (5.49 mmol) of trifluoromethanesulphonic anhydride in 5 ml of dichloromethane such that the internal temperature did not exceed −50° C. The mixture was stirred at −78° C. for another 15 min and spontaneously warmed to RT. The reaction mixture was diluted with 50 ml of methyl tert-butyl ether and washed three times with 25 ml of a mixture of saturated aqueous sodium chloride solution and saturated aqueous ammonium chloride solution (3:1), dried over magnesium sulphate, filtered and concentrated at 25° C. and a pressure of ≥100 mbar. Yield: 2.08 g (71% of theory)

$^1$H-NMR (400 MHz, DMSO-d$_6$): δ [ppm]=7.66-7.62 (m, 4H), 7.52-7.44 (m, 6H), 4.45-4.41 (m, 2H), 3.89-3.85 (m, 2H), 1.03 (s, 9H).

Example 57.1C

Benzyl 4-{[tert-butyl(diphenyl)silyl]oxy}-2-[4-(5-chloro-2-cyanophenyl)-5-methoxy-2-oxopyridin-1(2H)-yl]butanoate (racemate)

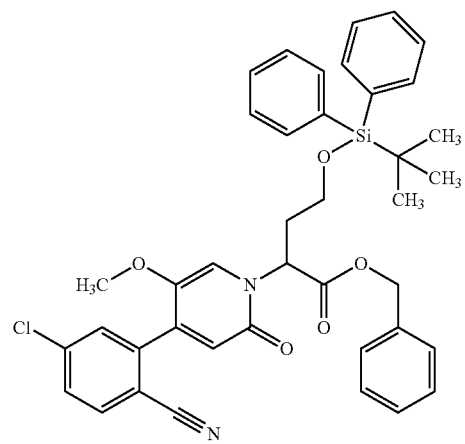 [SMILES: COc1cn(C(CCO[Si](c2ccccc2)(c2ccccc2)C(C)(C)C)C(=O)OCc2ccccc2)c(=O)cc1-c1cc(Cl)ccc1C#N]

1.00 g (2.45 mmol) of benzyl [4-(5-chloro-2-cyanophenyl)-5-methoxy-2-oxopyridin-1(2H)-yl]acetate in the presence of 2.69 ml (2.69 mmol, 1.1 eq.) of bis(trimethylsilyl)lithium amide (1M in tetrahydrofuran) and 1.59 g (3.67 mmol, 1.5 eq.) of 2-{[tert-butyl(diphenyl)silyl]oxy}ethyl trifluoromethanesulphonate were reacted according to General Method 7B. Yield: 708 mg (40% of theory)

LC/MS [Method 1]: $R_t$=1.55 min; MS (ESIpos): m/z=691 (M+H)$^+$ $^1$H-NMR (400 MHz, DMSO-d$_6$): δ [ppm]=8.00 (d, 1H), 7.74 (dd, 1H), 7.62-7.56 (m, 5H), 7.47-7.29 (m, 12H), 6.56 (s, 1H), 5.51 (dd, 1H), 5.19 (s, 2H), 3.75-3.69 (m, 1H), 3.63-3.57 (m, 1H), 3.56 (s, 3H), 2.52-2.40 (m, 2H), 0.97 (s, 9H).

Example 57.1D

4-{[tert-Butyl(diphenyl)silyl]oxy}-2-[4-(5-chloro-2-cyanophenyl)-5-methoxy-2-oxopyridin-1(2H)-yl]butanoic acid (racemate)

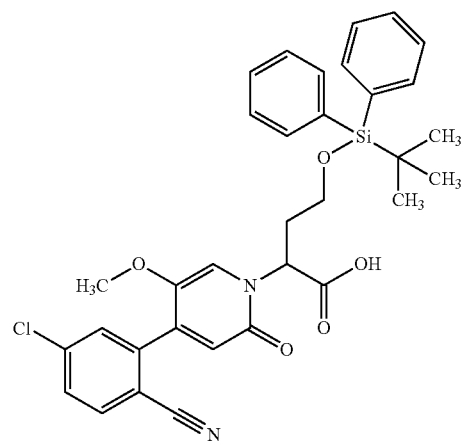 [SMILES: COc1cn(C(CCO[Si](c2ccccc2)(c2ccccc2)C(C)(C)C)C(=O)O)c(=O)cc1-c1cc(Cl)ccc1C#N]

605 mg (875 μmol) of benzyl 4-{[tert-butyl(diphenyl)silyl]oxy}-2-[4-(5-chloro-2-cyanophenyl)-5-methoxy-2-oxopyridin-1(2H)-yl]butanoate (racemate) were dissolved in 6 ml of tetrahydrofuran, and 2.2 ml (2.2 mmol, 2.5 eq.) of aqueous sodium hydroxide solution (1.0M) were added. The mixture was stirred at RT for another 1 h and then neutralized with aqueous hydrochloric acid (1N). The phases were separated and the aqueous phase was extracted twice with 25 ml of ethyl acetate. The combined organic phases were dried over magnesium sulphate and filtered, and the solvent was removed under reduced pressure. The crude product was used for the next step without further purification. Yield: 568 mg (93% of theory)

LC/MS [Method 1]: $R_t$=1.39 min; MS (ESIpos): m/z=601 (M+H)$^+$.

Example 57.1E

Ethyl 4-[(4-{[tert-butyl(diphenyl)silyl]oxy}-2-[4-(5-chloro-2-cyanophenyl)-5-methoxy-2-oxopyridin-1(2H)-yl]butanoyl)amino]benzoate (racemate)

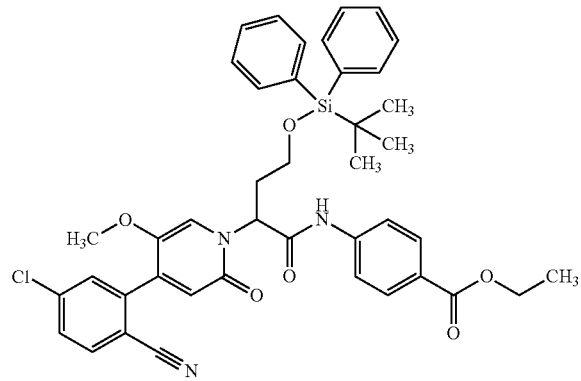 [SMILES: CCOC(=O)c1ccc(NC(=O)C(CCO[Si](c2ccccc2)(c2ccccc2)C(C)(C)C)n2cc(OC)c(-c3cc(Cl)ccc3C#N)cc2=O)cc1]

565 mg (940 μmol) of 4-{[tert-butyl(diphenyl)silyl]oxy}-2-[4-(5-chloro-2-cyanophenyl)-5-methoxy-2-oxopyridin-1(2H)-yl]butanoic acid (racemate), 155 mg (940 μmol) of ethyl 4-aminobenzoate, 134 mg (940 μmol) of Oxima and 146 μl (940 μmol) of DIC in 19 ml of dimethylformamide were reacted according to General Method 5B. The crude product was purified by flash chromatography (120 g cartridge, 85 ml/min, cyclohexane/ethyl acetate gradient). Yield: 268 mg (38% of theory)

LC/MS [Method 1]: $R_t$=1.54 min; MS (ESIpos): m/z=748 (M+H)$^+$ $^1$H-NMR (400 MHz, DMSO-$d_6$): δ [ppm]=10.8 (s, 1H), 8.00 (d, 1H), 7.94 (d, 2H), 7.79 (d, 2H), 7.74 (dd, 1H), 7.63-7.57 (m, 5H), 7.48 (s, 1H), 7.46-7.36 (m, 6H), 6.55 (s, 1H), 5.87 (dd, 1H), 4.29 (q, 2H), 3.72-3.67 (m, 2H), 3.64 (s, 3H), 2.52-2.48 (m, 2H, under solvent resonance), 1.32 (t, 3H), 0.94 (s, 9H).

Example 58.1A tert-Butyl 2-[4-(5-chloro-2-cyanophenyl)-5-methoxy-2-oxopyridin-1(2H)-yl]-3-(3-ethyloxetan-3-yl)prop-2-enoate (isomer mixture)

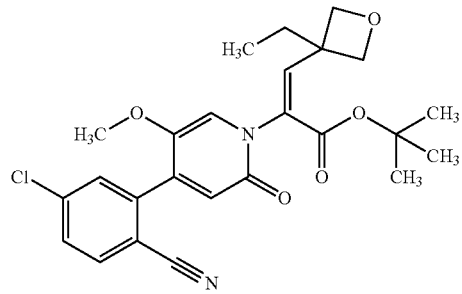 [SMILES: CCC1(/C=C(\C(=O)OC(C)(C)C)n2cc(OC)c(-c3cc(Cl)ccc3C#N)cc2=O)COC1]

38.4 mg (1.60 mmol, 2 eq., 60% in mineral oil) of sodium hydride and 457 mg (4.00 mmol) of 3-ethyloxetane-3-carbaldehyde in 1 ml of dimethylformamide were added in succession to a solution of 300 mg (800 μmol) of tert-butyl [4-(5-chloro-2-cyanophenyl)-5-methoxy-2-oxopyridin-1(2H)-yl]acetate in 8 ml of dimethylformamide. After 15 min at RT, the reaction was terminated by addition of 10 ml of saturated aqueous ammonium chloride solution and the reaction mixture was then extracted three times with 20 ml of ethyl acetate. The combined organic phases were dried over magnesium sulphate and filtered, and the solvent was removed under reduced pressure. The residue was purified by flash chromatography (24 g cartridge, 35 ml/min, cyclohexane/ethyl acetate gradient). Yield: 320 mg (82% of theory)

LC/MS [Method 1]: $R_t$=1.06 min; MS (ESIpos): m/z=471 (M+H)$^+$ $^1$H-NMR (400 MHz, DMSO-$d_6$): δ [ppm]=8.00 (d, 1H), 7.79-7.71 (m, 2H), 7.27 (s, 1H), 7.04 (s, 1H), 6.52 (s, 1H), 4.63 (d, 1H), 4.48 (d, 1H), 4.22 (d, 1H), 4.13 (d, 1H), 3.69/3.60 (2×s, 3H), 2.10-2.04/1.94-1.86 (2×q, 2H), 1.44-1.40 (2×s, 9H), 0.99/0.95 (2×t, 3H).

Example 58.1B tert-Butyl 2-[4-(5-chloro-2-cyanophenyl)-5-methoxy-2-oxopyridin-1(2H)-yl]-3-(3-ethyloxetan-3-yl)propanoate (racemate)

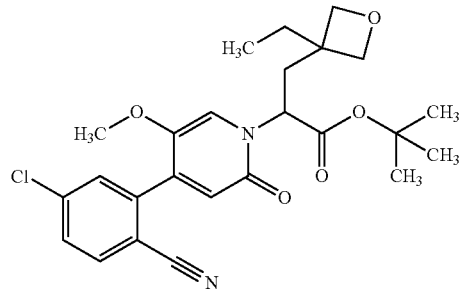 [SMILES: CCC1(CC(C(=O)OC(C)(C)C)n2cc(OC)c(-c3cc(Cl)ccc3C#N)cc2=O)COC1]

At RT, 302 mg (641 μmol) of tert-butyl 2-[4-(5-chloro-2-cyanophenyl)-5-methoxy-2-oxopyridin-1(2H)-yl]-3-(3-ethyloxetan-3-yl)prop-2-enoate (isomer mixture) were admixed with 20 ml of a "Hot Stryker's" reagent solution [B. A. Baker et al. *Org. Lett.* 2008, 10, 289-292]. The reaction mixture was stirred at RT for 1.5 h, and 20 ml of saturated aqueous ammonium chloride solution were then added. After phase separation, the aqueous phase was extracted three times with 25 ml of ethyl acetate. The combined organic phases were dried over magnesium sulphate and filtered, and the solvent was removed under reduced pressure. The residue was purified by flash chromatography (120 g silica cartridge, 85 ml/min, cyclohexane/ethyl acetate gradient). Yield: 275 mg (91% of theory)

LC/MS [Method 1]: $R_t$=1.11 min; MS (ESIpos): m/z=473 $(M+H)^+$ $^1$H-NMR (400 MHz, DMSO-$d_6$): δ [ppm]=7.98 (d, 1H), 7.75-7.71 (m, 2H), 7.51 (s, 1H), 6.49 (s, 1H), 5.22-5.13 (m, 1H), 4.31 (d, 1H), 4.23 (d, 1H), 4.04 (d, 1H), 3.93 (d, 1H), 3.65 (s, 3H), 2.65 (dd, 1H), 2.39 (dd, 1H), 1.83-1.72 (m, 2H), 1.41 (s, 9H), 0.83 (t, 3H).

Example 58.1C

2-[4-(5-Chloro-2-cyanophenyl)-5-methoxy-2-oxopyridin-1(2H)-yl]-3-(3-ethyloxetan-3-yl)propanoic acid (racemate)

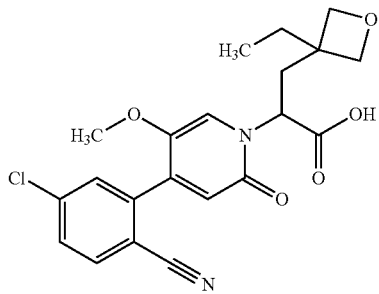 [SMILES: CCC1(CC(C(=O)O)n2cc(OC)c(-c3cc(Cl)ccc3C#N)cc2=O)COC1]

275 mg (599 μmol) of tert-butyl 2-[4-(5-chloro-2-cyanophenyl)-5-methoxy-2-oxopyridin-1(2H)-yl]-3-(3-ethyloxetan-3-yl)propanoate (racemate) and 3 ml of aqueous lithium hydroxide solution (1N) were reacted according to General Method 6B, giving the title compound. Yield: 193 mg (76% of theory)

LC/MS [Method 1]: $R_t$=0.82 min; MS (ESIpos): m/z=417 $(M+H)^+$ $^1$H-NMR (400 MHz, DMSO-$d_6$): δ [ppm]=13.1 (br. s, 1H), 7.99 (d, 1H), 7.77-7.71 (m, 2H), 7.56 (s, 1H), 6.49 (s, 1H), 5.25-5.13 (m, 1H), 4.30 (d, 1H), 4.22 (d, 1H), 4.02 (d, 1H), 3.92 (d, 1H), 3.65 (s, 3H), 2.69 (dd, 1H), 2.42 (dd, 1H), 1.84-1.73 (m, 2H), 0.82 (t, 3H).

Example 59.1A 1,1,2,2,2-Pentadeuteroethyl trifluoromethanesulphonate

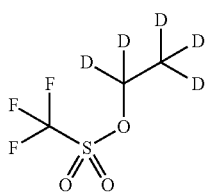 [SMILES: [2H]C([2H])([2H])C([2H])([2H])OS(=O)(=O)C(F)(F)F]

1.0 g (19.57 mmol) of 1,1,2,2,2-pentadeuteroethanol and 3.48 ml (20.55 mmol, 1.05 eq.) of trifluoromethanesulphonic anhydride in the presence of 2.51 ml (21.53 mmol, 1.1 eq.) of 2,6-dimethylpyridine were reacted according to General Method 8A. The crude product was reacted in the next step without further purification.

Example 59.1B tert-Butyl 2-[4-(5-chloro-2-cyanophenyl)-5-methoxy-2-oxopyridin-1(2H)-yl](3,3,4,4,4-pentadeutero)butanoate (racemate)

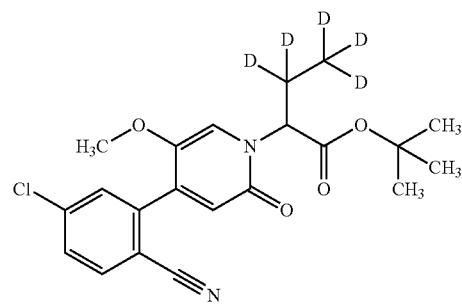 [SMILES: [2H]C([2H])([2H])C([2H])([2H])C(C(=O)OC(C)(C)C)n1cc(OC)c(-c2cc(Cl)ccc2C#N)cc1=O]

250 mg (0.67 mmol) of tert-butyl [4-(5-chloro-2-cyanophenyl)-5-methoxy-2-oxopyridin-1(2H)-yl]acetate in the presence of 0.80 ml (0.80 mmol, 1.2 eq.) of bis(trimethylsilyl)lithium amide (1M in THF) and 183 mg (1.00 mmol, 1.5 eq.) of 1,1,2,2,2-pentadeuteroethyl trifluoromethanesulphonate were reacted according to General Method 7B. Yield: 206 mg (purity 94%, 71% of theory)

LC/MS [Method 8]: $R_t$=1.37 min; MS (ESIpos): m/z=352 (M+H—COO-tert-butyl)$^+$, $^1$H-NMR (400 MHz, DMSO-$d_6$): δ [ppm]=7.99 (d, 1H), 7.76-7.69 (m, 2H), 7.36 (s, 1H), 6.50 (s, 1H), 5.01 (s, 1H), 3.63 (s, 3H), 1.40 (s, 9H).

Example 59.1C

2-[4-(5-Chloro-2-cyanophenyl)-5-methoxy-2-oxopyridin-1(2H)-yl](3,3,4,4,4-pentadeutero)butanoic acid (racemate)

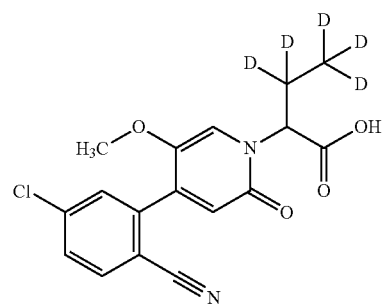 [SMILES: [2H]C([2H])([2H])C([2H])([2H])C(C(=O)O)n1cc(OC)c(-c2cc(Cl)ccc2C#N)cc1=O]

206 mg (purity 94%, 0.48 mmol) of tert-butyl 2-[4-(5-chloro-2-cyanophenyl)-5-methoxy-2-oxopyridin-1(2H)-yl](3,3,4,4,4-pentadeutero)butanoate (racemate) were hydrolysed with TFA according to General Method 6A. Yield: 208 mg (purity 71%, 88% of theory)

LC/MS [Method 1]: $R_t$=0.81 min; MS (ESIpos): m/z=352 (M+H)$^+$.

Example 59.1D tert-Butyl 4-({2-[4-(5-chloro-2-cyanophenyl)-5-methoxy-2-oxopyridin-1(2H)-yl](3,3,4,4,4-pentadeutero)butanoyl}amino)benzoate (racemate)

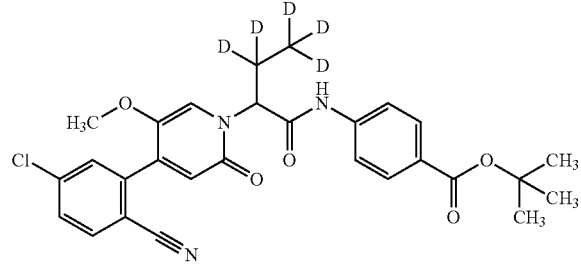 [SMILES: [2H]C([2H])([2H])C([2H])([2H])C(C(=O)Nc1ccc(C(=O)OC(C)(C)C)cc1)n1cc(OC)c(-c2cc(Cl)ccc2C#N)cc1=O]

208 mg (purity 71%, 0.42 mmol) of 2-[4-(5-chloro-2-cyanophenyl)-5-methoxy-2-oxopyridin-1(2H)-yl](3,3,4,4,4-pentadeutero)butanoic acid (racemate) and 89 mg (0.46 mmol, 1.1 eq.) of tert-butyl 4-aminobenzoate were reacted according to General Method 5A. Yield: 79 mg (purity 91%, 33% of theory)

LC/MS [Method 1]: $R_t$=1.21 min; MS (ESIpos): m/z=527 (M+H)$^+$.

Example 60.1A

[1-(Trifluoromethyl)cyclopropyl]methanol

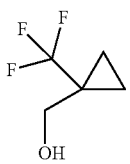

At 0° C., 26.7 ml (26.7 mmol) of diisobutylaluminum hydride (1M in dichloromethane) were slowly added dropwise to a solution of 1.89 g (10.7 mmol) of methyl 1-(trifluoromethyl)cyclopropanecarboxylate in 10 ml of dichloromethane. The mixture was then stirred at 0° C. for another 2 h and the reaction was subsequently terminated by addition of 10 ml of methanol. The reaction mixture was diluted with 30 ml of aqueous 20% strength sodium potassium tartrate solution and 30 ml of aqueous buffer solution (pH 7) and stirred vigorously at room temperature overnight. The phases were separated and the aqueous phase was extracted three times with dichloromethane. The combined organic phases were dried over magnesium sulphate and filtered, and the solvent was removed under reduced pressure. The crude product corresponded to the title compound. Yield: 0.96 g (64% of theory)

$^1$H-NMR (400 MHz, CDCl$_3$): δ [ppm]=3.74 (d, 2H), 1.65 (t, 1H), 1.06-1.02 (m, 2H), 0.81-0.76 (m, 2H).

Example 60.1B

[1-(Trifluoromethyl)cyclopropyl]methyl trifluoromethanesulphonate

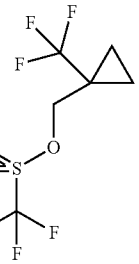

At −78° C., a solution of 428 mg (3.06 mmol) of [1-(trifluoromethyl)cyclopropyl]methanol and 468 µl (3.36 mmol) of triethylamine in 1.5 ml of dichloromethane was added dropwise to 569 µl (3.36 mmol) of trifluoromethanesulphonic anhydride in 1.5 ml of dichloromethane such that the internal temperature did not exceed −50° C. The mixture was stirred at −78° C. for another 30 min and spontaneously warmed to RT. The reaction mixture was diluted with 25 ml of methyl tert-butyl ether, washed three times with 20 ml of a mixture of saturated aqueous sodium chloride solution/1N hydrochloric acid (3:1), dried over magnesium sulphate, filtered and concentrated at 25° C. and a pressure of ≥100 mbar. The crude product was used for the next step without further purification. Yield: 701 mg (84% of theory)

Example 60.1C tert-Butyl 2-[4-(5-chloro-2-cyanophenyl)-5-methoxy-2-oxopyridin-1(2H)-yl]-3-[1-(trifluoromethyl)cyclopropyl]propanoate (racemate)

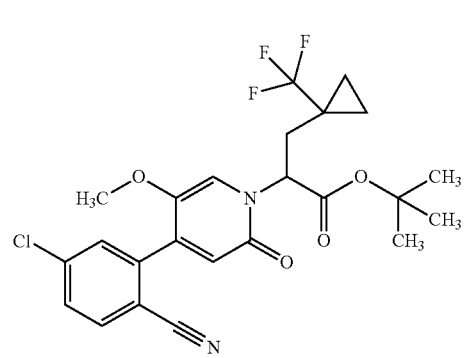 [SMILES: COc1cn(C(CC2(C(F)(F)F)CC2)C(=O)OC(C)(C)C)c(=O)cc1-c1cc(Cl)ccc1C#N]

500 mg (1.33 mmol) of tert-butyl [4-(5-chloro-2-cyanophenyl)-5-methoxy-2-oxopyridin-1(2H)-yl]acetate, 701 mg (2.58 mmol) of [1-(trifluoromethyl)cyclopropyl]methyl trifluoromethanesulphonate and 1.73 ml (1.73 mmol) of bis(trimethylsilyl)lithium amide (1M in THF) in 13 ml of THF were reacted according to General Method 7B. The crude product was purified by column chromatography (ethyl acetate/cyclohexane gradient, 40 g silica cartridge, flow rate 40 ml/min), giving the title compound. Yield: 295 mg (45% of theory)

LC/MS [Method 1]: $R_t$=1.20 min; MS (ESIpos): m/z=497 (M+H)$^+$,

¹H-NMR (400 MHz, DMSO-d₆): δ [ppm]=7.99 (d, 1H), 7.75-7.71 (m, 2H), 7.42 (s, 1H), 6.50 (s, 1H), 5.19-5.11 (m, 1H), 3.63 (s, 3H), 2.68 (dd, 1H), 2.33 (dd, 1H), 1.40 (s, 9H), 0.95-0.74 (m, 3H), 0.56-0.49 (m, 1H).

Example 60.1D

2-[4-(5-Chloro-2-cyanophenyl)-5-methoxy-2-oxopyridin-1(2H)-yl]-3-[1-(trifluoromethyl)cyclopropyl]propanoic acid (racemate)

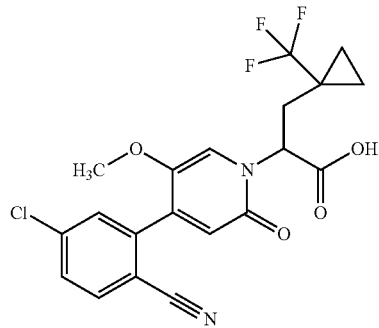 [SMILES: COc1cn(C(CC2(C(F)(F)F)CC2)C(=O)O)c(=O)cc1-c1cc(Cl)ccc1C#N]

295 mg (594 µmol) of tert-butyl 2-[4-(5-chloro-2-cyanophenyl)-5-methoxy-2-oxopyridin-1(2H)-yl]-3-[1-(trifluoromethyl)cyclopropyl]propanoate (racemate) in 6 ml of dichloromethane and 915 µl (11.9 mmol) of TFA were reacted according to General Method 6A. Yield: 258 mg (purity 92%, 91% of theory)

LC/MS [Method 1]: $R_t$=0.96 min; MS (ESIneg): m/z=439 (M−H)⁻,

¹H-NMR (400 MHz, DMSO-d₆): δ [ppm]=13.2 (br. s, 1H), 7.99 (d, 1H), 7.76-7.71 (m, 2H), 7.46 (s, 1H), 6.49 (s, 1H), 5.23-5.14 (m, 1H), 3.63 (s, 3H), 2.71 (dd, 1H), 2.37 (dd, 1H), 0.92-0.81 (m, 2H), 0.78-0.71 (m, 1H), 0.54-0.46 (m, 1H).

Example 60.1E tert-Butyl 4-({2-[4-(5-chloro-2-cyanophenyl)-5-methoxy-2-oxopyridin-1(2H)-yl]-3-[1-(trifluoromethyl)cyclopropyl]propanoyl}amino)benzoate (racemate)

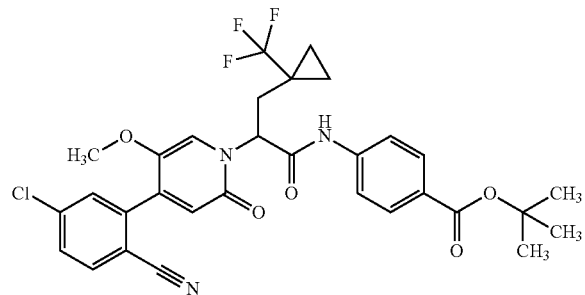 [SMILES: COc1cn(C(CC2(C(F)(F)F)CC2)C(=O)Nc2ccc(C(=O)OC(C)(C)C)cc2)c(=O)cc1-c1cc(Cl)ccc1C#N]

188 mg (426 µmol) of 2-[4-(5-chloro-2-cyanophenyl)-5-methoxy-2-oxopyridin-1(2H)-yl]-3-[1-(trifluoromethyl)cyclopropyl]propanoic acid (racemate), 82.4 mg (426 µmol) of tert-butyl 4-aminobenzoate, 6.1 mg (43 µmol) of Oxima and 66 µl (0.43 mmol) of DIC in 4 ml of dimethylformamide were reacted according to General Method 5B. Following preparative HPLC [column: Chromatorex C18, 10 µm, 125 mm×30 mm, mobile phase: acetonitrile/0.1% formic acid gradient (0 to 3 min 10% acetonitrile, to 35 min 90% acetonitrile and a further 3 min 90% acetonitrile)], the title compound was obtained. Yield: 157 mg (59% of theory)

LC/MS [Method 1]: $R_t$=1.35 min; MS (ESIpos): m/z=616 (M+H)⁺,

¹H-NMR (400 MHz, DMSO-d₆): δ [ppm]=10.8 (s, 1H), 7.99 (d, 1H), 7.88 (d, 2H), 7.78-7.71 (m, 4H), 7.53 (s, 1H), 6.55 (s, 1H), 5.86-5.80 (m, 1H), 3.67 (s, 3H), 2.60-2.47 (m, 2H), 1.54 (s, 9H), 0.97-0.80 (m, 4H).

Example 61.1A

[1-(Trifluoromethyl)cyclobutyl]methyl trifluoromethanesulphonate

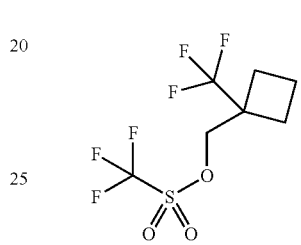

330 mg (2.03 mmol) of [1-(trifluoromethyl)cyclobutyl]methanol and 0.38 ml (2.24 mmol, 1.1 eq.) of trifluoromethanesulphonic anhydride in the presence of 312 µl (2.24 mmol, 1.1 eq.) of triethylamine were reacted according to General Method 8A. The crude product was reacted in the next step without further purification.

¹H-NMR (400 MHz, DMSO-d₆): δ [ppm]=4.56 (s, 2H), 2.28-2.19 (m, 2H), 2.11-1.89 (m, 4H).

Example 61.1B tert-Butyl 2-[4-(5-chloro-2-cyanophenyl)-5-methoxy-2-oxopyridin-1(2H)-yl]-3-[1-(trifluoromethyl)cyclobutyl]propanoate (racemate)

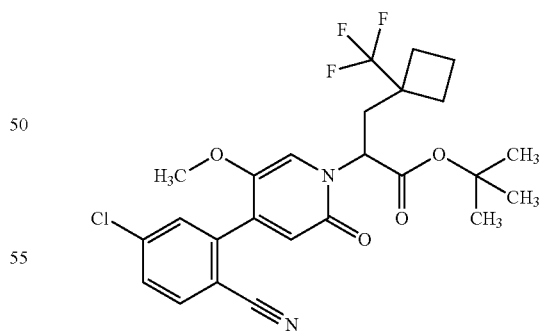

383 mg (1.02 mmol) of tert-butyl [4-(5-chloro-2-cyanophenyl)-5-methoxy-2-oxopyridin-1(2H)-yl]acetate in the presence of 1.23 ml (1.23 mmol, 1.2 eq.) of bis(trimethylsilyl)lithium amide (1M in THF) and 780 mg (purity 60%, 1.64 mmol, 1.6 eq.) of [1-(trifluoromethyl)cyclobutyl]methyl trifluoromethanesulphonate were reacted according to General Method 7B. Yield: 119 mg (purity 91%, 21% of theory)

LC/MS [Method 8]: $R_t$=1.54 min; MS (ESIpos): m/z=455 (M+H—COO-tert-butyl)$^+$.

Example 61.1C

2-[4-(5-Chloro-2-cyanophenyl)-5-methoxy-2-oxopyridin-1(2H)-yl]-3-[1-(trifluoromethyl)cyclobutyl]propanoic acid (racemate)

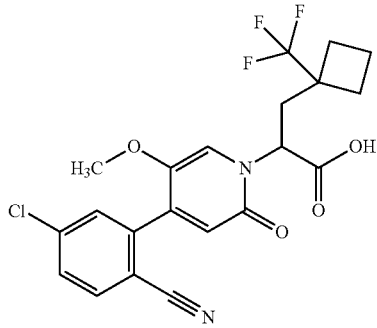 [SMILES: COc1cn(C(CC2(C(F)(F)F)CCC2)C(=O)O)c(=O)cc1-c1cc(Cl)ccc1C#N]

119 mg (purity 91%, 0.21 mmol) of tert-butyl 2-[4-(5-chloro-2-cyanophenyl)-5-methoxy-2-oxopyridin-1(2H)-yl]-3-[1-(trifluoromethyl)cyclobutyl]propanoate (racemate) were hydrolysed with TFA according to General Method 6A. Yield: 91 mg (purity 69%, 65% of theory)

LC/MS [Method 1]: $R_t$=1.01 min; MS (ESIpos): m/z=455 (M+H)$^+$.

Example 61.1D tert-Butyl 4-({2-[4-(5-chloro-2-cyanophenyl)-5-methoxy-2-oxopyridin-1(2H)-yl]-3-[1-(trifluoromethyl)-cyclobutyl]propanoyl}amino)benzoate (racemate)

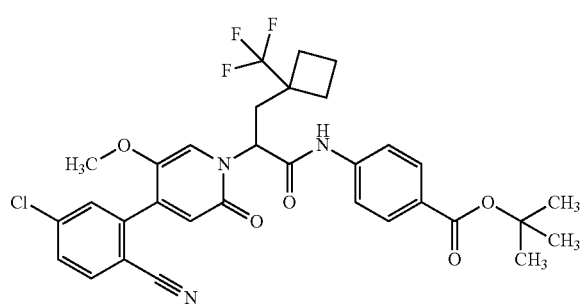 [SMILES: COc1cn(C(CC2(C(F)(F)F)CCC2)C(=O)Nc2ccc(C(=O)OC(C)(C)C)cc2)c(=O)cc1-c1cc(Cl)ccc1C#N]

90 mg (purity 69%, 0.14 mmol) of 2-[4-(5-chloro-2-cyanophenyl)-5-methoxy-2-oxopyridin-1(2H)-yl]-3-[1-(trifluoromethyl)cyclobutyl]propanoic acid (racemate) and 29 mg (0.15 mmol, 1.1 eq.) of tert-butyl 4-aminobenzoate were reacted according to General Method 5A. Yield: 58 mg (67% of theory)

LC/MS [Method 8]: $R_t$=1.65 min; MS (ESIneg): m/z=628 (M−H)$^-$.

Example 62.1A (3,3-Difluorocyclobutyl)methyl trifluoromethanesulphonate

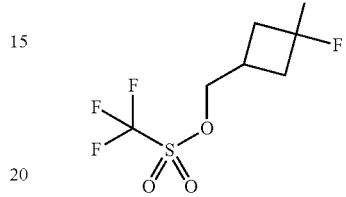

500 mg (4.09 mmol) of (3,3-difluorocyclobutyl)methanol and 0.76 ml (4.50 mmol, 1.1 eq.) of trifluoromethanesulphonic anhydride in the presence of 628 µl (4.50 mmol, 1.1 eq.) of triethylamine were reacted according to General Method 8A. The crude product was reacted in the next step without further purification.

$^1$H-NMR (400 MHz, DMSO-d$_6$): δ [ppm]=4.33 (d, 2H), 2.76-2.61 (m, 2H), 2.60-2.50 (m, 1H), 2.50-2.37 (m, 2H).

Example 62.1B tert-Butyl 2-[4-(5-chloro-2-cyanophenyl)-5-methoxy-2-oxopyridin-1(2H)-yl]-3-(3,3-difluorocyclobutyl)propanoate (racemate)

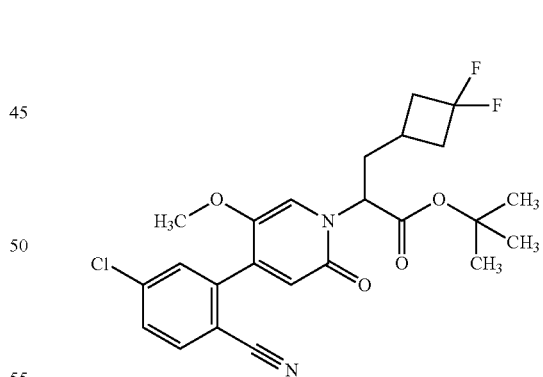

600 mg (1.60 mmol) of tert-butyl [4-(5-chloro-2-cyanophenyl)-5-methoxy-2-oxopyridin-1(2H)-yl]acetate in the presence of 1.92 ml (1.92 mmol, 1.2 eq.) of bis(trimethylsilyl)lithium amide (1M in THF) and 1162 mg (purity 70%, 3.20 mmol, 2.0 eq.) of (3,3-difluorocyclobutyl)methyl trifluoromethanesulphonate were reacted according to General Method 7B. Yield: 417 mg (52% of theory)

LC/MS [Method 8]: $R_t$=1.44 min; MS (ESIpos): m/z=423 (M+H—COO-tert-butyl)$^+$.

Example 62.1C

2-[4-(5-Chloro-2-cyanophenyl)-5-methoxy-2-oxopyridin-1(2H)-yl]-3-(3,3-difluorocyclobutyl)propanoic acid (racemate)

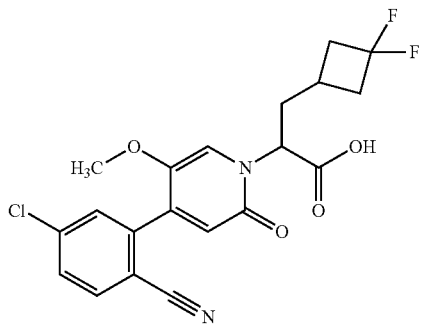 [SMILES: COc1cn(C(CC2CC(F)(F)C2)C(=O)O)c(=O)cc1-c1cc(Cl)ccc1C#N]

184 mg (0.37 mmol) of tert-butyl 2-[4-(5-chloro-2-cyanophenyl)-5-methoxy-2-oxopyridin-1(2H)-yl]-3-(3,3-difluorocyclobutyl)propanoate (racemate) were hydrolysed with TFA according to General Method 6A. Yield: 200 mg (purity 88%, quant.)

LC/MS [Method 1]: $R_t$=0.93 min; MS (ESIpos): m/z=423 (M+H)$^+$.

Example 62.1D tert-Butyl 4-({2-[4-(5-chloro-2-cyanophenyl)-5-methoxy-2-oxopyridin-1(2H)-yl]-3-(3,3-difluorocyclobutyl)propanoyl}amino)benzoate (racemate)

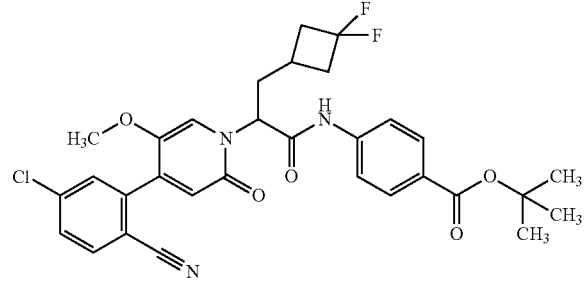 [SMILES: COc1cn(C(CC2CC(F)(F)C2)C(=O)Nc2ccc(C(=O)OC(C)(C)C)cc2)c(=O)cc1-c1cc(Cl)ccc1C#N]

200 mg (purity 88%, 0.42 mmol) of 2-{4-[5-chloro-2-(difluoromethoxy)phenyl]-5-methoxy-2-oxopyridin-1(2H)-yl}-4-methylpropanoic acid (racemate) and 89 mg (0.46 mmol, 1.1 eq.) of tert-butyl 4-aminobenzoate were reacted according to General Method 5A. Yield: 175 mg (70% of theory)

LC/MS [Method 1]: $R_t$=1.26 min; MS (ESIpos): m/z=598 (M+H)$^+$.

Example 63.1A

3-Methyloxetane-3-carbaldehyde

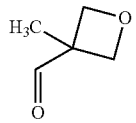

6.75 g (31.3 mmol) of pyridinium chlorochromate were initially charged in 100 ml of dichloromethane, and a solution of 2.00 g (19.6 mmol) of (3-methyloxetan-3-yl)methanol in 20 ml of dichloromethane was added at room temperature. 7 g of Celite® were then added, and the mixture was stirred at room temperature for another 4 h. The mixture was filtered off with suction through silica gel and the solvent was removed under reduced pressure at room temperature. The crude product was used for the next step without further purification. Yield: 1.55 g (79% of theory)

$^1$H-NMR (400 MHz, CDCl$_3$): δ [ppm]=9.95 (s, 1H), 4.89 (d, 2H), 4.51 (d, 2H), 1.48 (s, 3H).

Example 63.1B tert-Butyl 2-[4-(5-chloro-2-cyanophenyl)-5-methoxy-2-oxopyridin-1(2H)-yl]-3-(3-methyloxetan-3-yl)prop-2-enoate (isomer mixture)

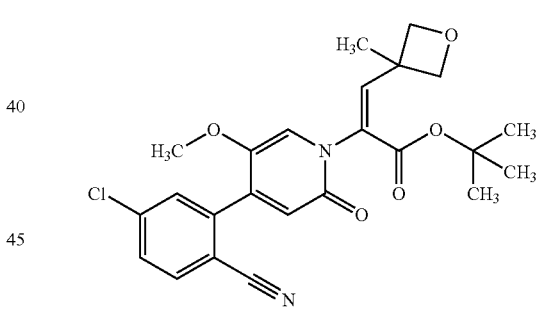

64.0 mg (1.60 mmol, 60% in mineral oil) of sodium hydride and 200 mg (2.00 mmol) of 3-methyloxetane-3-carbaldehyde in 1 ml of dimethylformamide were added in succession to a solution of 300 mg (800 μmol) of tert-butyl [4-(5-chloro-2-cyanophenyl)-5-methoxy-2-oxopyridin-1 (2H)-yl]acetate in 9 ml of dimethylformamide. After 15 min at room temperature, the reaction was terminated by addition of saturated aqueous ammonium chloride solution and the reaction mixture was then extracted three times with 20 ml of ethyl acetate. The combined organic phases were dried over magnesium sulphate and filtered, and the solvent was removed under reduced pressure. The residue was purified by flash chromatography (24 g silica cartridge, flow rate 35 ml/min, cyclohexane/ethyl acetate gradient). Yield: 356 mg (96% of theory)

LC/MS [Method 1]: $R_t$=1.03 min; MS (ESIpos): m/z=457 (M+H)$^+$.

Example 63.1C tert-Butyl 2-[4-(5-chloro-2-cyanophenyl)-5-methoxy-2-oxopyridin-1(2H)-yl]-3-(3-methyloxetan-3-yl)propanoate (racemate)

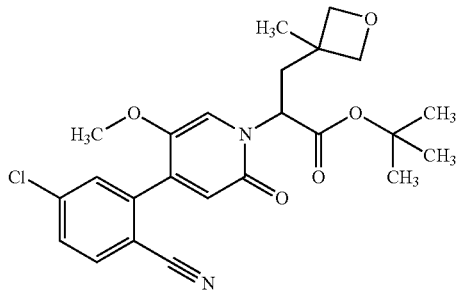 [SMILES: COc1cn(C(CC2(C)COC2)C(=O)OC(C)(C)C)c(=O)cc1-c1cc(Cl)ccc1C#N]

At room temperature, 350 mg (766 μmol) of tert-butyl 2-[4-(5-chloro-2-cyanophenyl)-5-methoxy-2-oxopyridin-1(2H)-yl]-3-(3-methyloxetan-3-yl)prop-2-enoate (isomer mixture) were admixed with 20 ml of a "Hot Stryker's" reagent solution [B. A. Baker et al. *Org. Lett.* 2008, 10, 289-292]. The reaction mixture was stirred at room temperature for 1 h, and saturated aqueous ammonium chloride solution was then added. After phase separation, the aqueous phase was extracted three times with ethyl acetate. The combined organic phases were dried over magnesium sulphate and filtered, and the solvent was removed under reduced pressure. The residue was purified by flash chromatography (40 g silica cartridge, flow rate 40 ml/min, cyclohexane/ethyl acetate gradient). Yield: 345 mg (97% of theory)

LC/MS [Method 1]: $R_t$=1.03 min; MS (ESIpos): m/z=459 (M+H)$^+$, $^1$H-NMR (400 MHz, DMSO-d$_6$): δ [ppm]=7.98 (d, 1H), 7.75-7.70 (m, 2H), 7.47 (s, 1H), 6.50 (s, 1H), 5.25-5.18 (m, 1H), 4.38 (d, 1H), 4.16 (d, 1H), 4.07 (d, 1H), 3.92 (d, 1H), 3.65 (s, 3H), 2.67 (dd, 1H), 2.31 (dd, 1H), 1.41 (s, 9H), 1.35 (s, 3H).

Example 63.1D

2-[4-(5-Chloro-2-cyanophenyl)-5-methoxy-2-oxopyridin-1(2H)-yl]-3-(3-methyloxetan-3-yl)propanoic acid (racemate)

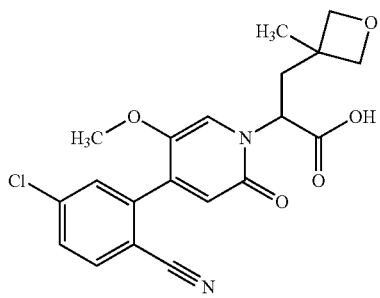 [SMILES: COc1cn(C(CC2(C)COC2)C(=O)O)c(=O)cc1-c1cc(Cl)ccc1C#N]

340 mg (741 μmol) of tert-butyl 2-[4-(5-chloro-2-cyanophenyl)-5-methoxy-2-oxopyridin-1(2H)-yl]-3-(3-methyloxetan-3-yl)propanoate (racemate) were dissolved in 5 ml of tetrahydrofuran, 2.5 ml of ethanol and 2.5 ml of water, and 3.7 ml (3.7 mmol, 5 eq.) of aqueous lithium hydroxide solution (1M) were added. The mixture was stirred at room temperature for another 7 h and then diluted with 20 ml of saturated aqueous ammonium chloride solution and 30 ml of ethyl acetate and adjusted to pH 4-5 using aqueous hydrochloric acid (1N). The phases were separated and the aqueous phase was extracted three times with 10 ml of ethyl acetate. The combined organic phases were dried over magnesium sulphate and filtered, and the solvent was removed under reduced pressure. The crude product was used for the next step without further purification. Yield: 275 mg (purity 95%, 88% of theory)

LC/MS [Method 1]: $R_t$=0.78 min; MS (ESIneg): m/z=401 (M-H)$^-$, $^1$H-NMR (400 MHz, DMSO-d$_6$): δ [ppm]=13.2 (br. s, 1H), 7.99 (d, 1H), 7.77-7.71 (m, 2H), 7.53 (s, 1H), 6.49 (s, 1H), 5.31-5.22 (m, 1H), 4.37 (d, 1H), 4.16 (d, 1H), 4.05 (d, 1H), 3.90 (d, 1H), 3.65 (s, 3H), 2.71 (dd, 1H), 2.33 (dd, 1H), 1.35 (s, 3H).

Example 63.1E

Allyl 4-({2-[4-(5-chloro-2-cyanophenyl)-5-methoxy-2-oxopyridin-1(2H)-yl]-3-(3-methyloxetan-3-yl)propanoyl}amino)benzoate (racemate)

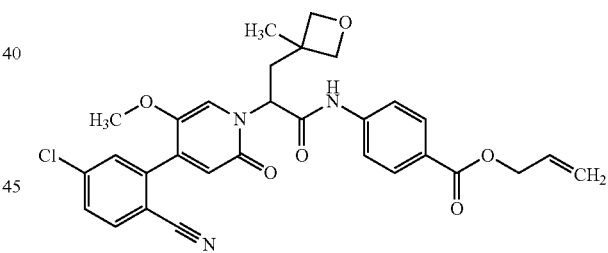

115 mg (285 μmol) of 2-[4-(5-chloro-2-cyanophenyl)-5-methoxy-2-oxopyridin-1(2H)-yl]-3-(3-methyloxetan-3-yl)propanoic acid (racemate), 51 mg (285 μmol) of allyl 4-aminobenzoate, 40.6 mg (285 μmol) of Oxima and 45 μl (0.29 mmol) of DIC in 2 ml of dimethylformamide were reacted according to General Method 5B. Preparative HPLC (acetonitrile/water gradient) gave the title compound. Yield: 25 mg (16% of theory)

LC/MS [Method 1]: $R_t$=1.06 min; MS (ESIpos): m/z=562 (M+H)$^+$, $^1$H-NMR (400 MHz, DMSO-d$_6$): δ [ppm]=10.9 (s, 1H), 8.01-7.96 (m, 3H), 7.80 (d, 2H), 7.74-7.71 (m, 2H), 7.65 (s, 1H), 6.53 (s, 1H), 6.09-5.99 (m, 1H), 5.87 (dd, 1H), 5.43-5.37 (m, 1H), 5.30-5.25 (m, 1H), 4.80-4.77 (m, 2H), 4.46 (d, 1H), 4.29 (d, 1H), 4.11 (d, 1H), 3.95 (d, 1H), 3.72 (s, 3H), 2.74-2.65 (m, 1H), 2.40-2.33 (m, 1H), 1.38 (s, 3H).

Example 64.1A

Methyl 4-methyltetrahydro-2H-pyran-4-carboxylate

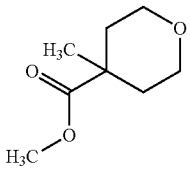

At −78° C., 22.1 ml of n-butyllithium (35.4 mmol, 1.6M in hexane) were slowly added dropwise to a solution of 4.91 ml (35.0 mmol) of diisopropylamine in 45 ml of tetrahydrofuran, and the mixture was stirred at −78° C. for another 10 min and at 0° C. for another 25 min. Subsequently, at −78° C., a solution of 5.00 g (34.7 mmol) of methyl tetrahydro-2H-pyran-4-carboxylate in 45 ml of tetrahydrofuran was added, and the mixture was stirred at −78° C. for another 15 min and at 0° C. for another 30 min. At −78° C., 2.16 ml (34.7 mmol) of methyl iodide were added dropwise, and the reaction mixture was slowly warmed to −25° C. and then to room temperature overnight. The reaction was terminated by addition of 80 ml of 0.1N hydrochloric acid, and the phases were separated. The aqueous phase was extracted twice with ethyl acetate, the combined organic phases were dried over magnesium sulphate and filtered and the solvent was removed under reduced pressure. The resulting suspension was triturated with 20 ml of methyl tert-butyl ether, the precipitate was filtered off with suction and the mother liquor was concentrated under reduced pressure, giving the title compound. Yield: 5.88 g (purity 95%, quant.)

$^1$H-NMR (400 MHz, DMSO-$d_6$): δ [ppm]=3.70-3.64 (m, 2H), 3.64 (s, 3H), 3.37-3.30 (m, 2H), 1.94-1.88 (m, 2H), 1.45-1.37 (m, 2H), 1.16 (s, 3H).

Example 64.1B (4-Methyltetrahydro-2H-pyran-4-yl)methanol

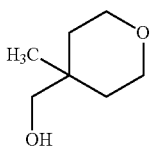

At −78° C., 73.3 ml (73.3 mmol, 1.0M in toluene) of diisobutylaluminium hydride were added dropwise to a solution of 5.80 g (36.7 mmol) of methyl 4-methyltetrahydro-2H-pyran-4-carboxylate in 220 ml of toluene such that the internal temperature did not exceed −70° C. The mixture was subsequently stirred at −78° C. for another 90 min and then further at room temperature overnight. The reaction was terminated by addition of 40 ml of methanol and 300 ml of 1N hydrochloric acid. The phases were separated and the aqueous phase was extracted three times with 150 ml of ethyl acetate. The combined organic phases were washed with saturated aqueous sodium chloride solution, dried over magnesium sulphate and filtered, and the solvent was removed under reduced pressure. The crude product corresponded to the title compound. Yield: 2.14 g (45% of theory)

$^1$H-NMR (400 MHz, CDCl$_3$): δ [ppm]=3.78-3.73 (m, 2H), 3.66-3.60 (m, 2H), 3.41 (s, 2H), 1.62-1.54 (m, 2H), 1.43 (br. s, 1H), 1.32-1.26 (m, 2H), 1.04 (s, 3H).

Example 64.1C (4-Methyltetrahydro-2H-pyran-4-yl)methyl trifluoromethanesulphonate

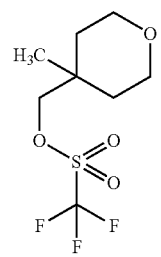

At −78° C., a solution of 1.00 g (7.68 mmol) of (4-methyltetrahydro-2H-pyran-4-yl)methanol and 1.18 ml (8.45 mmol) of triethylamine in 5 ml of dichloromethane was added dropwise to 1.42 ml (8.45 mmol) of trifluoromethanesulphonic anhydride in 5 ml of dichloromethane such that the internal temperature did not exceed −50° C. The mixture was stirred at −78° C. for another 15 min and spontaneously warmed to RT. The reaction mixture was diluted with 50 ml of methyl tert-butyl ether, washed three times with 25 ml of a mixture of saturated aqueous sodium chloride solution/1N hydrochloric acid (3:1), dried over magnesium sulphate, filtered and concentrated at 25° C. and a pressure of ≥100 mbar. Yield: 2.0 g (99% of theory)

$^1$H-NMR (400 MHz, CDCl$_3$): δ [ppm]=4.26 (s, 2H), 3.80-3.74 (m, 2H), 3.67-3.60 (m, 2H), 1.66-1.58 (m, 2H), 1.42-1.36 (m, 2H), 1.16 (s, 3H).

Example 64.1D tert-Butyl 2-[4-(5-chloro-2-cyanophenyl)-5-methoxy-2-oxopyridin-1(2H)-yl]-3-(4-methyltetrahydro-2H-pyran-4-yl)propanoate (racemate)

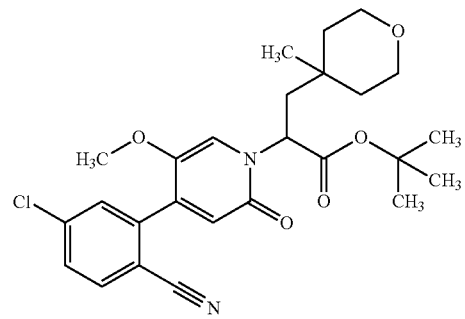 [SMILES: COc1cn(C(CC2(C)CCOCC2)C(=O)OC(C)(C)C)c(=O)cc1-c1cc(Cl)ccc1C#N]

1.91 g (5.08 mmol) of tert-butyl [4-(5-chloro-2-cyanophenyl)-5-methoxy-2-oxopyridin-1(2H)-yl]acetate, 2.00 g (7.63 mmol) of (4-methyltetrahydro-2H-pyran-4-yl)methyl trifluoromethanesulphonate and 6.61 ml (6.61 mmol) of bis(trimethylsilyl)lithium amide (1M in THF) in 10 ml of THF were reacted according to General Method 7B. Purification by preparative HPLC (acetonitrile/water gradient) gave the title compound. Yield: 212 mg (8% of theory)

LC/MS [Method 1]: $R_t$=1.10 min; MS (ESIpos): m/z=487 (M+H)$^+$, $^1$H-NMR (400 MHz, DMSO-d$_6$): δ [ppm]=8.00-7.96 (m, 1H), 7.74-7.70 (m, 2H), 7.50 (s, 1H), 6.48 (s, 1H), 5.48-5.41 (m, 1H), 3.66 (s, 3H), 3.55-3.42 (m, 4H), 2.30-2.22 (m, 1H), 2.15-2.09 (m, 1H), 1.49-1.10 (m, 4H), 1.41 (s, 9H), 0.95 (s, 3H).

Example 64.1E

2-[4-(5-Chloro-2-cyanophenyl)-5-methoxy-2-oxopyridin-1(2H)-yl]-3-(4-methyltetrahydro-2H-pyran-4-yl)propanoic acid (racemate)

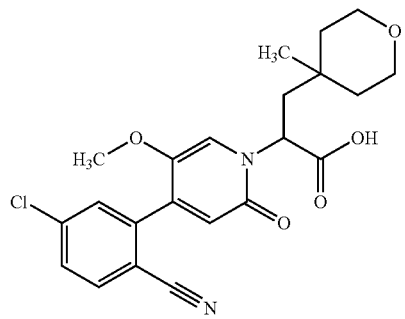 [SMILES: COc1cn(C(CC2(C)CCOCC2)C(=O)O)c(=O)cc1-c1cc(Cl)ccc1C#N]

210 mg (431 µmol) of tert-butyl 2-[4-(5-chloro-2-cyanophenyl)-5-methoxy-2-oxopyridin-1(2H)-yl]-3-(4-methyltetrahydro-2H-pyran-4-yl)propanoate (racemate) in 4.3 ml of dichloromethane and 598 µl (7.76 mmol) of TFA were reacted according to General Method 6A. Yield: 210 mg (purity 83%, 94% of theory)

LC/MS [Method 1]: $R_t$=0.86 min; MS (ESIneg): m/z=429 (M−H)$^-$, $^1$H-NMR (400 MHz, DMSO-d$_6$): δ [ppm]=13.2 (br. s, 1H), 7.98 (d, 1H), 7.75-7.70 (m, 2H), 7.55 (s, 1H), 6.48 (s, 1H), 5.58-5.43 (m, 1H), 3.65 (s, 3H), 3.55-3.38 (m, 4H), 2.37-2.31 (m, 1H), 2.18-2.12 (m, 1H), 1.48-1.41 (m, 1H), 1.35-1.28 (m, 1H), 1.27-1.19 (m, 1H), 1.13-1.06 (m, 1H), 0.96 (s, 3H).

Example 64.1F

Ethyl 4-({2-[4-(5-chloro-2-cyanophenyl)-5-methoxy-2-oxopyridin-1(2H)-yl]-3-(4-methyltetrahydro-2H-pyran-4-yl)propanoyl}amino)benzoate (racemate)

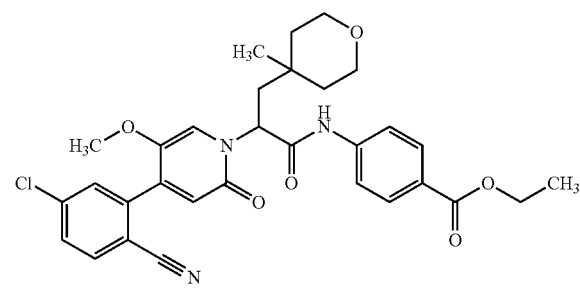 [SMILES: CCOC(=O)c1ccc(NC(=O)C(CC2(C)CCOCC2)n2cc(OC)c(-c3cc(Cl)ccc3C#N)cc2=O)cc1]

206 mg (478 µmol) of 2-[4-(5-chloro-2-cyanophenyl)-5-methoxy-2-oxopyridin-1(2H)-yl]-3-(4-methyltetrahydro-2H-pyran-4-yl)propanoic acid (racemate), 79 mg (0.48 mmol) of ethyl 4-aminobenzoate, 6.8 mg (48 µmol) of Oxima and 74 µl (0.48 mmol) of DIC in 4.8 ml of dimethylformamide were reacted according to General Method 5B. Preparative HPLC (acetonitrile/water gradient) gave the title compound. Yield: 70 mg (purity 95%, 24% of theory)

LC/MS [Method 1]: $R_t$=1.14 min; MS (ESIpos): m/z=578 (M+H)$^+$, $^1$H-NMR (400 MHz, DMSO-d$_6$): δ [ppm]=10.9 (s, 1H), 7.98 (d, 1H), 7.94 (d, 2H), 7.80 (d, 2H), 7.75-7.71 (m, 2H), 7.66 (s, 1H), 6.52 (s, 1H), 6.05 (dd, 1H), 4.29 (q, 2H), 3.71 (s, 3H), 3.65-3.39 (m, 4H), 2.34-2.27 (m, 1H), 2.07-2.00 (m, 1H), 1.57-1.48 (m, 1H), 1.40-1.25 (m, 2H), 1.31 (t, 3H), 1.16-1.09 (m, 1H), 1.03 (s, 3H).

Example 65.1A

Methyl 4-methoxycyclohexanecarboxylate (cis/trans isomer mixture)

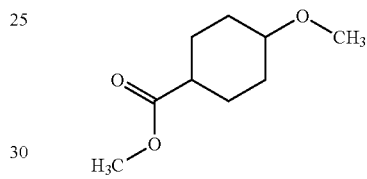

1.8 ml of concentrated sulphuric acid were added to a solution of 4.00 g (25.3 mmol) of 4-methoxycyclohexanecarboxylic acid in 32 ml of methanol, and the resulting reaction solution was heated under reflux overnight. The mixture was cooled to room temperature and the pH was adjusted to 7-8 using saturated aqueous sodium bicarbonate solution. The mixture was then extracted three times with 70 ml of ethyl acetate. The combined organic phases were dried over sodium sulphate and filtered, and the solvent was removed under reduced pressure. The crude product corresponded to the title compound. Yield: 4.30 g (99% of theory)

GC/MS [Method 9]: Rt=3.65 min; MS: m/z=172 (M)$^+$ $^1$H-NMR (400 MHz, DMSO-d$_6$): δ [ppm]=3.58 (s, 3H), 3.33-3.29/3.11-3.04 (2×m, 1H), 3.22/3.19 (2×s, 3H), 2.42-2.35/2.31-2.23 (2×m, 1H), 2.00-1.93/1.92-1.85 (2×m, 1H), 1.73-1.61 (m, 3H), 1.58-1.43 (m, 3H), 1.41-1.30/1.19-1.08 (2×m, 1H).

Example 65.1B (4-Methoxycyclohexyl)methanol (cis/trans isomer mixture)

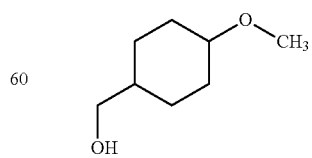

13.7 ml (27.5 mmol) of lithium aluminium hydride solution (2M in THF) was diluted with 82 ml of methyl tert-butyl ether, and a solution of 4.30 g (25.0 mmol) of methyl 4-methoxycyclohexanecarboxylate (cis/trans isomer mixture) in 82 ml of methyl tert-butyl ether was then added dropwise. The reaction solution was stirred at 40° C. for another 6 h and the reaction was then terminated by addition of 10 ml of water and 10 ml of aqueous 10% strength potassium hydroxide solution. The organic phase was decanted, dried over sodium sulphate and filtered, and the solvent was removed under reduced pressure. Yield: 3.24 g (90% of theory)

GC/MS [Method 9]: Rt=3.36/3.47 min; MS: m/z=144 (M)$^+$ $^1$H-NMR (400 MHz, CDCl$_3$): δ [ppm]=3.48/3.46 (2×d, 2H), 3.45-3.42/3.13-3.06 (2×m, 1H), 3.35/3.30 (2×s, 3H), 2.13-1.82 (m, 2H), 1.65 (br. s, 1H), 1.59-1.29 (m, 6H), 1.24-1.15/1.03-0.95 (2×m, 1H).

Example 65.1C (4-Methoxycyclohexyl)methyl trifluoromethanesulphonate (cis/trans isomer mixture)

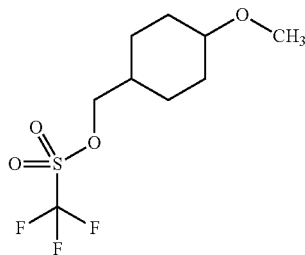 [SMILES: COC1CCC(COS(=O)(=O)C(F)(F)F)CC1]

4.30 g (29.8 mmol) of (4-methoxycyclohexyl)methanol (cis/trans isomer mixture) in 158 ml of dichloromethane and 5.21 ml (44.7 mmol) of lutidine and 7.57 ml (44.7 mmol) of trifluoromethanesulphonic anhydride were reacted according to General Method 8A. Yield: 6.00 g (73% of theory). The crude product was used for the next step without further purification.

Example 65.1D tert-Butyl 2-[4-(5-chloro-2-cyanophenyl)-5-methoxy-2-oxopyridin-1(2H)-yl]-3-(4-methoxycyclohexyl)propanoate (racemic cis/trans isomer mixture)

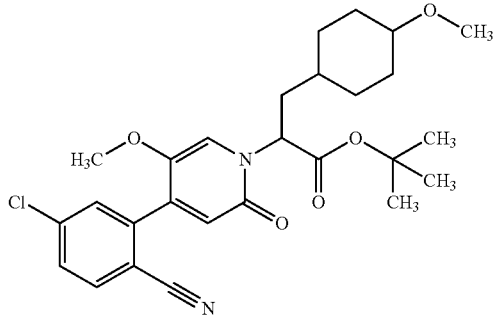 [SMILES: COc1cn(C(CC2CCC(OC)CC2)C(=O)OC(C)(C)C)c(=O)cc1-c1cc(Cl)ccc1C#N]

5.40 g (14.4 mmol) of tert-butyl [4-(5-chloro-2-cyanophenyl)-5-methoxy-2-oxopyridin-1(2H)-yl]acetate, 5.97 g (21.6 mmol) of (4-methoxycyclohexyl)methyl trifluoromethanesulphonate (cis/trans isomer mixture) and 15.8 ml (15.8 mmol) of bis(trimethylsilyl)lithium amide (1M in THF) in 114 ml of THF were reacted according to General Method 7B. Yield: 10.8 g (purity 51%) of crude product LC/MS [Method 1]: R$_t$=1.20/1.23 min; MS (ESIpos): m/z=501 (M+H)$^+$.

Example 65.1E tert-Butyl 2-[4-(5-chloro-2-cyanophenyl)-5-methoxy-2-oxopyridin-1(2H)-yl]-3-(cis-4-methoxycyclohexyl)propanoate (racemate)

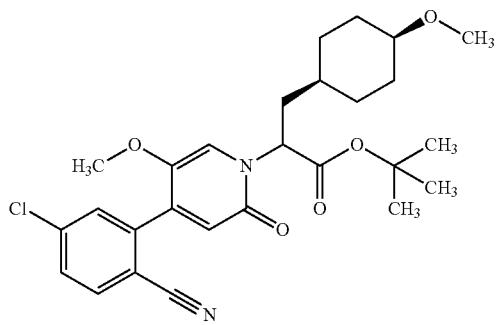 [SMILES: COc1cn(C(C[C@H]2CC[C@@H](OC)CC2)C(=O)OC(C)(C)C)c(=O)cc1-c1cc(Cl)ccc1C#N]

The crude product from Example 65.1D was purified by column chromatography (ethyl acetate/cyclohexane gradient, 340 g silica cartridge, flow rate 100 ml/min), giving the title compound. Yield: 2.1 g (29% of theory)

LC/MS [Method 1]: R$_t$=1.18 min; MS (ESIpos): m/z=501 (M+H)$^+$, $^1$H-NMR (400 MHz, DMSO-d$_6$): δ [ppm]=7.99 (d, 1H), 7.76-7.71 (m, 2H), 7.38 (s, 1H), 6.50 (s, 1H), 5.31-5.26 (m, 1H), 3.64 (s, 3H), 3.18 (s, 3H), 2.16-2.07 (m, 1H), 1.97-1.90 (m, 1H), 1.79-1.70 (m, 2H), 1.57-1.51 (m, 1H), 1.44-1.13 (m, 6H), 1.40 (s, 9H).

Example 65.2E tert-Butyl 2-[4-(5-chloro-2-cyanophenyl)-5-methoxy-2-oxopyridin-1(2H)-yl]-3-(trans-4-methoxycyclohexyl)propanoate (racemate)

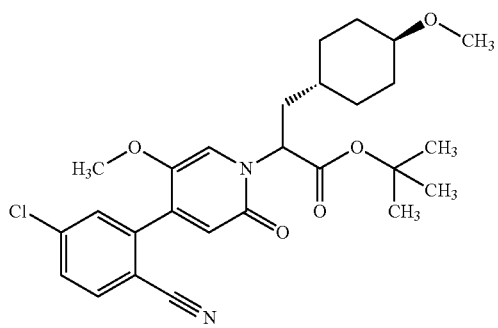 [SMILES: COc1cn(C(C[C@H]2CC[C@H](OC)CC2)C(=O)OC(C)(C)C)c(=O)cc1-c1cc(Cl)ccc1C#N]

The crude product from Example 65.1D was purified by column chromatography (ethyl acetate/cyclohexane gradient, 340 g silica cartridge, flow rate 100 ml/min), giving the title compound. Yield: 1.7 g (purity 87%, 21% of theory)

Example 65.1F

2-[4-(5-Chloro-2-cyanophenyl)-5-methoxy-2-oxopyridin-1(2H)-yl]-3-(cis-4-methoxycyclohexyl)propanoic acid (racemate)

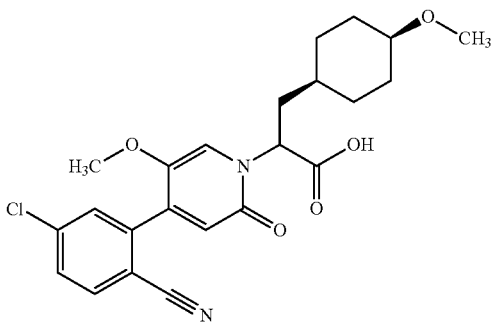 [SMILES: COc1cn(C(C[C@H]2CC[C@@H](OC)CC2)C(=O)O)c(=O)cc1-c1cc(Cl)ccc1C#N]

2.10 g (4.19 mmol) of tert-butyl 2-[4-(5-chloro-2-cyanophenyl)-5-methoxy-2-oxopyridin-1(2H)-yl]-3-(cis-4-methoxycyclohexyl)propanoate (racemate) in 6 ml of dichloromethane and 6.23 ml (83.8 mmol) of TFA were reacted according to General Method 6A. Yield: 2.10 g (quant.)

LC/MS [Method 1]: $R_t$=0.95 min; MS (ESIneg): m/z=443 (M−H)⁻.

Example 65.2F

2-[4-(5-Chloro-2-cyanophenyl)-5-methoxy-2-oxopyridin-1(2H)-yl]-3-(trans-4-methoxycyclohexyl)propanoic acid (racemate)

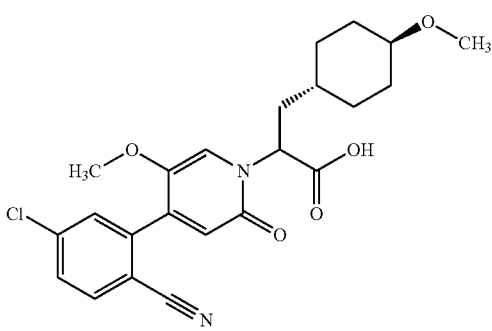 [SMILES: COc1cn(C(C[C@H]2CC[C@H](OC)CC2)C(=O)O)c(=O)cc1-c1cc(Cl)ccc1C#N]

1.70 g (purity 87%, 3.39 mmol) of tert-butyl 2-[4-(5-chloro-2-cyanophenyl)-5-methoxy-2-oxopyridin-1(2H)-yl]-3-(trans-4-methoxycyclohexyl)propanoate (racemate) in 6 ml of dichloromethane and 5.04 ml (67.9 mmol) of TFA were reacted according to General Method 6A. Yield: 1.70 g (quant.)

LC/MS [Method 1]: $R_t$=0.90 min; MS (ESIneg): m/z=443 (M−H)⁻,

¹H-NMR (400 MHz, DMSO-d₆): δ [ppm]=13.0 (br. s, 1H), 7.98 (d, 1H), 7.76-7.70 (m, 2H), 7.43 (s, 1H), 6.49 (s, 1H), 5.34-5.26 (m, 1H), 3.64 (s, 3H), 3.19 (s, 3H), 3.06-2.97 (m, 1H), 2.20-2.10 (m, 1H), 2.00-1.81 (m, 4H), 1.64-1.57 (m, 1H), 1.06-0.86 (m, 5H).

Example 65.1G

Ethyl 4-({2-[4-(5-chloro-2-cyanophenyl)-5-methoxy-2-oxopyridin-1(2H)-yl]-3-(cis-4-methoxycyclohexyl)propanoyl}amino)benzoate (racemate)

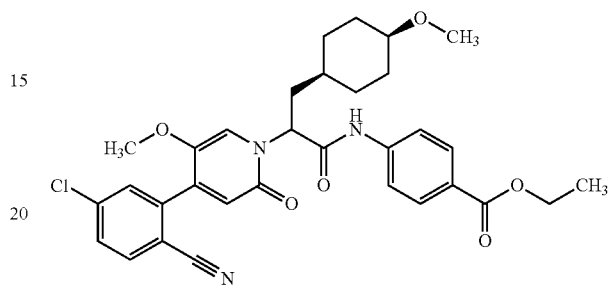

2.10 g (purity 74%, 4.72 mmol) of 2-[4-(5-chloro-2-cyanophenyl)-5-methoxy-2-oxopyridin-1(2H)-yl]-3-(cis-4-methoxycyclohexyl)propanoic acid (racemate), 780 mg (4.72 mmol) of ethyl 4-aminobenzoate, 671 mg (4.72 mmol) of Oxima and 735 µl (4.72 mmol) of DIC in 47 ml of dimethylformamide were reacted according to General Method 5B. After complete conversion, the reaction solution was diluted with 263 ml of 10% strength lithium chloride solution and 210 ml of ethyl acetate and the phases were separated. The aqueous phase was extracted twice with 210 ml of ethyl acetate. The combined organic phases were dried over magnesium sulphate and filtered, and the solvent was removed under reduced pressure. The crude product was purified by column chromatography (ethyl acetate/cyclohexane gradient, 100 g silica cartridge, flow rate 50 ml/min), giving the title compound. Yield: 2.1 g (75% of theory)

LC/MS [Method 1]: $R_t$=1.26 min; MS (ESIpos): m/z=592 (M+H)⁺,

¹H-NMR (400 MHz, DMSO-d₆): δ [ppm]=10.8 (s, 1H), 7.99 (d, 1H), 7.94 (d, 2H), 7.78 (d, 2H), 7.76-7.71 (m, 2H), 7.49 (s, 1H), 6.53 (s, 1H), 5.87-5.81 (m, 1H), 4.29 (q, 2H), 3.69 (s, 3H), 3.19 (s, 3H), 2.25-2.14 (m, 1H), 2.02-1.92 (m, 1H), 1.82-1.70 (m, 2H), 1.52-1.12 (m, 7H), 1.31 (t, 3H).

Example 65.2G

Ethyl 4-({2-[4-(5-chloro-2-cyanophenyl)-5-methoxy-2-oxopyridin-1(2H)-yl]-3-(trans-4-methoxycyclohexyl)propanoyl}amino)benzoate (racemate)

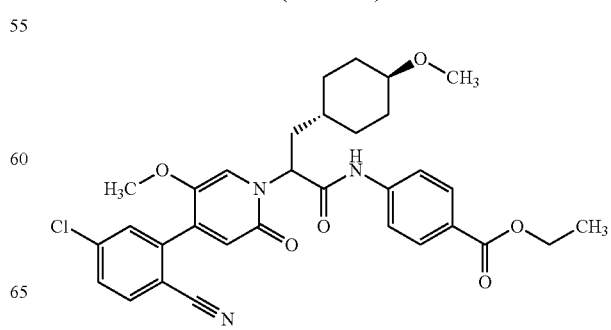

1.70 g (purity 82%, 3.82 mmol) of 2-[4-(5-chloro-2-cyanophenyl)-5-methoxy-2-oxopyridin-1(2H)-yl]-3-(trans-4-methoxycyclohexyl)propanoic acid (racemate), 631 mg (3.82 mmol) of ethyl 4-aminobenzoate, 543 mg (3.82 mmol) of Oxima and 595 μl (3.82 mmol) of DIC in 38 ml of dimethylformamide were reacted according to General Method 5B. After complete conversion, the reaction solution was diluted with 213 ml of 10% strength lithium chloride solution and 170 ml of ethyl acetate and the phases were separated. The aqueous phase was extracted twice with 170 ml of ethyl acetate. The combined organic phases were dried over magnesium sulphate and filtered, and the solvent was removed under reduced pressure. The crude product was purified by column chromatography (ethyl acetate/cyclohexane gradient, 100 g silica cartridge, flow rate 50 ml/min), giving the title compound. Yield: 1.1 g (purity 78%, 49% of theory)

LC/MS [Method 1]: $R_t$=1.23 min; MS (ESIpos): m/z=592 (M+H)$^+$, $^1$H-NMR (400 MHz, DMSO-d$_6$): δ [ppm]=10.8 (s, 1H), 7.99 (d, 1H), 7.94 (d, 2H), 7.80-7.71 (m, 4H), 7.49 (s, 1H), 6.54 (s, 1H), 5.87-5.81 (m, 1H), 4.29 (q, 2H), 3.69 (s, 3H), 3.20 (s, 3H), 3.08-2.98 (m, 1H), 2.24-2.15 (m, 1H), 2.00-1.88 (m, 3H), 1.83-1.72 (m, 2H), 1.31 (t, 3H), 1.12-0.89 (m, 5H).

Example 66.1A tert-Butyl 6-({2-[4-(5-chloro-2-cyanophenyl)-5-methoxy-2-oxopyridin-1(2H)-yl]-3-cyclobutylpropanoyl}amino)-2-methyl-3-oxo-2,3-dihydro-1H-indazole-1-carboxylate (racemate)

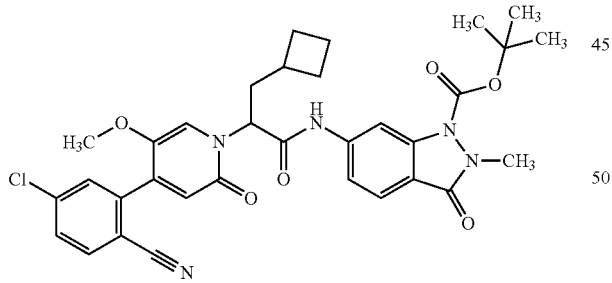

114 mg (purity 94%, 0.35 mmol) of 2-[4-(5-chloro-2-cyanophenyl)-5-methoxy-2-oxopyridin-1(2H)-yl]butanoic acid (racemate) and 103 mg (0.39 mmol, 1.1 eq.) of tert-butyl 6-amino-2-methyl-3-oxo-2,3-dihydro-1H-indazole-1-carboxylate were reacted according to General Method 5A. The crude product was purified by preparative HPLC (Reprosil C18, water/acetonitrile gradient). Yield: 101 mg (45% of theory)

LC/MS [Method 1]: $R_t$=1.27 min; MS (ESIpos): m/z=632 (M+H)$^+$.

Example 67.1A

Ethyl 2-[4-(5-chloro-2-cyanophenyl)-5-methoxy-2-oxopyridin-1(2H)-yl]-3-methylbutanoate (racemate)

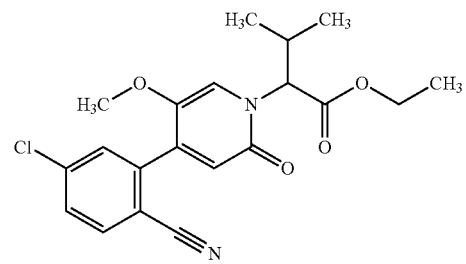 [SMILES: CCOC(=O)C(C(C)C)n1cc(OC)c(-c2cc(Cl)ccc2C#N)cc1=O]

3.50 g (13.4 mmol) of 4-chloro-2-(5-methoxy-2-oxo-1,2-dihydropyridin-4-yl)benzonitrile in the presence of 1.5 eq. of sodium hydride and 5.60 g (20.1 mmol, 1.5 eq.) of ethyl 3-methyl-2-{[(trifluoromethyl)sulphonyl]oxy}butanoate (racemate) were reacted at RT according to General Method 4E. The crude product was purified by flash chromatography (silica gel 50, cyclohexane/ethyl acetate mixtures). Yield: 3.70 g (66% of theory)

LC/MS [Method 1]: $R_t$=1.08 min; MS (ESIpos): m/z=389 (M+H)$^+$, $^1$H-NMR (400 MHz, DMSO-d$_6$): δ [ppm]=7.99 (d, 1H), 7.76 (d, 1H), 7.73 (dd, 1H), 7.43 (s, 1H), 6.51 (s, 1H), 5.00-4.95 (m, 1H), 4.21-4.11 (m, 2H), 3.65 (s, 3H), 2.65-2.56 (m, 1H), 1.19 (t, 3H), 1.11 (d, 3H), 0.76 (d, 3H).

Example 67.1B

2-[4-(5-Chloro-2-cyanophenyl)-5-methoxy-2-oxopyridin-1(2H)-yl]-3-methylbutanoic acid (racemate)

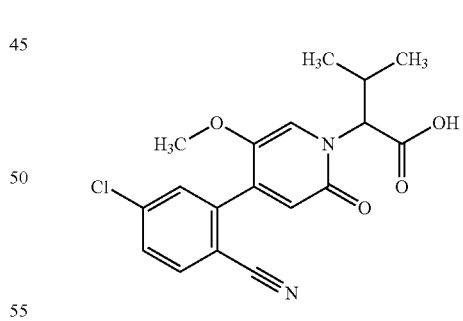

3.70 g (9.52 mmol) of ethyl 2-[4-(5-chloro-2-cyanophenyl)-5-methoxy-2-oxopyridin-1(2H)-yl]-3-methylbutanoate (racemate) were hydrolysed with lithium hydroxide according to General Method 6B. Yield: 2.80 g (82% of theory)

LC/MS [Method 1]: $R_t$=0.89 min; MS (ESIpos): m/z=361 (M+H)$^+$ $^1$H-NMR (400 MHz, DMSO-d$_6$): δ [ppm]=13.1 (br. s, 1H), 7.99 (d, 1H), 7.76 (d, 1H), 7.73 (dd, 1H), 7.41 (s, 1H), 6.51 (s, 1H), 4.94 (d, 1H), 3.64 (s, 3H), 2.62-2.56 (m, 1H), 1.12 (d, 3H), 0.75 (d, 3H).

Example 67.1C tert-Butyl 4-({2-[4-(5-chloro-2-cyanophenyl)-5-methoxy-2-oxopyridin-1(2H)-yl]-3-methylbutanoyl}amino)benzoate (racemate)

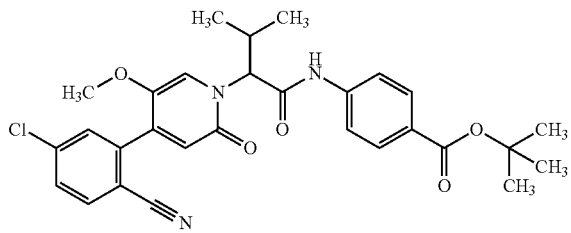 [SMILES: COc1cn(C(C(=O)Nc2ccc(C(=O)OC(C)(C)C)cc2)C(C)C)c(=O)cc1-c1cc(Cl)ccc1C#N]

120 mg (333 µmol) of 2-[4-(5-chloro-2-cyanophenyl)-5-methoxy-2-oxopyridin-1(2H)-yl]-3-methylbutanoic acid (racemate) and 70.7 mg (366 µmol, 1.1 eq.) of tert-butyl 4-aminobenzoate were reacted according to General Method 5A. The crude product was purified by flash chromatography (silica gel 50, cyclohexane/ethyl acetate mixtures). Yield: 134 mg (75% of theory)

LC/MS [Method 1]: $R_t$=1.29 min; MS (ESIpos): m/z=536 (M+H)$^+$, $^1$H-NMR (400 MHz, DMSO-d$_6$): δ [ppm]=11.0 (s, 1H), 8.00 (d, 1H), 7.88 (d, 2H), 7.78 (d, 2H), 7.76 (d, 1H), 7.73 (dd, 1H), 7.63 (s, 1H), 6.56 (s, 1H), 5.52 (d, 1H), 3.69 (s, 3H), 2.61-2.55 (m, 1H), 1.54 (s, 9H), 1.08 (d, 3H), 0.82 (d, 3H).

Example 67.2A

Methyl 4-({2-[4-(5-chloro-2-cyanophenyl)-5-methoxy-2-oxopyridin-1(2H)-yl]-3-methylbutanoyl}amino)-2-methylbenzoate (racemate)

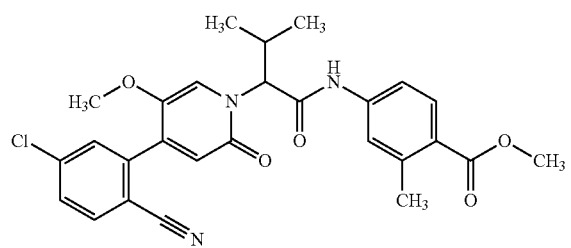 [SMILES: COC(=O)c1ccc(NC(=O)C(C(C)C)n2cc(OC)c(-c3cc(Cl)ccc3C#N)cc2=O)cc1C]

120 mg (333 µmol) of 2-[4-(5-chloro-2-cyanophenyl)-5-methoxy-2-oxopyridin-1(2H)-yl]-3-methylbutanoic acid (racemate) and 60.4 mg (366 µmol, 1.1 eq.) of methyl 4-amino-2-methylbenzoate were reacted according to General Method 5A. The crude product was purified by flash chromatography (silica gel 50, cyclohexane/ethyl acetate mixtures). Yield: 155 mg (88% of theory)

LC/MS [Method 1]: $R_t$=1.17 min; MS (ESIpos): m/z=508 (M+H)$^+$, $^1$H-NMR (400 MHz, DMSO-d$_6$): δ [ppm]=10.9 (s, 1H), 8.00 (d, 1H), 7.85 (d, 1H), 7.77-7.71 (m, 2H), 7.66-7.59 (m, 3H), 6.56 (s, 1H), 5.51 (d, 1H), 3.80 (s, 3H), 3.69 (s, 3H), 2.69 (s, 3H), 1.08 (d, 3H), 0.82 (d, 3H).

Example 67.3A

Ethyl 6-({2-[4-(5-chloro-2-cyanophenyl)-5-methoxy-2-oxopyridin-1(2H)-yl]-3-methylbutanoyl}amino)-1H-benzimidazole-2-carboxylate (racemate)

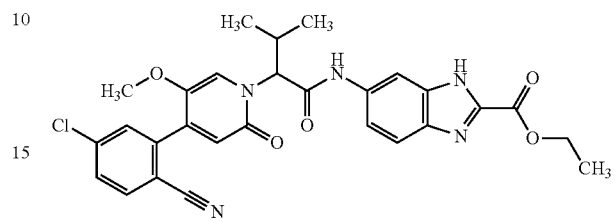

100 mg (277 µmol) of 2-[4-(5-chloro-2-cyanophenyl)-5-methoxy-2-oxopyridin-1(2H)-yl]-3-methylbutanoic acid (racemate), 57 mg (277 µmol, 1.0 eq.) of ethyl 6-amino-1H-benzimidazole-2-carboxylate, 39.4 mg (277 µmol) of Oxima and 42.9 µl (277 µmol) of DIC in 5.4 ml of dimethylformamide were reacted according to General Method 5B. The crude product was purified by flash chromatography (silica gel 50, cyclohexane/ethyl acetate mixtures). Yield: 139 mg (91% of theory)

LC/MS [Method 1]: $R_t$=0.99 min; MS (ESIpos): m/z=548 (M+H)$^+$.

Example 68.1A tert-Butyl 6-({2-[4-(5-chloro-2-cyanophenyl)-5-methoxy-2-oxopyridin-1(2H)-yl]-4-methoxybutanoyl}amino)-2-methyl-3-oxo-2,3-dihydro-1H-indazole-1-carboxylate (racemate)

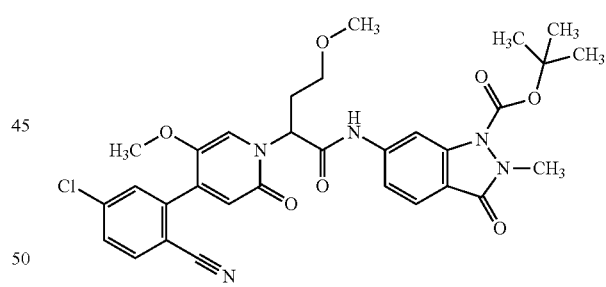

300 mg (796 µmol) of 2-[4-(5-chloro-2-cyanophenyl)-5-methoxy-2-oxopyridin-1(2H)-yl]-4-methoxybutanoic acid (racemate) and 231 mg (876 µmol, 1.1 eq.) of tert-butyl 6-amino-2-methyl-3-oxo-2,3-dihydro-1H-indazole-1-carboxylate were reacted according to General Method 5A. The crude product was purified by flash chromatography (silica gel 50, cyclohexane/ethyl acetate mixtures). Yield: 229 mg (46% of theory)

LC/MS [Method 1]: $R_t$=1.09 min; MS (ESIpos): m/z=622 (M+H)$^+$, $^1$H-NMR (400 MHz, DMSO-d$_6$): δ [ppm]=10.9 (s, 1H), 8.53 (d, 1H), 8.01-7.98 (m, 1H), 7.75-7.71 (m, 3H), 7.53 (s, 1H), 7.49 (dd, 1H), 6.53 (s, 1H), 5.79 (dd, 1H), 3.69 (s, 3H), 3.46 (s, 3H), 3.44-3.38 (m, 1H), 3.31 (s, 1H), 3.21 (s, 3H), 2.48-2.36 (m, 2H), 1.60 (s, 9H).

Example 68.2A

Ethyl 6-({2-[4-(5-chloro-2-cyanophenyl)-5-methoxy-2-oxopyridin-1(2H)-yl]-4-methoxybutanoyl}amino)-1H-indole-2-carboxylate (racemate)

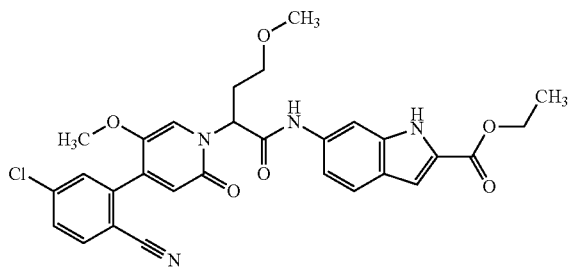 [SMILES: CCOC(=O)c1cc2ccc(NC(=O)C(CCOC)n3cc(OC)c(-c4cc(Cl)ccc4C#N)cc3=O)cc2[nH]1]

100 mg (265 µmol) of 2-[4-(5-chloro-2-cyanophenyl)-5-methoxy-2-oxopyridin-1(2H)-yl]-4-methoxybutanoic acid (racemate), 54.2 mg (265 µmol, 1.0 eq.) of ethyl 6-amino-1H-indole-2-carboxylate, 37.7 mg (265 µmol) of Oxima and 41.4 µl (265 µmol) of DIC in 5.5 ml of dimethylformamide were reacted according to General Method 5B. The crude product was purified by preparative HPLC (column: Chromatorex 125 mm×30 mm, 10 µm, mobile phase: water/0.1% formic acid and acetonitrile/0.1% formic acid, gradient 10% acetonitrile to 90% acetonitrile). Yield: 85 mg (54% of theory)

LC/MS [Method 1]: $R_t$=1.07 min; MS (ESIpos): m/z=563 (M+H)$^+$, $^1$H-NMR (400 MHz, DMSO-d$_6$): δ [ppm]=11.8 (d, 1H), 10.5 (s, 1H), 8.04 (br. s, 1H), 8.00 (d, 1H), 7.76-7.72 (m, 2H), 7.58 (d, 1H), 7.56 (s, 1H), 7.23 (dd, 1H), 7.11-7.08 (m, 1H), 6.53 (s, 1H), 5.80 (dd, 1H), 4.32 (q, 2H), 3.70 (s, 3H), 3.43-3.26 (m, 2H), 3.22 (s, 3H), 2.47-2.36 (m, 2H), 1.33 (t, 3H).

Example 68.3A

Ethyl 6-({2-[4-(5-chloro-2-cyanophenyl)-5-methoxy-2-oxopyridin-1(2H)-yl]-4-methoxybutanoyl}amino)-5-methoxy-1H-indole-2-carboxylate (racemate)

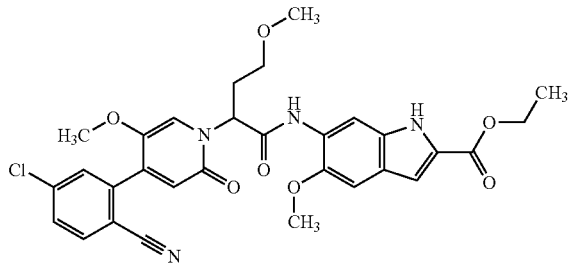

150 mg (398 µmol) of 2-[4-(5-chloro-2-cyanophenyl)-5-methoxy-2-oxopyridin-1(2H)-yl]-4-methoxybutanoic acid (racemate) and 103 mg (438 µmol, 1.1 eq.) of ethyl 6-amino-5-methoxy-1H-indole-2-carboxylate were reacted according to General Method 5A. The crude product was purified by preparative HPLC (column: Chromatorex 125 mm×30 mm, 10 µm, mobile phase: water and acetonitrile, gradient 10% acetonitrile to 90% acetonitrile). Yield: 87 mg (36% of theory)

LC/MS [Method 1]: $R_t$=1.13 min; MS (ESIpos): m/z=593 (M+H)$^+$, $^1$H-NMR (500 MHz, DMSO-d$_6$): δ [ppm]=11.7 (d, 1H), 9.43 (s, 1H), 8.26 (s, 1H), 8.00 (d, 1H), 7.76-7.72 (m, 2H), 7.51 (s, 1H), 7.20 (s, 1H), 7.04-7.03 (m, 1H), 6.58 (s, 1H), 5.79 (dd, 1H), 4.32 (q, 2H), 3.86 (s, 3H), 3.69 (s, 3H), 3.45-3.34 (m, 2H), 3.25 (s, 3H), 2.57-2.46 (m, 1H), 2.43-2.34 (m, 1H), 1.33 (t, 3H).

Example 69.1A tert-Butyl 2-[5-chloro-4-(5-chloro-2-cyanophenyl)-2-oxopyridin-1(2H)-yl]-4-methylpentanoate (racemate)

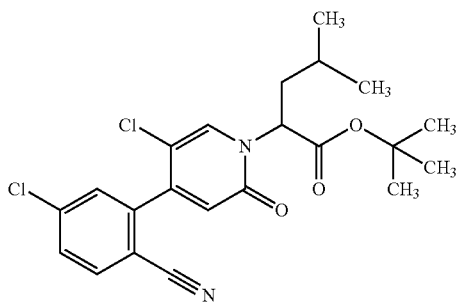 [SMILES: CC(C)CC(C(=O)OC(C)(C)C)n1cc(Cl)c(-c2cc(Cl)ccc2C#N)cc1=O]

416 mg (1.00 mmol) of tert-butyl [5-chloro-4-(5-chloro-2-cyanophenyl)-2-oxopyridin-1(2H)-yl]acetate in the presence of 0.95 ml (0.95 mmol, 1.2 eq.) of bis(trimethylsilyl) lithium amide (1M in THF) and 326 mg (1.58 mmol, 2.0 eq.) of isobutyl trifluoromethanesulphonate were reacted according to General Method 7B. Yield: 139 mg (purity 85%, 34% of theory)

LC/MS [Method 1]: $R_t$=1.27 min; MS (ESIpos): m/z=435 (M+H)$^+$.

Example 69.1B

2-[5-Chloro-4-(5-chloro-2-cyanophenyl)-2-oxopyridin-1(2H)-yl]-4-methylpentanoic acid (racemate)

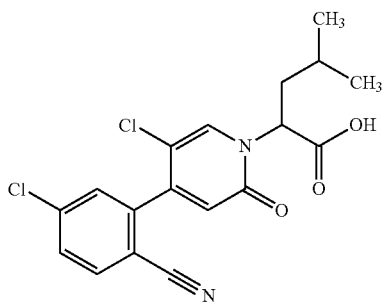 [SMILES: CC(C)CC(C(=O)O)n1cc(Cl)c(-c2cc(Cl)ccc2C#N)cc1=O]

139 mg (purity 85%, 0.27 mmol) of tert-butyl 2-[5-chloro-4-(5-chloro-2-cyanophenyl)-2-oxopyridin-1(2H)-yl]-4-methylpentanoate (racemate) were hydrolysed with TFA according to General Method 6A. Yield: 87 mg (84% of theory)

LC/MS [Method 1]: $R_t$=1.01 min; MS (ESIpos): m/z=379 (M+H)$^+$.

Example 69.1C tert-Butyl 4-({2-[5-chloro-4-(5-chloro-2-cyanophenyl)-2-oxopyridin-1(2H)-yl]-4-methylpentanoyl}amino)benzoate (racemate)

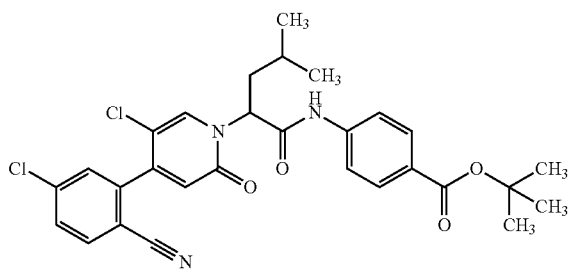 [SMILES: CC(C)CC(C(=O)Nc1ccc(C(=O)OC(C)(C)C)cc1)n1cc(Cl)c(-c2cc(Cl)ccc2C#N)cc1=O]

87 mg (0.23 mmol) of 2-[5-chloro-4-(5-chloro-2-cyanophenyl)-2-oxopyridin-1(2H)-yl]-4-methylpentanoic acid (racemate) and 49 mg (0.25 mmol, 1.1 eq.) of tert-butyl 4-aminobenzoate were reacted according to General Method 5A. Yield: 45 mg (35% of theory)

LC/MS [Method 1]: $R_t$=1.40 min; MS (ESIpos): m/z=554 (M+H)$^+$.

Example 70.1A tert-Butyl 2-[5-chloro-4-(5-chloro-2-cyanophenyl)-2-oxopyridin-1(2H)-yl]-4-(trifluoromethoxy)butanoate (racemate)

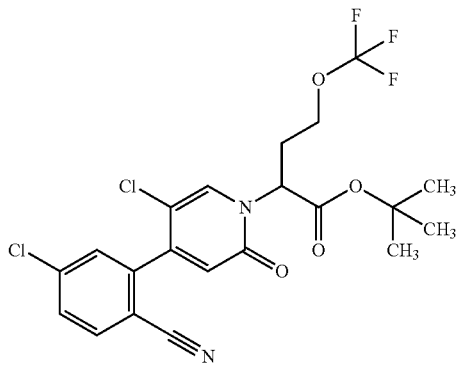 [SMILES: CC(C)(C)OC(=O)C(CCOC(F)(F)F)n1cc(Cl)c(-c2cc(Cl)ccc2C#N)cc1=O]

300 mg (0.79 mmol) of tert-butyl [5-chloro-4-(5-chloro-2-cyanophenyl)-2-oxopyridin-1(2H)-yl]acetate in the presence of 0.95 ml (0.95 mmol, 1.2 eq.) of bis(trimethylsilyl)lithium amide (1M in THF) and 207 mg (0.79 mmol, 1.0 eq.) of 2-(trifluoromethoxy)ethyl trifluoromethanesulphonate were reacted according to General Method 7B. Yield: 244 mg (purity 92%, 58% of theory)

LC/MS [Method 8]: $R_t$=1.53 min; MS (ESIpos): m/z=435 (M+H—COO-tert-butyl)$^+$.

Example 70.1B

2-[5-Chloro-4-(5-chloro-2-cyanophenyl)-2-oxopyridin-1(2H)-yl]-4-(trifluoromethoxy)butanoic acid (racemate)

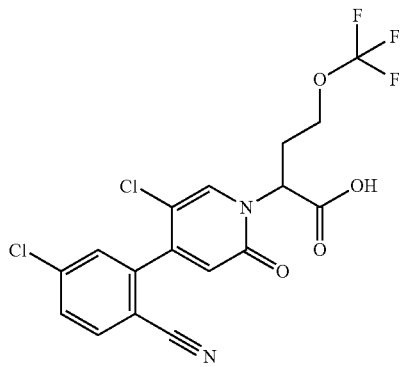 [SMILES: N#Cc1ccc(Cl)cc1-c1cc(=O)n(C(CCOC(F)(F)F)C(=O)O)cc1Cl]

244 mg (purity 92%, 0.46 mmol) of tert-butyl 2-[5-chloro-4-(5-chloro-2-cyanophenyl)-2-oxopyridin-1(2H)-yl]-4-(trifluoromethoxy)butanoate (racemate) were hydrolysed with TFA according to General Method 6A. Yield: 237 mg (purity 84%, quant.)

LC/MS [Method 1]: $R_t$=1.00 min; MS (ESIpos): m/z=435 (M+H)$^+$.

Example 70.1C tert-Butyl 4-({2-[5-chloro-4-(5-chloro-2-cyanophenyl)-2-oxopyridin-1(2H)-yl]-4-(trifluoromethoxy)butanoyl}amino)benzoate (racemate)

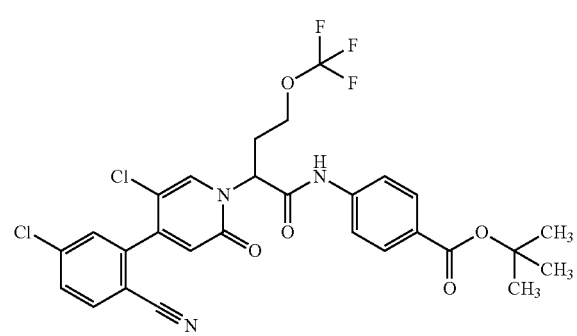 [SMILES: CC(C)(C)OC(=O)c1ccc(NC(=O)C(CCOC(F)(F)F)n2cc(Cl)c(-c3cc(Cl)ccc3C#N)cc2=O)cc1]

237 mg (purity 84%, 0.46 mmol) of 2-[5-chloro-4-(5-chloro-2-cyanophenyl)-2-oxopyridin-1(2H)-yl]-4-(trifluoromethoxy)butanoic acid (racemate) and 97 mg (0.50 mmol, 1.1 eq.) of tert-butyl 4-aminobenzoate were reacted according to General Method 5A. Yield: 142 mg (purity 81%, 41% of theory)

LC/MS [Method 1]: $R_t$=1.35 min; MS (ESIneg): m/z=608 (M−H)$^-$.

Example 71.1A tert-Butyl {4-[5-chloro-2-(difluoromethoxy)phenyl]-5-methoxy-2-oxopyridin-1(2H)-yl}acetate

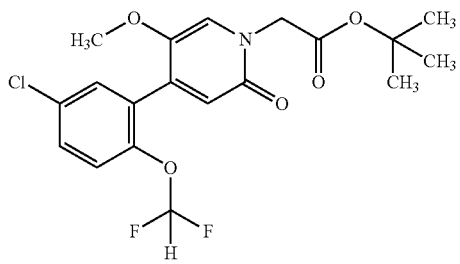 [SMILES: COc1cn(CC(=O)OC(C)(C)C)c(=O)cc1-c1cc(Cl)ccc1OC(F)F]

5.43 g (purity 80%, 14.4 mmol) of 4-[5-chloro-2-(difluoromethoxy)phenyl]-5-methoxypyridin-2(1H)-one and 1.2 eq. of tert-butyl bromoacetate in the presence of 1.5 eq. of potassium carbonate were reacted according to General Method 4B at 100° C. Yield: 3.64 g (61% of theory)

LC/MS [Method 1]: $R_t$=1.05 min; MS (ESIpos): m/z=416 (M+H)$^+$, $^1$H-NMR (400 MHz, DMSO-d$_6$): δ [ppm]=7.57 (dd, 1H), 7.45 (d, 1H), 7.43 (s, 1H), 7.30 (d, 1H), 7.13 (t, 1H), 6.35 (s, 1H), 4.58 (s, 2H), 3.56 (s, 3H), 1.44 (s, 9H).

Example 71.1B tert-Butyl 2-{4-[5-chloro-2-(difluoromethoxy)phenyl]-5-methoxy-2-oxopyridin-1(2H)-yl}-4-methylpentanoate (racemate)

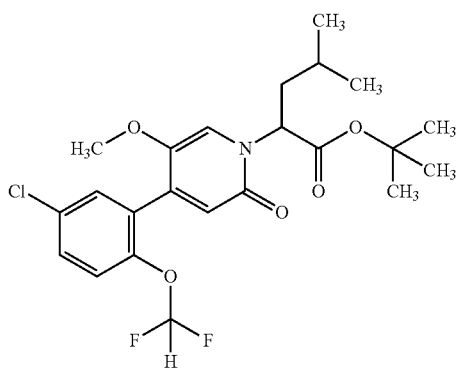 [SMILES: COc1cn(C(CC(C)C)C(=O)OC(C)(C)C)c(=O)cc1-c1cc(Cl)ccc1OC(F)F]

416 mg (1.00 mmol) of tert-butyl {4-[5-chloro-2-(difluoromethoxy)phenyl]-5-methoxy-2-oxopyridin-1(2H)-yl}acetate in the presence of 1.20 ml (1.20 mmol, 1.2 eq.) of bis(trimethylsilyl)lithium amide (1M in THF) and 309 mg (1.50 mmol, 1.5 eq.) of isobutyl trifluoromethanesulphonate were reacted according to General Method 7B. Yield: 370 mg (75% of theory)

LC/MS [Method 1]: $R_t$=1.23 min; MS (ESIpos): m/z=472 (M+H)$^+$, $^1$H-NMR (400 MHz, DMSO-d$_6$): δ [ppm]=7.57 (dd, 1H), 7.49 (d, 1H), 7.29 (d, 1H), 7.25 (s, 1H), 7.10 (t, 1H), 6.36 (s, 1H), 5.29 (dd, 1H), 3.59 (s, 3H), 2.19-2.08 (m, 1H), 1.91-1.81 (m 1H), 1.43-1.33 (m, 1H), 1.40 (s, 9H), 0.9 (dd, 6H).

Example 71.1C

2-{4-[5-Chloro-2-(difluoromethoxy)phenyl]-5-methoxy-2-oxopyridine-1(2H)-yl}-4-methylpentanoic acid (racemate)

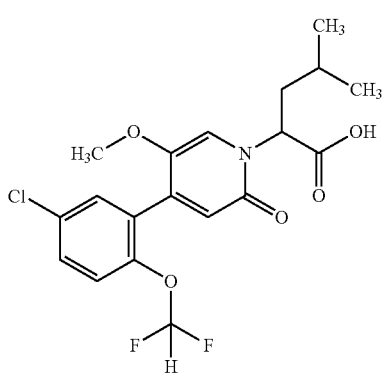 [SMILES: COc1cn(C(CC(C)C)C(=O)O)c(=O)cc1-c1cc(Cl)ccc1OC(F)F]

370 mg (0.75 mmol) of tert-butyl 2-{4-[5-chloro-2-(difluoromethoxy)phenyl]-5-methoxy-2-oxopyridin-1(2H)-yl}-4-methylpentanoate (racemate) were hydrolysed with TFA according to General Method 6A. Yield: 319 mg (purity 91%, 93% of theory)

LC/MS [Method 8]: $R_t$=1.27 min; MS (ESIpos): m/z=416 (M+H)$^+$.

Example 71.1D tert-Butyl 4-[(2-{4-[5-chloro-2-(difluoromethoxy)phenyl]-5-methoxy-2-oxopyridin-1(2H)-yl}-4-methylpentanoyl)amino]benzoate (racemate)

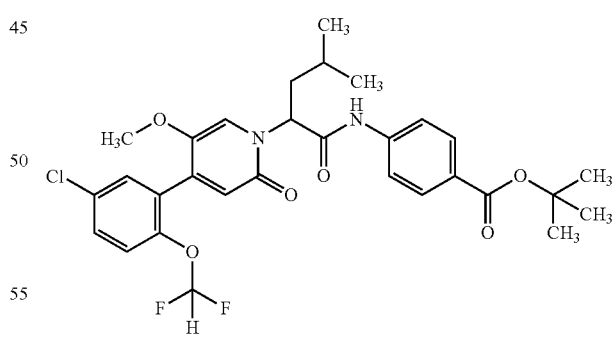

319 mg (purity 91%, 0.70 mmol) of 2-{4-[5-chloro-2-(difluoromethoxy)phenyl]-5-methoxy-2-oxopyridin-1(2H)-yl}-4-methylpentanoic acid (racemate) and 148 mg (0.77 mmol, 1.1 eq.) of tert-butyl 4-aminobenzoate were reacted according to General Method 5A. Yield: 263 mg (purity 88%, 56% of theory)

LC/MS [Method 1]: $R_t$=1.37 min; MS (ESIpos): m/z=591 (M+H)$^+$.

Example 72.1A tert-Butyl 2-{4-[5-chloro-2-(difluoromethoxy)phenyl]-5-methoxy-2-oxopyridin-1(2H)-yl}-4-methoxybutanoate (racemate)

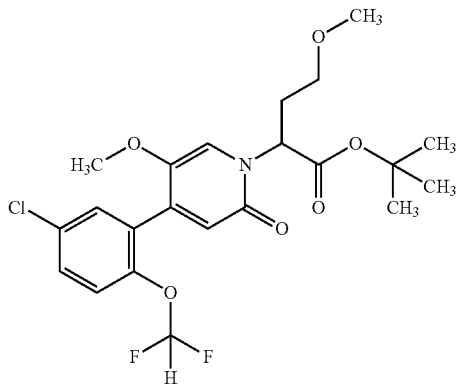 [SMILES: COCCC(C(=O)OC(C)(C)C)n1cc(OC)c(-c2cc(Cl)ccc2OC(F)F)cc1=O]

312 mg (0.75 mmol) of tert-butyl {4-[5-chloro-2-(difluoromethoxy)phenyl]-5-methoxy-2-oxopyridin-1(2H)-yl}acetate in the presence of 0.90 ml (0.90 mmol, 1.2 eq.) of bis(trimethylsilyl)lithium amide (1M in THF) and 312 mg (1.50 mmol, 1.5 eq.) of 2-methoxyethyl trifluoromethanesulphonate were reacted according to General Method 7B. Yield: 201 mg (purity 91%, 51% of theory)

LC/MS [Method 8]: $R_t$=1.40 min; MS (ESIpos): m/z=418 (M+H—COO-tert-butyl)$^+$.

Example 72.1B

2-{4-[5-Chloro-2-(difluoromethoxy)phenyl]-5-methoxy-2-oxopyridin-1(2H)-yl}-4-methoxybutanoic acid (racemate)

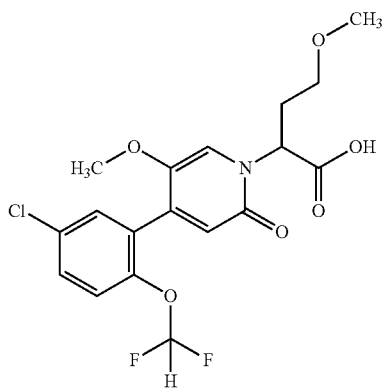 [SMILES: COCCC(C(=O)O)n1cc(OC)c(-c2cc(Cl)ccc2OC(F)F)cc1=O]

201 mg (purity 91%, 0.39 mmol) of tert-butyl 2-{4-[5-chloro-2-(difluoromethoxy)phenyl]-5-methoxy-2-oxopyridin-1(2H)-yl}-4-methoxybutanoate (racemate) were hydrolysed with TFA according to General Method 6A. Yield: 212 mg (purity 82%, quant.)

LC/MS [Method 8]: $R_t$=1.11 min; MS (ESIpos): m/z=418 (M+H)$^+$.

Example 72.1C tert-Butyl 4-[(2-{4-[5-chloro-2-(difluoromethoxy)phenyl]-5-methoxy-2-oxopyridin-1(2H)-yl}-4-methoxybutanoyl)amino]benzoate (racemate)

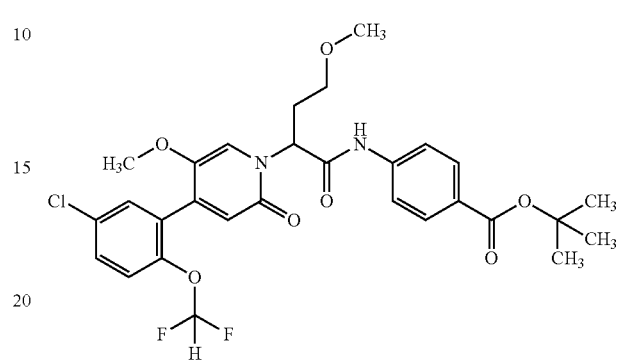

90 mg (purity 77%, 0.17 mmol) of 2-{4-[5-chloro-2-(difluoromethoxy)phenyl]-5-methoxy-2-oxopyridin-1(2H)-yl}-4-methoxybutanoic acid (racemate) and 35 mg (0.18 mmol, 1.1 eq.) of tert-butyl 4-aminobenzoate were reacted according to General Method 5A. Yield: 66 mg (67% of theory)

LC/MS [Method 8]: $R_t$=1.52 min; MS (ESIneg): m/z=591 (M–H)$^-$.

Example 72.2A tert-Butyl 6-[(2-{4-[5-chloro-2-(difluoromethoxy)phenyl]-5-methoxy-2-oxopyridin-1(2H)-yl}-4-methoxybutanoyl)amino]-2-methyl-3-oxo-2,3-dihydro-1H-indazole-1-carboxylate (racemate)

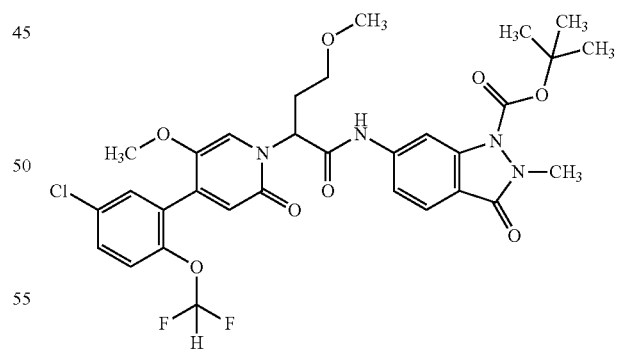

113 mg (purity 82%, 0.26 mmol) of 2-{4-[5-chloro-2-(difluoromethoxy)phenyl]-5-methoxy-2-oxopyridin-1(2H)-yl}-4-methoxybutanoic acid (racemate) and 79 mg (0.29 mmol, 1.1 eq.) of tert-butyl 6-amino-2-methyl-3-oxo-2,3-dihydro-1H-indazole-1-carboxylate were reacted according to General Method 5A. Yield: 132 mg (73% of theory)

LC/MS [Method 1]: $R_t$=1.15 min; MS (ESIpos): m/z=663 (M+H)$^+$.

Example 73.1A tert-Butyl 2-{4-[5-chloro-2-(difluoromethoxy)phenyl]-5-methoxy-2-oxopyridin-1(2H)-yl}-4-(trifluoromethoxy)butanoate (racemate)

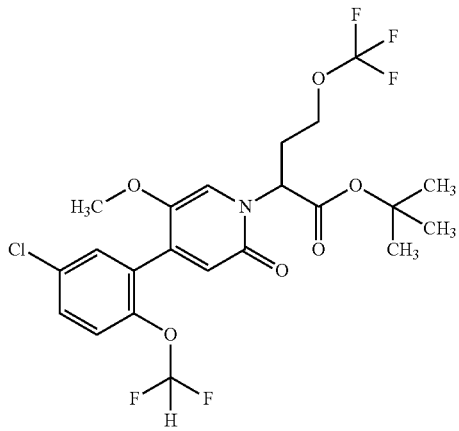 [SMILES: COc1cn(C(CCOC(F)(F)F)C(=O)OC(C)(C)C)c(=O)cc1-c1cc(Cl)ccc1OC(F)F]

416 mg (1.00 mmol) of tert-butyl {4-[5-chloro-2-(difluoromethoxy)phenyl]-5-methoxy-2-oxopyridin-1(2H)-yl}acetate in the presence of 1.20 ml (1.20 mmol, 1.2 eq.) of bis(trimethylsilyl)lithium amide (1M in THF) and 393 mg (1.50 mmol, 1.5 eq.) of 2-(trifluoromethoxy)ethyl trifluoromethanesulphonate were reacted according to General Method 7B. Yield: 327 mg (62% of theory)

LC/MS [Method 1]: $R_t$=1.23 min; MS (ESIpos): m/z=528 (M+H)$^+$, $^1$H-NMR (400 MHz, DMSO-d$_6$): δ [ppm]=7.57 (dd, 1H), 7.45 (d, 1H), 7.32 (s, 1H), 7.30 (d, 1H), 7.09 (t, 1H), 6.37 (s, 1H), 5.11 (dd, 1H), 4.21-4.13 (m, 1H), 4.05-3.95 (m, 1H), 3.57 (s, 3H), 1.40 (s, 9H).

Example 73.1B

2-{4-[5-chloro-2-(difluoromethoxy)phenyl]-5-methoxy-2-oxopyridin-1(2H)-yl}-4-(trifluoromethoxy)butanoic acid (racemate)

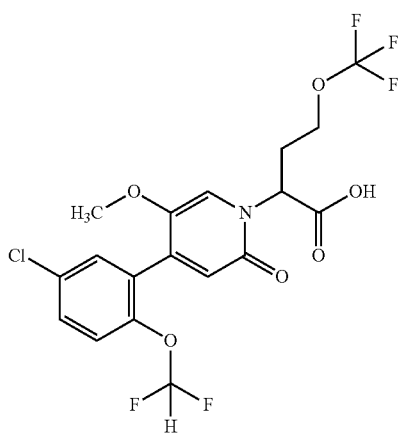 [SMILES: COc1cn(C(CCOC(F)(F)F)C(=O)O)c(=O)cc1-c1cc(Cl)ccc1OC(F)F]

327 mg (0.62 mmol) of tert-butyl 2-{4-[5-chloro-2-(difluoromethoxy)phenyl]-5-methoxy-2-oxopyridin-1(2H)-yl}-4-(trifluoromethoxy)butanoate (racemate) were hydrolysed with TFA according to General Method 6A. Yield: 290 mg (purity 93%, 92% of theory)

LC/MS [Method 1]: $R_t$=0.99 min; MS (ESIpos): m/z=472 (M+H)$^+$.

Example 73.1C tert-Butyl 4-{[2-{4-[5-chloro-2-(difluoromethoxy)phenyl]-5-methoxy-2-oxopyridin-1(2H)-yl}-4-(trifluoromethoxy)butanoyl]amino}benzoate (racemate)

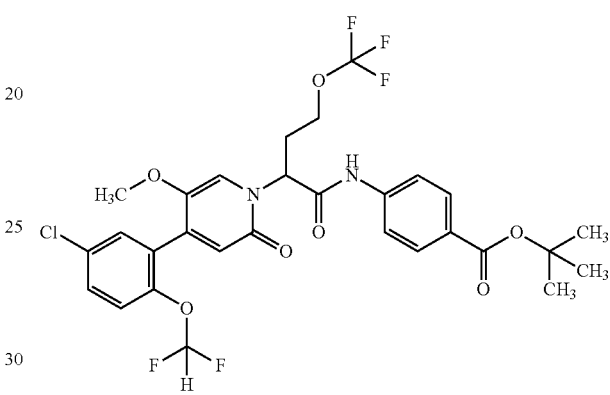

290 mg (purity 93%, 0.57 mmol) of 2-{4-[5-chloro-2-(difluoromethoxy)phenyl]-5-methoxy-2-oxopyridin-1(2H)-yl}-4-(trifluoromethoxy)butanoic acid (racemate) and 122 mg (0.63 mmol, 1.1 eq.) of tert-butyl 4-aminobenzoate were reacted according to General Method 5A. Yield: 195 mg (50% of theory)

LC/MS [Method 1]: $R_t$=1.33 min; MS (ESIpos): m/z=647 (M+H)$^+$.

Example 74.1A (2R)-Tetrahydro-2H-pyran-2-ylmethyl trifluoromethanesulphonate

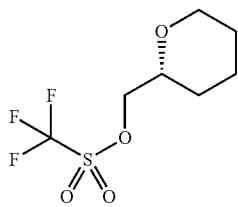 [SMILES: O=S(=O)(OC[C@H]1CCCCO1)C(F)(F)F]

568 mg (purity 69%, 3.48 mmol) of (2R)-tetrahydro-2H-pyran-2-ylmethanol and 0.71 ml (4.18 mmol, 1.2 eq.) of trifluoromethanesulphonic anhydride in the presence of 0.58 ml (4.18 mmol, 1.2 eq.) of triethylamine were reacted according to General Method 8A. The crude product was reacted in the next step without further purification.

Example 74.1B tert-Butyl 2-{4-[5-chloro-2-(difluoromethoxy)phenyl]-5-methoxy-2-oxopyridin-1(2H)-yl}-3-[(2R)-tetrahydro-2H-pyran-2-yl]propanoate (mixture of enantiomerically pure diastereomers 1 and 2)

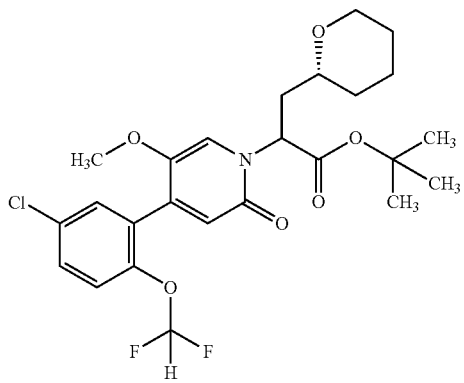 [SMILES: COc1cn(C(C[C@H]2CCCCO2)C(=O)OC(C)(C)C)c(=O)cc1-c1cc(Cl)ccc1OC(F)F]

333 mg (0.80 mmol) of tert-butyl {4-[5-chloro-2-(difluoromethoxy)phenyl]-5-methoxy-2-oxopyridin-1(2H)-yl}acetate in the presence of 0.96 ml (0.96 mmol, 1.2 eq.) of bis(trimethylsilyl)lithium amide (1M in THF) and 426 mg (purity 70%, 1.20 mmol, 1.5 eq.) of (2R)-tetrahydro-2H-pyran-2-ylmethyl trifluoromethanesulphonate were reacted according to General Method 7B. Yield: 85 mg (purity 94%, 19% of theory)

LC/MS [Method 1]: $R_t$=1.25 min; MS (ESIpos): m/z=514 (M+H)⁺.

Example 74.1C

2-{4-[5-Chloro-2-(difluoromethoxy)phenyl]-5-methoxy-2-oxopyridin-1(2H)-yl}-3-[(2R)-tetrahydro-2H-pyran-2-yl]propanoic acid (mixture of enantiomerically pure diastereomers 1 and 2)

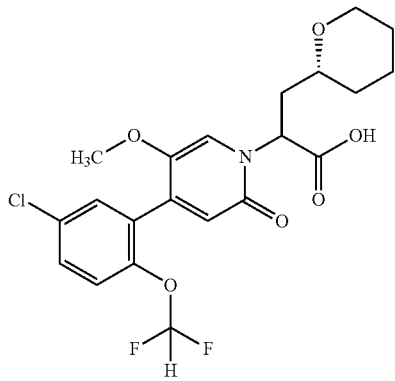 [SMILES: COc1cn(C(C[C@H]2CCCCO2)C(=O)O)c(=O)cc1-c1cc(Cl)ccc1OC(F)F]

85 mg (purity 94%, 0.16 mmol) of tert-butyl 2-{4-[5-chloro-2-(difluoromethoxy)phenyl]-5-methoxy-2-oxopyridin-1(2H)-yl}-3-[(2R)-tetrahydro-2H-pyran-2-yl]propanoate (mixture of enantiomerically pure diastereomers 1 and 2) were hydrolysed with TFA according to General Method 6A. Yield: 83 mg (purity 85%, 99% of theory)

LC/MS [Method 1]: $R_t$=0.98 min; MS (ESIpos): m/z=458 (M+H)⁺.

Example 74.1D tert-Butyl 4-[(2-{4-[5-chloro-2-(difluoromethoxy)phenyl]-5-methoxy-2-oxopyridin-1(2H)-yl}-3-[(2R)-tetrahydro-2H-pyran-2-yl]propanoyl)amino]benzoate (mixture of enantiomerically pure diastereomers 1 and 2)

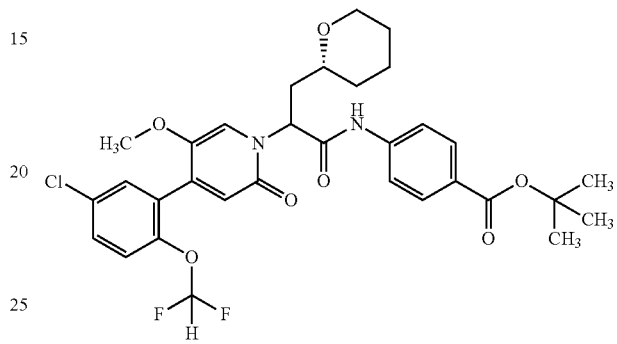

82 mg (purity 85%, 0.15 mmol) of 2-{4-[5-chloro-2-(difluoromethoxy)phenyl]-5-methoxy-2-oxopyridin-1(2H)-yl}-3-[(2R)-tetrahydro-2H-pyran-2-yl]propanoic acid (mixture of enantiomerically pure diastereomers 1 and 2) and 32 mg (0.17 mmol, 1.1 eq.) of tert-butyl 4-aminobenzoate were reacted according to General Method 5A. Yield: 67 mg (70% of theory)

LC/MS [Method 1]: diastereomer 1: $R_t$=1.35 min; MS (ESIpos): m/z=633 (M+H)⁺; diastereomer 2: $R_t$=1.36 min; MS (ESIpos): m/z=633 (M+H)⁺.

Example 75.1A tert-Butyl 4-({2-[4-(5-chloro-2-cyanophenyl)-5-methoxy-2-oxopyridin-1(2H)-yl]butanoyl}amino)-2-fluorobenzoate (racemate)

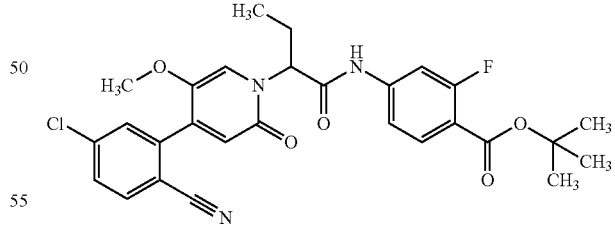

150 mg (0.43 mmol, 1.0 eq.) of 2-[4-(5-chloro-2-cyanophenyl)-5-methoxy-2-oxopyridin-1(2H)-yl]butanoic acid (racemate) and 152 mg (0.65 mmol, 1.5 eq.) of tert-butyl 2-fluoro-4-aminophenylcarboxylate were reacted according to General Method 5C. The crude product was purified by normal phase chromatography (mobile phase: cyclohexane/ethyl acetate 20%-50% mixtures). Yield: 250 mg (purity 93%, 99% of theory)

LC/MS [Method 8]: $R_t$=1.51 min; MS (ESIneg): m/z=538 (M−H)⁻

¹H-NMR (400 MHz, DMSO-d₆): δ [ppm]=10.95 (s, 1H), 8.02-7.97 (m, 1H), 7.81 (t, 1H), 7.75-7.66 (m, 3H), 7.47 (s, 1H), 7.42 (dd, 1H), 6.54 (s, 1H), 5.59 (dd, 1H), 3.69 (s, 3H), 2.25-2.13 (m, 2H), 1.53 (s, 9H), 0.90 (t, 3H).

Example 75.2A tert-Butyl 4-({2-[4-(5-chloro-2-cyanophenyl)-5-methoxy-2-oxopyridin-1(2H)-yl]butanoyl}amino)-3-fluorobenzoate (racemate)

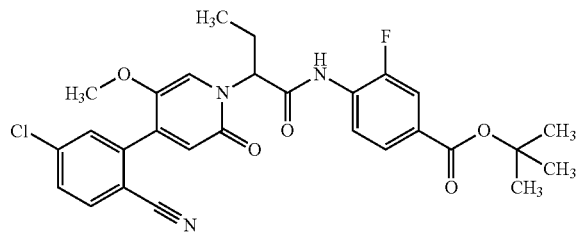 [SMILES: CCC(C(=O)Nc1ccc(C(=O)OC(C)(C)C)cc1F)n1cc(OC)c(-c2cc(Cl)ccc2C#N)cc1=O]

100 mg (0.29 mmol, 1.0 eq.) of 2-[4-(5-chloro-2-cyanophenyl)-5-methoxy-2-oxopyridin-1(2H)-yl]butanoic acid (racemate) and 91 mg (0.43 mmol, 1.5 eq.) of tert-butyl 4-amino-3-fluorobenzoate were reacted according to General Method 5C. The crude product was purified by normal phase chromatography (mobile phase: cyclohexane/ethyl acetate 35%-50% mixtures). Yield: 126 mg (81% of theory)

LC/MS [Method 1]: $R_t$=1.25 min; MS (ESIpos): m/z=540 (M+H)⁺,

¹H-NMR (400 MHz, DMSO-d₆): δ [ppm]=10.56 (s, 1H), 8.15-8.08 (m, 1H), 8.02-7.97 (m, 1H), 7.76-7.68 (m, 4H), 7.46 (s, 1H), 6.54 (s, 1H), 5.79 (dd, 1H), 3.68 (s, 3H), 2.25-2.15 (m, 2H), 1.54 (s, 9H), 0.91 (t, 3H).

Example 75.3A tert-Butyl 4-({2-[4-(5-chloro-2-cyanophenyl)-5-methoxy-2-oxopyridin-1(2H)-yl]butanoyl}amino)-2,5-difluorobenzoate (racemate)

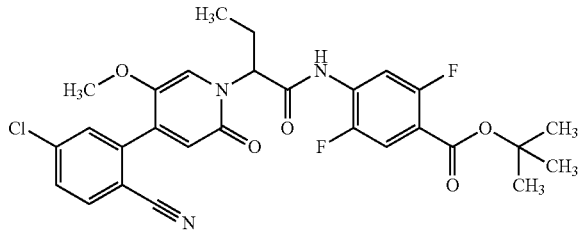 [SMILES: CCC(C(=O)Nc1cc(F)c(C(=O)OC(C)(C)C)cc1F)n1cc(OC)c(-c2cc(Cl)ccc2C#N)cc1=O]

150 mg (0.43 mmol) of 2-[4-(5-chloro-2-cyanophenyl)-5-methoxy-2-oxopyridin-1(2H)-yl]butanoic acid (racemate) and 154 mg (0.61 mmol, 1.4 eq.) of tert-butyl 4-amino-2,5-difluorobenzoate were reacted according to General Method 5B. The crude product was purified by normal phase chromatography (mobile phase: cyclohexane/ethyl acetate 20-40% mixtures). Yield: 180 mg (71% of theory)

LC/MS [Method 1]: $R_t$=1.31 min; MS (ESIpos): m/z=558 (M+H)⁺,

¹H-NMR (400 MHz, DMSO-d₆): δ [ppm]=10.75 (s, 1H), 8.05 (dd, 1H), 8.01-7.97 (m, 1H), 7.76-7.71 (m, 2H), 7.69 (dd, 1H), 7.45 (s, 1H), 6.55 (s, 1H), 5.84-5.78 (m, 1H), 3.69 (s, 3H), 2.24-2.15 (m, 2H), 1.53 (s, 9H), 0.90 (t, 3H).

Example 75.4A

Methyl 4-({2-[4-(5-chloro-2-cyanophenyl)-5-methoxy-2-oxopyridin-1(2H)-yl]butanoyl}amino)-2,3-difluorobenzoate (racemate)

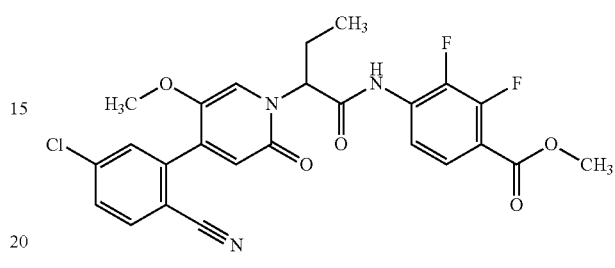

100 mg (0.29 mmol, 1.0 eq.) of 2-[4-(5-chloro-2-cyanophenyl)-5-methoxy-2-oxopyridin-1(2H)-yl]butanoic acid (racemate) and 85 mg (0.43 mmol, 1.5 eq.) of methyl 4-amino-2,3-difluorobenzoate were reacted according to General Method 5C. The crude product was purified by normal phase chromatography (mobile phase: cyclohexane/ethyl acetate 35-50% mixtures). Yield: 113 mg (76% of theory)

LC/MS [1]: $R_t$=1.08 min; MS (ESIpos): m/z=516 (M+H)⁺,

¹H-NMR (400 MHz, DMSO-d₆): δ [ppm]=10.77 (s, 1H), 8.02-7.97 (m, 1H), 7.96-7.89 (m, 1H), 7.76-7.66 (m, 3H), 7.45 (s, 1H), 6.55 (s, 1H), 5.79 (dd, 1H), 3.86 (s, 3H), 3.68 (s, 3H), 2.26-2.12 (m, 2H), 0.91 (t, 3H).

Example 75.5A

Methyl 4-({2-[4-(5-chloro-2-cyanophenyl)-5-methoxy-2-oxopyridin-1(2H)-yl]butanoyl}amino)-2,6-difluorobenzoate (racemate)

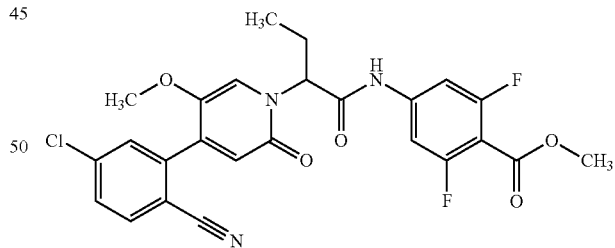

At 60-70° C., 110 μl (0.46 mmol, 4 eq.) of T3P (50% in ethyl acetate) were added dropwise to a solution of 46 mg (0.13 mmol) of 2-[4-(5-chloro-2-cyanophenyl)-5-methoxy-2-oxopyridin-1(2H)-yl]butanoic acid (racemate) and 51 mg (0.27 mmol, 2 eq.) of methyl 4-amino-2,6-difluorobenzoate in 1 ml of pyridine. The reaction mixture was heated to 90° C., stirred at 90° C. for 30 min and cooled to RT, and water and ethyl acetate were added. After phase separation, the aqueous phase was extracted with ethyl acetate. The combined organic phases were washed with saturated aqueous sodium chloride solution, dried (sodium sulphate), filtered and concentrated under reduced pressure. The crude product was purified by normal phase chromatography (mobile phase: cyclohexane/ethyl acetate 10-50% mixtures). Yield: 54 mg (79% of theory)

LC/MS [Method 1]: $R_t$=1.10 min; MS (ESIpos): m/z=516 (M+H)$^+$, $^1$H-NMR (400 MHz, DMSO-d$_6$): δ [ppm]=11.06 (s, 1H), 8.02-7.98 (m, 1H), 7.75-7.72 (m, 2H), 7.50-7.44 (m, 3H), 6.55 (s, 1H), 5.55 (dd, 1H), 3.85 (s, 3H), 3.69 (s, 3H), 2.24-2.14 (m, 2H), 0.90 (t, 3H).

Example 76.1A tert-Butyl 2-[4-(5-chloro-2-cyanophenyl)-5-methoxy-2-oxopyridin-1(2H)-yl]butanoate (racemate)

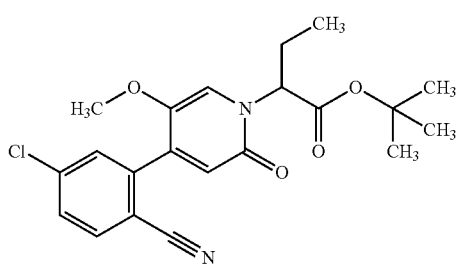 [SMILES: CCC(C(=O)OC(C)(C)C)n1cc(OC)c(-c2cc(Cl)ccc2C#N)cc1=O]

Under argon and at −78° C., 14.0 ml (1.0M in THF, 14.0 mmol, 1.05 eq.) of bis(trimethylsilyl)lithium amide were added dropwise to a solution of 5.0 g (13.3 mmol) of tert-butyl [4-(5-chloro-2-cyanophenyl)-5-methoxy-2-oxopyridin-1(2H)-yl]acetate in 100 ml of tetrahydrofuran, and the mixture was stirred at −78° C. for 15 min. 2.6 g (14.7 mmol, 1.1 eq.) of neat ethyl trifluoromethanesulphonate were then added dropwise. The cooling bath was removed and the reaction mixture was stirred at RT for another 1 h. The reaction mixture was cooled to 0° C., and saturated aqueous ammonium chloride solution was added. After phase separation, the aqueous phase was extracted twice with methyl tert-butyl ether. The combined organic phases were dried (sodium sulphate), filtered and concentrated under reduced pressure. The crude product was then purified by flash chromatography (340 g of silica gel, mobile phase: cyclohexane/ethyl acetate mixtures 8:1, 4:1). The product-containing fractions were combined and concentrated under reduced pressure. The residue was dissolved in hot methyl tert-butyl ether and the solution was left to stand without any cover, and after 10 min the mixture had crystallized almost completely. The crystals were filtered off and washed twice with methyl tert-butyl ether. The combined filtrates were concentrated under reduced pressure and the residue was re-crystallized as described. The two crystal batches were combined and dried under reduced pressure. Yield: 4.2 g (78% of theory)

LC/MS [Method 1]: $R_t$=1.05 min; MS (ESIpos): m/z=403 (M+H)$^+$, $^1$H-NMR (400 MHz, DMSO-d$_6$): δ [ppm]=7.99 (d, 1H), 7.77-7.70 (m, 2H), 7.36 (s, 1H), 6.50 (s, 1H), 5.03 (dd, 1H), 3.64 (s, 3H), 2.19-2.06 (m, 2H), 1.40 (s, 9H), 0.85 (t, 3H).

Example 76.1B

Ethyl 4-({2-[4-(5-chloro-2-cyanophenyl)-5-methoxy-2-oxopyridin-1(2H)-yl]butanoyl}amino)benzoate (racemate)

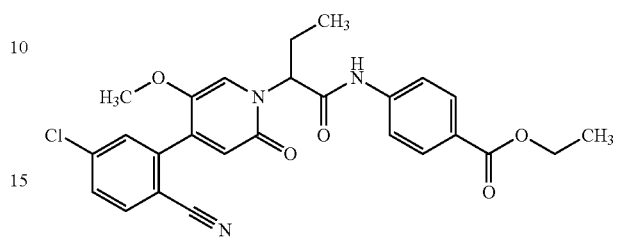

Under argon and at RT, 476 mg (2.9 mmol, 1.0 eq.) of ethyl 4-aminobenzoate and 41 mg (0.29 mmol, 0.1 eq.) of Oxima and then, dropwise, 452 μl (2.9 mmol, 1.0 eq.) of N,N'-diisopropylcarbodiimide (DIC) were added to a solution of 1.0 g (2.9 mmol) of 2-[4-(5-chloro-2-cyanophenyl)-5-methoxy-2-oxopyridin-1(2H)-yl]butanoic acid (racemate) in 10 ml of dimethylformamide. The reaction mixture was stirred at 40-45° C. for 3 h and cooled to RT, methyl tert-butyl ether and water were added and the mixture was stirred vigorously for 10 min, resulting in the formation of a precipitate. The precipitate was filtered off, washed twice with water and methyl tert-butyl ether and dried under reduced pressure (precipitate 1). After phase separation of the combined filtrates, the aqueous phase was extracted once with methyl tert-butyl ether. The combined organic phases were washed once with saturated aqueous sodium chloride solution, dried (sodium sulphate), filtered and concentrated under reduced pressure. The residue was triturated with methyl tert-butyl ether, filtered, washed twice with methyl tert-butyl ether and dried under reduced pressure. This precipitate was stirred in aqueous hydrochloric acid (1N) for 10 min, filtered off, washed twice with water and once with acetonitrile and dried under reduced pressure (precipitate 2). Yield: precipitate 1: 1.12 g (79% of theory), precipitate 2: 127 mg (still contains 1,3-diisopropylurea according to $^1$H NMR)

LC/MS [Method 1]: $R_t$=1.11 min; MS (ESIneg): m/z=492 (M−H)$^-$, $^1$H-NMR (400 MHz, DMSO-d$_6$): δ [ppm]=10.82 (s, 1H), 8.00 (d, 1H), 7.93 (d, 2H), 7.81-7.70 (m, 4H), 7.49 (s, 1H), 6.54 (s, 1H), 5.63 (dd, 1H), 4.29 (q, 2H), 3.69 (s, 3H), 2.26-2.11 (m, 2H), 1.31 (t, 3H), 0.91 (t, 3H).

Example 77.1A (1,1-Dioxidotetrahydro-2H-thiopyran-4-yl)methanol

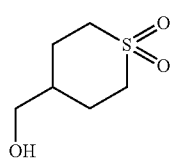

At room temperature, a solution of 500 mg (3.78 mmol) of tetrahydrothiopyran-4-ylmethanol in 10 ml of methanol was added with cooling to a solution of 1.86 g (8.70 mmol) of sodium periodate in 18 ml of water. The mixture was stirred at 60° C. for another 1 h, and methanol was then distilled off under reduced pressure and the resulting precipitate was filtered off with suction. The aqueous phase that remained was extracted twice with 10 ml of diethyl ether, twice with 10 ml of dichloromethane, twice with 10 ml of dichloromethane/methanol (1:1, v/v) and, after addition of 5 ml of water, twice with 10 ml of ethyl acetate. The combined organic phases were dried over sodium sulphate and filtered, and the solvent was removed under reduced pressure. The aqueous phase was extracted four more times with 20 ml of 2-methyltetrahydrofuran. The combined organic phases were dried over sodium sulphate and filtered, and the solvent was removed under reduced pressure. Combined yield: 406 mg (65% of theory)

$^1$H-NMR (400 MHz, CDCl$_3$): δ [ppm]=3.60-3.56 (m, 2H), 3.13-3.06 (m, 2H), 3.02-2.93 (m, 2H), 2.24-2.16 (m, 2H), 1.95-1.83 (m, 2H), 1.80-1.63 (m, 1H), 1.50 (t, 1H).

Example 77.1B (1,1-Dioxidotetrahydro-2H-thiopyran-4-yl)methyl trifluoromethanesulphonate

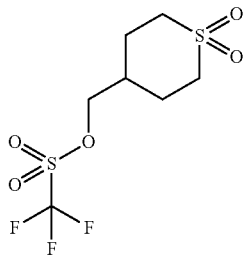 [SMILES: O=S1(=O)CCC(COS(=O)(=O)C(F)(F)F)CC1]

At −78° C., a solution of 380 mg (2.31 mmol) of (1,1-dioxidotetrahydro-2H-thiopyran-4-yl)methanol and 355 µl (2.55 mmol) of triethylamine in 3 ml of dichloromethane was added dropwise to 428 µl (2.55 mmol) of trifluoromethanesulphonic anhydride in 3 ml of dichloromethane such that the internal temperature did not exceed −50° C. The mixture was stirred at −78° C. for another 30 min and spontaneously warmed to RT. The reaction mixture was diluted with 30 ml of methyl tert-butyl ether and washed with saturated aqueous ammonium chloride solution, saturated aqueous sodium chloride solution and saturated aqueous sodium bicarbonate solution, dried over magnesium sulphate, filtered and concentrated at 25° C. and a pressure of ≥100 mbar. Yield: 503 mg (73% of theory)

$^1$H-NMR (400 MHz, CDCl$_3$): δ [ppm]=4.40 (d, 2H), 3.17-3.09 (m, 2H), 3.07-2.98 (m, 2H), 2.25-2.17 (m, 2H), 2.16-1.95 (m, 3H).

Example 77.1C tert-Butyl 2-[4-(5-chloro-2-cyanophenyl)-5-methoxy-2-oxopyridin-1(2H)-yl]-3-(1,1-dioxidotetrahydro-2H-thiopyran-4-yl)propanoate (racemate)

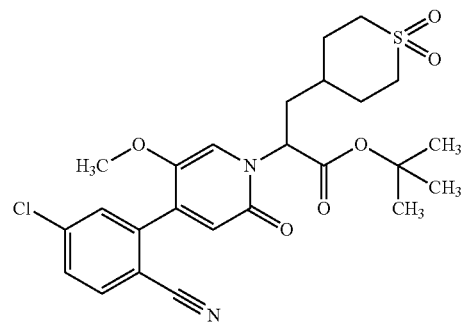 [SMILES: COc1cn(C(CC2CCS(=O)(=O)CC2)C(=O)OC(C)(C)C)c(=O)cc1-c1cc(Cl)ccc1C#N]

421 mg (1.13 mmol) of tert-butyl [4-(5-chloro-2-cyanophenyl)-5-methoxy-2-oxopyridin-1(2H)-yl]acetate, 500 mg (1.69 mmol) of (1,1-dioxidotetrahydro-2H-thiopyran-4-yl) methyl trifluoromethanesulphonate and 1.46 ml (1.46 mmol) of bis(trimethylsilyl)lithium amide (1M in THF) in 15 ml of THF were reacted according to General Method 7B. Aqueous work-up gave the title compound. Yield: 862 mg (purity 91%, quant.)

LC/MS [Method 1]: R$_t$=1.01 min; MS (ESIpos): m/z=521 (M+H)$^+$

Example 77.1D

2-[4-(5-Chloro-2-cyanophenyl)-5-methoxy-2-oxopyridin-1(2H)-yl]-3-(1,1-dioxidotetrahydro-2H-thiopyran-4-yl)propanoic acid (racemate)

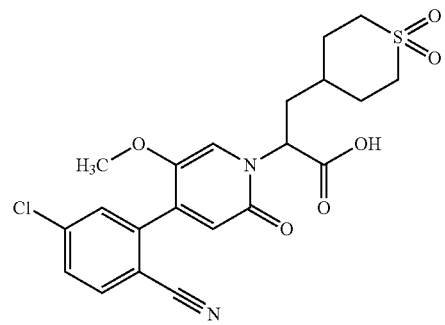 [SMILES: COc1cn(C(CC2CCS(=O)(=O)CC2)C(=O)O)c(=O)cc1-c1cc(Cl)ccc1C#N]

860 mg (1.65 mmol) of tert-butyl 2-[4-(5-chloro-2-cyanophenyl)-5-methoxy-2-oxopyridin-1(2H)-yl]-3-(1,1-dioxidotetrahydro-2H-thiopyran-4-yl)propanoate (racemate) in 16.6 ml of dichloromethane and 4.77 ml (61.9 mmol) of TFA were reacted according to General Method 6A. Yield: 1.18 g (purity 72%, quant.)

LC/MS [Method 1]: R$_t$=0.76 min; MS (ESIneg): m/z=463 (M−H)$^−$

Example 77.1E

Ethyl 4-({2-[4-(5-chloro-2-cyanophenyl)-5-methoxy-2-oxopyridin-1(2H)-yl]-3-(1,1-dioxidotetrahydro-2H-thiopyran-4-yl)propanoyl}amino)benzoate (racemate)

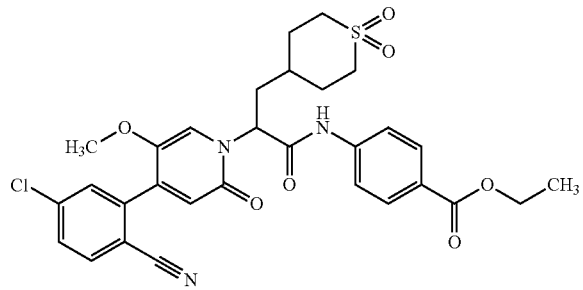 [SMILES: CCOC(=O)c1ccc(NC(=O)C(CC2CCS(=O)(=O)CC2)n2cc(OC)c(-c3cc(Cl)ccc3C#N)cc2=O)cc1]

768 mg (1.19 mmol) of 2-[4-(5-chloro-2-cyanophenyl)-5-methoxy-2-oxopyridin-1(2H)-yl]-3-(1,1-dioxidotetrahydro-2H-thiopyran-4-yl)propanoic acid (racemate, purity 72%), 786 mg (4.76 mmol) of ethyl 4-aminobenzoate, 67.6 mg (476 µmol) of Oxima and 741 µl (4.76 mmol) of DIC in 11.5 ml of dimethylformamide were reacted according to General Method 5B. Preparative HPLC (acetonitrile/water gradient) gave the title compound. Yield: 331 mg (45% of theory)

LC/MS [Method 1]: $R_t$=1.07 min; MS (ESIpos): m/z=612 (M+H)$^+$ $^1$H-NMR (400 MHz, DMSO-d$_6$): δ [ppm]=10.8 (s, 1H), 8.00 (d, 1H), 7.95 (d, 2H), 7.80-7.71 (m, 4H), 7.50 (s, 1H), 6.55 (s, 1H), 5.85 (dd, 1H), 4.29 (q, 2H), 3.70 (s, 3H), 3.14-2.95 (m, 4H), 2.37-2.28 (m, 1H), 2.15-2.02 (m, 3H), 1.81-1.66 (m, 2H), 1.56-1.43 (m, 1H), 1.31 (t, 3H).

Example 78.1A

2-[(Benzyloxy)methyl]tetrahydro-2H-pyran (racemate)

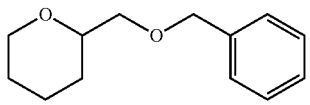 [SMILES: c1ccc(COCC2CCCCO2)cc1]

At 0° C., a solution of 25.0 g (215 mmol) of tetrahydro-2H-pyran-2-ylmethanol (racemate) in 500 ml of THF was slowly added dropwise to a suspension of 9.47 g (237 mmol, 60% in mineral oil) of sodium hydride in 500 ml of THF, and after the addition had ended, the mixture was stirred at 0° C. for another 30 min 25.7 ml (215 mmol) of benzyl bromide were then added, and the mixture was stirred at 0° C. for another 30 min and at room temperature for another 1 h. The reaction was terminated by addition of 200 ml of saturated aqueous ammonium chloride solution, and the phases were separated. The aqueous phase was extracted twice with 200 ml of methyl tert-butyl ether. The combined organic phases were dried over magnesium sulphate and filtered, and the solvent was removed under reduced pressure. The crude product was purified by column chromatography (ethyl acetate/cyclohexane gradient, 340 g silica cartridge, flow rate 100 ml/min), giving the title compound. Yield: 41.9 g (94% of theory)

LC/MS [Method 3]: $R_t$=2.18 min; MS (ESIpos): m/z=207 (M+H)$^+$ $^1$H-NMR (400 MHz, DMSO-d$_6$): δ [ppm]=7.37-7.25 (m, 5H), 4.47 (s, 2H), 3.87-3.81 (m, 1H), 3.47-3.28 (m, 4H), 1.80-1.72 (m, 1H), 1.58-1.37 (m, 4H), 1.25-1.13 (m, 1H).

Example 78.1B (R)-2-[(Benzyloxy)methyl]tetrahydro-2H-pyran

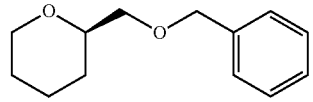 [SMILES: c1ccc(COC[C@H]2CCCCO2)cc1]

Enantiomer separation of 41.9 g of the racemate from Example 78.1A gave 16.7 g of the title compound Example 78.1B (enantiomer 1): Chiral HPLC: $R_t$=5.28 min; 99% ee, purity 93%.

Optical rotation: $[α]_{589}^{20.0}$=+14.9° (c 0.43 g/100 cm$^3$, CHCl$_3$)

Separation method: column: OD-H 5 µm 250 mm×20 mm; mobile phase: 95% isohexane, 5% 2-propanol; temperature: 25° C.; flow rate: 25 ml/min; UV detection: 210 nm.

Analysis: Column: OD-H 5 µm 250 mm×4.6 mm; mobile phase: 95% isohexane, 5% 2-propanol; flow rate: 1 ml/min; UV detection: 220 nm.

Example 78.2B (S)-2-[(Benzyloxy)methyl]tetrahydro-2H-pyran

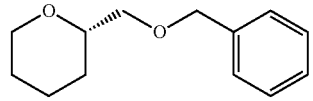 [SMILES: c1ccc(COC[C@@H]2CCCCO2)cc1]

Enantiomer separation of 41.9 g of the racemate from Example 78.1A gave 17.0 g of the title compound Example 78.2B (enantiomer 2): Chiral HPLC: $R_t$=7.36 min; 96% ee, purity 96%.

Optical rotation: $[α]_{589}^{20.0}$=13.9° (c 0.61 g/100 cm$^3$, CHCl$_3$)

Separation method: Column: OD-H 5 µm 250 mm×20 mm; mobile phase: 95% isohexane, 5% 2-propanol; temperature: 25° C.; flow rate: 25 ml/min; UV detection: 210 nm.

Analysis: Column: OD-H 5 µm 250 mm×4.6 mm; mobile phase: 95% isohexane, 5% 2-propanol; flow rate: 1 ml/min; UV detection: 220 nm.

Example 78.1C (2R)-Tetrahydro-2H-pyran-2-ylmethanol

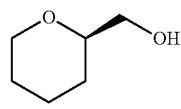

2.0 g of palladium on carbon (10%) were added to a solution of 16.7 g (75.3 mmol) of (R)-2-[(benzyloxy)methyl]tetrahydro-2H-pyran (purity 93%) in 150 ml of ethanol, and the mixture was hydrogenated under standard conditions overnight. The reaction mixture was then filtered through Celite and another 1.5 g of palladium on carbon (10%) were added. The mixture was hydrogenated for another 72 h. The reaction mixture was filtered through Celite, the filter cake was washed with ethanol, and the filtrate was concentrated under reduced pressure. The residue was purified chromatographically (silica, ethyl acetate/cyclohexane gradient) and the product fractions were freed from the solvent at <35° C. and >80 mbar. Yield: 5.47 g (63% of theory)

Optical rotation: $[\alpha]_{589}^{20.0}$=9.4° (c 0.4 g/100 cm$^3$, CHCl$_3$)
GC/MS [Method 9]: $R_t$=2.16 min; MS: m/z=116 (M)$^+$
$^1$H-NMR (400 MHz, DMSO-d$_6$): δ [ppm]=4.51 (t, 1H), 3.87-3.81 (m, 1H), 3.37-3.18 (m, 4H), 1.80-1.71 (m, 1H), 1.59-1.50 (m, 1H), 1.49-1.36 (m, 3H), 1.19-1.05 (m, 1H).

Example 78.2C (2S)-Tetrahydro-2H-pyran-2-ylmethanol

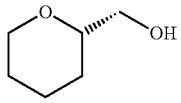

3.51 g (3.30 mmol) of palladium on carbon (10%) were added to a solution of 17.0 g (82.4 mmol) of (S)-2-[(benzyloxy)methyl]tetrahydro-2H-pyran (96% ee, purity 96%) in 120 ml of ethanol, and the mixture was hydrogenated at room temperature and under standard pressure overnight. Another 1.75 g (1.65 mmol) of palladium on carbon (10%) were then added, and the mixture was hydrogenated at room temperature for a further 72 h. Subsequently, the reaction mixture was filtered through Celite and the filtrate was concentrated. The residue was purified chromatographically (silica, dichloromethane/methanol gradient) and the product fractions were freed from the solvent at <25° C. and >50 mbar. Yield: 8.23 g (86% of theory)

Optical rotation: $[\alpha]_{589}^{20.0}$=9.1° (c 0.36 g/100 cm$^3$, CHCl$_3$), cf. A. Aponick, B. Biannic, *Org. Lett.* 2011, 13, 1330-1333.

GC/MS [Method 7]: $R_t$=1.82 min; MS: m/z=116 (M)$^+$
$^1$H-NMR (400 MHz, DMSO-d$_6$): δ [ppm]=4.51 (t, 1H), 3.87-3.81 (m, 1H), 3.37-3.18 (m, 4H), 1.80-1.71 (m, 1H), 1.59-1.50 (m, 1H), 1.49-1.36 (m, 3H), 1.19-1.05 (m, 1H).

Example 79.1A (2S)-Tetrahydro-2H-pyran-2-ylmethyl trifluoromethanesulphonate

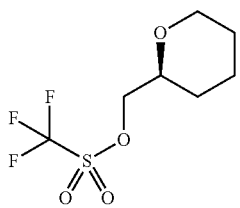 [SMILES: O=S(=O)(OC[C@@H]1CCCCO1)C(F)(F)F]

330 mg (2.84 mmol) of (2S)-tetrahydro-2H-pyran-2-ylmethanol were reacted with 0.57 ml (3.41 mmol, 1.2 eq.) of trifluoromethanesulphonic anhydride in the presence of 0.48 ml (3.41 mmol, 1.2 eq.) of triethylamine according to General Method 8A. The crude product was reacted in the next step without further purification.

$^1$H-NMR (400 MHz, DMSO-d$_6$): δ [ppm]=4.32 (dd, 1H), 4.18 (dd, 1H), 4.00-3.92 (m, 1H), 3.60-3.52 (m, 1H), 3.48-3.39 (m, 1H), 1.85-1.74 (m, 1H), 1.56-1.41 (m, 4H), 1.28-1.14 (m, 1H).

Example 79.1B tert-Butyl 2-{4-[5-chloro-2-(difluoromethoxy)phenyl]-5-methoxy-2-oxopyridin-1(2H)-yl}-3-[(2S)-tetrahydro-2H-pyran-2-yl]propanoate (mixture of enantiomerically pure diastereomers 1 and 2)

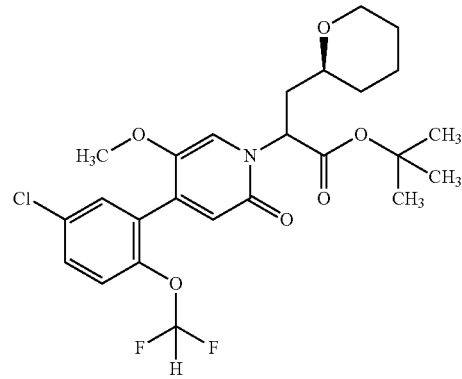 [SMILES: COc1cn(C(C[C@@H]2CCCCO2)C(=O)OC(C)(C)C)c(=O)cc1-c1cc(Cl)ccc1OC(F)F]

237 mg (0.55 mmol) of tert-butyl {4-[5-chloro-2-(difluoromethoxy)phenyl]-5-methoxy-2-oxopyridin-1(2H)-yl}acetate in the presence of 0.72 ml (0.72 mmol, 1.3 eq.) of bis(trimethylsilyl)lithium amide (1M in THF) were reacted with 274 mg (1.11 mmol, 2.0 eq.) of (2S)-tetrahydro-2H-pyran-2-ylmethyl trifluoromethanesulphonate according to General Method 7B. Yield: 130 mg (45% of theory)

LC/MS [Method 1]: $R_t$=1.25 min; MS (ESIpos): m/z=514 (M+H)$^+$.

Example 79.1C

2-{4-[5-Chloro-2-(difluoromethoxy)phenyl]-5-methoxy-2-oxopyridin-1(2H)-yl}-3-[(2S)-tetrahydro-2H-pyran-2-yl]propanoic acid (mixture of enantiomerically pure diastereomers 1 and 2)

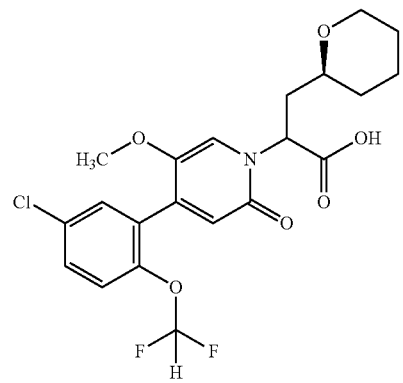 [SMILES: COc1cn(C(C[C@@H]2CCCCO2)C(=O)O)c(=O)cc1-c1cc(Cl)ccc1OC(F)F]

311 mg (purity 90%, 0.55 mmol) of tert-butyl 2-{4-[5-chloro-2-(difluoromethoxy)phenyl]-5-methoxy-2-oxopyridin-1(2H)-yl}-3-[(2S)-tetrahydro-2H-pyran-2-yl]propanoate (mixture of enantiomerically pure diastereomers 1 and 2) were hydrolysed with TFA according to General Method 6A. Yield: 312 mg (purity 87%, quant.)

LC/MS [Method 2]: diastereomer 1: $R_t$=2.86 min; MS (ESIpos): m/z=458 (M+H)$^+$; diastereomer 2: $R_t$=2.92 min; MS (ESIpos): m/z=458 (M+H)$^+$.

Example 79.1D

Ethyl 4-[(2-{4-[5-chloro-2-(difluoromethoxy)phenyl]-5-methoxy-2-oxopyridin-1(2H)-yl}-3-[(2S)-tetrahydro-2H-pyran-2-yl]propanoyl)amino]benzoate (mixture of enantiomerically pure diastereomers 1 and 2)

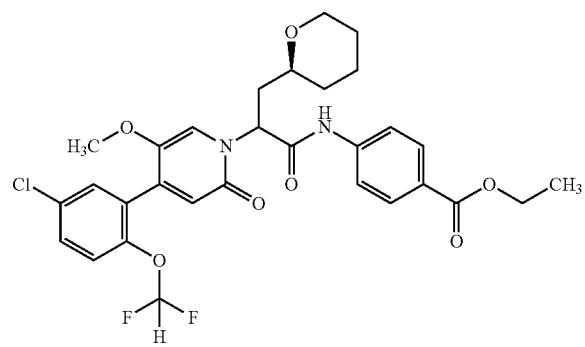 [SMILES: CCOC(=O)c1ccc(NC(=O)C(C[C@@H]2CCCCO2)n2cc(OC)c(-c3cc(Cl)ccc3OC(F)F)cc2=O)cc1]

Two fractions, 312 mg (purity 87%, 0.59 mmol) and 86 mg (0.19 mmol) of 2-{4-[5-chloro-2-(difluoromethoxy)phenyl]-5-methoxy-2-oxopyridin-1(2H)-yl}-3-[(2S)-tetrahydro-2H-pyran-2-yl]propanoic acid (mixture of enantiomerically pure diastereomers 1 and 2), were reacted with in total 202 mg (1.23 mmol, 1.6 eq.) of ethyl 4-aminobenzoate according to General Method 5B. Yield: 315 mg (83% of theory)

LC/MS [Method 1]: diastereomer 1: $R_t$=1.20 min; MS (ESIpos): m/z=605 (M+H)$^+$; diastereomer 2: $R_t$=1.22 min; MS (ESIpos): m/z=605 (M+H)$^+$.

Example 80.1A tert-Butyl 2-[5-chloro-4-(5-chloro-2-cyanophenyl)-2-oxopyridin-1(2H)-yl]-3-[(2S)-tetrahydro-2H-pyran-2-yl]propanoate (mixture of enantiomerically pure diastereomers 1 and 2)

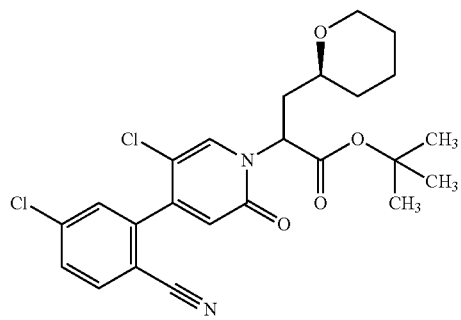 [SMILES: CC(C)(C)OC(=O)C(C[C@@H]1CCCCO1)n1cc(Cl)c(-c2cc(Cl)ccc2C#N)cc1=O]

570 mg (1.46 mmol) of tert-butyl [5-chloro-4-(5-chloro-2-cyanophenyl)-2-oxopyridin-1(2H)-yl]acetate in the presence of 1.75 ml (1.75 mmol, 1.2 eq.) of bis(trimethylsilyl)lithium amide (1M in THF) were reacted with 707 mg (purity 87%, 2.48 mmol, 1.7 eq.) of (2S)-tetrahydro-2H-pyran-2-ylmethyl trifluoromethanesulphonate according to General Method 7B. Yield: 396 mg (57% of theory)

LC/MS [Method 1]: $R_t$=1.25 min; MS (ESIpos): m/z=421 (M+H—COO-tert-butyl)$^+$.

Example 80.1B

2-[5-Chloro-4-(5-chloro-2-cyanophenyl)-2-oxopyridin-1(2H)-yl]-3-[(2S)-tetrahydro-2H-pyran-2-yl]propanoic acid (mixture of enantiomerically pure diastereomers 1 and 2)

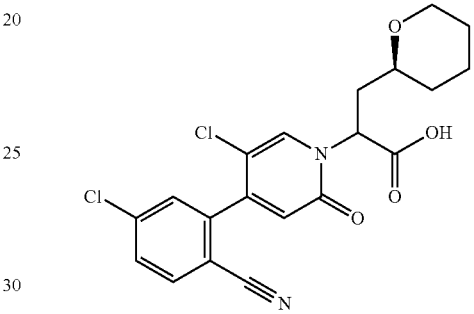

396 mg (0.83 mmol) of tert-butyl 2-[5-chloro-4-(5-chloro-2-cyanophenyl)-2-oxopyridin-1(2H)-yl]-3-[(2S)-tetrahydro-2H-pyran-2-yl]propanoate (mixture of enantiomerically pure diastereomers 1 and 2) were hydrolysed with TFA according to General Method 6A. Yield: 396 mg (quant.)

LC/MS [Method 1]: $R_t$=0.96 min; MS (ESIpos): m/z=421 (M+H)$^+$.

Example 80.1C tert-Butyl 4-({2-[5-chloro-4-(5-chloro-2-cyanophenyl)-2-oxopyridin-1(2H)-yl]-3-[(2S)-tetrahydro-2H-pyran-2-yl]propanoyl}amino)benzoate (mixture of enantiomerically pure diastereomers 1 and 2)

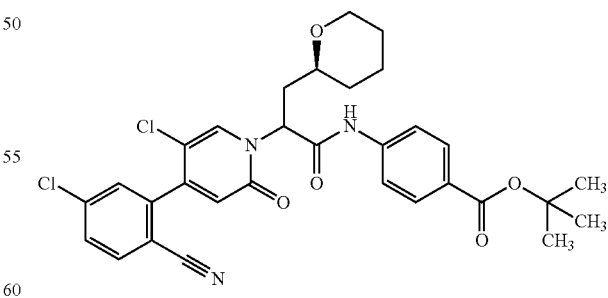

396 mg (0.90 mmol) of 2-[5-chloro-4-(5-chloro-2-cyanophenyl)-2-oxopyridin-1(2H)-yl]-3-[(2,9-tetrahydro-2H-pyran-2-yl]propanoic acid (mixture of enantiomerically pure diastereomers 1 and 2) were reacted with 192 mg (0.99 mmol, 1.1 eq.) of tert-butyl 4-aminobenzoate according to General Method 5A. Yield: 364 mg (68% of theory)

LC/MS [Method 1]: diastereomer 1: $R_t$=1.32 min; MS (ESIpos): m/z=596 (M+H)$^+$; diastereomer 2: $R_t$=1.34 min; MS (ESIpos): m/z=596 (M+H)$^+$.

Example 81.1A tert-Butyl 2-[5-chloro-4-(5-chloro-2-cyanophenyl)-2-oxopyridin-1(2H)-yl]-4-methoxybutanoate (racemate)

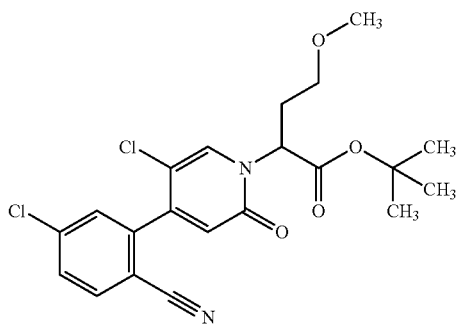 [SMILES: COCCC(C(=O)OC(C)(C)C)n1cc(Cl)c(-c2cc(Cl)ccc2C#N)cc1=O]

500 mg (1.32 mmol) of tert-butyl [5-chloro-4-(5-chloro-2-cyanophenyl)-2-oxopyridin-1(2H)-yl]acetate in the presence of 1.58 ml (1.58 mmol, 1.2 eq.) of bis(trimethylsilyl) lithium amide (1M in THF) were reacted with 556 mg (purity 74%, 1.98 mmol, 1.5 eq.) of 2-methoxyethyl trifluoromethanesulphonate according to General Method 7B. Yield: 455 mg (purity 80%, 63% of theory)

LC/MS [Method 1]: $R_t$=1.16 min; MS (ESIpos): m/z=381 (M+H—COO-tert.-butyl)$^+$.

Example 81.1B

2-[5-Chloro-4-(5-chloro-2-cyanophenyl)-2-oxopyridin-1(2H)-yl]-4-methoxybutanoic acid

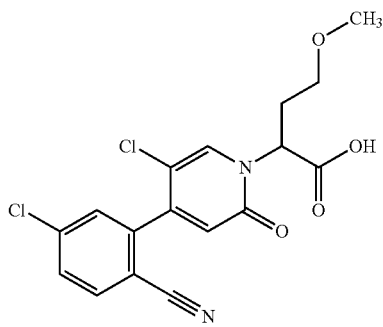 [SMILES: COCCC(C(=O)O)n1cc(Cl)c(-c2cc(Cl)ccc2C#N)cc1=O]

455 mg (purity 80%, 0.83 mmol) of tert-butyl 2-[5-chloro-4-(5-chloro-2-cyanophenyl)-2-oxopyridin-1(2H)-yl]-4-methoxybutanoate (racemate) were hydrolysed with TFA according to General Method 6A. Yield: 417 mg (purity 76%, quant.)

LC/MS [Method 8]: Rt=0.86 min; MS (ESIpos): m/z=381 (M+H)$^+$.

Example 81.1C tert-Butyl 4-({2-[5-chloro-4-(5-chloro-2-cyanophenyl)-2-oxopyridin-1(2H)-yl]-4-methoxybutanoyl}amino)benzoate (racemate)

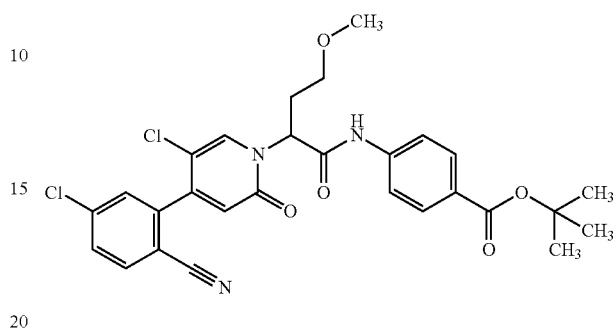

417 mg (purity 76%, 0.83 mmol) of 2-[5-chloro-4-(5-chloro-2-cyanophenyl)-2-oxopyridin-1(2H)-yl]-4-methoxybutanoic acid (racemate) were reacted with 177 mg (0.91 mmol, 1.1 eq.) of tert-butyl 4-aminobenzoate according to General Method 5A. Yield: 438 mg (92% of theory)

LC/MS [Method 1]: $R_t$=1.24 min; MS (ESIpos): m/z=556 (M+H)$^+$.

WORKING EXAMPLES

General Method 1

Amide Coupling Using HATU/DIEA

Under argon and at RT, the appropriate amine (1.1 eq.), N,N-diisopropylethylamine (DIEA) (2.2 eq.) and a solution of HATU (1.2 eq.) in a little DMF were added to a solution of the appropriate carboxylic acid (1.0 eq.) in dimethylformamide (about 12 ml/mmol). The reaction mixture was stirred at RT. After addition of water/ethyl acetate and phase separation, the organic phase was washed with water and with saturated aqueous sodium chloride solution, dried (sodium sulphate), filtered and concentrated under reduced pressure. The crude product was then purified by preparative HPLC (Reprosil C18, water/acetonitrile gradient or water/methanol gradient).

General Method 2

Hydrolysis of a Tert-Butyl Ester or a Boc-Protected Amine Using TFA

At RT, TFA (20 eq.) was added to a solution of the appropriate tert-butyl ester derivative or a Boc-protected amine (1.0 eq.) in dichloromethane (about 25 ml/mmol), and the mixture was stirred at RT for 1-8 h. Subsequently, the reaction mixture was concentrated under reduced pressure. The residue was co-evaporated repeatedly with dichloromethane and/or toluene. The crude product was then purified by preparative RP-HPLC (mobile phase: acetonitrile/water gradient or water/methanol gradient).

General Method 3

Hydrolysis of a Methyl or Ethyl Ester with Lithium Hydroxide

At RT, lithium hydroxide (2-4 eq.) was added to a solution of the appropriate ester (1.0 eq.) in a mixture of tetrahydrofuran/water (3:1, about 15 ml/mmol), and the mixture was stirred at RT. The reaction mixture was then adjusted to pH 1 using aqueous hydrochloric acid solution (1N). After addition of water/ethyl acetate, the aqueous phase was extracted three times with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 4

Hydrolysis of a Methyl or Ethyl Ester with Caesium Carbonate

Caesium carbonate (2 eq.) was added to a solution of the appropriate methyl or ethyl ester (1 eq.) in a mixture of methanol/water (4/1, 0.05-0.2M), and the resulting suspension was stirred at RT to 60° C. for 3-8 h. The reaction mixture was cooled to RT if required and adjusted to pH 3 using aqueous hydrochloric acid (1N). Methanol was removed at 30° C. under reduced pressure. The aqueous phase was extracted with ethyl acetate. The combined organic phases were dried (sodium sulphate or magnesium sulphate), filtered and concentrated under reduced pressure. The residue was purified by means of preparative HPLC.

General Method 5

Amide Coupling Using OXIMA/DIC

N,N'-Diisopropylcarbodiimide (DIC) (1 eq.) was added dropwise to a degassed solution of the appropriate carboxylic acid (1 eq.), aniline (1 eq.) and ethyl hydroxyiminocyanoacetate (Oxima) (0.1-1 eq.) in dimethylformamide (0.1M), and the resulting reaction solution was stirred at RT-40° C. for 8-24 h. The solvent was removed under reduced pressure. The residue was either admixed with water and the desired product was filtered off or purified by normal phase chromatography (cyclohexane/ethyl acetate gradient) or preparative RP-HPLC (water/acetonitrile gradient or water/methanol gradient).

General Method 6

Amide Coupling Using T3P/DIEA

Under argon and at 0° C., N,N-diisopropylethylamine (3 eq.) and propylphosphonic anhydride (T3P, 50% in dimethylformamide, 3 eq.) were added dropwise to a solution of the carboxylic acid and the appropriate amine (1.1-1.5 eq.) in dimethylformamide (0.15-0.05 mmol). The reaction mixture was stirred at RT and then concentrated under reduced pressure. After addition of water/ethyl acetate and phase separation, the aqueous phase was extracted twice with ethyl acetate. The combined organic phases were dried (sodium sulphate or magnesium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 7

Amide Coupling Using T3P/Pyridine

Under argon and at 0° C., propylphosphonic anhydride (T3P, 50% in ethyl acetate, 4 eq.) was added dropwise to a solution of the carboxylic acid (1 eq.) and the appropriate amine (1.5 eq.) in pyridine (0.15-0.05 M). This mixture was heated to 90° C. and stirred at 90° C. for 1-20 h. The reaction mixture was cooled to RT, and water and ethyl acetate were added. After phase separation, the aqueous phase was extracted with ethyl acetate. The combined organic phases were washed with aqueous buffer solution (pH 5), with saturated aqueous sodium bicarbonate solution and with saturated aqueous sodium chloride solution, dried (sodium sulphate or magnesium sulphate), filtered and concentrated under reduced pressure. The crude product was then optionally purified either by normal phase chromatography (mobile phase: cyclohexane/ethyl acetate mixtures or dichloromethane/methanol mixtures) or by preparative RP-HPLC (water/acetonitrile gradient or water/methanol gradient).

Example 1

2-[4-(5-Chloro-2-cyanophenyl)-2-oxopyridin-1(2H)-yl]-N-[4-(1H-tetrazol-5-yl)phenyl]propanamide (racemate)

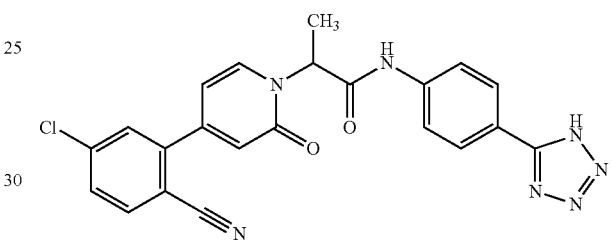

65 mg (purity 83%, 0.18 mmol) of 2-[4-(5-chloro-2-cyanophenyl)-2-oxopyridin-1(2H)-yl]propanoic acid (racemate) (Example 2.2B) and 1.2 eq. of 4-(1H-tetrazol-5-yl)aniline were reacted according to General Method 1. Yield: 17 mg (22% of theory)

LC/MS [Method 1]: $R_t$=0.82 min; MS (ESIpos): m/z=446 (M+H)$^+$ $^1$H-NMR (400 MHz, DMSO-d$_6$): δ [ppm]=10.78 (s, 1H), 8.08-7.94 (m, 4H), 7.87-7.80 (m, 3H), 7.78 (dd, 1H), 6.67 (d, 1H), 6.58 (d, 1H), 5.59 (q, 1H), 1.71 (d, 3H).

Example 2

2-[4-(5-Chloro-2-cyanophenyl)-2-oxopyridin-1(2H)-yl]-N-{4-[3-(trifluoromethyl)-1H-1,2,4-triazol-5-yl]phenyl}propanamide (racemate)

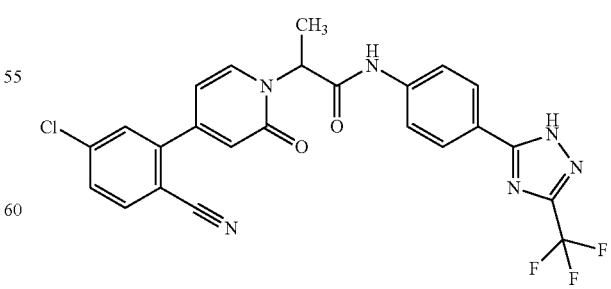

95 mg (purity 83%, 0.26 mmol) of 2-[4-(5-chloro-2-cyanophenyl)-2-oxopyridin-1(2H)-yl]propanoic acid (racemate) (Example 2.2B) and 75 mg (0.31 mmol) of 4-[3-

(trifluoromethyl)-1H-1,2,4-triazol-5-yl]aniline (Example 1.1C) were reacted according to General Method 1. Yield: 30 mg (purity 92%, 21% of theory)

LC/MS [Method 1]: R$_t$=1.06 min; MS (ESIpos): m/z=513 (M+H)$^+$ $^1$H-NMR (400 MHz, DMSO-d$_6$): δ [ppm]=15.17 (s, 1H), 10.75 (s, 1H), 8.04 (d, 1H), 8.00 (d, 2H), 7.96 (d, 1H), 7.81 (m, 3H), 7.77 (dd, 1H), 6.67 (d, 1H), 6.57 (dd, 1 h), 5.59 (q, 1H), 1.71 (d, 3H).

Example 3

2-[4-(5-Chloro-2-cyanophenyl)-2-oxopyridin-1(2H)-yl]-N-{4-[3-(methoxymethyl)-1H-1,2,4-triazol-5-yl]phenyl}propanamide (racemate)

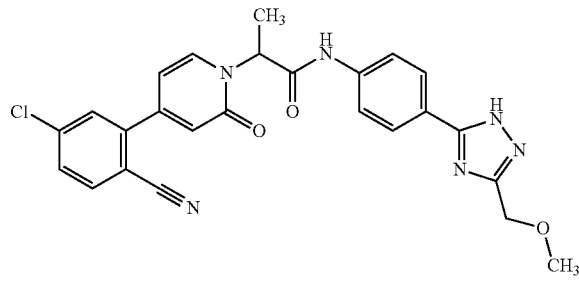 [SMILES: COCc1n[nH]c(-c2ccc(NC(=O)C(C)n3ccc(-c4cc(Cl)ccc4C#N)cc3=O)cc2)n1]

90 mg (purity 93%, 0.28 mmol) of 2-[4-(5-chloro-2-cyanophenyl)-2-oxopyridin-1(2H)-yl]propanoic acid (racemate) (Example 2.2B) and 80 mg (0.33 mmol) of 4-[3-(methoxymethyl)-1H-1,2,4-triazol-5-yl]aniline monohydrochloride were reacted according to General Method 1. Yield: 45 mg (33% of theory)

LC/MS [Method 1]: R$_t$=0.87 min; MS (ESIpos): m/z=489 (M+H)$^+$ $^1$H-NMR (400 MHz, DMSO-d$_6$): δ [ppm]=10.62 (br. s, 1H), 8.04 (d, 1H), 7.99-7.92 (m, 3H), 7.82 (d, 1H), 7.77 (dd, 1H), 7.73 (m, 2H), 6.67 (d, 1H), 6.56 (dd, 1H), 5.60 (q, 1H), 1.70 (d, 3H).

Example 4

2-[4-(5-Chloro-2-cyanophenyl)-2-oxopyridin-1(2H)-yl]-N-[4-(1H-imidazol-2-yl)phenyl]propanamide (racemate)

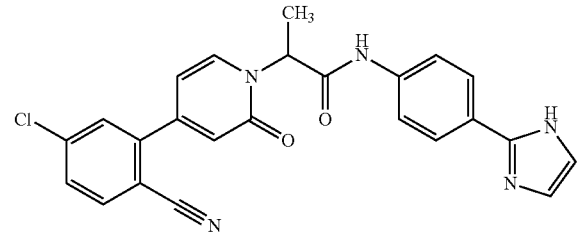 [SMILES: CC(C(=O)Nc1ccc(-c2ncc[nH]2)cc1)n1ccc(-c2cc(Cl)ccc2C#N)cc1=O]

71 mg (0.23 mmol) of 2-[4-(5-chloro-2-cyanophenyl)-2-oxopyridin-1(2H)-yl]propanoic acid (racemate) (Example 2.2B) and 40 mg (0.25 mmol) of 4-(1H-imidazol-2-yl)aniline (Example 1.2A) were reacted according to General Method 1. Yield: 4 mg (4% of theory)

LC/MS [Method 1]: R$_t$=0.66 min; MS (ESIpos): m/z=444 (M+H)$^+$ $^1$H-NMR (400 MHz, DMSO-d$_6$): δ [ppm]=12.39 (br. s, 1H), 10.56 (br. s, 1H), 8.05 (d, 1H), 7.96 (d, 1H), 7.88 (d, 2H), 7.82 (d, 1H), 7.77 (dd, 1H), 7.67 (d, 2H), 7.21 (br. s, 1H), 6.99 (br. s, 1H), 6.67 (d, 1H), 6.56 (dd, 1H), 5.60 (q, 1H), 1.70 (d, 3H).

Example 5

2-[4-(5-Chloro-2-cyanophenyl)-2-oxopyridin-1(2H)-yl]-N-[4-(1H-imidazol-4-yl)phenyl]propanamide (racemate)

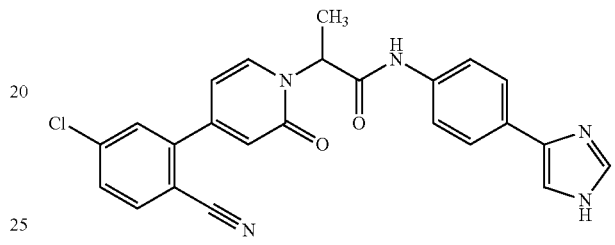

78 mg (0.25 mmol) of 2-[4-(5-chloro-2-cyanophenyl)-2-oxopyridin-1(2H)-yl]propanoic acid (racemate) (Example 2.2B) and 44 mg (0.28 mmol) of 4-(1H-imidazol-4-yl)aniline were reacted according to General Method 1. Yield: 40 mg (36% of theory)

LC/MS [Method 1]: R$_t$=0.74 min; MS (ESIpos): m/z=444 (M+H)$^+$ $^1$H-NMR (400 MHz, DMSO-d$_6$): δ [ppm]=12.13 (br. s, 1H), 10.45 (s, 1H), 8.05 (d, 1H), 7.96 (d, 1H), 7.83 (d, 1H), 7.77 (dd, 1H), 7.74-7.66 (m, 3H), 7.61 (d, 2H), 7.52 (br. s, 1H), 6.67 (d, 1H), 6.56 (dd, 1H), 5.61 (q, 1H), 1.69 (d, 3H).

Example 6

2-[4-(5-Chloro-2-cyanophenyl)-2-oxopyridin-1(2H)-yl]-N-{4-[2-(trifluoromethyl)-1H-imidazol-5-yl]phenyl}propanamide (racemate)

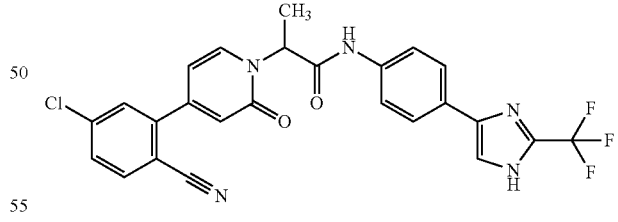

67 mg (0.22 mmol) of 2-[4-(5-chloro-2-cyanophenyl)-2-oxopyridin-1(2H)-yl]propanoic acid (racemate) (Example 2.2B) and 49 mg (0.22 mmol) of 4-[2-(trifluoromethyl)-1H-imidazol-5-yl]aniline (Example 1.3B) were reacted according to General Method 1. Yield: 26 mg (22% of theory)

LC/MS [Method 1]: R$_t$=1.00 min; MS (ESIpos): m/z=512 (M+H)$^+$ $^1$H-NMR (400 MHz, DMSO-d$_6$): δ [ppm]=13.66 (br. s, 1H), 10.51 (s, 1H), 8.05 (d, 1H), 7.96 (d, 1H), 7.89 (s, 1H), 7.83 (d, 1H), 7.81-7.74 (m, 3H), 7.65 (d, 2H), 6.67 (d, 1H), 6.56 (dd, 1H), 5.61 (q, 1H), 1.70 (d, 3H).

Example 7

2-[4-(5-Chloro-2-cyanophenyl)-2-oxopyridin-1(2H)-yl]-N-[4-(5-oxo-2,5-dihydro-1H-pyrazol-3-yl)phenyl]propanamide (racemate)

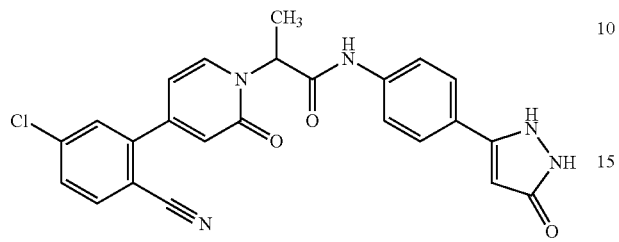

110 mg (0.20 mmol) of tert-butyl 5-[4-({2-[4-(5-chloro-2-cyanophenyl)-2-oxopyridin-1(2H)-yl]propanoyl}amino)phenyl]-3-oxo-2,3-dihydro-1H-pyrazole-1-carboxylate (racemate) (Example 2.3A) were hydrolysed with TFA according to General Method 2. Yield: 24 mg (27% of theory)

LC/MS [Method 1]: $R_t$=0.87 min; MS (ESIpos): m/z=460 (M+H)$^+$ $^1$H-NMR (400 MHz, DMSO-d$_6$): δ [ppm]=11.79 (br. s, 1H), 10.55 (s, 1H), 9.57 (br. s, 1H), 8.04 (d, 1H), 7.96 (d, 1H), 7.83 (d, 1H), 7.77 (dd, 1H), 7.68-7.59 (m, 4H), 6.67 (d, 1H), 6.56 (dd, 1H), 5.84 (br. s, 1H), 5.60 (q, 1H), 1.70 (d, 3H).

Example 8

2-[4-(5-Chloro-2-cyanophenyl)-2-oxopyridin-1(2H)-yl]-N-[4-(5-oxo-4,5-dihydro-1,2,4-oxadiazol-3-yl)phenyl]propanamide (racemate)

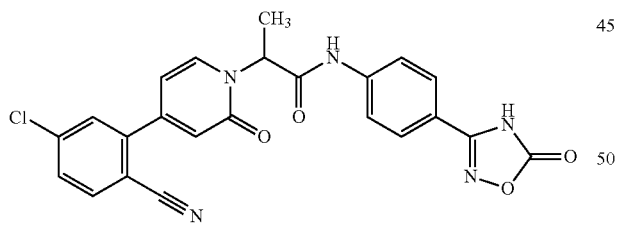

120 mg (purity 93%, 0.37 mmol) of 2-[4-(5-chloro-2-cyanophenyl)-2-oxopyridin-1(2H)-yl]propanoic acid (racemate) (Example 2.2B) and 1.2 eq. of 3-(4-aminophenyl)-1,2,4-oxadiazol-5(4H)-one (Example 1.5A) were reacted according to General Method 1. Yield: 23 mg (13% of theory)

LC/MS [Method 1]: $R_t$=0.91 min; MS (ESIpos): m/z=462 (M+H)$^+$ $^1$H-NMR (400 MHz, DMSO-d$_6$): δ [ppm]=12.88 (br. s, 1H), 10.81 (s, 1H), 8.05 (d, 1H), 7.96 (d, 1H), 7.82 (d, 1H), 7.81-7.78 (m, 4H), 7.77 (dd, 1H), 6.67 (s, 1H), 6.57 (d, 1H), 5.57 (q, 1H), 1.71 (d, 3H).

Example 9

4-({2-[4-(5-Chloro-2-cyanophenyl)-2-oxopyridin-1(2H)-yl]propanoyl}amino)benzoic acid (racemate)

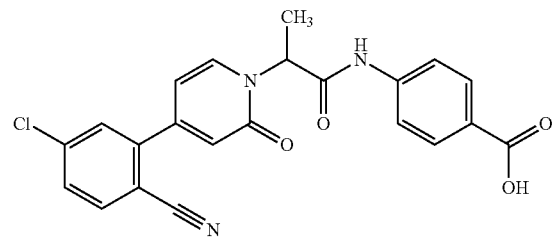 [SMILES: CC(C(=O)Nc1ccc(C(=O)O)cc1)n1ccc(-c2cc(Cl)ccc2C#N)cc1=O]

43 mg (0.09 mmol) of tert-butyl 4-({2-[4-(5-chloro-2-cyanophenyl)-2-oxopyridin-1(2H)-yl]propanoyl}amino)benzoate (racemate) (Example 2.2C) were hydrolysed with TFA according to General Method 2. Yield: 20 mg (purity 89%, 48% of theory)

LC/MS [Method 1]: $R_t$=0.88 min; MS (ESIpos): m/z=422 (M+H)$^+$ $^1$H-NMR (400 MHz, DMSO-d$_6$): δ [ppm]=12.73 (br. s, 1H), 10.74 (s, 1H), 8.04 (d, 1H), 7.95 (d, 1H), 7.91 (d, 2H), 7.82 (d, 1H), 7.76 (dd, 1H), 7.72 (d, 2H), 6.66 (d, 1H), 6.56 (dd, 1H), 5.58 (q, 1H), 1.70 (s, 3H).

Example 10

4-({2-[4-(5-Chloro-2-ethynylphenyl)-2-oxopyridin-1(2H)-yl]propanoyl}amino)benzoic acid (racemate)

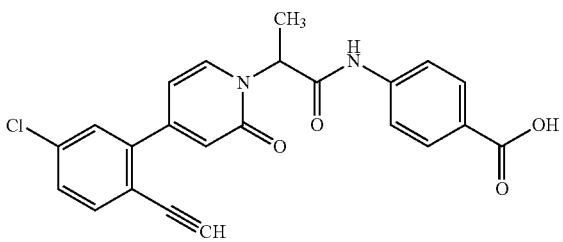 [SMILES: C#Cc1ccc(Cl)cc1-c1ccn(C(C)C(=O)Nc2ccc(C(=O)O)cc2)c(=O)c1]

15 mg (0.03 mmol) of methyl 4-({2-[4-(5-chloro-2-ethynylphenyl)-2-oxopyridin-1(2H)-yl]propanoyl}amino)benzoate (racemate) (Example 2.8F) were hydrolysed with lithium hydroxide according to General Method 3. Yield: 4 mg (purity 92%, 28% of theory)

LC/MS [Method 1]: $R_t$=0.98 min; MS (ESIpos): m/z=421 (M+H)$^+$ $^1$H-NMR (400 MHz, DMSO-d$_6$): δ [ppm]=12.72 (br. s, 1H), 10.75 (s, 1H), 7.91 (d, 2H), 7.86 (d, 1H), 7.73 (d, 2H), 7.65 (d, 1H), 7.58 (d, 1H), 7.54 (dd, 1H), 6.60 (d, 1H), 6.53 (dd, 1H), 5.57 (q, 1H), 3.57 (s, 1H), 1.68 (d, 3H).

Example 11

4-({2-[4-(2,5-Dichlorophenyl)-2-oxopyridin-1(2H)-yl]propanoyl}amino)benzoic acid (racemate)

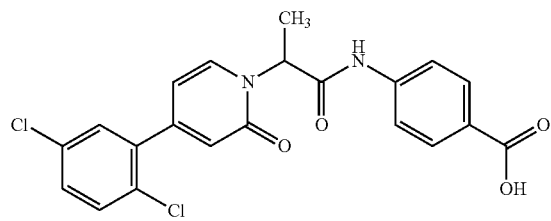 [SMILES: CC(C(=O)Nc1ccc(C(=O)O)cc1)n1ccc(-c2cc(Cl)ccc2Cl)cc1=O]

83 mg (0.17 mmol) of tert-butyl 4-({2-[4-(2,5-dichlorophenyl)-2-oxopyridin-1(2H)-yl]propanoyl}amino)benzoate (racemate) (Example 2.9C) were hydrolysed with TFA according to General Method 2. Yield: 21 mg (purity 88%, 23% of theory)

LC/MS [Method 1]: $R_t$=0.99 min; MS (ESIpos): m/z=431 (M+H)$^+$ $^1$H-NMR (400 MHz, DMSO-d$_6$): δ [ppm]=10.70 (s, 1H), 7.92-7.84 (m, 3H), 7.68 (d, 2H), 7.63 (d, 1H), 7.59-7.52 (m, 2H), 6.48 (d, 1H), 6.42 (dd, 1H), 5.58 (q, 1H), 1.68 (d, 3H).

Example 12

4-({2-[4-(2-Bromo-5-chlorophenyl)-2-oxopyridin-1(2H)-yl]propanoyl}amino)benzoic acid (racemate)

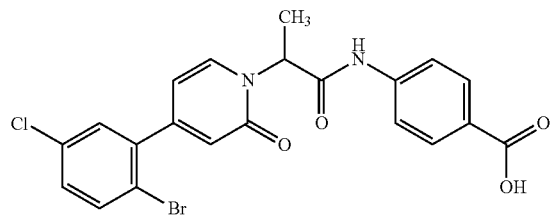 [SMILES: CC(C(=O)Nc1ccc(C(=O)O)cc1)n1ccc(-c2cc(Cl)ccc2Br)cc1=O]

96 mg (0.18 mmol) of tert-butyl 4-({2-[4-(2-bromo-5-chlorophenyl)-2-oxopyridin-1(2H)-yl]propanoyl}amino)benzoate (racemate) (Example 2.10C) were hydrolysed with TFA according to General Method 2. Yield: 69 mg (82% of theory)

LC/MS [Method 1]: $R_t$=1.03 min; MS (ESIpos): m/z=475 (M+H)$^+$ $^1$H-NMR (400 MHz, DMSO-d$_6$): δ [ppm]=12.77 (br. s, 1H), 10.76 (s, 1H), 7.91 (d, 2H), 7.87 (d, 1H), 7.79 (d, 1H), 7.73 (d, 2H), 7.53 (d, 1H), 7.46 (dd, 1H), 6.43 (s, 1H), 6.38 (dd, 1H), 5.57 (q, 1H), 1.68 (d, 3H).

Example 13

4-{[2-{4-[5-Chloro-2-(trifluoromethyl)phenyl]-2-oxopyridin-1(2H)-yl}propanoyl]amino}benzoic acid (racemate)

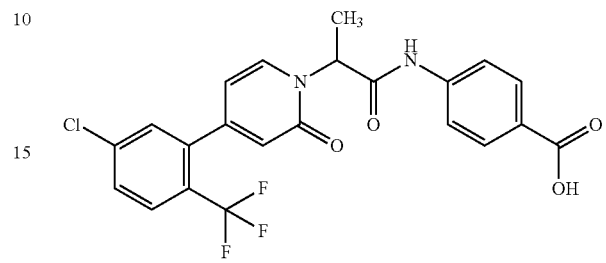

104 mg (0.20 mmol) of tert-butyl 4-[(2-{4-[5-chloro-2-(trifluoromethyl)phenyl]-2-oxopyridin-1(2H)-yl}propanoyl)amino]benzoate (racemate) (Example 2.11C) were hydrolysed with TFA according to General Method 2. Yield: 67 mg (73% of theory)

LC/MS [Method 1]: $R_t$=1.01 min; MS (ESIpos): m/z=465 (M+H)$^+$ $^1$H-NMR (400 MHz, DMSO-d$_6$): δ [ppm]=12.76 (br. s, 1H), 10.74 (s, 1H), 7.93-7.84 (m, 4H), 7.78-7.70 (m, 3H), 7.60 (d, 1H), 6.38 (d, 1H), 6.33 (dd, 1H), 5.57 (q, 1H), 1.68 (d, 3H).

Example 14

4-({2-[4-(5-Chloro-2-cyanophenyl)-2-oxopyridin-1(2H)-yl]propanoyl}amino)-2-fluorobenzoic acid (racemate)

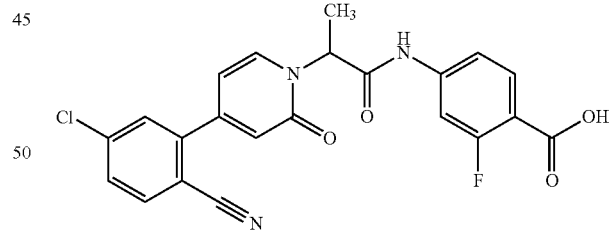

82 mg (0.17 mmol) of methyl 4-({2-[4-(5-chloro-2-cyanophenyl)-2-oxopyridin-1(2H)-yl]propanoyl}amino)-2-fluorobenzoate (racemate) (Example 2.4A) were hydrolysed with lithium hydroxide according to General Method 3. Yield: 8 mg (purity 93%, 10% of theory)

LC/MS [Method 1]: $R_t$=0.92 min; MS (ESIpos): m/z=440 (M+H)$^+$ $^1$H-NMR (400 MHz, DMSO-d$_6$): δ [ppm]=13.05 (br. s, 1H), 10.93 (s, 1H), 8.05 (d, 1H), 7.95 (d, 1H), 7.86 (t, 1H), 7.83 (d, 1H), 7.77 (dd, 1H), 7.66 (d, 1H), 7.40 (d, 1H), 6.66 (d, 1H), 6.56 (dd, 1H), 5.53 (q, 1H), 1.70 (d, 3H).

Example 15

2-Chloro-4-({2-[4-(5-chloro-2-cyanophenyl)-2-oxopyridin-1(2H)-yl]propanoyl}amino)benzoic acid (racemate)

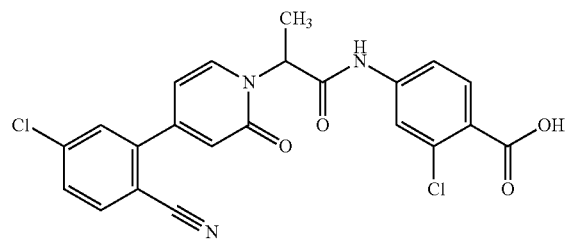 [SMILES: CC(C(=O)Nc1ccc(C(=O)O)c(Cl)c1)n1ccc(-c2cc(Cl)ccc2C#N)cc1=O]

100 mg (purity 94%, 0.20 mmol) of methyl 2-chloro-4-({2-[4-(5-chloro-2-cyanophenyl)-2-oxopyridin-1(2H)-yl]propanoyl}amino)benzoate (racemate) (Example 2.5A) were hydrolysed with lithium hydroxide according to General Method 3. Yield: 8 mg (purity 93%, 10% of theory)

LC/MS [Method 1]: $R_t$=0.93 min; MS (ESIpos): m/z=456 (M+H)$^+$ $^1$H-NMR (400 MHz, DMSO-d$_6$): δ [ppm]=13.14 (br. s, 1H), 10.83 (s, 1H), 8.04 (d, 1H), 7.94 (d, 1H), 7.90 (d, 1H), 7.86 (d, 1H), 7.81 (d, 1H), 7.76 (dd, 1H), 7.57 (dd, 1H), 6.67 (d, 1H), 6.56 (dd, 1H), 5.52 (q, 1H), 1.70 (d, 3H).

Example 16

4-({2-[4-(5-Chloro-2-cyanophenyl)-2-oxopyridin-1(2H)-yl]propanoyl}amino)-2-methylbenzoic acid (racemate)

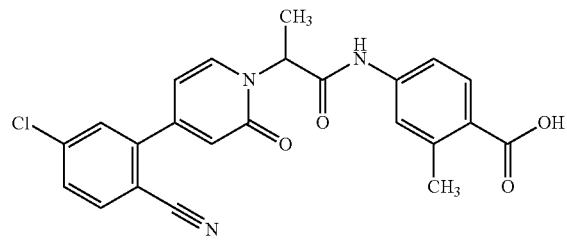 [SMILES: Cc1cc(NC(=O)C(C)n2ccc(-c3cc(Cl)ccc3C#N)cc2=O)ccc1C(=O)O]

120 mg (0.27 mmol) of methyl 4-({2-[4-(5-chloro-2-cyanophenyl)-2-oxopyridin-1(2H)-yl]propanoyl}amino)-2-methylbenzoate (racemate) (Example 2.6A) were hydrolysed with lithium hydroxide according to General Method 3. Yield: 39 mg (purity 93%, 33% of theory)

LC/MS [Method 1]: $R_t$=0.91 min; MS (ESIpos): m/z=436 (M+H)$^+$ $^1$H-NMR (400 MHz, DMSO-d$_6$): δ [ppm]=12.61 (br. s, 1H), 10.64 (s, 1H), 8.05 (d, 1H), 7.94 (d, 1H), 7.86-7.81 (m, 2H), 7.76 (dd, 1H), 7.56-7.49 (m, 2H), 6.66 (d, 1H), 6.56 (dd, 1H), 5.56 (q, 1H), 1.69 (d, 3H).

Example 17

2-[4-(5-Chloro-2-cyanophenyl)-2-oxopyridin-1(2H)-yl]-N-(2-methyl-3-oxo-2,3-dihydro-1H-indazol-6-yl)propanamide (racemate)

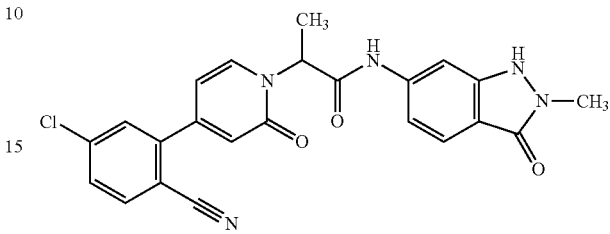

75 mg (0.14 mmol) of tert-butyl 6-({2-[4-(5-chloro-2-cyanophenyl)-2-oxopyridin-1(2H)-yl]propanoyl}amino)-2-methyl-3-oxo-2,3-dihydro-1H-indazole-1-carboxylate (racemate) (Example 2.7A) were hydrolysed with TFA according to General Method 2. Yield: 37 mg (60% of theory)

LC/MS [Method 1]: $R_t$=0.79 min; MS (ESIpos): m/z=448 (M+H)$^+$ $^1$H-NMR (400 MHz, DMSO-d$_6$): δ [ppm]=10.65 (s, 1H), 10.20 (s, 1H), 8.05 (d, 1H), 7.96 (d, 1H), 7.82 (d, 1H), 7.77 (dd, 1H), 7.74 (s, 1H), 7.56 (d, 1H), 7.13 (dd, 1H), 6.66 (d, 1H), 6.56 (dd, 1H), 5.58 (q, 1H), 1.70 (d, 3H).

Example 18

N-(1H-Benzimidazol-6-yl)-2-[4-(5-chloro-2-cyanophenyl)-2-oxopyridin-1(2H)-yl]propanamide (racemate)

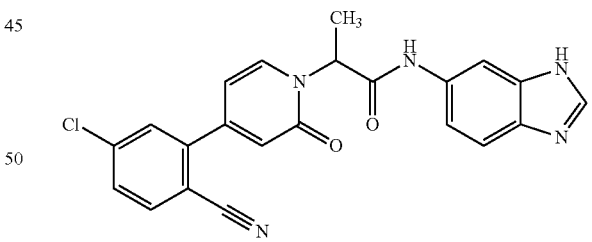

65 mg (purity 83%, 0.18 mmol) of 2-[4-(5-chloro-2-cyanophenyl)-2-oxopyridin-1(2H)-yl]propanoic acid (racemate) (Example 2.2B) and 26 mg (0.20 mmol) of 1H-benzimidazole-6-amine were reacted according to General Method 1. Yield: 11 mg (15% of theory)

LC/MS [Method 1]: $R_t$=0.64 min; MS (ESIpos): m/z=418 (M+H)$^+$ $^1$H-NMR (400 MHz, DMSO-d$_6$): δ [ppm]=12.39 (s, 1H), 10.46 (s, 1H), 8.15 (s, 1H), 8.08-7.95 (m, 3H), 7.83 (d, 1H), 7.77 (dd, 1H), 7.61-7.21 (m, 2H), 6.68 (d, 1H), 6.57 (dd, 1H), 5.63 (m, 1H), 1.69 (d, 3H).

Example 19

2-[4-(5-Chloro-2-cyanophenyl)-2-oxopyridin-1(2H)-yl]-N-[4-(1H-tetrazol-5-yl)phenyl]butanamide (racemate)

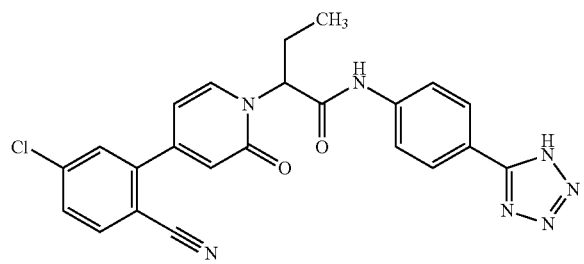 [SMILES: CCC(C(=O)Nc1ccc(-c2nnn[nH]2)cc1)n1ccc(-c2cc(Cl)ccc2C#N)cc1=O]

212 mg (purity 60%, 0.4 mmol) of 2-[4-(5-chloro-2-cyanophenyl)-2-oxopyridin-1(2H)-yl]butanoic acid (racemate) (Example 3.1C) and 31 mg (0.19 mmol) of 4-(1H-tetrazol-5-yl)aniline were reacted according to General Method 1. Yield: 143 mg (77% of theory)

LC/MS [Method 1]: $R_t$=0.88 min; MS (ESIpos): m/z=460 (M+H)$^+$ $^1$H-NMR (400 MHz, DMSO-d$_6$): δ [ppm]=16.77 (br. s, 1H), 10.87 (s, 1H), 8.05 (d, 1H), 8.01 (d, 2H), 7.98 (d, 1H), 7.87-7.82 (m, 3H), 7.77 (dd, 1H), 6.69 (d, 1H), 6.57 (dd, 1H), 5.62 (q, 1H), 2.25-2.15 (m, 1H), 2.15-2.04 (m, 1H), 0.92 (t, 3H).

Example 20

2-[4-(5-Chloro-2-cyanophenyl)-2-oxopyridin-1(2H)-yl]-N-[4-(1H-tetrazol-5-yl)phenyl]butanamide (enantiomer 1)

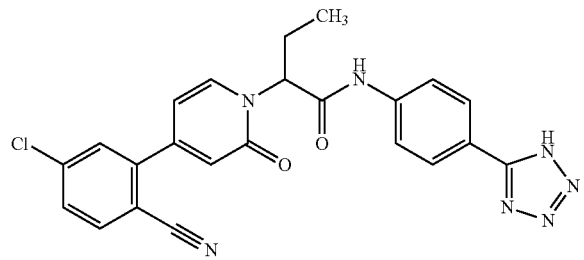 [SMILES: CCC(C(=O)Nc1ccc(-c2nnn[nH]2)cc1)n1ccc(-c2cc(Cl)ccc2C#N)cc1=O]

Enantiomer separation of 140 mg of the racemate from Example 19 gave 51 mg of the title compound Example 20 (enantiomer 1): Chiral HPLC: $R_t$=4.7 min; 99% ee.

Separation method: column: Daicel Chiralpak AZ-H 5 μm 250×20 mm; mobile phase A: isohexane, mobile phase B: ethanol+0.2% acetic acid; gradient: 0.0 min 70% A→3 min 70% A→20 min 0% A→30 min 0% A; oven: 45° C.; flow rate: 15 ml/min; UV detection: 220 nm.

Analysis: column: Daicel Chiralpak AZ-H 5 μm 250×4.6 mm; mobile phase: 90% isohexane, 10% ethanol; oven: 30° C.; flow rate: 1 ml/min; UV detection: 220 nm.

Example 21

2-[4-(5-Chloro-2-cyanophenyl)-2-oxopyridin-1(2H)-yl]-N-[4-(1H-tetrazol-5-yl)phenyl]butanamide (enantiomer 2)

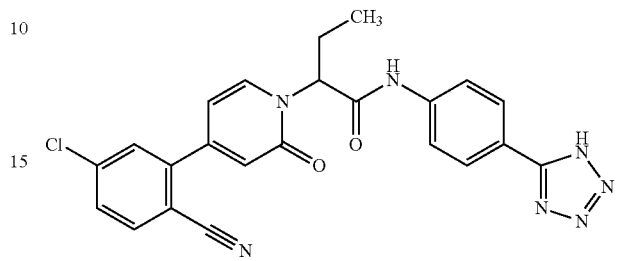

Enantiomer separation of 140 mg of the racemate from Example 19 gave 59 mg of the title compound Example 21 (enantiomer 2): Chiral HPLC: $R_t$=10.7 min; 99% ee.

Separation method: column: Daicel Chiralpak AZ-H 5 μm 250×20 mm; mobile phase A: isohexane, mobile phase B: ethanol+0.2% acetic acid; gradient: 0.0 min 70% A→3 min 70% A→20 min 0% A→30 min 0% A; oven: 45° C.; flow rate: 15 ml/min; UV detection: 220 nm; sample preparation: 140 mg of racemate dissolved in 0.5 ml of triethanolamine/5.5 ml of ethanol.

Analysis: column: Daicel Chiralpak AZ-H 5 μm 250×4.6 mm; mobile phase: 90% isohexane, 10% ethanol; oven: 30° C.; flow rate: 1 ml/min; UV detection: 220 nm.

Example 22

2-[4-(5-Chloro-2-cyanophenyl)-2-oxopyridin-1(2H)-yl]-3-methyl-N-[4-(1H-tetrazol-5-yl)phenyl]butanamide (racemate)

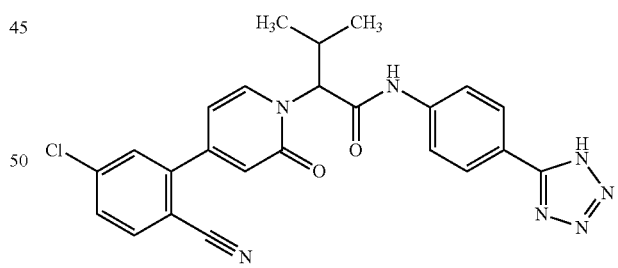

79 mg (purity 86%, 0.21 mmol) of 2-[4-(5-chloro-2-cyanophenyl)-2-oxopyridin-1(2H)-yl]-3-methylbutanoic acid (racemate) (Example 4.1C) and 40 mg (0.25 mmol) of 4-(1H-tetrazol-5-yl)aniline were reacted according to General Method 1. Yield: 45 mg (46% of theory)

LC/MS [Method 1]: $R_t$=1.01 min; MS (ESIpos): m/z=474 (M+H)$^+$ $^1$H-NMR (400 MHz, DMSO-d$_6$): δ [ppm]=11.03 (s, 1H), 8.10 (d, 1H), 8.04 (d, 3H), 8.01 (d, 2H), 7.87 (d, 2H), 7.84 (d, 1H), 7.76 (dd, 1H), 6.70 (d, 1H), 6.57 (dd, 1H), 5.52 (d, 1H), 1.10 (d, 3H), 0.82 (d, 3H).

Example 23

2-[4-(5-Chloro-2-cyanophenyl)-2-oxopyridin-1(2H)-yl]-N-[4-(1H-tetrazol-5-yl)phenyl]hexanamide (racemate)

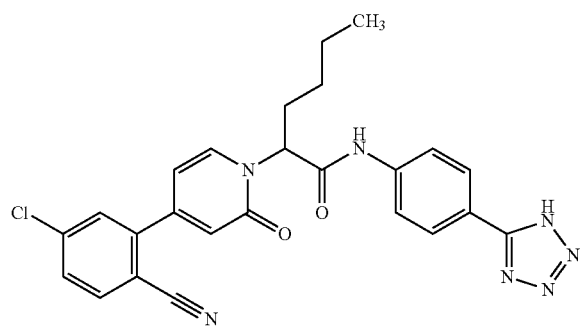 [SMILES: CCCCC(C(=O)Nc1ccc(-c2nnn[nH]2)cc1)n1ccc(-c2cc(Cl)ccc2C#N)cc1=O]

95 mg (purity 78%, 0.22 mmol) of 2-[4-(5-chloro-2-cyanophenyl)-2-oxopyridin-1(2H)-yl]hexanoic acid (racemate) (Example 5.1C) and 42 mg (0.26 mmol) of 4-(1H-tetrazol-5-yl)aniline were reacted according to General Method 1. Yield: 32 mg (30% of theory)

LC/MS [Method 1]: $R_t$=1.07 min; MS (ESIpos): m/z=488 (M+H)$^+$ $^1$H-NMR (400 MHz, DMSO-d$_6$): δ [ppm]=16.77 (br. s, 1H), 10.88 (s, 1H), 8.05 (d, 1H), 8.03-7.97 (m, 2H), 7.87-7.82 (m, 3H), 7.77 (dd, 1H), 6.68 (d, 1H), 6.56 (dd, 1H), 5.71 (dd, 1H), 2.21-2.04 (m, 2H), 1.41-1.31 (m, 2H), 1.29-1.20 (m, 2H), 0.88 (t, 3H).

Example 24

4-[(2-{4-[5-Chloro-2-(trifluoromethyl)phenyl]-2-oxopyridin-1(2H)-yl}-3-cyclopropylpropanoyl)-amino]benzoic acid (racemate)

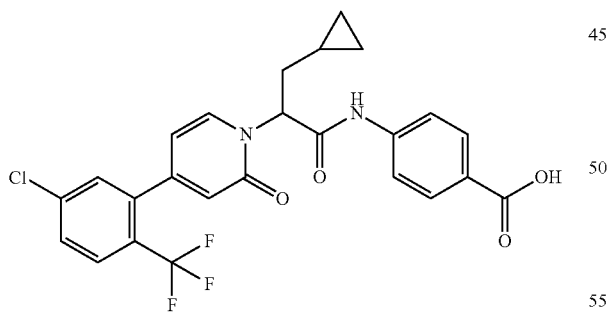

200 mg (purity 48%, 0.19 mmol) of methyl 4-[(2-{4-[5-chloro-2-(trifluoromethyl)phenyl]-2-oxopyridin-1(2H)-yl}-3-cyclopropylpropanoyl)amino]benzoate (racemate) (Example 6.1G) were hydrolysed with lithium hydroxide according to General Method 3. Yield: 46 mg (49% of theory)

LC/MS [Method 1]: $R_t$=1.14 min; MS (ESIpos): m/z=505 (M+H)$^+$ $^1$H-NMR (400 MHz, DMSO-d$_6$): δ [ppm]=12.78 (br. s, 1H), 10.84 (s, 1H), 7.90 (t, 4H), 7.78-7.71 (m, 3H), 7.64 (d, 1H), 6.39 (d, 1H), 6.33 (dd, 1H), 5.88-5.77 (m, 1H), 5.74-5.67 (m, 1H), 5.05-4.96 (m, 2H), 2.27-2.15 (m, 2H), 2.11-1.93 (m, 2H).

Example 25

4-[(2-{4-[5-Chloro-2-(trifluoromethoxy)phenyl]-2-oxopyridin-1(2H)-yl}-3-cyclopropylpropanoyl)-amino]benzoic acid (racemate)

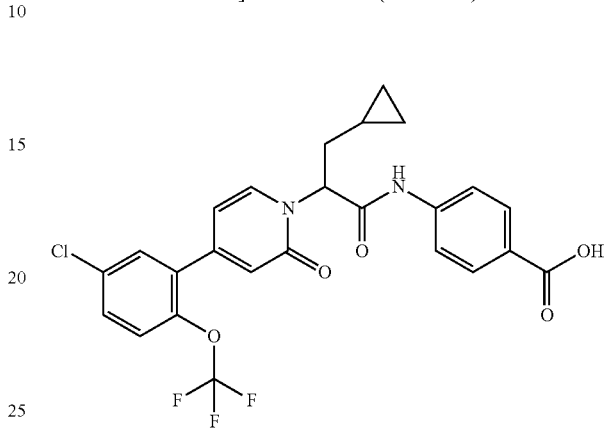

77 mg (purity 92%, 0.12 mmol) of tert-butyl 4-[(2-{4-[5-chloro-2-(trifluoromethoxy)phenyl]-2-oxopyridin-1(2H)-yl}-3-cyclopropylpropanoyl)amino]benzoate (racemate) (Example 6.2C) were hydrolysed with TFA according to General Method 2. Yield: 41 mg (64% of theory)

LC/MS [Method 3]: $R_t$=2.60 min; MS (ESIpos): m/z=521 (M+H)$^+$ $^1$H-NMR (400 MHz, DMSO-d$_6$): δ [ppm]=12.78 (br. s, 1H), 10.84 (s, 1H), 7.94-7.88 (m, 3H), 7.76-7.71 (m, 3H), 7.67 (dd, 1H), 6.58 (dd, 1H), 6.55 (d, 1H), 6.45 (dd, 1H), 5.87-5.76 (m, 1H), 5.72-5.65 (m, 1H), 5.03-4.95 (m, 2H), 2.27-2.17 (m, 2H), 2.09-1.92 (m, 2H).

Example 26

2-[4-(5-Chloro-2-cyanophenyl)-2-oxopyridin-1(2H)-yl]-3-phenyl-N-[4-(1H-tetrazol-5-yl)phenyl]propanamide/diethylamine adduct (racemate)

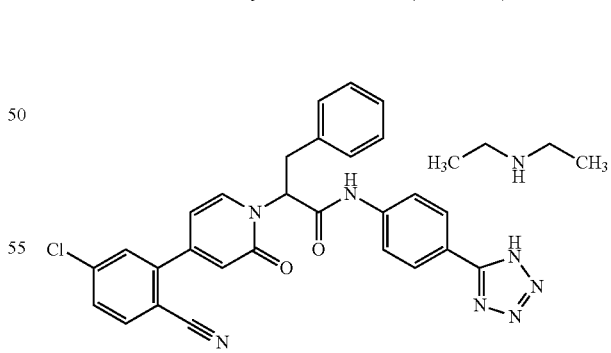

77 mg (purity 85%, 0.17 mmol) of 2-[4-(5-chloro-2-cyanophenyl)-2-oxopyridin-1(2H)-yl]-3-phenylpropanoic acid (racemate) (Example 7.1C) and 31 mg (0.19 mmol) of 4-(1H-tetrazol-5-yl)aniline were reacted according to General Method 1. Yield: 17 mg (purity 94%, 16% of theory)

LC/MS [Method 1]: $R_t$=1.02 min; MS (ESIpos): m/z=522 (M+H)$^+$

¹H-NMR (400 MHz, DMSO-d₆): δ [ppm]=10.66 (s, 1H), 8.16 (d, 1H), 8.01 (d, 1H), 7.92 (d, 2H), 7.77 (d, 1H), 7.74 (dd, 1H), 7.65 (d, 2H), 7.33-7.24 (m, 4H), 7.21-7.16 (m, 1H), 6.56 (d, 1H), 6.50 (dd, 1H), 6.10 (dd, 1H), 2.93 (q, 4H), 1.15 (t, 6H).

Example 27

4-{[2-{4-[5-Chloro-2-(trifluoromethyl)phenyl]-2-oxopyridin-1(2H)-yl}-3-(pyridin-2-yl)propanoyl]amino}benzoic acid (racemate)

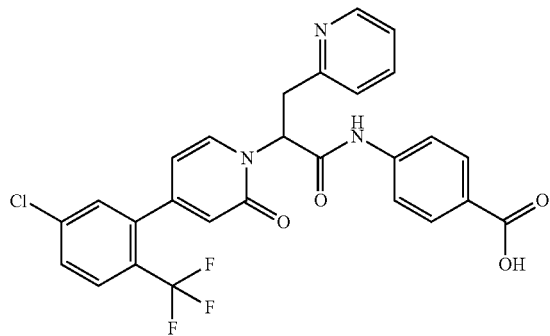 [SMILES: O=C(O)c1ccc(NC(=O)C(Cc2ccccn2)n2ccc(-c3cc(Cl)ccc3C(F)(F)F)cc2=O)cc1]

163 mg (purity 93%, 0.25 mmol) of tert-butyl 4-[(2-{4-[5-chloro-2-(trifluoromethoxy)phenyl]-2-oxopyridin-1(2H)-yl}-3-cyclopropylpropanoyl)amino]benzoate (racemate) (Example 8.1E) were hydrolysed with TFA according to General Method 2. Yield: 98 mg (71% of theory)

LC/MS [Method 1]: R$_t$=1.01 min; MS (ESIpos): m/z=542 (M+H)⁺

¹H-NMR (400 MHz, DMSO-d₆): δ [ppm]=12.77 (br. s, 1H), 10.92 (s, 1H), 8.48 (d, 1H), 7.95-7.89 (m, 3H), 7.86 (d, 1H), 7.78-7.69 (m, 4H), 7.54 (d, 1H), 7.35 (d, 1H), 7.25 (dd, 1H), 6.28 (d, 1H), 6.23-6.16 (m, 2H), 3.71-3.56 (m, 2H).

Example 28

4-{[2-{4-[5-Chloro-2-(trifluoromethyl)phenyl]-2-oxopyridin-1(2H)-yl}-3-(pyridin-3-yl)propanoyl]amino}benzoic acid (racemate)

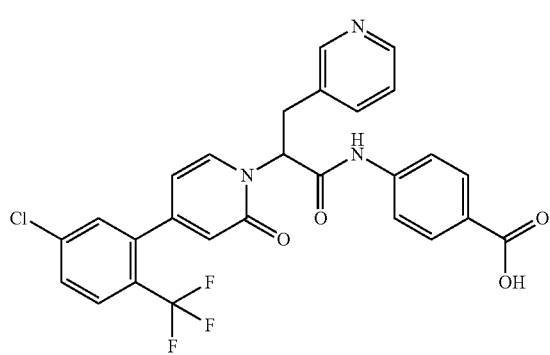 [SMILES: O=C(O)c1ccc(NC(=O)C(Cc2cccnc2)n2ccc(-c3cc(Cl)ccc3C(F)(F)F)cc2=O)cc1]

33 mg (purity 94%, 0.05 mmol) of tert-butyl 4-{[2-{4-[5-chloro-2-(trifluoromethyl)phenyl]-2-oxopyridin-1(2H)-yl}-3-(pyridin-3-yl)propanoyl]amino}benzoate (racemate) (Example 9.1C) were hydrolysed with TFA according to General Method 2. Yield: 11 mg (40% of theory)

LC/MS [Method 1]: R$_t$=0.91 min; MS (ESIpos): m/z=542 (M+H)⁺

¹H-NMR (400 MHz, DMSO-d₆): δ [ppm]=12.79 (br. s, 1H), 10.87 (s, 1H), 8.48 (s, 1H), 8.41 (d, 1H), 8.05 (d, 1H), 7.93 (d, 2H), 7.86 (d, 1H), 7.76-7.71 (m, 3H), 7.61 (d, 1H), 7.54 (s, 1H), 7.28 (dd, 1H), 6.30.6.26 (m, 2H), 6.05 (dd, 1H), 3.56-3.43 (m, 2H).

Example 29

4-({2-[4-(2-Bromo-5-chlorophenyl)-2-oxopyridin-1(2H)-yl]-3-(pyridin-3-yl)propanoyl}amino)benzoic acid (racemate)

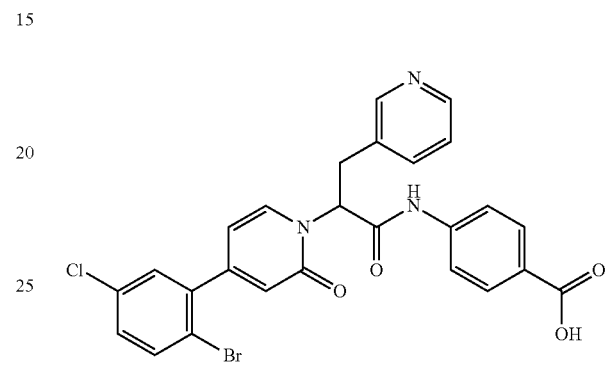

65 mg (purity 85%, 0.10 mmol) of methyl 4-({2-[4-(2-bromo-5-chlorophenyl)-2-oxopyridin-1(2H)-yl]-3-(pyridin-3-yl)propanoyl}amino)benzoate (racemate) (Example 9.2E) were hydrolysed with lithium hydroxide according to General Method 3. Yield: 14 mg (26% of theory)

LC/MS [Method 1]: R$_t$=0.90 min; MS (ESIpos): m/z=552 (M+H)⁺

¹H-NMR (400 MHz, DMSO-d₆): δ [ppm]=12.79 (br. s, 1H), 10.86 (s, 1H), 8.48 (s, 1H), 8.40 (d, 1H), 8.06 (d, 1H), 7.93 (d, 2H), 7.78-7.70 (m, 3H), 7.65 (dd, 1H), 7.45 (d, 1H), 7.44 (dd, 1H), 7.31 (dd, 1H), 6.35-6.31 (m, 2H), 6.05 (dd, 1H), 3.56-3.43 (m, 2H).

Example 30

4-{[2-{4-[5-Chloro-2-(trifluoromethyl)phenyl]-2-oxopyridin-1(2H)-yl}-3-(pyridin-4-yl)propanoyl]amino}benzoic acid (racemate)

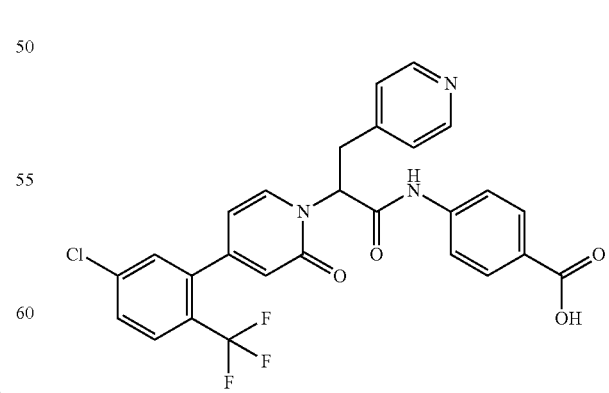

383 mg (0.62 mmol) of tert-butyl 4-{[2-{4-[5-chloro-2-(trifluoromethyl)phenyl]-2-oxopyridin-1(2H)-yl}-3-(pyridin-4-yl)propanoyl]amino}benzoate (racemate) (Example 10.1C) were hydrolysed with TFA according to General Method 2. Yield: 180 mg (53% of theory)

LC/MS [Method 1]: $R_t$=0.86 min; MS (ESIpos): m/z=542 (M+H)$^+$ $^1$H-NMR (400 MHz, DMSO-d$_6$): δ [ppm]=12.85 (br. s, 1H), 10.88 (s, 1H), 8.64 (d, 2H), 8.01 (d, 1H), 7.94 (d, 2H), 7.87 (d, 1H), 7.77-7.70 (m, 3H), 7.58-7.52 (m, 3H), 6.31-6.26 (m, 2H), 6.13 (dd, 1H), 3.72-3.59 (m, 2H).

Example 31

4-{[2-{4-[5-Chloro-2-(trifluoromethyl)phenyl]-2-oxopyridin-1(2H)-yl}-3-(pyridin-4-yl)propanoyl]amino}benzoic acid (enantiomer 1)

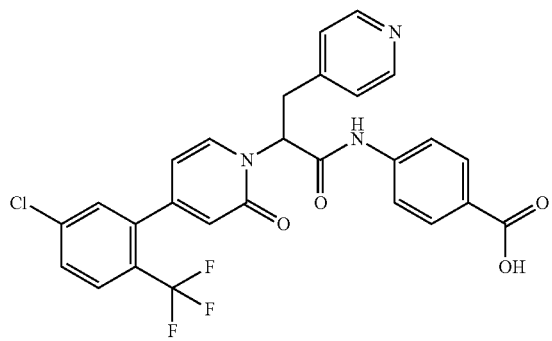 [SMILES: O=C(O)c1ccc(NC(=O)C(Cc2ccncc2)n2ccc(-c3cc(Cl)ccc3C(F)(F)F)cc2=O)cc1]

Enantiomer separation of 155 mg of the racemate from Example 30 gave 56 mg (purity 89%) of the title compound Example 31 (enantiomer 1): Chiral HPLC: $R_t$=6.8 min; 100% ee.

Separation method: column: Daicel Chiralpak AZ-H 5 μm 250×20 mm; mobile phase: 50% isohexane, 46% ethanol, 4% 2% strength trifluoroacetic acid in ethanol; oven: 25° C.; flow rate: 20 ml/min; UV detection: 230 nm.

Analysis: column: Daicel Chiralpak AZ-H 5 μm 250×4.6 mm; mobile phase: 50% isohexane, 50% ethanol+0.2% TFA in 1% water; oven: 30° C.; flow rate: 1 ml/min; UV detection: 220 nm.

Example 32

4-{[2-{4-[5-Chloro-2-(trifluoromethyl)phenyl]-2-oxopyridin-1(2H)-yl}-3-(pyridin-4-yl)propanoyl]amino}benzoic acid (enantiomer 2)

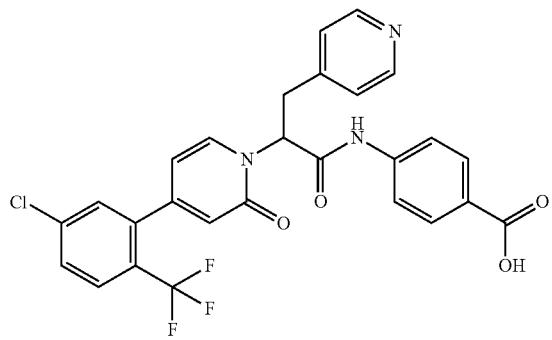 [SMILES: O=C(O)c1ccc(NC(=O)C(Cc2ccncc2)n2ccc(-c3cc(Cl)ccc3C(F)(F)F)cc2=O)cc1]

Enantiomer separation of 155 mg of the racemate from Example 30 gave 21 mg of the title compound Example 32 (enantiomer 2): Chiral HPLC: $R_t$=10.6 min; 95% ee.

Separation method: column: Daicel Chiralpak AZ-H 5 μm 250×20 mm; mobile phase: 50% isohexane, 46% ethanol, 4% 2% strength trifluoroacetic acid in ethanol; oven: 25° C.; flow rate: 20 ml/min; UV detection: 230 nm.

Analysis: column: Daicel Chiralpak AZ-H 5 μm 250×4.6 mm; mobile phase: 50% isohexane, 50% ethanol+0.2% TFA in 1% water; oven: 30° C.; flow rate: 1 ml/min; UV detection: 220 nm.

Example 33

4-({2-[4-(2-Bromo-5-chlorophenyl)-2-oxopyridin-1(2H)-yl]-3-(pyridin-4-yl)propanoyl}amino)benzoic acid (racemate)

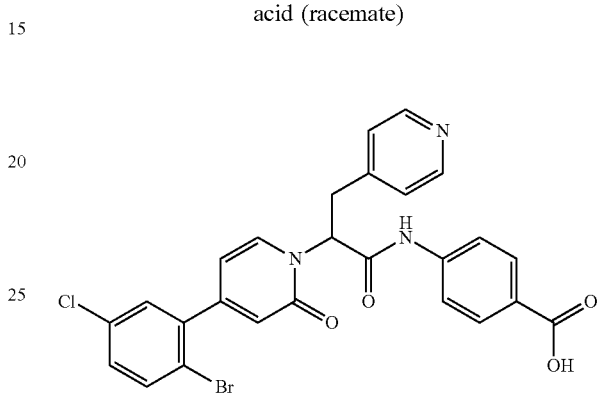

734 mg (purity 92%, 1.11 mmol) of tert-butyl 4-({2-[4-(2-bromo-5-chlorophenyl)-2-oxopyridin-1(2H)-yl]-3-(pyridin-4-yl)propanoyl}amino)benzoate (racemate) (Example 10.2C) were hydrolysed with TFA according to General Method 2. Yield: 126 mg (21% of theory)

LC/MS [Method 1]: $R_t$=0.83 min; MS (ESIpos): m/z=552 (M+H)$^+$ $^1$H-NMR (400 MHz, DMSO-d$_6$): δ [ppm]=12.85 (br. s, 1H), 10.88 (s, 1H), 8.48 (d, 2H), 8.02 (d, 1H), 7.93 (d, 2H), 7.78-7.71 (m 3H), 7.48 (d, 1H), 7.44 (dd, 1H), 7.31 (d, 1H), 6.34 (d, 1H), 6.31 (dd, 1H), 6.09 (dd, 1H), 3.57-3.49 (m, 2H).

Example 34

4-({2-[4-(5-Chloro-2-cyanophenyl)-5-fluoro-2-oxopyridin-1(2H)-yl]propanoyl}amino)benzoic acid (racemate)

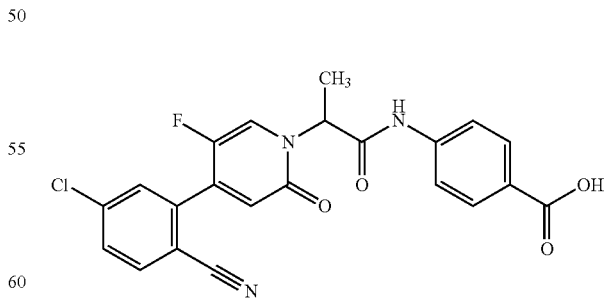

53 mg (0.11 mmol) of tert-butyl 4-({2-[4-(5-chloro-2-cyanophenyl)-5-fluoro-2-oxopyridin-1(2H)-yl] propanoyl}amino)benzoate (racemate) (Example 11.1E) were hydrolysed with TFA according to General Method 2. Yield: 36 mg (77% of theory).

LC/MS [Method 1]: $R_t$=0.90 min; MS (ESIpos): m/z=440 (M+H)$^+$ $^1$H-NMR (400 MHz, DMSO-d$_6$): δ [ppm]=12.78 (br. s, 1H), 10.77 (s, 1H), 8.24 (d, 1H), 8.09 (d, 1H), 7.91 (d, 2H), 7.88 (d, 1H), 7.82 (dd, 1H), 7.72 (d, 2H), 6.67 (d, 1H), 5.55 (q, 1H), 1.72 (d, 3H).

Example 35

4-({2-[5-Chloro-4-(5-chloro-2-cyanophenyl)-2-oxopyridin-1(2H)-yl]propanoyl}amino)benzoic acid (racemate)

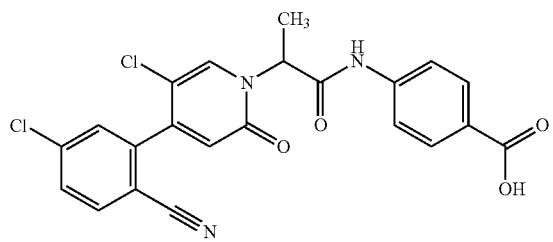 [SMILES: CC(C(=O)Nc1ccc(C(=O)O)cc1)n1cc(Cl)c(-c2cc(Cl)ccc2C#N)cc1=O]

281 mg (purity 58%, 0.32 mmol) of tert-butyl 4-({2-[5-chloro-4-(5-chloro-2-cyanophenyl)-2-oxopyridin-1(2H)-yl]propanoyl}amino)benzoate (racemate) (Example 12.1E) were hydrolysed with TFA according to General Method 2. Yield: 97 mg (67% of theory)

LC/MS [Method 1]: $R_t$=0.96 min; MS (ESIpos): m/z=456 (M+H)$^+$ $^1$H-NMR (400 MHz, DMSO-d$_6$): δ [ppm]=12.78 (s, 1H), 10.77 (s, 1H), 8.19 (s, 1H), 8.08 (d, 1H), 7.92 (d, 2H), 7.80 (d, 2H), 7.73 (d, 2H), 6.68 (s, 1H), 5.56 (q, 1H), 1.74 (d, 3H).

Example 36

4-({2-[5-Chloro-4-(5-chloro-2-cyanophenyl)-2-oxopyridin-1(2H)-yl]propanoyl}amino)benzoic acid (enantiomer 1)

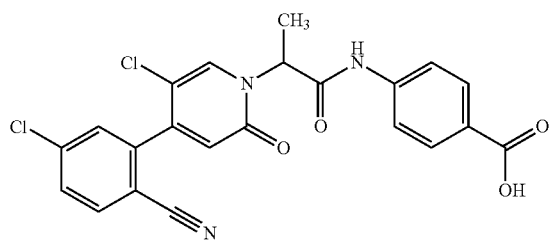 [SMILES: CC(C(=O)Nc1ccc(C(=O)O)cc1)n1cc(Cl)c(-c2cc(Cl)ccc2C#N)cc1=O]

Enantiomer separation of 59 mg of the racemate from Example 35 gave 24 mg of the title compound Example 36 (enantiomer 1): Chiral HPLC: $R_t$=8.6 min; 100% ee.

Separation method: column: Daicel Chiralpak AZ-H 5 μm 250×30 mm; mobile phase: 50% isohexane, 50% ethanol; oven: 25° C.; flow rate: 40 ml/min; UV detection: 220 nm.

Analysis: column: Daicel Chiralpak AZ-H 5 μm 250×4.6 mm; mobile phase: 50% isohexane, 50% ethanol+0.2% TFA in 1% water; oven: 30° C.; flow rate: 1 ml/min; UV detection: 220 nm.

Example 37

4-({2-[5-Chloro-4-(5-chloro-2-cyanophenyl)-2-oxopyridin-1(2H)-yl]propanoyl}amino)benzoic acid (enantiomer 2)

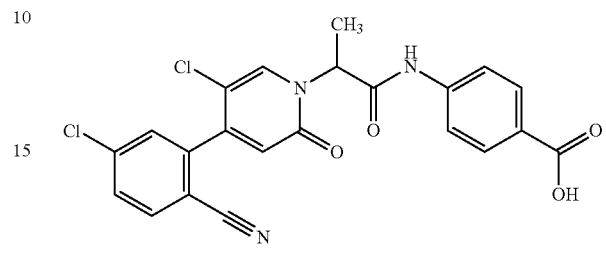

Enantiomer separation of 59 mg of the racemate from Example 35 gave 15 mg of the title compound Example 37 (enantiomer 2): Chiral HPLC: $R_t$=15.5 min; 100% ee.

Separation method: column: Daicel Chiralpak AZ-H 5 μm 250×30 mm; mobile phase: 50% isohexane, 50% ethanol; oven: 25° C.; flow rate: 40 ml/min; UV detection: 220 nm.

Analysis: column: Daicel Chiralpak AZ-H 5 μm 250×4.6 mm; mobile phase: 50% isohexane, 50% ethanol+0.2% TFA in 1% water; oven: 30° C.; flow rate: 1 ml/min; UV detection: 220 nm.

Example 38

4-[(2-{5-Chloro-4-[5-chloro-2-(difluoromethyl)phenyl]-2-oxopyridin-1(2H)-yl}propanoyl)amino]benzoic acid (racemate)

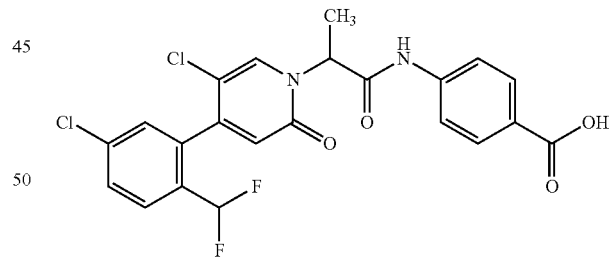

79 mg (0.15 mmol) of tert-butyl 4-[(2-{5-chloro-4-[5-chloro-2-(difluoromethyl)phenyl]-2-oxopyridin-1(2H)-yl}propanoyl)amino]benzoate (racemate) (Example 14.1E) were hydrolysed with TFA according to General Method 2. Yield: 54 mg (76% of theory)

LC/MS [Method 1]: $R_t$=1.03 min; MS (ESIpos): m/z=481 (M+H)$^+$ $^1$H-NMR (400 MHz, DMSO-d$_6$): δ [ppm]=12.79 (br. s, 1H), 10.75/10.72 (2s, 1H), 8.14/8.12 (2s, 1H), 7.92 (d, 2H), 7.80-7.70 (m, 4H), 7.54 (br. d, 1H), 7.02-6.75 (br. t, 1H), 6.50/6.49 (2s, 1H), 5.57 (q, 1H), 1.73/1.71 (2d, 3H).

Example 39

4-[(2-{5-Chloro-4-[5-chloro-2-(trifluoromethyl)phenyl]-2-oxopyridin-1(2H)-yl}propanoyl)amino]benzoic acid (racemate)

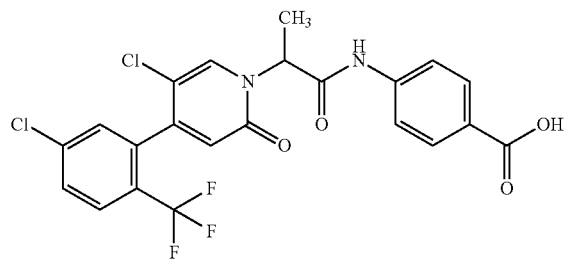 [SMILES: CC(C(=O)Nc1ccc(C(=O)O)cc1)n1cc(Cl)c(-c2cc(Cl)ccc2C(F)(F)F)cc1=O]

75 mg (0.14 mmol) of tert-butyl 4-[(2-{5-chloro-4-[5-chloro-2-(trifluoromethyl)phenyl]-2-oxopyridin-1(2H)-yl}propanoyl)amino]benzoate (racemate) (Example 15.1E) were hydrolysed with TFA according to General Method 2. Yield: 56 mg (83% of theory)

LC/MS [Method 1]: $R_t$=1.07 min; MS (ESIpos): m/z=499 (M+H)$^+$ $^1$H-NMR (400 MHz, DMSO-d$_6$): δ [ppm]=12.79 (s, 1H), 10.78/10.75 (2s, 1H), 8.12/8.11 (2s, 1H), 7.95-7.89 (m, 3H), 7.80 (s, 1H), 7.72 (d, 2H), 7.69 (br. t, 1H), 6.52/6.50 (2s, 1H), 5.57 (q, 1H), 1.73/1.71 (2d, 3H).

Example 40

4-({2-[5-Chloro-4-(5-chloro-2-cyanophenyl)-2-oxopyridin-1(2H)-yl]propanoyl}amino)-2-fluorobenzoic acid (racemate)

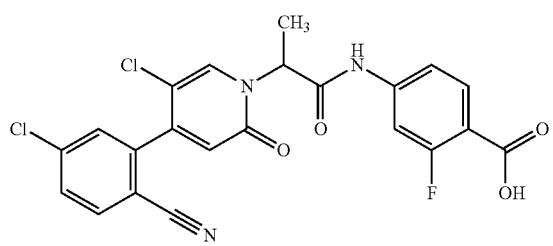 [SMILES: CC(C(=O)Nc1ccc(C(=O)O)c(F)c1)n1cc(Cl)c(-c2cc(Cl)ccc2C#N)cc1=O]

Under argon and at RT, 37 mg (0.30 mmol, 1.0 eq.) of N,N'-diisopropylcarbodiimide were added to a solution of 100 mg (0.30 mmol) of 2-[5-chloro-4-(5-chloro-2-cyanophenyl)-2-oxopyridin-1(2H)-yl]propanoic acid (racemate) (Example 12.1D) in 2 ml of dichloroethane, the mixture was stirred for 10 min, 46 mg (0.30 mmol) of 4-amino-2-fluorobenzoic acid were added and the mixture was stirred under reflux overnight. Subsequently, the reaction mixture was concentrated under reduced pressure and the crude product was purified by preparative HPLC (Reprosil C18, water/methanol gradient). Yield: 41 mg (29% of theory)

LC/MS [Method 1]: $R_t$=0.98 min; MS (ESIpos): m/z=474 (M+H)$^+$ $^1$H-NMR (400 MHz, DMSO-d$_6$): δ [ppm]=13.04 (br. s, 1H), 10.93 (s, 1H), 8.19 (s, 1H), 8.07 (d, 1H), 7.87 (t, 1H), 7.83-7.76 (m, 1H), 7.80 (dd, 1H), 7.65 (dd, 1H), 7.41 (dd, 1H), 6.69 (s, 1H), 5.52 (q, 1H), 1.75 (d, 3H).

Example 41

2-[5-Chloro-4-(5-chloro-2-cyanophenyl)-2-oxopyridin-1(2H)-yl]-N-{4-[3-(trifluoromethyl)-1H-1,2,4-triazol-5-yl]phenyl}propanamide (racemate)

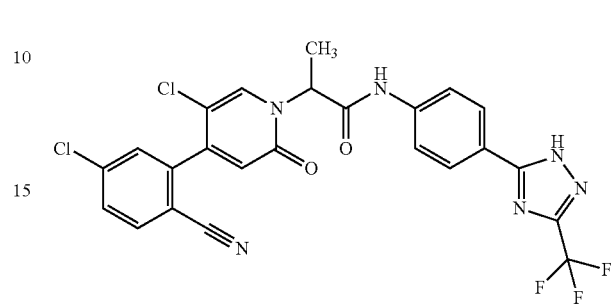

126 mg (purity 66%, 0.25 mmol) of 2-[5-chloro-4-(5-chloro-2-cyanophenyl)-2-oxopyridin-1(2H)-yl]propanoic acid (racemate) (Example 12.1D) and 64 mg (0.27 mmol) of 4-[3-(trifluoromethyl)-1H-1,2,4-triazol-5-yl]aniline (Example 1.1C) were reacted according to General Method 1. Yield: 76 mg (57% of theory)

LC/MS [Method 1]: $R_t$=1.10 min; MS (ESIpos): m/z=547 (M+H)$^+$ $^1$H-NMR (400 MHz, DMSO-d$_6$): δ [ppm]=15.20 (s, 1H), 10.77 (s, 1H), 8.20 (s, 1H), 8.08 (d, 1H), 8.01 (d, 2H), 7.84-7.77 (m, 4H), 6.69 (s, 1H), 5.58 (q, 1H), 1.76 (d, 3H).

Example 42

2-[5-Chloro-4-(5-chloro-2-cyanophenyl)-2-oxopyridin-1(2H)-yl]-N-[4-(5-oxo-2,5-dihydro-1H-pyrazol-3-yl)phenyl]propanamide (racemate)

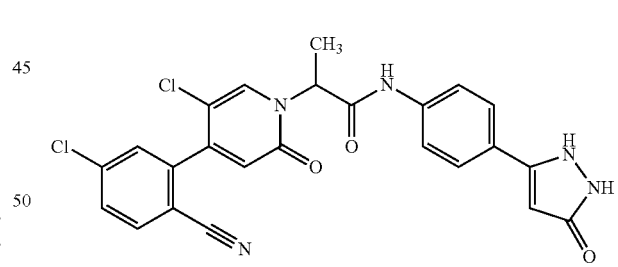

17.8 mg (purity 78%, 0.02 mmol) of tert-butyl 5-[4-({2-[5-chloro-4-(5-chloro-2-cyanophenyl)-2-oxopyridin-1(2H)-yl]propanoyl}amino)phenyl]-3-oxo-2,3-dihydro-1H-pyrazole-1-carboxylate (racemate) (Example 12.2A) were reacted with TFA according to General Method 2. Yield: 6 mg (55% of theory)

LC/MS [Method 1]: $R_t$=0.92 min; MS (ESIpos): m/z=494 (M+H)$^+$ $^1$H-NMR (400 MHz, DMSO-d$_6$): δ [ppm]=11.96 (br. s, 1H), 10.54 (s, 1H), 9.56 (br. s, 1H), 8.18 (s, 1H), 8.07 (d, 1H), 7.80 (m, 2H), 7.63 (m, 4H), 6.67 (s, 1H), 5.85 (br. s, 1H), 5.59 (q, 1H), 1.73 (d, 3H).

Example 43

2-[5-Chloro-4-(5-chloro-2-cyanophenyl)-2-oxopyridin-1(2H)-yl]-N-[4-(1H-imidazol-4-yl)phenyl]propanamide (racemate)

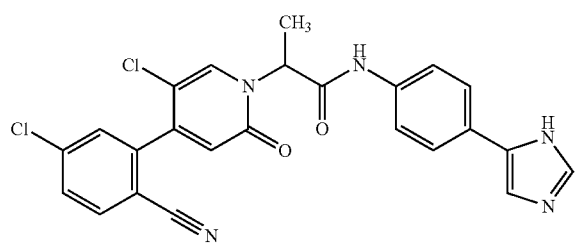 [SMILES: CC(C(=O)Nc1ccc(-c2cnc[nH]2)cc1)n1cc(Cl)c(-c2cc(Cl)ccc2C#N)cc1=O]

102 mg (purity 82%, 0.25 mmol) of 2-[5-chloro-4-(5-chloro-2-cyanophenyl)-2-oxopyridin-1(2H)-yl]propanoic acid (racemate) (Example 12.1D) and 43 mg (0.27 mmol) of 4-0H-imidazol-4-yl)aniline were reacted according to General Method 1. Yield: 5 mg (purity 94%, 4% of theory)

LC/MS [Method 1]: $R_t$=0.75 min; MS (ESIpos): m/z=478 (M+H)$^+$ $^1$H-NMR (400 MHz, DMSO-$d_6$): δ [ppm]=12.22 (br. s, 1H), 10.46 (s, 1H), 8.20 (s, 1H), 8.08 (d, 1H), 7.82 (m, 2H), 7.73 (m, 3H), 7.61 (d, 2H), 7.53 (br. s, 1H), 6.69 (s, 1H), 5.62 (q, 1H), 1.75 (d, 3H).

Example 44

2-[5-Chloro-4-(5-chloro-2-cyanophenyl)-2-oxopyridin-1(2H)-yl]-N-[2-(trifluoromethyl)-1H-benzimidazol-6-yl]propanamide (racemate)

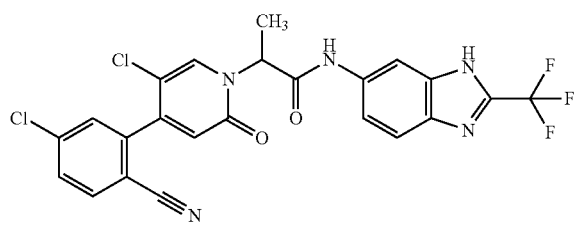 [SMILES: CC(C(=O)Nc1ccc2nc(C(F)(F)F)[nH]c2c1)n1cc(Cl)c(-c2cc(Cl)ccc2C#N)cc1=O]

68 mg (purity 94%, 0.20 mmol) of 2-[5-chloro-4-(5-chloro-2-cyanophenyl)-2-oxopyridin-1(2H)-yl]propanoic acid (racemate) (Example 12.1D) and 44 mg (0.22 mmol) of 2-(trifluoromethyl)-1H-benzimidazole-6-amine were reacted according to General Method 1. Yield: 63 mg (60% of theory)

LC/MS [Method 1]: $R_t$=1.01 min; MS (ESIpos): m/z=520 (M+H)$^+$ $^1$H-NMR (400 MHz, DMSO-$d_6$): δ [ppm]=13.85 (s, 1H), 10.64 (s, 1H), 8.22 (s, 1H), 8.18 (s, 1H), 8.08 (d, 1H), 7.80 (m, 2H), 7.74 (br. s, 1H), 7.41 (br. s, 1H), 6.69 (s, 1H), 1.06 (q, 1H), 1.76 (d, 3H).

Example 45

4-({2-[5-Chloro-4-(5-chloro-2-cyanophenyl)-2-oxopyridin-1(2H)-yl]-3-cyclopropylpropanoyl}amino)benzoic acid (racemate)

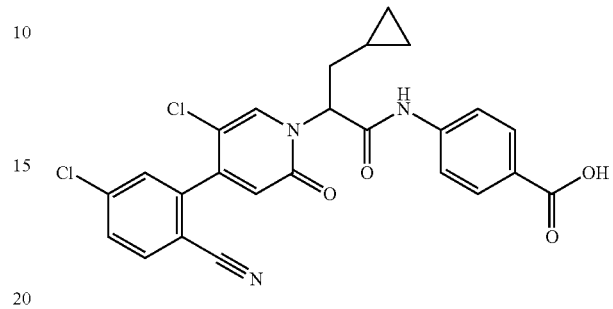

192 mg (0.34 mmol) of tert-butyl 4-({2-[5-chloro-4-(5-chloro-2-cyanophenyl)-2-oxopyridin-1(2H)-yl]-3-cyclopropylpropanoyl}amino)benzoate (racemate) (Example 13.1D) were hydrolysed with TFA according to General Method 2. Yield: 141 mg (82% of theory)

LC/MS [Method 1]: $R_t$=1.07 min; MS (ESIpos): m/z=496 (M+H)$^+$ $^1$H-NMR (400 MHz, DMSO-$d_6$): δ [ppm]=12.80 (s, 1H), 10.83 (s, 1H), 8.25 (s, 1H), 8.07 (d, 1H), 7.92 (d, 2H), 7.84-7.78 (m, 2H), 7.73 (d, 2H), 6.69 (s, 1H), 5.76 (m, 1H), 2.25 (m, 1H), 1.91 (m, 1H), 0.70-0.60 (m, 1H), 0.48-0.32 (m, 2H), 0.22-0.09 (m, 2H).

Example 46

4-({2-[5-Chloro-4-(5-chloro-2-cyanophenyl)-2-oxopyridin-1(2H)-yl]-3-cyclopropylpropanoyl}amino)benzoic acid (enantiomer 1)

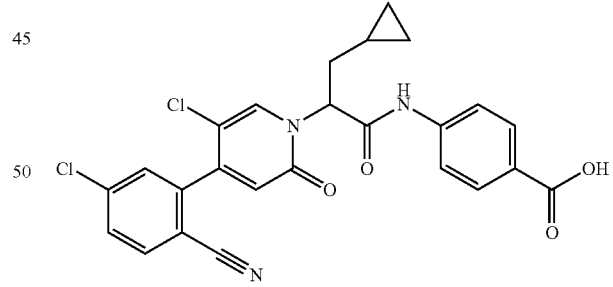

Enantiomer separation of 138 mg of the racemate from Example 45 gave 42 mg of the title compound Example 46 (enantiomer 1): Chiral HPLC: $R_t$=5.7 min; 100% ee.

Separation method: column: Daicel Chiralpak AZ-H 5 µm 250×30 mm; mobile phase: 50% isohexane, 50% 2-propanol; oven: 20° C.; flow rate: 50 ml/min; UV detection: 270 nm.

Analysis: column: Daicel Chiralpak AZ-H 5 µm 250×4.6 mm; mobile phase: 50% isohexane, 50% 2-propanol+0.2% TFA in 1% water; oven: 20° C.; flow rate: 1 ml/min; UV detection: 220 nm.

Example 47

4-({2-[5-Chloro-4-(5-chloro-2-cyanophenyl)-2-oxopyridin-1(2H)-yl]-3-cyclopropylpropanoyl}amino)benzoic acid (enantiomer 2)

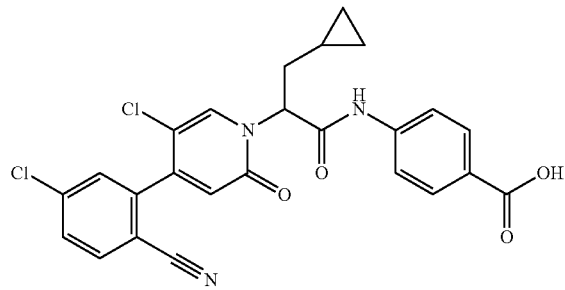 [SMILES: N#Cc1ccc(Cl)cc1-c1cc(=O)n(C(CC2CC2)C(=O)Nc2ccc(C(=O)O)cc2)cc1Cl]

Enantiomer separation of 138 mg of the racemate from Example 45 gave 41 mg of the title compound Example 47 (enantiomer 2): Chiral HPLC: $R_t$=11.9 min; 97% ee.

Separation method: column: Daicel Chiralpak AZ-H 5 μm 250×30 mm; mobile phase: 50% isohexane, 50% 2-propanol; oven: 20° C.; flow rate: 50 ml/min; UV detection: 270 nm.

Analysis: column: Daicel Chiralpak AZ-H 5 μm 250×4.6 mm; mobile phase: 50% isohexane, 50% 2-propanol+0.2% TFA in 1% water; oven: 20° C.; flow rate: 1 ml/min; UV detection: 220 nm.

Example 48

4-({2-[4-(5-Chloro-2-cyanophenyl)-5-cyano-2-oxopyridin-1(2H)-yl]propanoyl}amino)benzoic acid (racemate)

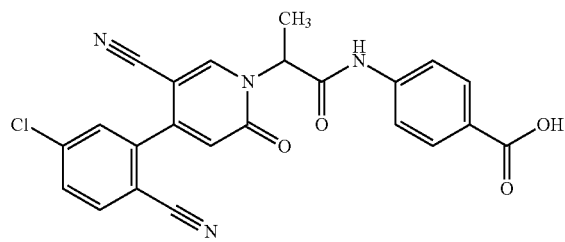 [SMILES: CC(C(=O)Nc1ccc(C(=O)O)cc1)n1cc(C#N)c(-c2cc(Cl)ccc2C#N)cc1=O]

93 mg (0.19 mmol) of tert-butyl 4-({2-[4-(5-chloro-2-cyanophenyl)-5-cyano-2-oxopyridin-1(2H)-yl]propanoyl}amino)benzoate (racemate) (Example 16.1E) were hydrolysed with TFA according to General Method 2. Yield: 91 mg (quant.)

LC/MS [Method 1]: $R_t$=0.90 min; MS (ESIpos): m/z=447 (M+H)$^+$ $^1$H-NMR (400 MHz, DMSO-d$_6$): δ [ppm]=12.80 (br. s, 1H), 10.83 (s, 1H), 8.87 (s, 1H), 8.13 (d, 1H), 7.95-7.89 (m, 3H), 7.86 (dd, 1H), 7.72 (d, 2H), 6.78 (s, 1H), 5.57 (q, 1H), 1.78 (d, 3H).

Example 49

4-[(2-{4-[5-Chloro-2-(difluoromethyl)phenyl]-5-cyano-2-oxopyridin-1(2H)-yl}propanoyl)amino]benzoic acid (racemate)

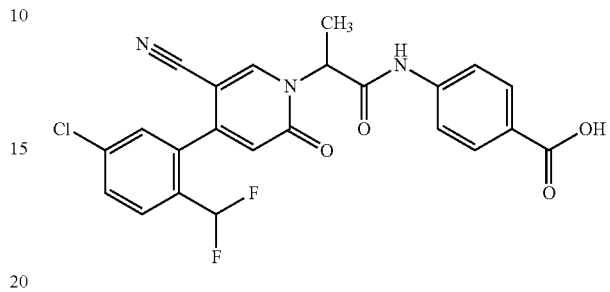

48 mg (0.09 mmol) of tert-butyl 4-[(2-{4-[5-chloro-2-(difluoromethyl)phenyl]-5-cyano-2-oxopyridin-1(2H)-yl}propanoyl)amino]benzoate (racemate) (Example 17.1D) were hydrolysed with TFA according to General Method 2. Yield: 30 mg (70% of theory)

LC/MS [Method 1]: $R_t$=0.96 min; MS (ESIpos): m/z=472 (M+H)$^+$ $^1$H-NMR (400 MHz, DMSO-d$_6$): δ [ppm]=12.80 (s, 1H), 10.80 (s, 1H), 8.79 (s, 1H), 7.92 (d, 2H), 7.84-7.58 (m, 5H), 7.12-6.85 (br. t, 1H), 6.54 (s, 1H), 5.58 (q, 1H), 1.75 (d, 3H).

Example 50

4-[(2-{4-[5-Chloro-2-(trifluoromethyl)phenyl]-5-cyano-2-oxopyridin-1(2H)-yl}propanoyl)amino]benzoic acid (racemate)

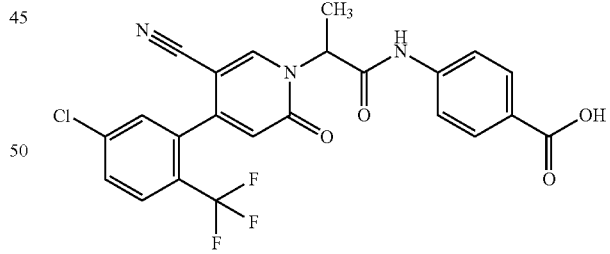

124 mg (0.22 mmol) of tert-butyl 4-[(2-{4-[5-chloro-2-(trifluoromethyl)phenyl]-5-cyano-2-oxopyridin-1(2H)-yl}propanoyl)amino]benzoate (racemate) (Example 18.1E) were hydrolysed with TFA according to General Method 2. Yield: 85 mg (79% of theory)

LC/MS [Method 1]: $R_t$=0.99 min; MS (ESIpos): m/z=490 (M+H)$^+$ $^1$H-NMR (400 MHz, DMSO-d$_6$): δ [ppm]=12.79 (s, 1H), 10.82 (d, 1H), 8.79 (s, 1H), 7.96 (dd, 1H), 7.92 (d, 2H), 7.87-7.69 (m, 4H), 6.85 (s, 1H), 5.57 (q, 1H), 1.76 (d, 3H).

Example 51

4-[(2-{4-[5-Chloro-2-(trifluoromethoxy)phenyl]-5-cyano-2-oxopyridin-1(2H)-yl}propanoyl)amino]benzoic acid (racemate)

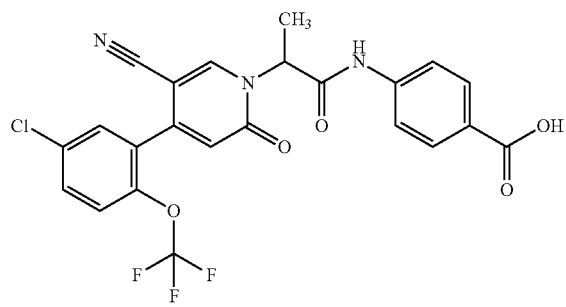 [SMILES: CC(C(=O)Nc1ccc(C(=O)O)cc1)n1cc(C#N)c(-c2cc(Cl)ccc2OC(F)(F)F)cc1=O]

107 mg (purity 94%, 0.18 mmol) of tert-butyl 4-[(2-{4-[5-chloro-2-(trifluoromethoxy)phenyl]-5-cyano-2-oxopyridin-1(2H)-yl}propanoyl)amino]benzoate (racemate) (Example 18.2A) were hydrolysed with TFA according to General Method 2. Yield: 59 mg (65% of theory)

LC/MS [Method 1]: $R_t$=1.00 min; MS (ESIpos): m/z=506 (M+H)$^+$ $^1$H-NMR (400 MHz, DMSO-d$_6$): δ [ppm]=12.79 (s, 1H), 10.80 (s, 1H), 8.79 (s, 1H), 7.92 (d, 2H), 7.78-7.61 (m, 5H), 6.65 (s, 1H), 5.55 (q, 1H), 1.76 (d, 3H).

Example 52

4-({2-[4-(5-Chloro-2-cyclopropylphenyl)-5-cyano-2-oxopyridin-1(2H)-yl]propanoyl}amino)benzoic acid (racemate)

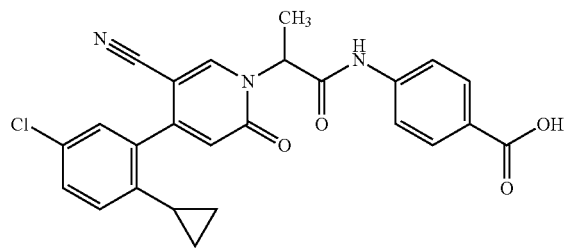 [SMILES: CC(C(=O)Nc1ccc(C(=O)O)cc1)n1cc(C#N)c(-c2cc(Cl)ccc2C2CC2)cc1=O]

66 mg (0.13 mmol) of tert-butyl 4-({2-[4-(5-chloro-2-cyclopropylphenyl)-5-cyano-2-oxopyridin-1(2H)-yl]propanoyl}amino)benzoic acid (racemate) (Example 18.3A) were hydrolysed with TFA according to General Method 2. Yield: 39 mg (68% of theory)

LC/MS [Method 1]: $R_t$=1.02 min; MS (ESIpos): m/z=462 (M+H)$^+$ $^1$H-NMR (400 MHz, DMSO-d$_6$): δ [ppm]=12.79 (s, 1H), 10.79 (s, 1H), 8.76 (s, 1H), 7.92 (d, 2H), 7.71 (d, 2H), 7.45 (dd, 1H), 7.34 (s, 1H), 7.06 (d, 1H), 6.54 (s, 1H), 5.57 (q, 1H), 1.76 (d, 3H), 1.70 (m, 1H), 0.93 (d, 2H), 0.74 (d, 2H).

Example 53

4-({2-[4-(5-Chloro-2-cyanophenyl)-5-(difluoromethyl)-2-oxopyridin-1(2H)-yl]propanoyl}amino)benzoic acid (racemate)

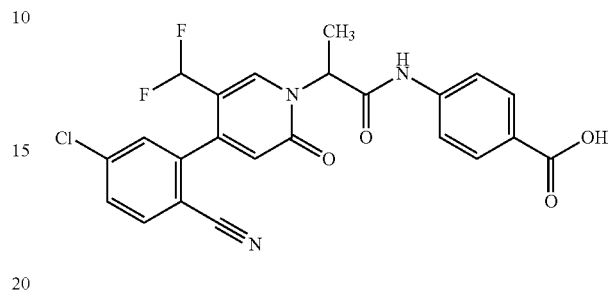

64 mg (0.12 mmol) of tert-butyl 4-({2-[4-(5-chloro-2-cyanophenyl)-5-(difluoromethyl)-2-oxopyridin-1(2H)-yl]propanoyl}amino)benzoate (racemate) (Example 19.1F) were hydrolysed with TFA according to General Method 2. Yield: 46 mg (80% of theory)

LC/MS [Method 1]: $R_t$=0.95 min; MS (ESIpos): m/z=472 (M+H)$^+$ $^1$H-NMR (400 MHz, DMSO-d$_6$): δ [ppm]=12.79 (s, 1H), 10.83 (s, 1H), 8.30 (s, 1H), 8.02 (d, 1H), 7.91 (d, 2H), 7.79-7.69 (m, 4H), 6.85 (br. t, 1H), 6.57 (s, 1H), 5.58 (q, 1H), 1.74 (d, 3H).

Example 54

4-({2-[4-(5-Chloro-2-cyanophenyl)-2-oxo-5-(trifluoromethyl)pyridin-1(2H)-yl]propanoyl}amino)benzoic acid (racemate)

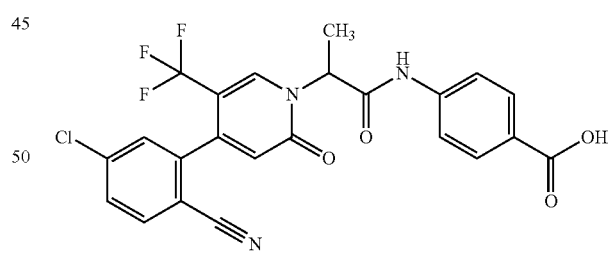

251 mg (purity 79%, 0.36 mmol) of tert-butyl 4-({2-[4-(5-chloro-2-cyanophenyl)-2-oxo-5-(trifluoromethyl)pyridin-1(2H)-yl]propanoyl}amino)benzoate (racemate) (Example 20.1E) were hydrolysed with TFA according to General Method 2. Yield: 35 mg (20% of theory)

LC/MS [Method 1]: $R_t$=1.02 min; MS (ESIpos): m/z=490 (M+H)$^+$ $^1$H-NMR (400 MHz, DMSO-d$_6$): δ [ppm]=12.80 (s, 1H), 10.80 (d, 1H), 8.33 (d, 1H), 8.06 (dd, 1H), 7.92 (d, 2H), 7.85-7.68 (m, 4H), 6.68 (d, 1H), 5.63 (q, 1H), 1.79 (t, 3H).

Example 55

4-({2-[4-(5-Chloro-2-cyanophenyl)-5-methoxy-2-oxopyridin-1(2H)-yl]propanoyl}amino)benzoic acid (racemate)

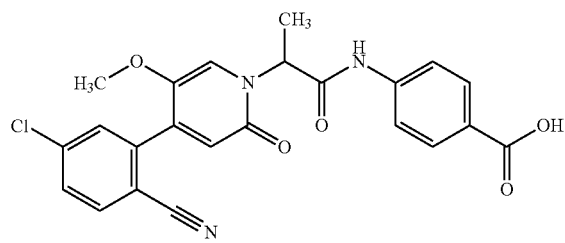 [SMILES: COc1cn(C(C)C(=O)Nc2ccc(C(=O)O)cc2)c(=O)cc1-c1cc(Cl)ccc1C#N]

42 mg (0.08 mmol) of tert-butyl 4-({2-[4-(5-chloro-2-cyanophenyl)-5-methoxy-2-oxopyridin-1(2H)-yl]propanoyl}amino)benzoate (racemate) (Example 21.1E) were hydrolysed with TFA according to General Method 2. Yield: 24 mg (64% of theory)

LC/MS [Method 1]: $R_t$=0.92 min; MS (ESIpos): m/z=452 (M+H)$^+$ $^1$H-NMR (400 MHz, DMSO-d$_6$): δ [ppm]=12.77 (s, 1H), 10.71 (s, 1H), 8.01 (d, 1H), 7.91 (d, 2H), 7.77-7.71 (m, 4H), 7.47 (s, 1H), 6.53 (s, 1H), 5.60 (q, 1H), 3.70 (s, 3H), 1.74 (d, 3H).

Example 56

4-({2-[4-(5-Chloro-2-cyanophenyl)-5-methoxy-2-oxopyridin-1(2H)-yl]propanoyl}amino)benzoic acid (enantiomer 1)

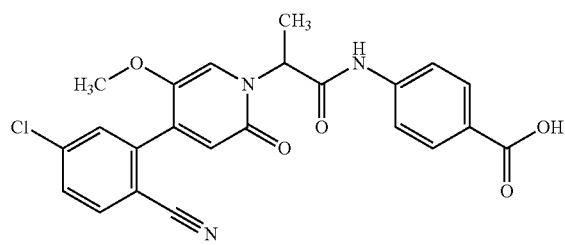 [SMILES: COc1cn(C(C)C(=O)Nc2ccc(C(=O)O)cc2)c(=O)cc1-c1cc(Cl)ccc1C#N]

Enantiomer separation of 430 mg of the racemate from Example 55 gave 214 mg of the title compound Example 56 (enantiomer 1): Chiral HPLC: $R_t$=4.3 min; 99% ee.

Separation method: column: Daicel Chiralpak OZ 5 μm 250×20 mm; mobile phase: 50% isohexane, 50% ethanol; oven: 40° C.; flow rate: 15 ml/min; UV detection: 220 nm.

Analysis: column: Daicel Chiralpak OZ 5 μm 250×4.6 mm; mobile phase: 30% isohexane, 70% ethanol+0.2% TFA in 1% water; oven: 45° C.; flow rate: 1 ml/min; UV detection: 220 nm.

Example 57

4-({2-[4-(5-Chloro-2-cyanophenyl)-5-methoxy-2-oxopyridin-1(2H)-yl]propanoyl}amino)benzoic acid (enantiomer 2)

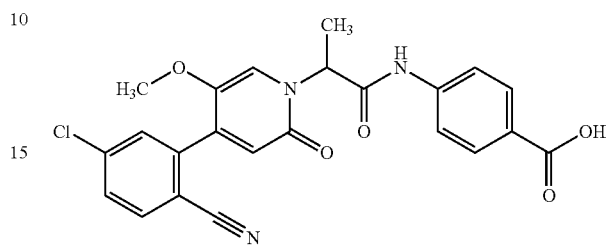

Enantiomer separation of 430 mg of the racemate from Example 55 gave 223 mg of the title compound Example 57 (enantiomer 2): Chiral HPLC: $R_t$=5.9 min; 99% ee.

Separation method: column: Daicel Chiralpak OZ 5 μm 250×20 mm; mobile phase: 50% isohexane, 50% ethanol; oven: 40° C.; flow rate: 15 ml/min; UV detection: 220 nm.

Analysis: column: Daicel Chiralpak OZ 5 μm 250×4.6 mm; mobile phase: 30% isohexane, 70% ethanol+0.2% TFA in 1% water; oven: 45° C.; flow rate: 1 ml/min; UV detection: 220 nm.

Example 58

4-({2-[4-(5-Chloro-2-nitrophenyl)-5-methoxy-2-oxopyridin-1(2H)-yl]propanoyl}amino)benzoic acid (racemate)

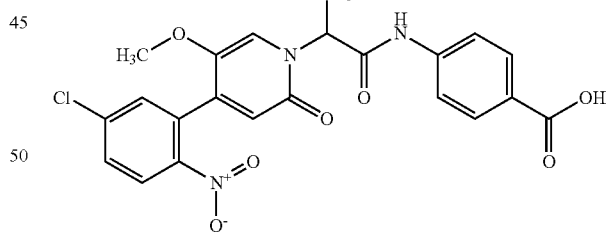

32 mg (0.06 mmol) of tert-butyl 4-({2-[4-(5-chloro-2-nitrophenyl)-5-methoxy-2-oxopyridin-1(2H)-yl]propanoyl}amino)benzoate (racemate) (Example 21.2D) were hydrolysed with TFA according to General Method 2. Yield: 10 mg (36% of theory)

LC/MS [Method 1]: $R_t$=0.93 min; MS (ESIpos): m/z=472 (M+H)$^+$ $^1$H-NMR (400 MHz, DMSO-d$_6$): δ [ppm]=12.77 (br. s, 1H), 10.69 (s, 1H), 8.14 (d, 1H), 7.91 (d, 2H), 7.80 (dd, 1H), 7.77-7.70 (m, 3H), 7.34 (s, 1H), 6.59 (s, 1H), 5.59 (q, 1H), 3.55 (s, 3H), 1.71 (d, 3H).

Example 59

4-({2-[4-(5-Chloro-2-cyanophenyl)-5-methoxy-2-oxopyridin-1(2H)-yl]-3-cyclopropylpropanoyl}amino)benzoic acid (enantiomer 1)

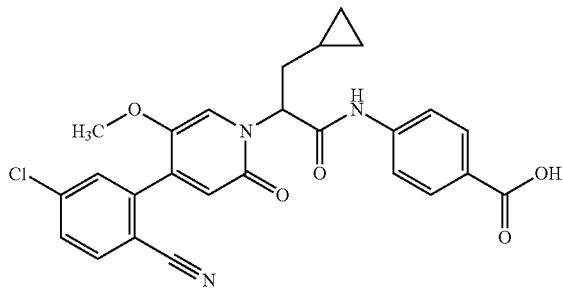 [SMILES: COc1cn(C(CC2CC2)C(=O)Nc2ccc(C(=O)O)cc2)c(=O)cc1-c1cc(Cl)ccc1C#N]

161 mg (0.29 mmol) of tert-butyl 4-({2-[4-(5-chloro-2-cyanophenyl)-5-methoxy-2-oxopyridin-1(2H)-yl]-3-cyclopropylpropanoyl}amino)benzoate (racemate) (Example 22.1D) were hydrolysed with TFA according to General Method 2.

Subsequent enantiomer separation of 88 mg of the racemate gave 56 mg of the title compound Example 59 (enantiomer 1): Chiral HPLC: $R_t$=4.1 min; 99% ee.

Separation method: column: Daicel Chiralpak IF 5 μm 250×20 mm; mobile phase: 25% isohexane, 75% ethanol; oven: 45° C.; flow rate: 15 ml/min; UV detection: 220 nm.

Analysis: column: Daicel Chiralpak IF 5 μm 250×4.6 mm; mobile phase: 25% isohexane, 75% ethanol+0.2% TFA in 1% water; oven: 30° C.; flow rate: 1 ml/min; UV detection: 220 nm.

LC/MS [Method 1]: $R_t$=1.01 min; MS (ESIpos): m/z=492 (M+H)$^+$ $^1$H-NMR (400 MHz, DMSO-d$_6$): δ [ppm]=12.77 (br. s, 1H), 10.79 (s, 1H), 8.00 (d, 1H), 7.91 (d, 2H), 7.78-7.71 (m, 4H), 7.54 (s, 1H), 6.53 (s, 1H), 5.80 (dd, 1H), 3.70 (s, 3H), 2.28-2.18 (m, 1H), 1.96-1.87 (m, 1H), 0.71-0.61 (m, 1H), 0.47-0.33 (m, 2H), 0.23-0.10 (m, 2H).

Example 60

4-({2-[4-(5-Chloro-2-cyanophenyl)-5-methoxy-2-oxopyridin-1(2H)-yl]-3-cyclopropylpropanoyl}amino)benzoic acid (enantiomer 2)

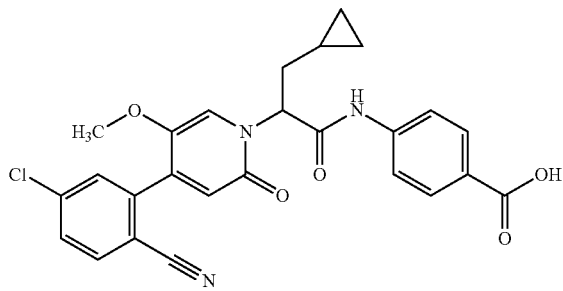 [SMILES: COc1cn(C(CC2CC2)C(=O)Nc2ccc(C(=O)O)cc2)c(=O)cc1-c1cc(Cl)ccc1C#N]

150 mg (0.27 mmol) of tert-butyl 4-({2-[4-(5-chloro-2-cyanophenyl)-5-methoxy-2-oxopyridin-1(2H)-yl]-3-cyclopropylpropanoyl}amino)benzoate (Example 22.1D) were hydrolysed with TFA according to General Method 2.

Subsequent enantiomer separation of 81 mg of the racemate gave 52 mg of the title compound Example 60 (enantiomer 2): Chiral HPLC: $R_t$=5.4 min; 98% ee.

Separation method: column: Daicel Chiralpak IF 5 μm 250×20 mm; mobile phase: 25% isohexane, 75% ethanol; oven: 45° C.; flow rate: 15 ml/min; UV detection: 220 nm.

Analysis: column: Daicel Chiralpak IF 5 μm 250×4.6 mm; mobile phase: 25% isohexane, 75% ethanol+0.2% TFA in 1% water; oven: 30° C.; flow rate: 1 ml/min; UV detection: 220 nm.

LC/MS [Method 1]: $R_t$=1.02 min; MS (ESIpos): m/z=492 (M+H)$^+$ $^1$H-NMR (400 MHz, DMSO-d$_6$): δ [ppm]=12.77 (br. s, 1H), 10.79 (s, 1H), 8.00 (d, 1H), 7.91 (d, 2H), 7.78-7.71 (m, 4H), 7.54 (s, 1H), 6.53 (s, 1H), 5.80 (dd, 1H), 3.70 (s, 3H), 2.28-2.18 (m, 1H), 1.96-1.87 (m, 1H), 0.71-0.61 (m, 1H), 0.47-0.33 (m, 2H), 0.23-0.10 (m, 2H).

Example 61

4-({2-[4-(5-Chloro-2-cyanophenyl)-5-methoxy-2-oxopyridin-1(2H)-yl]pent-4-ynoyl}amino)benzoic acid (racemate)

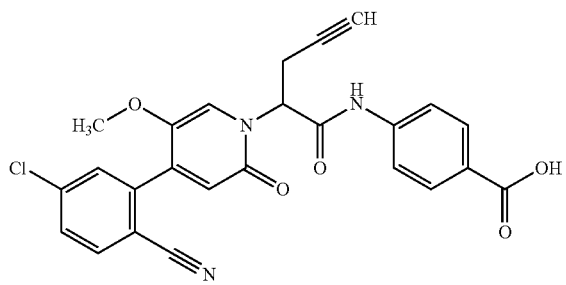 [SMILES: C#CCC(C(=O)Nc1ccc(C(=O)O)cc1)n1cc(OC)c(-c2cc(Cl)ccc2C#N)cc1=O]

91 mg (0.17 mmol) of tert-butyl 4-({2-[4-(5-chloro-2-cyanophenyl)-5-methoxy-2-oxopyridin-1(2H)-yl]pent-4-ynoyl}amino)benzoate (racemate) (Example 23.1C) were hydrolysed with TFA according to General Method 2. Yield: 55 mg (67% of theory)

LC/MS [Method 1]: $R_t$=0.94 min; MS (ESIpos): m/z=476 (M+H)$^+$ $^1$H-NMR (400 MHz, DMSO-d$_6$): δ [ppm]=12.78 (s, 1H), 10.78 (s, 1H), 8.01 (d, 1H), 7.92 (d, 2H), 7.78-7.71 (m, 4H), 7.60 (s, 1H), 6.55 (s, 1H), 5.78 (dd, 1H), 3.69 (s, 3H), 3.30-3.22 (m, 1H), 3.18-3.10 (m, 1H), 3.01-2.97 (m, 1H).

Example 62

4-({2-[4-(5-Chloro-2-cyanophenyl)-2-oxo-5-(propan-2-yloxy)pyridin-1(2H)-yl]propanoyl}amino)benzoic acid (racemate)

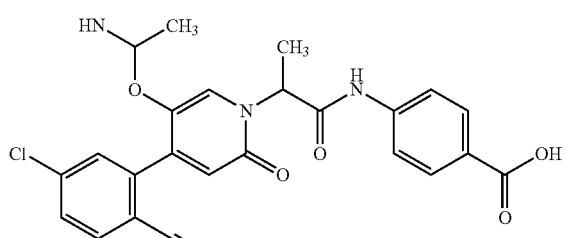

31 mg (0.06 mmol) of tert-butyl 4-({2-[4-(5-chloro-2-cyanophenyl)-2-oxo-5-(propan-2-yloxy)pyridin-1(2H)-yl]

propanoyl}amino)benzoate (racemate) (Example 24.11) were hydrolysed with TFA according to General Method 2. Yield: 5 mg (18% of theory)

LC/MS [Method 1]: $R_t$=1.00 min; MS (ESIpos): m/z=480 (M+H)$^+$ $^1$H-NMR (400 MHz, DMSO-d$_6$): δ [ppm]=12.78 (s, 1H), 10.73 (s, 1H), 8.01 (d, 1H), 7.92 (d, 2H), 7.77-7.70 (m, 4H), 7.55 (s, 1H), 6.53 (s, 1H), 5.65 (q, 1H), 4.10-4.02 (m, 1H), 1.71 (d, 3H), 1.07 (dd, 6H).

Example 63

4-({2-[4-(5-Chloro-2-cyanophenyl)-5-methoxy-2-oxopyridin-1(2H)-yl]-4-methylpentanoyl}amino)benzoic acid (racemate)

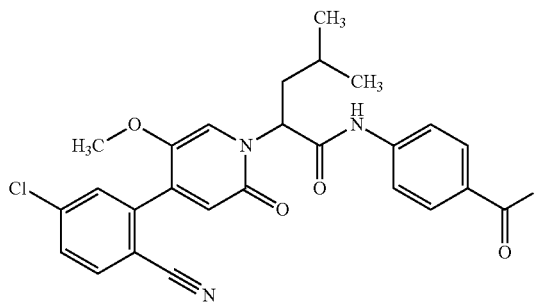

127 mg (0.23 mmol) of tert-butyl 4-({2-[4-(5-chloro-2-cyanophenyl)-5-methoxy-2-oxopyridin-1(2H)-yl]-4-methylpentanoyl}amino)benzoate (racemate) (Example 25.1C) were hydrolysed with TFA according to General Method 2. Yield: 79 mg (71% of theory)

LC/MS [Method 1]: $R_t$=1.07 min; MS (ESIpos): m/z=494 (M+H)$^+$ $^1$H-NMR (400 MHz, DMSO-d$_6$): δ [ppm]=12.78 (s, 1H), 10.85 (s, 1H), 8.00 (d, 1H), 7.92 (d, 2H), 7.79-7.71 (m, 4H), 7.50 (s, 1H), 6.54 (s, 1H), 5.86 (dd, 1H), 3.69 (s, 3H), 2.27-2.17 (br. m, 1H), 1.93-1.84 (br. m, 1H), 1.49-1.39 (br. m, 1H), 0.95 (t, 6H).

Example 64

4-({2-[4-(5-Chloro-2-cyanophenyl)-5-methoxy-2-oxopyridin-1(2H)-yl]-4-methylpentanoyl}amino)benzoic acid (enantiomer 1)

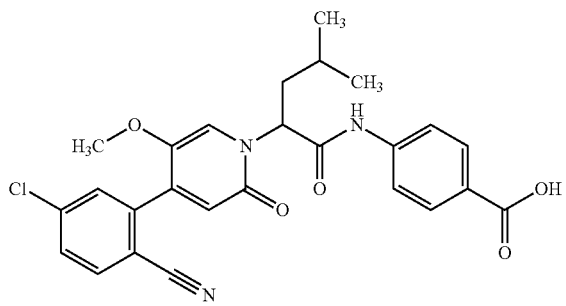 [SMILES: COc1cn(C(CC(C)C)C(=O)Nc2ccc(C(=O)O)cc2)c(=O)cc1-c1cc(Cl)ccc1C#N]

Enantiomer separation of 73 mg of the racemate from Example 63 gave 37 mg of the title compound Example 64 (enantiomer 1): Chiral HPLC: $R_t$=4.6 min; 99% ee.

Separation method: column: Daicel Chiralpak IF 5 μm 250×20 mm; mobile phase: 50% isohexane, 50% ethanol; oven: 40° C.; flow rate: 15 ml/min; UV detection: 220 nm.

Analysis: column: Daicel Chiralpak AZ-H 5 μm 250×4.6 mm; mobile phase: 50% isohexane, 50% ethanol+0.2% TFA in 1% water; oven: 40° C.; flow rate: 1 ml/min; UV detection: 220 nm.

Example 65

4-({2-[4-(5-Chloro-2-cyanophenyl)-5-methoxy-2-oxopyridin-1(2H)-yl]-4-methylpentanoyl}amino)benzoic acid (enantiomer 2)

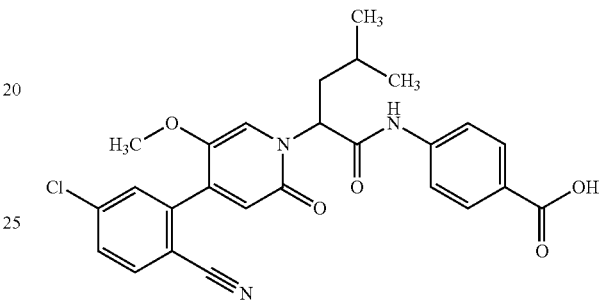

Enantiomer separation of 73 mg of the racemate from Example 63 gave 33 mg of the title compound Example 65 (enantiomer 2): Chiral HPLC: $R_t$=7.0 min; 99% ee.

Separation method: column: Daicel Chiralpak IF 5 μm 250×20 mm; mobile phase: 50% isohexane, 50% ethanol; oven: 40° C.; flow rate: 15 ml/min; UV detection: 220 nm.

Analysis: column: Daicel Chiralpak AZ-H 5 μm 250×4.6 mm; mobile phase: 50% isohexane, 50% ethanol+0.2% TFA in 1% water; oven: 40° C.; flow rate: 1 ml/min; UV detection: 220 nm.

Example 66

4-({2-[4-(5-Chloro-2-cyanophenyl)-5-methoxy-2-oxopyridin-1(2H)-yl]butanoyl}amino)benzoic acid (racemate)

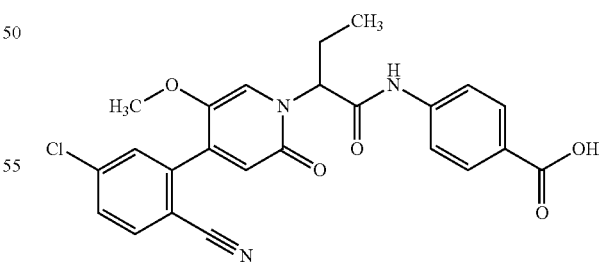

68 mg (0.13 mmol) of tert-butyl 4-({2-[4-(5-chloro-2-cyanophenyl)-5-methoxy-2-oxopyridin-1(2H)-yl]butanoyl}amino)benzoate (racemate) (Example 26.1B) were hydrolysed with TFA according to General Method 2. Yield: 51 mg (84% of theory)

LC/MS [Method 1]: $R_t$=0.94 min; MS (ESIpos): m/z=466 (M+H)$^+$ $^1$H-NMR (400 MHz, DMSO-d$_6$): δ [ppm]=12.78 (s, 1H), 10.81 (s, 1H), 8.00 (d, 1H), 7.92 (d, 2H), 7.79-7.71 (m, 4H), 7.50 (s, 1H), 6.54 (s, 1H), 5.64 (dd, 1H), 3.69 (s, 3H), 2.25-2.11 (m, 2H), 0.91 (t, 3H).

Alternative Synthesis:

At RT, 0.2 ml of water and 97 mg (1.22 mmol, 3.0 eq.) of sodium hydroxide were added to a suspension of 200 mg (0.41 mmol) of ethyl 4-({2-[4-(5-chloro-2-cyanophenyl)-5-methoxy-2-oxopyridin-1(2H)-yl]butanoyl}amino)benzoate (racemate) in 2.0 ml of ethanol. The reaction mixture was stirred at RT for 1 h and at an oil bath temperature of 60° C. for 6 h, allowed to stand at RT overnight and then added to aqueous hydrochloric acid (1N). After dilution with water a precipitate was formed which was filtered off, washed twice with water and dried under reduced pressure. The precipitate was then purified by flash chromatography (25 g of silica gel, mobile phase: dichloromethane→dichloromethane/methanol 50:1). Yield: 144 mg (38% of theory based on 0.82 mmol, since two crude product batches of the stated size were purified together)

LC/MS [Method 1]: R$_t$=0.92 min; MS (ESIneg): m/z=464 (M−H)$^-$, $^1$H-NMR (400 MHz, DMSO-d$_6$): δ [ppm]=12.74 (s, 1H), 10.80 (s, 1H), 8.00 (d, 1H), 7.92 (d, 2H), 7.79-7.70 (m, 4H), 7.50 (s, 1H), 6.54 (s, 1H), 5.65 (dd, 1H), 3.69 (s, 3H), 2.26-2.11 (m, 2H), 0.91 (t, 3H).

Example 67

4-({2-[4-(5-Chloro-2-cyanophenyl)-5-methoxy-2-oxopyridin-1(2H)-yl]butanoyl}amino)benzoic acid (enantiomer 1)

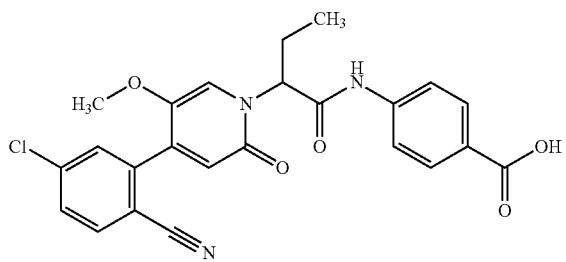 [SMILES: CCC(C(=O)Nc1ccc(C(=O)O)cc1)n1cc(OC)c(-c2cc(Cl)ccc2C#N)cc1=O]

Enantiomer separation of 433 mg of the racemate from Example 66 gave 196 mg of the title compound Example 67 (enantiomer 1): Chiral HPLC: R$_t$=5.22 min; 99% ee.

Separation method: column: Daicel Chiralpak IF 5 μm 250 mm×20 mm; mobile phase: 50% isohexane, 50% ethanol+0.2% acetic acid; temperature: 40° C.; flow rate: 15 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; temperature: 40° C.; flow rate: 1 ml/min; UV detection: 220 nm.

$^1$H-NMR (400 MHz, DMSO-d$_6$): δ [ppm]=12.77 (s, 1H), 10.81 (s, 1H), 8.00 (d, 1H), 7.91 (d, 2H), 7.79-7.71 (m, 4H), 7.50 (s, 1H), 6.54 (s, 1H), 5.64 (dd, 1H), 3.69 (s, 3H), 2.26-2.11 (m, 2H), 0.91 (t, 3H).

Example 68

4-({2-[4-(5-Chloro-2-cyanophenyl)-5-methoxy-2-oxopyridin-1(2H)-yl]butanoyl}amino)benzoic acid (enantiomer 2)

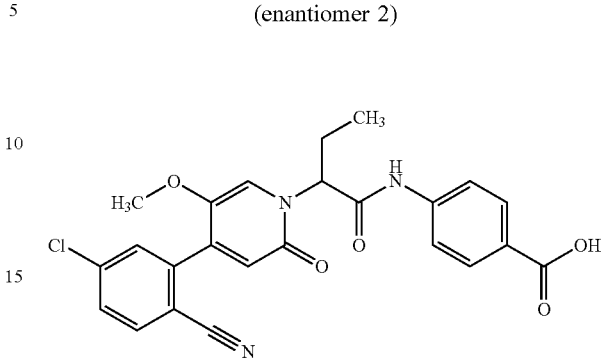

Enantiomer separation of 433 mg of the racemate from Example 66 gave 201 mg of the title compound Example 68 (enantiomer 2): Chiral HPLC: R$_t$=8.19 min; 99% ee.

Separation method: column: Daicel Chiralpak IF 5 μm 250 mm×20 mm; mobile phase: 50% isohexane, 50% ethanol+0.2% acetic acid; temperature: 40° C.; flow rate: 15 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; temperature: 40° C.; flow rate: 1 ml/min; UV detection: 220 nm.

$^1$H-NMR (400 MHz, DMSO-d$_6$): δ [ppm]=12.77 (s, 1H), 10.81 (s, 1H), 8.00 (d, 1H), 7.91 (d, 2H), 7.79-7.71 (m, 4H), 7.50 (s, 1H), 6.54 (s, 1H), 5.64 (dd, 1H), 3.69 (s, 3H), 2.26-2.11 (m, 2H), 0.91 (t, 3H).

Example 69

2-[4-(5-Chloro-2-cyanophenyl)-5-methoxy-2-oxopyridin-1(2H)-yl]-N-[4-(5-oxo-2,5-dihydro-1H-pyrazol-3-yl)phenyl]butanamide (racemate)

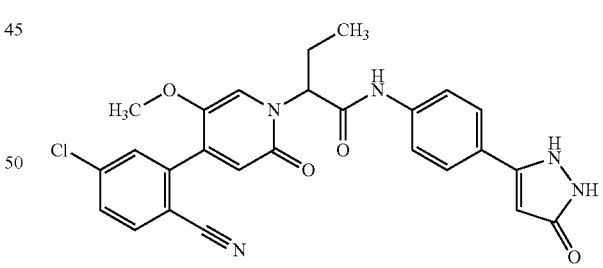

17 mg (purity 70%, 0.02 mmol) of tert-butyl 5-[4-({2-[4-(5-chloro-2-cyanophenyl)-5-methoxy-2-oxopyridin-1(2H)-yl]butanoyl}amino)phenyl]-3-oxo-2,3-dihydro-1H-pyrazole-1-carboxylate (racemate) were hydrolysed with TFA according to General Method 2. Yield: 8 mg (78% of theory)

LC/MS [Method 1]: R$_t$=0.89 min; MS (ESIpos): m/z=504 (M+H)$^+$ $^1$H-NMR (400 MHz, DMSO-d$_6$): δ [ppm]=11.96 (br. s, 1H), 10.57 (s, 1H), 9.54 (br. s, 1H), 8.00 (d, 1H), 7.74 (s, 1H), 7.73 (d, 1H), 7.66 (d, 2H), 7.61 (d, 2H), 7.51 (s, 1H), 6.54 (s, 1H), 5.84 (br. s, 1H), 5.64 (dd, 1H), 3.69 (s, 3H), 2.24-2.10 (m, 2H), 0.91 (t, 3H).

Example 70

2-[4-(5-Chloro-2-cyanophenyl)-5-methoxy-2-oxopyridin-1(2H)-yl]-N-(2-methyl-3-oxo-2,3-dihydro-1H-indazol-6-yl)butanamide (racemate)

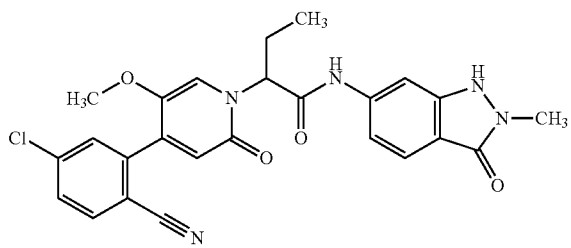 [SMILES: CCC(C(=O)Nc1ccc2c(=O)n(C)[nH]c2c1)n1cc(OC)c(-c2cc(Cl)ccc2C#N)cc1=O]

112 mg (0.19 mmol) of tert-butyl 6-({2-[4-(5-chloro-2-cyanophenyl)-5-methoxy-2-oxopyridin-1(2H)-yl]butanoyl}amino)-2-methyl-3-oxo-2,3-dihydro-1H-indazole-1-carboxylate (racemate) were hydrolysed with TFA according to General Method 2. Yield: 34 mg (35% of theory)

LC/MS [Method 1]: $R_t$=0.85 min; MS (ESIpos): m/z=492 (M+H)$^+$ $^1$H-NMR (400 MHz, DMSO-d$_6$): δ [ppm]=10.73 (s, 1H), 10.21 (s, 1H), 8.00 (d, 1H), 7.81-7.71 (m, 3H), 7.57 (d, 1H), 7.51 (s, 1H), 7.16 (dd, 1H), 6.55 (s, 1H), 5.65 (dd, 1H), 3.69 (s, 3H), 2.27-2.10 (m, 2H), 0.91 (t, 3H).

Example 71

2-[4-(5-Chloro-2-cyanophenyl)-5-methoxy-2-oxopyridin-1(2H)-yl]-N-(2-oxo-2,3-dihydro-1H-benzimidazol-5-yl)butanamide (racemate)

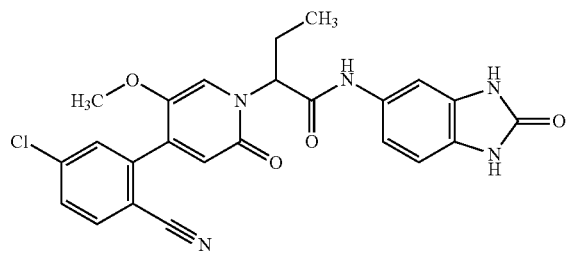 [SMILES: CCC(C(=O)Nc1ccc2[nH]c(=O)[nH]c2c1)n1cc(OC)c(-c2cc(Cl)ccc2C#N)cc1=O]

71 mg (0.20 mmol) of 2-[4-(5-chloro-2-cyanophenyl)-5-methoxy-2-oxopyridin-1(2H)-yl]butanoic acid (racemate) and 33 mg (0.22 mmol, 1.1 eq.) of 5-amino-1,3-dihydro-2H-benzimidazol-2-one were reacted according to General Method 1. Yield: 74 mg (76% of theory)

LC/MS [Method 1]: $R_t$=0.86 min; MS (ESIpos): m/z=478 (M+H)$^+$ $^1$H-NMR (400 MHz, DMSO-d$_6$): δ [ppm]=10.58 (s, 1H), 10.53 (s, 1H), 10.37 (s, 1H), 8.00 (d, 1H), 7.77-7.70 (m, 2H), 7.53 (s, 1H), 7.45 (d, 1H), 7.08 (dd, 1H), 6.85 (d, 1H), 6.53 (s, 1H), 5.63 (dd, 1H), 3.69 (s, 3H), 2.22-2.03 (m, 2H), 0.90 (t, 3H).

Example 72

2-[4-(5-Chloro-2-cyanophenyl)-5-methoxy-2-oxopyridin-1(2H)-yl]-N-[4-(2-oxo-2,3-dihydro-1,3-oxazol-5-yl)phenyl]butanamide (racemate)

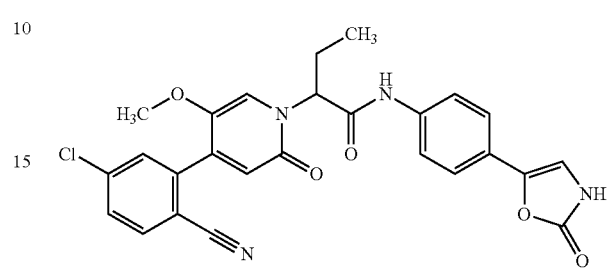

87 mg (0.25 mmol) of 2-[4-(5-chloro-2-cyanophenyl)-5-methoxy-2-oxopyridin-1(2H)-yl]butanoic acid (racemate) and 60 mg (0.30 mmol, 1.2 eq.) of 5-(4-aminophenyl)-1,3-oxazol-2(3H)-one were reacted according to General Method 1. Yield: 23 mg (purity 93%, 17% of theory)

LC/MS [Method 8]: $R_t$=1.16 min; MS (ESIneg): m/z=503 (M−H)$^-$ $^1$H-NMR (400 MHz, DMSO-d$_6$): δ [ppm]=10.77 (s, 1H), 10.60 (s, 1H), 8.00 (d, 1H), 7.76-7.70 (m, 2H), 7.67 (d, 2H), 7.50 (s, 1H), 7.46 (d, 2H), 7.39 (d, 1H), 6.53 (s, 1H), 5.63 (dd, 1H), 3.69 (s, 3H), 2.25-2.09 (m, 2H), 0.90 (t, 3H).

Example 73

6-({2-[4-(5-Chloro-2-cyanophenyl)-5-methoxy-2-oxopyridin-1(2H)-yl]butanoyl}amino)-1H-benzimidazole-2-carboxylic acid (racemate)

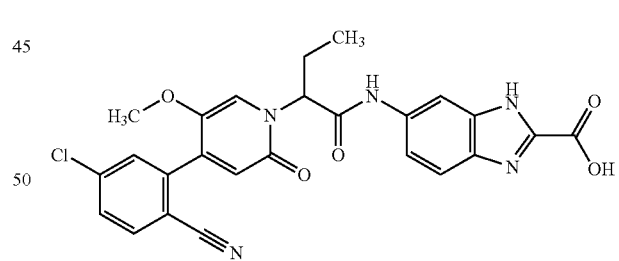

86 mg (0.16 mmol) of ethyl 6-({2-[4-(5-chloro-2-cyanophenyl)-5-methoxy-2-oxopyridin-1(2H)-yl]butanoyl}amino)-1H-benzimidazole-2-carboxylate (racemate) were hydrolysed with lithium hydroxide according to General Method 3. Yield: 67 mg (82% of theory)

LC/MS [Method 1]: $R_t$=0.76 min; MS (ESIpos): m/z=506 (M+H)$^+$ $^1$H-NMR (400 MHz, DMSO-d$_6$): δ [ppm]=10.68 (s, 1H), 8.17 (s, 1H), 8.01 (d, 1H), 7.78-7.71 (m, 2H), 7.64 (d, 1H), 7.54 (s, 1H), 7.46 (dd, 1H), 6.55 (s, 1H), 5.66 (dd, 1H), 3.70 (s, 3H), 2.28-2.10 (m, 2H), 0.91 (t, 3H).

Example 74

6-({2-[4-(5-Chloro-2-cyanophenyl)-5-methoxy-2-oxopyridin-1(2H)-yl]butanoyl}amino)-1H-indole-2-carboxylic acid (racemate)

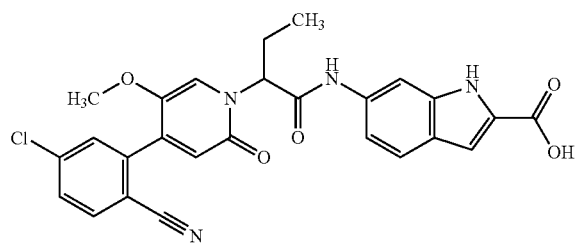 [SMILES: CCC(C(=O)Nc1ccc2cc(C(=O)O)[nH]c2c1)n1cc(OC)c(-c2cc(Cl)ccc2C#N)cc1=O]

75 mg (0.14 mmol) of ethyl 6-({2-[4-(5-chloro-2-cyanophenyl)-5-methoxy-2-oxopyridin-1(2H)-yl]butanoyl}amino)-1H-indole-2-carboxylate (racemate) were hydrolysed with lithium hydroxide according to General Method 3. Yield: 38 mg (48% of theory)

LC/MS [Method 1]: $R_t$=1.18 min; MS (ESIneg): m/z=503 (M−H)⁻

¹H-NMR (400 MHz, DMSO-$d_6$): δ [ppm]=12.84 (br. s, 1H), 11.70 (s, 1H), 10.55 (s, 1H), 8.06-7.98 (m, 2H), 7.79-7.70 (m, 2H), 7.57 (d, 1H), 7.54 (s, 1H), 7.19 (dd, 1H), 7.03 (s, 1H), 6.54 (s, 1H), 5.68 (dd, 1H), 3.70 (s, 3H), 2.27-2.08 (m, 2H), 0.92 (t, 3H).

Example 75

5-({2-[4-(5-Chloro-2-cyanophenyl)-5-methoxy-2-oxopyridin-1(2H)-yl]butanoyl}amino)-1H-indole-2-carboxylic acid (racemate)

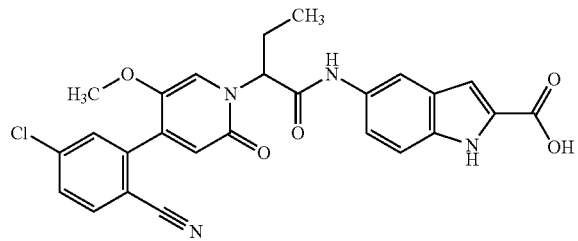 [SMILES: CCC(C(=O)Nc1ccc2[nH]c(C(=O)O)cc2c1)n1cc(OC)c(-c2cc(Cl)ccc2C#N)cc1=O]

94 mg (0.18 mmol) of ethyl 5-({2-[4-(5-chloro-2-cyanophenyl)-5-methoxy-2-oxopyridin-1(2H)-yl]butanoyl}amino)-1H-indole-2-carboxylate (racemate) were hydrolysed with lithium hydroxide according to General Method 3. Yield: 39 mg (43% of theory)

LC/MS [Method 1]: $R_t$=1.15 min; MS (ESIneg): m/z=503 (M−H)⁻

¹H-NMR (400 MHz, DMSO-$d_6$): δ [ppm]=10.77 (s, 1H), 10.26 (s, 1H), 8.00 (d, 1H), 7.82 (s, 1H), 7.75 (s, 1H), 7.73 (dd, 1H), 7.56 (s, 1H), 7.22 (d, 1H), 7.15 (d, 1H), 6.54 (s, 1H), 6.43 (s, 1H), 5.68 (dd, 1H), 3.70 (s, 3H), 2.25-2.02 (m, 2H), 0.90 (t, 3H).

Example 76

4-({2-[4-(5-Chloro-2-cyanophenyl)-5-methoxy-2-oxopyridin-1(2H)-yl]-4-methoxybutanoyl}amino)benzoic acid (racemate)

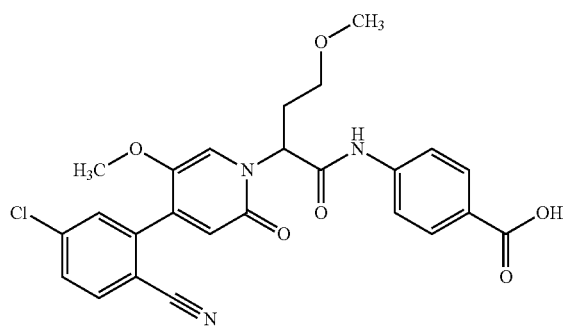 [SMILES: COCCC(C(=O)Nc1ccc(C(=O)O)cc1)n1cc(OC)c(-c2cc(Cl)ccc2C#N)cc1=O]

1.80 g (3.40 mmol) of ethyl 4-({2-[4-(5-chloro-2-cyanophenyl)-5-methoxy-2-oxopyridin-1(2H)-yl]-4-methoxybutanoyl}amino)benzoate (racemate) in 45 ml of methanol/water (4/1) were reacted with 2.24 g (6.87 mmol) of caesium carbonate according to General Method 4, giving the title compound. Yield: 1.66 g (88% of theory)

LC/MS [Method 1]: $R_t$=0.89 min; MS (ESIneg): m/z=494 (M−H)⁻

¹H-NMR (400 MHz, DMSO-$d_6$): δ [ppm]=12.8 (s, 1H), 10.8 (s, 1H), 8.00 (d, 1H), 7.91 (d, 2H), 7.77 (d, 2H), 7.75 (s, 1H), 7.74 (dd, 1H), 7.51 (s, 1H), 6.53 (s, 1H), 5.76 (t, 1H), 3.69 (s, 3H), 3.43-3.25 (m, 2H), 3.20 (s, 3H), 2.44-2.39 (m, 2H).

Example 77

(+)-4-({2-[4-(5-Chloro-2-cyanophenyl)-5-methoxy-2-oxopyridin-1(2H)-yl]-4-methoxybutanoyl}amino)benzoic acid (enantiomer 1)

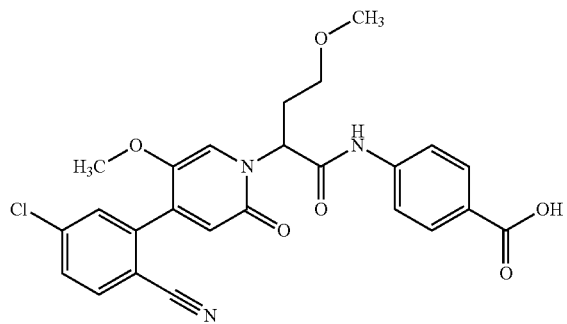 [SMILES: COCCC(C(=O)Nc1ccc(C(=O)O)cc1)n1cc(OC)c(-c2cc(Cl)ccc2C#N)cc1=O]

Enantiomer separation of 1.66 g of the racemate from Example 76 gave 707 mg of the title compound Example 77 (enantiomer 1): Chiral HPLC: $R_t$=4.59 min; 99% ee.

Optical rotation: $[\alpha]_{589}^{20.1}$=+95.82° (c 0.255 g/100 ml, methanol)

Separation method (SFC): column: AZ-H 5 µm 250 mm×20 mm; mobile phase: 70% carbon dioxide, 30% ethanol; temperature: 40° C.; flow rate: 80 ml/min; pressure: 100 bar; UV detection: 210 nm.

Analysis (SFC): column: AZ-H 5 μm 250 mm×4.6 mm; mobile phase: 70% carbon dioxide, 30% ethanol; temperature: 40° C.; flow rate: 3 ml/min; pressure: 100 bar; UV detection: 210 nm.

Example 78

(−)-4-({2-[4-(5-Chloro-2-cyanophenyl)-5-methoxy-2-oxopyridin-1(2H)-yl]-4-methoxybutanoyl}amino)benzoic acid (enantiomer 2)

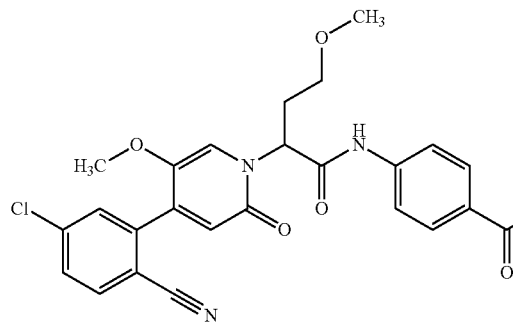

Enantiomer separation of 1.66 g of the racemate from Example 76 gave 631 mg of the title compound Example 78 (enantiomer 2): Chiral HPLC: $R_t$=8.11 min; 98% ee.

Optical rotation: $[\alpha]_{589}^{19.9}$=−95.05° (c 0.33 g/100 ml, methanol)

Separation method (SFC): column: AZ-H 5 μm 250×20 mm; mobile phase: 70% carbon dioxide, 30% ethanol; temperature: 40° C.; flow rate: 80 ml/min; pressure: 100 bar; UV detection: 210 nm.

Analysis (SFC): column: AZ-H 5 μm 250×4.6 mm; mobile phase: 70% carbon dioxide, 30% ethanol; temperature: 40° C.; flow rate: 3 ml/min; pressure: 100 bar; UV detection: 210 nm.

Example 79

4-({(4S)-2-[4-(5-Chloro-2-cyanophenyl)-5-methoxy-2-oxopyridin-1(2H)-yl]-4-methoxypentanoyl}amino)benzoic acid (mixture of enantiomerically pure diastereomers 1 and 2)

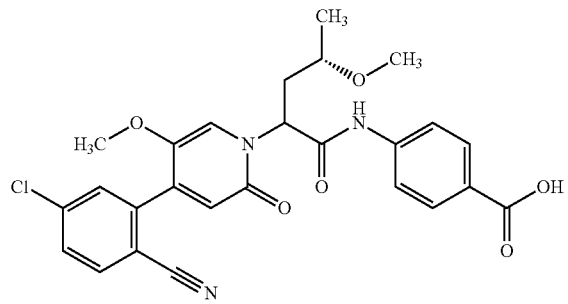 [SMILES: COc1cn(C(C[C@H](C)OC)C(=O)Nc2ccc(C(=O)O)cc2)c(=O)cc1-c1cc(Cl)ccc1C#N]

387 mg (0.66 mmol) of tert-butyl 4-({(4S)-2-[4-(5-chloro-2-cyanophenyl)-5-methoxy-2-oxopyridin-1(2H)-yl]-4-methoxypentanoyl}amino)benzoate (mixture of enantiomerically pure diastereomers 1 and 2) were hydrolysed with TFA according to General Method 2. Yield: 245 mg (70% of theory)

LC/MS [Method 1]: $R_t$=0.96 min; MS (ESIpos): m/z=510 (M+H)$^+$ $^1$H-NMR (400 MHz, DMSO-d$_6$): δ [ppm]=12.77 (br. s, 1H), 10.80/10.75 (2×s, 1H), 8.00 (d, 1H), 7.94-7.87 (m, 2H), 7.81-7.71 (m, 4H), 7.57/7.51 (2×s, 1H), 6.53 (2×s, 1H), 5.89-5.80 (m, 1H), 3.69 (s, 3H), 3.25-3.19/3.17-3.09 (2×m, 1H), 3.19/3.12 (2×s, 3H), 2.43-2.28 (m, 1H), 2.28-2.17 (m, 1H), 1.16/1.14 (2×d, 3H).

Example 80

4-({(4S)-2-[4-(5-Chloro-2-cyanophenyl)-5-methoxy-2-oxopyridin-1(2H)-yl]-4-methoxypentanoyl}amino)benzoic acid (enantiomerically pure diastereomer 1)

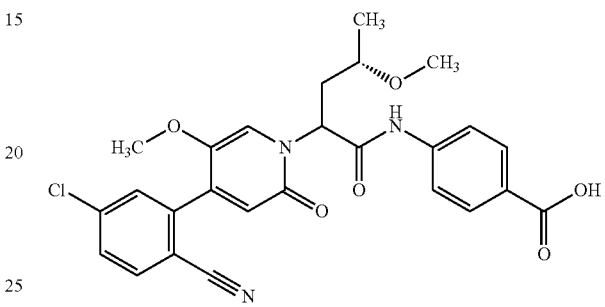

Diastereomer separation of 240 mg of the mixture from Example 79 gave 57 mg of the title compound Example 80 (enantiomerically pure diastereomer 1): Chiral HPLC: $R_t$=8.1 min; diastereomeric purity: >99%.

Separation method: column: Daicel Chiralpak IF 5 μm 250 mm×20 mm; mobile phase: 50% isohexane, 50% ethanol+0.2% TFA+1% water; temperature: 23° C.; flow rate: 20 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; temperature: 40° C.; flow rate: 1 ml/min; UV detection: 220 nm.

$^1$H-NMR (400 MHz, DMSO-d$_6$): δ [ppm]=12.8 (br. s, 1H), 10.75 (s, 1H), 8.00 (d, 1H), 7.90 (d, 2H), 7.81-7.70 (m, 4H), 7.51 (s, 1H), 6.53 (s, 1H), 5.84 (dd, 1H), 3.69 (s, 3H), 3.17-3.08 (m, 1H), 3.12 (s, 3H), 2.44-2.34 (m, 1H), 2.29-2.18 (m, 1H), 1.14 (d, 3H).

Example 81

4-({(4S)-2-[4-(5-Chloro-2-cyanophenyl)-5-methoxy-2-oxopyridin-1(2H)-yl]-4-methoxypentanoyl}amino)benzoic acid (enantiomerically pure diastereomer 2)

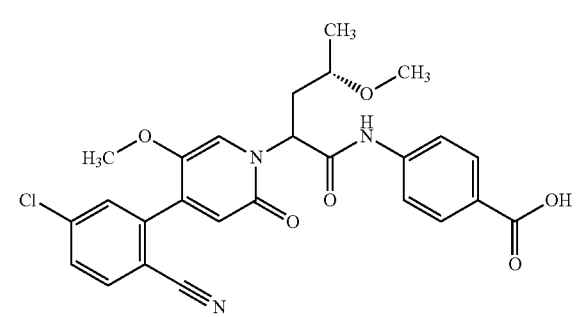 [SMILES: COc1cn(C(C[C@H](C)OC)C(=O)Nc2ccc(C(=O)O)cc2)c(=O)cc1-c1cc(Cl)ccc1C#N]

Diastereomer separation of 240 mg of the mixture from Example 79 gave 10 mg of the title compound Example 81 (enantiomerically pure diastereomer 2): Chiral HPLC: $R_t$=10.9 min; diastereomeric purity: 98%.

Separation method: column: Daicel Chiralpak IF 5 μm 250 mm×20 mm; mobile phase: 50% isohexane, 50% ethanol+0.2% TFA+1% water; temperature: 23° C.; flow rate: 20 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; temperature: 40° C.; flow rate: 1 ml/min; UV detection: 220 nm.

$^1$H-NMR (400 MHz, DMSO-$d_6$): δ [ppm]=12.75 (br. s, 1H), 10.77 (s, 1H), 7.99 (d, 1H), 7.91 (d, 2H), 7.81-7.70 (m, 4H), 7.57 (s, 1H), 6.53 (s, 1H), 5.85 (dd, 1H), 3.69 (s, 3H), 3.26-3.20 (m, 1H), 3.19 (s, 3H), 2.36-2.27 (m, 1H), 2.26-2.18 (m, 1H), 1.16 (d, 3H).

Example 82

4-({(4R)-2-[4-(5-Chloro-2-cyanophenyl)-5-methoxy-2-oxopyridin-1(2H)-yl]-4-methoxypentanoyl}amino)benzoic acid (mixture of enantiomerically pure diastereomers 1 and 2)

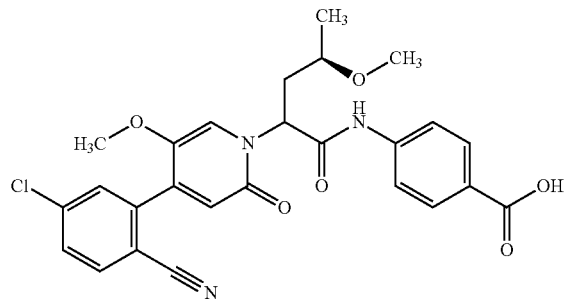 [SMILES: COc1cn(C(C[C@@H](C)OC)C(=O)Nc2ccc(C(=O)O)cc2)c(=O)cc1-c1cc(Cl)ccc1C#N]

51 mg (0.09 mmol) of tert-butyl 4-({(4R)-2-[4-(5-chloro-2-cyanophenyl)-5-methoxy-2-oxopyridin-1(2H)-yl]-4-methoxypentanoyl}amino)benzoate (mixture of enantiomerically pure diastereomers 1 and 2) were hydrolysed with TFA according to General Method 2. Yield: 27 mg (58% of theory)

LC/MS [Method 8]: $R_t$=1.20 min; MS (ESIneg): m/z=508 (M−H)$^-$ $^1$H-NMR (400 MHz, DMSO-$d_6$): δ [ppm]=12.76 (br. s, 1H), 10.80/10.74 (2×s, 1H), 8.00 (d, 1H), 7.94-7.86 (m, 2H), 7.81-7.70 (m, 4H), 7.57/7.51 (2×s, 1H), 6.53 (2×s, 1H), 5.89-5.79 (m, 1H), 3.69 (s, 3H), 3.25-3.19/3.17-3.09 (2×m, 1H), 3.19/3.12 (2×s, 3H), 2.43-2.28 (m, 1H), 2.28-2.17 (m, 1H), 1.16/1.14 (2×d, 3H).

Example 83

4-({(4R)-2-[4-(5-Chloro-2-cyanophenyl)-5-methoxy-2-oxopyridin-1 (2H)-yl]-4-methoxypentanoyl}amino)benzoic acid (enantiomerically pure diastereomer 1)

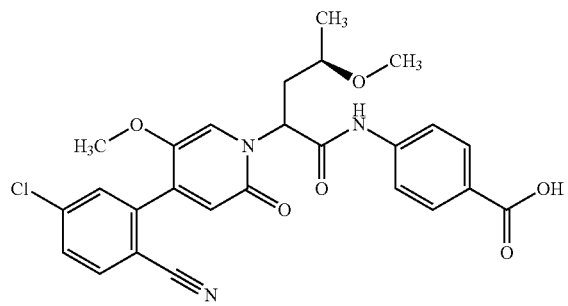

26 mg (0.05 mmol) of tert-butyl 4-({(4R)-2-[4-(5-chloro-2-cyanophenyl)-5-methoxy-2-oxopyridin-1(2H)-yl]-4-methoxypentanoyl}amino)benzoate (enantiomerically pure diastereomer 1) were hydrolysed with TFA according to General Method 2. Yield: 11 mg (45% of theory)

LC/MS [Method 8]: $R_t$=1.20 min; MS (ESIneg): m/z=508 (M−H)$^-$ $^1$H-NMR (400 MHz, DMSO-$d_6$): δ [ppm]=12.76 (br. s, 1H), 10.74 (s, 1H), 8.00 (d, 1H), 7.94-7.86 (m, 2H), 7.81-7.70 (m, 4H), 7.51 (s, 1H), 6.53 (s, 1H), 5.84 (dd, 1H), 3.69 (s, 3H), 3.25-3.09 (m, 1H), 3.12 (s, 3H), 2.43-2.28 (m, 1H), 2.28-2.17 (m, 1H), 1.14 (d, 3H).

Example 84

4-({2-[4-(5-Chloro-2-cyanophenyl)-5-methoxy-2-oxopyridin-1(2H)-yl]-3-[(2R)-tetrahydrofuran-2-yl]propanoyl}amino)benzoic acid (mixture of enantiomerically pure diastereomers 1 and 2)

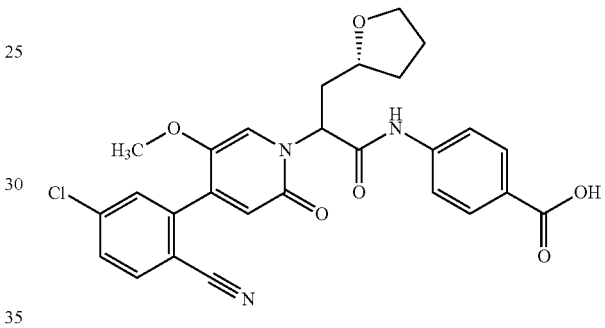

327 mg (0.57 mmol) of tert-butyl 4-({2-[4-(5-chloro-2-cyanophenyl)-5-methoxy-2-oxopyridin-1(2H)-yl]-3-[(2R)-tetrahydrofuran-2-yl]propanoyl}amino)benzoate (mixture of enantiomerically pure diastereomers 1 and 2) were hydrolysed with TFA according to General Method 2. Yield: 227 mg (purity 94%, 72% of theory)

LC/MS [Method 1]: $R_t$=0.94 min; MS (ESIpos): m/z=522 (M+H)$^+$.

Example 85

4-({2-[4-(5-Chloro-2-cyanophenyl)-5-methoxy-2-oxopyridin-1(2H)-yl]-3-[(2R)-tetrahydrofuran-2-yl]propanoyl}amino)benzoic acid (enantiomerically pure diastereomer 1)

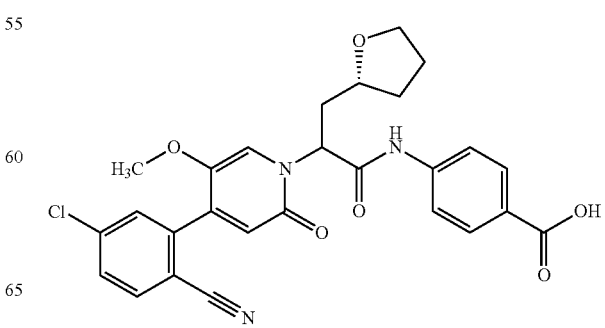

Diasteromer separation of 227 mg of the mixture from Example 84 gave 61 mg of the title compound Example 85 (enantiomerically pure diastereomer 1): Chiral HPLC: $R_t$=4.04 min; diastereomeric purity: >99%.

Separation method (SFC): column: Daicel Chiralpak IF 5 μm 250 mm×20 mm; mobile phase: 80% carbon dioxide, 20% ethanol; temperature: 40° C.; flow rate: 100 ml/min; UV detection: 210 nm.

Analysis (SFC): column: Daicel Chiralpak AZ-H 5 μm 250 mm×4.6 mm; mobile phase: 60% carbon dioxide, 40% ethanol; flow rate: 3 ml/min; UV detection: 220 nm.

$^1$H-NMR (400 MHz, DMSO-d$_6$): δ [ppm]=10.80 (s, 1H), 8.00 (d, 1H), 7.91 (d, 2H), 7.81-7.70 (m, 4H), 7.55 (s, 1H), 6.52 (s, 1H), 5.83 (t, 1H), 3.80-3.70 (m, 2H), 3.68 (s, 3H), 3.59 (q, 1H), 2.39-2.24 (m, 2H), 2.01-1.72 (3×m, 3H), 1.69-1.57 (m, 1H).

Example 86

4-({2-[4-(5-Chloro-2-cyanophenyl)-5-methoxy-2-oxopyridin-1(2H)-yl]-3-[(2R)-tetrahydrofuran-2-yl] propanoyl}amino)benzoic acid (enantiomerically pure diastereomer 2)

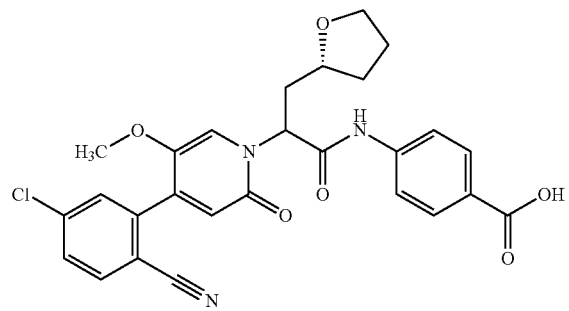 [SMILES: COc1cn(C(C[C@H]2CCCO2)C(=O)Nc2ccc(C(=O)O)cc2)c(=O)cc1-c1cc(Cl)ccc1C#N]

Diasteromer separation of 227 mg of the mixture from Example 84 gave 70 mg of the title compound Example 86 (enantiomerically pure diastereomer 2): Chiral HPLC: $R_t$=6.62 min; diastereomeric purity: 95%.

Separation method (SFC): column: Daicel Chiralpak IF 5 μm 250 mm×20 mm; mobile phase: 80% carbon dioxide, 20% ethanol; temperature: 40° C.; flow rate: 100 ml/min; UV detection: 210 nm.

Analysis (SFC): column: Daicel Chiralpak AZ-H 5 μm 250 mm×4.6 mm; mobile phase: 60% carbon dioxide, 40% ethanol; flow rate: 3 ml/min; UV detection: 220 nm.

$^1$H-NMR (400 MHz, DMSO-d$_6$): δ [ppm]=10.79 (s, 1H), 8.00 (d, 1H), 7.91 (d, 2H), 7.81-7.70 (m, 4H), 7.51 (s, 1H), 6.52 (s, 1H), 5.81 (dd, 1H), 3.81-3.73 (m, 1H), 3.73-3.65 (m, 1H), 3.69 (s, 3H), 3.63-3.54 (q, 1H), 2.50-2.41 (m, 1H), 2.31-2.21 (m, 1H), 2.01-1.72 (3×m, 3H), 1.55-1.42 (m, 1H).

Example 87

4-({2-[4-(5-Chloro-2-cyanophenyl)-5-methoxy-2-oxopyridin-1(2H)-yl]-3-[(2S)-tetrahydrofuran-2-yl] propanoyl}amino)benzoic acid (mixture of enantiomerically pure diastereomers 1 and 2)

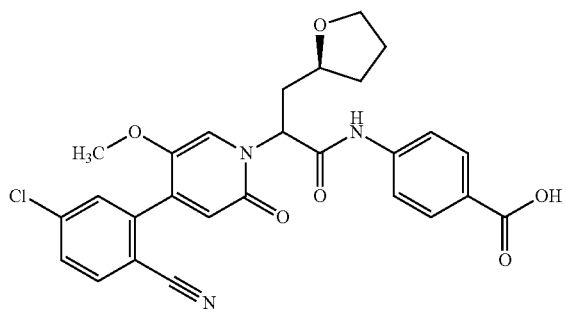 [SMILES: COc1cn(C(C[C@@H]2CCCO2)C(=O)Nc2ccc(C(=O)O)cc2)c(=O)cc1-c1cc(Cl)ccc1C#N]

1612 mg (2.78 mmol) of tert-butyl 4-({2-[4-(5-chloro-2-cyanophenyl)-5-methoxy-2-oxopyridin-1(2H)-yl]-3-[(2S)-tetrahydrofuran-2-yl]propanoyl}amino)benzoate (mixture of enantiomerically pure diastereomers 1 and 2) were hydrolysed with TFA according to General Method 2. Yield: 1270 mg (purity 90%, 79% of theory)

LC/MS [Method 8]: $R_t$=1.19 min; MS (ESIpos): m/z=522 (M+H)$^+$.

Example 88

4-({2-[4-(5-Chloro-2-cyanophenyl)-5-methoxy-2-oxopyridin-1(2H)-yl]-3-[(2S)-tetrahydrofuran-2-yl] propanoyl}amino)benzoic acid (enantiomerically pure diastereomer 1)

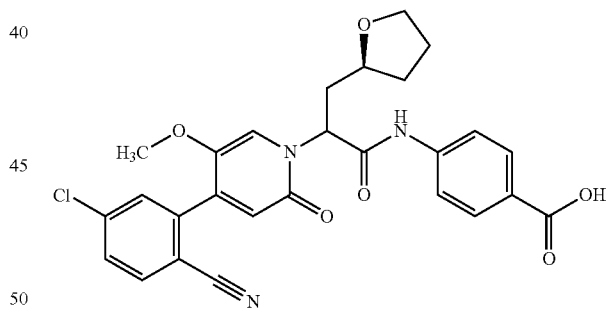

Diasteromer separation of 1270 mg of the mixture from Example 87 gave 350 mg of the title compound Example 88 (enantiomerically pure diastereomer 1): Chiral HPLC: $R_t$=4.31 min; diastereomeric purity: >99%.

Separation method (SFC): column: Daicel Chiralpak IC 5 μm 250 mm×20 mm; mobile phase: 25% carbon dioxide, 75% ethanol; temperature: 40° C.; flow rate: 100 ml/min; UV detection: 210 nm.

Analysis (SFC): column: Daicel IC 5 μm 250 mm×4.6 mm; mobile phase: 70% carbon dioxide, 30% ethanol; flow rate: 3 ml/min; UV detection: 210 nm.

$^1$H-NMR (400 MHz, DMSO-d$_6$): δ [ppm]=12.75 (br. s, 1H), 10.77 (s, 1H), 7.91 (d, 2H), 7.77 (d, 2H), 7.75-7.70 (m, 2H), 7.55 (s, 1H), 6.52 (s, 1H), 5.83 (t, 1H), 3.80-3.70 (m, 2H), 3.68 (s, 3H), 3.59 (q, 1H), 2.36-2.24 (m, 2H), 2.01-1.72 (3×m, 3H), 1.69-1.57 (m, 1H).

Example 89

4-({2-[4-(5-Chloro-2-cyanophenyl)-5-methoxy-2-oxopyridin-1(2H)-yl]-3-[(2S)-tetrahydrofuran-2-yl]propanoyl}amino)benzoic acid (enantiomerically pure diastereomer 2)

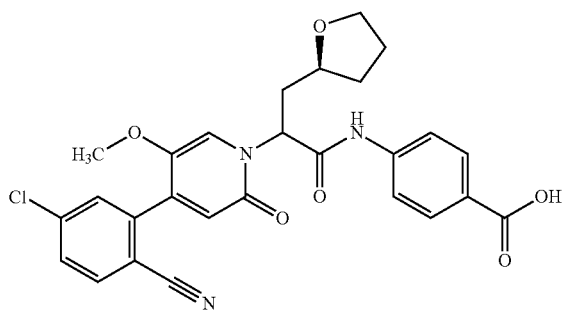 [SMILES: COc1cn(C(C[C@@H]2CCCO2)C(=O)Nc2ccc(C(=O)O)cc2)c(=O)cc1-c1cc(Cl)ccc1C#N]

Diastereomer separation of 1270 mg of the mixture from Example 87 gave 452 mg of the title compound Example 89 (enantiomerically pure diastereomer 2): Chiral HPLC: $R_t$=6.69 min; diastereomeric purity: >99%.

Separation method (SFC): column: Daicel Chiralpak IC 5 μm 250 mm×20 mm; mobile phase: 25% carbon dioxide, 75% ethanol; temperature: 40° C.; flow rate: 100 ml/min; UV detection: 210 nm.

Analysis (SFC): column: Daicel IC 5 μm 250 mm×4.6 mm; mobile phase: 70% carbon dioxide, 30% ethanol; flow rate: 3 ml/min; UV detection: 210 nm.

$^1$H-NMR (400 MHz, DMSO-$d_6$): δ [ppm]=12.74 (s, 1H), 10.77 (s, 1H), 7.99 (d, 1H), 7.90 (d, 2H), 7.80-7.70 (m, 4H), 7.51 (s, 1H), 6.52 (s, 1H), 5.81 (dd, 1H), 3.81-3.73 (m, 1H), 3.73-3.65 (m, 1H), 3.69 (s, 3H), 3.59 (q, 1H), 2.50-2.41 (m, 1H), 2.31-2.22 (m, 1H), 2.01-1.72 (3×m, 3H), 1.54-1.43 (m, 1H).

Example 90

4-({2-[4-(5-Chloro-2-cyanophenyl)-5-methoxy-2-oxopyridin-1(2H)-yl]-3-(tetrahydrofuran-3-yl)propanoyl}amino)benzoic acid (mixture of racemic diastereomers)

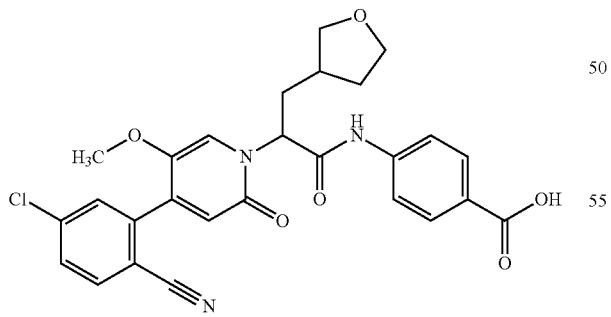

795 mg (1.3 mmol) of tert-butyl 4-({2-[4-(5-chloro-2-cyanophenyl)-5-methoxy-2-oxopyridin-1(2H)-yl]-3-(tetrahydrofuran-3-yl)propanoyl}amino)benzoate (mixture of racemic diastereomers) were hydrolysed with TFA according to General Method 2. Yield: 405 mg (59% of theory)

LC/MS [Method 1]: $R_t$=0.92 min; MS (ESIpos): m/z=522 (M+H)$^+$ $^1$H-NMR (400 MHz, DMSO-$d_6$): δ [ppm]=12.78 (s, 1H), 10.86/10.85 (2×s, 1H), 8.00 (d, 1H), 7.92 (d, 2H), 7.80-7.70 (m, 4H), 7.56/7.53 (2×s, 1H), 6.55 (s, 1H), 5.81/5.76 (2×dd, 1H), 3.82-3.68 (m, 2H), 3.70 (s, 3H), 3.60 (q, 1H), 3.44/3.26 (2×dd, 1H), 2.39-2.26 (m, 1H), 2.23-2.10 (m, 1H), 2.05-1.88 (m, 2H), 1.74-1.62/1.58-1.45 (2×m, 1H).

Example 91

4-({2-[4-(5-Chloro-2-cyanophenyl)-5-methoxy-2-oxopyridin-1(2H)-yl]-3-(tetrahydrofuran-3-yl)propanoyl}amino)benzoic acid (enantiomer 1 of the second diastereomer)

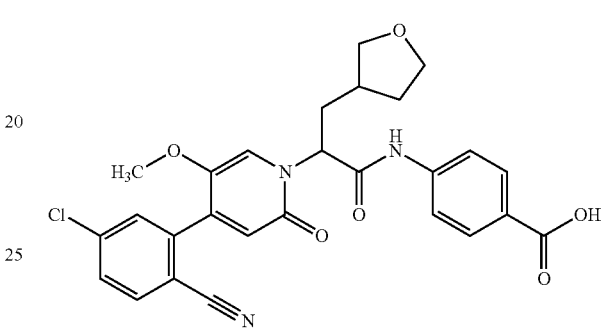

Diastereomer and enantiomer separation of 400 mg of the mixture from Example 90 gave 8 mg of the title compound Example 91 (enantiomer 1 of the second diastereomer): Chiral HPLC: $R_t$=5.73 min; >99% ee.

Separation method (SFC): column: Daicel Chiralpak AD-H 5 μm 250 mm×20 mm; mobile phase: 80% carbon dioxide, 20% ethanol; temperature: 40° C.; flow rate: 80 ml/min; UV detection: 210 nm.

Analysis (SFC): column: Daicel Chiralpak AZ-H 5 μm 250 mm×4.6 mm; mobile phase: 70% carbon dioxide, 30% ethanol; flow rate: 3 ml/min; UV detection: 220 nm.

$^1$H-NMR (400 MHz, DMSO-$d_6$): δ [ppm]=12.74 (s, 1H), 10.84 (s, 1H), 8.00 (d, 1H), 7.92 (d, 2H), 7.82-7.68 (m, 4H), 7.53 (s, 1H), 6.55 (s, 1H), 5.81 (br. s, 1H), 3.82-3.65 (m, 2H), 3.70 (s, 3H), 3.65-3.53 (m, 1H), 3.30-3.23 (m, 1H), 2.39-2.26 (m, 1H), 2.23-2.10 (m, 1H), 2.07-1.88 (m, 2H), 1.74-1.62 (m, 1H).

Example 92

4-({2-[4-(5-Chloro-2-cyanophenyl)-5-methoxy-2-oxopyridin-1(2H)-yl]-3-(tetrahydrofuran-3-yl)propanoyl}amino)benzoic acid (enantiomer 2 of the second diastereomer)

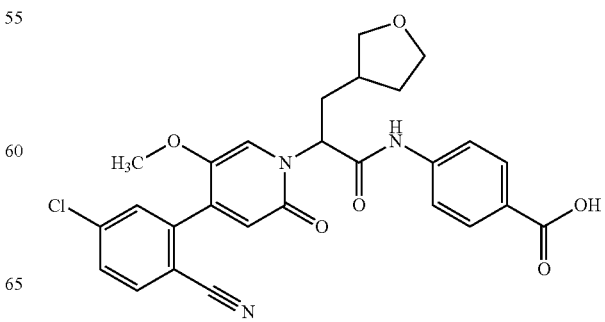

Diastereomer and enantiomer separation of 400 mg of the mixture from Example 90 gave 32 mg of the title compound Example 92 (enantiomer 2 of the second diastereomer): Chiral HPLC: $R_t$=8.96 min; >99% ee.

Separation method (SFC): column: Daicel Chiralpak OJ-H 5 μm 250 mm×20 mm; mobile phase: 75% carbon dioxide, 25% ethanol; temperature: 40° C.; flow rate: 80 ml/min; UV detection: 210 nm.

Analysis (SFC): column: Daicel Chiralpak AZ-H 5 μm 250 mm×4.6 mm; mobile phase: 70% carbon dioxide, 30% ethanol; flow rate: 3 ml/min; UV detection: 220 nm.

$^1$H-NMR (400 MHz, DMSO-$d_6$): δ [ppm]=12.74 (s, 1H), 10.83 (s, 1H), 8.00 (d, 1H), 7.92 (d, 2H), 7.79-7.70 (m, 4H), 7.53 (s, 1H), 6.55 (s, 1H), 5.81 (dd, 1H), 3.80-3.72 (m, 2H), 3.70 (s, 3H), 3.60 (q, 1H), 3.28 (dd, 1H), 2.38-2.28 (m, 1H), 2.21-2.11 (m, 1H), 2.06-1.89 (m, 2H), 1.73-1.63 (m, 1H).

Example 93

4-({2-[4-(5-Chloro-2-cyanophenyl)-5-methoxy-2-oxopyridin-1(2H)-yl]-3-(tetrahydrofuran-3-yl)propanoyl}amino)benzoic acid (enantiomer 2 of the first diastereomer)

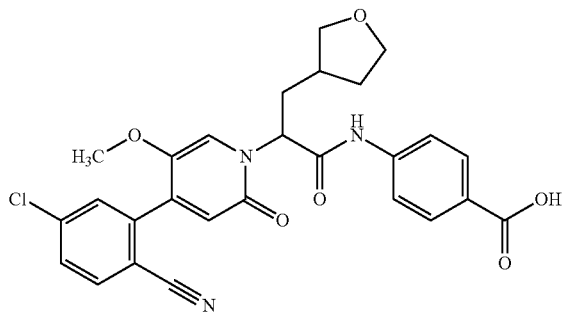 [SMILES: COc1cn(C(CC2CCOC2)C(=O)Nc2ccc(C(=O)O)cc2)c(=O)cc1-c1cc(Cl)ccc1C#N]

Diastereomer and enantiomer separation of 400 mg of the mixture from Example 90 gave 43 mg of the title compound Example 93 (enantiomer 2 of the first diastereomer): Chiral HPLC: $R_t$=10.27 min; >99% ee.

Separation method (SFC): column: Daicel Chiralpak OJ-H 5 μm 250 mm×20 mm; mobile phase: 75% carbon dioxide, 25% ethanol; temperature: 40° C.; flow rate: 80 ml/min; UV detection: 210 nm.

Analysis (SFC): column: Daicel Chiralpak AZ-H 5 μm 250 mm×4.6 mm; mobile phase: 70% carbon dioxide, 30% ethanol; flow rate: 3 ml/min; UV detection: 220 nm.

$^1$H-NMR (400 MHz, DMSO-$d_6$): δ [ppm]=12.78 (s, 1H), 10.85 (s, 1H), 8.00 (d, 1H), 7.92 (d, 2H), 7.80-7.70 (m, 4H), 7.56 (s, 1H), 6.55 (s, 1H), 5.77 (dd, 1H), 3.79-3.67 (m, 2H), 3.70 (s, 3H), 3.60 (q, 1H), 3.44 (dd, 1H), 2.37-2.27 (m, 1H), 2.23-2.13 (m, 1H), 2.05-1.93 (m, 2H), 1.58-1.45 (m, 1H).

Example 94

4-({2-[4-(5-Chloro-2-cyanophenyl)-5-methoxy-2-oxopyridin-1(2H)-yl]-3-(tetrahydro-2H-pyran-4-yl)propanoyl}amino)benzoic acid (racemate)

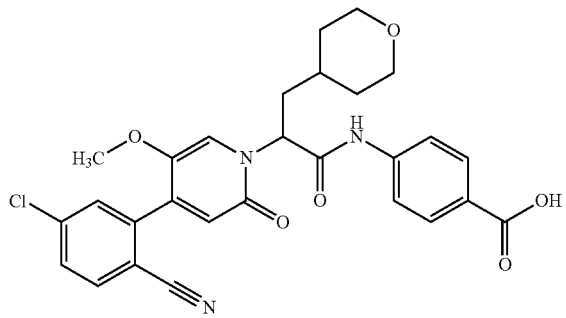

1.07 g (1.89 mmol) of ethyl ({2-[4-(5-chloro-2-cyanophenyl)-5-methoxy-2-oxopyridin-1(2H)-yl]-3-(tetrahydro-2H-pyran-4-yl)propanoyl}amino)benzoate (racemate) in 24 ml of methanol/water (4/1) were reacted with 1.24 g (3.79 mmol) of caesium carbonate according to General Method 4. Yield: 1.24 g (purity 73%, 88% of theory)

LC/MS [Method 1]: $R_t$=0.92 min; MS (ESIneg): m/z=534 (M−H)⁻

$^1$H-NMR (400 MHz, DMSO-$d_6$): δ [ppm]=12.8 (s, 1H), 10.8 (s, 1H), 8.00 (d, 1H), 7.92 (d, 2H), 7.78-7.72 (m, 4H), 7.52 (s, 1H), 6.54 (s, 1H), 5.92-5.85 (m, 1H), 3.86-3.76 (m, 2H), 3.69 (s, 3H), 3.24-3.12 (m, 2H), 2.30-2.20 (m, 1H), 2.03-1.94 (m, 1H), 1.65-1.56 (m, 2H), 1.42-1.18 (m, 3H).

Example 95

4-({2-[4-(5-Chloro-2-cyanophenyl)-5-methoxy-2-oxopyridin-1(2H)-yl]-3-(tetrahydro-2H-pyran-4-yl)propanoyl}amino)benzoic acid (enantiomer 1)

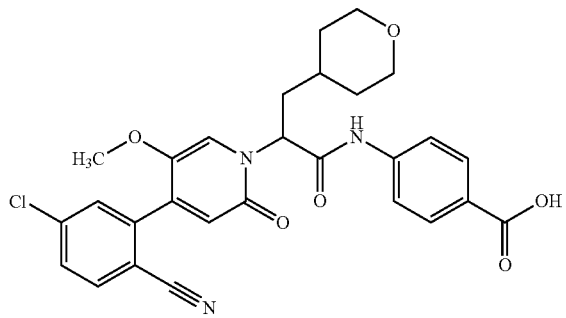

Enantiomer separation of 1.24 g (purity 73%) of the racemate from Example 94 gave 57.6 mg of the title compound Example 95 (enantiomer 1): Chiral HPLC: $R_t$=3.77 min; 99% ee.

Separation method (SFC): column: AD-H 5 μm 250 mm×20 mm; mobile phase: 80% carbon dioxide, 20% 2-propanol; temperature: 40° C.; flow rate: 80 ml/min; pressure: 100 bar; UV detection: 210 nm.

Analysis (SFC): column: AD-3 5 μm 250 mm×4.6 mm; mobile phase: 95-50% carbon dioxide, 5-50% 2-propanol; temperature: 40° C.; flow rate: 3 ml/min; UV detection: 210 nm.

Example 96

4-({2-[4-(5-Chloro-2-cyanophenyl)-5-methoxy-2-oxopyridin-1(2H)-yl]-3-(tetrahydro-2H-pyran-4-yl)propanoyl}amino)benzoic acid (enantiomer 2)

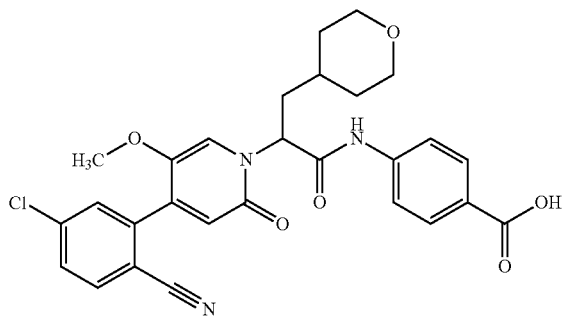 [SMILES: COc1cn(C(CC2CCOCC2)C(=O)Nc2ccc(C(=O)O)cc2)c(=O)cc1-c1cc(Cl)ccc1C#N]

Enantiomer separation of 1.24 g (purity 73%) of the racemate from Example 94 gave 132 mg of the title compound Example 96 (enantiomer 2): Chiral HPLC: R$_t$=4.17 min; 98% ee.

Separation method (SFC): column: AD-H 5 μm 250 mm×20 mm; mobile phase: 80% carbon dioxide, 20% 2-propanol; temperature: 40° C.; flow rate: 80 ml/min; pressure: 100 bar; UV detection: 210 nm.

Analysis (SFC): column: AD-3 5 μm 250 mm×4.6 mm; mobile phase: 95-50% carbon dioxide, 5-50% 2-propanol; temperature: 40° C.; flow rate: 3 ml/min; UV detection: 210 nm.

Example 97

4-({2-[4-(5-Chloro-2-cyanophenyl)-5-methoxy-2-oxopyridin-1(2H)-yl]-3-(tetrahydro-2H-pyran-3-yl)propanoyl}amino)benzoic acid (mixture of racemic diastereomers)

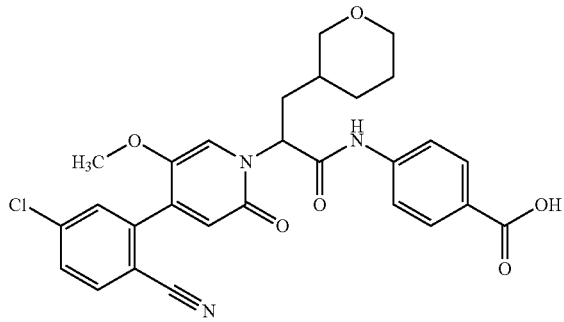 [SMILES: COc1cn(C(CC2CCCOC2)C(=O)Nc2ccc(C(=O)O)cc2)c(=O)cc1-c1cc(Cl)ccc1C#N]

712 mg (purity 85%, 1.02 mmol) of tert-butyl 4-({2-[4-(5-chloro-2-cyanophenyl)-5-methoxy-2-oxopyridin-1(2H)-yl]-3-(tetrahydro-2H-pyran-3-yl)propanoyl}amino)benzoate (mixture of racemic diastereomers) were hydrolysed with TFA according to General Method 2. Yield: 209 mg (38% of theory)

LC/MS [Method 2]: R$_t$=2.81 min; MS (ESIpos): m/z=536 (M+H)$^+$; R$_t$=2.88 min; MS (ESIpos): m/z=536 (M+H)$^+$ $^1$H-NMR (400 MHz, DMSO-d$_6$): δ [ppm]=10.86/10.83 (2×s, 1H), 8.00 (d, 1H), 7.92 (d, 2H), 7.81-7.70 (m, 4H), 7.53/7.50 (2×s, 1H), 6.56/6.55 (2×s, 1H), 5.86/5.82 (2×dd, 1H), 3.87-3.74 (m, 1H), 3.75-3.66 (m, 1H), 3.70 (s, 3H), 3.17-3.02 (m, 1H), 2.23-2.08 (m, 1H), 2.02-1.77 (m, 2H), 1.64-1.49 (m, 1H), 1.48-1.30 (m, 2H), 1.30-1.13 (m, 1H).

Example 98

4-(2-[4-(5-Chloro-2-cyanophenyl)-5-methoxy-2-oxopyridin-1(2H)-yl]-3-(tetrahydro-2H-pyran-3-yl)propanoyl amino)benzoic acid (enantiomer 1 of the first diastereomer)

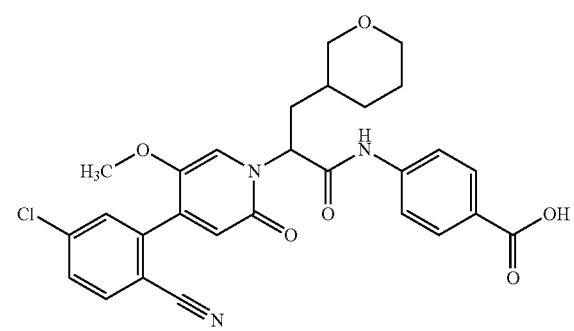

Diastereomer and enantiomer separation of 205 mg of the mixture from Example 97 gave 27 mg of the title compound Example 98 (enantiomer 1 of the first diastereomer): Chiral HPLC: R$_t$=9.48 min; >99% ee.

Separation method: column: Daicel Chiralpak AZ-H 5 μm 250 mm×20 mm; mobile phase: 50% isohexane, 50% ethanol+0.2% TFA; temperature: 30° C.; flow rate: 15 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; flow rate: 3 ml/min; UV detection: 220 nm.

$^1$H-NMR (400 MHz, DMSO-d$_6$): δ [ppm]=12.78 (br. s, 1H), 10.83 (s, 1H), 8.00 (d, 1H), 7.92 (d, 2H), 7.81-7.70 (m, 4H), 7.53 (s, 1H), 6.56 (s, 1H), 5.82 (dd, 1H), 3.87-3.78 (m, 1H), 3.76-3.66 (m, 1H), 3.70 (s, 3H), 3.30-3.21 (m, 1H), 3.12 (dd, 1H), 2.18-2.07 (m, 1H), 2.02-1.91 (m, 1H), 1.86-1.75 (m, 1H), 1.59-1.49 (m, 1H), 1.49-1.30 (m, 2H), 1.29-1.13 (m, 1H).

Example 99

4-({2-[4-(5-Chloro-2-cyanophenyl)-5-methoxy-2-oxopyridin-1(2H)-yl]-3-(tetrahydro-2H-pyran-3-yl)propanoyl}amino)benzoic acid (enantiomer 1 of the second diastereomer)

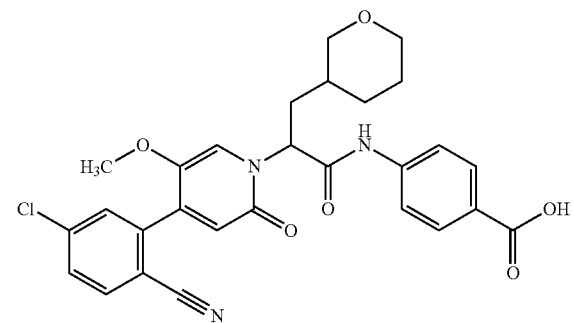 [SMILES: COc1cn(C(CC2CCCOC2)C(=O)Nc2ccc(C(=O)O)cc2)c(=O)cc1-c1cc(Cl)ccc1C#N]

Diastereomer and enantiomer separation of 205 mg of the mixture from Example 97 gave 27 mg (purity 88%) of the title compound Example 99 (enantiomer 1 of the second diastereomer): Chiral HPLC: $R_t$=10.86 min; >99% ee.

Separation method: column: Daicel Chiralpak AZ-H 5 μm 250 mm×20 mm; mobile phase: 50% isohexane, 50% ethanol+0.2% TFA; temperature: 30° C.; flow rate: 15 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; flow rate: 3 ml/min; UV detection: 220 nm.

$^1$H-NMR (400 MHz, DMSO-$d_6$): δ [ppm]=12.78 (br. s, 1H), 10.86 (s, 1H), 8.00 (d, 1H), 7.92 (d, 2H), 7.81-7.70 (m, 4H), 7.50 (s, 1H), 6.55 (s, 1H), 5.86 (dd, 1H), 3.81-3.74 (m, 1H), 3.74-3.65 (m, 1H), 3.70 (s, 3H), 3.33-3.22 (m, 1H), 3.07 (dd, 1H), 2.23-2.11 (m, 1H), 1.94-1.78 (m, 2H), 1.64-1.54 (m, 1H), 1.44-1.20 (m, 3H).

Example 100

4-({2-[4-(5-Chloro-2-cyanophenyl)-5-methoxy-2-oxopyridin-1(2H)-yl]-3-(tetrahydro-2H-pyran-3-yl) propanoyl}amino)benzoic acid (mixture of enantiomer 2 of the first diastereomer and enantiomer 2 of the second diastereomer)

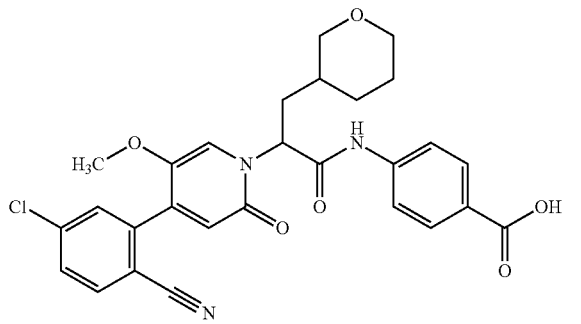 [SMILES: COc1cn(C(CC2CCCOC2)C(=O)Nc2ccc(C(=O)O)cc2)c(=O)cc1-c1cc(Cl)ccc1C#N]

Diastereomer and enantiomer separation of 205 mg of the mixture from Example 97 gave 74 mg (purity 95%) of the title compound Example 100 (mixture of enantiomer 2 of the first diastereomer and enantiomer 2 of the second diastereomer): Chiral HPLC: $R_t$=14.38 min.

Separation method: column: Daicel Chiralpak AZ-H 5 μm 250 mm×20 mm; mobile phase: 50% isohexane, 50% ethanol+0.2% TFA; temperature: 30° C.; flow rate: 15 ml/min; UV detection: 220 nm.

Analysis: column: Daicel Chiralpak AZ-H 5 μm 250 mm×4.6 mm; mobile phase: 50% isohexane, 50% ethanol+0.2% TFA+1% water; flow rate: 3 ml/min; UV detection: 220 nm.

$^1$H-NMR (400 MHz, DMSO-$d_6$): δ [ppm]=12.78 (br. s, 1H), 10.86/10.83 (2×s, 1H), 8.00 (d, 1H), 7.92 (d, 2H), 7.81-7.70 (m, 4H), 7.53/7.50 (2×s, 1H), 6.56/6.55 (2×s, 1H), 5.86/5.82 (2×dd, 1H), 3.87-3.74 (m, 1H), 3.74-3.65 (m, 1H), 3.70 (s, 3H), 3.34-3.22 (m, 1H), 3.17-3.02 (m, 1H), 2.23-2.08 (m, 1H), 2.02-1.77 (m, 2H), 1.64-1.49 (m, 1H), 1.48-1.30 (m, 2H), 1.30-1.13 (m, 1H).

Example 101

({2-[4-(5-Chloro-2-cyanophenyl)-5-methoxy-2-oxopyridin-1(2H)-yl]-3-[tetrahydro-2H-pyran-2-yl] propanoyl}amino)benzoic acid (mixture of racemic diastereomers)

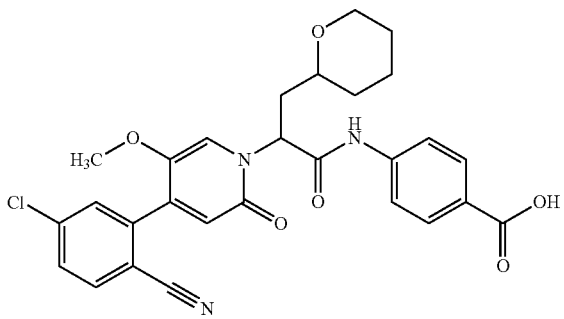 [SMILES: COc1cn(C(CC2CCCCO2)C(=O)Nc2ccc(C(=O)O)cc2)c(=O)cc1-c1cc(Cl)ccc1C#N]

1.24 g (2.25 mmol) of methyl ({2-[4-(5-chloro-2-cyanophenyl)-5-methoxy-2-oxopyridin-1(2H)-yl]-3-[tetrahydro-2H-pyran-2-yl]propanoyl}amino)benzoate (mixture of racemic diastereomers) in 30 ml of methanol/water (4/1) were reacted with 1.47 g (4.51 mmol) of caesium carbonate according to General Method 4. Yield: 1.17 g (85% of theory)

LC/MS [Method 1]: $R_t$=1.00 min; MS (ESIneg): m/z=534 (M−H)⁻

$^1$H-NMR (400 MHz, DMSO-$d_6$): δ [ppm]=12.8 (s, 1H), 10.8/10.7 (2×s, 1H), 8.02-7.98 (m, 1H), 7.93-7.87 (m, 2H), 7.80-7.71 (m, 4H), 7.53/7.49 (2×s, 1H), 6.52/6.51 (2×s, 1H), 5.85-5.71 (m, 1H), 3.90-3.78 (m, 1H), 3.69-3.68 (2×s, 3H), 3.29-3.15 (m, 1H), 3.13-3.05 (m, 1H), 2.42-2.11 (m, 2H), 1.78-1.70 (m, 1H), 1.67-1.56 (m, 1H), 1.47-1.35 (m, 3H), 1.30-1.19 (m, 1H).

Example 102

({2-[4-(5-Chloro-2-cyanophenyl)-5-methoxy-2-oxopyridin-1(2H)-yl]-3-[tetrahydro-2H-pyran-2-yl] propanoyl}amino)benzoic acid (enantiomer 1 of the first diastereomer)

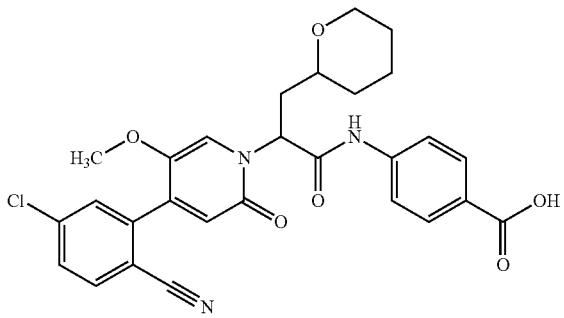 [SMILES: COc1cn(C(CC2CCCCO2)C(=O)Nc2ccc(C(=O)O)cc2)c(=O)cc1-c1cc(Cl)ccc1C#N]

Diastereomer and enantiomer separation of 1.17 g of the mixture from Example 101 gave 231 mg of the title compound Example 102 (enantiomer 1 of the first diastereomer): Chiral HPLC: $R_t$=9.96 min; 87% ee.

Separation method (SFC): column: AD-H 5 µm 250 mm×20 mm; mobile phase: 80% carbon dioxide, 20% 2-propanol; temperature: 40° C.; flow rate: 80 ml/min; pressure: 100 bar; UV detection: 210 nm.

Analysis: column: AZ-H 5 µm 250 mm×4.6 mm; mobile phase: 50% isohexane, 50% 2-propanol+0.2% TFA+1% water; temperature: 40° C.; flow rate: 3 ml/min; UV detection: 210 nm.

$^1$H-NMR (400 MHz, DMSO-d$_6$): δ [ppm]=12.7 (s, 1H), 10.7 (s, 1H), 8.00 (d, 1H), 7.90 (d, 2H), 7.77-7.72 (m, 4H), 7.49 (s, 1H), 6.51 (s, 1H), 5.78-5.71 (m, 1H), 3.84-3.79 (m, 1H), 3.69 (s, 3H), 3.23-3.15 (m, 1H), 3.13-3.05 (m, 1H), 2.42-2.32 (m, 1H), 2.26-2.18 (m, 1H), 1.78-1.71 (m, 1H), 1.62-1.56 (m, 1H), 1.46-1.37 (m, 3H), 1.30-1.20 (m, 1H).

Example 103

({2-[4-(5-Chloro-2-cyanophenyl)-5-methoxy-2-oxopyridin-1(2H)-yl]-3-[tetrahydro-2H-pyran-2-yl]propanoyl}amino)benzoic acid (enantiomer 1 of the second diastereomer)

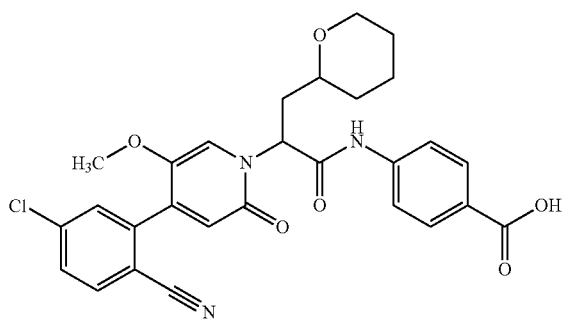 [SMILES: COc1cn(C(CC2CCCCO2)C(=O)Nc2ccc(C(=O)O)cc2)c(=O)cc1-c1cc(Cl)ccc1C#N]

Diastereomer and enantiomer separation of 1.17 g of the mixture from Example 101 gave 54 mg of the title compound Example 103 (enantiomer 1 of the second diastereomer): Chiral HPLC: R$_t$=15.34 min; 99% ee.

Separation method (SFC): column: AD-H 5 µm 250 mm×20 mm; mobile phase: 80% carbon dioxide, 20% 2-propanol; temperature: 40° C.; flow rate: 80 ml/min; pressure: 100 bar; UV detection: 210 nm.

Analysis: column: AZ-H 5 µm 250 mm×4.6 mm; mobile phase: 50% isohexane, 50% 2-propanol+0.2% TFA+1% water; temperature: 40° C.; flow rate: 3 ml/min; UV detection: 210 nm.

$^1$H-NMR (400 MHz, DMSO-d$_6$): δ [ppm]=12.8 (s, 1H), 10.7 (s, 1H), 7.99 (d, 1H), 7.90 (d, 2H), 7.77 (d, 2H), 7.74-7.71 (m, 2H), 7.52 (s, 1H), 6.52 (s, 1H), 5.82 (t, 1H), 3.90-3.84 (m, 1H), 3.68 (s, 3H), 3.28-3.22 (m, 2H), 2.34-2.27 (m, 1H), 2.19-2.10 (m, 1H), 1.78-1.73 (m, 1H), 1.67-1.60 (m, 1H), 1.47-1.36 (m, 3H), 1.33-1.23 (m, 1H).

Example 104

({2-[4-(5-Chloro-2-cyanophenyl)-5-methoxy-2-oxopyridin-1(2H)-yl]-3-[tetrahydro-2H-pyran-2-yl]propanoyl}amino)benzoic acid (enantiomer 2 of the second diastereomer)

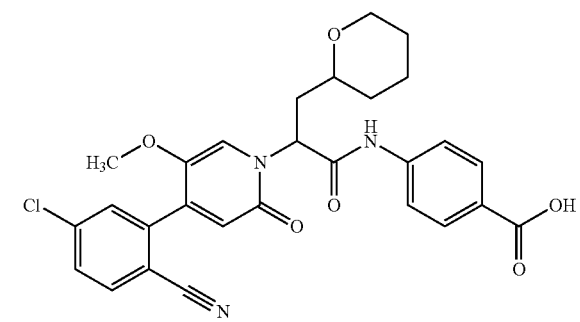 [SMILES: COc1cn(C(CC2CCCCO2)C(=O)Nc2ccc(C(=O)O)cc2)c(=O)cc1-c1cc(Cl)ccc1C#N]

Diastereomer and enantiomer separation of 1.17 g of the mixture from Example 101 gave 91 mg of the title compound Example 104 (enantiomer 2 of the second diastereomer): Chiral HPLC: R$_t$=20.83 min; 99% ee.

Separation method (SFC): column: AD-H 5 µm 250 mm×20 mm; mobile phase: 80% carbon dioxide, 20% 2-propanol; temperature: 40° C.; flow rate: 80 ml/min; pressure: 100 bar; UV detection: 210 nm.

Analysis: column: AZ-H 5 µm 250 mm×4.6 mm; mobile phase: 50% isohexane, 50% 2-propanol+0.2% TFA+1% water; temperature: 40° C.; flow rate: 3 ml/min; UV detection: 210 nm.

$^1$H-NMR (400 MHz, DMSO-d$_6$): δ [ppm]=12.8 (s, 1H), 10.7 (s, 1H), 7.99 (d, 1H), 7.90 (d, 2H), 7.77 (d, 2H), 7.74-7.71 (m, 2H), 7.52 (s, 1H), 6.52 (s, 1H), 5.82 (t, 1H), 3.90-3.84 (m, 1H), 3.68 (s, 3H), 3.28-3.22 (m, 2H), 2.34-2.27 (m, 1H), 2.19-2.10 (m, 1H), 1.78-1.73 (m, 1H), 1.67-1.60 (m, 1H), 1.47-1.36 (m, 3H), 1.33-1.23 (m, 1H).

Example 105

({2-[4-(5-Chloro-2-cyanophenyl)-5-methoxy-2-oxopyridin-1(2H)-yl]-3-[tetrahydro-2H-pyran-2-yl]propanoyl}amino)benzoic acid (enantiomer 2 of the first diastereomer)

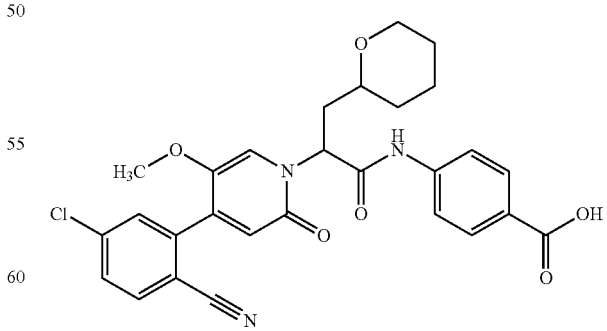

Diastereomer and enantiomer separation of 1.17 g of the mixture from Example 101 gave 183 mg of the title compound Example 105 (enantiomer 2 of the first diastereomer): Chiral HPLC: R$_t$=27.14 min; 99% ee.

Separation method (SFC): column: AD-H 5 μm 250 mm×20 mm; mobile phase: 80% carbon dioxide, 20% 2-propanol; temperature: 40° C.; flow rate: 80 ml/min; pressure: 100 bar; UV detection: 210 nm.

Analysis: column: AZ-H 5 μm 250 mm×4.6 mm; mobile phase: 50% isohexane, 50% 2-propanol+0.2% TFA+1% water; temperature: 40° C.; flow rate: 3 ml/min; UV detection: 210 nm.

$^1$H-NMR (400 MHz, DMSO-$d_6$): δ [ppm]=12.7 (s, 1H), 10.7 (s, 1H), 8.00 (d, 1H), 7.90 (d, 2H), 7.77-7.72 (m, 4H), 7.49 (s, 1H), 6.51 (s, 1H), 5.78-5.71 (m, 1H), 3.84-3.79 (m, 1H), 3.69 (s, 3H), 3.23-3.15 (m, 1H), 3.13-3.05 (m, 1H), 2.42-2.32 (m, 1H), 2.26-2.18 (m, 1H), 1.78-1.71 (m, 1H), 1.62-1.56 (m, 1H), 1.46-1.37 (m, 3H), 1.30-1.20 (m, 1H).

Example 106

4-({2-[4-(5-Chloro-2-cyanophenyl)-5-methoxy-2-oxopyridin-1(2H)-yl]-3-(1,4-dioxan-2-yl)propanoyl}amino)benzoic acid (mixture of racemic diastereomers)

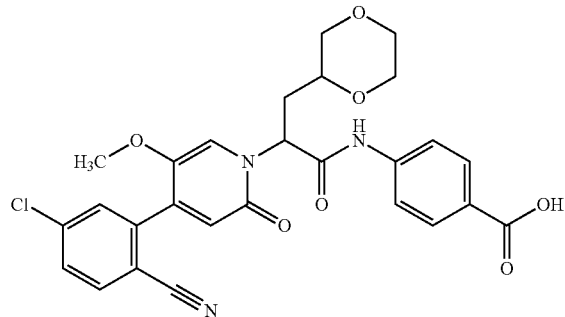 [SMILES: COc1cn(C(CC2COCCO2)C(=O)Nc2ccc(C(=O)O)cc2)c(=O)cc1-c1cc(Cl)ccc1C#N]

103 mg (0.17 mmol) of tert-butyl 4-({2-[4-(5-chloro-2-cyanophenyl)-5-methoxy-2-oxopyridin-1(2H)-yl]-3-(1,4-dioxan-2-yl)propanoyl}amino)benzoate (mixture of racemic diastereomers) were hydrolysed with TFA according to General Method 2. Yield: 60 mg (64% of theory)

LC/MS [Method 8]: $R_t$=1.12 min; MS (ESIneg): m/z=536 (M-H)$^-$; $R_t$=1.13 min; MS (ESIneg): m/z=536 (M-H)$^-$ $^1$H-NMR (400 MHz, DMSO-$d_6$): δ [ppm]=12.77 (br. s, 1H), 10.75/10.73 (2×s, 1H), 8.03-7.97 (m, 1H), 7.94-7.86 (m, 2H), 7.80-7.70 (m, 4H), 7.53/7.48 (2×s, 1H), 6.54/6.53 (2×s, 1H), 5.83-5.73 (m, 1H), 3.79-3.65 (m, 2H), 3.70/3.68 (2×s, 3H), 3.65-3.56 (m, 1H), 3.55-3.39 (m, 2H), 3.30-3.20 (m, 2H), 2.41-2.09 (m, 2H).

Example 107

4-({2-[4-(5-Chloro-2-cyanophenyl)-5-methoxy-2-oxopyridin-1(2H)-yl]-4-fluorobutanoyl}amino)benzoic acid (racemate)

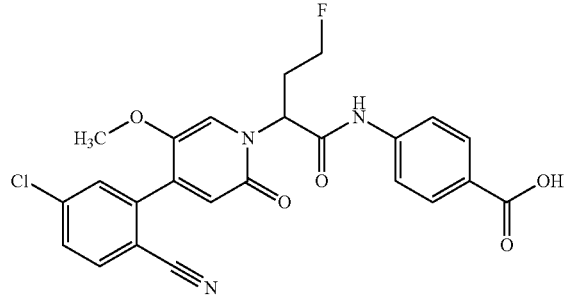 [SMILES: COc1cn(C(CCF)C(=O)Nc2ccc(C(=O)O)cc2)c(=O)cc1-c1cc(Cl)ccc1C#N]

114 mg (211 μmol) of tert-butyl 4-({2-[4-(5-chloro-2-cyanophenyl)-5-methoxy-2-oxopyridin-1(2H)-yl]-4-fluorobutanoyl}amino)benzoate (racemate) and 325 μl (4.22 mmol) of TFA were reacted according to General Method 2. The crude product was purified by preparative HPLC [column: Chromatorex C18, 10 μm, 125 mm×30 mm, mobile phase: acetonitrile/water gradient (0 to 3 min 15% acetonitrile, to 35 min 90% acetonitrile and a further 3 min 90% acetonitrile)]. Yield: 45 mg (44% of theory)

LC/MS [Method 1]: $R_t$=0.91 min; MS (ESIneg): m/z=482 (M-H)$^-$ $^1$H-NMR (400 MHz, DMSO-$d_6$): δ [ppm]=12.8 (br. s, 1H), 10.8 (s, 1H), 8.00 (d, 1H), 7.92 (d, 2H), 7.79-7.72 (m, 4H), 7.52 (s, 1H), 6.55 (s, 1H), 5.85 (t, 1H), 4.67-4.49 (m, 1H), 4.48-4.29 (m, 1H), 3.69 (s, 3H), 2.69-2.55 (m, 2H).

Example 108

4-({2-[4-(5-Chloro-2-cyanophenyl)-5-methoxy-2-oxopyridin-1(2H)-yl]-4,4-difluorobutanoyl}amino)benzoic acid (racemate)

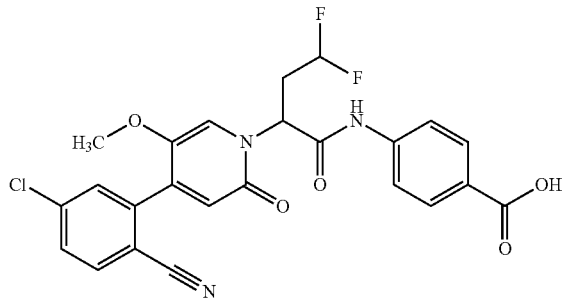 [SMILES: COc1cn(C(CC(F)F)C(=O)Nc2ccc(C(=O)O)cc2)c(=O)cc1-c1cc(Cl)ccc1C#N]

80 mg (151 μmol) of ethyl 4-({2-[4-(5-chloro-2-cyanophenyl)-5-methoxy-2-oxopyridin-1(2H)-yl]-4,4-difluorobutanoyl}amino)benzoate (racemate) in 2 ml of methanol/water (4/1) were reacted with 326 mg (302 μmol) of caesium carbonate according to General Method 4. The crude product was purified by preparative HPLC [column: Chromatorex C18, 10 μm, 125 mm×30 mm, mobile phase: acetonitrile/0.05% formic acid gradient (0 to 3 min 10% acetonitrile, to 35 min 90% acetonitrile and a further 3 min 90% acetonitrile)]. Yield: 18 mg (23% of theory)

LC/MS [Method 1]: $R_t$=0.92 min; MS (ESIneg): m/z=500 (M-H)$^-$ $^1$H-NMR (400 MHz, DMSO-$d_6$): δ [ppm]=12.8 (br. s, 1H), 10.7 (s, 1H), 8.00 (d, 1H), 7.91 (d, 2H), 7.76-7.70 (m, 4H), 7.56 (s, 1H), 6.55 (s, 1H), 6.15 (tt, 1H), 5.91 (dd, 1H), 3.69 (s, 3H), 2.99-2.75 (m, 2H).

Example 109

4-({2-[4-(5-Chloro-2-cyanophenyl)-5-methoxy-2-oxopyridin-1(2H)-yl]-4,4,4-trifluorobutanoyl}amino)benzoic acid (racemate)

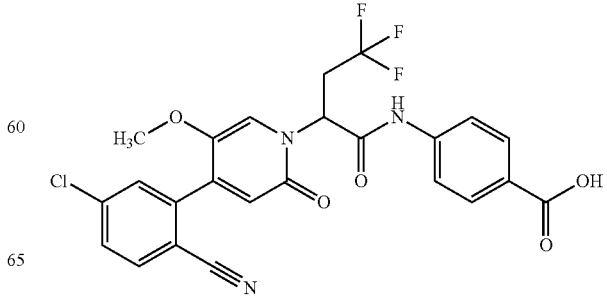

21 mg (38 µmol) of ethyl 4-({2-[4-(5-chloro-2-cyanophenyl)-5-methoxy-2-oxopyridin-1(2H)-yl]-4,4,4-trifluorobutanoyl}amino)benzoate (racemate) in 0.75 ml of methanol/water (4/1) were reacted with 25 mg (77 µmol) of caesium carbonate according to General Method 4. The crude product was purified by preparative HPLC [column: Chromatorex C18, 10 µm, 125 mm×30 mm, mobile phase: acetonitrile/0.05% formic acid gradient (0 to 3 min 10% acetonitrile, to 35 min 90% acetonitrile and a further 3 min 90% acetonitrile)]. Yield: 9 mg (46% of theory)

LC/MS [Method 1]: $R_t$=0.98 min; MS (ESIneg): m/z=518 (M−H)−

$^1$H-NMR (400 MHz, DMSO-d$_6$): δ [ppm]=12.8 (s, 1H), 10.8 (s, 1H), 8.00 (d, 1H), 7.92 (d, 2H), 7.75-7.72 (m, 4H), 7.63 (s, 1H), 6.56 (s, 1H), 6.11-6.05 (m, 1H), 3.69 (s, 3H), 3.56-3.25 (m, 2H).

Example 110

4-({2-[4-(5-Chloro-2-cyanophenyl)-5-methoxy-2-oxopyridin-1(2H)-yl]-4-fluoropentanoyl}amino)benzoic acid (mixture of racemic diastereomers)

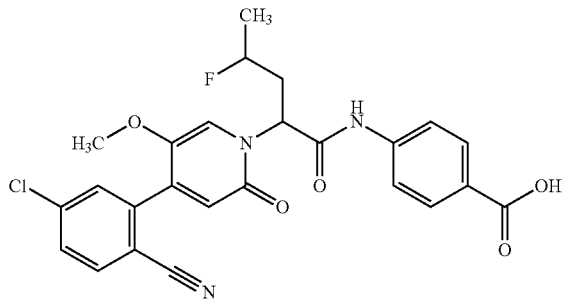 [SMILES: COc1cn(C(CC(C)F)C(=O)Nc2ccc(C(=O)O)cc2)c(=O)cc1-c1cc(Cl)ccc1C#N]

170 mg (purity 91%, 0.29 mmol) of ethyl 4-({2-[4-(5-chloro-2-cyanophenyl)-5-methoxy-2-oxopyridin-1(2H)-yl]-4-fluoropentanoyl}amino)benzoate (mixture of racemic diastereomers) were hydrolysed with lithium hydroxide according to General Method 3. Yield: 67 mg (45% of theory)

LC/MS [Method 8]: $R_t$=1.19 min; MS (ESIpos): m/z=498 (M+H)+

$^1$H-NMR (400 MHz, DMSO-d$_6$): δ [ppm]=10.83 (s, 1H), 8.00 (d, 1H), 7.95-7.87 (m, 2H), 7.81-7.70 (m, 4H), 7.55/7.51 (2×s, 1H), 6.54 (s, 1H), 5.94-5.83 (m, 1H), 4.84-4.45 (2×dm, 2H), 3.69 (s, 3H), 2.46-2.41 (m, 1H), 1.39/1.33 (2×t, 3H).

Example 111

4-({2-[4-(5-Chloro-2-cyanophenyl)-5-methoxy-2-oxopyridin-1(2H)-yl]-5,5,5-trifluoro-4-methylpentanoyl}amino)benzoic acid (mixture of racemic diastereomers)

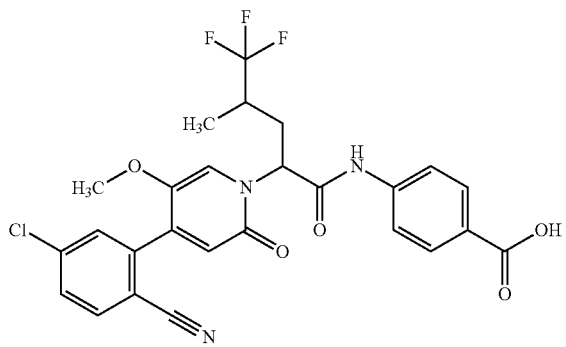 [SMILES: COc1cn(C(CC(C)C(F)(F)F)C(=O)Nc2ccc(C(=O)O)cc2)c(=O)cc1-c1cc(Cl)ccc1C#N]

48 mg (0.08 mmol) of tert-butyl 4-({2-[4-(5-chloro-2-cyanophenyl)-5-methoxy-2-oxopyridin-1(2H)-yl]-5,5,5-trifluoro-4-methylpentanoyl}amino)benzoate (mixture of racemic diastereomers) were hydrolysed with TFA according to General Method 2. Yield: 24 mg (56% of theory)

LC/MS [Method 1]: $R_t$=1.07 min; MS (ESIpos): m/z=548 (M+H)+

$^1$H-NMR (400 MHz, DMSO-d$_6$): δ [ppm]=10.89/10.78 (2×s, 1H), 8.00 (d, 1H), 7.96-7.88 (m, 2H), 7.81-7.70 (m, 4H), 7.53 (s, 1H), 6.59/6.58 (2×s, 1H), 5.91/5.78 (2×dd, 1H), 3.69/3.67 (2×s, 3H), 2.72-2.62 (m, 1H), 2.44-2.31 (m, 1H), 2.22-1.98 (m, 1H), 1.19/1.14 (2×d, 3H).

Example 112

4-({2-[4-(5-Chloro-2-cyanophenyl)-5-methoxy-2-oxopyridin-1(2H)-yl]-4,4-dimethylpentanoyl}amino)benzoic acid (racemate)

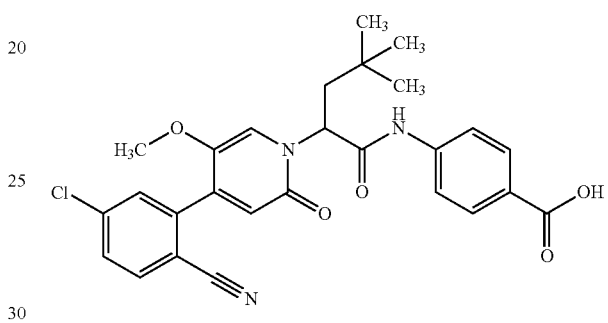

99 mg (176 µmol) of tert-butyl 4-({2-[4-(5-chloro-2-cyanophenyl)-5-methoxy-2-oxopyridin-1(2H)-yl]-4,4-dimethylpentanoyl}amino)benzoate (racemate) and 270 µl (3.51 µmol) of TFA were reacted according to General Method 2. The crude product was purified by preparative HPLC [column: Chromatorex C18, 10 µm, 125 mm×30 mm, mobile phase: acetonitrile/water gradient (0 to 3 min 15% acetonitrile, to 35 min 90% acetonitrile and a further 3 min 90% acetonitrile)]. Yield: 57 mg (64% of theory)

LC/MS [Method 1]: $R_t$=1.07 min; MS (ESIneg): m/z=506 (M−H)−

$^1$H-NMR (400 MHz, DMSO-d$_6$): δ [ppm]=12.8 (s, 1H), 10.9 (s, 1H), 7.99 (d, 1H), 7.91 (d, 2H), 7.77 (d, 2H), 7.74-7.71 (m, 2H), 7.60 (s, 1H), 6.54 (s, 1H), 5.99 (dd, 1H), 3.70 (s, 3H), 2.12 (dd, 1H), 2.03 (dd, 1H), 0.92 (s, 9H).

Example 113

4-({2-[4-(5-Chloro-2-cyanophenyl)-5-methoxy-2-oxopyridin-1(2H)-yl]-3-[2,2-difluorocyclopropyl]propanoyl}amino)benzoic acid (mixture of racemic diastereomers)

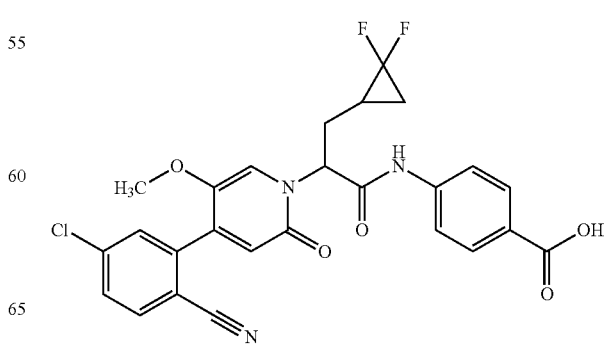

74.0 mg (127 µmol) of tert-butyl 4-({2-[4-(5-chloro-2-cyanophenyl)-5-methoxy-2-oxopyridin-1(2H)-yl]-3-[2,2-difluorocyclopropyl]propanoyl}amino)benzoate (mixture of racemic diastereomers) and 195 µl (2.53 mmol) of TFA were reacted according to General Method 2. The crude product was purified by preparative HPLC [column: Chromatorex C18, 10 µm, 125 mm×30 mm, mobile phase: acetonitrile/water gradient (0 to 3 min 15% acetonitrile, to 35 min 90% acetonitrile and a further 3 min 90% acetonitrile)]. Yield: 45 mg (52% of theory)

LC/MS [Method 1]: $R_t$=0.99 min; MS (ESIneg): m/z=526 (M-H)⁻

¹H-NMR (400 MHz, DMSO-$d_6$): δ [ppm]=12.8 (s, 1H), 10.8/10.7 (2×s, 1H), 8.00 (d, 1H), 7.93-7.90 (m, 2H), 7.77-7.71 (m, 4H), 7.53 (s, 1H), 6.56 (s, 1H), 5.80-5.70 (m, 1H), 3.70/3.69 (2×s, 3H), 2.60-2.37 (m, 1H), 2.30-2.09 (2×m, 1H), 1.70-1.49 (m, 2H), 1.32-1.05 (2×m, 1H).

Example 114

4-({2-[4-(5-Chloro-2-cyanophenyl)-5-methoxy-2-oxopyridin-1(2H)-yl]-3-[2,2-difluorocyclopropyl]propanoyl}amino)benzoic acid (enantiomer 1 of the first diastereomer and enantiomer 1 of the second diastereomer)

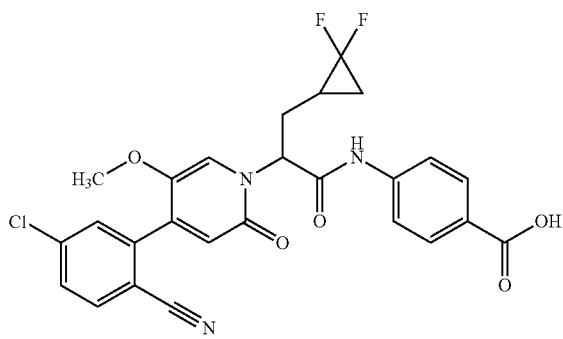 [SMILES: COc1cn(C(CC2CC2(F)F)C(=O)Nc2ccc(C(=O)O)cc2)c(=O)cc1-c1cc(Cl)ccc1C#N]

Enantiomer separation of 44 mg of the mixture of racemic diastereomers from Example 113 gave 15 mg of the title compound Example 114: Chiral HPLC: $R_t$=5.42/5.81 min; 99% ee, diastereomer ratio 1:1.

Separation method: column: AZ-H 5 µm 250 mm×20 mm; mobile phase: 50% isohexane, 50% 2-propanol+0.2% TFA+1% water; temperature: 30° C.; flow rate: 20 ml/min; UV detection: 220 nm.

Analysis: column: AZ-H 5 µm 250 mm×4.6 mm; mobile phase: 50% isohexane, 50% 2-propanol+0.2% TFA+1% water; temperature: 30° C.; flow rate: 1 ml/min; UV detection: 220 nm.

¹H-NMR (400 MHz, DMSO-$d_6$): δ [ppm]=12.8 (s, 1H), 10.8/10.7 (2×s, 1H), 8.00 (d, 1H), 7.93-7.90 (m, 2H), 7.77-7.71 (m, 4H), 7.53 (s, 1H), 6.56 (s, 1H), 5.80-5.70 (m, 1H), 3.70/3.69 (2×s, 3H), 2.60-2.37 (m, 1H), 2.30-2.09 (2×m, 1H), 1.70-1.49 (m, 2H), 1.32-1.05 (2×m, 1H).

Example 115

4-({2-[4-(5-Chloro-2-cyanophenyl)-5-methoxy-2-oxopyridin-1(2H)-yl]-3-[2,2-difluorocyclopropyl]propanoyl}amino)benzoic acid (enantiomer 2 of the first diastereomer and enantiomer 2 of the second diastereomer)

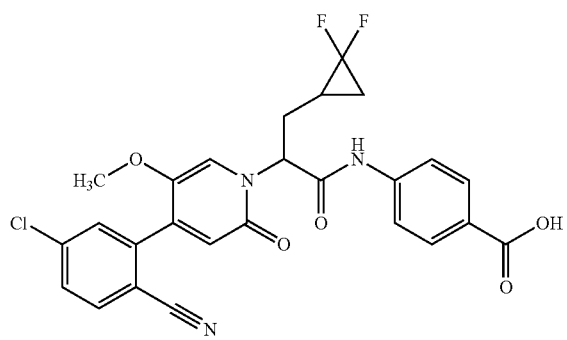 [SMILES: COc1cn(C(CC2CC2(F)F)C(=O)Nc2ccc(C(=O)O)cc2)c(=O)cc1-c1cc(Cl)ccc1C#N]

Enantiomer separation of 44 mg of the mixture of racemic diastereomers from Example 113 gave 15 mg of the title compound Example 115: Chiral HPLC: $R_t$=8.75/9.79 min; 99% ee, diastereomer ratio 1:1.

Separation method: column: AZ-H 5 µm 250 mm×20 mm; mobile phase: 50% isohexane, 50% 2-propanol+0.2% TFA+1% water; temperature: 30° C.; flow rate: 20 ml/min; UV detection: 220 nm.

Analysis: column: AZ-H 5 µm 250 mm×4.6 mm; mobile phase: 50% isohexane, 50% 2-propanol+0.2% TFA+1% water; temperature: 30° C.; flow rate: 1 ml/min; UV detection: 220 nm.

¹H-NMR (400 MHz, DMSO-$d_6$): δ [ppm]=12.8 (s, 1H), 10.8/10.7 (2×s, 1H), 8.00 (d, 1H), 7.93-7.90 (m, 2H), 7.77-7.71 (m, 4H), 7.53 (s, 1H), 6.56 (s, 1H), 5.80-5.70 (m, 1H), 3.70/3.69 (2×s, 3H), 2.60-2.37 (m, 1H), 2.30-2.09 (2×m, 1H), 1.70-1.49 (m, 2H), 1.32-1.05 (2×m, 1H).

Example 116

4-({2-[4-(5-Chloro-2-cyanophenyl)-5-methoxy-2-oxopyridin-1(2H)-yl]-3-(1-methylcyclopropyl)propanoyl}amino)benzoic acid (racemate)

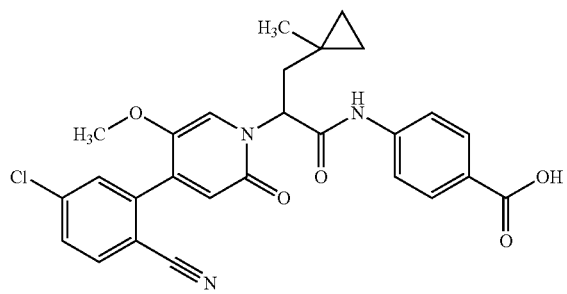 [SMILES: COc1cn(C(CC2(C)CC2)C(=O)Nc2ccc(C(=O)O)cc2)c(=O)cc1-c1cc(Cl)ccc1C#N]

100 mg (178 µmol) of tert-butyl 4-({2-[4-(5-chloro-2-cyanophenyl)-5-methoxy-2-oxopyridin-1(2H)-yl]-3-(1-methylcyclopropyl)propanoyl}amino)benzoate (racemate) and 274 µl (3.56 mmol) of TFA were reacted according to General Method 2. The reaction mixture was purified by preparative HPLC [column: Chromatorex C18, 10 μm, 125 mm×30 mm, mobile phase: acetonitrile/water gradient (0 to 3 min 15% acetonitrile, to 35 min 90% acetonitrile and a further 3 min 90% acetonitrile)]. Yield: 107 mg (27% of theory)

LC/MS [Method 1]: $R_t$=1.05 min; MS (ESIneg): m/z=504 (M−H)⁻

$^1$H-NMR (400 MHz, DMSO-$d_6$): δ [ppm]=12.8 (s, 1H), 10.8 (s, 1H), 8.00 (d, 1H), 7.91 (d, 2H), 7.79-7.72 (m, 4H), 7.55 (s, 1H), 6.53 (s, 1H), 5.97 (dd, 1H), 3.68 (s, 3H), 2.20 (dd, 1H), 2.04 (dd, 1H), 1.08 (s, 3H), 0.35-0.25 (m, 2H), 0.21-0.12 (m, 2H).

Example 117

4-({2-[4-(5-Chloro-2-cyanophenyl)-5-methoxy-2-oxopyridin-1(2H)-yl]-3-cyclobutylpropanoyl}amino)benzoic acid (racemate)

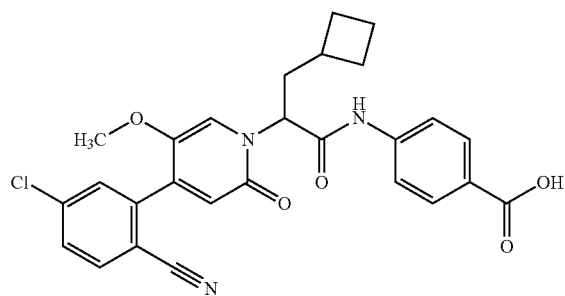 [SMILES: COc1cn(C(CC2CCC2)C(=O)Nc2ccc(C(=O)O)cc2)c(=O)cc1-c1cc(Cl)ccc1C#N]

64 mg (purity 86%, 0.10 mmol) of tert-butyl 4-({2-[4-(5-chloro-2-cyanophenyl)-5-methoxy-2-oxopyridin-1(2H)-yl]-3-cyclobutylpropanoyl}amino)benzoate (racemate) were hydrolysed with TFA according to General Method 2. Yield: 33 mg (67% of theory)

LC/MS [Method 1]: $R_t$=1.07 min; MS (ESIpos): m/z=506 (M+H)⁺

$^1$H-NMR (400 MHz, DMSO-$d_6$): δ [ppm]=12.77 (s, 1H), 10.80 (s, 1H), 8.00 (s, 1H), 7.91 (d, 2H), 7.80-7.70 (m, 4H), 7.51 (s, 1H), 6.51 (s, 1H), 5.75-5.65 (m, 1H), 3.69 (s, 3H), 2.35-2.16 (m, 3H), 2.01-1.88 (m, 2H), 1.85-1.60 (m, 4H).

Example 118

4-({[4-(5-Chloro-2-cyanophenyl)-5-methoxy-2-oxopyridin-1(2H)-yl](ethoxy)acetyl}amino)benzoic acid (racemate)

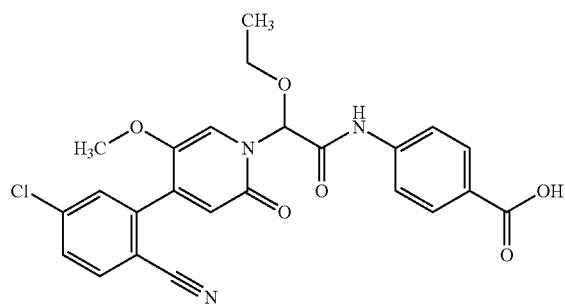 [SMILES: CCOC(C(=O)Nc1ccc(C(=O)O)cc1)n1cc(OC)c(-c2cc(Cl)ccc2C#N)cc1=O]

260 mg (0.48 mmol) of tert-butyl 4-({[4-(5-chloro-2-cyanophenyl)-5-methoxy-2-oxopyridin-1(2H)-yl](ethoxy)acetyl}amino)benzoate (racemate) were hydrolysed with TFA according to General Method 2. Yield: 184 mg (79% of theory)

LC/MS [Method 1]: $R_t$=0.96 min; MS (ESIpos): m/z=482 (M+H)⁺

$^1$H-NMR (400 MHz, DMSO-$d_6$): δ [ppm]=12.81 (br. s, 1H), 10.72 (s, 1H), 8.01 (d, 1H), 7.94 (d, 2H), 7.84-7.71 (m, 4H), 7.35 (s, 1H), 6.57 (s, 1H), 6.41 (s, 1H), 3.82-3.73 (m, 1H), 3.73-3.62 (m, 1H), 3.67 (s, 3H), 1.27 (t, 3H).

Example 119

4-({[4-(5-Chloro-2-cyanophenyl)-5-methoxy-2-oxopyridin-1(2H)-yl]acetyl}amino)benzoic acid

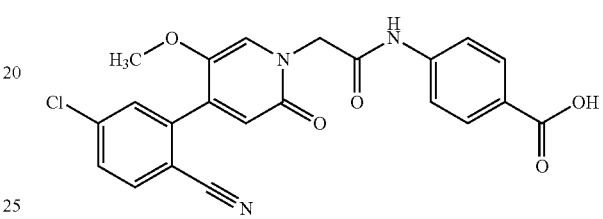

49.0 mg (99.0 μmol) of tert-butyl 4-({[4-(5-chloro-2-cyanophenyl)-5-methoxy-2-oxopyridin-1(2H)-yl]acetyl}amino)benzoate and 153 μl (1.98 mmol) of TFA were reacted according to General Method 2. Yield: 20 mg (44% of theory)

LC/MS [Method 1]: $R_t$=0.81 min; MS (ESIneg): m/z=436 (M−H)⁻

$^1$H-NMR (400 MHz, DMSO-$d_6$): δ [ppm]=12.7 (s, 1H), 10.7 (s, 1H), 8.01 (d, 1H), 7.92 (d, 2H), 7.75-7.71 (m, 4H), 7.60 (s, 1H), 6.52 (s, 1H), 4.82 (s, 2H), 3.64 (s, 3H).

Example 120

4-[(2-{4-[5-Chloro-2-(trifluoromethoxy)phenyl]-5-methoxy-2-oxopyridin-1(2H)-yl}propanoyl)amino]benzoic acid (racemate)

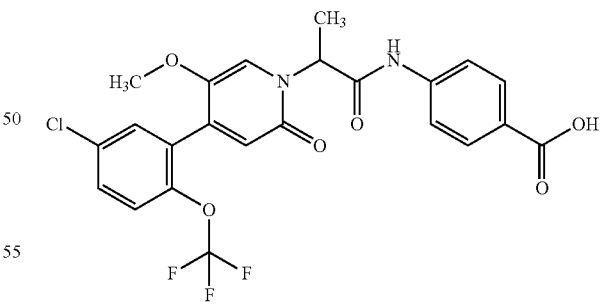

155 mg (0.23 mmol) of tert-butyl 4-[(2-{4-[5-chloro-2-(trifluoromethoxy)phenyl]-5-methoxy-2-oxopyridin-1(2H)-yl}propanoyl)amino]benzoate were hydrolysed with TFA according to General Method 2. Yield: 67 mg (purity 94%, 54% of theory)

LC/MS [Method 1]: $R_t$=1.03 min; MS (ESIpos): m/z=511 (M+H)⁺

$^1$H-NMR (400 MHz, DMSO-$d_6$): δ [ppm]=12.76 (br. s, 1H), 10.68 (s, 1H), 7.91 (d, 2H), 7.73 (d, 2H), 7.65 (dd, 1H), 7.59 (d, 1H), 7.51 (dd, 1H), 7.40 (s, 1H), 6.41 (s, 1H), 5.59 (q, 1H), 3.65 (s, 3H), 1.72 (d, 3H).

Example 121

4-({2-[4-(2-Bromo-5-chlorophenyl)-5-methoxy-2-oxopyridin-1(2H)-yl]propanoyl}amino)benzoic acid (racemate)

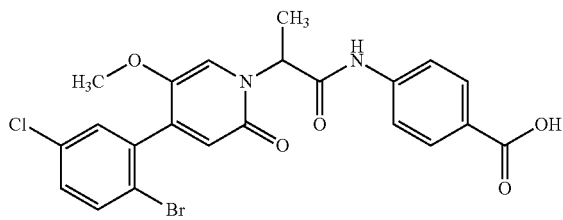 [SMILES: COc1cn(C(C)C(=O)Nc2ccc(C(=O)O)cc2)c(=O)cc1-c1cc(Cl)ccc1Br]

72 mg (purity 73%, 0.09 mmol) of tert-butyl 4-({2-[4-(2-bromo-5-chlorophenyl)-5-methoxy-2-oxopyridin-1(2H)-yl]propanoyl}amino)benzoate (racemate) were hydrolysed with TFA according to General Method 2. Yield: 20 mg (42% of theory)

LC/MS [Method 1]: $R_t$=0.98 min; MS (ESIpos): m/z=505 (M+H)$^+$ $^1$H-NMR (400 MHz, DMSO-d$_6$): δ [ppm]=12.76 (s, 1H), 10.70 (s, 1H), 7.91 (d, 2H), 7.78-7.69 (m, 3H), 7.51-7.41 (m, 2H), 7.40 (s, 1H), 6.32 (s, 1H), 5.61 (q, 1H), 3.66 (s, 3H), 1.72 (d, 3H).

Example 122

4-({2-[4-(5-Chloro-2-methylphenyl)-5-methoxy-2-oxopyridin-1(2H)-yl]propanoyl}amino)benzoic acid (racemate)

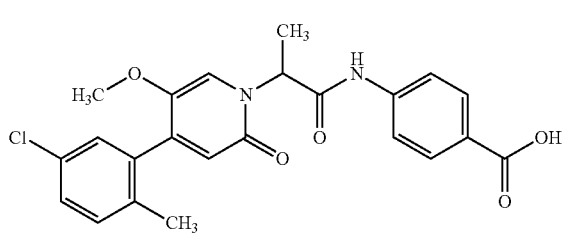 [SMILES: COc1cn(C(C)C(=O)Nc2ccc(C(=O)O)cc2)c(=O)cc1-c1cc(Cl)ccc1C]

105 mg (purity 91%, 0.19 mmol) of tert-butyl 4-({2-[4-(5-chloro-2-methylphenyl)-5-methoxy-2-oxopyridin-1(2H)-yl]propanoyl}amino)benzoate (racemate) were hydrolysed with TFA according to General Method 2. Yield: 47 mg (60% of theory)

LC/MS [Method 1]: $R_t$=0.99 min; MS (ESIpos): m/z=441 (M+H)$^+$ $^1$H-NMR (400 MHz, DMSO-d$_6$): δ [ppm]=12.76 (s, 1H), 10.67 (s, 1H), 7.91 (d, 2H), 7.74 (d, 2H), 7.42-7.34 (m, 2H), 7.31 (d, 1H), 7.22 (d, 1H), 6.26 (s, 1H), 5.60 (q, 1H), 3.63 (s, 3H), 2.11 (s, 3H), 1.72 (d, 3H).

Example 123

4-[(2-{4-[5-Chloro-2-(trifluoromethyl)phenyl]-5-methoxy-2-oxopyridin-1(2H)-yl}propanoyl)amino]benzoic acid (racemate)

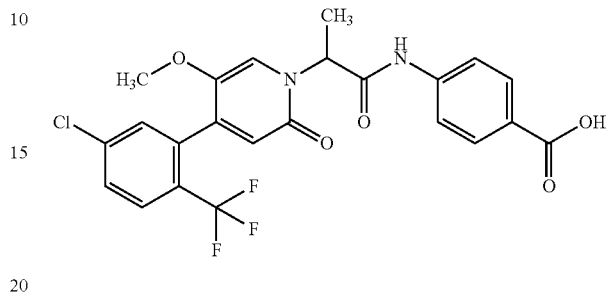

145 mg (purity 84%, 0.22 mmol) of tert-butyl 4-[(2-{4-[5-chloro-2-(trifluoromethyl)phenyl]-5-methoxy-2-oxopyridin-1(2H)-yl}propanoyl)amino]benzoate (racemate) were hydrolysed with TFA according to General Method 2. Yield: 41 mg (37% of theory)

LC/MS [Method 1]: $R_t$=1.00 min; MS (ESIpos): m/z=495 (M+H)$^+$ $^1$H-NMR (400 MHz, DMSO-d$_6$): δ [ppm]=12.76 (s, 1H), 10.70/10.68 (2×s, 1H), 7.91 (d, 2H), 7.87 (d, 1H), 7.79-7.69 (m, 3H), 7.58/7.54 (2×s, 1H), 7.37 (s, 1H), 6.36/6.34 (2×s, 1H), 5.61 (q, 1H), 3.63 (s, 3H), 1.72 (2×d, 3H).

Example 124

4-({2-[4-(5-Chloro-2-cyclopropylphenyl)-5-methoxy-2-oxopyridin-1(2H)-yl]propanoyl}amino)benzoic acid (racemate)

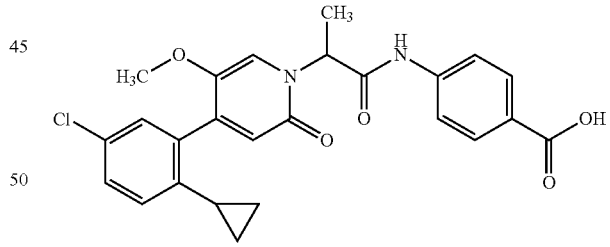

114 mg (0.22 mmol) of tert-butyl 4-({2-[4-(5-chloro-2-cyclopropylphenyl)-5-methoxy-2-oxopyridin-1(2H)-yl]propanoyl}amino)benzoate (racemate) were hydrolysed with TFA according to General Method 2. Yield: 73 mg (78% of theory)

LC/MS [Method 1]: $R_t$=1.03 min; MS (ESIpos): m/z=467 (M+H)$^+$ $^1$H-NMR (400 MHz, DMSO-d$_6$): δ [ppm]=12.77 (s, 1H), 10.68 (s, 1H), 7.91 (d, 2H), 7.74 (d, 2H), 7.38 (s, 1H), 7.35 (dd, 1H), 7.19 (d, 1H), 6.95 (d, 1H), 6.31 (s, 1H), 5.61 (q, 1H), 3.65 (s, 3H), 1.72 (d, 3H), 1.70-1.59 (m, 1H), 0.85 (d, 2H), 0.65 (br. s, 2H).

Example 125

4-({2-[4-(5-Chloro-2-cyanophenyl)-5-methoxy-2-oxopyridin-1(2H)-yl]-4-methoxyhexanoyl}amino)benzoic acid (mixture of racemic diastereomers)

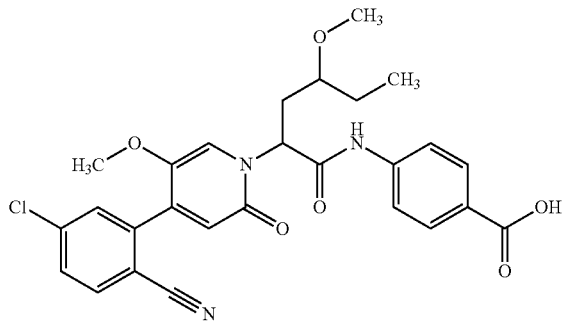 [SMILES: CCC(CC(C(=O)Nc1ccc(C(=O)O)cc1)n1cc(OC)c(-c2cc(Cl)ccc2C#N)cc1=O)OC]

631 mg (1.14 mmol) of ethyl 4-({2-[4-(5-chloro-2-cyanophenyl)-5-methoxy-2-oxopyridin-1(2H)-yl]-4-methoxyhexanoyl}amino)benzoate (mixture of racemic diastereomers) in 22.5 ml of methanol/water (4/1) were reacted with 745 mg (2.29 mmol) of caesium carbonate according to General Method 4. Yield: 580 mg (purity 87%, 84% of theory)

LC/MS [Method 1]: $R_t$=1.00 min; MS (ESIpos): m/z=524 (M+H)$^+$ $^1$H-NMR (400 MHz, DMSO-d$_6$): δ [ppm]=12.7 (br. s, 1H), 10.8 (2×s, 1H), 8.01-7.89 (m, 1H), 7.93-7.88 (m, 2H), 7.80-7.72 (m, 4H), 7.59/7.52 (2×s, 1H), 6.54 (s, 1 h), 5.88-5.81 (m, 1H), 3.69 (s, 3H), 3.19/3.13 (2×s, 3H), 3.08-3.02/2.95-2.89 (2×m, 1H), 2.44-2.31 (m, 1H) 2.27-2.16 (m, 1H), 1.62-1.45 (m, 2H), 0.86/0.85 (2×t, 3H).

Example 126

4-({2-[4-(5-Chloro-2-cyanophenyl)-5-methoxy-2-oxopyridin-1(2H)-yl]-4-hydroxybutanoyl}amino)benzoic acid (racemate)

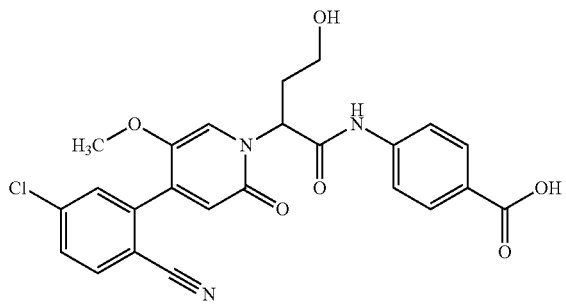 [SMILES: COc1cn(C(CCO)C(=O)Nc2ccc(C(=O)O)cc2)c(=O)cc1-c1cc(Cl)ccc1C#N]

266 mg (355 µmol) of ethyl 4-[(4-{[tert-butyl(diphenyl)silyl]oxy}-2-[4-(5-chloro-2-cyanophenyl)-5-methoxy-2-oxopyridin-1(2H)-yl]butanoyl)amino]benzoate (racemate) in 7 ml of methanol/water (4/1) were reacted with 232 mg (711 µmol) of caesium carbonate according to General Method 4. The crude product was purified by preparative HPLC [column: Chromatorex C18, 10 µm, 125 mm×30 mm, mobile phase: acetonitrile/0.05% formic acid gradient (0 to 3 min 10% acetonitrile, to 35 min 90% acetonitrile and a further 3 min 90% acetonitrile)]. Yield: 16.5 mg (9% of theory)

LC/MS [Method 1]: $R_t$=0.80 min; MS (ESIpos): m/z=482 (M+H)$^+$ $^1$H-NMR (400 MHz, DMSO-d$_6$): δ [ppm]=12.8 (br. s, 1H), 10.7 (s, 1H), 8.00 (d, 1H), 7.90 (d, 2H), 7.78-7.71 (m, 4H), 7.49 (s, 1H), 6.53 (s, 1H), 5.76 (dd, 1H), 4.76 (t, 1H), 3.69 (s, 3H), 3.51-3.38 (m, 2H), 2.38-2.26 (m, 2H).

Example 127

4-[(2-{4-[5-Chloro-2-(difluoromethoxy)phenyl]-5-methoxy-2-oxopyridin-1(2H)-yl}propanoyl)amino]benzoic acid (racemate)

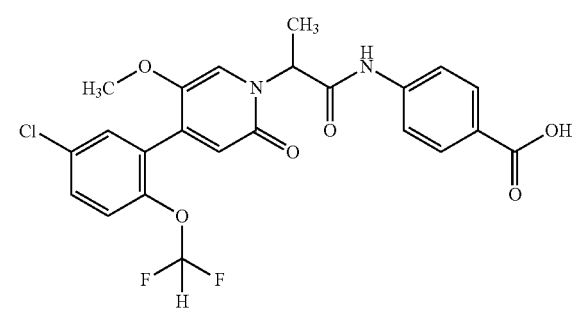

47 mg (0.09 mmol) of tert-butyl 4-[(2-{4-[5-chloro-2-(difluoromethoxy)phenyl]-5-methoxy-2-oxopyridin-1(2H)-yl}propanoyl)amino]benzoate (racemate) were hydrolysed with TFA according to General Method 2. Yield: 33 mg (78% of theory)

LC/MS [Method 1]: $R_t$=0.93 min; MS (ESIpos): m/z=493 (M+H)$^+$ $^1$H-NMR (400 MHz, DMSO-d$_6$): δ [ppm]=12.76 (br. s, 1H), 10.68 (s, 1H), 7.91 (d, 2H), 7.73 (d, 2H), 7.58 (dd, 1H), 7.47 (d, 1H), 7.36 (s, 1H), 7.30 (d, 1H), 7.16 (t, 1H), 6.38 (s, 1H), 5.59 (q, 1H), 3.65 (s, 3H), 1.72 (d, 3H).

Example 128

4-[(2-{4-[5-Chloro-2-(difluoromethoxy)phenyl]-5-methoxy-2-oxopyridin-1(2H)-yl}butanoyl)amino]benzoic acid (racemate)

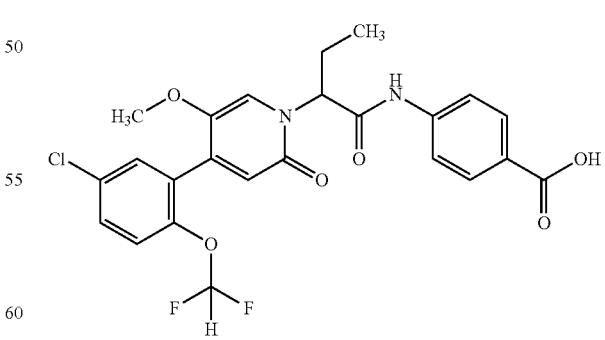

127 mg (0.23 mmol) of tert-butyl 4-[(2-{4-[5-chloro-2-(difluoromethoxy)phenyl]-5-methoxy-2-oxopyridin-1(2H)-yl}butanoyl)amino]benzoate (racemate) were hydrolysed with TFA according to General Method 2. Yield: 72 mg (63% of theory)

LC/MS [Method 1]: $R_t$=0.99 min; MS (ESIpos): m/z=507 (M+H)$^+$ $^1$H-NMR (400 MHz, DMSO-d$_6$): δ [ppm]=12.75 (br. s, 1H), 10.78 (s, 1H), 7.91 (d, 2H), 7.75 (d, 2H), 7.58 (dd, 1H), 7.49 (dd, 1H), 7.39 (s, 1H), 7.30 (d, 1H), 7.13 (t, 1H), 6.40 (s, 1H), 5.63 (dd, 1H), 3.64 (s, 3H), 2.24-2.06 (m, 2H), 0.90 (t, 3H).

Example 129

4-({2-[4-(5-Chloro-2-cyanophenyl)-5-ethoxy-2-oxopyridin-1(2H)-yl]propanoyl}amino)benzoic acid (racemate)

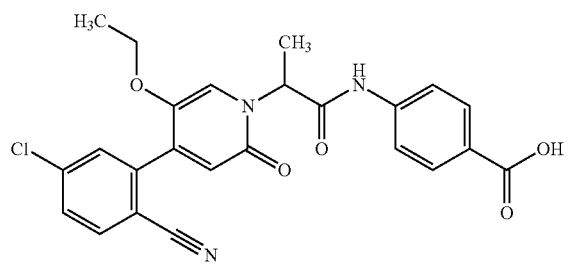 [SMILES: CCOc1cn(C(C)C(=O)Nc2ccc(C(=O)O)cc2)c(=O)cc1-c1cc(Cl)ccc1C#N]

32 mg (purity 89%, 0.06 mmol) of tert-butyl 4-({2-[4-(5-chloro-2-cyanophenyl)-5-ethoxy-2-oxopyridin-1(2H)-yl]propanoyl}amino)benzoate (racemate) were hydrolysed with TFA according to General Method 2. Yield: 11 mg (44% of theory)

LC/MS [Method 3]: $R_t$=2.25 min; MS (ESIpos): m/z=466 (M+H)$^+$ $^1$H-NMR (400 MHz, DMSO-d$_6$): δ [ppm]=12.76 (s, 1H), 10.70 (s, 1H), 8.01 (d, 1H), 7.91 (d, 2H), 7.78-7.68 (m, 4H), 7.49 (s, 1H), 6.53 (s, 1H), 5.60 (q, 1H), 3.92 (q, 2H), 1.72 (d, 3H), 1.18 (t, 3H).

Example 130

4-({2-[4-(5-Chloro-2-cyanophenyl)-5-(difluoromethoxy)-2-oxopyridin-1(2H)-yl]propanoyl}amino)benzoic acid (racemate)

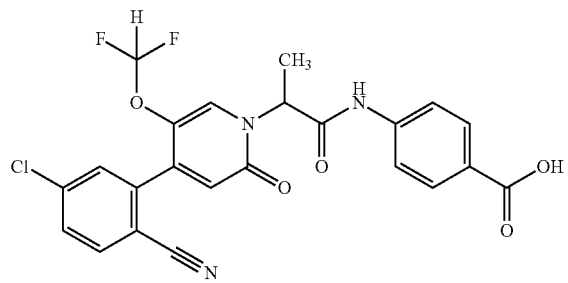 [SMILES: CC(C(=O)Nc1ccc(C(=O)O)cc1)n1cc(OC(F)F)c(-c2cc(Cl)ccc2C#N)cc1=O]

99 mg (0.18 mmol) of tert-butyl 4-({2-[4-(5-chloro-2-cyanophenyl)-5-(difluoromethoxy)-2-oxopyridin-1(2H)-yl]propanoyl}amino)benzoate (racemate) were hydrolysed with TFA according to General Method 2. Yield: 75 mg (84% of theory)

LC/MS [Method 1]: $R_t$=0.94 min; MS (ESIpos): m/z=488 (M+H)$^+$ $^1$H-NMR (400 MHz, DMSO-d$_6$): δ [ppm]=12.77 (s, 1H), 10.78 (s, 1H), 8.05 (d, 1H), 7.99 (s, 1H), 7.91 (d, 2H), 7.82-7.68 (m, 4H), 6.89 (t, 1H), 6.65 (s, 1H), 5.57 (q, 1H), 1.72 (d, 3H).

Example 131

4-({2-[4-(5-Chloro-2-cyanophenyl)-2-oxo-5-(2,2,2-trifluoroethoxy)pyridin-1(2H)-yl]propanoyl}amino) benzoic acid (racemate)

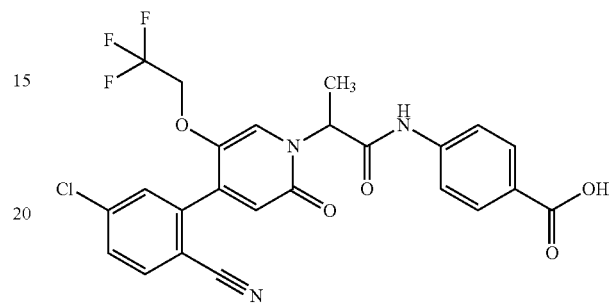

113 mg (0.14 mmol) of tert-butyl 4-({2-[4-(5-chloro-2-cyanophenyl)-2-oxo-5-(2,2,2-trifluoroethoxy)pyridin-1(2H)-yl]propanoyl}amino)benzoate (racemate) were hydrolysed with TFA according to General Method 2. Yield: 39 mg (purity 90%, 49% of theory)

LC/MS [Method 1]: $R_t$=0.98 min; MS (ESIpos): m/z=520 (M+H)$^+$ $^1$H-NMR (400 MHz, DMSO-d$_6$): δ [ppm]=12.77 (br. s, 1H), 10.73 (s, 1H), 8.03 (d, 1H), 7.92 (d, 2H), 7.82-7.70 (m, 5H), 6.59 (s, 1H), 5.58 (q, 1H), 4.66 (dq, 2H), 1.74 (d, 3H).

Example 132

4-({2-[4-(5-Chloro-2-cyanophenyl)-5-methoxy-2-oxopyridin-1(2H)-yl]-3-(4-hydroxycyclohexyl)propanoyl amino)benzoic acid (mixture of racemic diastereomers)

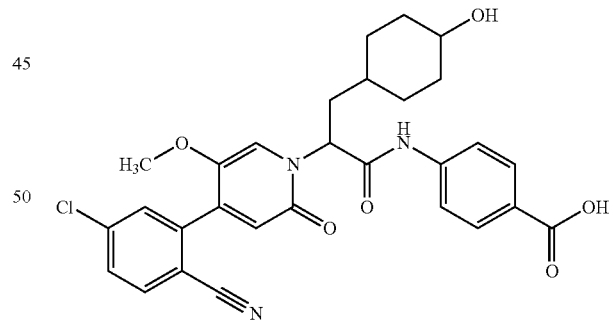

341 mg (473 μmol) of tert-butyl 4-({3-(4-[tert-butyl(dimethyl)silyl]oxy}cyclohexyl)-2-[4-(5-chloro-2-cyanophenyl)-5-methoxy-2-oxopyridin-1(2H)-yl]propanoyl}amino) benzoate (mixture of racemic diastereomers) were reacted with 912 μl (11.8 mmol) of TFA according to General Method 2. The crude product was purified by preparative HPLC [column: Chromatorex C18, 10 μm, 125 mm×30 mm, mobile phase: acetonitrile/water gradient (0 to 3 min 15% acetonitrile, to 35 min 90% acetonitrile and a further 3 min 90% acetonitrile)]. Yield: 107 mg (27% of theory)

LC/MS [Method 1]: $R_t$=0.87-0.89 min; MS (ESIneg): m/z=548 (M−H)$^−$

¹H-NMR (400 MHz, DMSO-d₆): δ [ppm]=12.8 (s, 1H), 10.8 (2×s, 1H), 8.00 (d, 1H), 7.92 (d, 2H), 7.79-7.71 (m, 4H), 7.50/7.49 (2×s, 1H), 6.54/6.53 (2×s, 1H), 5.88-5.81 (m, 1H), 4.45/4.28 (2×d, 1H), 3.69 (s, 3H), 2.23-2.13 (m, 1H), 2.04-1.84 (m, 1H), 1.82-1.69 (m, 2H), 1.63-1.28 (m, 4H), 1.24-1.13 (m, 1H), 1.10-0.95 (m, 2H).

Example 133

4-(2-[4-(5-Chloro-2-cyanophenyl)-5-methoxy-2-oxopyridin-1(2H)-yl]-3-(4-hydroxycyclohexyl)propanoyl amino)benzoic acid (enantiomer 1 of the first diastereomer and enantiomer 1 of the second diastereomer)

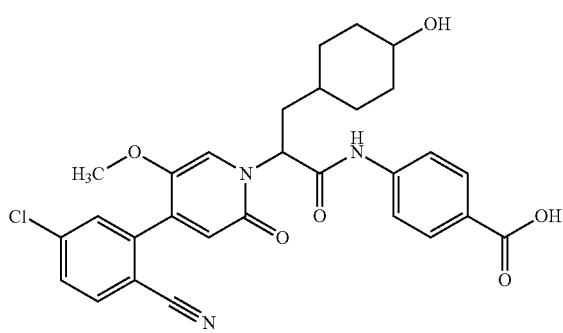 [SMILES: COc1cn(C(CC2CCC(O)CC2)C(=O)Nc2ccc(C(=O)O)cc2)c(=O)cc1-c1cc(Cl)ccc1C#N]

Enantiomer separation of 107 mg of the mixture of racemic diastereomers from Example 132 gave 23 mg of the title compound Example 133: Chiral HPLC: R_t=5.77/5.84 min; 99% ee, diastereomer ratio: 1:1.

Separation method: column: AZ-H 5 μm 250 mm×20 mm; mobile phase: 50% isohexane, 50% ethanol+0.2% acetic acid; temperature: 30° C.; flow rate: 15 ml/min; UV detection: 230 nm.

Analysis: column: AZ-H 5 μm 250 mm×4.6 mm; mobile phase: 50% isohexane, 50% ethanol+0.2% TFA+1% water; temperature: 30° C.; flow rate: 1 ml/min; UV detection: 220 nm.

¹H-NMR (400 MHz, DMSO-d₆): δ [ppm]=12.8 (s, 1H), 10.8 (2×s, 1H), 8.00 (d, 1H), 7.92 (d, 2H), 7.79-7.71 (m, 4H), 7.50/7.49 (2×s, 1H), 6.54/6.53 (2×s, 1H), 5.88-5.81 (m, 1H), 4.45/4.28 (2×d, 1H), 3.69 (s, 3H), 2.23-2.13 (m, 1H), 2.04-1.84 (m, 1H), 1.82-1.69 (m, 2H), 1.63-1.28 (m, 4H), 1.24-1.13 (m, 1H), 1.10-0.95 (m, 2H).

Example 134

4-({2-[4-(5-Chloro-2-cyanophenyl)-5-methoxy-2-oxopyridin-1(2H)-yl]-3-(4-hydroxycyclohexyl)propanoyl}amino)benzoic acid (enantiomer 2 of the first diastereomer)

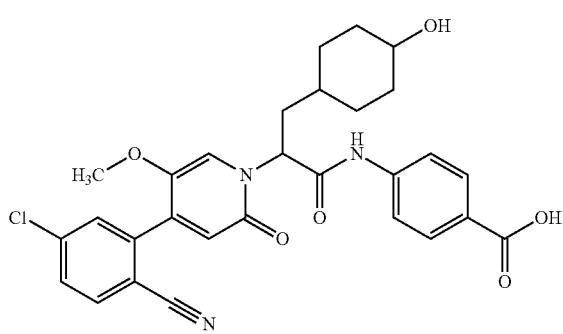 [SMILES: COc1cn(C(CC2CCC(O)CC2)C(=O)Nc2ccc(C(=O)O)cc2)c(=O)cc1-c1cc(Cl)ccc1C#N]

Enantiomer separation of 107 mg of the mixture of racemic diastereomers from Example 132 gave 11 mg of the title compound Example 134: Chiral HPLC: R_t=9.44 min; 99% ee.

Separation method: column: AZ-H 5 μm 250 mm×20 mm; mobile phase: 50% isohexane, 50% ethanol+0.2% acetic acid; temperature: 30° C.; flow rate: 15 ml/min; UV detection: 230 nm.

Analysis: column: AZ-H 5 μm 250 mm×4.6 mm; mobile phase: 50% isohexane, 50% ethanol+0.2% TFA+1% water; temperature: 30° C.; flow rate: 1 ml/min; UV detection: 220 nm.

¹H-NMR (400 MHz, DMSO-d₆): δ [ppm]=12.8 (s, 1H), 10.8 (s, 1H), 8.00 (d, 1H), 7.91 (d, 2H), 7.78-7.71 (m, 4H), 7.49 (s, 1H), 6.54 (s, 1H), 5.87-5.80 (m, 1H), 4.45 (d, 1H), 3.69 (s, 3H), 2.23-2.13 (m, 1H), 1.95-1.85 (m, 1H), 1.84-1.69 (m, 4H), 1.10-0.93 (m, 5H).

Example 135

4-({2-[4-(5-Chloro-2-cyanophenyl)-5-methoxy-2-oxopyridin-1(2H)-yl]-3-(4-hydroxycyclohexyl)propanoyl}amino)benzoic acid (enantiomer 2 of the second diastereomer)

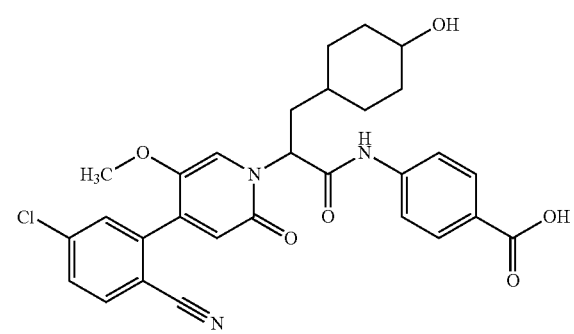 [SMILES: COc1cn(C(CC2CCC(O)CC2)C(=O)Nc2ccc(C(=O)O)cc2)c(=O)cc1-c1cc(Cl)ccc1C#N]

Enantiomer separation of 107 mg of the mixture of racemic diastereomers from Example 132 gave 14 mg of the title compound Example 135: Chiral HPLC: R_t=11.77 min; 89% ee.

Separation method: column: AZ-H 5 μm 250 mm×20 mm; mobile phase: 50% isohexane, 50% ethanol+0.2% acetic acid; temperature: 30° C.; flow rate: 15 ml/min; UV detection: 230 nm.

Analysis: column: AZ-H 5 μm 250 mm×4.6 mm; mobile phase: 50% isohexane, 50% ethanol+0.2% TFA+1% water; temperature: 30° C.; flow rate: 1 ml/min; UV detection: 220 nm.

¹H-NMR (400 MHz, DMSO-d₆): δ [ppm]=12.8 (s, 1H), 10.8 (s, 1H), 8.00 (d, 1H), 7.91 (d, 2H), 7.79-7.71 (m, 4H), 7.50 (s, 1H), 6.53 (s, 1H), 5.89-5.81 (m, 1H), 4.29 (d, 1H), 3.69 (s, 3H), 2.22-2.12 (m, 1H), 2.05-1.95 (m, 1H), 1.64-1.14 (m, 9H).

Example 136

4-({2-[4-(5-Chloro-2-cyanophenyl)-5-methoxy-2-oxopyridin-1(2H)-yl]-4-(trifluoromethoxy)butanoyl}amino)benzoic acid (racemate)

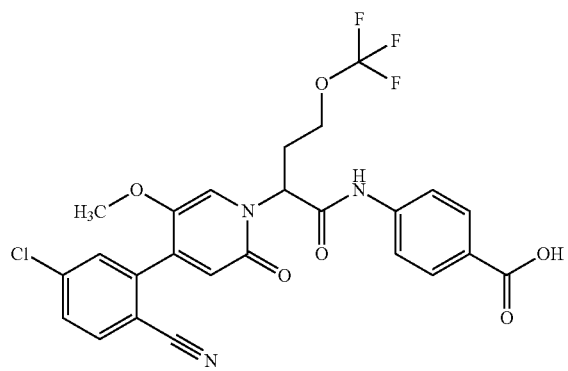 [SMILES: COc1cn(C(CCOC(F)(F)F)C(=O)Nc2ccc(C(=O)O)cc2)c(=O)cc1-c1cc(Cl)ccc1C#N]

151 mg (248 µmol) of tert-butyl 4-({2-[4-(5-chloro-2-cyanophenyl)-5-methoxy-2-oxopyridin-1(2H)-yl]-4-(trifluoromethoxy)butanoyl}amino)benzoate (racemate) and 574 µl (7.45 mmol) of TFA were reacted according to General Method 2. The crude product was purified by preparative HPLC [column: Chromatorex C18, 10 µm, 125 mm×30 mm, mobile phase: acetonitrile/water gradient (0 to 3 min 15% acetonitrile, to 35 min 90% acetonitrile and a further 3 min 90% acetonitrile)]. Yield: 65 mg (47% of theory)

LC/MS [Method 1]: $R_t$=1.02 min; MS (ESIneg): m/z=548 (M–H)⁻

$^1$H-NMR (400 MHz, DMSO-$d_6$): δ [ppm]=12.8 (s, 1H), 10.8 (s, 1H), 8.00 (d, 1H), 7.91 (d, 2H), 7.76-7.70 (m, 4H), 7.51 (s, 1H), 6.56 (s, 1H), 5.81 (t, 1H), 4.20-4.15 (m, 1H), 4.03-3.99 (m, 1H), 3.69 (s, 3H), 2.66-2.60 (m, 2H).

Example 137

4-({2-[4-(5-Chloro-2-cyanophenyl)-5-methoxy-2-oxopyridin-1(2H)-yl]-4-(trifluoromethoxy)butanoyl}amino)benzoic acid (enantiomer 1)

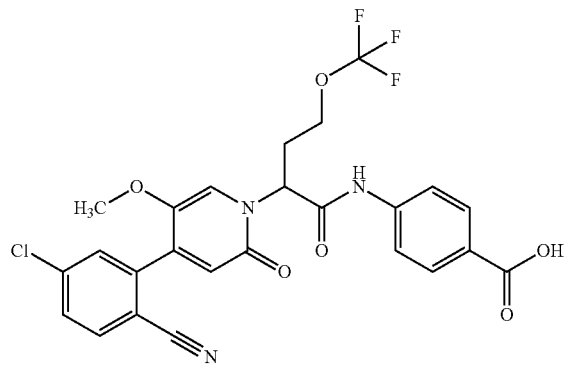 [SMILES: COc1cn(C(CCOC(F)(F)F)C(=O)Nc2ccc(C(=O)O)cc2)c(=O)cc1-c1cc(Cl)ccc1C#N]

Enantiomer separation of 165 mg of the mixture of racemic diastereomers from Example 136 gave 65 mg of the title compound Example 137: Chiral HPLC: $R_t$=1.00 min; 99% ee.

Separation method (SFC): column: AZ-H 5 µm 250 mm×30 mm; mobile phase: 70% carbon dioxide, 30% ethanol; temperature: 40° C.; flow rate: 100 ml/min; UV detection: 210 nm.

Analysis (SFC): column: AZ-3 5 µm 250 mm×4.6 mm; mobile phase: 85% carbon dioxide, 15% ethanol; temperature: 30° C.; flow rate: 3 ml/min; UV detection: 220 nm.

Example 138

4-({2-[4-(5-Chloro-2-cyanophenyl)-5-methoxy-2-oxopyridin-1(2H)-yl]-4-(trifluoromethoxy)butanoyl}amino)benzoic acid (enantiomer 2)

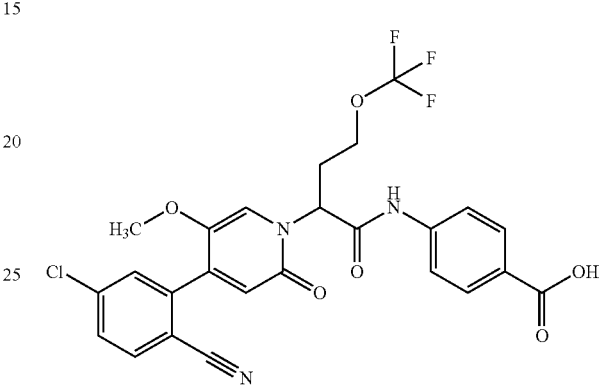

Enantiomer separation of 165 mg of the mixture of racemic diastereomers from Example 136 gave 69 mg of the title compound Example 138: Chiral HPLC: $R_t$=2.01 min; 94% ee.

Separation method (SFC): column: AZ-H 5 µm 250 mm×30 mm; mobile phase: 70% carbon dioxide, 30% ethanol; temperature: 40° C.; flow rate: 100 ml/min; UV detection: 210 nm.

Analysis (SFC): column: AZ-3 5 µm 250 mm×4.6 mm; mobile phase: 85% carbon dioxide, 15% ethanol; temperature: 30° C.; flow rate: 3 ml/min; UV detection: 220 nm.

Example 139

2-[4-(5-Chloro-2-cyanophenyl)-5-methoxy-2-oxopyridin-1(2H)-yl]-3-(3-ethyloxetan-3-yl)-N-[4-(5-oxo-4,5-dihydro-1,2,4-oxadiazol-3-yl)phenyl]propanamide (racemate)

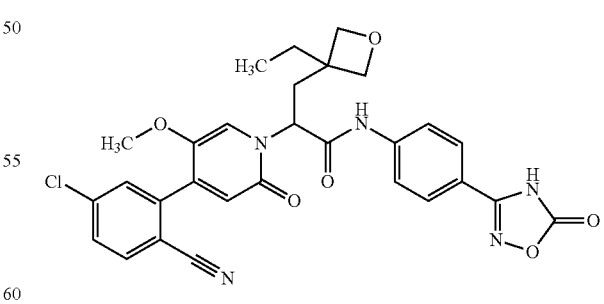

37.4 mg (89.6 µmol) of 2-[4-(5-chloro-2-cyanophenyl)-5-methoxy-2-oxopyridin-1(2H)-yl]-3-(3-ethyloxetan-3-yl)propanoic acid (racemate), 15.9 mg (89.6 µmol) of 3-(4-aminophenyl)-1,2,4-oxadiazol-5(4H)-one, 12.7 mg (89.6 µmol) of Oxima and 14.0 µl (89.6 µmol) of DIC in 950 µl of dimethylformamide were reacted according to General Method 5. The crude product was purified by preparative HPLC [column: Chromatorex C18, 10 nm, 125 mm×30 mm, mobile phase: acetonitrile/0.05% formic acid gradient (0 to 3 min 10% acetonitrile, to 35 min 90% acetonitrile and a further 3 min 90% acetonitrile)] and then using Method 10. Yield: 2 mg (4% of theory)

LC/MS [Method 1]: $R_t$=0.96 min; MS (ESIpos): m/z=576 (M+H)$^+$ $^1$H-NMR (400 MHz, DMSO-d$_6$): δ [ppm]=12.9 (br. s, 1H), 10.9 (s, 1H), 7.99 (d, 1H), 7.83 (d, 2H), 7.79 (m, 2H), 7.74-7.70 (m, 3H), 6.54 (s, 1H), 5.82-5.76 (m, 1H), 4.40 (d, 1H), 4.26 (d, 1H), 4.15 (d, 1H), 4.05 (d, 1H), 3.72 (s, 3H), 2.56-2.44 (m, 2H), 1.83-1.75 (m, 2H), 0.90 (t, 3H).

Example 140

4-({2-[4-(5-Chloro-2-cyanophenyl)-5-methoxy-2-oxopyridin-1(2H)-yl](3,3,4,4,4-pentadeutero)butanoyl}amino)benzoic acid (racemate)

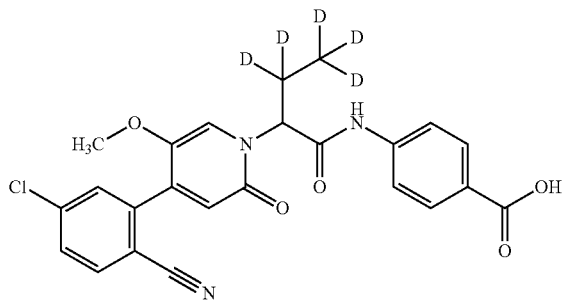 [SMILES: [2H]C([2H])([2H])C([2H])([2H])C(C(=O)Nc1ccc(C(=O)O)cc1)n1cc(OC)c(-c2cc(Cl)ccc2C#N)cc1=O]

79 mg (purity 91%, 0.14 mmol) of tert-butyl 4-({2-[4-(5-chloro-2-cyanophenyl)-5-methoxy-2-oxopyridin-1(2H)-yl](3,3,4,4,4-pentadeutero)butanoyl}amino)benzoate (racemate) were hydrolysed with TFA according to General Method 2. The crude product was purified by preparative HPLC (Reprosil C18, water/acetonitrile gradient). Yield: 30 mg (46% of theory)

LC/MS [Method 1]: $R_t$=0.93 min; MS (ESIpos): m/z=471 (M+H)$^+$, $^1$H-NMR (400 MHz, DMSO-d$_6$): δ [ppm]=12.74 (br. s, 1H), 10.78 (s, 1H), 8.00 (d, 1H), 7.91 (d, 2H), 7.79-7.70 (m, 4H), 7.49 (s, 1H), 6.54 (s, 1H), 5.63 (s, 1H), 3.69 (s, 3H).

Example 141

4-({2-[4-(5-Chloro-2-cyanophenyl)-5-methoxy-2-oxopyridin-1(2H)-yl]-4-methoxyhexanoyl}amino)benzoic acid (enantiomer 1 of the first diastereomer)

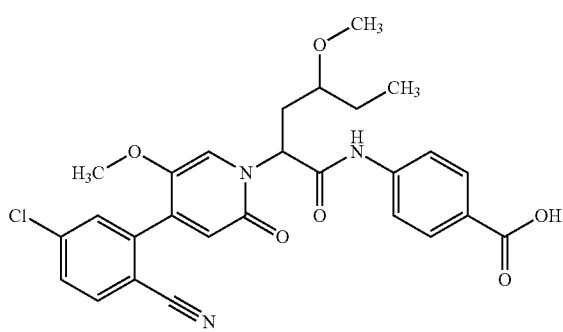 [SMILES: CCC(CC(C(=O)Nc1ccc(C(=O)O)cc1)n1cc(OC)c(-c2cc(Cl)ccc2C#N)cc1=O)OC]

Diastereomer and enantiomer separation of 528 mg of the mixture from Example 125 gave, after further preparative HPLC, 32.5 mg of the title compound Example 141 (enantiomer 1 of the first diastereomer): Chiral HPLC: $R_t$=3.44 min; 99% ee.

Separation method (SFC): column: AD-H 5 µm 250 mm×20 mm; mobile phase: 85% carbon dioxide, 15% 2-propanol; temperature: 40° C.; flow rate: 80 ml/min; pressure: 100 bar; UV detection: 210 nm.

Analysis: column: AD-3 5 µm 250 mm×4.6 mm; mobile phase: 95-50% carbon dioxide, 5-50% 2-propanol; temperature: 40° C.; flow rate: 3 ml/min; UV detection: 220 nm.

$^1$H-NMR (400 MHz, DMSO-d$_6$): δ [ppm]=12.7 (br. s, 1H), 10.8 (s, 1H), 7.99 (d, 1H), 7.90 (d, 2H), 7.79-7.71 (m, 4H), 7.52 (s, 1H), 6.54 (s, 1H), 5.87-5.81 (m, 1H), 3.68 (s, 3H), 3.13 (s, 3H), 2.96-2.89 (m, 1H), 2.43-2.31 (m, 1H), 2.26-2.17 (m, 1H), 1.58-1.46 (m, 2H), 0.85 (t, 3H).

Example 142

4-({2-[4-(5-Chloro-2-cyanophenyl)-5-methoxy-2-oxopyridin-1(2H)-yl]-4-methoxyhexanoyl}amino)benzoic acid (enantiomer 2 of the first diastereomer)

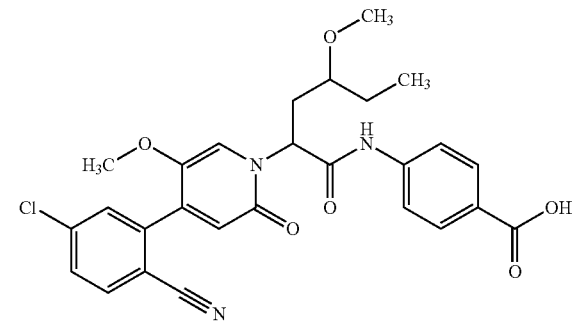 [SMILES: CCC(CC(C(=O)Nc1ccc(C(=O)O)cc1)n1cc(OC)c(-c2cc(Cl)ccc2C#N)cc1=O)OC]

Diastereomer and enantiomer separation of 528 mg of the mixture from Example 125 gave, after further preparative HPLC, 32.4 mg of the title compound Example 142 (enantiomer 2 of the first diastereomer): Chiral HPLC: $R_t$=3.53 min; 99% ee.

Separation method (SFC): column: AD-H 5 µm 250 mm×20 mm; mobile phase: 85% carbon dioxide, 15% 2-propanol; temperature: 40° C.; flow rate: 80 ml/min; pressure: 100 bar; UV detection: 210 nm.

Analysis: column: AD-3 5 µm 250 mm×4.6 mm; mobile phase: 95-50% carbon dioxide, 5-50% 2-propanol; temperature: 40° C.; flow rate: 3 ml/min; UV detection: 220 nm.

$^1$H-NMR (400 MHz, DMSO-d$_6$): δ [ppm]=12.7 (br. s, 1H), 10.8 (s, 1H), 7.99 (d, 1H), 7.90 (d, 2H), 7.79-7.71 (m, 4H), 7.52 (s, 1H), 6.54 (s, 1H), 5.87-5.81 (m, 1H), 3.68 (s, 3H), 3.13 (s, 3H), 2.96-2.89 (m, 1H), 2.43-2.31 (m, 1H), 2.26-2.17 (m, 1H), 1.58-1.46 (m, 2H), 0.85 (t, 3H).

Example 143

4-({2-[4-(5-Chloro-2-cyanophenyl)-5-methoxy-2-oxopyridin-1(2H)-yl]-4-methoxyhexanoyl}amino)benzoic acid (enantiomer 1 of the second diastereomer)

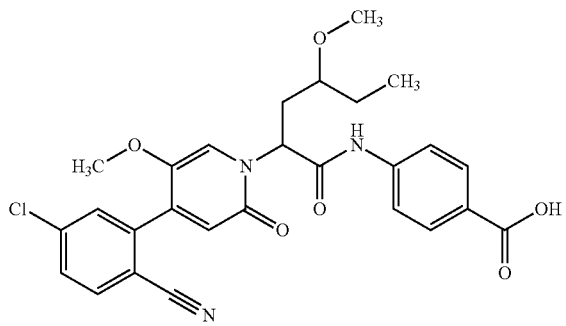 [SMILES: CCC(CC(C(=O)Nc1ccc(C(=O)O)cc1)n1cc(OC)c(-c2cc(Cl)ccc2C#N)cc1=O)OC]

Diastereomer and enantiomer separation of 528 mg of the mixture from Example 125 gave, after further preparative HPLC, 25.9 mg of the title compound Example 143 (enantiomer 1 of the second diastereomer): Chiral HPLC: $R_t$=3.71 min; 99% ee.

Separation method (SFC): column: AD-H 5 μm 250 mm×20 mm; mobile phase: 85% carbon dioxide, 15% 2-propanol; temperature: 40° C.; flow rate: 80 ml/min; pressure: 100 bar; UV detection: 210 nm.

Analysis: column: AD-3 5 μm 250 mm×4.6 mm; mobile phase: 95-50% carbon dioxide, 5-50% 2-propanol; temperature: 40° C.; flow rate: 3 ml/min; UV detection: 220 nm.

$^1$H-NMR (400 MHz, DMSO-d$_6$): δ [ppm]=12.8 (br. s, 1H), 10.8 (s, 1H), 7.99 (d, 1H), 7.91 (d, 2H), 7.77 (d, 2H), 7.75-7.71 (m, 2H), 7.59 (s, 1H), 6.54 (s, 1H), 5.86-5.81 (m, 1H), 3.68 (s, 3H), 3.19 (s, 3H), 3.09-3.02 (m, 1H), 2.28-2.21 (m, 2H), 1.63-1.45 (m, 2H), 0.86 (t, 3H).

Example 144

4-({2-[4-(5-Chloro-2-cyanophenyl)-5-methoxy-2-oxopyridin-1(2H)-yl]-4-methoxyhexanoyl}amino)benzoic acid (enantiomer 2 of the second diastereomer)

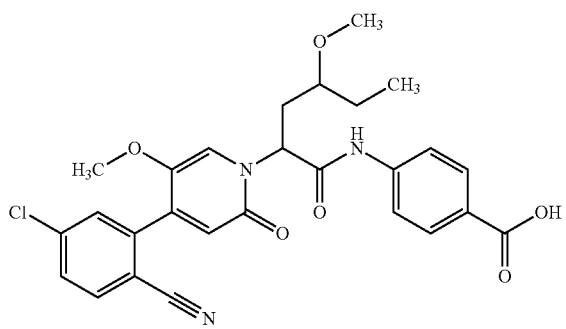 [SMILES: CCC(CC(C(=O)Nc1ccc(C(=O)O)cc1)n1cc(OC)c(-c2cc(Cl)ccc2C#N)cc1=O)OC]

Diastereomer and enantiomer separation of 528 mg of the mixture from Example 125 gave, after further preparative HPLC, 21.9 mg of the title compound Example 144 (enantiomer 2 of the second diastereomer): Chiral HPLC: $R_t$=4.27 min; 99% ee.

Separation method (SFC): column: AD-H 5 μm 250 mm×20 mm; mobile phase: 85% carbon dioxide, 15% 2-propanol; temperature: 40° C.; flow rate: 80 ml/min; pressure: 100 bar; UV detection: 210 nm.

Analysis: column: AD-3 5 μm 250 mm×4.6 mm; mobile phase: 95-50% carbon dioxide, 5-50% 2-propanol; temperature: 40° C.; flow rate: 3 ml/min; UV detection: 220 nm.

$^1$H-NMR (400 MHz, DMSO-d$_6$): δ [ppm]=12.8 (br. s, 1H), 10.8 (s, 1H), 7.99 (d, 1H), 7.91 (d, 2H), 7.77 (d, 2H), 7.75-7.71 (m, 2H), 7.59 (s, 1H), 6.54 (s, 1H), 5.86-5.81 (m, 1H), 3.68 (s, 3H), 3.19 (s, 3H), 3.09-3.02 (m, 1H), 2.28-2.21 (m, 2H), 1.63-1.45 (m, 2H), 0.86 (t, 3H).

Example 145

4-({2-[4-(5-Chloro-2-cyanophenyl)-5-methoxy-2-oxopyridin-1(2H)-yl]-3-[1-(trifluoromethyl)cyclopropyl]propanoyl}amino)benzoic acid (racemate)

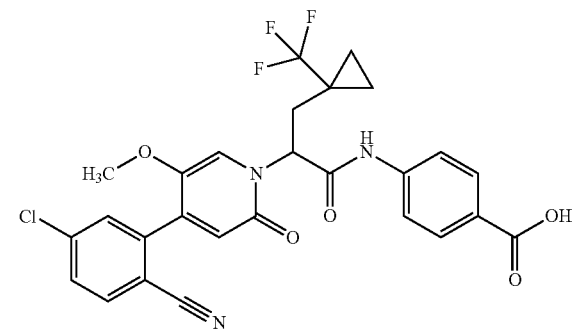 [SMILES: COc1cn(C(CC2(C(F)(F)F)CC2)C(=O)Nc2ccc(C(=O)O)cc2)c(=O)cc1-c1cc(Cl)ccc1C#N]

157 mg (255 μmol) of tert-butyl 4-({2-[4-(5-chloro-2-cyanophenyl)-5-methoxy-2-oxopyridin-1(2H)-yl]-3-[1-(trifluoromethyl)cyclopropyl]propanoyl}amino)benzoate (racemate) were hydrolysed with 393 μl (5.10 mmol) of trifluoroacetic acid according to General Method 2, and after preparative HPLC [column: Chromatorex C18, 10 μm, 125 mm×30 mm, mobile phase: acetonitrile/0.1% formic acid gradient (0 to 3 min 10% acetonitrile, to 35 min 90% acetonitrile and a further 3 min 90% acetonitrile)], the title compound was obtained. Yield: 94 mg (65% of theory)

LC/MS [Method 1]: $R_t$=1.03 min; MS (ESIneg): m/z=558 (M−H)$^−$, $^1$H-NMR (400 MHz, DMSO-d$_6$): δ [ppm]=12.8 (br. s, 1H), 10.8 (s, 1H), 7.99 (d, 1H), 7.92 (d, 2H), 7.78-7.71 (m, 4H), 7.52 (s, 1H), 6.55 (s, 1H), 5.86-5.79 (m, 1H), 3.67 (s, 3H), 2.60-2.44 (m, 2H), 0.97-0.79 (m, 4H).

Example 146

4-({2-[4-(5-Chloro-2-cyanophenyl)-5-methoxy-2-oxopyridin-1(2H)-yl]-3-[1-(trifluoromethyl)cyclopropyl]propanoyl}amino)benzoic acid (enantiomer 1)

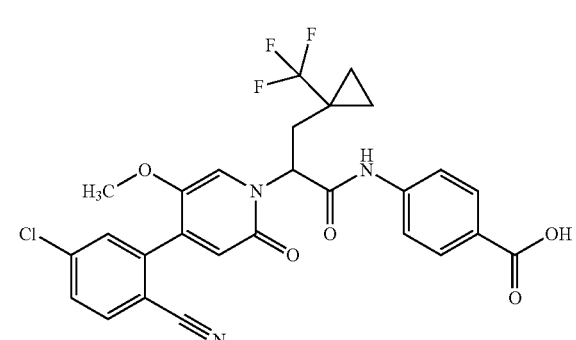

Enantiomer separation of 94 mg of the racemate from Example 145 gave 29.9 mg of the title compound Example 146 (enantiomer 1): Chiral HPLC: $R_t$=3.71 min; 99% ee.

Separation method (SFC): column: AZ-H 5 μm 250 mm×30 mm; mobile phase: 75% carbon dioxide, 25% ethanol; temperature: 40° C.; flow rate: 100 ml/min; pressure: 100 bar; UV detection: 210 nm.

Analysis (SFC): column: AZ-H 5 μm 250 mm×4.6 mm; mobile phase: 80% carbon dioxide, 20% ethanol; temperature: 40° C.; flow rate: 3 ml/min; UV detection: 210 nm.

Example 147

4-({2-[4-(5-Chloro-2-cyanophenyl)-5-methoxy-2-oxopyridin-1(2H)-yl]-3-[1-(trifluoromethyl)cyclopropyl]propanoyl}amino)benzoic acid (enantiomer 2)

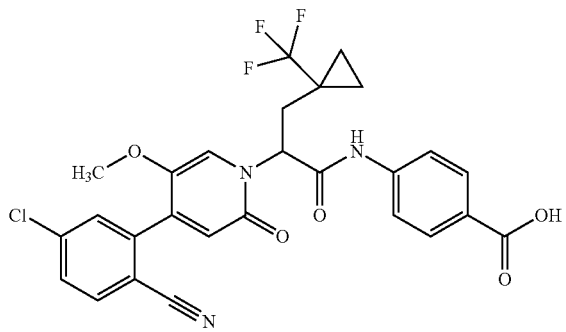 [SMILES: COc1cn(C(CC2(C(F)(F)F)CC2)C(=O)Nc2ccc(C(=O)O)cc2)c(=O)cc1-c1cc(Cl)ccc1C#N]

Enantiomer separation of 94 mg of the racemate from Example 145 gave 27.8 mg of the title compound Example 147 (enantiomer 2): Chiral HPLC: $R_t$=5.32 min; 99% ee.

Separation method (SFC): column: AZ-H 5 μm 250 mm×30 mm; mobile phase: 75% carbon dioxide, 25% ethanol; temperature: 40° C.; flow rate: 100 ml/min; pressure: 100 bar; UV detection: 210 nm.

Analysis (SFC): column: AZ-H 5 μm 250 mm×4.6 mm; mobile phase: 80% carbon dioxide, 20% ethanol; temperature: 40° C.; flow rate: 3 ml/min; UV detection: 210 nm.

Example 148

4-({2-[4-(5-Chloro-2-cyanophenyl)-5-methoxy-2-oxopyridin-1(2H)-yl]-3-[1-(trifluoromethyl)cyclobutyl]propanoyl}amino)benzoic acid (racemate)

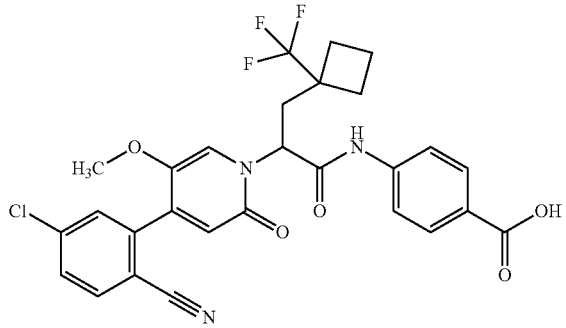 [SMILES: COc1cn(C(CC2(C(F)(F)F)CCC2)C(=O)Nc2ccc(C(=O)O)cc2)c(=O)cc1-c1cc(Cl)ccc1C#N]

58 mg (0.09 mmol) of tert-butyl 4-({2-[4-(5-chloro-2-cyanophenyl)-5-methoxy-2-oxopyridin-1(2H)-yl]-3-[1-(trifluoromethyl)cyclobutyl]propanoyl}amino)benzoate (racemate) were hydrolysed with TFA according to General Method 2. The crude product was purified by preparative HPLC (Reprosil C18, water/acetonitrile gradient). Yield: 35 mg (65% of theory)

LC/MS [Method 1]: $R_t$=1.09 min; MS (ESIpos): m/z=574 (M+H)$^+$, $^1$H-NMR (400 MHz, DMSO-d$_6$): δ [ppm]=10.88 (s, 1H), 7.99 (d, 1H), 7.92 (d, 2H), 7.81-7.70 (m, 4H), 7.58 (s, 1H), 6.58 (s, 1H), 5.95 (t, 1H), 3.68 (s, 3H), 2.61 (dd, 1H), 2.48 (dd, 1H), 2.21 (t, 2H), 2.18-2.12 (m, 1H), 2.12-2.02 (m, 1H), 1.99-1.83 (m, 2H).

Example 149

4-({2-[4-(5-Chloro-2-cyanophenyl)-5-methoxy-2-oxopyridin-1(2H)-yl]-3-(3,3-difluorocyclobutyl)propanoyl}amino)benzoic acid (racemate)

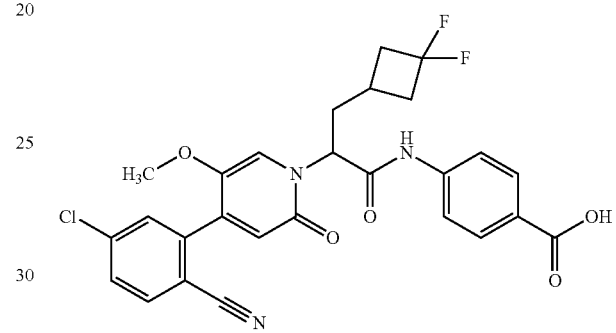

175 mg (0.29 mmol) of tert-butyl 4-({2-[4-(5-chloro-2-cyanophenyl)-5-methoxy-2-oxopyridin-1(2H)-yl]-3-(3,3-difluorocyclobutyl)propanoyl}amino)benzoate (racemate) were hydrolysed with TFA according to General Method 2. The crude product was purified by preparative HPLC (Reprosil C18, water/acetonitrile gradient). Yield: 122 mg (77% of theory)

LC/MS [Method 1]: $R_t$=1.01 min; MS (ESIpos): m/z=542 (M+H)$^+$, $^1$H-NMR (400 MHz, DMSO-d$_6$): δ [ppm]=12.77 (s, 1H), 10.79 (s, 1H), 8.00 (d, 1H), 7.92 (d, 2H), 7.79-7.69 (m, 4H), 7.53 (s, 1H), 6.54 (s, 1H), 5.73 (dd, 1H), 3.70 (s, 3H), 2.68-2.50 (m, 2H), 2.50-2.39 (m, 2H), 2.39-2.21 (m, 2H), 2.08-1.95 (m, 1H).

Example 150

4-({2-[4-(5-Chloro-2-cyanophenyl)-5-methoxy-2-oxopyridin-1(2H)-yl]-3-(3-methyloxetan-3-yl)propanoyl}amino)benzoic acid (racemate)

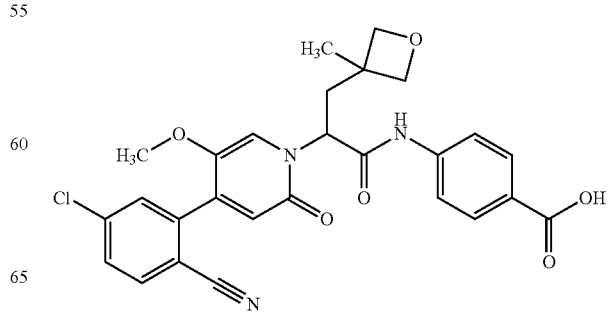

25 mg (44 µmol) of allyl 4-({2-[4-(5-chloro-2-cyanophenyl)-5-methoxy-2-oxopyridin-1(2H)-yl]-3-(3-methyloxetan-3-yl)propanoyl}amino)benzoate (racemate) and 48.2 µl (445 µmol) of N-methylaniline were initially charged in 1 ml of tetrahydrofuran, and the resulting solution was degassed. 5 mg (4 µmol) of tetrakis(triphenylphosphine)palladium(0) were then added, and the mixture was stirred at room temperature for another 30 min. The reaction solution was purified directly by preparative HPLC (neutral) and the title compound was obtained after final preparative thin-layer chromatography (ethyl acetate/cyclohexane=1:1). Yield: 10.1 mg (purity 92%, 42% of theory)

LC/MS [Method 1]: $R_t$=0.89 min; MS (ESIpos): m/z=522 (M+H)$^+$, $^1$H-NMR (400 MHz, DMSO-d$_6$): δ [ppm]=12.8 (br. s, 1H), 10.8 (s, 1H), 7.99 (d, 1H), 7.92 (d, 2H), 7.77-7.71 (m, 4H), 7.66 (s, 1H), 6.52 (s, 1H), 5.87 (dd, 1H), 4.46 (d, 1H), 4.29 (d, 1H), 4.11 (d, 1H), 3.95 (d, 1H), 3.72 (s, 3H), 2.68 (dd, 1H), 2.37 (dd, 1H), 1.38 (s, 3H).

Example 151

4-({2-[4-(5-Chloro-2-cyanophenyl)-5-methoxy-2-oxopyridin-1(2H)-yl]-3-(4-methyltetrahydro-2H-pyran-4-yl)propanoyl}amino)benzoic acid (racemate)

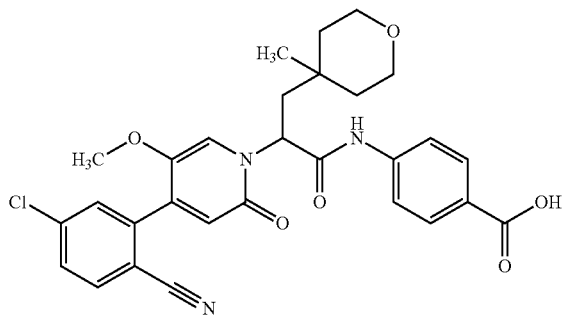 [SMILES: COc1cn(C(CC2(C)CCOCC2)C(=O)Nc2ccc(C(=O)O)cc2)c(=O)cc1-c1cc(Cl)ccc1C#N]

69.0 mg (119 µmol) of ethyl 4-({2-[4-(5-chloro-2-cyanophenyl)-5-methoxy-2-oxopyridin-1(2H)-yl]-3-(4-methyltetrahydro-2H-pyran-4-yl)propanoyl}amino)benzoate (racemate) in 4.3 ml of ethanol/water (3/1) were reacted with 198 mg (609 µmol) of caesium carbonate according to General Method 4, giving the title compound after preparative HPLC [column: Chromatorex C18, 10 µm, 125 mm×30 mm, mobile phase: acetonitrile/0.1% formic acid gradient (0 to 3 min 10% acetonitrile, to 35 min 90% acetonitrile and a further 3 min 90% acetonitrile)]. Yield: 38 mg (57% of theory)

LC/MS [Method 1]: $R_t$=0.96 min; MS (ESIpos): m/z=550 (M+H)$^+$, $^1$H-NMR (400 MHz, DMSO-d$_6$): δ [ppm]=12.8 (br. s, 1H), 10.9 (s, 1H), 7.98 (d, 1H), 7.92 (d, 2H), 7.77 (d, 2H), 7.74-7.71 (m, 2H), 7.66 (s, 1H), 6.52 (s, 1H), 6.05 (dd, 1H), 3.71 (s, 3H), 3.65-3.40 (m, 4H), 2.29 (dd, 1H), 2.04 (dd, 1H), 1.57-1.49 (m, 1H), 1.41-1.25 (m, 2H), 1.16-1.09 (m, 1H), 1.03 (s, 3H).

Example 152

4-({2-[4-(5-Chloro-2-cyanophenyl)-5-methoxy-2-oxopyridin-1(2H)-yl]-3-(cis-4-methoxycyclohexyl)propanoyl}amino)benzoic acid (racemate)

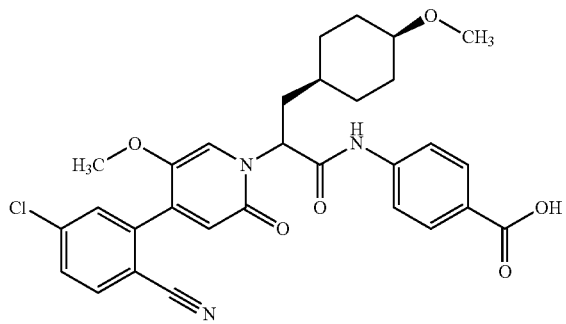 [SMILES: COc1cn(C(C[C@H]2CC[C@@H](OC)CC2)C(=O)Nc2ccc(C(=O)O)cc2)c(=O)cc1-c1cc(Cl)ccc1C#N]

2.10 g (3.55 mmol) of ethyl 4-({2-[4-(5-chloro-2-cyanophenyl)-5-methoxy-2-oxopyridin-1(2H)-yl]-3-(cis-4-methoxycyclohexyl)propanoyl}amino)benzoate (racemate) in 129 ml of ethanol/water (2.6/1) were reacted with 5.89 g (18.1 mmol) of caesium carbonate according to General Method 4. After complete conversion, the pH was adjusted to 5-6 with hydrochloric acid (1N) and the mixture was stirred for another 30 min. The precipitate was filtered off with suction, washed with a little water and dried under high vacuum and it corresponded to the title compound. Yield: 1.24 g (60% of theory)

LC/MS [Method 1]: $R_t$=1.03 min; MS (ESIpos): m/z=564 (M+H)$^+$, $^1$H-NMR (400 MHz, DMSO-d$_6$): δ [ppm]=12.8 (s, 1H), 10.8 (s, 1H), 7.99 (d, 1H), 7.92 (d, 2H), 7.79-7.71 (m, 4H), 7.50 (s, 1H), 6.53 (s, 1H), 5.88-5.82 (m, 1H), 3.69 (s, 3H), 3.19 (s, 3H), 2.23-2.13 (m, 1H), 2.02-1.92 (m, 1H), 1.82-1.70 (m, 2H), 1.52-1.42 (m, 2H), 1.40-1.16 (m, 5H).

Example 153

4-({2-[4-(5-Chloro-2-cyanophenyl)-5-methoxy-2-oxopyridin-1(2H)-yl]-3-(cis-4-methoxycyclohexyl)propanoyl}amino)benzoic acid (enantiomer 1)

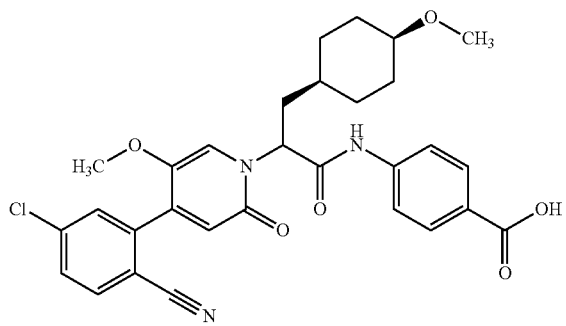 [SMILES: COc1cn(C(C[C@H]2CC[C@@H](OC)CC2)C(=O)Nc2ccc(C(=O)O)cc2)c(=O)cc1-c1cc(Cl)ccc1C#N]

Enantiomer separation of 1.24 g of the racemate from Example 152 gave 562 mg of the title compound Example 153 (enantiomer 1): Chiral HPLC: $R_t$=3.18 min; 99% ee.

Separation method (SFC): column: AD-H 5 µm 250 mm×20 mm; mobile phase: 80% carbon dioxide, 20%

2-propanol; temperature: 40° C.; flow rate: 80 ml/min; pressure: 100 bar; UV detection: 210 nm.

Analysis (SFC): column: AD-3 5 µm 250 mm×4.6 mm; mobile phase: 95-50% carbon dioxide, 5-50% 2-propanol; temperature: 40° C.; flow rate: 3 ml/min; UV detection: 220 nm.

Example 154

4-({2-[4-(5-Chloro-2-cyanophenyl)-5-methoxy-2-oxopyridin-1(2H)-yl]-3-(cis-4-methoxycyclohexyl)propanoyl}amino)benzoic acid (enantiomer 2)

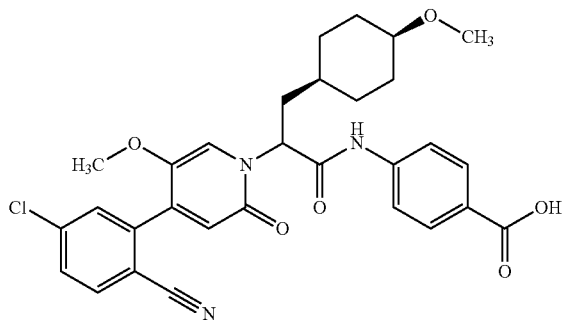 [SMILES: COc1cn(C(C[C@H]2CC[C@@H](OC)CC2)C(=O)Nc2ccc(C(=O)O)cc2)c(=O)cc1-c1cc(Cl)ccc1C#N]

Enantiomer separation of 1.24 g of the racemate from Example 152 gave 566 mg of the title compound Example 154 (enantiomer 2): Chiral HPLC: $R_t$=3.82 min; 98% ee.

Separation method (SFC): column: AD-H 5 µm 250 mm×20 mm; mobile phase: 80% carbon dioxide, 20% 2-propanol; temperature: 40° C.; flow rate: 80 ml/min; pressure: 100 bar; UV detection: 210 nm.

Analysis (SFC): column: AD-3 5 µm 250 mm×4.6 mm; mobile phase: 95-50% carbon dioxide, 5-50% 2-propanol; temperature: 40° C.; flow rate: 3 ml/min; UV detection: 220 nm.

Example 155

4-({2-[4-(5-Chloro-2-cyanophenyl)-5-methoxy-2-oxopyridin-1(2H)-yl]-3-(trans-4-methoxycyclohexyl)propanoyl}amino)benzoic acid (racemate)

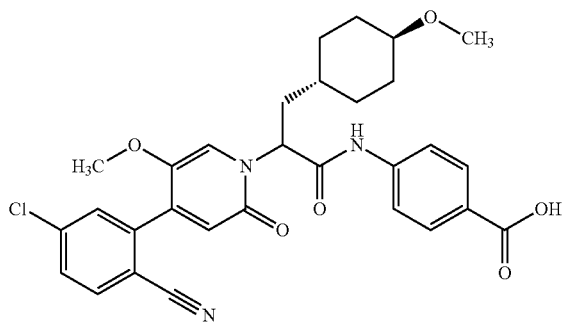 [SMILES: COc1cn(C(C[C@H]2CC[C@H](OC)CC2)C(=O)Nc2ccc(C(=O)O)cc2)c(=O)cc1-c1cc(Cl)ccc1C#N]

1.10 g (1.86 mmol) of ethyl 4-({2-[4-(5-chloro-2-cyanophenyl)-5-methoxy-2-oxopyridin-1(2H)-yl]-3-(trans-4-methoxycyclohexyl)propanoyl}amino)benzoate (racemate) in 67 ml of ethanol/water (2.6/1) were reacted with 3.09 g (9.48 mmol) of caesium carbonate according to General Method 4. After complete conversion, the pH was adjusted to 5-6 with hydrochloric acid (1N) and the mixture was stirred for another 30 min. The precipitate was filtered off with suction, washed with a little water and dried under high vacuum. Yield: 690 mg (purity 89%, 59% of theory)

100 mg of the crude product was purified by preparative HPLC [column: Chromatorex C18, 10 µm, 125 mm×30 mm, mobile phase: acetonitrile/0.1% formic acid gradient (0 to 3 min 10% acetonitrile, to 35 min 90% acetonitrile and a further 3 min 90% acetonitrile)], giving the title compound. Yield: 30 mg (3% of theory)

LC/MS [Method 1]: $R_t$=1.00 min; MS (ESIpos): m/z=564 (M+H)$^+$, $^1$H-NMR (400 MHz, DMSO-d$_6$): δ [ppm]=12.8 (s, 1H), 10.8 (s, 1H), 7.99 (d, 1H), 7.91 (d, 2H), 7.77-7.71 (m, 4H), 7.49 (s, 1H), 6.54 (s, 1H), 5.87-5.81 (m, 1H), 3.69 (s, 3H), 3.20 (s, 3H), 3.07-2.99 (m, 1H), 2.24-2.15 (m, 1H), 2.00-1.88 (m, 3H), 1.85-1.73 (m, 2H), 1.15-0.88 (m, 5H).

Example 156

4-({2-[4-(5-Chloro-2-cyanophenyl)-5-methoxy-2-oxopyridin-1(2H)-yl]-3-(trans-4-methoxycyclohexyl)propanoyl}amino)benzoic acid (enantiomer 1)

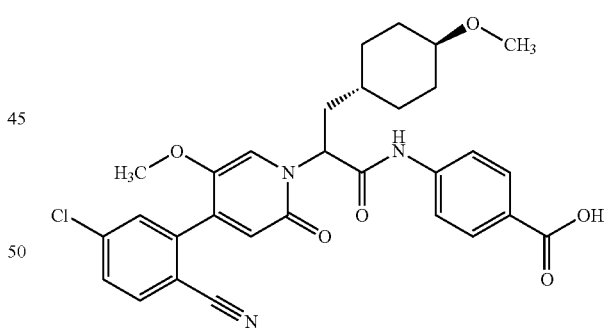

Enantiomer separation of 586 mg of the racemate from Example 155 gave, after further preparative HPLC, 145 mg of the title compound Example 156 (enantiomer 1): Chiral HPLC: $R_t$=5.62 min; 99% ee.

Separation method (SFC): column: AZ-H 5 µm 250 mm×20 mm; mobile phase: 75% carbon dioxide, 25% ethanol; temperature: 40° C.; flow rate: 100 ml/min; pressure: 100 bar; UV detection: 210 nm.

Analysis (SFC): column: AZ-H 5 µm 250 mm×4.6 mm; mobile phase: 70% carbon dioxide, 30% ethanol; temperature: 40° C.; flow rate: 3 ml/min; UV detection: 220 nm.

Example 157

4-({2-[4-(5-Chloro-2-cyanophenyl)-5-methoxy-2-oxopyridin-1(2H)-yl]-3-(trans-4-methoxycyclohexyl)propanoyl}amino)benzoic acid (enantiomer 2)

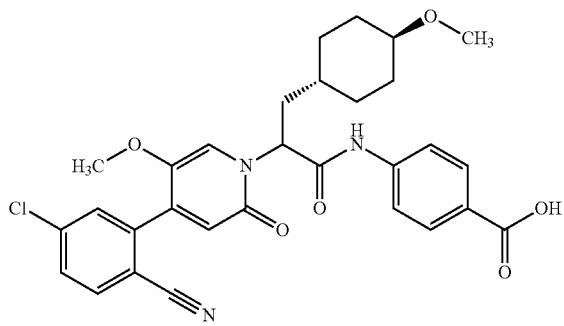 [SMILES: COc1cn(C(C[C@H]2CC[C@H](OC)CC2)C(=O)Nc2ccc(C(=O)O)cc2)c(=O)cc1-c1cc(Cl)ccc1C#N]

Enantiomer separation of 586 mg of the racemate from Example 155 gave, after further preparative HPLC, 110 mg of the title compound Example 157 (enantiomer 2): Chiral HPLC: $R_t$=8.17 min; 99% ee.

Separation method (SFC): column: AZ-H 5 µm 250 mm×20 mm; mobile phase: 75% carbon dioxide, 25% ethanol; temperature: 40° C.; flow rate: 100 ml/min; pressure: 100 bar; UV detection: 210 nm.

Analysis (SFC): column: AZ-H 5 µm 250 mm×4.6 mm; mobile phase: 70% carbon dioxide, 30% ethanol; temperature: 40° C.; flow rate: 3 ml/min; UV detection: 220 nm.

Example 158

2-[4-(5-Chloro-2-cyanophenyl)-5-methoxy-2-oxopyridin-1(2H)-yl]-3-cyclobutyl-N-[4-(2-oxo-2,3-dihydro-1,3-oxazol-5-yl)phenyl]propanamide (racemate)

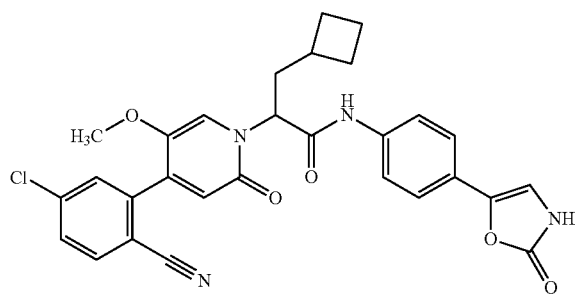 [SMILES: COc1cn(C(CC2CCC2)C(=O)Nc2ccc(-c3c[nH]c(=O)o3)cc2)c(=O)cc1-c1cc(Cl)ccc1C#N]

103 mg (purity 94%, 0.25 mmol) of 2-[4-(5-chloro-2-cyanophenyl)-5-methoxy-2-oxopyridin-1(2H)-yl]-3-cyclobutylpropanoic acid (racemate) and 55 mg (0.28 mmol, 1.1 eq.) of 5-(4-aminophenyl)-1,3-oxazol-2(3H)-one were reacted according to General Method 1. The crude product was purified by preparative HPLC (Reprosil C18, water/acetonitrile gradient). Yield: 36 mg (27% of theory)

LC/MS [Method 8]: $R_t$=1.30 min; MS (ESIneg): m/z=543 (M−H)⁻,

¹H-NMR (400 MHz, DMSO-d₆): δ [ppm]=10.78 (s, 1H), 10.59 (s, 1H), 8.00 (d, 1H), 7.76-7.70 (m, 2H), 7.68 (d, 2H), 7.52 (s, 1H), 7.46 (d, 2H), 7.40 (s, 1H), 6.51 (s, 1H), 5.68 (t, 1H), 3.69 (s, 3H), 2.30-2.17 (m, 3H), 2.01-1.88 (m, 2H), 1.84-1.61 (m, 4H).

Example 159

2-[4-(5-Chloro-2-cyanophenyl)-5-methoxy-2-oxopyridin-1(2H)-yl]-3-cyclobutyl-N-(2-methyl-3-oxo-2,3-dihydro-1H-indazol-6-yl)propanamide (racemate)

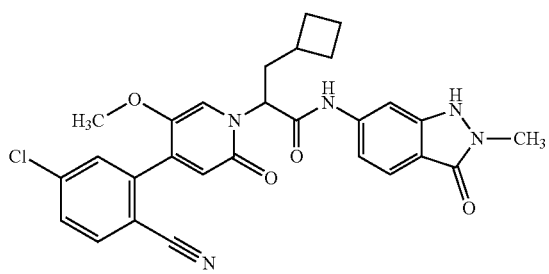 [SMILES: COc1cn(C(CC2CCC2)C(=O)Nc2ccc3c(=O)n(C)[nH]c3c2)c(=O)cc1-c1cc(Cl)ccc1C#N]

101 mg (0.16 mmol) of tert-butyl 6-({2-[4-(5-chloro-2-cyanophenyl)-5-methoxy-2-oxopyridin-1(2H)-yl]-3-cyclobutylpropanoyl}amino)-2-methyl-3-oxo-2,3-dihydro-1H-indazole-1-carboxylate (racemate) were hydrolysed with TFA according to General Method 2. The crude product was purified by preparative HPLC (Reprosil C18, water/acetonitrile gradient). Yield: 52 mg (62% of theory)

LC/MS [Method 1]: $R_t$=0.95 min; MS (ESIpos): m/z=532 (M+H)⁺,

¹H-NMR (400 MHz, DMSO-d₆): δ [ppm]=10.73 (s, 1H), 10.21 (s, 1H), 8.00 (d, 1H), 7.80-7.70 (m, 3H), 7.57 (d, 1H), 7.53 (s, 1H), 7.18 (dd, 1H), 6.52 (s, 1H), 5.70 (t, 1H), 3.70 (s, 3H), 2.30-2.17 (m, 3H), 2.01-1.88 (m, 2H), 1.84-1.61 (m, 4H).

Example 160

4-({2-[4-(5-Chloro-2-cyanophenyl)-5-methoxy-2-oxopyridin-1(2H)-yl]-3-methylbutanoyl}amino)benzoic acid (racemate)

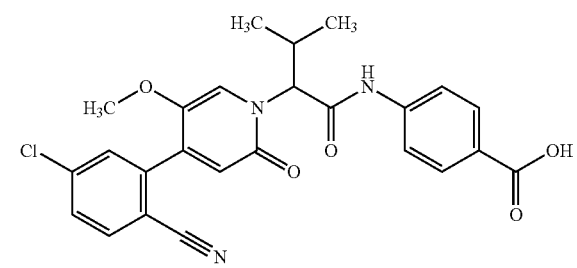 [SMILES: COc1cn(C(C(=O)Nc2ccc(C(=O)O)cc2)C(C)C)c(=O)cc1-c1cc(Cl)ccc1C#N]

95 mg (177 µmol) of tert-butyl 4-({2-[4-(5-chloro-2-cyanophenyl)-5-methoxy-2-oxopyridin-1(2H)-yl]-3-methylbutanoyl}amino)benzoate (racemate) were hydrolysed with TFA according to General Method 2. The crude product was purified by preparative HPLC (column: Chromatorex 125 mm×30 mm, 10 µm, mobile phase: 0.1% aqueous ammonium formate solution and acetonitrile, gradient 30% acetonitrile to 70% acetonitrile). Yield: 28 mg (33% of theory)

LC/MS [Method 1]: $R_t$=1.00 min; MS (ESIpos): m/z=480 (M+H)$^+$, $^1$H-NMR (400 MHz, DMSO-d$_6$): δ [ppm]=11.0 (s, 1H), 8.00 (d, 1H), 7.89 (d, 2H), 7.78-7.71 (m, 4H), 7.65 (s, 1H), 6.56 (s, 1H), 5.52 (d, 1H), 3.69 (s, 3H), 1.08 (d, 3H), 0.82 (d, 3H).

Example 161

4-({2-[4-(5-Chloro-2-cyanophenyl)-5-methoxy-2-oxopyridin-1(2H)-yl]-3-methylbutanoyl}amino)-2-methylbenzoic acid (racemate)

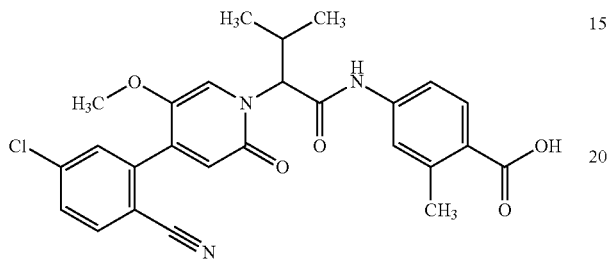

105 mg (207 µmol) of methyl 4-({2-[4-(5-chloro-2-cyanophenyl)-5-methoxy-2-oxopyridin-1(2H)-yl]-3-methylbutanoyl}amino)-2-methylbenzoate (racemate) were dissolved in 4.0 ml of methanol. 0.83 ml of a 1N sodium hydroxide solution was added and the mixture was heated to reflux for 1 h. The reaction mixture was then concentrated under reduced pressure and the residue was taken up in water and acidified with 1N aqueous hydrochloric acid. The mixture was extracted with ethyl acetate, the organic phase was dried over sodium sulphate and the solvent was removed under reduced pressure. The residue was purified by preparative HPLC (column: Chromatorex 125 mm×30 mm, 10 µm, mobile phase: 0.1% aqueous ammonium formate solution and acetonitrile, gradient 30% acetonitrile to 70% acetonitrile). The isolated product was finally triturated with water and filtered off with suction. Yield: 15 mg (15% of theory)

LC/MS [Method 1]: $R_t$=1.03 min; MS (ESIpos): m/z=494 (M+H)$^+$, $^1$H-NMR (400 MHz, DMSO-d$_6$): δ [ppm]=12.6 (br. s, 1H), 10.9 (s, 1H), 8.00 (d, 1H), 7.84 (d, 1H), 7.76-7.71 (m, 2H), 7.64-7.60 (m, 2H), 7.57 (dd, 1H), 6.55 (s, 1H), 5.51 (d, 1H), 3.69 (s, 3H), 2.51 (s, 3H), 1.08 (d, 3H), 0.82 (d, 3H).

Example 162

6-({2-[4-(5-Chloro-2-cyanophenyl)-5-methoxy-2-oxopyridin-1(2H)-yl]-3-methylbutanoyl}amino)-1H-benzimidazole-2-carboxylic acid (racemate)

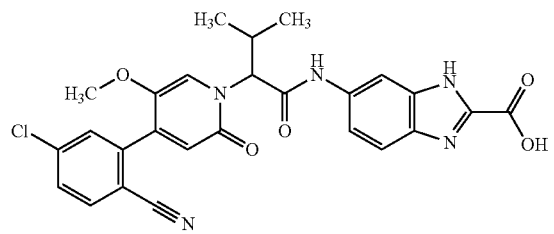 [SMILES: COc1cn(C(C(=O)Nc2ccc3nc(C(=O)O)[nH]c3c2)C(C)C)c(=O)cc1-c1cc(Cl)ccc1C#N]

130 mg (237 µmol) of ethyl 6-({2-[4-(5-chloro-2-cyanophenyl)-5-methoxy-2-oxopyridin-1(2H)-yl]-3-methylbutanoyl}amino)-1H-benzimidazole-2-carboxylate (racemate) were hydrolysed with lithium hydroxide according to General Method 3. Yield: 56 mg (44% of theory)

LC/MS [Method 1]: $R_t$=0.83 min; MS (ESIpos): m/z=520 (M+H)$^+$, $^1$H-NMR (400 MHz, DMSO-d$_6$): δ [ppm]=10.9 (s, 1H), 8.20 (s, 1H), 8.14 (s, 1H), 8.00 (d, 1H), 7.76 (d, 1H), 7.75-7.72 (m, 1H), 7.68 (s, 1H), 7.63 (d, 1H), 7.49 (dd, 1H), 5.53 (d, 1H), 3.70 (s, 3H), 2.61-2.55 (m, 1H), 1.10 (d, 3H), 0.83 (d, 3H).

Example 163

2-[4-(5-Chloro-2-cyanophenyl)-5-methoxy-2-oxopyridin-1(2H)-yl]-4-methoxy-N-(2-oxo-2,3-dihydro-1H-benzimidazol-5-yl)butanamide (racemate)

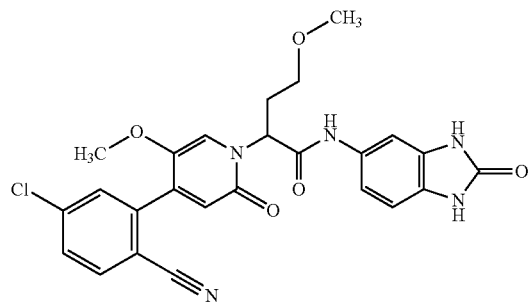 [SMILES: COCCC(C(=O)Nc1ccc2[nH]c(=O)[nH]c2c1)n1cc(OC)c(-c2cc(Cl)ccc2C#N)cc1=O]

70 mg (186 µmol) of 2-[4-(5-chloro-2-cyanophenyl)-5-methoxy-2-oxopyridin-1(2H)-yl]-4-methoxybutanoic acid (racemate), 27.7 mg (186 µmol, 1.0 eq.) of 5-aminobenzimidazolone, 26.4 mg (186 µmol) of Oxima and 28.9 µl (186 µmol) of DIC in 3.9 ml of dimethylformamide were reacted according to General Method 5. The crude product was purified by preparative HPLC (column: Chromatorex 125 mm×30 mm, 10 µm, mobile phase: water/0.1% formic acid and acetonitrile/0.1% formic acid, gradient 10% acetonitrile to 90% acetonitrile) and then subjected to basic extraction (aqueous sodium hydroxide solution/ethyl acetate). Yield: 44 mg (47% of theory)

LC/MS [Method 2]: $R_t$=2.22 min; MS (ESIpos): m/z=508 (M+H)$^+$, $^1$H-NMR (400 MHz, DMSO-d$_6$): δ [ppm]=10.6 (s, 1H), 10.5 (s, 1H), 10.4 (s, 1H), 8.02-7.98 (m, 1H), 7.76-7.71 (m, 2H), 7.54 (s, 1H), 7.45 (d, 1H), 7.09 (dd, 1H), 6.84 (d, 1H), 6.52 (s, 1H), 5.75 (dd, 1H), 3.68 (s, 3H), 3.43-3.23 (m, 2H), 3.21 (s, 3H), 2.44-2.29 (m, 2H).

Example 164

2-[4-(5-Chloro-2-cyanophenyl)-5-methoxy-2-oxopyridin-1(2H)-yl]-4-methoxy-N-(3-oxo-2,3-dihydro-1H-indazol-6-yl)butanamide (racemate)

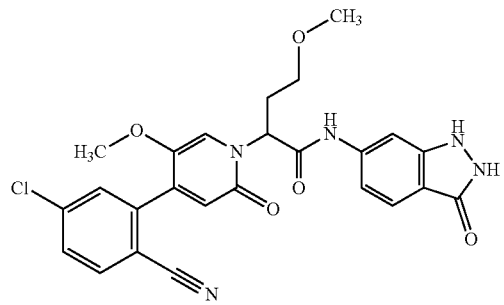 [SMILES: COCCC(C(=O)Nc1ccc2c(=O)[nH][nH]c2c1)n1cc(OC)c(-c2cc(Cl)ccc2C#N)cc1=O]

150 mg (377 µmol) of 2-[4-(5-chloro-2-cyanophenyl)-5-methoxy-2-oxopyridin-1(2H)-yl]-4-methoxybutanoic acid (racemate) and 65 mg (438 µmol, 1.1 eq.) of 6-amino-1H-indazol-3(2H)-one were reacted according to General Method 1. The crude product was purified by flash chromatography (silica gel 50, dichloromethane/methanol mixtures). Yield: 105 mg (52% of theory)

LC/MS [Method 1]: $R_t$=0.79 min; MS (ESIpos): m/z=508 (M+H)$^+$, $^1$H-NMR (400 MHz, DMSO-d$_6$): δ [ppm]=11.1 (br. s, 1H), 10.6-10.6 (m, 2H), 8.01-7.98 (m, 1H), 7.86 (d, 1H), 7.75-7.72 (m, 2H), 7.55-7.51 (m, 2H), 7.08 (dd, 1H), 6.53 (s, 1H), 5.79 (dd, 1H), 3.69 (s, 3H), 3.43-3.36 (m, 1H), 3.31-3.26 (m, 1H), 3.21 (s, 3H), 2.46-2.34 (m, 2H).

Example 165

2-[4-(5-Chloro-2-cyanophenyl)-5-methoxy-2-oxopyridin-1(2H)-yl]-4-methoxy-N-(2-methyl-3-oxo-2,3-dihydro-1H-indazol-6-yl)butanamide (racemate)

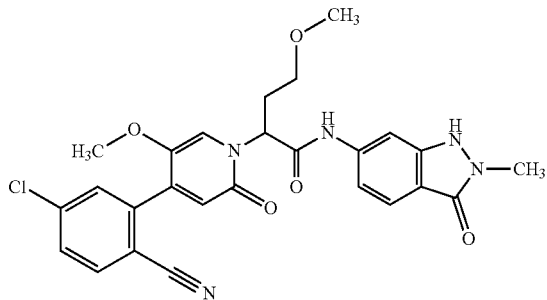 [SMILES: COCCC(C(=O)Nc1ccc2c(=O)n(C)[nH]c2c1)n1cc(OC)c(-c2cc(Cl)ccc2C#N)cc1=O]

225 mg (362 µmol) of tert-butyl 6-({2-[4-(5-chloro-2-cyanophenyl)-5-methoxy-2-oxopyridin-1(2H)-yl]-4-methoxybutanoyl}amino)-2-methyl-3-oxo-2,3-dihydro-1H-indazole-1-carboxylate (racemate) were hydrolysed with TFA according to General Method 2. Yield: 205 mg (purity 92%, 100% of theory)

LC/MS [Method 1]: $R_t$=0.82 min; MS (ESIpos): m/z=522 (M+H)$^+$, $^1$H-NMR (400 MHz, DMSO-d$_6$): δ [ppm]=10.7 (s, 1H), 10.2 (s, 1H), 8.02-7.97 (m, 1H), 7.77 (d, 1H), 7.75-7.72 (m, 2H), 7.56 (d, 1H), 7.52 (s, 1H), 7.20 (dd, 1H), 6.53 (s, 1H), 5.77 (dd, 1H), 3.69 (s, 3H), 3.44-3.37 (m, 1H), 3.32 (s, 3H), 3.31-3.26 (m, 1H), 3.21 (s, 3H), 2.47-2.36 (m, 2H).

Example 166

2-[4-(5-Chloro-2-cyanophenyl)-5-methoxy-2-oxopyridin-1(2H)-yl]-N-(1H-indazol-5-yl)-4-methoxybutanamide (racemate)

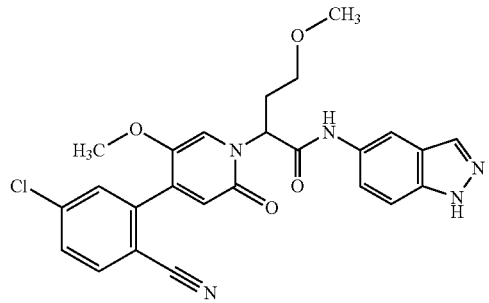 [SMILES: COCCC(C(=O)Nc1ccc2[nH]ncc2c1)n1cc(OC)c(-c2cc(Cl)ccc2C#N)cc1=O]

150 mg (398 µmol) of 2-[4-(5-chloro-2-cyanophenyl)-5-methoxy-2-oxopyridin-1(2H)-yl]-4-methoxybutanoic acid (racemate) and 58.3 mg (438 µmol, 1.1 eq.) of 5-aminoindazole were reacted according to General Method 1. The crude product was purified by preparative HPLC (column: Chromatorex 125 mm×30 mm, 10 µm, mobile phase: water and acetonitrile, gradient 10% acetonitrile to 90% acetonitrile). Yield: 88 mg (42% of theory)

LC/MS [Method 1]: $R_t$=0.87 min; MS (ESIpos): m/z=492 (M+H)$^+$, $^1$H-NMR (400 MHz, DMSO-d$_6$): δ [ppm]=13.0 (s, 1H), 10.5 (s, 1H), 8.14 (s, 1H), 8.02 (s, 1H), 8.01-7.98 (m, 1H), 7.75-7.70 (m, 2H), 7.56 (s, 1H), 7.49 (s, 2H), 6.53 (s, 1H), 5.80 (dd, 1H), 3.69 (s, 3H), 3.44-3.37 (m, 1H), 3.34-3.26 (m, 1H), 3.22 (s, 3H), 2.48-2.31 (m, 2H).

Example 167

2-[4-(5-Chloro-2-cyanophenyl)-5-methoxy-2-oxopyridin-1(2H)-yl]-N-(3-chloro-1H-indazol-5-yl)-4-methoxybutanamide (racemate)

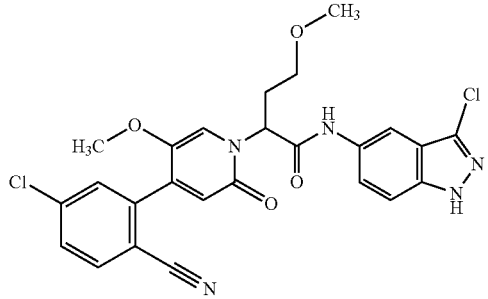 [SMILES: COCCC(C(=O)Nc1ccc2[nH]nc(Cl)c2c1)n1cc(OC)c(-c2cc(Cl)ccc2C#N)cc1=O]

170 mg (451 µmol) of 2-[4-(5-chloro-2-cyanophenyl)-5-methoxy-2-oxopyridin-1(2H)-yl]-4-methoxybutanoic acid (racemate) and 92.4 mg (purity 90%, 496 µmol, 1.1 eq.) of 5-amino-3-chloro-1H-indazole were reacted according to General Method 1. The crude product was purified by flash chromatography (silica gel 50, cyclohexane/ethyl acetate mixtures). Yield: 113 mg (48% of theory)

LC/MS [Method 1]: $R_t$=0.97 min; MS (ESIpos): m/z=526 (M+H)$^+$, $^1$H-NMR (400 MHz, DMSO-d$_6$): δ [ppm]=13.3 (s, 1H), 10.6 (s, 1H), 8.16 (s, 1H), 8.02-7.98 (m, 1H), 7.76-7.70 (m, 2H), 7.55 (s, 3H), 6.53 (s, 1H), 5.79 (dd, 1H), 3.70 (s, 3H), 3.45-3.37 (m, 1H), 3.31-3.26 (m, 1H), 3.22 (s, 3H), 2.48-2.31 (m, 2H).

Example 168

6-({2-[4-(5-Chloro-2-cyanophenyl)-5-methoxy-2-oxopyridin-1(2H)-yl]-4-methoxybutanoyl}amino)-1H-indole-2-carboxylic acid (racemate)

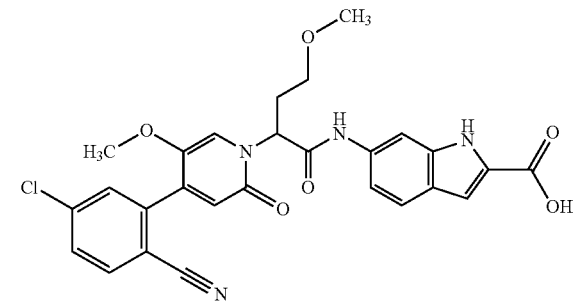 [SMILES: COCCC(C(=O)Nc1ccc2cc(C(=O)O)[nH]c2c1)n1cc(OC)c(-c2cc(Cl)ccc2C#N)cc1=O]

80 mg (142 µmol) of ethyl 6-({2-[4-(5-chloro-2-cyanophenyl)-5-methoxy-2-oxopyridin-1(2H)-yl]-4-methoxybutanoyl}amino)-1H-indole-2-carboxylate (racemate) were hydrolysed with lithium hydroxide at RT according to General Method 3. Yield: 50 mg (66% of theory)

LC/MS [Method 1]: R$_t$=0.92 min; MS (ESIpos): m/z=535 (M+H)$^+$, $^1$H-NMR (400 MHz, DMSO-d$_6$): δ [ppm]=12.8 (br. s, 1H), 11.7-11.6 (m, 1H), 10.5 (s, 1H), 8.03-7.98 (m, 2H), 7.75-7.71 (m, 2H), 7.58-7.54 (m, 2H), 7.21 (dd, 1H), 7.04-7.02 (m, 1H), 6.52 (s, 1H), 5.80 (dd, 1H), 3.70 (s, 3H), 3.43-3.35 (m, 1H), (1H under H$_2$O signal), 3.22 (s, 3H), 2.46-2.36 (m, 2H).

Example 169

6-({2-[4-(5-Chloro-2-cyanophenyl)-5-methoxy-2-oxopyridin-1(2H)-yl]-4-methoxybutanoyl}amino)-5-methoxy-1H-indole-2-carboxylic acid (racemate)

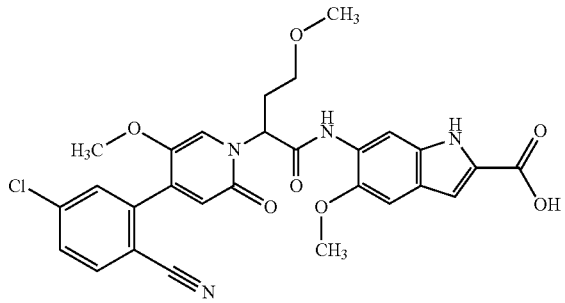 [SMILES: COCCC(C(=O)Nc1cc2[nH]c(C(=O)O)cc2cc1OC)n1cc(OC)c(-c2cc(Cl)ccc2C#N)cc1=O]

80 mg (135 µmol) of ethyl 6-({2-[4-(5-chloro-2-cyanophenyl)-5-methoxy-2-oxopyridin-1(2H)-yl]-4-methoxybutanoyl}amino)-5-methoxy-1H-indole-2-carboxylate (racemate) were hydrolysed with lithium hydroxide at RT according to General Method 3. Yield: 63 mg (purity 90%, 74% of theory)

LC/MS [Method 1]: R$_t$=0.93 min; MS (ESIpos): m/z=565 (M+H)$^+$, $^1$H-NMR (400 MHz, DMSO-d$_6$): δ [ppm]=12.7 (br. s, 1H), 11.6 (s, 1H), 9.41 (s, 1H), 8.23 (s, 1H), 8.00 (d, 1H), 7.78-7.70 (m, 2H), 7.51 (s, 1H), 7.19 (s, 1H), 6.99-6.97 (m, 1H), 6.57 (s, 1H), 5.79 (dd, 1H), 3.86 (s, 3H), 3.69 (s, 3H), 3.45-3.35 (m, 2H), 3.24 (s, 3H), 2.44-2.31 (m, 2H).

Example 170

4-({2-[5-Chloro-4-(5-chloro-2-cyanophenyl)-2-oxopyridin-1(2H)-yl]-4-methylpentanoyl}amino)benzoic acid (racemate)

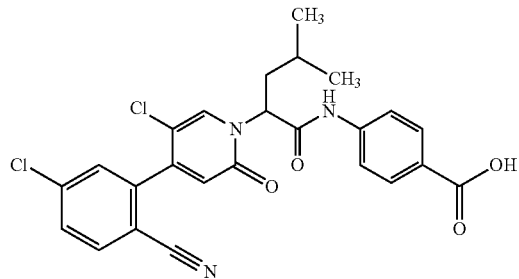 [SMILES: CC(C)CC(C(=O)Nc1ccc(C(=O)O)cc1)n1cc(Cl)c(-c2cc(Cl)ccc2C#N)cc1=O]

45 mg (0.08 mmol) of tert-butyl 4-({2-[5-chloro-4-(5-chloro-2-cyanophenyl)-2-oxopyridin-1(2H)-yl]-4-methylpentanoyl}amino)benzoate (racemate) were hydrolysed with TFA according to General Method 2. The crude product was purified by preparative HPLC (Reprosil C18, water/acetonitrile gradient). Yield: 28 mg (purity 90%, 62% of theory)

LC/MS [Method 1]: R$_t$=1.08 min; MS (ESIpos): m/z=498 (M+H)$^+$, $^1$H-NMR (400 MHz, DMSO-d$_6$): δ [ppm]=12.79 (s, 1H), 10.89 (s, 1H), 8.22 (s, 1H), 8.07 (d, 1H), 7.92 (d, 2H), 7.84 (d, 1H), 7.79 (dd, 1H), 7.74 (d, 2H), 6.70 (s, 1H), 5.84 (dd, 1H), 2.32-2.22 (m, 1H), 1.93-1.82 (m, 1H), 1.48-1.35 (m, 1H), 0.94 (dd, 6H).

Example 171

4-({2-[5-Chloro-4-(5-chloro-2-cyanophenyl)-2-oxopyridin-1(2H)-yl]-4-(trifluoromethoxy)butanoyl}amino)benzoic acid (racemate)

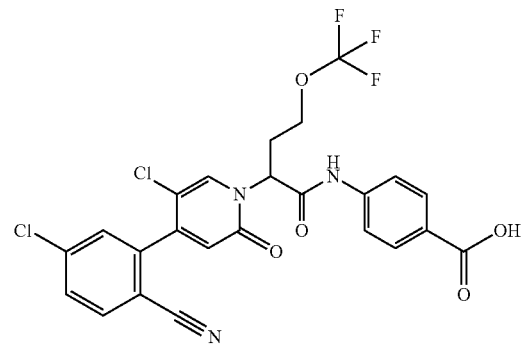 [SMILES: N#Cc1ccc(Cl)cc1-c1cc(=O)n(C(CCOC(F)(F)F)C(=O)Nc2ccc(C(=O)O)cc2)cc1Cl]

142 mg (purity 81%, 0.19 mmol) of tert-butyl 4-({2-[5-chloro-4-(5-chloro-2-cyanophenyl)-2-oxopyridin-1(2H)-yl]-4-(trifluoromethoxy)butanoyl}amino)benzoate (racemate) were hydrolysed with TFA according to General Method 2. The crude product was purified by preparative HPLC (Reprosil C18, water/acetonitrile gradient). Yield: 54 mg (52% of theory)

LC/MS [Method 2]: R$_t$=3.32 min; MS (ESIpos): m/z=554 (M+H)$^+$, $^1$H-NMR (400 MHz, DMSO-d$_6$): δ [ppm]=12.79 (s, 1H), 10.87 (s, 1H), 8.26 (s, 1H), 8.07 (d, 1H), 7.92 (d, 2H), 7.80 (dd, 1H), 7.77 (d, 1H), 7.74 (d, 2H), 6.71 (s, 1H), 5.81 (dd, 1H), 4.24-4.15 (m, 1H), 4.03-3.84 (m, 1H), 2.71-2.59 (m, 2H).

Example 172

4-[(2-{4-[5-Chloro-2-(difluoromethoxy)phenyl]-5-methoxy-2-oxopyridin-1(2H)-yl}-4-methylpentanoyl)amino]benzoic acid (racemate)

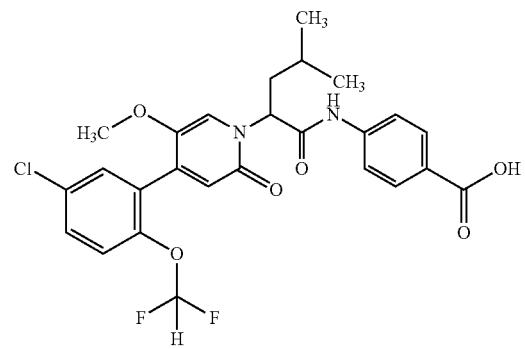 [SMILES: COc1cn(C(CC(C)C)C(=O)Nc2ccc(C(=O)O)cc2)c(=O)cc1-c1cc(Cl)ccc1OC(F)F]

263 mg (purity 88%, 0.39 mmol) of tert-butyl 4-[(2-{4-[5-chloro-2-(difluoromethoxy)phenyl]-5-methoxy-2-oxopyridin-1(2H)-yl}-4-methylpentanoyl)amino]benzoate (racemate) were hydrolysed with TFA according to General Method 2. The crude product was purified by preparative HPLC (Reprosil C18, water/acetonitrile gradient). Yield: 140 mg (67% of theory)

LC/MS [Method 1]: $R_t$=1.10 min; MS (ESIpos): m/z=535 (M+H)$^+$, $^1$H-NMR (400 MHz, DMSO-d$_6$): δ [ppm]=12.78 (s, 1H), 10.84 (s, 1H), 7.91 (d, 2H), 7.76 (d, 2H), 7.58 (dd, 1H), 7.50 (d, 1H), 7.40 (s, 1H), 7.29 (d, 1H), 7.13 (t, 1H), 6.40 (s, 1H), 5.84 (dd, 1H), 3.63 (s, 3H), 2.22-2.12 (m, 1H), 1.92-1.82 (m, 1H), 1.49-1.36 (m, 1H), 0.94 (t, 6H).

Example 173

4-[(2-{4-[5-Chloro-2-(difluoromethoxy)phenyl]-5-methoxy-2-oxopyridin-1(2H)-yl}-4-methoxybutanoyl)amino]benzoic acid (racemate)

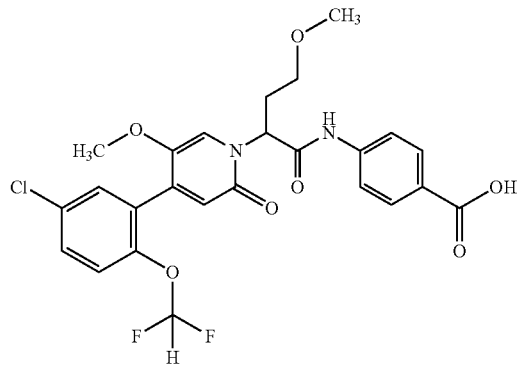 [SMILES: COCCC(C(=O)Nc1ccc(C(=O)O)cc1)n1cc(OC)c(-c2cc(Cl)ccc2OC(F)F)cc1=O]

66 mg (0.11 mmol) of tert-butyl 4-[(2-{4-[5-chloro-2-(difluoromethoxy)phenyl]-5-methoxy-2-oxopyridin-1(2H)-yl}4-methoxybutanoyl)amino]benzoate (racemate) were hydrolysed with TFA according to General Method 2. The crude product was purified by preparative HPLC (Reprosil C18, water/acetonitrile gradient). Yield: 31 mg (52% of theory)

LC/MS [Method 1]: $R_t$=0.96 min; MS (ESIpos): m/z=537 (M+H)$^+$, $^1$H-NMR (400 MHz, DMSO-d$_6$): δ [ppm]=12.73 (s, 1H), 10.73 (s, 1H), 7.90 (d, 2H), 7.76 (d, 2H), 7.57 (dd, 1H), 7.49 (d, 1H), 7.40 (s, 1H), 7.30 (d, 1H), 7.13 (t, 1H), 6.39 (s, 1H), 5.74 (dd, 1H), 3.63 (s, 3H), 3.42-3.34 (m, 1H), 3.30-3.24 (m, 1H), 3.20 (s, 3H), 2.45-2.34 (m, 2H).

Example 174

2-{4-[5-Chloro-2-(difluoromethoxy)phenyl]-5-methoxy-2-oxopyridin-1(2H)-yl}-4-methoxy-N-(2-methyl-3-oxo-2,3-dihydro-1H-indazol-6-yl)butanamide (racemate)

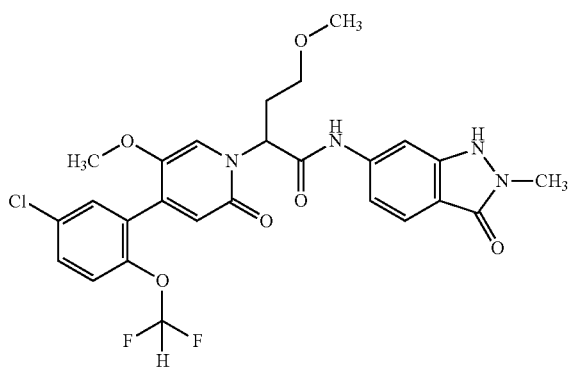 [SMILES: COCCC(C(=O)Nc1ccc2c(=O)n(C)[nH]c2c1)n1cc(OC)c(-c2cc(Cl)ccc2OC(F)F)cc1=O]

132 mg (0.19 mmol) of tert-butyl 6-[(2-{4-[5-chloro-2-(difluoromethoxy)phenyl]-5-methoxy-2-oxopyridin-1(2H)-yl}-4-methoxybutanoyl)amino]-2-methyl-3-oxo-2,3-dihydro-1H-indazole-1-carboxylate (racemate) were hydrolysed with TFA according to General Method 2. The crude product was purified by preparative HPLC (Reprosil C18, water/acetonitrile gradient). Yield: 48 mg (45% of theory)

LC/MS [Method 1]: $R_t$=0.89 min; MS (ESIpos): m/z=563 (M+H)$^+$, $^1$H-NMR (400 MHz, DMSO-d$_6$): δ [ppm]=10.65 (s, 1H), 10.19 (s, 1H), 7.77 (d, 1H), 7.61-7.51 (m, 2H), 7.49 (d, 1H), 7.42 (s, 1H), 7.33-7.25 (m, 2H), 7.19 (dd, 1H), 7.13 (t, 1H), 6.39 (s, 1H), 5.75 (dd, 1H), 3.63 (s, 3H), 3.32 (s, 3H), 3.20 (s, 3H), 2.43-2.30 (m, 2H).

Example 175

2-{4-[5-Chloro-2-(difluoromethoxy)phenyl]-5-methoxy-2-oxopyridin-1(2H)-yl}-4-methoxy-N-(2-oxo-2,3-dihydro-1H-benzimidazol-5-yl)butanamide (racemate)

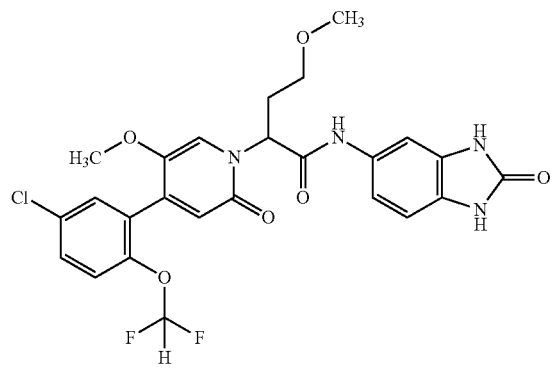 [SMILES: COCCC(C(=O)Nc1ccc2[nH]c(=O)[nH]c2c1)n1cc(OC)c(-c2cc(Cl)ccc2OC(F)F)cc1=O]

76 mg (purity 82%, 0.15 mmol) of 2-{4-[5-chloro-2-(difluoromethoxy)phenyl]-5-methoxy-2-oxopyridin-1(2H)-yl}-4-methoxybutanoic acid (racemate) and 25 mg (0.17 μmol, 1.1 eq.) of 5-aminobenzimidazolone were reacted according to General Method 1. The crude product was purified by preparative HPLC (Reprosil C18, water/acetonitrile gradient). Yield: 37 mg (45% of theory)

LC/MS [Method 1]: $R_t$=0.86 min; MS (ESIpos): m/z=549 (M+H)$^+$, $^1$H-NMR (400 MHz, DMSO-d$_6$): δ [ppm]=10.56 (s, 1H), 10.50 (s, 1H), 10.30 (s, 1H), 7.57 (dd, 1H), 7.48 (d, 1H), 7.46-7.40 (m, 2H), 7.30 (d, 1H), 7.12 (t, 1H), 7.09 (dd, 1H), 6.84 (d, 1H), 6.37 (s, 1H), 5.73 (dd, 1H), 3.62 (s, 3H), 3.34-3.23 (m, 2H), 3.20 (s, 3H), 2.40-2.25 (m, 2H).

Example 176

4-{[2-{4-[5-Chloro-2-(difluoromethoxy)phenyl]-5-methoxy-2-oxopyridin-1(2H)-yl}-4-(trifluoromethoxy)butanoyl]amino}benzoic acid (racemate)

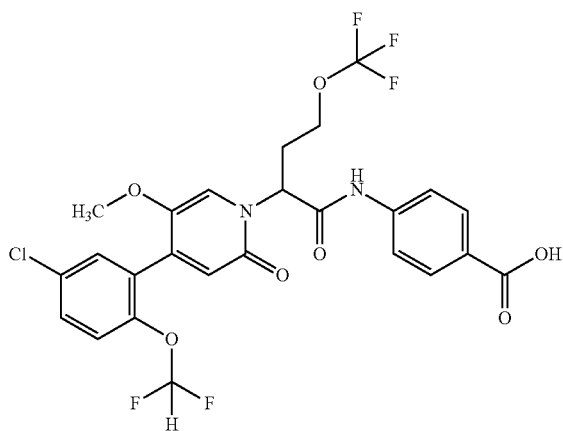 [SMILES: COc1cn(C(CCOC(F)(F)F)C(=O)Nc2ccc(C(=O)O)cc2)c(=O)cc1-c1cc(Cl)ccc1OC(F)F]

195 mg (0.29 mmol) of tert-butyl 4-{[2-{4-[5-chloro-2-(difluoromethoxy)phenyl]-5-methoxy-2-oxopyridin-1(2H)-yl}-4-(trifluoromethoxy)butanoyl]amino}benzoate (racemate) were hydrolysed with TFA according to General Method 2. The crude product was purified by preparative HPLC (Reprosil C18, water/acetonitrile gradient). Yield: 84 mg (50% of theory)

LC/MS [Method 1]: $R_t$=1.07 min; MS (ESIpos): m/z=591 (M+H)$^+$, $^1$H-NMR (400 MHz, DMSO-$d_6$): δ [ppm]=12.76 (s, 1H), 10.75 (s, 1H), 7.91 (d, 2H), 7.75 (d, 2H), 7.58 (dd, 1H), 7.46 (d, 1H), 7.40 (s, 1H), 7.30 (d, 1H), 7.11 (t, 1H), 6.41 (s, 1H), 5.79 (t, 1H), 4.19-4.11 (m, 1H), 4.04-3.95 (m, 1H), 3.63 (s, 3H), 2.65-2.57 (m, 2H).

Example 177

4-[(2-{4-[5-Chloro-2-(difluoromethoxy)phenyl]-5-methoxy-2-oxopyridin-1(2H)-yl}-3-[(2R)-tetrahydro-2H-pyran-2-yl]propanoyl)amino]benzoic acid (mixture of enantiomerically pure diastereomers 1 and 2)

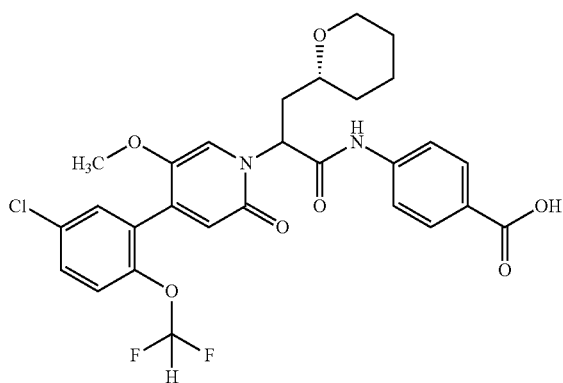 [SMILES: COc1cn(C(C[C@H]2CCCCO2)C(=O)Nc2ccc(C(=O)O)cc2)c(=O)cc1-c1cc(Cl)ccc1OC(F)F]

67 mg (0.11 mmol) of tert-butyl 4-[(2-{4-[5-chloro-2-(difluoromethoxy)phenyl]-5-methoxy-2-oxopyridin-1(2H)-yl}-3-[(2R)-tetrahydro-2H-pyran-2-yl]propanoyl)amino]benzoate (mixture of enantiomerically pure diastereomers 1 and 2) were hydrolysed with TFA according to General Method 2. The crude product was purified by preparative HPLC (Reprosil C18, water/acetonitrile gradient). Yield: 25 mg (41% of theory)

LC/MS [Method 1]: $R_t$=1.05 min; MS (ESIpos): m/z=577 (M+H)$^+$, $^1$H-NMR (400 MHz, DMSO-$d_6$): δ [ppm]=12.75 (s, 1H), 10.74/10.65 (2×s, 1H), 7.94-7.86 (m, 2H), 7.81-7.72 (m, 2H), 7.59/7.56 (2×t, 1H), 7.50/7.48 (2×d, 1H), 7.42/7.38 (2×s, 1H), 7.33-7.27 (m, 1H), 7.13/7.12 (2×t, 1H), 6.38/6.37 (2×s, 1H), 5.80/5.72 (t/dd, 1H), 3.90-3.78 (m, 1H), 3.63/3.62 (2×s, 3H), 3.29-3.03 (m, 2H), 2.39-2.09 (m, 2H), 1.79-1.70 (m, 1H), 1.67-1.54 (m, 1H), 1.48-1.18 (m, 4H).

Example 178

4-({2-[4-(5-Chloro-2-cyanophenyl)-5-methoxy-2-oxopyridin-1(2H)-yl]butanoyl}amino)-2-fluorobenzoic acid (racemate)

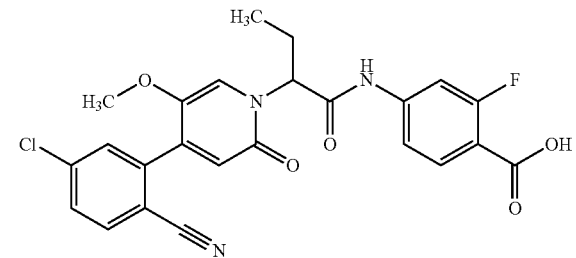 [SMILES: CCC(C(=O)Nc1ccc(C(=O)O)c(F)c1)n1cc(OC)c(-c2cc(Cl)ccc2C#N)cc1=O]

249 mg (0.43 mmol) of tert-butyl 4-({2-[4-(5-chloro-2-cyanophenyl)-5-methoxy-2-oxopyridin-1(2H)-yl]butanoyl}amino)-2-fluorobenzoate (racemate) were reacted according to General Method 2. The crude product was purified by preparative HPLC (water/acetonitrile/0.1% formic acid gradient). Yield: 145 mg (65% of theory)

LC/MS [Method 8]: $R_t$=1.19 min; MS (ESIpos): m/z=484 (M+H)$^+$, $^1$H-NMR (400 MHz, DMSO-$d_6$): δ [ppm]=12.99 (br. s, 1H), 10.94 (s, 1H), 8.02-7.97 (m, 1H), 7.86 (t, 1H), 7.77-7.67 (m, 3H), 6.54 (s, 1H), 5.60 (dd, 1H), 3.69 (s, 3H), 3.26-2.11 (m, 2H), 0.91 (t, 3H), $^{19}$F-NMR (376.54 MHz, DMSO-$d_6$): δ [ppm]=−107.7.

Example 179

4-({(2S)-2-[4-(5-Chloro-2-cyanophenyl)-5-methoxy-2-oxopyridin-1(2H)-yl]butanoyl}amino)-2-fluorobenzoic acid (enantiomer 2)

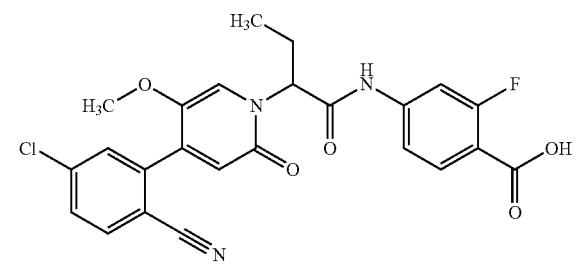 [SMILES: CCC(C(=O)Nc1ccc(C(=O)O)c(F)c1)n1cc(OC)c(-c2cc(Cl)ccc2C#N)cc1=O]

Enantiomer separation of 135 mg of the racemate from Example 178 gave 36 mg of the title compound Example 179 (enantiomer 2): chiral SFC: $R_t$=2.67 min; 99% ee.

Separation method (SFC): column: Chiralpak AZ-H 5 μm 250 mm×30 mm; mobile phase: 60% carbon dioxide, 40% ethanol; temperature: 40° C.; flow rate: 100 ml/min; pressure: 80 bar; UV detection: 220 nm.

Analysis: column: Chiralpak AZ-H 5μ 250 mm×4.6 mm; mobile phase: 60% carbon dioxide, 40% ethanol; flow rate: 3 ml/min; UV detection: 220 nm.

Example 180

4-({2-[4-(5-Chloro-2-cyanophenyl)-5-methoxy-2-oxopyridin-1(2H)-yl]butanoyl}amino)-3-fluorobenzoic acid (racemate)

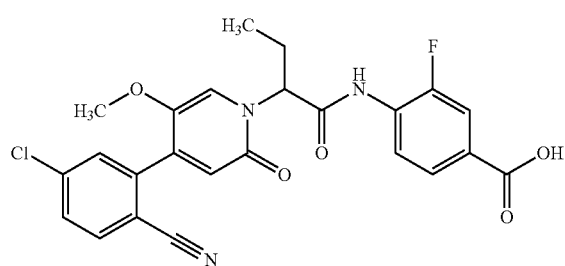 [SMILES: CCC(C(=O)Nc1ccc(C(=O)O)cc1F)n1cc(OC)c(-c2cc(Cl)ccc2C#N)cc1=O]

125 mg (0.23 mmol) of tert-butyl 4-(2-[4-(5-chloro-2-cyanophenyl)-5-methoxy-2-oxopyridin-1(2H)-yl]butanoyl}amino)-3-fluorobenzoate (racemate) were reacted according to General Method 2. The crude product was purified by preparative HPLC (water/acetonitrile/0.1% formic acid gradient). Yield: 57 mg (51% of theory)

LC/MS [Method 1]: $R_t$=0.94 min; MS (ESIpos): m/z=484 (M+H)$^+$, $^1$H-NMR (400 MHz, DMSO-d$_6$): δ [ppm]=13.13 (br. s, 1H), 10.55 (s, 1H), 8.11 (t, 1H), 8.02-7.97 (m, 1H), 7.79-7.70 (m, 4H), 7.46 (s, 1H), 6.55 (s, 1H), 5.80 (dd, 1H), 3.68 (s, 3H), 2.27-2.10 (m, 2H), 0.91 (t, 3H), $^{19}$F-NMR (376.54 MHz, DMSO-d$_6$): δ [ppm]=−123.9.

Example 181

4-({(2S)-2-[4-(5-Chloro-2-cyanophenyl)-5-methoxy-2-oxopyridin-1(2H)-yl]butanoyl}amino)-3-fluorobenzoic acid (enantiomer 2)

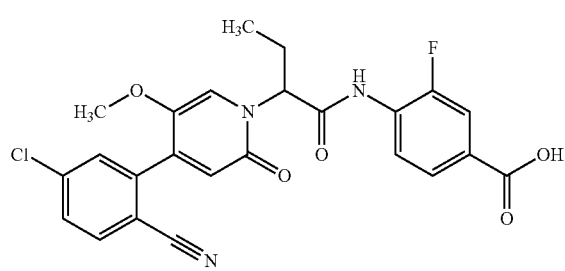 [SMILES: CCC(C(=O)Nc1ccc(C(=O)O)cc1F)n1cc(OC)c(-c2cc(Cl)ccc2C#N)cc1=O]

Enantiomer separation of 55 mg of the racemate from Example 180 gave 27 mg of the title compound Example 181 (enantiomer 2): chiral SFC: $R_t$=7.07 min; >99% ee.

Separation method (SFC): column: AD-H 5 μm 250 mm×20 mm; mobile phase: 85% carbon dioxide, 15% ethanol; temperature: 40° C.; flow rate: 100 ml/min; pressure: 100 bar; UV detection: 210 nm.

Analysis: column: AD-H 5 μm 250 mm×4.6 mm; mobile phase: 80% carbon dioxide, 20% ethanol; flow rate: 3 ml/min; UV detection: 220 nm.

Example 182

4-({2-[4-(5-Chloro-2-cyanophenyl)-5-methoxy-2-oxopyridin-1(2H)-yl]butanoyl}amino)-2,5-difluorobenzoic acid (racemate)

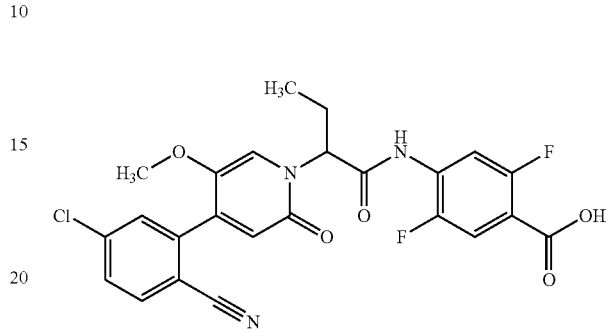

179 mg (0.32 mmol) of tert-butyl 4-({2-[4-(5-chloro-2-cyanophenyl)-5-methoxy-2-oxopyridin-1(2H)-yl]butanoyl}amino)-2,5-difluorobenzoate (racemate) were reacted according to General Method 6A. The crude product was purified by preparative HPLC (water/acetonitrile/0.1% formic acid gradient). Yield: 105 mg (65% of theory)

LC/MS [Method 8]: $R_t$=1.21 min; MS (ESIpos): m/z=502 (M+H)$^+$, $^1$H-NMR (400 MHz, DMSO-d$_6$): δ [ppm]=13.36 (br. s, 1H), 10.74 (s, 1H), 8.08-7.97 (m, 2H), 7.77-7.68 (m, 3H), 7.45 (s, 1H), 6.55 (s, 1H), 5.85-5.78 (m, 1H), 3.69 (s, 3H), 2.25-2.14 (m, 2H), 0.90 (t, 3H), $^{19}$F-NMR (376.54 MHz, DMSO-d$_6$): δ [ppm]=−112.6, −129.8.

Example 183

4-({(2S)-2-[4-(5-Chloro-2-cyanophenyl)-5-methoxy-2-oxopyridin-1(2H)-yl]butanoyl}amino)-2,5-difluorobenzoic acid (enantiomer 2)

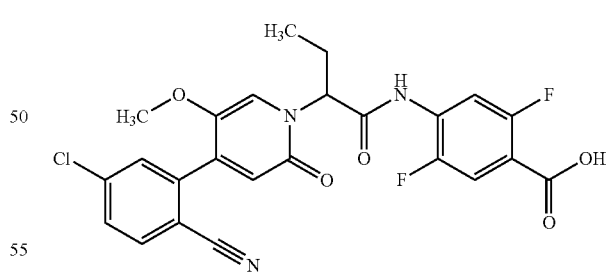

Enantiomer separation of 100 mg of the racemate from Example 182 gave 33 mg of the title compound Example 183 (enantiomer 2): chiral SFC: $R_t$=3.05 min; >99% ee.

Separation method (SFC): column: Chiralpak AZ-H 5 μ 250 mm×30 mm; mobile phase: 75% carbon dioxide, 25% ethanol; temperature: 40° C.; flow rate: 100 ml/min; pressure: 100 bar; UV detection: 210 nm.

Analysis: column: Chiralpak AZ-H 5μ 250 mm×4.6 mm; mobile phase: 70% carbon dioxide, 30% ethanol; flow rate: 3 ml/min; UV detection: 220 nm.

Example 184

4-({2-[4-(5-Chloro-2-cyanophenyl)-5-methoxy-2-oxopyridin-1(2H)-yl]butanoyl}amino)-2,3-difluorobenzoic acid (racemate)

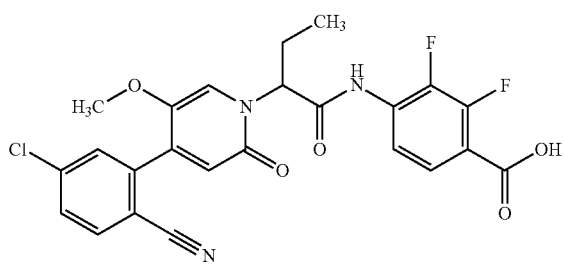 [SMILES: CCC(C(=O)Nc1ccc(C(=O)O)c(F)c1F)n1cc(OC)c(-c2cc(Cl)ccc2C#N)cc1=O]

80 mg (0.15 mmol) of methyl 4-({2-[4-(5-chloro-2-cyanophenyl)-5-methoxy-2-oxopyridin-1(2H)-yl]butanoyl}amino)-2,3-difluorobenzoate (racemate) were reacted according to General Method 6B. The crude product was purified by preparative HPLC (water/acetonitrile/0.1% formic acid gradient). Yield: 58 mg (74% of theory)

LC/MS [1]: $R_t$=0.96 min; MS (ESIpos): m/z=502 (M+H)$^+$, $^1$H-NMR (400 MHz, DMSO-d$_6$): δ [ppm]=13.40 (br. s, 1H), 10.73 (s, 1H), 8.02-7.97 (m, 1H), 7.90-7.84 (m, 1H), 7.76-7.71 (m, 2H), 7.71-7.64 (m, 1H), 7.45 (s, 1H), 6.55 (s, 1H), 5.78 (dd, 1H), 3.68 (s, 3H), 2.27-2.13 (m, 2H), 0.91 (t, 3H), $^{19}$F-NMR (376.54 MHz, DMSO-d$_6$): δ [ppm]=−135.72, −147.97.

Example 185

4-({2-[4-(5-Chloro-2-cyanophenyl)-5-methoxy-2-oxopyridin-1(2H)-yl]butanoyl}amino)-2,6-difluorobenzoic acid (racemate)

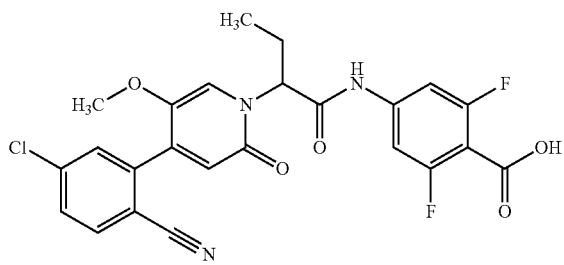 [SMILES: CCC(C(=O)Nc1cc(F)c(C(=O)O)c(F)c1)n1cc(OC)c(-c2cc(Cl)ccc2C#N)cc1=O]

67 mg (0.20 mmol, 2 eq.) of caesium carbonate were added to a solution of 53 mg (0.10 mmol) of methyl 4-({2-[4-(5-chloro-2-cyanophenyl)-5-methoxy-2-oxopyridin-1(2H)-yl]butanoyl}amino)-2,6-difluorobenzoate (racemate) in 1.25 ml of a mixture of methanol/water (4/1), and the resulting suspension was stirred at 60° C. for 1 h. Methanol was removed at 30° C. under reduced pressure. The reaction mixture was cooled to RT and adjusted to pH 3 using aqueous hydrochloric acid (1N). The aqueous phase was extracted with ethyl acetate. The combined organic phases were dried (sodium sulphate), filtered and concentrated under reduced pressure. The crude product was purified by preparative HPLC (water/acetonitrile/0.1% formic acid gradient). Yield: 11 mg (21% of theory)

LC/MS [Method 1]: $R_t$=0.96 min; MS (ESIpos): m/z=502 (M+H)$^+$, $^1$H-NMR (400 MHz, DMSO-d$_6$): δ [ppm]=13.63 (br. s, 1H), 10.88 (br. s, 1H), 8.00 (d, 1H), 7.76-7.71 (m, 2H), 7.47 (s, 1H), 7.40-7.28 (m, 2H), 6.54 (s, 1H), 5.56 (dd, 1H), 3.69 (s, 3H), 2.24-2.11 (m, 2H), 0.89 (t, 3H).

Example 186

2-[4-(5-Chloro-2-cyanophenyl)-5-methoxy-2-oxopyridin-1(2H)-yl]-N-[4-(5-oxo-4,5-dihydro-1,2,4-thiadiazol-3-yl)phenyl]butanamide (racemate)

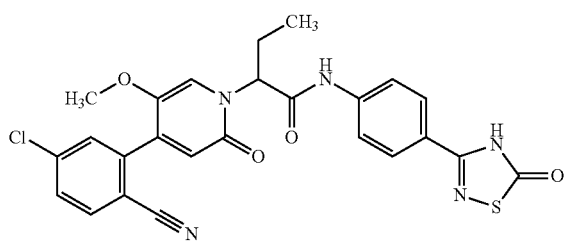 [SMILES: CCC(C(=O)Nc1ccc(-c2nsc(=O)[nH]2)cc1)n1cc(OC)c(-c2cc(Cl)ccc2C#N)cc1=O]

65 mg (0.19 mmol) of 2-[4-(5-chloro-2-cyanophenyl)-5-methoxy-2-oxopyridin-1(2H)-yl]butanoic acid (racemate) and 54 mg (0.28 mmol, 1.5 eq.) of 3-(4-aminophenyl)-1,2,4-thiadiazol-5(4H)-one were reacted according to General Method 7. The crude product was purified by preparative HPLC (water/acetonitrile/0.1% formic acid gradient). Yield: 45 mg (46% of theory)

LC/MS [Method 8]: Rt=1.25 min; MS (ESIpos): m/z=521 (M+H)$^+$, $^1$H-NMR (400 MHz, DMSO-d$_6$): δ [ppm]=13.31 (br. s, 1H), 10.78 (s, 1H), 8.02-7.98 (m, 1H), 7.94-7.89 (m, 2H), 7.80-7.71 (m, 4H), 7.50 (s, 1H), 6.54 (s, 1H), 5.64 (dd, 1H), 3.69 (s, 3H), 2.26-2.10 (m, 2H), 0.91 (t, 3H).

Example 187

(2S)-2-[4-(5-Chloro-2-cyanophenyl)-5-methoxy-2-oxopyridin-1(2H)-yl]-N-[4-(5-oxo-4,5-dihydro-1,2,4-thiadiazol-3-yl)phenyl]butanamide (enantiomer 2)

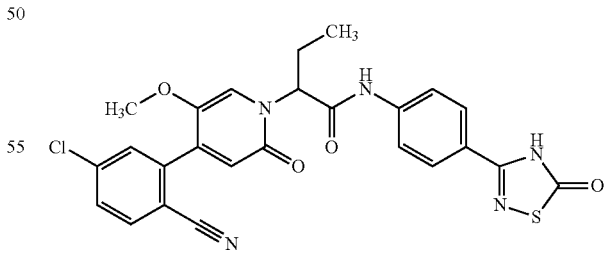

Enantiomer separation of 40 mg of the racemate from Example 186 gave 10 mg of the title compound Example 187 (enantiomer 2): Chiral HPLC: $R_t$=6.83 min; >99% ee.

Separation method (HPLC): column: Chiralpak IB 5 μm 250 mm×20 mm; mobile phase: 50% hexane, 50% 2-propanol; temperature: 35° C.; flow rate: 20 ml/min; UV detection: 220 nm.

Analysis: column: Chiralcel OD-H 5 µm 250 mm×4.6 mm; mobile phase: 50% hexane, 50% 2-propanol; flow rate: 1 ml/min; temperature: 30° C.; UV detection: 220 nm.

Example 188

2-[4-(5-Chloro-2-cyanophenyl)-5-methoxy-2-oxopyridin-1(2H)-yl]-N-[4-(5-thioxo-4,5-dihydro-1,2,4-oxadiazol-3-yl)phenyl]butanamide (racemate)

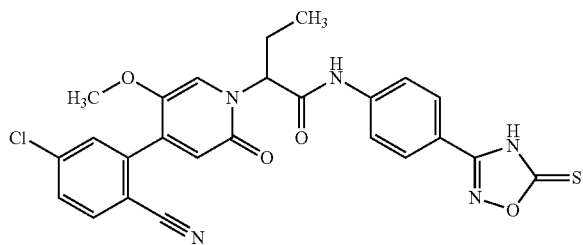 [SMILES: CCC(C(=O)Nc1ccc(-c2nsc(=O)[nH]2)cc1)n1cc(OC)c(-c2cc(Cl)ccc2C#N)cc1=O]

36 mg (0.10 mmol) of 2-[4-(5-chloro-2-cyanophenyl)-5-methoxy-2-oxopyridin-1(2H)-yl]butanoic acid (racemate) and 30 mg (0.16 mmol, 1.5 eq.) of 3-(4-aminophenyl)-1,2,4-oxadiazole-5(4H)-thione were reacted according to General Method 7. The crude product was purified by preparative HPLC (water/acetonitrile/0.1% formic acid gradient). Yield: 21 mg (38% of theory)

LC/MS [Method 8]: Rt=1.26 min; MS (ESIneg): m/z=520 (M−H)⁻,

¹H-NMR (400 MHz, DMSO-d₆): δ [ppm]=10.85 (s, 1H), 8.02-7.97 (m, 1H), 7.89-7.80 (m, 4H), 7.76-7.71 (m, 2H), 7.50 (s, 1H), 6.54 (s, 1H), 5.64 (dd, 1H), 3.69 (s, 3H), 2.26-2.11 (m, 2H), 0.91 (t, 3H).

Example 189

2-[4-(5-Chloro-2-cyanophenyl)-5-methoxy-2-oxopyridin-1(2H)-yl]-N-[4-(1,3-oxazol-2-yl)phenyl]butanamide (racemate)

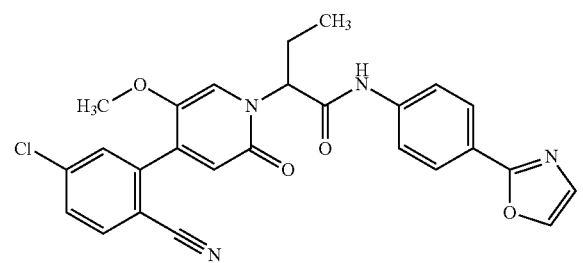 [SMILES: CCC(C(=O)Nc1ccc(-c2ncco2)cc1)n1cc(OC)c(-c2cc(Cl)ccc2C#N)cc1=O]

100 mg (0.29 mmol) of 2-[4-(5-chloro-2-cyanophenyl)-5-methoxy-2-oxopyridin-1(2H)-yl]butanoic acid (racemate) and 73 mg (0.43 mmol, 1.5 eq.) of 4-(1,3-oxazol-2-yl)aniline were reacted according to General Method 7. The crude product was purified by normal phase chromatography (mobile phase: dichloromethane/methanol 1-10% mixtures). Yield: 89 mg (63% of theory)

LC/MS [Method 1]: Rt=1.04 min; MS (ESIpos): m/z=489 (M+H)⁺,

¹H-NMR (400 MHz, DMSO-d₆): δ [ppm]=10.76 (s, 1H), 8.18 (d, 1H), 8.00 (d, 1H), 7.98-7.93 (m, 2H), 7.83-7.78 (m, 2H), 7.76-7.71 (m, 2H), 7.51 (s, 1H), 7.35 (d, 1H), 6.54 (s, 1H), 5.65 (dd, 1H), 3.69 (s, 3H), 2.26-2.10 (m, 2H), 0.91 (t, 3H).

Example 190

2-[4-(5-Chloro-2-cyanophenyl)-5-methoxy-2-oxopyridin-1(2H)-yl]-N-[4-(1,2,4-oxadiazol-3-yl)phenyl]butanamide (racemate)

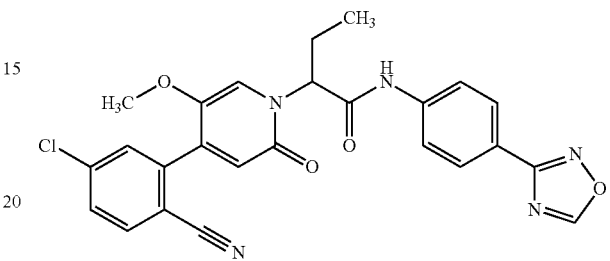

100 mg (0.29 mmol) of 2-[4-(5-chloro-2-cyanophenyl)-5-methoxy-2-oxopyridin-1(2H)-yl]butanoic acid (racemate) and 73 mg (0.43 mmol, 1.5 eq.) of 4-(1,2,4-oxadiazol-3-yl)aniline were reacted according to General Method 7. The crude product was purified by normal phase chromatography (mobile phase: dichloromethane/methanol 2-5% mixtures) and subsequently by preparative HPLC (water/acetonitrile/0.1% formic acid gradient). Yield: 81 mg (55% of theory)

LC/MS [Method 1]: Rt=0.95 min; MS (ESIpos): m/z=490 (M+H)⁺,

¹H-NMR (400 MHz, DMSO-d₆): δ [ppm]=10.85 (s, 1H), 9.30 (s, 1H), 8.03-7.97 (m, 3H), 7.89-7.84 (m, 2H), 7.76-7.71 (m, 2H), 7.51 (s, 1H), 6.55 (s, 1H), 5.65 (dd, 1H), 3.70 (s, 3H), 2.27-2.12 (m, 2H), 0.92 (t, 3H).

Example 191

2-[4-(5-Chloro-2-cyanophenyl)-5-methoxy-2-oxopyridin-1(2H)-yl]-N-[4-(5-methyl-1,3,4-oxadiazol-2-yl)phenyl]butanamide (racemate)

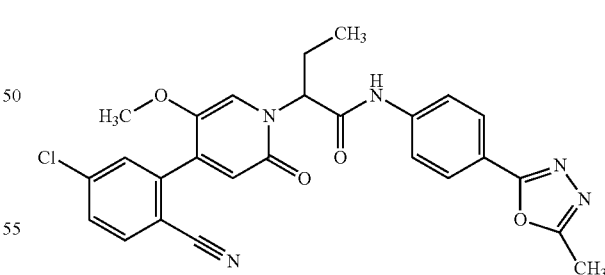

100 mg (0.29 mmol) of 2-[4-(5-chloro-2-cyanophenyl)-5-methoxy-2-oxopyridin-1(2H)-yl]butanoic acid (racemate) and 76 mg (0.43 mmol, 1.5 eq.) of 4-(5-methyl-1,3,4-oxadiazol-2-yl)aniline were reacted according to General Method 7. The crude product was purified by normal phase chromatography (mobile phase: dichloromethane/methanol 1-10% mixtures). Yield: 144 mg (99% of theory)

LC/MS [Method 1]: Rt=0.98 min; MS (ESIpos): m/z=504 (M+H)⁺,

¹H-NMR (400 MHz, DMSO-d₆): δ [ppm]=10.83 (s, 1H), 8.02-7.97 (m, 1H), 7.97-7.91 (m, 2H), 7.88-7.82 (m, 2H), 7.76-7.71 (m, 2H), 7.50 (s, 1H), 6.54 (s, 1H), 5.65 (dd, 1H), 3.69 (s, 3H), 2.56 (s, 3H), 2.27-2.11 (m, 2H), 0.92 (t, 3H).

Example 192

Methyl 3-{5-[4-({2-[4-(5-chloro-2-cyanophenyl)-5-methoxy-2-oxopyridin-1(2H)-yl]butanoyl}amino)phenyl]-4H-1,2,4-triazol-3-yl}-2,2,3,3-tetrafluoropropanoate (racemate)

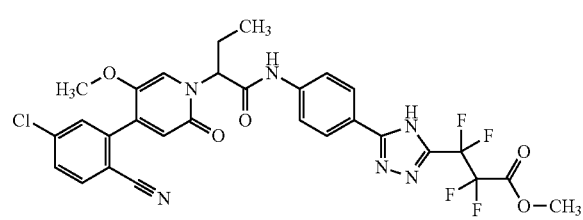 [SMILES: CCC(C(=O)Nc1ccc(-c2nnc(C(F)(F)C(F)(F)C(=O)OC)[nH]2)cc1)n1cc(OC)c(-c2cc(Cl)ccc2C#N)cc1=O]

87 mg (0.25 mmol) of 2-[4-(5-chloro-2-cyanophenyl)-5-methoxy-2-oxopyridin-1(2H)-yl]butanoic acid (racemate) and 88 mg (0.28 mmol, 1.1 eq.) of methyl 3-[5-(4-aminophenyl)-4H-1,2,4-triazol-3-yl]-2,2,3,3-tetrafluoropropanoate were reacted according to General Method 1. The crude product was purified by preparative HPLC (Reprosil C18, water/acetonitrile gradient). Yield: 96 mg (purity 94%, 56% of theory)

LC/MS [Method 1]: R$_t$=1.08 min; MS (ESIpos): m/z=647 (M+H)⁺.

Example 193

3-{5-[4-({2-[4-(5-Chloro-2-cyanophenyl)-5-methoxy-2-oxopyridin-1 (2H)-yl]butanoyl}amino)phenyl]-4H-1,2,4-triazol-3-yl}-2,2,3,3-tetrafluoropropanoic acid (racemate)

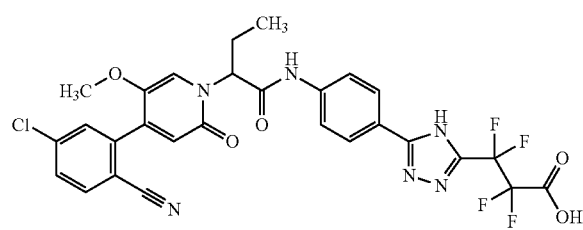 [SMILES: CCC(C(=O)Nc1ccc(-c2nnc(C(F)(F)C(F)(F)C(=O)O)[nH]2)cc1)n1cc(OC)c(-c2cc(Cl)ccc2C#N)cc1=O]

96 mg (purity 94%, 0.14 mmol) of methyl 3-{5-[4-({2-[4-(5-chloro-2-cyanophenyl)-5-methoxy-2-oxopyridin-1 (2H)-yl]butanoyl}amino)phenyl]-4H-1,2,4-triazol-3-yl}-2,2,3,3-tetrafluoropropanoate (racemate) were hydrolysed with lithium hydroxide according to General Method 3. The crude product was purified by preparative HPLC (Reprosil C18, water/acetonitrile gradient). Yield: 28 mg (32% of theory)

LC/MS [Method 1]: R$_t$=0.86 min; MS (ESIpos): m/z=633 (M+H)⁺,

¹H-NMR (400 MHz, DMSO-d₆): δ [ppm]=15.01 (br. s, 1H), 10.77 (s, 1H), 8.03-7.94 (m, 3H), 7.82 (d, 2H), 7.77-7.71 (m, 2H), 7.51 (s, 1H), 6.55 (s, 1H), 5.65 (dd, 1H), 3.70 (s, 3H), 2.31-2.10 (m, 2H), 0.92 (t, 3H).

Example 194

2-[4-(5-Chloro-2-cyanophenyl)-5-methoxy-2-oxopyridin-1(2H)-yl]-N-(4-fluoro-3-oxo-2,3-dihydro-1H-indazol-6-yl)butanamide (racemate)

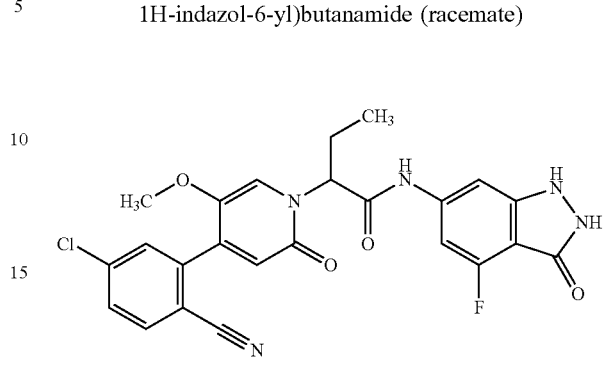

100 mg (0.28 mmol) of 2-[4-(5-chloro-2-cyanophenyl)-5-methoxy-2-oxopyridin-1(2H)-yl]butanoic acid (racemate) and 51 mg (0.31 mmol, 1.1 eq.) of 6-amino-4-fluoro-1,2-dihydro-3H-indazol-3-one were reacted according to General Method 6. The crude product was purified by preparative HPLC (Reprosil C18, water/acetonitrile gradient). Yield: 6 mg (4% of theory)

LC/MS [Method 1]: R$_t$=0.86 min; MS (ESIpos): m/z=496 (M+H)⁺,

¹H-NMR (400 MHz, DMSO-d₆): δ [ppm]=11.63 (br. s, 1H), 10.77 (br. s, 1H), 10.66 (s, 1H), 8.00 (d, 1H), 7.78-7.69 (m, 2H), 7.60 (s, 1H), 7.51 (s, 1H), 6.87 (d, 1H), 6.56 (s, 1H), 5.62 (dd, 1H), 3.70 (s, 3H), 2.25-2.08 (m, 2H), 0.91 (t, 3H).

Example 195

2-[4-(5-Chloro-2-cyanophenyl)-5-methoxy-2-oxopyridin-1(2H)-yl]-N-[3-(trifluoromethyl)-1H-indazol-6-yl]butanamide (racemate)

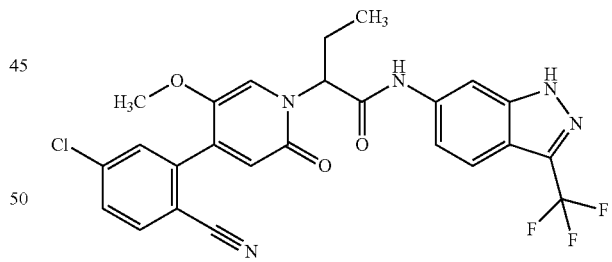

82 mg (0.23 mmol) of 2-[4-(5-chloro-2-cyanophenyl)-5-methoxy-2-oxopyridin-1(2H)-yl]butanoic acid (racemate) and 51 mg (0.25 mmol, 1.1 eq.) of 3-(trifluoromethyl)-1H-indazole-6-amine were reacted according to General Method 6. The crude product was purified by preparative HPLC (Reprosil C18, water/acetonitrile gradient). Yield: 30 mg (25% of theory)

LC/MS [Method 1]: R$_t$=1.08 min; MS (ESIpos): m/z=530 (M+H)⁺,

¹H-NMR (400 MHz, DMSO-d₆): δ [ppm]=13.83 (s, 1H), 10.81 (s, 1H), 8.28 (s, 1H), 8.00 (d, 1H), 7.79-7.71 (m, 3H), 7.53 (s, 1H), 7.39 (dd, 1H), 6.56 (s, 1H), 5.67 (dd, 1H), 3.70 (s, 3H), 2.27-2.11 (m, 2H), 0.92 (t, 3H).

Example 196

2-[4-(5-Chloro-2-cyanophenyl)-5-methoxy-2-oxopyridin-1(2H)-yl]-N-(3-chloro-1H-indazol-5-yl)butanamide (racemate)

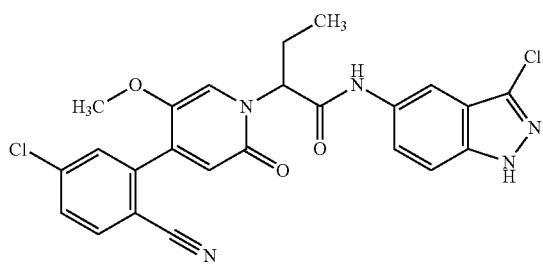 [SMILES: CCC(C(=O)Nc1ccc2[nH]nc(Cl)c2c1)n1cc(OC)c(-c2cc(Cl)ccc2C#N)cc1=O]

In two batches, a total of 242 mg (0.68 mmol) of 2-[4-(5-chloro-2-cyanophenyl)-5-methoxy-2-oxopyridin-1(2H)-yl]butanoic acid (racemate) and 404 mg (purity 31%, 0.75 mmol, 1.1 eq.) of 3-chloro-1H-indazole-5-amine were reacted according to General Method 1. The combined crude products were purified by repeated preparative HPLC (Reprosil C18, water/acetonitrile gradient). Yield: 18 mg (purity 94%, 13% of theory) of the title compound Example 196 and 65 mg (55% of theory) of the title compound Example 197, which was isolated as a by-product due to the starting material 3-chloro-1H-indazole-5-amine employed being contaminated with 1H-indazole-5-amine.

LC/MS [Method 1]: $R_t$=1.01 min; MS (ESIpos): m/z=496 (M+H)$^+$,
$^1$H-NMR (400 MHz, DMSO-d$_6$): δ [ppm]=13.25 (s, 1H), 10.64 (s, 1H), 8.16 (s, 1H), 8.00 (d, 1H), 7.77-7.70 (m, 2H), 7.59-7.49 (m, 3H), 6.55 (s, 1H), 5.66 (dd, 1H), 3.70 (s, 3H), 2.28-2.09 (m, 2H), 0.92 (t, 3H).

Example 197

2-[4-(5-Chloro-2-cyanophenyl)-5-methoxy-2-oxopyridin-1(2H)-yl]-N-(1H-indazol-5-yl)butanamide (racemate)

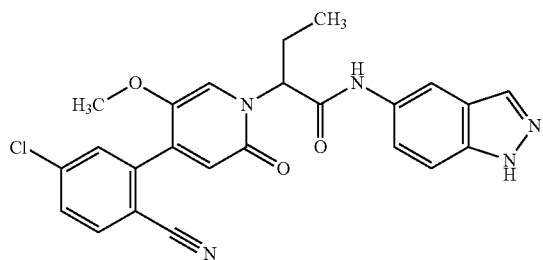 [SMILES: CCC(C(=O)Nc1ccc2[nH]ncc2c1)n1cc(OC)c(-c2cc(Cl)ccc2C#N)cc1=O]

The title compound Example 197 was isolated as a by-product in the preparation of the title compound Example 196. Yield: 65 mg (55% of theory)

LC/MS [Method 1]: $R_t$=0.90 min; MS (ESIpos): m/z=462 (M+H)$^+$,
$^1$H-NMR (400 MHz, DMSO-d$_6$): δ [ppm]=13.00 (s, 1H), 10.50 (s, 1H), 8.15 (s, 1H), 8.05-7.96 (m, 2H), 7.77-7.70 (m, 2H), 7.55 (s, 1H), 7.73-7.45 (m, 2H), 6.54 (s, 1H), 5.68 (dd, 1H), 3.69 (s, 3H), 2.26-2.08 (m, 2H), 0.92 (t, 3H).

Example 198

4-({2-[4-(5-Chloro-2-cyanophenyl)-5-methoxy-2-oxopyridin-1(2H)-yl]-3-(1,1-dioxidotetrahydro-2H-thiopyran-4-yl)propanoyl}amino)benzoic acid (racemate)

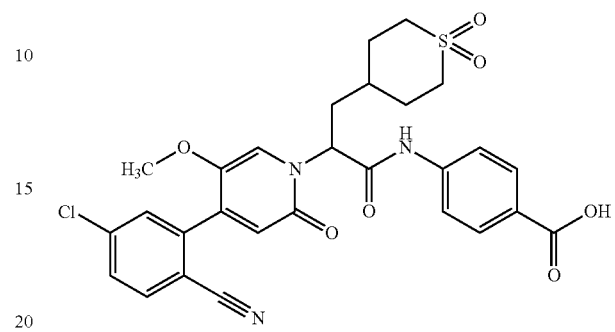

329 mg (537 µmol) of ethyl 4-({2-[4-(5-chloro-2-cyanophenyl)-5-methoxy-2-oxopyridin-1(2H)-yl]-dioxidotetrahydro-2H-thiopyran-4-yl)propanoyl}amino)benzoate (racemate) in 19.4 ml of ethanol/water (2.6/1) were reacted with 893 mg (2.74 mmol) of caesium carbonate according to General Method 6C, giving the title compound after preparative HPLC [column: Chromatorex C18, 10 µm, 125 mm×30 mm, mobile phase: acetonitrile/0.05% formic acid gradient (0 to 3 min 10% acetonitrile to 35 min 90% acetonitrile and a further 3 min 90% acetonitrile)]. Yield: 136 mg (43% of theory)

LC/MS [Method 1]: $R_t$=0.89 min; MS (ESIpos): m/z=584 (M+H)$^+$
$^1$H-NMR (400 MHz, DMSO-d$_6$): δ [ppm]=12.8 (br. s, 1H), 10.8 (s, 1H), 8.01 (d, 1H), 7.92 (d, 2H), 7.77-7.71 (m, 4H), 7.51 (s, 1H), 6.56 (s, 1H), 5.85 (dd, 1H), 3.71 (s, 3H), 3.14-2.96 (m, 4H), 2.37-2.27 (m, 1H), 2.15-2.03 (m, 3H), 1.81-1.65 (m, 2H), 1.55-1.43 (m, 1H).

Example 199

4-[(2-{4-[5-Chloro-2-(difluoromethoxy)phenyl]-5-methoxy-2-oxopyridin-1(2H)-yl}-3-[(2,9-tetrahydro-2H-pyran-2-yl]propanoyl)amino]benzoic acid (mixture of enantiomerically pure diastereomers 1 and 2)

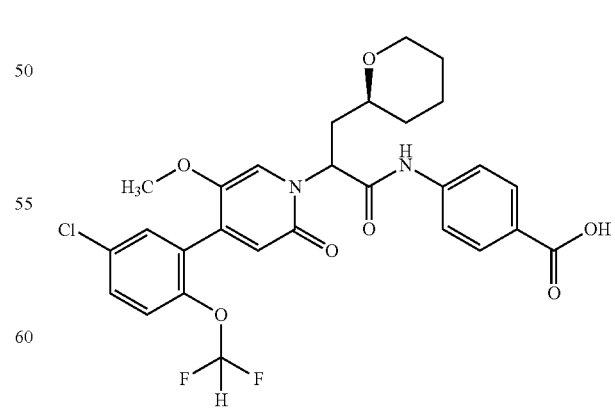

315 mg (0.49 mmol) of ethyl 4-[(2-{4-[5-chloro-2-(difluoromethoxy)phenyl]-5-methoxy-2-oxopyridin-1(2H)-yl}-3-[(2S)-tetrahydro-2H-pyran-2-yl]propanoyl)amino]benzoate (mixture of enantiomerically pure diastereomers 1 and 2)

in 6.5 ml of ethanol/water (4/1) were hydrolyzed with 322 mg (0.99 mmol, 2.0 eq.) of caesium carbonate according to General Method 4. The crude product was purified by preparative HPLC (Reprosil C18, water/acetonitrile gradient). Yield: 111 mg (39% of theory)

LC/MS [Method 1]: $R_t$=1.05 min; MS (ESIpos): m/z=577 (M+H)$^+$, $^1$H-NMR (400 MHz, DMSO-d$_6$): δ [ppm]=12.76 (s, 1H), 10.74/10.65 (2×s, 1H), 7.94-7.86 (m, 2H), 7.81-7.72 (m, 2H), 7.59/7.57 (2×t, 1H), 7.50/7.48 (2×d, 1H), 7.42/7.38 (2×s, 1H), 7.33-7.27 (m, 1H), 7.13/7.12 (2×t, 1H), 6.38/6.37 (2×s, 1H), 5.80/5.72 (t/dd, 1H), 3.90-3.78 (m, 1H), 3.63/3.62 (2×s, 3H), 3.29-3.03 (m, 2H), 2.39-2.09 (m, 2H), 1.79-1.70 (m, 1H), 1.67-1.54 (m, 1H), 1.48-1.18 (m, 4H).

Example 200

4-[(2-{4-[5-Chloro-2-(difluoromethoxy)phenyl]-5-methoxy-2-oxopyridin-1(2H)-yl}-3-[(2,9-tetrahydro-2H-pyran-2-yl]propanoyl)amino]benzoic acid (enantiomerically pure diastereomer 1)

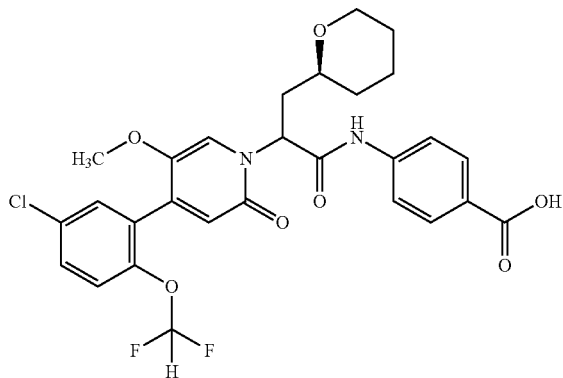 [SMILES: COc1cn(C(C[C@@H]2CCCCO2)C(=O)Nc2ccc(C(=O)O)cc2)c(=O)cc1-c1cc(Cl)ccc1OC(F)F]

Diastereomer separation of the compound from Example 199 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 201

4-[(2-{4-[5-Chloro-2-(difluoromethoxy)phenyl]-5-methoxy-2-oxopyridin-1(2H)-yl}-3-[(2,9-tetrahydro-2H-pyran-2-yl]propanoyl)amino]benzoic acid (enantiomerically pure diastereomer 2)

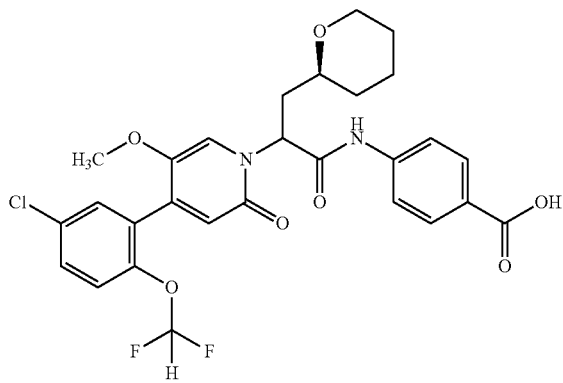 [SMILES: COc1cn(C(C[C@@H]2CCCCO2)C(=O)Nc2ccc(C(=O)O)cc2)c(=O)cc1-c1cc(Cl)ccc1OC(F)F]

Diastereomer separation of the compound from Example 199 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 202

4-({2-[5-Chloro-4-(5-chloro-2-cyanophenyl)-2-oxopyridin-1(2H)-yl]-3-[(2S)-tetrahydro-2H-pyran-2-yl]propanoyl}amino)benzoic acid (mixture of enantiomerically pure diastereomers 1 and 2)

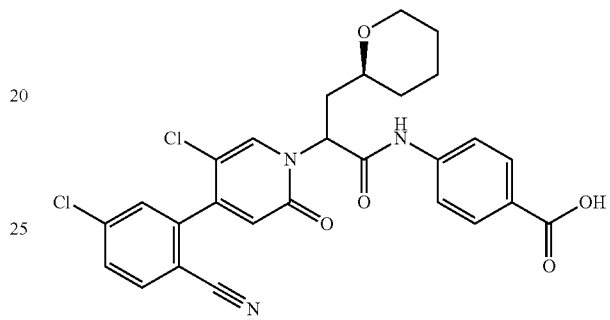

364 mg (0.61 mmol) of tert-butyl 4-({2-[5-chloro-4-(5-chloro-2-cyanophenyl)-2-oxopyridin-1(2H)-yl]-3-[(2S)-tetrahydro-2H-pyran-2-yl]propanoyl}amino)benzoate (mixture of enantiomerically pure diastereomers 1 and 2) were hydrolysed with TFA according to General Method 2. The crude product was purified by preparative flash chromatography (silica gel 50, eluent: dichloromethane/methanol gradient). Yield: 264 mg (76% of theory)

LC/MS [Method 1]: $R_t$=1.05 min; MS (ESIpos): m/z=540 (M+H)$^+$, $^1$H-NMR (400 MHz, DMSO-d$_6$): δ [ppm]=12.75 (s, 1H), 10.78 (s, 1H), 8.20 (d, 1H), 8.06 (dd, 1H), 7.94-7.87 (m, 2H), 7.84-7.71 (m, 4H), 6.65 (s, 1H), 5.81 (br. s, 1H), 3.89-3.77 (m, 1H), 3.26-3.01 (m, 2H), 2.47-2.15 (m, 2H), 1.80-1.70 (m, 1H), 1.65-1.55 (m, 1H), 1.47-1.21 (m, 4H).

Example 203

4-({2-[5-Chloro-4-(5-chloro-2-cyanophenyl)-2-oxopyridin-1(2H)-yl]-3-[(2S)-tetrahydro-2H-pyran-2-yl]propanoyl}amino)benzoic acid (enantiomerically pure diastereomer 1)

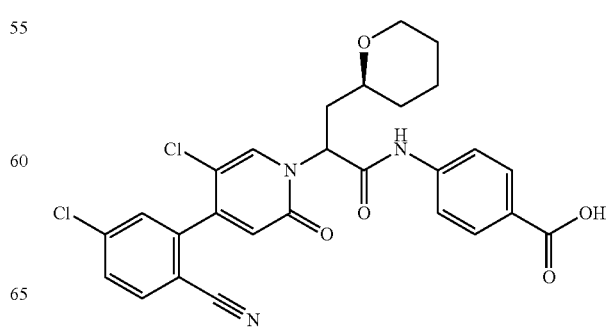

Example 204

4-({2-[5-Chloro-4-(5-chloro-2-cyanophenyl)-2-oxopyridin-1(2H)-yl]-3-[(2S)-tetrahydro-2H-pyran-2-yl]propanoyl}amino)benzoic acid (enantiomerically pure diastereomer 2)

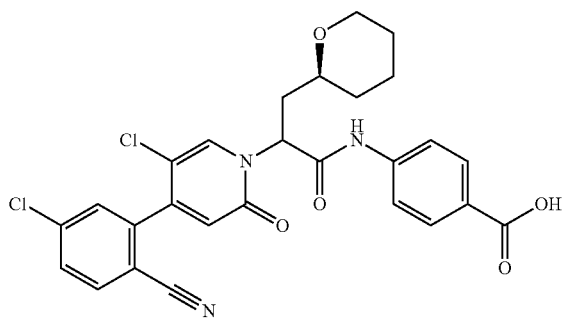 [SMILES: N#Cc1ccc(Cl)cc1-c1cc(=O)n(C(C[C@@H]2CCCCO2)C(=O)Nc2ccc(C(=O)O)cc2)cc1Cl]

Diastereomer separation of the compound from Example 202 to give the title compound can be carried out by SFC on a chiral phase (for example Daicel Chiralpak AD-H 5 µm, Daicel Chiralpak AZ-H 5 µm, Daicel Chiralpak IF 5 µm, Daicel Chiralpak IC 5 µm or Daicel Chiralpak OJ-H 5 µm) with carbon dioxide/ethanol or carbon dioxide/2-propanol mixtures as eluents.

Example 205

4-({2-[5-Chloro-4-(5-chloro-2-cyanophenyl)-2-oxopyridin-1(2H)-yl]-4-methoxybutanoyl}amino)-benzoic acid (racemate)

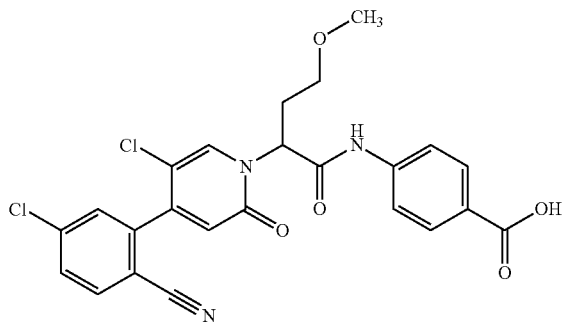 [SMILES: COCCC(C(=O)Nc1ccc(C(=O)O)cc1)n1cc(Cl)c(-c2cc(Cl)ccc2C#N)cc1=O]

438 mg (0.76 mmol) of tert-butyl 4-({2-[5-chloro-4-(5-chloro-2-cyanophenyl)-2-oxopyridin-1(2H)-yl]-4-methoxybutanoyl}amino)benzoate (racemate) were hydrolysed with TFA according to General Method 2. The crude product was purified by preparative HPLC (Reprosil C18, water/acetonitrile gradient). Yield: 123 mg (32% of theory) LC/MS [Method 1]: $R_t$=0.96 min; MS (ESIpos): m/z=500 (M+H)$^+$, $^1$H-NMR (400 MHz, DMSO-d$_6$): δ [ppm]=12.77 (br. s, 1H), 10.82 (s, 1H), 8.22 (s, 1H), 8.07 (d, 1H), 7.91 (d, 2H), 7.84-7.77 (m, 2H), 7.75 (d, 2H), 6.67 (s, 1H), 5.77 (br. s, 1H), 3.45-3.38 (m, 1H), 3.30-3.22 (m, 1H), 3.19 (s, 3H), 2.46-2.39 (m, 2H).

Example 206

4-({2-[5-Chloro-4-(5-chloro-2-cyanophenyl)-2-oxopyridin-1(2H)-yl]-4-methoxybutanoyl}amino)-benzoic acid (enantiomer 1)

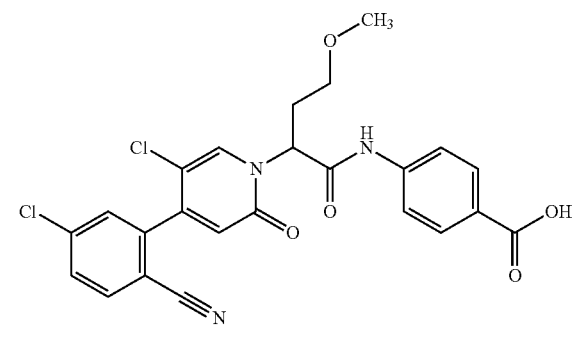 [SMILES: COCCC(C(=O)Nc1ccc(C(=O)O)cc1)n1cc(Cl)c(-c2cc(Cl)ccc2C#N)cc1=O]

Enantiomer separation of the compound from Example 205 to give the title compound can be carried out by SFC on a chiral phase (for example Daicel Chiralpak AD-H 5 µm, Daicel Chiralpak AZ-H 5 µm, Daicel Chiralpak IF 5 µm, Daicel Chiralpak IC 5 µm or Daicel Chiralpak OJ-H 5 µm) with carbon dioxide/ethanol or carbon dioxide/2-propanol mixtures as eluents.

Example 207

4-({2-[5-Chloro-4-(5-chloro-2-cyanophenyl)-2-oxopyridin-1(2H)-yl]-4-methoxybutanoyl}amino)-benzoic acid (enantiomer 2)

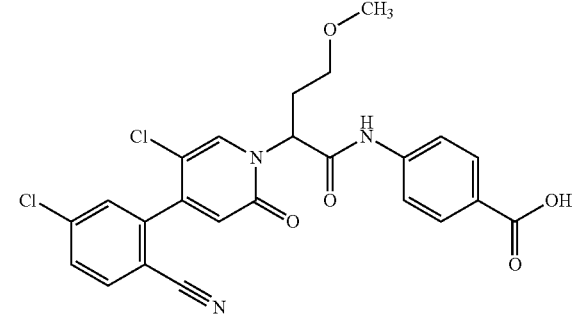 [SMILES: COCCC(C(=O)Nc1ccc(C(=O)O)cc1)n1cc(Cl)c(-c2cc(Cl)ccc2C#N)cc1=O]

Enantiomer separation of the compound from Example 205 to give the title compound can be carried out by SFC on a chiral phase (for example Daicel Chiralpak AD-H 5 µm, Daicel Chiralpak AZ-H 5 µm, Daicel Chiralpak IF 5 µm, Daicel Chiralpak IC 5 µm or Daicel Chiralpak OJ-H 5 µm) with carbon dioxide/ethanol or carbon dioxide/2-propanol mixtures as eluents.

Example 208

4-({2-[5-Chloro-4-(5-chloro-2-cyanophenyl)-2-oxopyridin-1(2H)-yl]-4-(trifluoromethoxy)butanoyl}amino)benzoic acid (enantiomer 1)

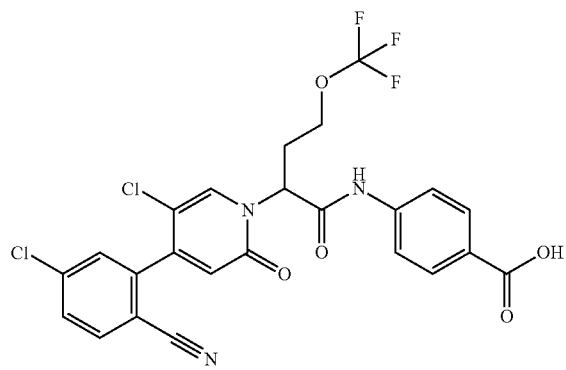 [SMILES: N#Cc1ccc(Cl)cc1-c1cc(=O)n(C(CCOC(F)(F)F)C(=O)Nc2ccc(C(=O)O)cc2)cc1Cl]

Enantiomer separation of the compound from Example 171 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 209

4-({2-[5-Chloro-4-(5-chloro-2-cyanophenyl)-2-oxopyridin-1(2H)-yl]-4-(trifluoromethoxy)butanoyl}amino)benzoic acid (enantiomer 2)

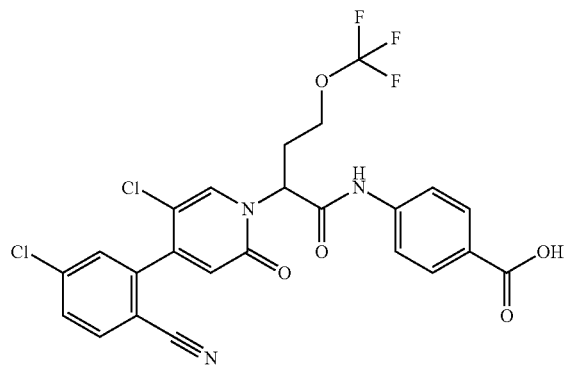 [SMILES: N#Cc1ccc(Cl)cc1-c1cc(=O)n(C(CCOC(F)(F)F)C(=O)Nc2ccc(C(=O)O)cc2)cc1Cl]

Enantiomer separation of the compound from Example 171 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 210

4-[(2-{4-[5-Chloro-2-(difluoromethoxy)phenyl]-5-methoxy-2-oxopyridin-1(2H)-yl}-4-methoxybutanoyl)amino]benzoic acid (enantiomer 1)

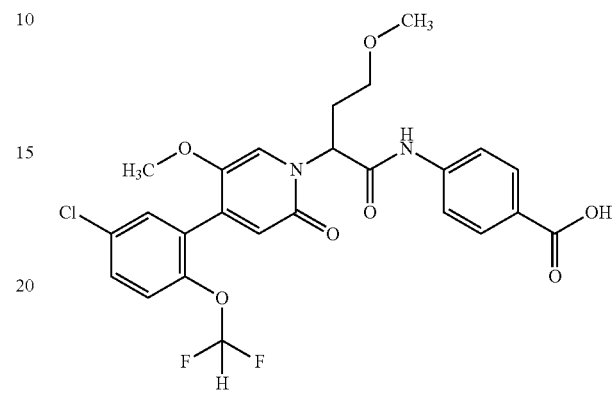

Enantiomer separation of the compound from Example 173 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 211

4-[(2-{4-[5-Chloro-2-(difluoromethoxy)phenyl]-5-methoxy-2-oxopyridin-1(2H)-yl}-4-methoxybutanoyl)amino]benzoic acid (enantiomer 2)

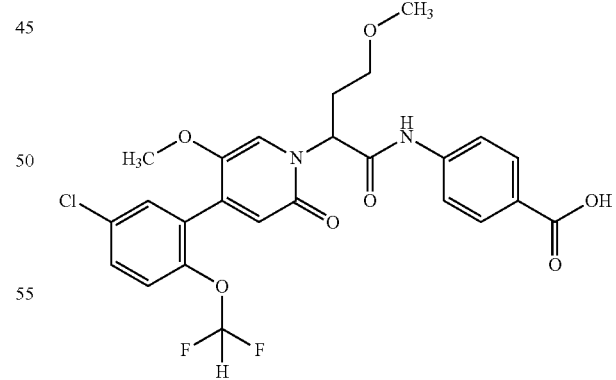

Enantiomer separation of the compound from Example 173 to the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 212

4-{[2-{4-[5-Chloro-2-(difluoromethoxy)phenyl]-5-methoxy-2-oxopyridin-1(2H)-yl}-4-(trifluoromethoxy)butanoyl]amino}benzoic acid (enantiomer 1)

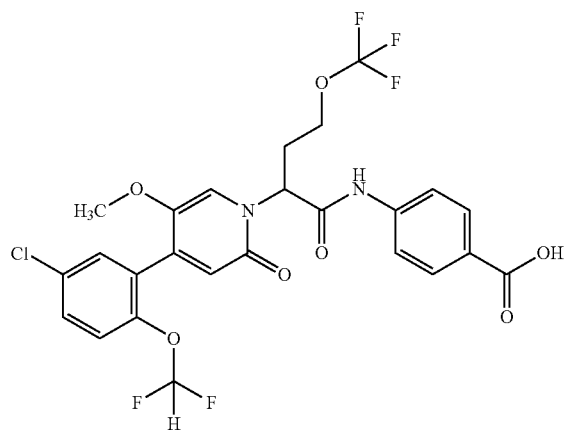 [SMILES: COc1cn(C(CCOC(F)(F)F)C(=O)Nc2ccc(C(=O)O)cc2)c(=O)cc1-c1cc(Cl)ccc1OC(F)F]

Enantiomer separation of the compound from Example 176 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 213

4-{[2-{4-[5-Chloro-2-(difluoromethoxy)phenyl]-5-methoxy-2-oxopyridin-1(2H)-yl}-4-(trifluoromethoxy)butanoyl]amino}benzoic acid (enantiomer 2)

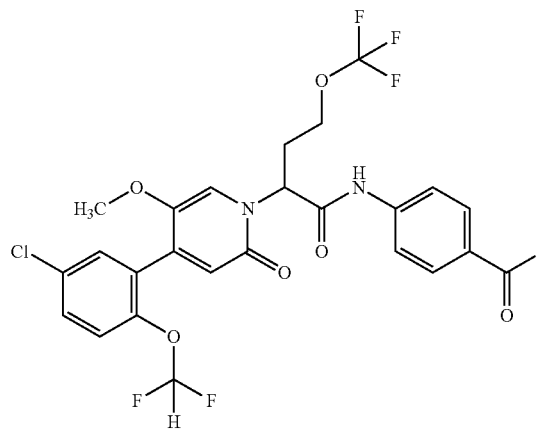

Enantiomer separation of the compound from Example 176 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 214

4-[(2-{4-[5-Chloro-2-(difluoromethoxy)phenyl]-5-methoxy-2-oxopyridin-1(2H)-yl}-3-[(2R)-tetrahydro-2H-pyran-2-yl]propanoyl)amino]benzoic acid (enantiomerically pure diastereomer 1)

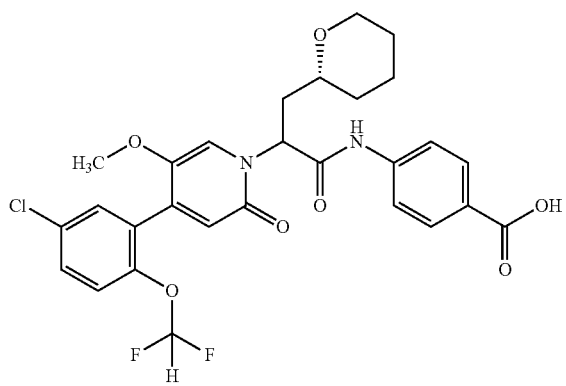 [SMILES: COc1cn(C(C[C@H]2CCCCO2)C(=O)Nc2ccc(C(=O)O)cc2)c(=O)cc1-c1cc(Cl)ccc1OC(F)F]

Enantiomer separation of the compound from Example 177 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 μm or Daicel Chiralpak OJ-H 5 μm) with carbon dioxide/ethanol or carbon dioxide/2-propanol mixtures as eluents.

Example 215

4-[(2-{4-[5-Chloro-2-(difluoromethoxy)phenyl]-5-methoxy-2-oxopyridin-1(2H)-yl}-3-[(2R)-tetrahydro-2H-pyran-2-yl]propanoyl)amino]benzoic acid (enantiomerically pure diastereomer 2)

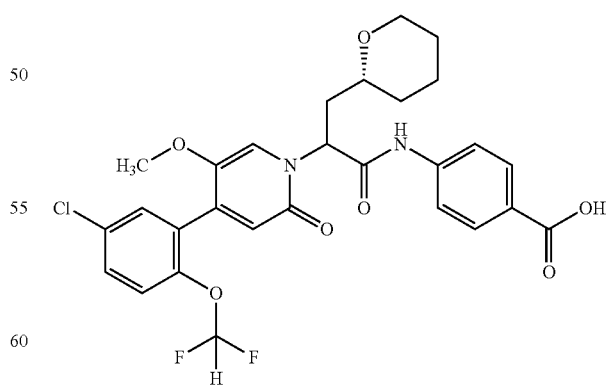

Enantiomer separation of the compound from Example 177 to give the title compound can be carried out by SFC on a chiral phase (for example Daicel Chiralpak AD-H 5 μm, Daicel Chiralpak AZ-H 5 μm, Daicel Chiralpak IF 5 μm, Daicel Chiralpak IC 5 µm or Daicel Chiralpak OJ-H 5 µm) with carbon dioxide/ethanol or carbon dioxide/2-propanol mixtures as eluents.

B) ASSESSMENT OF PHYSIOLOGICAL EFFICACY

The suitability of the compounds according to the invention for treating thromboembolic disorders can be demonstrated in the following assay systems:
a) Test Descriptions (In Vitro)
a.1) Measurement of FXIa Inhibition To determine the factor XIa inhibition of the substances according to the invention, a biochemical test system is used which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions are placed into the wells of white microtitre plates from Greiner (384 wells). 20 µl of assay buffer (50 mM of Tris/HCl pH 7.4; 100 mM of sodium chloride solution; 5 mM of calcium chloride solution; 0.1% of bovine serum albumin) and 20 µl of factor XIa from Kordia (0.45 nM in assay buffer) are then added successively. After 15 min of incubation, the enzyme reaction is started by addition of 20 µl of the factor XIa substrate Boc-Glu(OBzl)-Ala-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and the $IC_{50}$ values are calculated from the concentration/activity relationships. Activity data from this test are listed in Table A below:

TABLE A

| Example No. | $IC_{50}$ [nM] | Example No. | $IC_{50}$ [nM] |
|---|---|---|---|
| 1 | 53 | 2 | 260 |
| 3 | 430 | 4 | 240 |
| 5 | 150 | 6 | 440 |
| 7 | 82 | 8 | 110 |
| 9 | 170 | 10 | 730 |
| 11 | 750 | 12 | 500 |
| 13 | 600 | 14 | 330 |
| 15 | 430 | 16 | 910 |
| 17 | 960 | 18 | 840 |
| 19 | 59 | 20 | 27000 |
| 21 | 26 | 22 | 1700 |
| 23 | 150 | 24 | 240 |
| 25 | 220 | 26 | 7.6 |
| 27 | 42 | 28 | 49 |
| 29 | 36 | 30 | 50 |
| 31 | 24000 | 32 | 65 |
| 33 | 33 | 34 | 74 |
| 35 | 27 | 36 | 17000 |
| 37 | 14 | 38 | 230 |
| 39 | 1100 | 40 | 35 |
| 41 | 54 | 42 | 14 |
| 43 | 40 | 44 | 140 |
| 45 | 13 | 46 | 3300 |
| 47 | 9.8 | 48 | 42 |

TABLE A-continued

| Example No. | $IC_{50}$ [nM] | Example No. | $IC_{50}$ [nM] |
|---|---|---|---|
| 49 | 43 | 50 | 470 |
| 51 | 500 | 52 | 700 |
| 53 | 630 | 54 | 3500 |
| 55 | 5.9 | 56 | 3400 |
| 57 | 2.0 | 58 | 3.9 |
| 59 | 950 | 60 | 1.6 |
| 61 | 4.8 | 62 | 290 |
| 63 | 9.1 | 64 | 4000 |
| 65 | 4.7 | 66 | 4.7 |
| 67 | 1700 | 68 | 1.8 |
| 69 | 3.5 | 70 | 24 |
| 71 | 32 | 72 | 34 |
| 73 | 6.2 | 74 | 17 |
| 75 | 4.3 | 76 | 1.6 |
| 77 | 2000 | 78 | 1.3 |
| 79 | 3.2 | 80 | 4000 |
| 81 | 0.7 | 82 | 18 |
| 83 | 5.8 | 84 | 4.4 |
| 85 | 1900 | 86 | 2.4 |
| 87 | 2.8 | 88 | 1.3 |
| 89 | 75 | 90 | 8.5 |
| 91 | 470 | 92 | 3.2 |
| 93 | 4.0 | 94 | 5.5 |
| 95 | 520 | 96 | 2.4 |
| 97 | 4.2 | 98 | 890 |
| 99 | 920 | 100 | 1.5 |
| 101 | 1.3 | 102 | 660 |
| 103 | 0.5 | 104 | 7.3 |
| 105 | 1.4 | 106 | 2.3 |
| 107 | 5.3 | 108 | 6.4 |
| 109 | 31 | 110 | 9.2 |
| 111 | 34 | 112 | 32 |
| 113 | 4.3 | 114 | 600 |
| 115 | 3.0 | 116 | 2.3 |
| 117 | 1.9 | 118 | 53 |
| 119 | 28 | 120 | 46 |
| 121 | 17 | 122 | 52 |
| 123 | 63 | 124 | 170 |
| 125 | 3.6 | 126 | 7.1 |
| 127 | 10 | 128 | 11 |
| 129 | 24 | 130 | 50 |
| 131 | 81 | 132 | 2.0 |
| 133 | 130 | 134 | 0.3 |
| 135 | 2.7 | 136 | 1.6 |
| 137 | 1200 | 138 | 1.0 |
| 139 | 2.5 | 140 | 3.8 |
| 141 | 190 | 142 | 3.9 |
| 143 | 0.6 | 144 | 98 |
| 145 | 17 | 146 | 130 |
| 147 | 14 | 148 | 59 |
| 149 | 5.0 | 150 | 4.7 |
| 151 | 14 | 152 | 5.4 |
| 153 | 1100 | 154 | 2.4 |
| 155 | 2.0 | 156 | 600 |
| 157 | 0.8 | 158 | 22 |
| 159 | 18 | 160 | 120 |
| 161 | 2000 | 162 | 1100 |
| 163 | 6.0 | 164 | 2.2 |
| 165 | 11 | 166 | 6.8 |
| 167 | 28 | 168 | 3.9 |
| 169 | 160 | 170 | 49 |
| 171 | 5.2 | 172 | 21 |
| 173 | 2.6 | 174 | 19 |
| 175 | 15 | 176 | 4.5 |
| 177 | 3.4 | 178 | 3.0 |
| 179 | 2.3 | 180 | 13 |
| 181 | 11 | 182 | 31 |
| 183 | 14 | 184 | 10 |
| 185 | 5.5 | 186 | 5.3 |
| 187 | 2.8 | 188 | 4.5 |
| 189 | 66 | 190 | 80 |
| 191 | 49 | 192 | 3.0 |
| 193 | 2.6 | 194 | 6.8 |
| 195 | 150 | 196 | 110 |
| 197 | 17 | 198 | 12 |
| 199 | 1.3 | 202 | 2.9 |
| 205 | 4.0 | | | a.2) Determination of the Selectivity

To demonstrate the selectivity of the substances with respect to FXIa inhibition, the test substances are examined for their inhibition of other human serin proteases, such as factor Xa, trypsin and plasmin To determine the enzymatic activity of factor Xa (1.3 nmol/l from Kordia), trypsin (83 mU/ml from Sigma) and plasmin (0.1 µg/ml from Kordia), these enzymes are dissolved (50 mmol/l of Tris buffer [C,C,C-tris(hydroxymethyl)aminomethane], 100 mmol/l of sodium chloride, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 µmol/l of Boc-Ile-Glu-Gly-Arg-AMC from Bachem for factor Xa and trypsin, 50 µmol/l of MeOSuc-Ala-Phe-Lys-AMC from Bachem for plasmin) After an incubation time of 30 min at 22° C., fluorescence is measured (excitation: 360 nm, emission: 460 nm). The measured emissions of the test batches with test substance are compared to the control batches without test substance (only dimethyl sulphoxide instead of test substance in dimethyl sulphoxide), and the $IC_{50}$ values are calculated from the concentration/activity relationships.

a.3) Thrombin Generation Assay (Thrombogram)

The effect of the test substances on the thrombogram (thrombin generation assay according to Hemker) is determined in vitro in human plasma (Octaplas® from Octapharma).

In the thrombin generation assay according to Hemker, the activity of thrombin in coagulating plasma is determined by measuring the fluorescent cleavage products of the substrate I-1140 (Z-Gly-Gly-Arg-AMC, Bachem). The reactions are carried out in the presence of varying concentrations of test substance or the corresponding solvent. To start the reaction, reagents from Thrombinoscope (30 pM or 0.1 pM recombinant tissue factor, 24 µM phospholipids in HEPES) are used. Moreover, a thrombin calibrator from Thrombinoscope is used whose amidolytic activity is required for calculating the thrombin activity in a sample containing an unknown amount of thrombin. The test is carried out according to the specifications of the manufacturer (Thrombinoscope BV): 4 µl of test substance or of the solvent, 76 µl of plasma and 20 µl of PPP reagent or thrombin calibrator are incubated at 37° C. for 5 min. After addition of 20 µl of 2.5 mM thrombin substrate in 20 mM HEPES, 60 mg/ml of BSA, 102 mM of calcium chloride, the thrombin generation is measured every 20 s over a period of 120 min. Measurement is carried out using a fluorometer (Fluoroskan Ascent) from Thermo Electron fitted with a 390/460 nM filter pair and a dispenser.

Using the Thrombinoscope software, the thrombogram is calculated and represented graphically. The following parameters are calculated: lag time, time to peak, peak, ETP (endogenous thrombin potential) and start tail.

a.4) Determination of the Anticoagulatory Activity

The anticoagulatory activity of the test substances is determined in vitro in human plasma and rat plasma. To this end, blood is drawn off in a mixing ratio of sodium citrate/blood of 1/9 using a 0.11 molar sodium citrate solution as receiver. Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (Cephalin, Kaolin) at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions are placed into the wells of white microtitre plates from Greiner (384 wells). 20 µl of assay buffer (50 mM Tris/HCl pH 7.4; 100 mM sodium chloride solution; 5 mM of calcium chloride solution; 0.1% of bovine serum albumin) and 20 µl of plasma kallikrein from Kordia (0.6 nM in assay buffer) are then added successively. After 15 min of incubation, the enzyme reaction is started by addition of 20 µl of the substrate H-Pro-Phe-Arg-AMC dissolved in assay buffer (10 µl in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and the $IC_{50}$ values are calculated from the concentration/activity relationships.

TABLE B

| Example No. | $IC_{50}$ [nM] | Example No. | $IC_{50}$ [nM] |
|---|---|---|---|
| 1 | 600 | 3 | 650 |
| 4 | 590 | 5 | 330 |
| 6 | 640 | 7 | 220 |
| 8 | 490 | 9 | 840 |
| 17 | 630 | 18 | 490 |
| 21 | 120 | 22 | 595 |
| 23 | 520 | 26 | 67 |
| 27 | 780 | 28 | 570 |
| 29 | 350 | 30 | 620 |
| 32 | 800 | 33 | 320 |
| 34 | 310 | 35 | 510 |
| 37 | 275 | 40 | 550 |
| 41 | 1600 | 42 | 110 |
| 43 | 230 | 44 | 140 |
| 45 | 200 | 47 | 150 |
| 55 | 31 | 57 | 17 |
| 58 | 46 | 60 | 15.5 |
| 61 | 29 | 63 | 67 |

TABLE B-continued

| Example No. | IC$_{50}$ [nM] | Example No. | IC$_{50}$ [nM] |
|---|---|---|---|
| 65 | 25 | 66 | 31 |
| 68 | 14.5 | 69 | 11 |
| 70 | 16 | 71 | 17 |
| 72 | 29 | 73 | 16 |
| 74 | 10 | 75 | 28 |
| 76 | 12 | 78 | 4.1 |
| 79 | 15 | 81 | 7.6 |
| 82 | 45 | 83 | 15 |
| 84 | 40 | 86 | 16.5 |
| 87 | 14 | 88 | 7.9 |
| 89 | 850 | 90 | 54 |
| 92 | 35 | 93 | 18 |
| 94 | 48 | 96 | 19 |
| 97 | 26 | 100 | 15 |
| 101 | 19 | 103 | 5.9 |
| 104 | 67 | 105 | 13 |
| 106 | 21 | 107 | 56 |
| 108 | 59 | 109 | 220 |
| 110 | 78 | 111 | 220 |
| 112 | 200 | 113 | 39 |
| 115 | 16 | 116 | 11 |
| 117 | 12 | 118 | 210 |
| 119 | 200 | 121 | 220 |
| 122 | 700 | 123 | 1100 |
| 125 | 23 | 126 | 64 |
| 127 | 160 | 128 | 180 |
| 129 | 390 | 130 | 1300 |
| 132 | 18 | 134 | 5.8 |
| 135 | 19 | 136 | 9.4 |
| 138 | 6.5 | 139 | 9.4 |
| 140 | 32 | 141 | 1600 |
| 142 | 18 | 143 | 4.6 |
| 144 | 1000 | 145 | 98 |
| 146 | 1500 | 147 | 70 |
| 148 | 430 | 149 | 27 |
| 150 | 18 | 151 | 110 |
| 152 | 75 | 154 | 45 |
| 155 | 10 | 157 | 5.2 |
| 158 | 29 | 159 | 16 |
| 160 | 240 | 161 | 1500 |
| 162 | 250 | 163 | 3.6 |
| 164 | 1.9 | 165 | 8.2 |
| 166 | 6.3 | 167 | 8.4 |
| 168 | 3.1 | 169 | 54 |
| 170 | 670 | 171 | 89 |
| 172 | 360 | 173 | 54 |
| 174 | 28 | 175 | 20 |
| 176 | 58 | 177 | 120 |
| 178 | 33 | 179 | 24 |
| 180 | 78 | 181 | 45 |
| 182 | 130 | 183 | 62 |
| 184 | 110 | 185 | 40 |
| 186 | 31 | 187 | 14 |
| 188 | 31 | 189 | 63 |
| 190 | 35 | 191 | 35 |
| 192 | 61 | 193 | 46 |
| 194 | 6.3 | 195 | 59 |
| 196 | 21 | 197 | 10 |
| 198 | 39 | 199 | 34 |
| 202 | 82 | 205 | 68 | a.6) Determination of Endothel Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, N.Y.), it is possible to measure continuously variations in the transendothelial electrical resistance (TEER) across an endothelial cell monolayer plated over gold electrodes. HUVECs are shown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1\times10^{-10}$ to $1\times10^{-6}$ M.

a.7) Determination of the In Vitro Permeability of Endothelial Cells

In a further hyperpermeability model, the activity of the substances on the modulation of macromolecular permeability is determined HUVECs are shown on a fibronectin-coated Transwell filter membrane (24-well plates, 6.5 mm insert with 0.4 µM polycarbonate membrane; Costar #3413). The filter membrane separates the upper from the lower cell culture chamber, with the confluent endothelial cell layer on the floor of the upper cell culture chamber. 250 g/ml of 40 kDa FITC dextan (Invitrogen, D1844) is added to the medium of the upper chamber. Hyperpermeability of the monolayer formed is induced by stimulation with kininogen, prekallikrein and factor XII (100 nM each). Every 30 min, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1\times10^{-10}$ to $1\times10^{-6}$ M.

b) Determination of Antithrombotic Activity (In Vivo)

b.1) Arterial Thrombosis Model (Iron(II) Chloride-Induced Thrombosis) in Combination with Ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the tissue injury is then caused by wrapping a piece of filter paper (10 mm×10 mm) on a Parafilm® strip (25 mm×12 mm) around the carotid artery without disturbing the blood flow. The filter paper contains 100 µl of a 13% strength solution of iron(II) chloride (Sigma) in water. After 5 min, the filter paper is removed and the vessel is rinsed twice with aqueous 0.9% strength sodium chloride solution. 30 min after the injury the injured region of the carotid artery is extracted surgically and any thrombotic material is removed and weighed.

The test substances are administered either intravenously to the anaesthetized animals via the femoral vein or orally to the awake animals via gavage, in each case 5 min and 2 h, respectively, before the injury.

Ear bleeding time is determined 2 min after injury to the carotid artery. To this end, the left ear is shaved and a defined 3-mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Oedema Formation and/or Neovascularization in the Eye (In Vivo)

c.1) Test of the Efficacy of Substances in the Laser-Induced Choroidal Neovascularization Model This study serves to investigate the efficacy of a test substance on reduction of extravasation/oedema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine). Following instillation of a drop of a 0.5% strength tropicamide solution to dilate the pupils, choroidal neovascularization is triggered on six defined locations around the optical nerve using a 532 nm argon laser photocoagulator (diameter 50-75 µm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 min later, pictures of the eye background are taken. The degree of extravasation/the oedema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and $\mu m^3$, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57Bl/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% Formalin. After washing in phosphate-buffered saline, the retina is excised, a flat preparation thereof is produced and this is stained with isolectin B4 antibody. Quantification of neovascularization is carried out using a Zeiss ApoTome.

C) WORKING EXAMPLES FOR PHARMACEUTICAL COMPOSITIONS

The substances according to the invention can be converted to pharmaceutical preparations as follows:

Tablet:
Composition:
100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg, diameter 8 mm, radius of curvature 12 mm

Production:
The mixture of the compound of Example 1, lactose and starch is granulated with a 5% strength solution (m/m) of the PVP in water. After drying, the granules are mixed with the magnesium stearate for 5 min. This mixture is pressed with a conventional tableting press (for tablet dimensions see above).

Oral Suspension:
Composition:
1000 mg of the compound of Example 1, 1000 mg of ethanol (96%), 400 mg of Rhodigel (xanthan gum) (from FMC, USA) and 99 g of water.

A single dose of 100 mg of the compound according to the invention corresponds to 10 ml of oral suspension.

Production:
The Rhodigel is suspended in ethanol, and the compound of Example 1 is added to the suspension. The water is added while stirring. The mixture is stirred for approx. 6 h until the Rhodigel has finished swelling.

Solution or Suspension for Topical Administration to the Eye (Eye Drops):

A sterile pharmaceutical preparation for topical administration to the eye can be prepared by reconstituting a lyophilisate of the compound according to the invention in sterile saline. Suitable preservatives for such a solution or suspension are, for example, benzalkonium chloride, thiomersal or phenylmercury nitrate in a concentration range of from 0.001 to 1 percent by weight.

The invention claimed is:

1. A compound of the formula

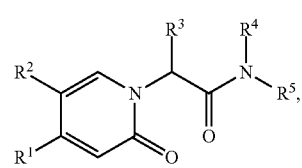

in which $R^1$ represents a group of the formula

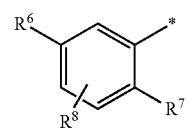

where * is the point of attachment to the oxopyridine ring, $R^6$ represents bromine, chlorine, fluorine, methyl, difluoromethyl, trifluoromethyl, methoxy, difluoromethoxy or trifluoromethoxy, $R^7$ represents bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl, $R^8$ represents hydrogen, chlorine or fluorine, $R^2$ represents hydrogen, bromine, chlorine, fluorine, cyano, $C_1$-$C_3$-alkyl, difluoromethyl, trifluoromethyl, 1,1-difluoroethyl, 2,2-difluoroethyl, 2,2,2-trifluoroethyl, $C_1$-$C_3$-alkoxy, difluoromethoxy, trifluoromethoxy, 1,1-difluoroethoxy, 2,2-difluoroethoxy, 2,2,2-trifluoroethoxy, methylcarbonyl or cyclopropyl, $R^3$ represents hydrogen, $C_1$-$C_5$-alkyl, $C_1$-$C_4$-alkoxy, difluoromethyl, trifluoromethyl, 1,1-difluoroethyl, 1,1,2,2,2-pentadeuteroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy, where alkyl may be substituted by a substituent selected from the group consisting of fluorine, cyano, hydroxy, difluoromethyl, trifluoromethyl, methoxy, ethoxy, difluoromethoxy, trifluoromethoxy, $C_3$-$C_6$-cycloalkyl, 4- to 6-membered oxoheterocyclyl, 4- to 6-membered thioheterocyclyl, 1,4-dioxanyl, phenyl and pyridyl, where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy, and where oxoheterocyclyl and thioheterocyclyl may be substituted by 1 to 2 substituents independently of one another selected from the group consisting of oxo, fluoro, methyl, ethyl, difluoromethyl and trifluoromethyl, $R^4$ represents hydrogen, $R^5$ represents a group of the formula

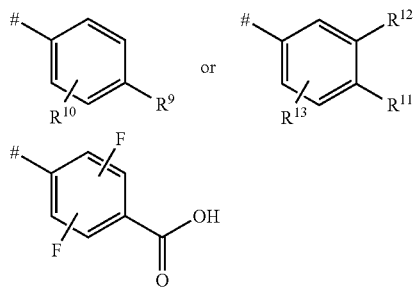

where # is the point of attachment to the nitrogen atom, $R^9$ represents hydroxycarbonyl or 5-membered heterocyclyl, where heterocyclyl may be substituted by 1 to 2 substituents independently of one another selected from the group consisting of oxo, hydroxy, thioxo, sulphanyl, methyl, difluoromethyl, trifluoromethyl, 2-hydroxycarbonyl-1,1,2,2-tetrafluoroethyl and 2-methoxycarbonyl-1,1,2,2-tetrafluoroethyl, where methyl may be substituted by a methoxy substituent, $R^{10}$ represents hydrogen, chlorine, fluorine or methyl, $R^{11}$ and $R^{12}$ together with the carbon atoms to which they are attached form a 5-membered heterocycle, where the heterocycle may be substituted by 1 to 2 substituents independently of one another selected from the group consisting of oxo, chlorine, hydroxy, hydroxycarbonyl, methyl, difluoromethyl, trifluoromethyl, 1,1,2,2,2-pentafluoroethyl, 2-hydroxycarbonyl-1,1,2,2-tetrafluoroethyl and 2-methoxycarbonyl-1,1,2,2-tetrafluoroethyl, $R^{13}$ represents hydrogen, chlorine, fluorine, methyl or methoxy, or a salt thereof, solvate thereof or solvate of a salt thereof.

2. The compound of claim 1, wherein $R^1$ represents a group of the formula

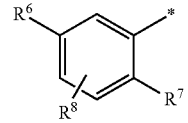

where * is the point of attachment to the oxopyridine ring, $R^6$ represents chlorine, $R^7$ represents bromine, chlorine, cyano, nitro, methyl, difluoromethyl, trifluoromethyl, difluoromethoxy, trifluoromethoxy, ethynyl or cyclopropyl, $R^8$ represents hydrogen, $R^2$ represents hydrogen, chlorine, fluorine, cyano, difluoromethyl, trifluoromethyl, 2,2,2-trifluoroethyl, methoxy, ethoxy, isopropoxy, difluoromethoxy or 2,2,2-trifluoroethoxy, $R^3$ represents hydrogen, $C_1$-$C_5$-alkyl, ethoxy, 1,1,2,2,2-pentadeuteroethyl or prop-2-yn-1-yl, where $C_1$-alkyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl, tetrahydro-2H-thiopyranyl, 1,4-dioxanyl, phenyl and pyridyl, where cyclopropyl, cyclobutyl, cyclohexyl and oxetanyl may be substituted by 1 to 2 substituents independently of one another selected from the group consisting of fluorine, hydroxy, methyl, ethyl, methoxy and trifluoromethyl, and where tetrahydrofuranyl, tetrahydro-2H-pyranyl and tetrahydro-2H-thiopyranyl may be substituted by 1 to 2 substituents independently of one another selected from the group consisting of oxo, methyl and ethyl, and where $C_2$-$C_4$-alkyl may be substituted by a substituent selected from the group consisting of fluorine, hydroxy, trifluoromethyl, methoxy and trifluoromethoxy, $R^4$ represents hydrogen, $R^5$ represents a group of the formula

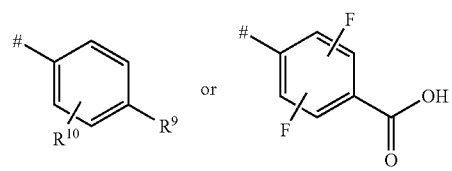

where # is the point of attachment to the nitrogen atom, $R^9$ represents hydroxycarbonyl, oxazolyl, oxadiazolyl, thiadiazolyl, pyrazolyl, imidazolyl, triazolyl, tetrazolyl or dihydrooxazolyl, where oxazolyl, oxadiazolyl, thiadiazolyl, pyrazolyl, imidazolyl, triazolyl and dihydrooxazolyl may be substituted by 1 to 2 substituents independently of one another selected from the group consisting of oxo, hydroxy, thioxo, sulphanyl, methyl, trifluoromethyl and 2-hydroxycarbonyl-1,1,2,2-tetrafluoroethyl,
where methyl may be substituted by a methoxy substituent,
$R^{10}$ represents hydrogen, chlorine, fluorine or methyl,
or
$R^5$ represents 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl or 1H-indazol-5-yl,
where the 5-membered heterocycle in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by 1 to 2 substituents independently of one another selected from the group consisting of oxo, chlorine, hydroxycarbonyl, methyl and trifluoromethyl,
and
where the benzyl ring in 2,3-dihydro-1H-indazol-6-yl, 1H-benzimidazol-6-yl, indol-6-yl, 2,3-dihydro-1H-indazol-5-yl, 2,3-dihydro-1H-benzimidazol-5-yl, indol-5-yl, 1H-indazol-6-yl and 1H-indazol-5-yl may be substituted by a substituent selected from the group consisting of fluorine and methoxy,
or a salt thereof, solvate thereof or solvate of a salt thereof.

3. The compound of claim 1, wherein
$R^1$ represents a group of the formula

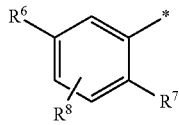

where * is the point of attachment to the oxopyridine ring,
$R^6$ represents chlorine,
$R^7$ represents cyano or difluoromethoxy,
$R^8$ represents hydrogen,
$R^2$ represents chlorine, cyano, methoxy, ethoxy or difluoromethoxy,
$R^3$ represents methyl, ethyl, n-propyl, 2-methylprop-1-yl or n-butyl,
where methyl may be substituted by a substituent selected from the group consisting of difluoromethyl, trifluoromethyl, cyclopropyl, cyclobutyl, cyclohexyl, tetrahydrofuranyl, tetrahydro-2H-pyranyl, 1,4-dioxanyl, phenyl and pyridyl,
where cyclopropyl, cyclobutyl and cyclohexyl may be substituted by 1 to 2 substituents independently of one another selected from the group consisting of fluorine, hydroxy, methyl, methoxy and trifluoromethyl,
and
where ethyl, n-propyl and n-butyl may be substituted by a substituent selected from the group consisting of fluorine, methoxy and trifluoromethoxy,
$R^4$ represents hydrogen,
$R^5$ represents a group of the formula

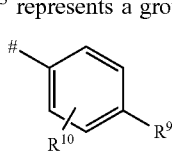

where # is the point of attachment to the nitrogen atom,
$R^9$ represents hydroxycarbonyl, oxadiazolyl, pyrazolyl, triazolyl or tetrazolyl,
where oxadiazolyl and pyrazolyl may be substituted by 1 to 2 substituents independently of one another selected from the group consisting of oxo, hydroxy and trifluoromethyl,
and
where triazolyl may be substituted by a substituent selected from the group consisting of trifluoromethyl and 2-hydroxycarbonyl-1,1,2,2-tetrafluoroethyl,
$R^{10}$ represents hydrogen or fluorine,
or
$R^5$ represents 2,3-dihydro-1H-indazol-6-yl, 1H-benzimidazol-6-yl, 2,3-dihydro-1H-benzimidazol-5-yl or 1H-indazol-5-yl,
where the 5-membered heterocycle in 2,3-dihydro-1H-indazol-6-yl may be substituted by 1 to 2 substituents independently of one another selected from the group consisting of oxo and methyl,
and
where the benzyl ring in 2,3-dihydro-1H-indazol-6-yl may be substituted by a fluorine substituent,
and
where the 5-membered heterocycle in 1H-benzimidazol-6-yl may be substituted by a hydroxycarbonyl substituent,
and
where the 5-membered heterocycle in 2,3-dihydro-1H-benzimidazol-5-yl may be substituted by an oxo substituent,
and
where the 5-membered heterocycle in 1H-indazol-5-yl may be substituted by a chlorine substituent,
or a salt thereof, solvate thereof or solvate of a salt thereof.

4. A process for preparing a compound of formula (I) or a salt thereof, solvate thereof or solvate of a salt thereof according to claim 1, comprising
[A] reacting a compound of the formula

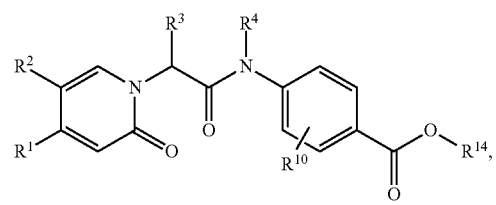

in which
$R^1$, $R^2$, $R^3$, $R^4$ and $R^{10}$ have the meaning given in claim 1, and
$R^{14}$ represents tert-butyl,
with an acid to give a compound of the formula

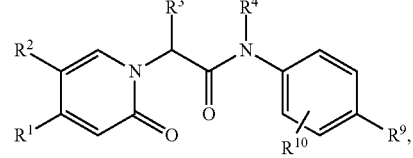

in which
$R^1$, $R^2$, $R^3$, $R^4$ and $R^{10}$ have the meaning given in claim 1, and
$R^9$ represents hydroxycarbonyl,
or
[B] reacting a compound of the formula

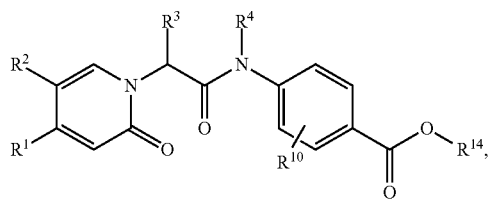
(IIb)

in which
$R^1$, $R^2$, $R^3$, $R^4$ and $R^{10}$ have the meaning given in claim 1, and
$R^{14}$ represents methyl or ethyl,
with a base to give a compound of the formula

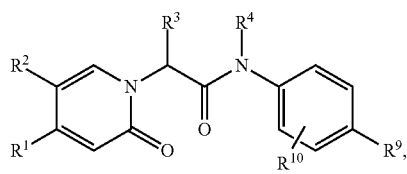
(Ib)

in which
$R^1$, $R^2$, $R^3$, $R^4$ and $R^{10}$ have the meaning given in claim 1, and
$R^9$ represents hydroxycarbonyl,
or
[C] reacting a compound of the formula

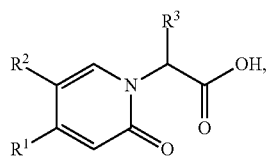
(III)

in which
$R^1$, $R^2$ and $R^3$ have the meaning given in claim 1, with a compound of the formula

(IV)

in which
$R^4$ and $R^5$ have the meaning given in claim 1, in the presence of a dehydrating agent to give a compound of the formula (I),
or
[D] reacting a compound of the formula

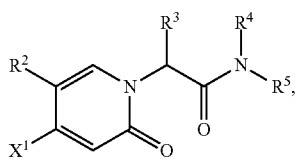
(V)

in which
$R^2$, $R^3$, $R^4$ and $R^5$ have the meaning given in claim 1, and
$X^1$ represents chlorine, bromine or iodine,
with a compound of the formula $R^1$-Q (VI), in which
$R^1$ has the meaning given in claim 1, and
Q represents —B(OH)$_2$, a boronic ester, or radical —BF$_3^-$ K$^+$,
under Suzuki coupling conditions to give a compound of the formula (I).

5. The process of claim 4, wherein the boronic ester is boronic acid pinacol ester.

6. A pharmaceutical composition comprising a compound according to claim 1 and an inert, nontoxic, pharmaceutically suitable excipient.

7. A method for the treatment of a thrombotic or thromboembolic disorder comprising administering a therapeutically effective amount of at least one compound of claim 1 to a human or animal in need thereof.

8. A method for the treatment of an ophthalmic disorder comprising administering a therapeutically effective amount of at least one compound of claim 1 to a human or animal in need thereof.

* * * * *